US010053469B2

(12) United States Patent
Barbosa et al.

(10) Patent No.: US 10,053,469 B2
(45) Date of Patent: Aug. 21, 2018

(54) PYRIDONE AND AZA-PYRIDONE COMPOUNDS AND METHODS OF USE

(71) Applicants: GILEAD CONNECTICUT, INC., Foster City, CA (US); GENENTECH INC., South Franciso, CA (US)

(72) Inventors: Antonio J. M. Barbosa, Middlebury, CT (US); Peter A. Blomgren, North Branford, CT (US); Kevin S. Currie, North Branford, CT (US); Ravi Krishnamoorthy, Guilderland, NY (US); Jeffrey E. Kropf, Branford, CT (US); Seung H. Lee, Branford, CT (US); Scott A. Mitchell, East Haven, CT (US); Daniel Ortwine, San Ramon, CA (US); Aaron C. Schmitt, Hamden, CT (US); Xiaojing Wang, Foster City, CA (US); Jianjun Xu, Madison, CT (US); Wendy Young, San Mateo, CA (US); Honglu Zhang, Guilderland, NY (US); Zhongdong Zhao, Guilford, CT (US); Pavel E. Zhichkin, Delmar, NY (US)

(73) Assignees: GILEAD CONNECTICUT, INC., Foster City, CA (US); GENENTECH INC., South Franciso, CA (US)

( * ) Notice: Subject to any disclaimer, the term of this patent is extended or adjusted under 35 U.S.C. 154(b) by 0 days.

(21) Appl. No.: 15/281,923

(22) Filed: Sep. 30, 2016

(65) Prior Publication Data

US 2017/0073356 A1   Mar. 16, 2017

Related U.S. Application Data

(62) Division of application No. 14/059,626, filed on Oct. 22, 2013, now Pat. No. 9,505,785, which is a division
(Continued)

(51) Int. Cl.

| C07D 519/00 | (2006.01) |
|---|---|
| C07D 487/04 | (2006.01) |
| C07D 495/04 | (2006.01) |
| C07D 498/04 | (2006.01) |
| A61K 31/497 | (2006.01) |
| A61K 31/4985 | (2006.01) |
| A61K 31/501 | (2006.01) |
| A61K 31/5025 | (2006.01) |
| A61K 31/506 | (2006.01) |

(Continued)

(52) U.S. Cl.
CPC .......... *C07D 519/00* (2013.01); *A61K 31/497* (2013.01); *A61K 31/4985* (2013.01); *A61K 31/501* (2013.01); *A61K 31/506* (2013.01); *A61K 31/5025* (2013.01); *A61K 31/5377* (2013.01); *A61K 31/5383* (2013.01); *A61K 31/5386* (2013.01); *A61K 31/551* (2013.01); *A61K 45/06* (2013.01); *C07C 69/65* (2013.01); *C07D 209/52* (2013.01); *C07D 471/14* (2013.01); *C07D 487/04* (2013.01); *C07D 495/04* (2013.01); *C07D 498/04* (2013.01); *C07F 5/04* (2013.01)

(58) Field of Classification Search
CPC ..................................................... C07D 487/04
See application file for complete search history.

(56) References Cited

U.S. PATENT DOCUMENTS

| 7,884,108 B2 | 2/2011 | Blomgren et al. |
|---|---|---|
| 7,902,194 B2 | 3/2011 | Dewdney et al. |

(Continued)

FOREIGN PATENT DOCUMENTS

| EP | 2566869 B1 | 3/2013 |
|---|---|---|
| WO | 2008033854 A1 | 3/2008 |

(Continued)

OTHER PUBLICATIONS

Canadian Office Action dated Apr. 6, 2017 for corresponding Canadian Application No. 2,798,634.
(Continued)

*Primary Examiner* — Paul V Ward
(74) *Attorney, Agent, or Firm* — Millen, White, Zelano & Branigan, PC

(57) ABSTRACT

Pyridone and aza-pyridone compounds of Formula I are provided, including stereoisomers, tautomers, and pharmaceutically acceptable salts thereof, useful for inhibiting Btk kinase, and for treating immune disorders such as inflammation mediated by Btk kinase. Methods of using compounds of Formula I for in vitro, in situ, and in vivo diagnosis, and treatment of such disorders in mammalian cells, or associated pathological conditions, are disclosed.

27 Claims, 8 Drawing Sheets

Related U.S. Application Data of application No. 13/102,720, filed on May 6, 2011, now Pat. No. 8,618,107.

(60) Provisional application No. 61/443,952, filed on Feb. 17, 2011, provisional application No. 61/332,353, filed on May 7, 2010.

(51) Int. Cl.
*A61K 31/5377* (2006.01)
*A61K 31/5383* (2006.01)
*A61K 31/5386* (2006.01)
*A61K 31/551* (2006.01)
*A61K 45/06* (2006.01)
*C07D 471/14* (2006.01)
*C07C 69/65* (2006.01)
*C07D 209/52* (2006.01)
*C07F 5/04* (2006.01)

(56) References Cited

U.S. PATENT DOCUMENTS

| | | | |
|---|---|---|---|
| 8,058,446 B2 | 11/2011 | Blomgren et al. | |
| 8,618,107 B2* | 12/2013 | Barbosa | C07D 487/04 514/252.01 |
| 9,505,785 B2* | 11/2016 | Barbosa | C07D 487/04 |
| 2008/0139557 A1 | 6/2008 | Blomgren et al. | |
| 2009/0082330 A1 | 3/2009 | Blomgren et al. | |
| 2009/0318448 A1 | 12/2009 | Dewdney et al. | |
| 2010/0004231 A1 | 1/2010 | Dewdney et al. | |
| 2011/0059944 A1 | 3/2011 | Blomgren et al. | |
| 2011/0105479 A1 | 5/2011 | Dewdney et al. | |

FOREIGN PATENT DOCUMENTS

| | | |
|---|---|---|
| WO | 2009/039397 A2 | 3/2009 |
| WO | 2009156284 A1 | 12/2009 |
| WO | 2010000633 A1 | 1/2010 |
| WO | 2011/140488 A1 | 11/2011 |

OTHER PUBLICATIONS

International Search Report, dated Sep. 8, 2011, issued in corresponding PCT/US2011/035596.
Chinese Notification of Examination for corresponding Chinese Application No. 201180033536.8; published Apr. 28, 2016.
English language translation of Chinese Notification of Examination for corresponding Chinese Application No. 201180033536.8; published Apr. 28, 2016.
English language Abstract for WO 2011/140488; published Nov. 10, 2011.

* cited by examiner

PYRIDONE AND AZA-PYRIDONE COMPOUNDS AND METHODS OF USE

CROSS REFERENCE TO RELATED APPLICATIONS

This non-provisional application filed under 37 CFR § 1.53(b), claims the benefit under 35 USC § 119(e) of U.S. Provisional Application Ser. No. 61/443,952 filed on 17 Feb. 2011, and U.S. Provisional Application Ser. No. 61/332,353 filed on 7 May 2010, which are incorporated by reference in entirety

FIELD OF THE INVENTION

The invention relates generally to compounds for treating disorders mediated by Bruton's Tyrosine Kinase (Btk) including inflammation, immunological, and cancer, and more specifically to compounds which inhibit Btk activity. The invention also relates to methods of using the compounds for in vitro, in situ, and in vivo diagnosis or treatment of mammalian cells, or associated pathological conditions.

BACKGROUND OF THE INVENTION

Protein kinases, the largest family of human enzymes, encompass well over 500 proteins. Bruton's Tyrosine Kinase (Btk) is a member of the Tec family of tyrosine kinases, and is a regulator of early B-cell development as well as mature B-cell activation, signaling, and survival.

B-cell signaling through the B-cell receptor (BCR) can lead to a wide range of biological outputs, which in turn depend on the developmental stage of the B-cell. The magnitude and duration of BCR signals must be precisely regulated. Aberrant BCR-mediated signaling can cause disregulated B-cell activation and/or the formation of pathogenic auto-antibodies leading to multiple autoimmune and/or inflammatory diseases. Mutation of Btk in humans results in X-linked agammaglobulinaemia (XLA). This disease is associated with the impaired maturation of B-cells, diminished immunoglobulin production, compromised T-cell-independent immune responses and marked attenuation of the sustained calcium sign upon BCR stimulation.

Evidence for the role of Btk in allergic disorders and/or autoimmune disease and/or inflammatory disease has been established in Btk-deficient mouse models. For example, in standard murine preclinical models of systemic lupus erythematosus (SLE), Btk deficiency has been shown to result in a marked amelioration of disease progression. Moreover, Btk deficient mice can also be resistant to developing collagen-induced arthritis and can be less susceptible to *Staphylococcus*-induced arthritis.

A large body of evidence supports the role of B-cells and the humoral immune system in the pathogenesis of autoimmune and/or inflammatory diseases. Protein-based therapeutics (such as Rituxan) developed to deplete B-cells, represent an approach to the treatment of a number of autoimmune and/or inflammatory diseases. Because of Btk's role in B-cell activation, inhibitors of Btk can be useful as inhibitors of B-cell mediated pathogenic activity (such as autoantibody production).

Btk is also expressed in osteoclasts, mast cells and monocytes and has been shown to be important for the function of these cells. For example, Btk deficiency in mice is associated with impaired IgE-mediated mast cell activation (marked diminution of TNF-alpha and other inflammatory cytokine release), and Btk deficiency in humans is associated with greatly reduced TNF-alpha production by activated monocytes.

Thus, inhibition of Btk activity can be useful for the treatment of allergic disorders and/or autoimmune and/or inflammatory diseases such as: SLE, rheumatoid arthritis, multiple vasculitides, idiopathic thrombocytopenic purpura (ITP), myasthenia gravis, allergic rhinitis, and asthma. In addition, Btk has been reported to play a role in apoptosis; thus, inhibition of Btk activity can be useful for cancer, as well as the treatment of B-cell lymphoma and leukemia. Moreover, given the role of Btk in osteoclast function, the inhibition of Btk activity can be useful for the treatment of bone disorders such as osteoporosis.

SUMMARY OF THE INVENTION

The invention relates generally to Formula I compounds with Bruton's Tyrosine Kinase (Btk) modulating activity.

Formula I compounds have the structures:

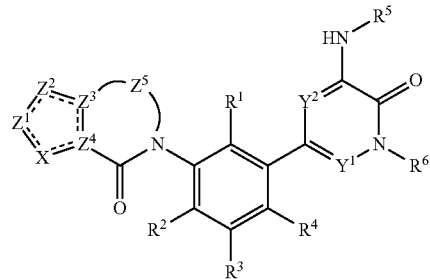

including stereoisomers, tautomers, or pharmaceutically acceptable salts thereof. The various substituents are defined herein below.

One aspect of the invention is a pharmaceutical composition comprised of a Formula I compound and a pharmaceutically acceptable carrier, glidant, diluent, or excipient. The pharmaceutical composition may further comprise a second therapeutic agent.

Another aspect of the invention is a process for making a pharmaceutical composition which comprises combining a Formula I compound with a pharmaceutically acceptable carrier.

The invention includes a method of treating a disease or disorder which method comprises administering a therapeutically effective amount of a Formula I compound to a patient with a disease or disorder selected from immune disorders, cancer, cardiovascular disease, viral infection, inflammation, metabolism/endocrine function disorders and neurological disorders, and mediated by Bruton's tyrosine kinase.

The invention includes a kit for treating a condition mediated by Bruton's tyrosine kinase, comprising: a) a first pharmaceutical composition comprising a Formula I compound; and b) instructions for use.

The invention includes a Formula I compound for use as a medicament, and for use in treating a disease or disorder selected from immune disorders, cancer, cardiovascular disease, viral infection, inflammation, metabolism/endocrine function disorders and neurological disorders, and mediated by Bruton's tyrosine kinase.

The invention includes use of a Formula I compound in the manufacture of a medicament for the treatment of immune disorders, cancer, cardiovascular disease, viral infection, inflammation, metabolism/endocrine function disorders and neurological disorders, and where the medicament mediates Bruton's tyrosine kinase.

The invention includes methods of making a Formula I compound.

DETAILED DESCRIPTION OF EXEMPLARY EMBODIMENTS

Figure 1:
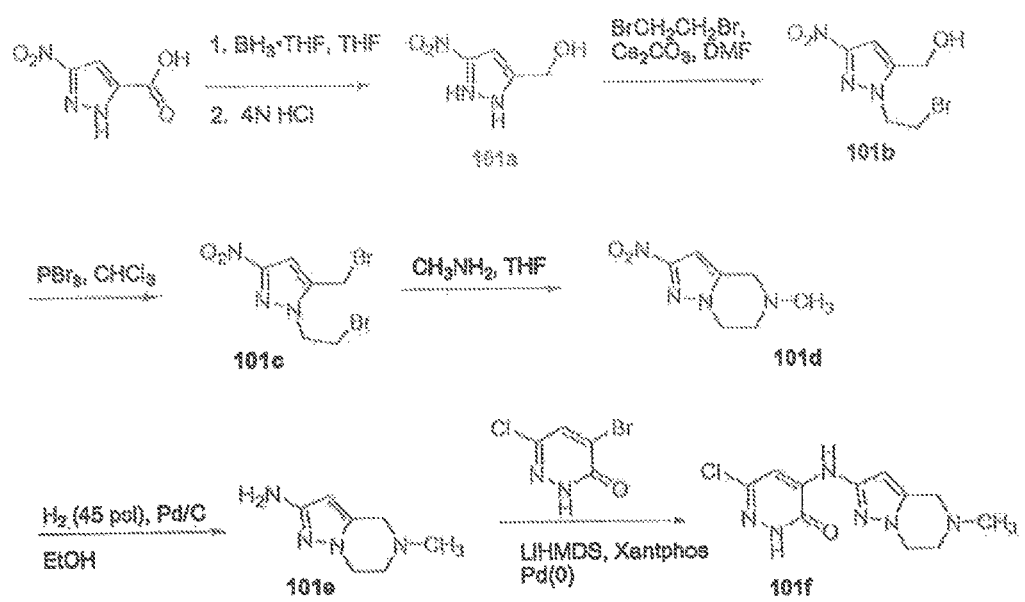
FIG. 1 shows an exemplary synthetic route to prepare 6-chloro,4-amino pyridazinone compounds, including 6-chloro-4-(5-methyl-4,5,6,7-tetrahydropyrazolo[1,5-a]pyrazin-2-ylamino)pyridazin-3(2H)-one 101f, from 3-nitropyrazole-5-carboxylic acid.

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls.

Definitions

The term "alkyl" as used herein refers to a saturated linear or branched-chain monovalent hydrocarbon radical of one to twelve carbon atoms ($C_1$-$C_{12}$), wherein the alkyl radical may be optionally substituted independently with one or more substituents described below. In another embodiment, an alkyl radical is one to eight carbon atoms ($C_1$-$C_8$), or one to six carbon atoms ($C_1$-$C_6$). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl, 1-octyl, and the like.

The term "alkylene" as used herein refers to a saturated linear or branched-chain divalent hydrocarbon radical of one to twelve carbon atoms ($C_1$-$C_{12}$), wherein the alkylene radical may be optionally substituted independently with one or more substituents described below. In another embodiment, an alkylene radical is one to eight carbon atoms ($C_1$-$C_8$), or one to six carbon atoms ($C_1$-$C_6$). Examples of alkylene groups include, but are not limited to, methylene (—$CH_2$—), ethylene (—$CH_2CH_2$—), propylene (—$CH_2CH_2CH_2$—), and the like.

The terms "carbocycle", "carbocyclyl", "carbocyclic ring" and "cycloalkyl" refer to a monovalent non-aromatic, saturated or partially unsaturated ring having 3 to 12 carbon atoms ($C_3$-$C_{12}$) as a monocyclic ring or 7 to 12 carbon atoms as a bicyclic ring. Bicyclic carbocycles having 7 to 12 atoms can be arranged, for example, as a bicyclo[4,5], [5,5], [5,6] or [6,6] system, and bicyclic carbocycles having 9 or 10 ring atoms can be arranged as a bicyclo[5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

"Aryl" means a monovalent aromatic hydrocarbon radical of 6-20 carbon atoms ($C_6$-$C_{20}$) derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein.

"Arylene" means a divalent aromatic hydrocarbon radical of 6-20 carbon atoms ($C_6$-$C_{20}$) derived by the removal of two hydrogen atom from a two carbon atoms of a parent aromatic ring system. Some arylene groups are represented in the exemplary structures as "Ar". Arylene includes bicyclic radicals comprising an aromatic ring fused to a saturated, partially unsaturated ring, or aromatic carbocyclic ring. Typical arylene groups include, but are not limited to, radicals derived from benzene (phenylene), substituted benzenes, naphthalene, anthracene, biphenylene, indenylene, indanylene, 1,2-dihydronaphthalene, 1,2,3,4-tetrahydronaphthyl, and the like. Arylene groups are optionally substituted The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus, sulfur, and silicon, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo[4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, morpholin-4-yl, piperidin-1-yl, piperidonyl, oxopiperazinyl, piperazinyl, piperazin-4-yl-2-one, piperazin-4-yl-3-one, pyrrolidin-1-yl, thiomorpholin-4-yl, S-dioxothiomorpholin-4-yl, azocan-1-yl, azetidin-1-yl, octahydropyrido[1,2-a]pyrazin-2-yl, [1,4]diazepan-1-yl, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. Examples of a heterocyclic group wherein 2 ring atoms are substituted with oxo (=O) moieties are pyrimidinonyl and 1,1-dioxo-thiomorpholinyl. The heterocycle groups herein are optionally substituted independently with one or more substituents described herein.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The heterocycle or heteroaryl groups may be carbon (carbon-linked), or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The terms "treat" and "treatment" refer to therapeutic treatment, wherein the object is to slow down (lessen) an undesired physiological change or disorder, such as the development or spread of arthritis or cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those with the condition or disorder.

The phrase "therapeutically effective amount" means an amount of a compound of the present invention that (i) treats the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop)

cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

"Inflammatory disorder" as used herein can refer to any disease, disorder, or syndrome in which an excessive or unregulated inflammatory response leads to excessive inflammatory symptoms, host tissue damage, or loss of tissue function "Inflammatory disorder" also refers to a pathological state mediated by influx of leukocytes and/or neutrophil chemotaxis.

"Inflammation" as used herein refers to a localized, protective response elicited by injury or destruction of tissues, which serves to destroy, dilute, or wall off (sequester) both the injurious agent and the injured tissue Inflammation is notably associated with influx of leukocytes and/or neutrophil chemotaxis Inflammation can result from infection with pathogenic organisms and viruses and from noninfectious means such as trauma or reperfusion following myocardial infarction or stroke, immune response to foreign antigen, and autoimmune responses. Accordingly, inflammatory disorders amenable to treatment with Formula I compounds encompass disorders associated with reactions of the specific defense system as well as with reactions of the non-specific defense system.

"Specific defense system" refers to the component of the immune system that reacts to the presence of specific antigens. Examples of inflammation resulting from a response of the specific defense system include the classical response to foreign antigens, autoimmune diseases, and delayed type hypersensitivity response mediated by T-cells. Chronic inflammatory diseases, the rejection of solid transplanted tissue and organs, e.g., kidney and bone marrow transplants, and graft versus host disease (GVHD), are further examples of inflammatory reactions of the specific defense system.

The term "nonspecific defense system" as used herein refers to inflammatory disorders that are mediated by leukocytes that are incapable of immunological memory (e.g., granulocytes, and macrophages). Examples of inflammation that result, at least in part, from a reaction of the nonspecific defense system include inflammation associated with conditions such as adult (acute) respiratory distress syndrome (ARDS) or multiple organ injury syndromes; reperfusion injury; acute glomerulonephritis; reactive arthritis; dermatoses with acute inflammatory components; acute purulent meningitis or other central nervous system inflammatory disorders such as stroke; thermal injury; inflammatory bowel disease; granulocyte transfusion associated syndromes; and cytokine-induced toxicity.

"Autoimmune disease" as used herein refers to any group of disorders in which tissue injury is associated with humoral or cell-mediated responses to the body's own constituents.

"Allergic disease" as used herein refers to any symptoms, tissue damage, or loss of tissue function resulting from allergy. "Arthritic disease" as used herein refers to any disease that is characterized by inflammatory lesions of the joints attributable to a variety of etiologies. "Dermatitis" as used herein refers to any of a large family of diseases of the skin that are characterized by inflammation of the skin attributable to a variety of etiologies. "Transplant rejection" as used herein refers to any immune reaction directed against grafted tissue, such as organs or cells (e.g., bone marrow), characterized by a loss of function of the grafted and surrounding tissues, pain, swelling, leukocytosis, and thrombocytopenia. The therapeutic methods of the present invention include methods for the treatment of disorders associated with inflammatory cell activation.

"Inflammatory cell activation" refers to the induction by a stimulus (including, but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including, but not limited to, major histocompatability antigens or cell adhesion molecules) in inflammatory cells (including but not limited to monocytes, macrophages, T lymphocytes, B lymphocytes, granulocytes (i.e., polymorphonuclear leukocytes such as neutrophils, basophils, and eosinophils), mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory disorder.

The term "NSAID" is an acronym for "non-steroidal anti-inflammatory drug" and is a therapeutic agent with analgesic, antipyretic (lowering an elevated body temperature and relieving pain without impairing consciousness) and, in higher doses, with anti-inflammatory effects (reducing inflammation). The term "non-steroidal" is used to distinguish these drugs from steroids, which (among a broad range of other effects) have a similar eicosanoid-depressing, anti-inflammatory action. As analgesics, NSAIDs are unusual in that they are non-narcotic. NSAIDs include aspirin, ibuprofen, and naproxen. NSAIDs are usually indicated for the treatment of acute or chronic conditions where pain and inflammation are present. NSAIDs are generally indicated for the symptomatic relief of the following conditions: rheumatoid arthritis, osteoarthritis, inflammatory arthropathies (e.g. ankylosing spondylitis, psoriatic arthritis, Reiter's syndrome, acute gout, dysmenorrhoea, metastatic bone pain, headache and migraine, postoperative pain, mild-to-moderate pain due to inflammation and tissue injury, pyrexia, ileus, and renal colic. Most NSAIDs act as non-selective inhibitors of the enzyme cyclooxygenase, inhibiting both the cyclooxygenase-1 (COX-1) and cyclooxygenase-2 (COX-2) isoenzymes. Cyclooxygenase catalyzes the formation of prostaglandins and thromboxane from arachidonic acid (itself derived from the cellular phospholipid bilayer by phospholipase $A_2$). Prostaglandins act (among other things) as messenger molecules in the process of inflammation. COX-2 inhibitors include celecoxib, etoricoxib, lumiracoxib, parecoxib, rofecoxib, rofecoxib, and valdecoxib.

The terms "cancer" refers to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy. Examples of chemotherapeutic agents include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo[4.3.0]nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCIN®), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE® (Cremophor-free), albumin-engineered nanoparticle formulations of paclitaxel (American Pharmaceutical Partners, Schaumberg, Ill.), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gamma1I, calicheamicin omega1 (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®)); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG™, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents in combination with the Btk inhibitors of the invention include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a Formula I compound of this invention with a mammal for a period of time sufficient to yield a metabolic product thereof.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity. In one aspect, a stereoisomer of this invention can be present in predominant form, e.g. greater than 50% ee (enantiomeric excess), greater than 80% ee, greater than 90% ee, greater than 95% ee, or greater than 99% ee.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The term "diastereomer" refers to stereoisomeric molecules which are not enantiomers. Diastereomers include cis-trans isomers and conformational isomers which have the same molecular formula but which have a different geometric structure.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The phrase "pharmaceutically acceptable" indicates that the substance or composition must be compatible chemically and/or toxicologically, with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, DMSO, ethylacetate, acetic acid, and ethanolamine.

The terms "compound of this invention," and "compounds of the present invention" include compounds of Formulas I and stereoisomers, tautomers, solvates, metabolites, and pharmaceutically acceptable salts and prodrugs thereof.

Any formula or structure given herein, including Formula I compounds, is also intended to represent hydrates, solvates, and polymorphs of such compounds, and mixtures thereof.

Any formula or structure given herein, including Formula I compounds, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as, but not limited to 2H (deuterium, D), 3H (tritium), 11C, 13C, 14C, 15N, 18F, 31P, 32P, 35S, 36Cl, and 125I. Various isotopically labeled compounds of the present invention, for example those into which radioactive isotopes such as 3H, 13C, and 14C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labelled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent in the compound of the formula (I). The concentration of such a heavier isotope, specifically deuterium, may be defined by an isotopic enrichment factor. In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this invention any atom specifically designated as a deuterium (D) is meant to represent deuterium.

Pyridone and Aza-Pyridone Compounds

The present invention provides pyridone and aza-pyridone compounds of Formula I, including Formulas Ia-bf, and pharmaceutical formulations thereof, which are potentially useful in the treatment of diseases, conditions and/or disorders modulated by Btk kinase

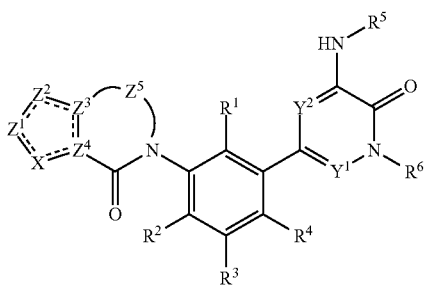

I

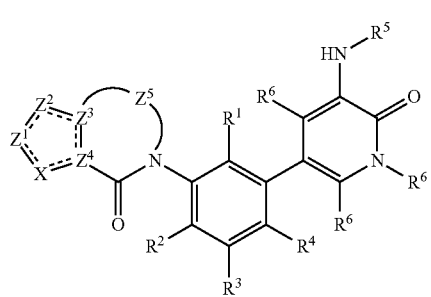

Ia

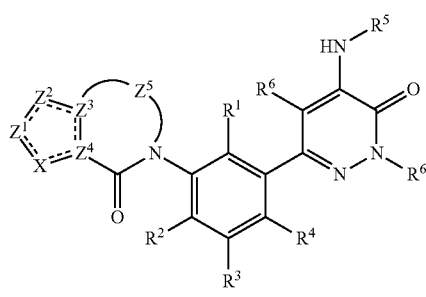

Ib including stereoisomers, tautomers, or pharmaceutically acceptable salts thereof, wherein:

$R^1$ is H, D, F, Cl, CN, —$NH_2$, —$NHCH_3$, —$N(CH_3)_2$, —OH, —$OCH_3$, —$OCH_2CH_3$, —$OCH_2CH_2OH$, heteroaryl selected from imidazolyl and pyrazolyl, heterocyclyl selected from oxetanyl and azetidinyl, and $C_1$-$C_3$ alkyl;

$R^2$, $R^3$ and $R^4$ are independently selected from H, D, F, Cl, —$NH_2$, —$NHCH_3$, —$N(CH_3)_2$, —OH, —$OCH_3$, —$OCH_2CH_3$, —$OCH_2CH_2OH$, and $C_1$-$C_3$ alkyl;

$R^5$ is optionally substituted $C_6$-$C_{20}$ aryl, $C_3$-$C_{12}$ carbocyclyl, $C_2$-$C_{20}$ heterocyclyl, $C_1$-$C_{20}$ heteroaryl, —($C_6$-$C_{20}$ aryl)-($C_2$-$C_{20}$ heterocyclyl), —($C_1$-$C_{20}$ heteroaryl)-($C_2$-$C_{20}$ heterocyclyl), —($C_1$-$C_{20}$ heteroaryl)-($C_1$-$C_6$ alkyl), or —($C_1$-$C_{20}$ heteroaryl)-C(=O)—($C_2$-$C_{20}$ heterocyclyl);

$R^6$ is H, F, —$NH_2$, —OH, or optionally substituted $C_1$-$C_3$ alkyl;

X is S, S(=O), S(=O)$_2$, N, $NR^6$, O, or $CR^7$;

$R^7$ is independently selected from H, D, F, Cl, —$CH_3$, —$CH_2CH_3$, —CN, —$CH_2F$, —$CHF_2$, —$CF_3$, —$NH_2$, —OH, and —$OCH_3$;

$Y^1$ and $Y^2$ are independently selected from $CR^6$ and N;

$Z^1$, $Z^2$, $Z^3$, and $Z^4$ are independently selected from C, $CR^7$, and N;

$Z^5$ is selected from —$C(R^3)_2$—, —$C(=O)$—, —$N(R^6)$—, —$C(R^3)_2C(R^3)_2$—, —$C(R^3)_2C(=O)$—, —$CR^3=CR^3$—, —$CR^3=N$—, —$N(R^6)C(R^3)_2$—, —$N(R^6)C(R^3)_2C(R^3)_2$—, and —$OC(R^3)_2C(R^3)_2$—;

one of $Z^1$ and $Z^2$, or X and $Z^1$, where X is not S, S(=O), or S(=O)$_2$, forms a five-, six-, or seven-membered aryl, carbocyclyl, heterocyclyl or heteroaryl ring;

where alkyl, carbocyclyl, heterocyclyl, aryl, and heteroaryl are optionally substituted with one or more groups independently selected from D, F, Cl, Br, I, —$CH_3$, —$CH_2CH_3$, —$CH_2CH(CH_3)_2$, —$CH_2OH$, —$CH_2CH_2OH$, —$C(CH_3)_2OH$, —$CH(OH)CH(CH_3)_2$, —$C(CH_3)_2CH_2OH$, —$CH_2CH_2SO_2CH_3$, —$CH_2OP(O)(OH)_2$, —CN, —$CH_2F$, —$CHF_2$, —$CF_3$, —$CO_2H$, —$COCH_3$, —$CO_2CH_3$, —$CO_2C(CH_3)_3$, —$COCH(OH)CH_3$, —$CONH_2$, —$CONHCH_3$, —$CON(CH_3)_2$, —$C(CH_3)_2CONH_2$, —$NO_2$, —$NH_2$, —$NHCH_3$, —$N(CH_3)_2$, —$NHCOCH_3$, —$N(CH_3)COCH_3$, —$NHS(O)_2CH_3$, —$N(CH_3)C(CH_3)_2CONH_2$, —$N(CH_3)CH_2CH_2S(O)_2CH_3$, =O, —OH, —$OCH_3$, —$OCH_2CH_2N(CH_3)_2$, —$OP(O)(OH)_2$, —$S(O)_2N(CH_3)_2$, —$SCH_3$, —$CH_2OCH_3$, —$S(O)_2CH_3$, cyclopropyl, azetidinyl, 1-methylazetidin-3-yl)oxy, N-methyl-N-oxetan-3-ylamino, azetidin-1-ylmethyl, oxetanyl, and morpholino.

In one aspect, Formula I compounds are 3-amino-5-phenyl pyridine-2(1H)-one Ia where $Y^1$ and $Y^2$ are $CR^6$, 4-amino-6-phenyl pyridazin-3(2H)-one Ib where $Y^1$ is N and $Y^2$ is $CR^6$, and 3-amino-5-phenyl pyrazin-2(1H)-ones Ic where $Y^1$ is $CR^6$ and $Y^2$ is N.

Exemplary embodiments of Formula I compounds include compounds of Formulas Ia-Ibf:

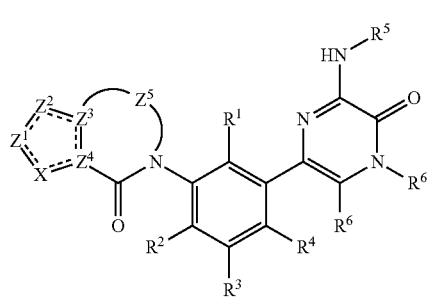

Ic

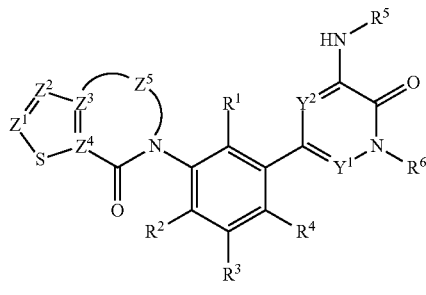

Id

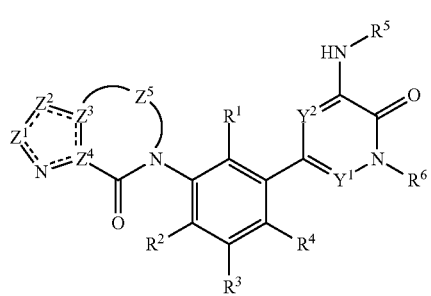

Ie

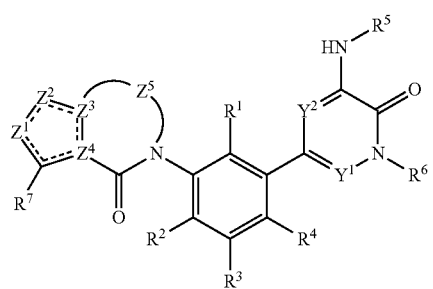
If
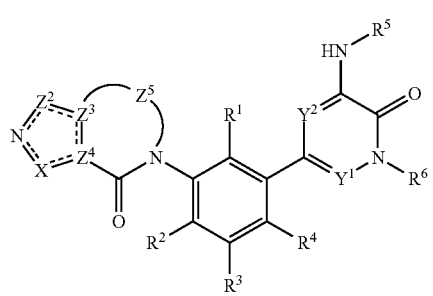
Ig
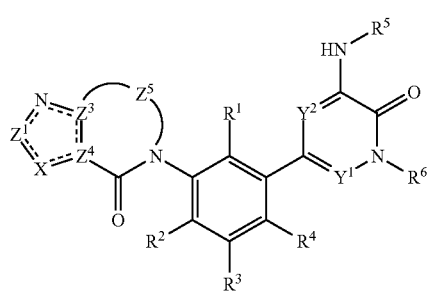
Ih
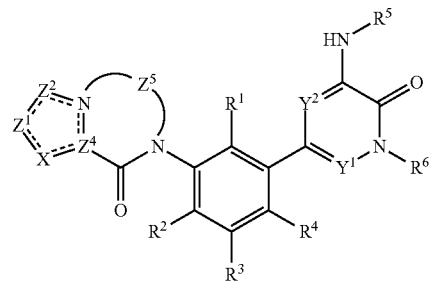
Ii
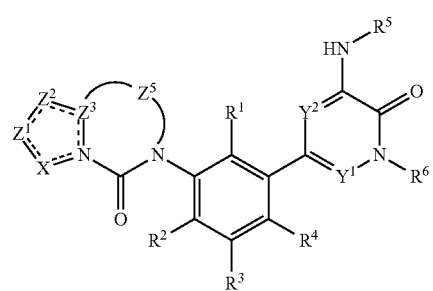
Ij
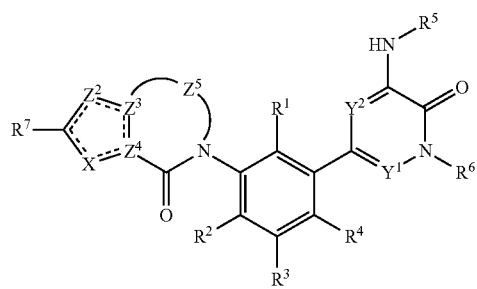
Ik
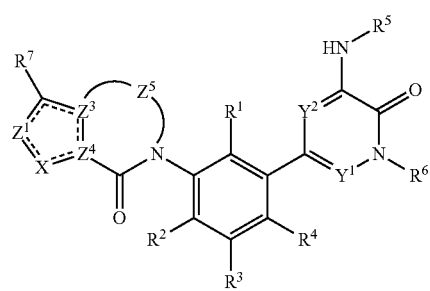
Il
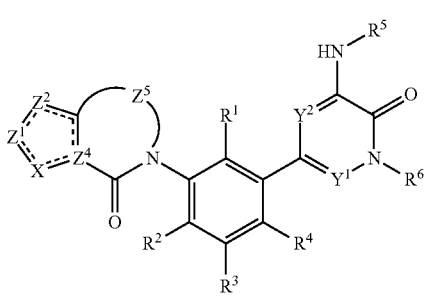
Im
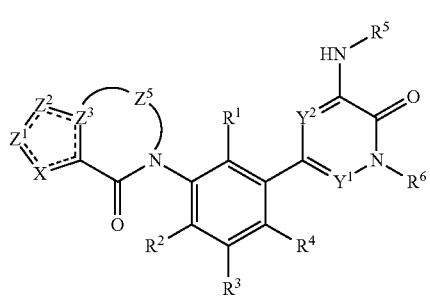
In
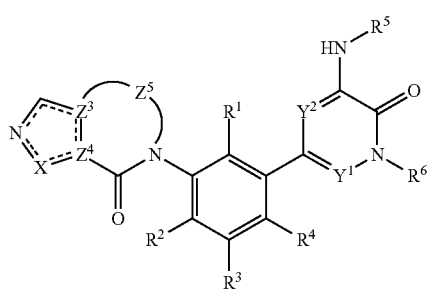
Io

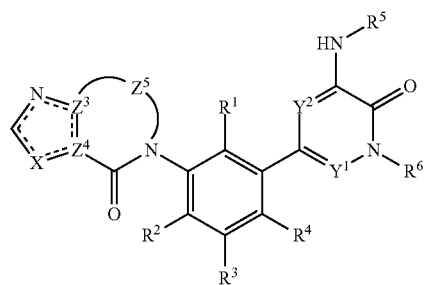
Ip
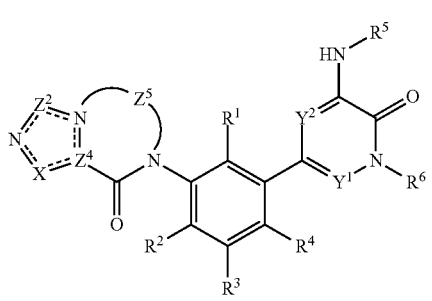
Iq
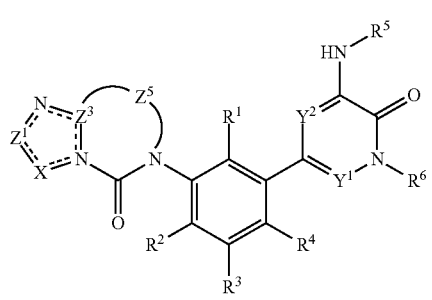
Ir
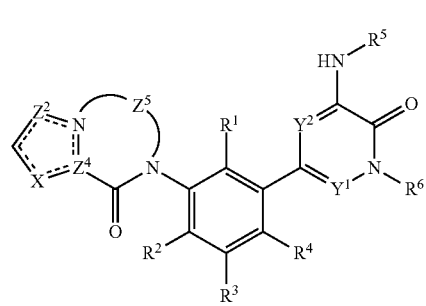
Is
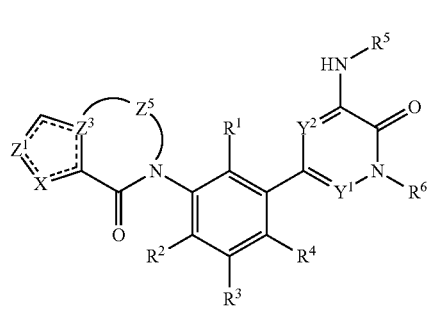
It
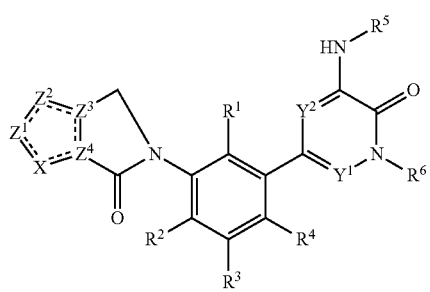
Iu
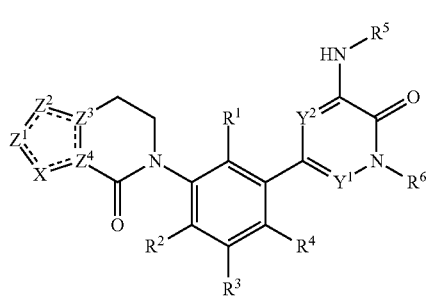
Iv
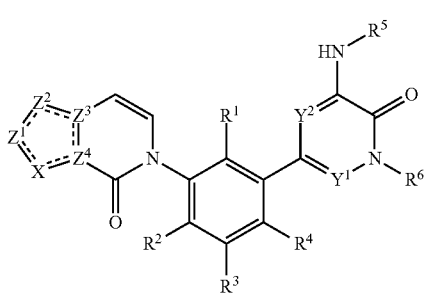
Iw
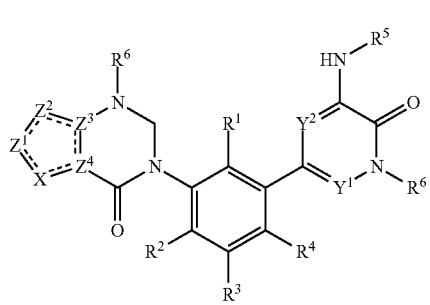
Ix
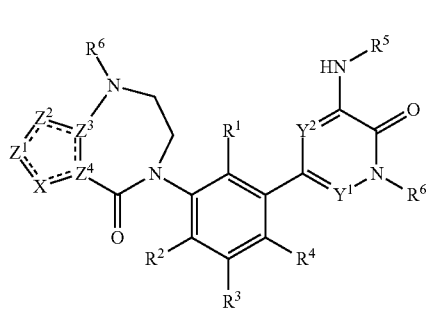
Iy Iz
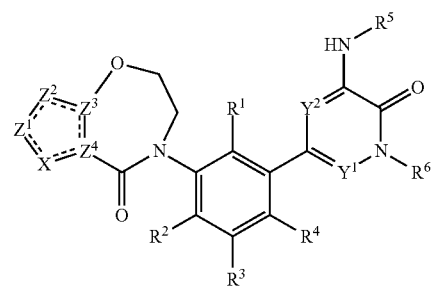
Iaa
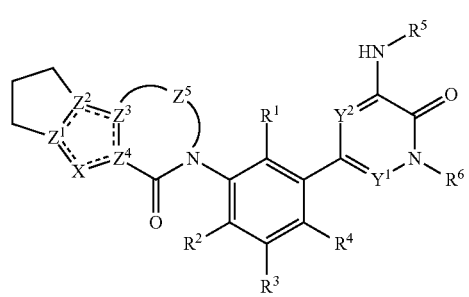
Iab
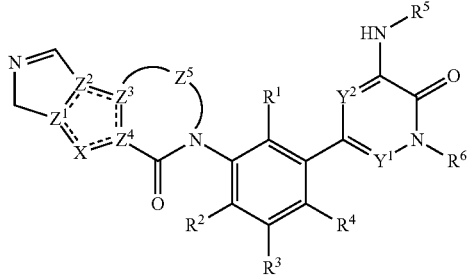
Iac
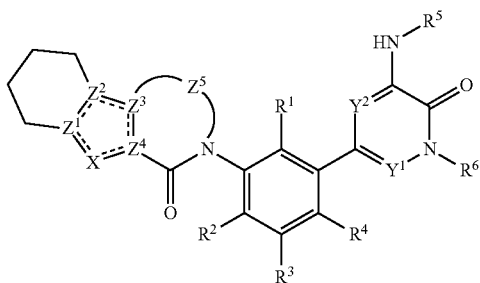
Iad
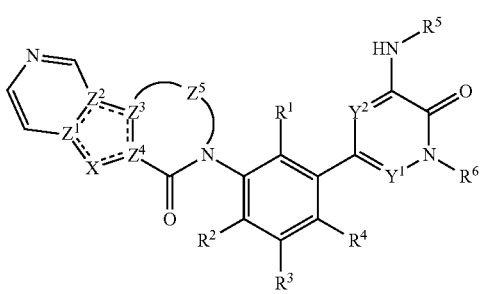
Iae
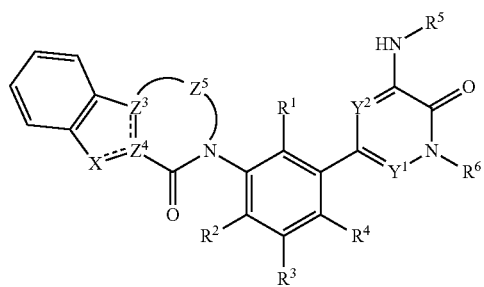
Iaf
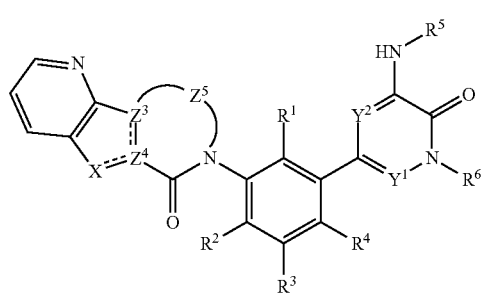
Iag
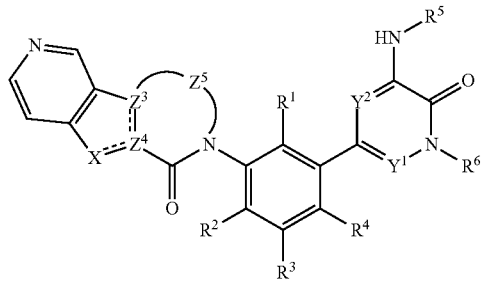
Iah
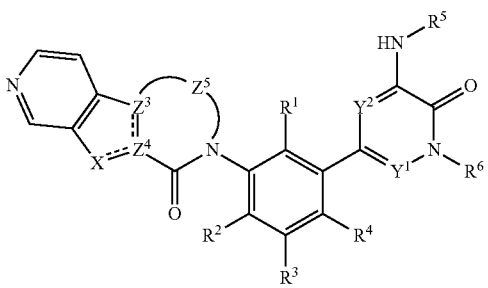
Iai
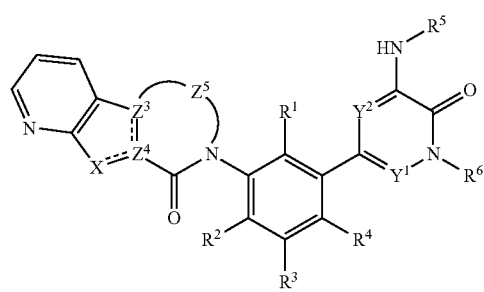

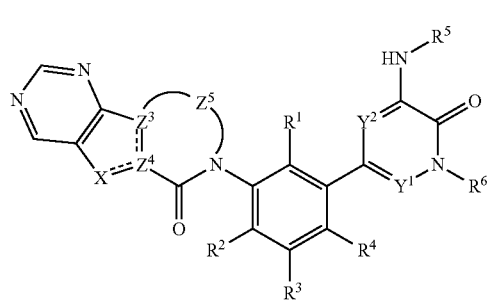
Iaj
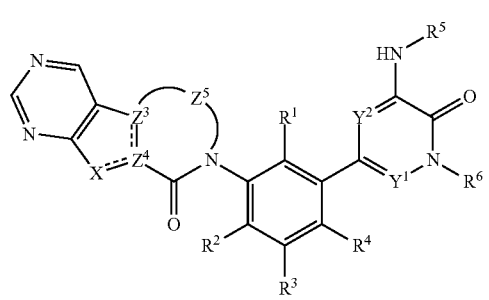
Iak
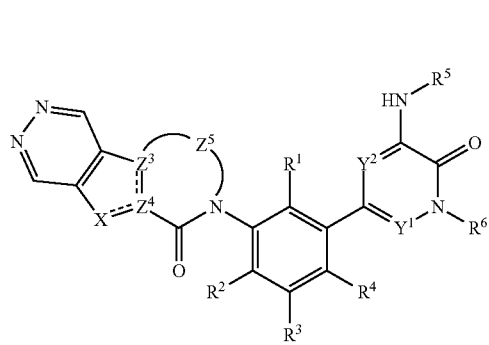
Ial
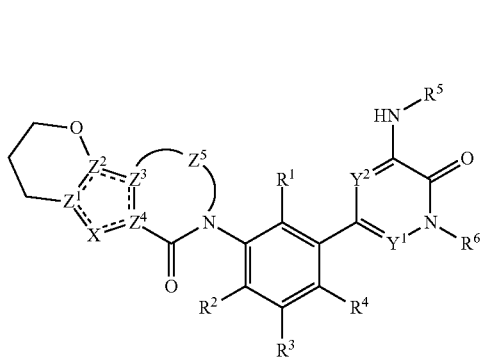
Iam
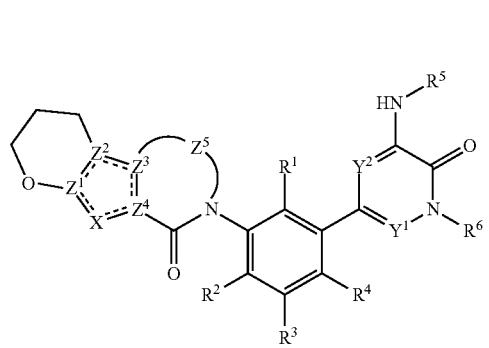
Ian
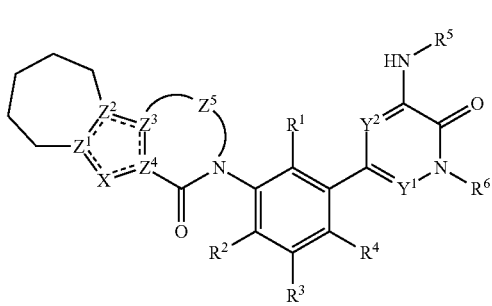
Iao
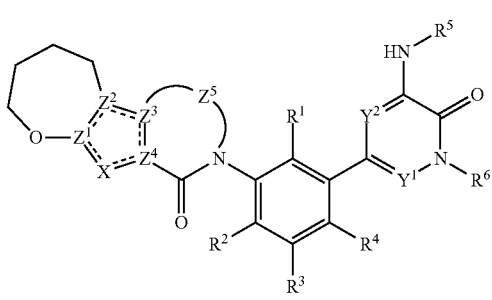
Iap
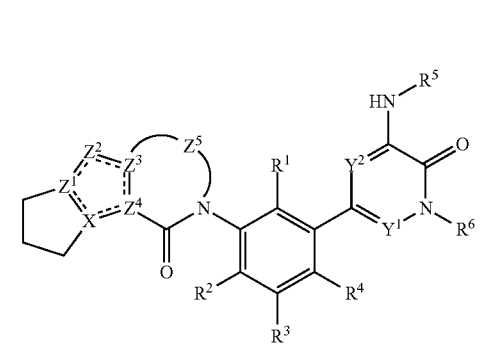
Iaq
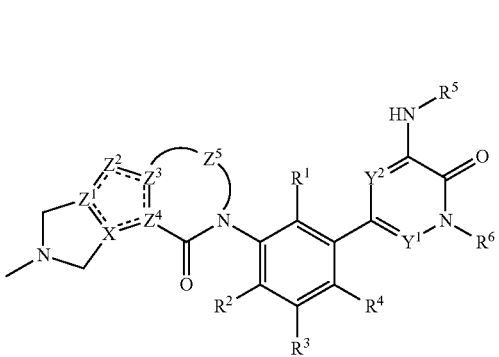
Iar
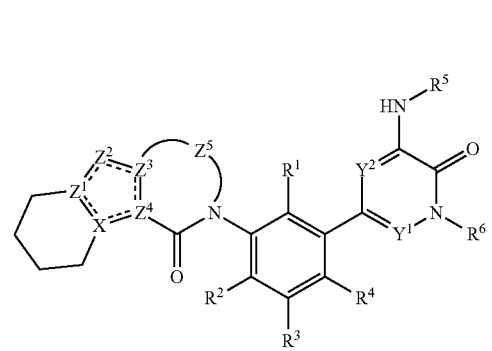
Ias

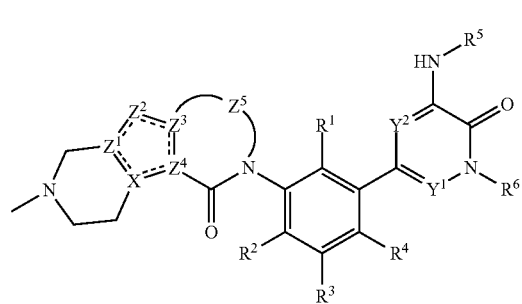 Iat
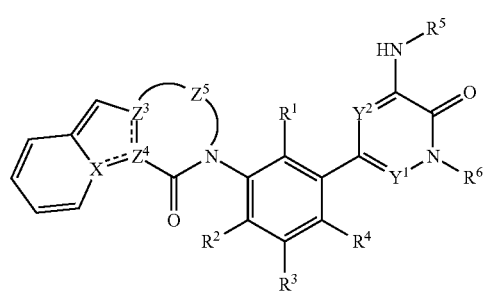 Iau
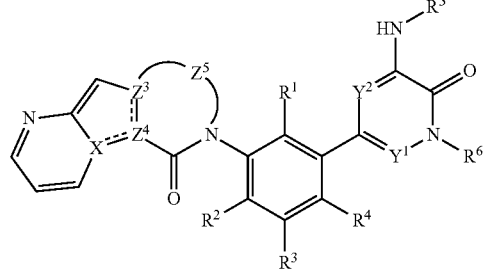 Iav
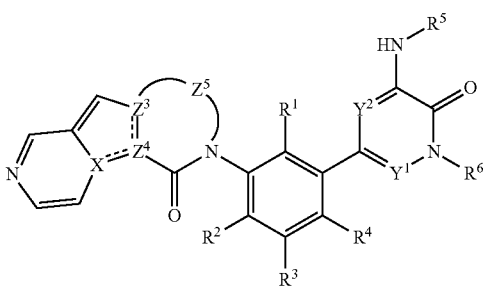 Iaw
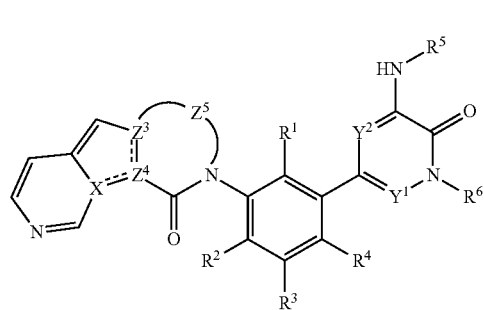 Iax
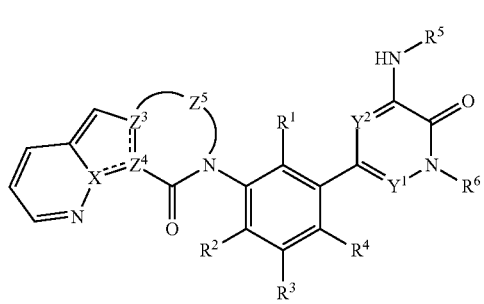 Iay
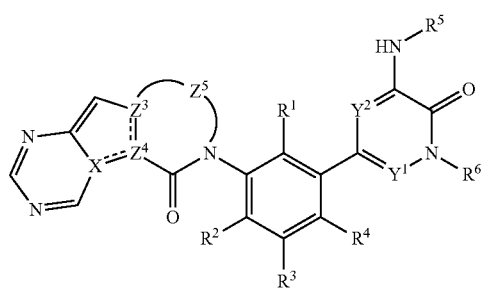 Iaz
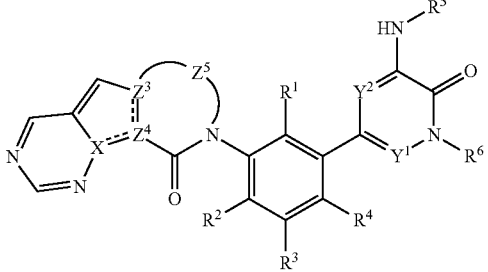 Iba
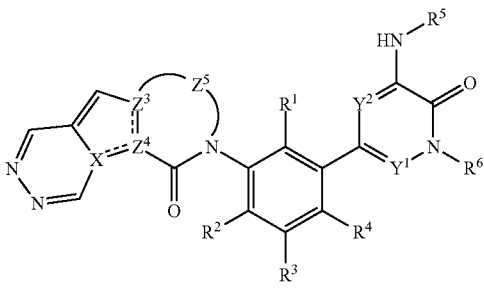 Ibb
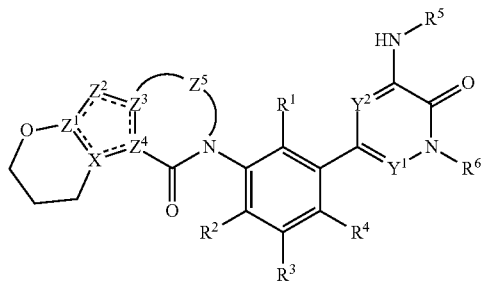 Ibc

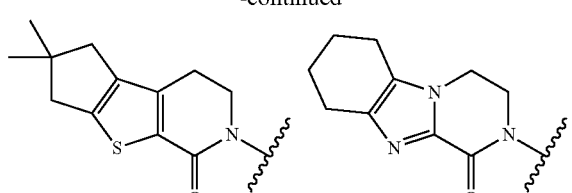
Ibd
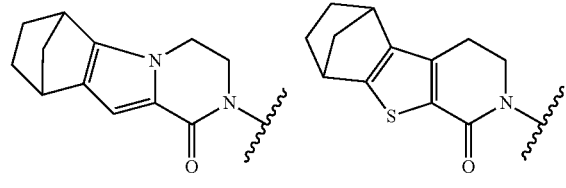
Ibe
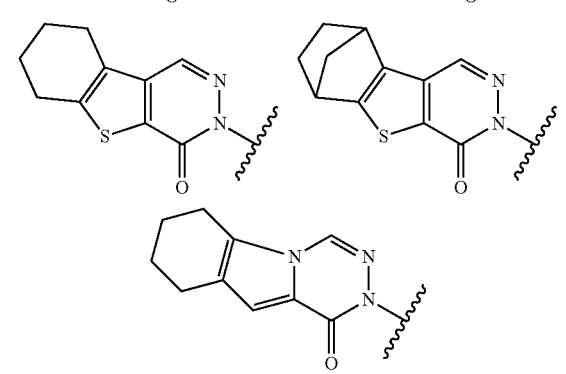
Ibf
Exemplary embodiments of Formula I compounds include where the group:
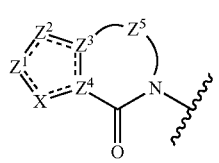
forms the structures:
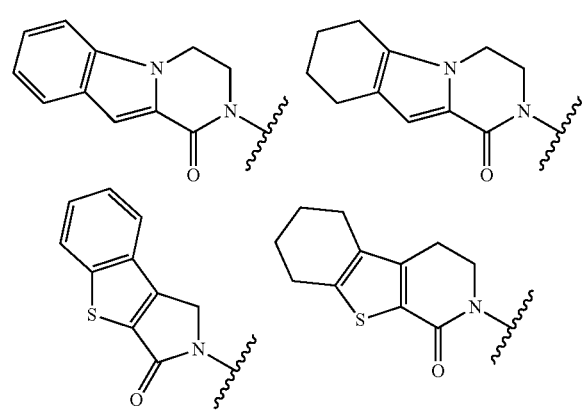
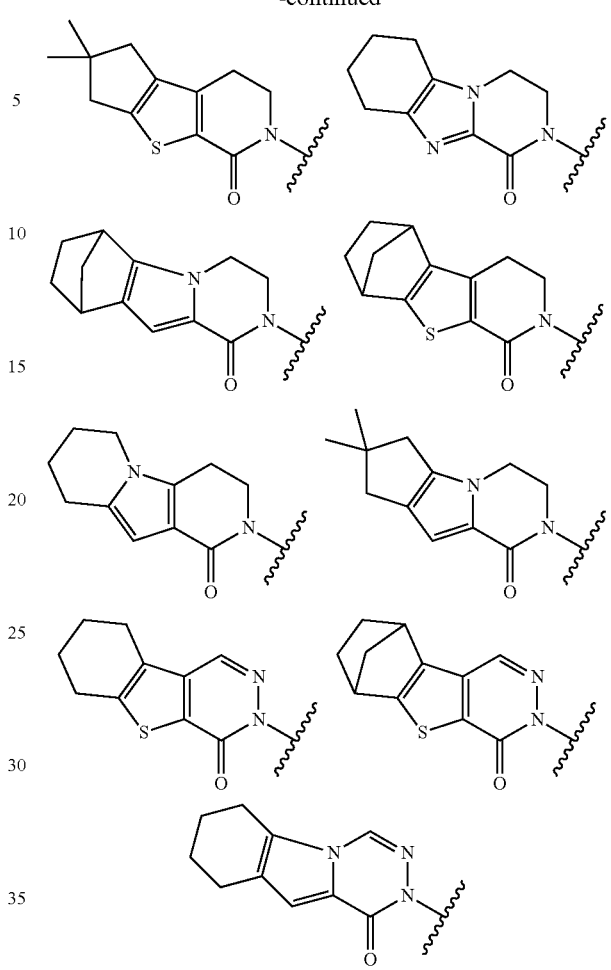
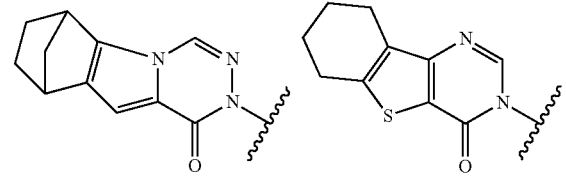
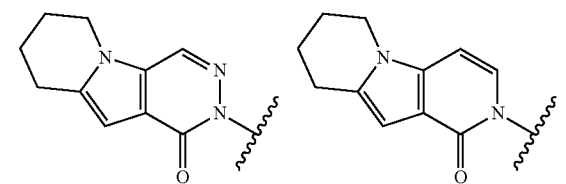

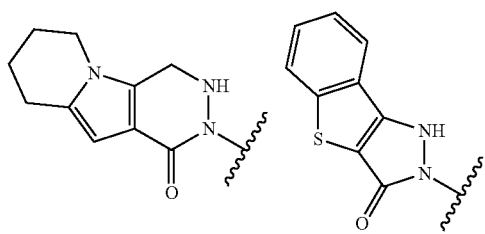
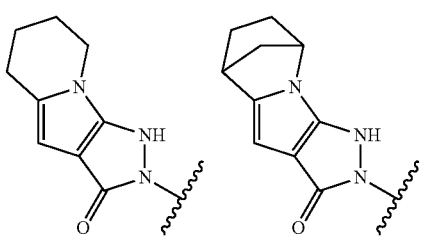 [SMILES: *n1[nH]c2c(cc3n2CCCC3)c1=O ; *n1[nH]c2c(cc3n2C2CCC3C2)c1=O]

where the wavy line indicates the site of attachment.

Exemplary embodiments of Formula I compounds include wherein the center phenyl ring group is substituted or not substituted such as: (i) $R^1$, $R^2$, $R^3$, and $R^4$ are each H; (ii) or one or more of $R^1$, $R^2$, $R^3$, and $R^4$ are F; (iii) $R^1$ is selected from F, —$CH_3$, —$CH_2F$, —$CHF_2$, and —$CF_3$; (iv) $R^1$ is —$CH_2OH$; (v) $R^3$ is F; and (vi) $R^1$ is —$CH_2OH$, $R^2$ and $R^4$ are each H, and $R^3$ is F.

Exemplary embodiments of Formula I compounds include wherein $R^5$ is optionally substituted $C_6$-$C_{20}$ aryl selected from phenyl and naphthyl.

Exemplary embodiments of Formula I compounds include wherein $R^5$ is optionally substituted $C_3$-$C_{12}$ carbocyclyl selected from cyclopropyl, cyclobutyl, cyclopentyl, cyclohexyl, and cycloheptyl.

Exemplary embodiments of Formula I compounds include wherein $R^5$ is optionally substituted $C_2$-$C_{20}$ heterocyclyl selected from oxetanyl, azetidinyl, pyrrolidinyl, tetrahydrofuryl, piperidinyl, piperazinyl, morpholinyl, and tetrahydropyranyl.

Exemplary embodiments of Formula I compounds include wherein $R^5$ is optionally substituted $C_1$-$C_{20}$ heteroaryl selected from pyrazolyl, pyridinyl, pyrimidinyl, 5-methyl-4,5,6,7-tetrahydropyrazolo[1,5-a]pyrazin-2-yl, 5-acetyl-4,5,6,7-tetrahydropyrazolo[1,5-a]pyrazin-2-yl, 6,7-dihydro-4H-pyrazolo[5,1-c][1,4]oxazin-2-yl, and 1-methyl-5-(5-(4-methylpiperazin-1-yl)pyridine-2-yl.

Exemplary embodiments of Formula I compounds include wherein $R^5$ is selected from the structures:

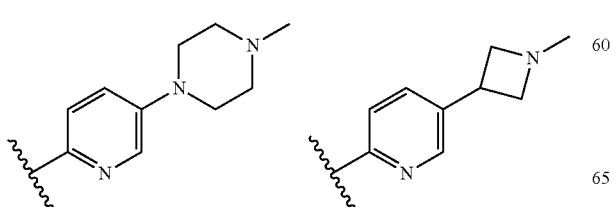
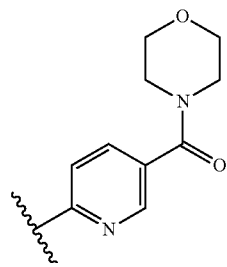
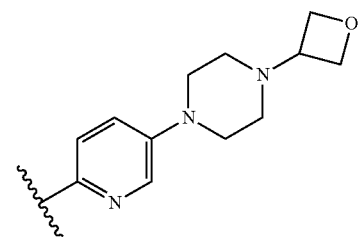
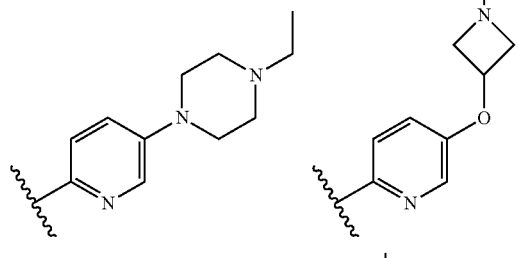
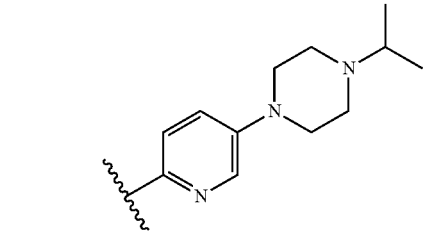
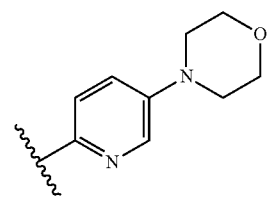
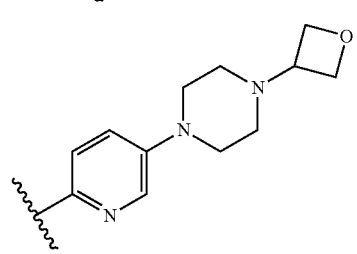
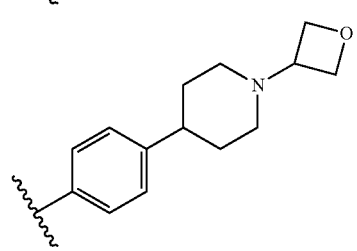

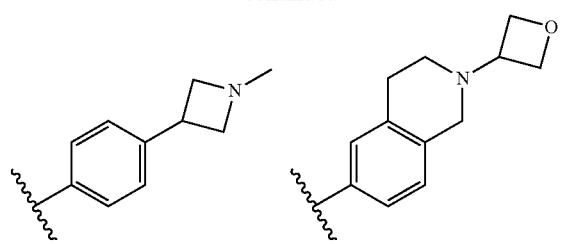
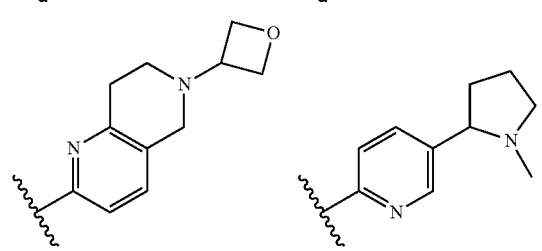
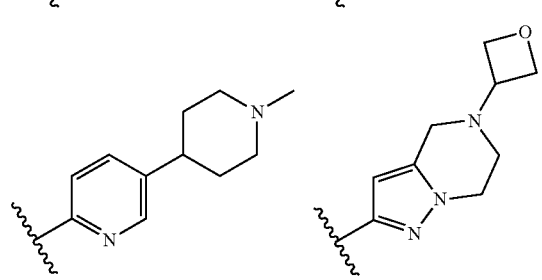
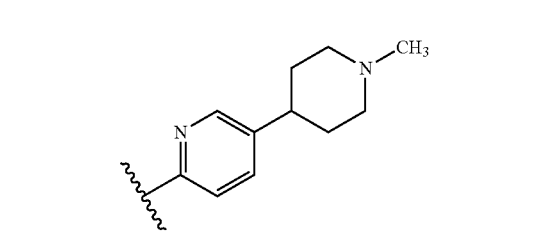
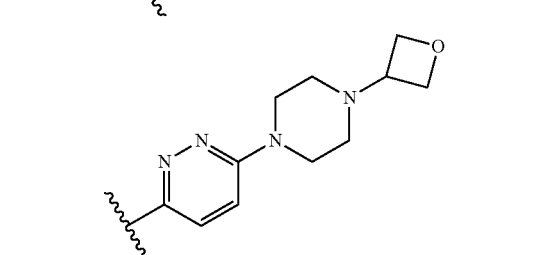
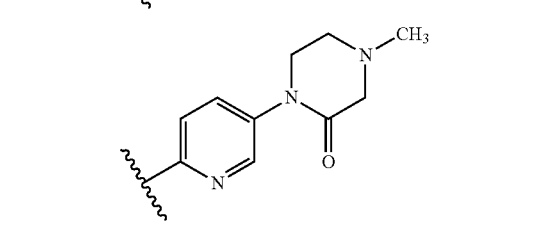
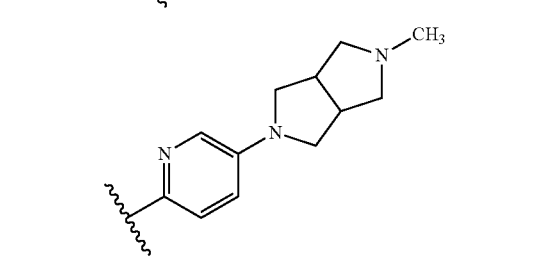

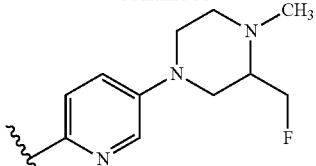
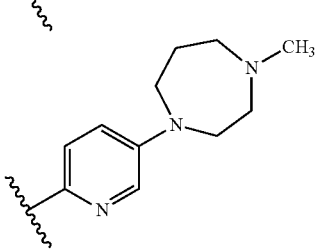

where the wavy line indicates the site of attachment.

Exemplary embodiments of Formula I compounds include wherein $R^6$ is H.

Exemplary embodiments of Formula I compounds include wherein $Y^1$ is $CR^6$ and $Y^2$ is N.

Exemplary embodiments of Formula I compounds include wherein $Y^1$ is N and $Y^2$ is $CR^6$.

Exemplary embodiments of Formula I compounds include wherein $Y^1$ and $Y^2$ are each $CR^6$.

Each solid/dashed line, ⚌, in the five-membered ring formed by X, $Z^1$, $Z^2$, $Z^3$, and $Z^4$ in the structures of Formula I compounds represents a single bond or a double bond, with the proviso that any two double bonds in the ring are not adjacent.

The Formula I compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention.

In addition, the present invention embraces all diastereomers, including cis-trans (geometric) and conformational isomers. For example, if a Formula I compound incorporates a double bond or a fused ring, the cis- and trans-forms, as well as mixtures thereof, are embraced within the scope of the invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the present invention may exist in unsolvated as well as solvated forms with pharmaceutically acceptable solvents such as water, ethanol, and the like, and it is intended that the invention embrace both solvated and unsolvated forms.

The compounds of the present invention may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations.

Valence tautomers include interconversions by reorganization of some of the bonding electrons.

Biological Evaluation

The relative efficacies of Formula I compounds as inhibitors of an enzyme activity (or other biological activity) can be established by determining the concentrations at which each compound inhibits the activity to a predefined extent and then comparing the results. Typically, the preferred determination is the concentration that inhibits 50% of the activity in a biochemical assay, i.e., the 50% inhibitory concentration or "$IC_{50}$". Determination of $IC_{50}$ values can be accomplished using conventional techniques known in the art. In general, an $IC_{50}$ can be determined by measuring the activity of a given enzyme in the presence of a range of concentrations of the inhibitor under study. The experimentally obtained values of enzyme activity then are plotted against the inhibitor concentrations used. The concentration of the inhibitor that shows 50% enzyme activity (as compared to the activity in the absence of any inhibitor) is taken as the $IC_{50}$ value. Analogously, other inhibitory concentrations can be defined through appropriate determinations of activity. For example, in some settings it can be desirable to establish a 90% inhibitory concentration, i.e., $IC_{90}$, etc.

Formula I compounds were tested by a standard biochemical Btk Kinase Assay (Example 901).

A general procedure for a standard cellular Btk Kinase Assay that can be used to test Formula I compounds is a Ramos Cell Btk Assay (Example 902).

A standard cellular B-cell proliferation assay can be used to test Formula I compounds with B-cells purified from spleen of Balb/c mice (Example 903).

A standard T cell proliferation assay can be used to test Formula I compounds with T-cells purified from spleen of Balb/c mice (Example 904).

A CD86 Inhibition assay can be conducted on Formula I compounds for the inhibition of B cell activity using total mouse splenocytes purified from spleens of 8-16 week old Balb/c mice (Example 905).

A B-ALL Cell Survival Assay can be conducted on Formula I compounds to measure the number of viable B-ALL cells in culture (Example 906).

A CD69 Whole Blood Assay can be conducted on Formula I compounds to determine the ability of compounds to inhibit the production of CD69 by B lymphocytes in human whole blood activated by crosslinking surface IgM with goat F(ab')2 anti-human IgM (Example 907).

Exemplary Formula I compounds in Tables 1, 2, and 3 were made, characterized, and tested for inhibition of Btk according to the methods of this invention, and have the following structures and corresponding names (ChemDraw Ultra, Version 9.0.1, and ChemBioDraw, Version 11.0, CambridgeSoft Corp., Cambridge Mass.). Where more than one name is associated with a Formula I compound or intermediate, the chemical structure shall define the compound.

TABLE 1

| No. | Structure | Name | M + H m/z | Btk $IC_{50}$ (μMol) |
|---|---|---|---|---|
| 101 | 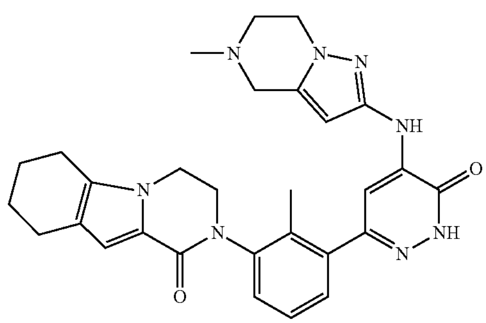 [SMILES: Cc1c(-c2cc(Nc3cc4n(n3)CCN(C)C4)c(=O)[nH]n2)cccc1N1CCn2c(cc3c2CCCC3)C1=O] | 2-(2-methyl-3-(5-(5-methyl-4,5,6,7-tetrahydropyrazolo[1,5-a]pyrazin-2-ylamino)-6-oxo-1,6-dihydropyridazin-3-yl)phenyl)-3,4,6,7,8,9-hexahydropyrazino[1,2-a]indol-1(2H)-one | 525.2 | 0.002 |
| 102 | 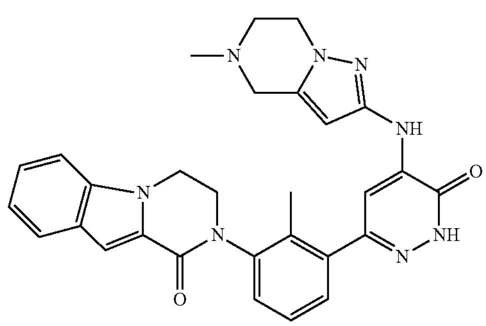 [SMILES: Cc1c(-c2cc(Nc3cc4n(n3)CCN(C)C4)c(=O)[nH]n2)cccc1N1CCn2c(cc3ccccc32)C1=O] | 2-(2-methyl-3-(5-(5-methyl-4,5,6,7-tetrahydropyrazolo[1,5-a]pyrazin-2-ylamino)-6-oxo-1,6-dihydropyridazin-3-yl)phenyl)-3,4-dihydropyrazino[1,2-a]indol-1(2H)-one | 521.2 | 0.0229 |

TABLE 1-continued

| No. | Structure | Name | M + H m/z | Btk IC$_{50}$ (μMol) |
|---|---|---|---|---|
| 103 | 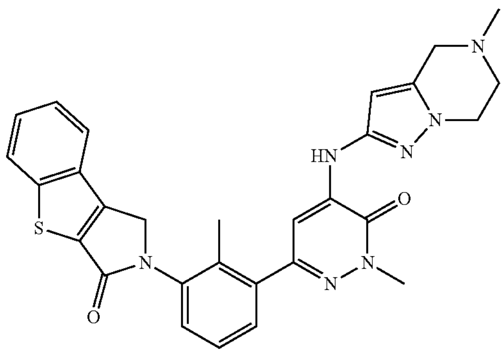 [SMILES: Cc1c(-c2cc(Nc3cc4n(n3)CCN(C)C4)c(=O)n(C)n2)cccc1N1Cc2c(sc3ccccc23)C1=O] | 4-{2-Methyl-3-[1-methyl-5-({5-methyl-4H,5H,6H,7H-pyrazolo[1,5-a]pyrazin-2-yl}amino)-6-oxo-1,6-dihydropyridazin-3-yl]phenyl}-7-thia-4-azatricyclo[6.4.0.0²,⁶]dodeca-1(8),2(6),9,11-tetraen-5-one | 538.2 | 3.2 |
| 104 | 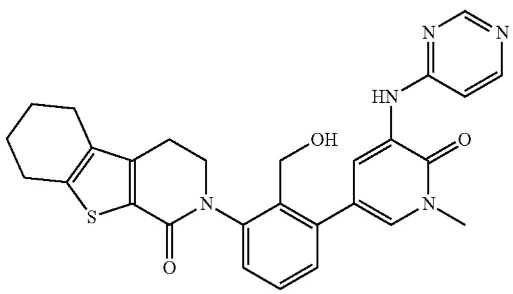 [SMILES: Cn1cc(-c2cccc(N3CCc4c(sc5c4CCCC5)C3=O)c2CO)cc(Nc2ccncn2)c1=O] | 5-[2-(Hydroxymethyl)-3-[1-methyl-6-oxo-5-(pyrimidin-4-ylamino)-1,6-dihydropyridin-3-yl]phenyl]-8-thia-5-azatricyclo[7.4.0.0²,⁷]trideca-1(9),2(7)-dien-6-one | 514.2 | 0.00087 |
| 105 | 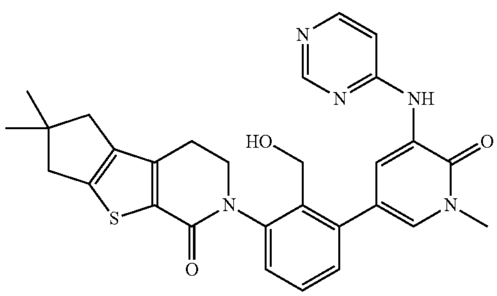 | 10-[2-(Hydroxymethyl)-3-[1-methyl-6-oxo-5-(pyrimidin-4-ylamino)-1,6-dihydropyridin-3-yl]phenyl]-4,4-dimethyl-7-thia-10-azatricyclo[6.4.0.02,6]dodeca-1(8),2(6)-dien-9-one | 528.2 | 0.010 |
| 106 | 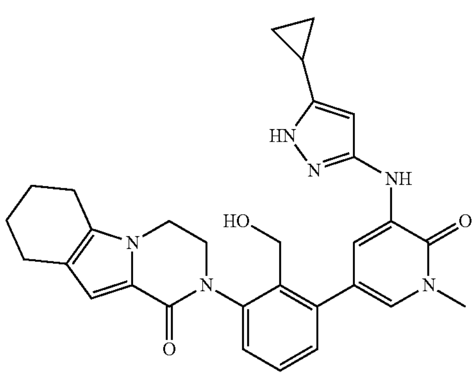 [SMILES: Cn1cc(-c2cccc(N3CCn4c(cc5c4CCCC5)C3=O)c2CO)cc(Nc2cc(C3CC3)[nH]n2)c1=O] | 2-(3-(5-(5-cyclopropyl-1H-pyrazol-3-ylamino)-1-methyl-6-oxo-1,6-dihydropyridin-3-yl)-2-(hydroxymethyl)phenyl)-3,4,6,7,8,9-hexahydropyrazino[1,2-a]indol-1(2H)-one | 525 | 0.0010 |

TABLE 1-continued

| No. | Structure | Name | M + H m/z | Btk IC$_{50}$ (μMol) |
|---|---|---|---|---|
| 107 | 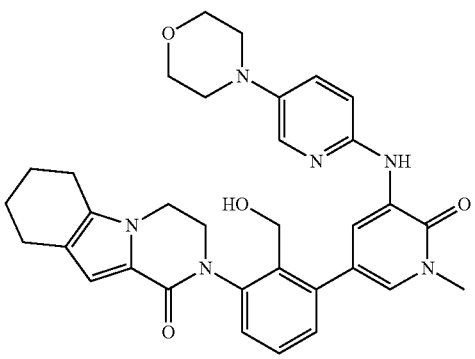 [SMILES: Cn1cc(-c2cccc(N3CCn4c(cc5c4CCCC5)C3=O)c2CO)cc(Nc2ccc(N3CCOCC3)cn2)c1=O] | 2-(2-(hydroxymethyl)-3-(1-methyl-5-(5-morpholinopyridin-2-ylamino)-6-oxo-1,6-dihydropyridin-3-yl)phenyl)-3,4,6,7,8,9-hexahydropyrazino[1,2-a]indol-1(2H)-one | 581 | 0.0101 |
| 108 | 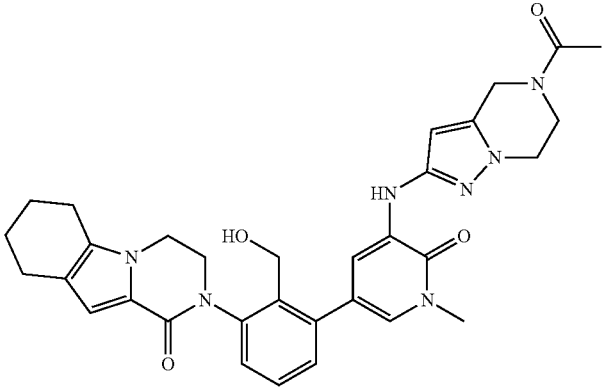 [SMILES: CC(=O)N1CCn2nc(Nc3cc(-c4cccc(N5CCn6c(cc7c6CCCC7)C5=O)c4CO)cn(C)c3=O)cc2C1] | 2-(3-(5-(5-acetyl-4,5,6,7-tetrahydropyrazolo[1,5-a]pyrazin-2-ylamino)-1-methyl-6-oxo-1,6-dihydropyridin-3-yl)-2-(hydroxymethyl)phenyl)-3,4,6,7,8,9-hexahydropyrazino[1,2-a]indol-1(2H)-one | 582.3 | 0.0061 |
| 109 | 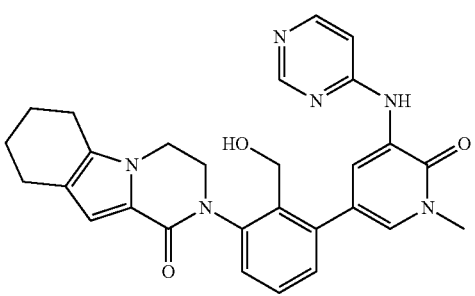 [SMILES: Cn1cc(-c2cccc(N3CCn4c(cc5c4CCCC5)C3=O)c2CO)cc(Nc2ccncn2)c1=O] | 2-(2-(hydroxymethyl)-3-(1-methyl-6-oxo-5-(pyrimidin-4-ylamino)-1,6-dihydropyridin-3-yl)phenyl)-3,4,6,7,8,9-hexahydropyrazino[1,2-a]indol-1(2H)-one | 497.2 | 0.0062 |
| 110 | 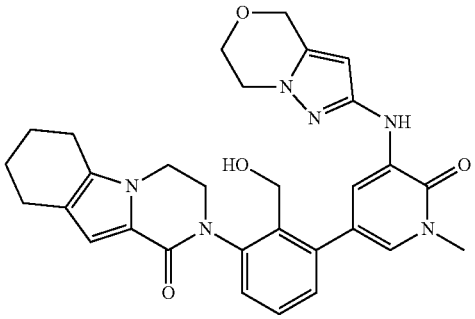 [SMILES: Cn1cc(-c2cccc(N3CCn4c(cc5c4CCCC5)C3=O)c2CO)cc(Nc2cc3n(n2)CCOC3)c1=O] | 2-(3-(5-(6,7-dihydro-4H-pyrazolo[5,1-c][1,4]oxazin-2-ylamino)-1-methyl-6-oxo-1,6-dihydropyridin-3-yl)-2-(hydroxymethyl)phenyl)-3,4,6,7,8,9-hexahydropyrazino[1,2-a]indol-1(2H)-one | 541.4 | 0.0077 |

TABLE 1-continued

| No. | Structure | Name | M + H m/z | Btk IC$_{50}$ (μMol) |
|---|---|---|---|---|
| 111 | 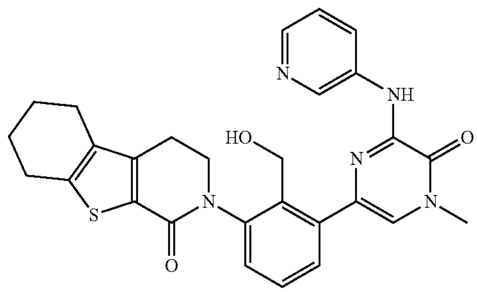 [SMILES: Cn1cc(-c2cccc(N3CCc4c(sc5c4CCCC5)C3=O)c2CO)nc(Nc2cccnc2)c1=O] | 5-[2-(Hydroxymethyl)-3-[4-methyl-5-oxo-6-(pyridine-3-ylamino)-4,5-dihydropyrazin-2-yl]phenyl]-8-thia-5-azatricyclo[7.4.0.02,7]trideca-1(9),2(7)-dien-6-one | 514.2 | |
| 112 | 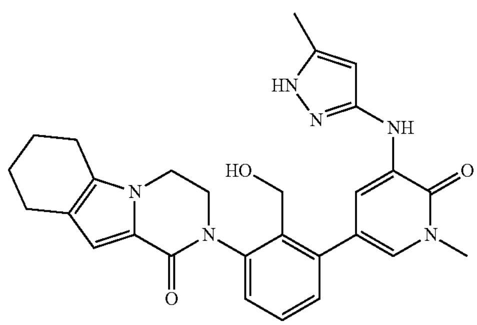 [SMILES: Cc1cc(Nc2cc(-c3cccc(N4CCn5c(cc6c5CCCC6)C4=O)c3CO)cn(C)c2=O)n[nH]1] | 2-(2-(hydroxymethyl)-3-(1-methyl-5-(5-methyl-1H-pyrazol-3-ylamino)-6-oxo-1,6-dihydropyridin-3-yl)phenyl)-3,4,6,7,8,9-hexahydropyrazino[1,2-a]indol-1(2H)-one | 499.3 | |
| 113 | 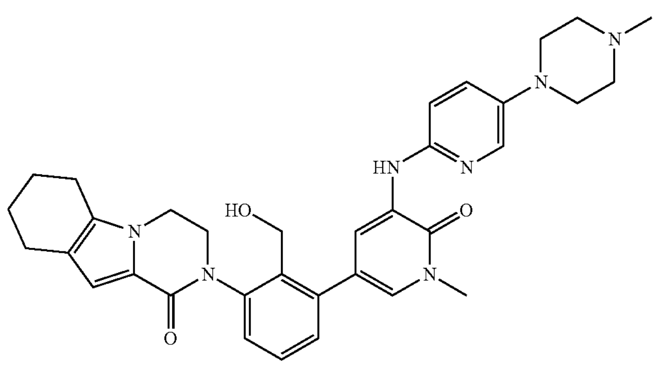 [SMILES: CN1CCN(c2ccc(Nc3cc(-c4cccc(N5CCn6c(cc7c6CCCC7)C5=O)c4CO)cn(C)c3=O)nc2)CC1] | 2-(2-(hydroxymethyl)-3-(1-methyl-5-(5-(4-methylpiperazin-1-yl)pyridine-2-ylamino)-6-oxo-1,6-dihydropyridin-3-yl)phenyl)-3,4,6,7,8,9-hexahydropyrazino[1,2-a]indol-1(2H)-one | 594.3 | 0.005 |
| 114 | 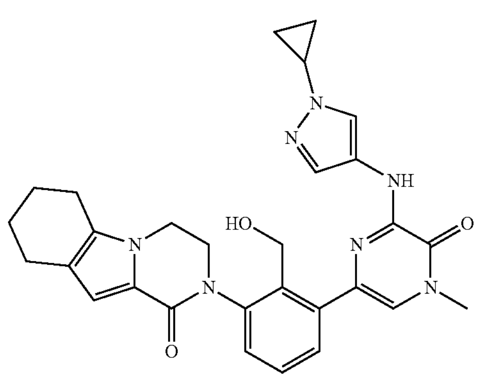 [SMILES: Cn1cc(-c2cccc(N3CCn4c(cc5c4CCCC5)C3=O)c2CO)nc(Nc2cnn(C3CC3)c2)c1=O] | 2-(3-(6-(1-cyclopropyl-1H-pyrazol-4-ylamino)-4-methyl-5-oxo-4,5-dihydropyrazin-2-yl)-2-(hydroxymethyl)phenyl)-3,4,6,7,8,9-hexahydropyrazino[1,2-a]indol-1(2H)-one | 526.3 | |

TABLE 1-continued

| No. | Structure | Name | M + H m/z | Btk IC$_{50}$ (μMol) |
|---|---|---|---|---|
| 115 | 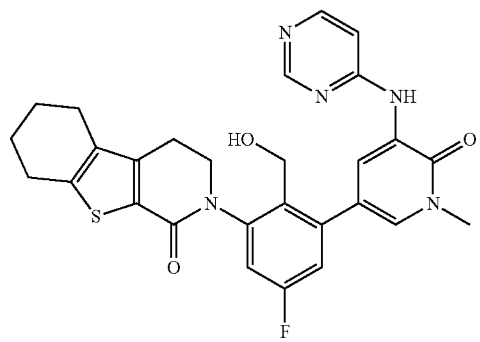 [SMILES: Cn1cc(-c2cc(F)cc(N3CCc4c(sc5c4CCCC5)C3=O)c2CO)cc(Nc2ccncn2)c1=O] | 5-[5-Fluoro-2-(hydroxymethyl)-3-[1-methyl-6-oxo-5-(pyrimidin-4-ylamino)-1,6-dihydropyridin-3-yl]phenyl]-8-thia-5-azatricyclo[7.4.0.02,7]trideca-1(9),2(7)-dien-6-one | 532.2 | |
| 116 | 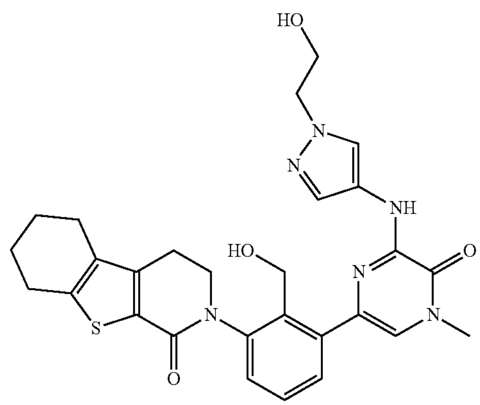 [SMILES: Cn1cc(-c2cccc(N3CCc4c(sc5c4CCCC5)C3=O)c2CO)nc(Nc2cnn(CCO)c2)c1=O] | 5-[3-(6-{[1-(2-Hydroxyethyl)-1H-pyrazol-4-yl]amino}-4-methyl-5-oxo-4,5-dihydropyrazin-2-yl)-2-(hydroxymethyl)phenyl]-8-thia-5-azatricyclo[7.40.02,7]trideca-1(9),2(7)-dien-6-one | 547.2 | 0.006 |
| 117 | 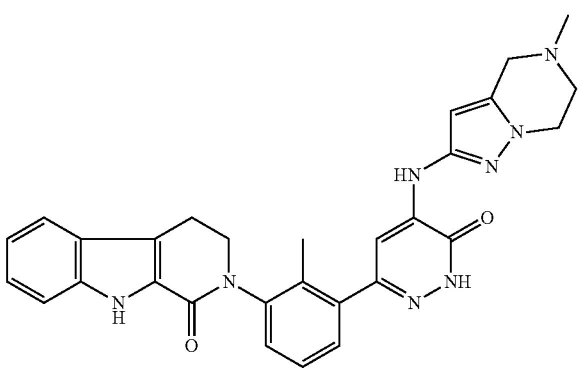 [SMILES: Cc1c(-c2cc(Nc3cc4n(n3)CCN(C)C4)c(=O)[nH]n2)cccc1N1CCc2c([nH]c3ccccc23)C1=O] | 2-(2-methyl-3-(5-(5-methyl-4,5,6,7-tetrahydropyrazolo[1,5-a]pyrazin-2-ylamino)-6-oxo-1,6-dihydropyridazin-3-yl)phenyl)-2,3,4,9-tetrahydro-1H-pyrido[3,4-b]indol-1-one | 521.2 | |
| 118 | 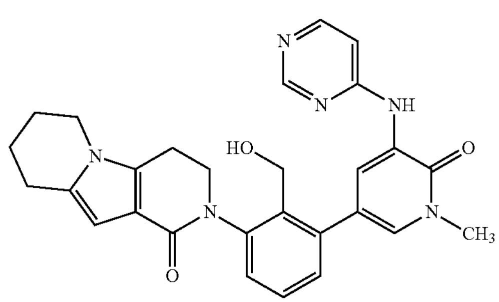 [SMILES: Cn1cc(-c2cccc(N3CCc4c(cc5n4CCCC5)C3=O)c2CO)cc(Nc2ccncn2)c1=O] | 2-(2-(hydroxymethyl)-3-(1-methyl-6-oxo-5-(pyrimidin-4-ylamino)-1,6-dihydropyridin-3-yl)phenyl)-3,4,6,7,8,9-hexahydropyrido[3,4-b]indolizin-1(2H)-one | 497.2 | |

TABLE 1-continued

| No. | Structure | Name | M + H m/z | Btk IC$_{50}$ (µMol) |
|---|---|---|---|---|
| 119 | 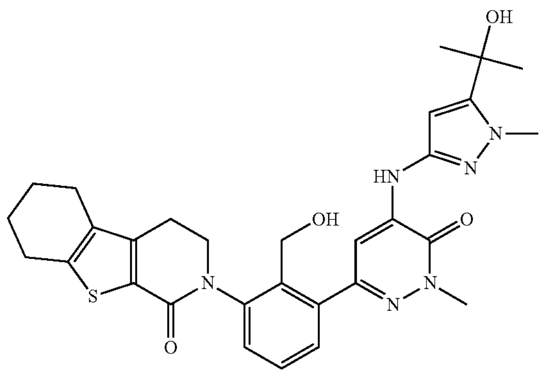 [SMILES: Cn1nc(Nc2cc(-c3cccc(N4CCc5c(sc6c5CCCC6)C4=O)c3CO)nn(C)c2=O)cc1C(C)(C)O] | 5-[2-(hydroxymethyl)-3-(5-{[5-(2-hydroxypropan-2-yl)-1-methyl-1H-pyrazol-3-yl]amino}-1-methyl-6-oxo-1,6-dihydropyridazin-3-yl)phenyl]-8-thia-5-azatricyclo[7.4.0.0 2,7]trideca-1(9),2(7)-dien-6-one | 575.2 | 0.007 |
| 120 | 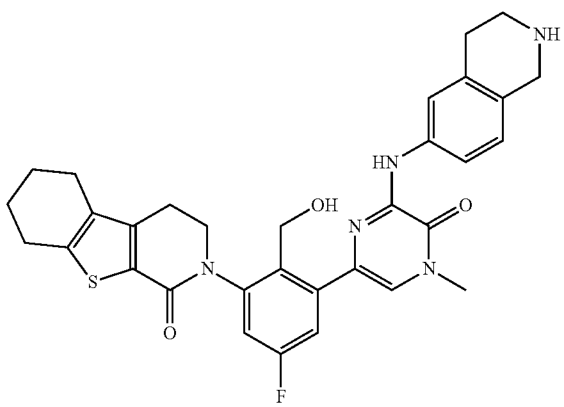 [SMILES: Cn1cc(-c2cc(F)cc(N3CCc4c(sc5c4CCCC5)C3=O)c2CO)nc(Nc2ccc3c(c2)CCNC3)c1=O] | 5-[5-fluoro-2-(hydroxymethyl)-3-[4-methyl-5-oxo-6-(1,2,3,4-tetrahydroisoquinolin-6-ylamino)-4,5-dihydropyrazin-2-yl]phenyl]-8-thia-5-azatricyclo[7.4.0.02,7]trideca-1(9),2(7)-dien-6-one | 586 | |
| 121 | 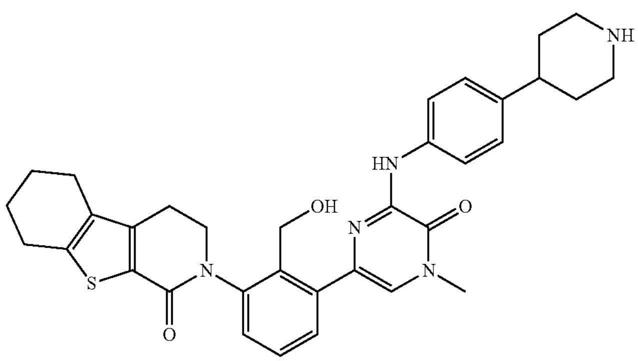 [SMILES: Cn1cc(-c2cccc(N3CCc4c(sc5c4CCCC5)C3=O)c2CO)nc(Nc2ccc(C3CCNCC3)cc2)c1=O] | 5-[2-(hydroxymethyl)-3-(4-methyl-5-oxo-6-{[4-(piperidin-4-yl)phenyl]amino}-4,5-dihydropyrazin-2-yl)phenyl]-8-thia-5-azatricyclo[7.4.0.02,7]trideca-1(9),2(7)-dien-one | 596.3 | |
| 122 | 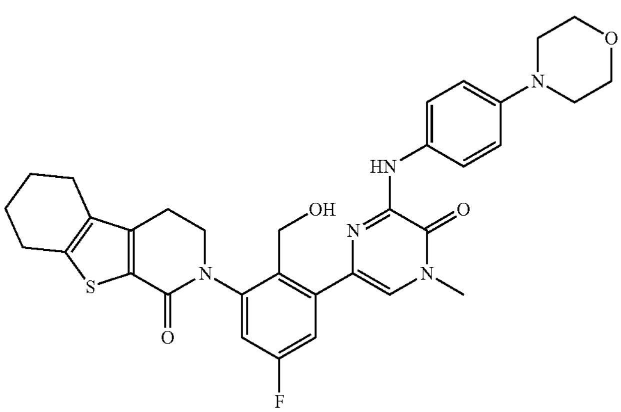 [SMILES: Cn1cc(-c2cc(F)cc(N3CCc4c(sc5c4CCCC5)C3=O)c2CO)nc(Nc2ccc(N3CCOCC3)cc2)c1=O] | 5-[5-fluoro-2-(hydroxymethyl)-3-(4-methyl-6-{[4-(morpholin-4-yl)phenyl]amino}-5-oxo-4,5-dihydropyrazin-2-yl)phenyl]-8-thia-5-azatricyclo[7.4.0.02,7]trideca-1(9),2(7)-dien-6-one | 616 | |

TABLE 1-continued

| No. | Structure | Name | M + H m/z | Btk IC$_{50}$ (μMol) |
|---|---|---|---|---|
| 123 | 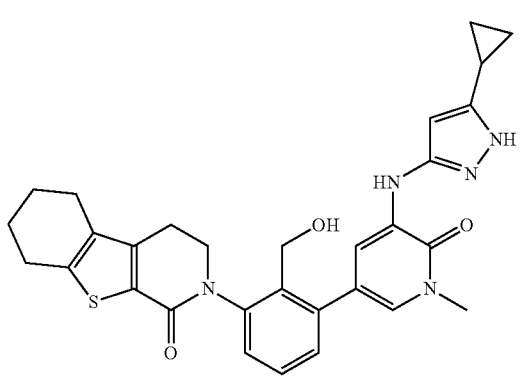 [SMILES: Cn1cc(-c2cccc(N3CCc4c(sc5c4CCCC5)C3=O)c2CO)cc(Nc2cc(C3CC3)[nH]n2)c1=O] | 5-(3-{5-[(5-cyclopropyl-1H-pyrazol-3-yl)amino]-1-methyl-6-oxo-1,6-dihydropyridin-3-yl}-2-(hydroxymethyl)phenyl)-8-thia-5-azatricyclo[7.4.0.0$^{2,7}$]trideca-1(9),2(7)-dien-6-one | 542.1 | 0.003 |
| 124 | 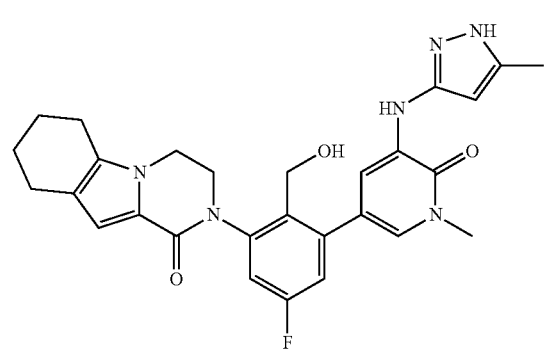 [SMILES: Cc1cc(Nc2cc(-c3cc(F)cc(N4CCn5c(cc6c5CCCC6)C4=O)c3CO)cn(C)c2=O)n[nH]1] | 5-[5-fluoro-2-(hydroxymethyl)-3-{1-oxo-1H,2H,3H,4H,6H,7H,8H,9H-pyrazino[1,2-a]indol-2-yl}phenyl]-1-methyl-3-[(5-methyl-1H-pyrazol-3-yl)amino]-1,2-dihydropyridin-2-one | 517 | |
| 125 | 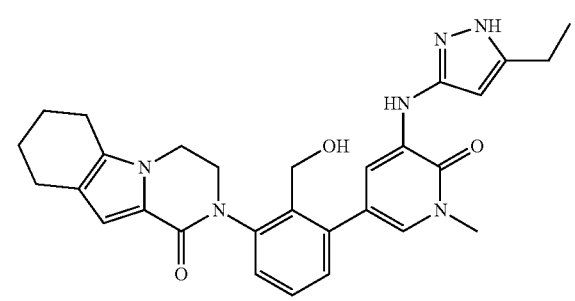 [SMILES: CCc1cc(Nc2cc(-c3cccc(N4CCn5c(cc6c5CCCC6)C4=O)c3CO)cn(C)c2=O)n[nH]1] | 3-[(5-ethyl-1H-pyrazol-3-yl)amino]-5-[2-(hydroxymethyl)-3-{1-oxo-1H,2H,3H,4H,6H,7H,8H,9H-pyrazino[1,2-a]indol-2-yl}phenyl]-1-methyl-1,2-dihydropyridin-2-one | 513.3 | |
| 126 | 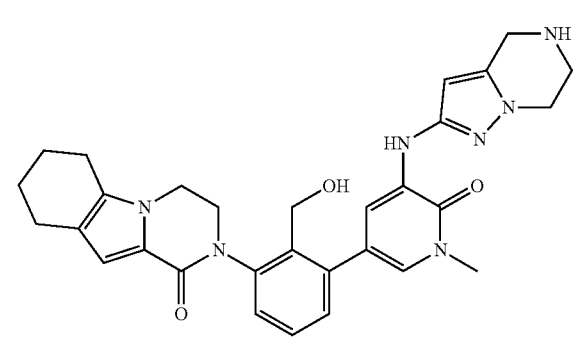 [SMILES: Cn1cc(-c2cccc(N3CCn4c(cc5c4CCCC5)C3=O)c2CO)cc(Nc2cc3n(n2)CCNC3)c1=O] | 2-(2-(Hydroxymethyl)-3-(1-methyl-6-oxo-5-(4,5,6,7-tetrahydropyrazolo[1,5-a]pyrazin-2-ylamino)-1,6-dihydropyridin-3-yl)phenyl)-3,4,6,7,8,9-hexahydropyrazino[1,2-a]indol-1(2H)-one | 540.3 | |

TABLE 1-continued

| No. | Structure | Name | M + H m/z | Btk IC$_{50}$ (μMol) |
|---|---|---|---|---|
| 127 | 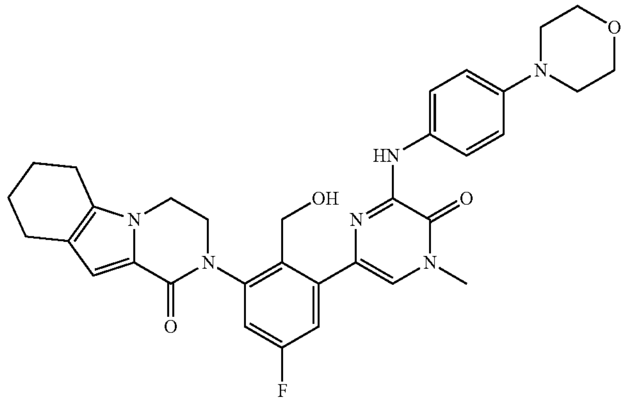 [SMILES: Cn1cc(-c2cc(F)cc(N3CCn4c(cc5c4CCCC5)C3=O)c2CO)nc(Nc2ccc(N3CCOCC3)cc2)c1=O] | 2-(5-fluoro-2-(hydroxymethyl)-3-(4-methyl-6-(4-morpholinophenylamino)-5-oxo-4,5-dihydropyrazin-2-yl)phenyl)-3,4,6,7,8,9-hexahydropyrazino[1,2-a]indol-1(2H)-one | 599 | |
| 128 | 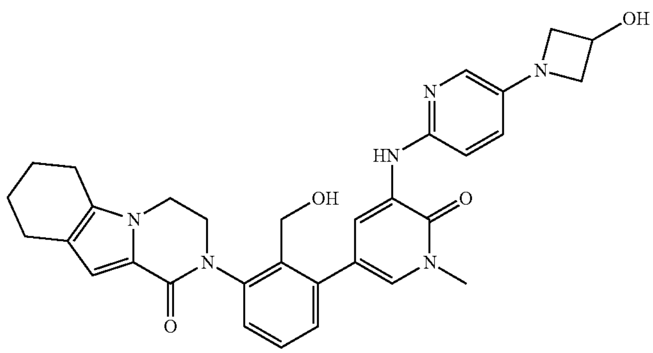 [SMILES: Cn1cc(-c2cccc(N3CCn4c(cc5c4CCCC5)C3=O)c2CO)cc(Nc2ccc(N3CC(O)C3)cn2)c1=O] | 2-(3-(5-(5-(3-hydroxyazetidin-1-yl)pyridin-2-ylamino)-1-methyl-6-oxo-1,6-dihydropyridin-3-yl)-2-(hydroxymethyl)phenyl)-3,4,6,7,8,9-hexahydropyrazino[1,2-a]indol-1(2H)-one | 567.2 | |
| 129 | 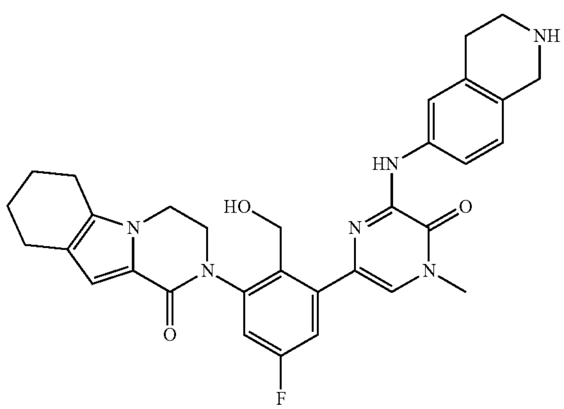 [SMILES: Cn1cc(-c2cc(F)cc(N3CCn4c(cc5c4CCCC5)C3=O)c2CO)nc(Nc2ccc3c(c2)CCNC3)c1=O] | 2-(5-fluoro-2-(hydroxymethyl)-3-(4-methyl-5-oxo-6-(1,2,3,4-tetrahydroisoquinolin-6-ylamino)-4,5-dihydropyrazin-2-yl)phenyl)-3,4,6,7,8,9-hexahydropyrazino[1,2-a]indol-1(2H)-one | 569 | |
| 130 | 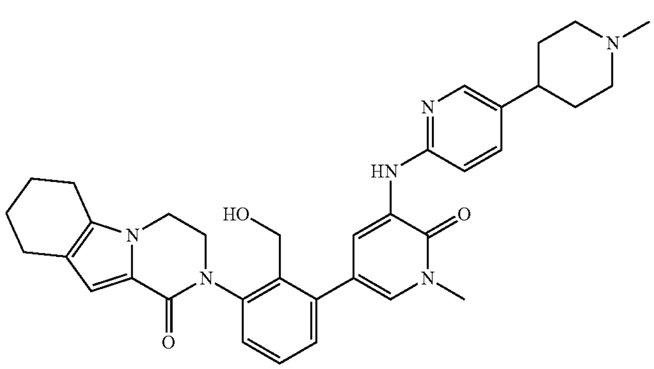 [SMILES: CN1CCC(c2ccc(Nc3cc(-c4cccc(N5CCn6c(cc7c6CCCC7)C5=O)c4CO)cn(C)c3=O)nc2)CC1] | 2-(2-(hydroxymethyl)-3-(1-methyl-5-(5-(1-methylpiperidin-4-yl)pyridin-2-ylamino)-6-oxo-1,6-dihydropyridin-3-yl)phenyl)-3,4,6,7,8,9-hexahydropyrazino[1,2-a]indol-(2H)-one | 593.4 | |

TABLE 1-continued

| No. | Structure | Name | M + H m/z | Btk IC$_{50}$ (μMol) |
|---|---|---|---|---|
| 131 | 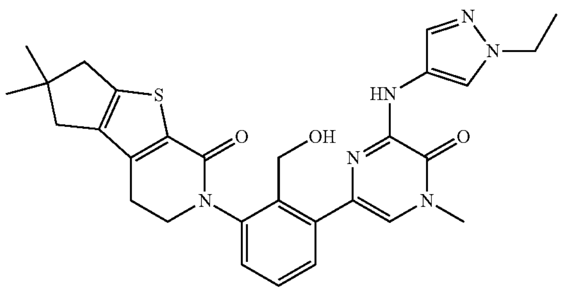 [SMILES: CCn1cc(Nc2nc(-c3cccc(N4CCc5c(sc6c5CC(C)(C)C6)C4=O)c3CO)cn(C)c2=O)cn1] | 5-(3-(6,6-Dimethyl-3,4,6,7-tetrahydro-5H-cyclopenta[4,5]thieno[2,3-c]pyridine-1(2H)-yl)-2-(hydroxymethyl)phenyl)-1-methyl-3-(1-ethyl-1H-pyrazol-4-ylamino)pyrazin-2(1H)-one | 545.1 | 0.002 |

TABLE 2

| No. | Structure | Name | MH+ m/z | Btk IC$_{50}$ (μMol) |
|---|---|---|---|---|
| 132 | 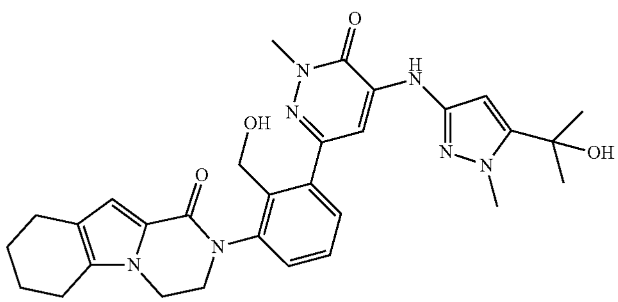 [SMILES: Cn1nc(Nc2cc(-c3cccc(N4CCn5c(cc6c5CCCC6)C4=O)c3CO)nn(C)c2=O)cc1C(C)(C)O] | 2-(2-(hydroxymethyl)-3-(5-(5-(2-hydroxypropan-2-yl)-1-methyl-1H-pyrazol-3-ylamino)-1-methyl-6-oxo-1,6-dihydropyridazin-3-yl)phenyl)-3,4,6,7,8,9-hexahydropyrazino[1,2-a]indol-1(2H)-one | 558.3 | |
| 133 | 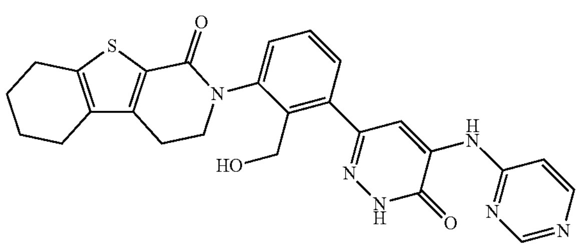 [SMILES: O=C1c2sc3c(c2CCN1c1cccc(-c2cc(Nc4ccncn4)c(=O)[nH]n2)c1CO)CCCC3] | 5-[2-(hydroxymethyl)-3-[6-oxo-5-(pyrimidin-4-ylamino)-1,6-dihydropyridazin-3-yl]phenyl]-8-thia-5-azatricyclo[7.4.0.0$^{2,7}$]trideca-1(9),2(7)-dien-6-one | 501.1 | |
| 134 | 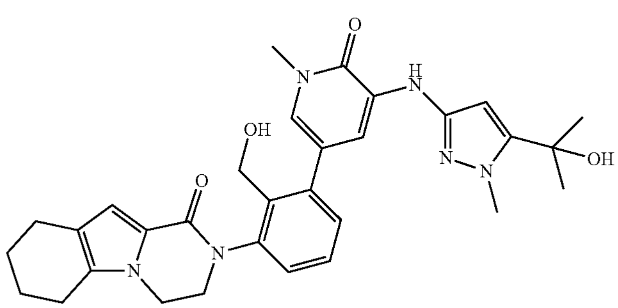 [SMILES: Cn1nc(Nc2cc(-c3cccc(N4CCn5c(cc6c5CCCC6)C4=O)c3CO)cn(C)c2=O)cc1C(C)(C)O] | 5-[2-(hydroxymethyl)-3-{1-oxo-1H,2H,3H,4H,6H,7H,8H,9H-pyrazino[1,2-a]indol-2-yl}phenyl]-3-{[5-(2-hydroxypropan-2-yl)-1-methyl-1H-pyrazol-3-yl]amino}-1-methyl-1,2-dihydropyridin-2-one | 557.3 | |

TABLE 2-continued

| No. | Structure | Name | MH+ m/z | Btk IC$_{50}$ (μMol) |
|---|---|---|---|---|
| 135 | 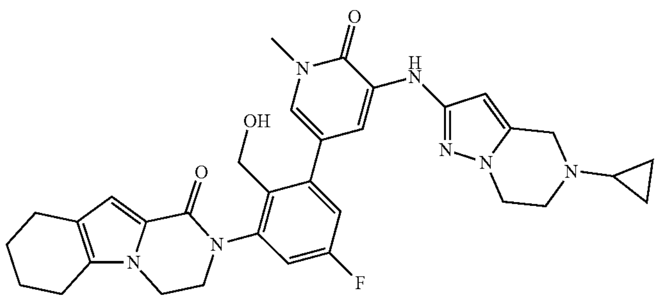 [SMILES: Cn1cc(-c2cc(F)cc(N3CCn4c(cc5c4CCCC5)C3=O)c2CO)cc(Nc2cc3n(n2)CCN(C2CC2)C3)c1=O] | 3-({5-cyclopropyl-4H,5H,6H,7H-pyrazolo[1,5-a]pyrazin-2-yl}amino)-5-[5-fluoro-2-(hydroxymethyl)-3-{1-oxo-1H,2H,3H,4H,6H,7H,8H,9H-pyrazino[1,2-a]indol-2-yl}phenyl]-1-methyl-1,2-dihydropyridin-2-one | 598 | |
| 136 | 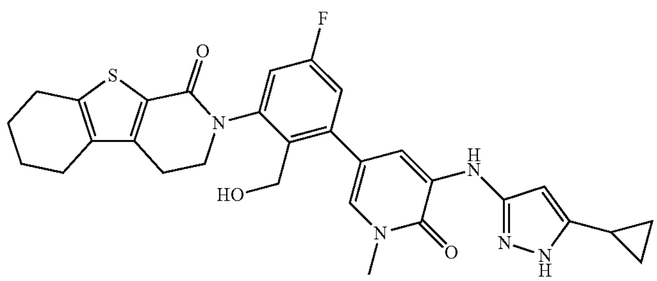 [SMILES: Cn1cc(-c2cc(F)cc(N3CCc4c(sc5c4CCCC5)C3=O)c2CO)cc(Nc2cc(C3CC3)[nH]n2)c1=O] | 5-(3-{5-[(5-cyclopropyl-1H-pyrazol-3-yl)amino]-1-methyl-6-oxo-1,6-dihydropyridin-3-yl}-5-fluoro-2-(hydroxymethyl)phenyl)-8-thia-5-azatricyclo[7.4.0.0$^{2,7}$]trideca-1(9),2(7)-dien-6-one | 560 | |
| 137 | 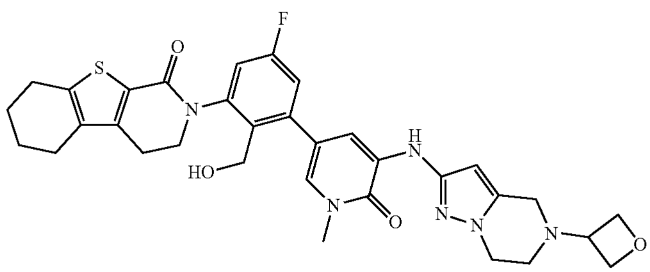 [SMILES: Cn1cc(-c2cc(F)cc(N3CCc4c(sc5c4CCCC5)C3=O)c2CO)cc(Nc2cc3n(n2)CCN(C2COC2)C3)c1=O] | 5-[5-fluoro-2-(hydroxymethyl)-3-(1-methyl-5-{[5-(oxetan-3-yl)-4H,5H,6H,7H-pyrazolo[1,5-a]pyrazin-2-yl]amino}-6-oxo-1,6-dihydropyridin-3-yl)phenyl]-8-thia-5-azatricyclo[7.4.0.0$^{2,7}$]trideca-1(9),2(7)-dien-6-one | 631 | |
| 138 | 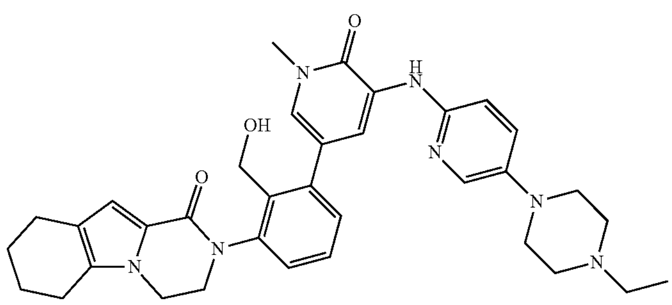 [SMILES: CCN1CCN(c2ccc(Nc3cc(-c4cccc(N5CCn6c(cc7c6CCCC7)C5=O)c4CO)cn(C)c3=O)nc2)CC1] | 3-{[5-(4-ethylpiperazin-1-yl)pyridine-2-yl]amino}-5-[2-(hydroxymethyl)-3-{1-oxo-1H,2H,3H,4H,6H,7H,8H,9H-pyrazino[1,2-a]indol-2-yl}phenyl]-1-methyl-1,2-dihydropyridin-2-one | 608.3 | |
| 139 | 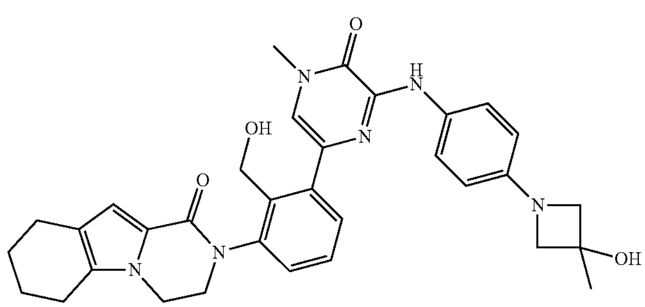 [SMILES: Cn1cc(-c2cccc(N3CCn4c(cc5c4CCCC5)C3=O)c2CO)nc(Nc2ccc(N3CC(C)(O)C3)cc2)c1=O] | 3-{[4-(3-hydroxy-3-methylazetidin-1-yl)phenyl]amino}-5-[2-(hydroxymethyl)-3-{1-oxo-1H,2H,3H,4H,6H,7H,8H,9H-pyrazino[1,2-a]indol-2-yl}phenyl]-1-methyl-1,2-dihydropyrazin-2-one | 581 | |

TABLE 2-continued

| No. | Structure | Name | MH+ m/z | Btk IC$_{50}$ (μMol) |
|---|---|---|---|---|
| 140 | 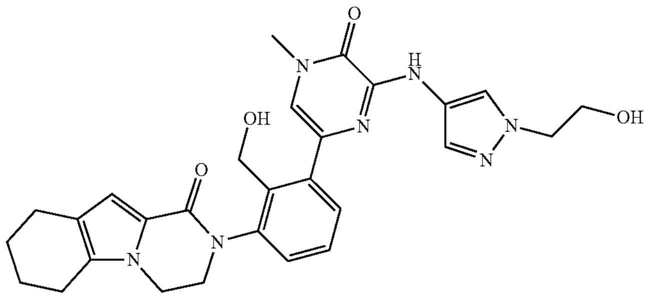 [SMILES: Cn1cc(-c2cccc(N3CCn4c(cc5c4CCCC5)C3=O)c2CO)nc(Nc2cnn(CCO)c2)c1=O] | 3-{[1-(2-hydroxyethyl)-1H-pyrazol-4-yl]amino}-5-[2-(hydroxymethyl)-3-{1-oxo-1H,2H,3H,4H,6H,7H,8H,9H-pyrazino[1,2-a]indol-2-yl}phenyl]-1-methyl-1,2-dihydropyrazin-2-one | 529.59 | |
| 141 | 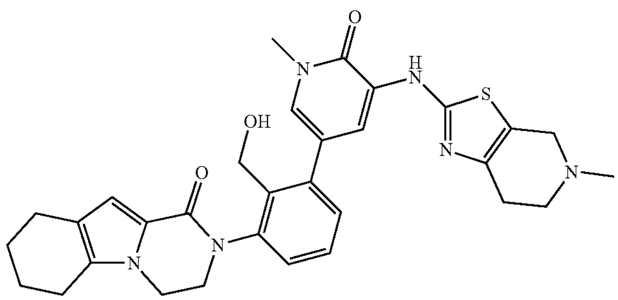 [SMILES: CN1CCc2nc(Nc3cc(-c4cccc(N5CCn6c(cc7c6CCCC7)C5=O)c4CO)cn(C)c3=O)sc2C1] | 2-(2-(hydroxymethyl)-3-(1-methyl-5-(5-methyl-4,5,6,7-tetrahydrothiazolo[5,4-c]pyridin-2-ylamino)-6-oxo-1,6-dihydropyridin-3-yl)phenyl)-3,4,6,7,8,9-hexahydropyrazino[1,2-a]indol-1(2H)-one | 570.71 | |
| 142 | 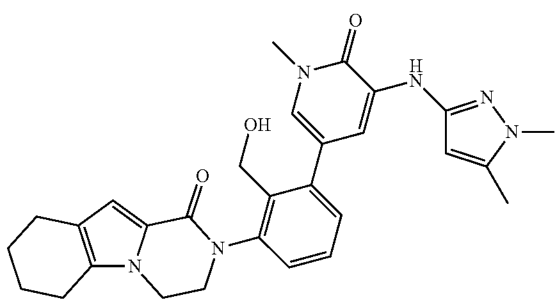 [SMILES: Cc1cc(Nc2cc(-c3cccc(N4CCn5c(cc6c5CCCC6)C4=O)c3CO)cn(C)c2=O)nn1C] | 3-[(1,5-dimethyl-1H-pyrazol-3-yl)amino]-5-[2-(hydroxymethyl)-3-{1-oxo-1H,2H,3H,4H,6H,7H,8H,9H-pyrazino[1,2-a]indol-2-yl}phenyl]-1-methyl-1,2-dihydropyridin-2-one | 512.6 | |
| 143 | 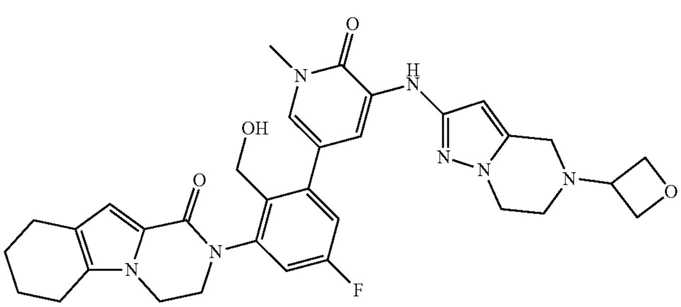 [SMILES: Cn1cc(-c2cc(F)cc(N3CCn4c(cc5c4CCCC5)C3=O)c2CO)cc(Nc2cc3n(n2)CCN(C2COC2)C3)c1=O] | 5-[5-fluoro-2-(hydroxymethyl)-3-{1-oxo-1H,2H,3H,4H,6H,7H,8H,9H-pyrazino[1,2-a]indol-2-yl}phenyl]-1-methyl-3-{[5-(oxetan-3-yl)-4H,5H,6H,7H-pyrazolo[1,5-a]pyrazin-2-yl]amino}-1,2-dihydropyridin-2-one | 613.68 | |
| 144 | 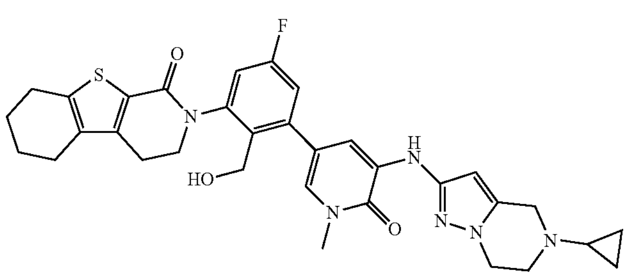 [SMILES: Cn1cc(-c2cc(F)cc(N3CCc4c(sc5c4CCCC5)C3=O)c2CO)cc(Nc2cc3n(n2)CCN(C2CC2)C3)c1=O] | 5-{3-[5-({5-cyclopropyl-4H,5H,6H,7H-pyrazolo[1,5-a]pyrazin-2-yl}amino)-1-methyl-6-oxo-1,6-dihydropyridin-3-yl]-5-fluoro-2-(hydroxymethyl)phenyl}-8-thia-5-azatricyclo[7.4.0.0$^{2,7}$]trideca-1(9),2(7)-dien-6-one | 614.73 | |

TABLE 2-continued

| No. | Structure | Name | MH+ m/z | Btk IC$_{50}$ (μMol) |
|---|---|---|---|---|
| 145 | 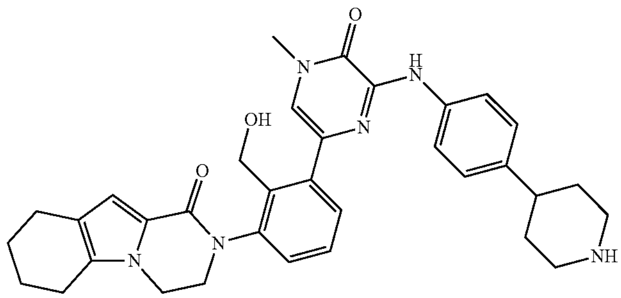 [SMILES: Cn1cc(-c2cccc(N3CCn4c(cc5c4CCCC5)C3=O)c2CO)nc(Nc2ccc(C3CCNCC3)cc2)c1=O] | 5-[2-(hydroxymethyl)-3-{1-oxo-1H,2H,3H,4H,6H,7H,8H,9H-pyrazino[1,2-a]indol-2-yl}phenyl]-1-methyl-3-{[4-(piperidin-4-yl)phenyl]amino}-1,2-dihydropyrazin-2-one | 579.4 | |
| 146 | 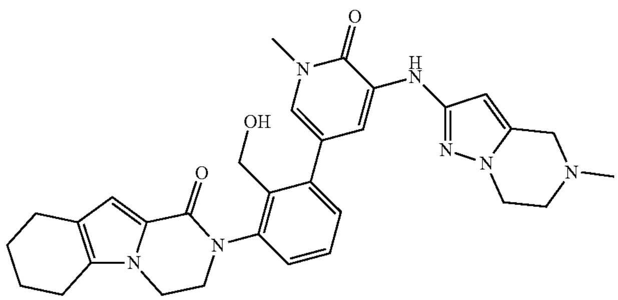 [SMILES: CN1CCn2nc(Nc3cc(-c4cccc(N5CCn6c(cc7c6CCCC7)C5=O)c4CO)cn(C)c3=O)cc2C1] | 5-[2-(hydroxymethyl)-3-{1-oxo-1H,2H,3H,4H,6H,7H,8H,9H-pyrazino[1,2-a]indol-2-yl}phenyl]-1-methyl-3-({5-methyl-4H,5H,6H,7H-pyrazolo[1,5-a]pyrazin-2-yl}amino)-1,2-dihydropyridin-2-one | 554 | |
| 147 | 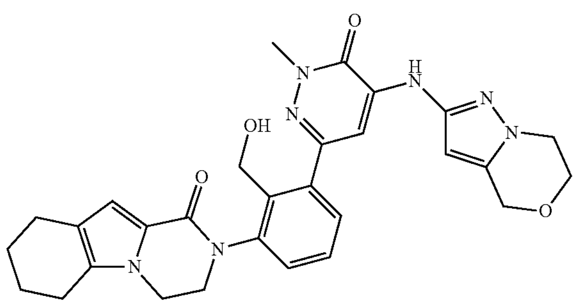 [SMILES: Cn1nc(-c2cccc(N3CCn4c(cc5c4CCCC5)C3=O)c2CO)cc(Nc2cc3n(n2)CCOC3)c1=O] | 6-[2-(hydroxymethyl)-3-{1-oxo-1H,2H,3H,4H,6H,7H,8H,9H-pyrazino[1,2-a]indol-2-yl}phenyl]-2-methyl-4-{4H,6H,7H-pyrazolo[3,2-c][1,4]oxazin-2-ylamino}-2,3-dihydropyridazin-3-one | 542 | |
| 148 | 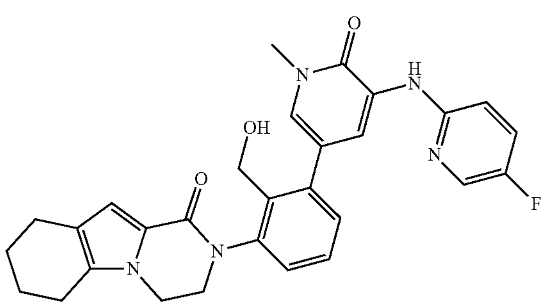 [SMILES: Cn1cc(-c2cccc(N3CCn4c(cc5c4CCCC5)C3=O)c2CO)cc(Nc2ccc(F)cn2)c1=O] | 3-[(5-fluoropyridin-2-yl)amino]-5-[2-(hydroxymethyl)-3-{1-oxo-1H,2H,3H,4H,6H,7H,8H,9H-pyrazino[1,2-a]indol-2-yl}phenyl]-1-methyl-1,2-dihydropyridin-2-one | 514 | |
| 149 | 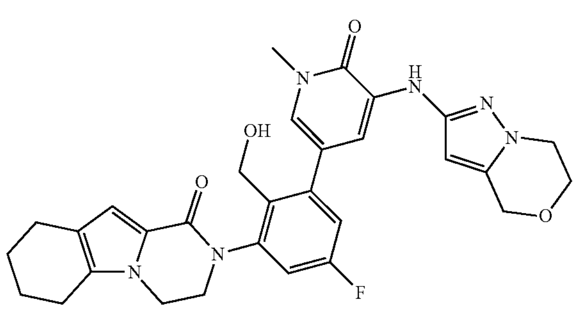 [SMILES: Cn1cc(-c2cc(F)cc(N3CCn4c(cc5c4CCCC5)C3=O)c2CO)cc(Nc2cc3n(n2)CCOC3)c1=O] | 5-[5-fluoro-2-(hydroxymethyl)-3-{1-oxo-1H,2H,3H,4H,6H,7H,8H,9H-pyrazino[1,2-a]indol-2-yl}phenyl]-1-methyl-3-{4H,6H,7H-pyrazolo[3,2-c][1,4]oxazin-2-ylamino}-1,2-dihydropyridin-2-one | 559 | 0.005 |

TABLE 2-continued

| No. | Structure | Name | MH+ m/z | Btk IC$_{50}$ (μMol) |
|---|---|---|---|---|
| 150 | 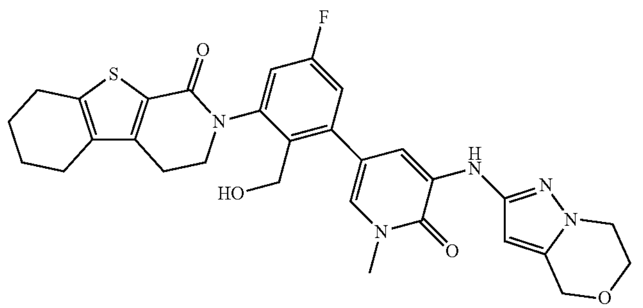 [SMILES: Cn1cc(-c2cc(F)cc(N3CCc4c(sc5c4CCCC5)C3=O)c2CO)cc(Nc2cc3n(n2)CCOC3)c1=O] | 5-[5-fluoro-2-(hydroxymethyl)-3-(1-methyl-6-oxo-5-{4H,6H,7H-pyrazolo[3,2-c][1,4]oxazin-2-ylamino}-1,6-dihydropyridin-3-yl)phenyl]-8-thia-5-azatricyclo[7.4.0.0$^{2,7}$]trideca-1(9),2(7)-dien-6-one | 576 | |
| 151 | 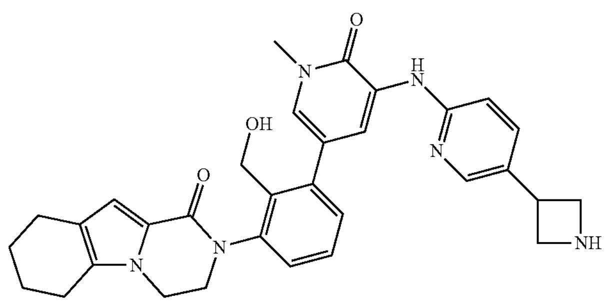 [SMILES: Cn1cc(-c2cccc(N3CCn4c(cc5c4CCCC5)C3=O)c2CO)cc(Nc2ccc(C3CNC3)cn2)c1=O] | 3-{[5-(azetidin-3-yl)pyridine-2-yl]amino}-5-[2-(hydroxymethyl)-3-{1-oxo-1H,2H,3H,4H,6H,7H,8H,9H-pyrazino[1,2-a]indol-2-yl}phenyl]-1-methyl-1,2-dihydropyridin-2-one | 551.3 | |
| 152 | 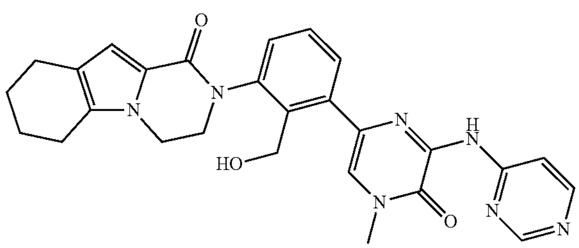 [SMILES: Cn1cc(-c2cccc(N3CCn4c(cc5c4CCCC5)C3=O)c2CO)nc(Nc2ccncn2)c1=O] | 11-[2-(hydroxymethyl)-3-[1-methyl-6-oxo-5-(pyrimidin-4-ylamino)-1,6-dihydropyridin-3-yl]phenyl]-1,8,11-triazatricyclo[7.4.0.0$^{2,7}$]trideca-2(7),8-dien-10-one | 498.2 | |
| 153 | 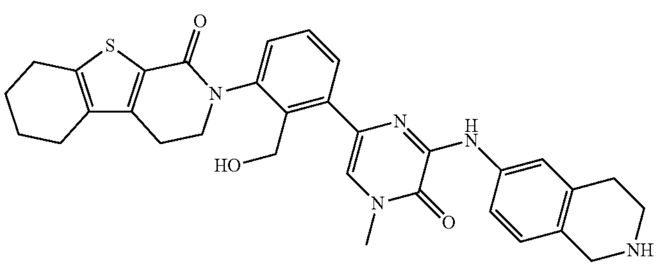 [SMILES: Cn1cc(-c2cccc(N3CCc4c(sc5c4CCCC5)C3=O)c2CO)nc(Nc2ccc3c(c2)CCNC3)c1=O] | 5-[2-(hydroxymethyl)-3-[4-methyl-5-oxo-6-(1,2,3,4-tetrahydroisoquinolin-6-ylamino)-4,5-dihydropyrazin-2-yl]phenyl]-8-thia-5-azatricyclo[7.4.0.0$^{2,7}$]trideca-1(9),2(7)-dien-6-one | 568.1 | |
| 154 | 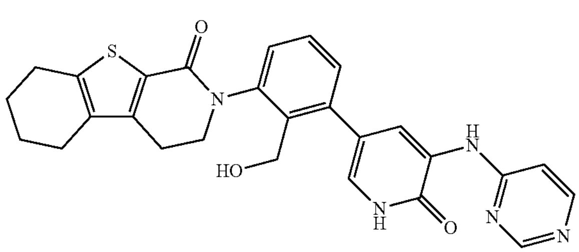 [SMILES: O=C1c2sc3c(c2CCN1c1cccc(-c2c[nH]c(=O)c(Nc4ccncn4)c2)c1CO)CCCC3] | 5-[2-(hydroxymethyl)-3-[6-oxo-5-(pyrimidin-4-ylamino)-1,6-dihydropyridin-3-yl]phenyl]-8-thia-5-azatricyclo[7.4.0.0$^{2,7}$]trideca-1(9),2(7)-dien-6-one | 500.1 | |

TABLE 2-continued

| No. | Structure | Name | MH+ m/z | Btk IC$_{50}$ (μMol) |
|---|---|---|---|---|
| 155 | 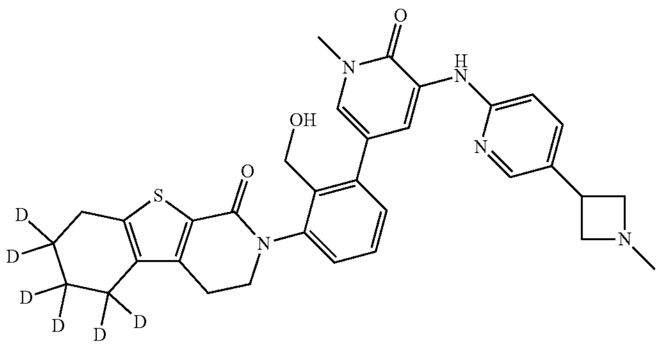 [SMILES: [2H]C1([2H])Cc2sc3c(c2C([2H])([2H])C1([2H])[2H])CCN(c1cccc(-c2cc(Nc4ccc(C5CN(C)C5)cn4)c(=O)n(C)c2)c1CO)C3=O] | 11,11,12,12,13,13-hexahydrogenio-5-[2-(hydroxymethyl)-3-(1-methyl-5-{[5-(1-methylazetidin-3-yl)pyridine-2-yl]amino}-6-oxo-1,6-dihydropyridin-3-yl)phenyl]-8-thia-5-azatricyclo[7.4.0.0$^{2,7}$]trideca-1(9),2(7)-dien-6-one | 588.2 | |
| 156 | 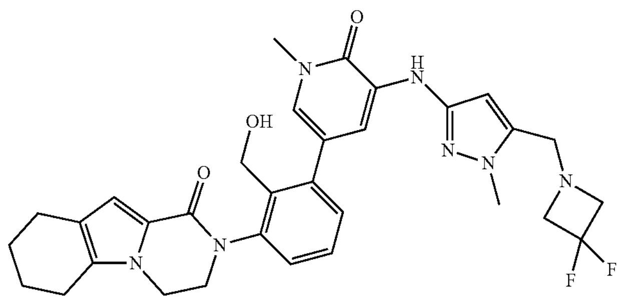 [SMILES: Cn1nc(Nc2cc(-c3cccc(N4CCn5c(cc6c5CCCC6)C4=O)c3CO)cn(C)c2=O)cc1CN1CC(F)(F)C1] | 3-({5-[(3,3-difluoroazetidin-1-yl)methyl]-1-methyl-1H-pyrazol-3-yl}amino)-5-[2-(hydroxymethyl)-3-{1-oxo-1H,2H,3H,4H,6H,7H,8H,9H-pyrazino[1,2-a]indol-2-yl}phenyl]-1-methyl-1,2-dihydropyridin-2-one | 604.4 | |
| 157 | 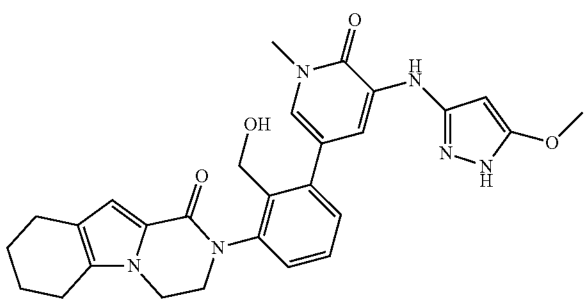 [SMILES: COc1cc(Nc2cc(-c3cccc(N4CCn5c(cc6c5CCCC6)C4=O)c3CO)cn(C)c2=O)n[nH]1] | 5-[2-(hydroxymethyl)-3-{1-oxo-1H,2H,3H,4H,6H,7H,8H,9H-pyrazino[1,2-a]indol-2-yl}phenyl]-3-[(5-methoxy-1H-pyrazol-3-yl)amino]-1-methyl-1,2-dihydropyridin-2-one | 515.4 | |
| 158 | 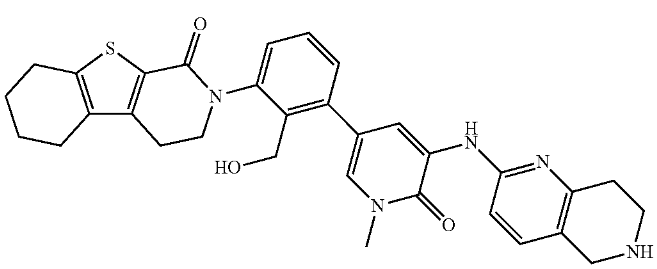 [SMILES: Cn1cc(-c2cccc(N3CCc4c(sc5c4CCCC5)C3=O)c2CO)cc(Nc2ccc3c(n2)CCNC3)c1=O] | 5-[2-(hydroxymethyl)-3-[1-methyl-6-oxo-5-(5,6,7,8-tetrahydro-1,6-naphthyridin-2-ylamino)-1,6-dihydropyridin-3-yl]phenyl]-8-thia-5-azatricyclo[7.4.0.0$^{2,7}$]trideca-1(9),2(7)-dien-6-one | 568.3 | |
| 159 | 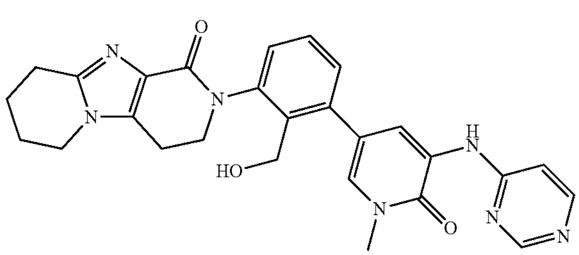 [SMILES: Cn1cc(-c2cccc(N3CCc4c(nc5n4CCCC5)C3=O)c2CO)cc(Nc2ccncn2)c1=O] | 5-[2-(hydroxymethyl)-3-[1-methyl-6-oxo-5-(pyrimidin-4-ylamino)-1,6-dihydropyridin-3-yl]phenyl]-1,5,8-triazatricyclo[7.4.0.0$^{2,7}$]trideca-2(7),8-dien-6-one | 498.2 | |

TABLE 2-continued

| No. | Structure | Name | MH+ m/z | Btk IC$_{50}$ (μMol) |
|---|---|---|---|---|
| 160 | 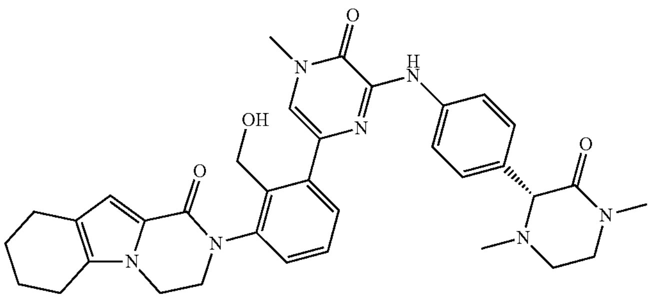 [SMILES: CN1CCN(C)[C@H](c2ccc(Nc3nc(-c4cccc(N5CCn6c(cc7c6CCCC7)C5=O)c4CO)cn(C)c3=O)cc2)C1=O] | 3-({4-[(2R)-1,4-dimethyl-3-oxopiperazin-2-yl]phenyl}amino)-5-[2-(hydroxymethyl)-3-{1-oxo-1H,2H,3H,4H,6H,7H,8H,9H-pyrazino[1,2-a]indol-2-yl]phenyl]-1-methyl-1,2-dihydropyrazin-2-one | 622.4 | |
| 161 | 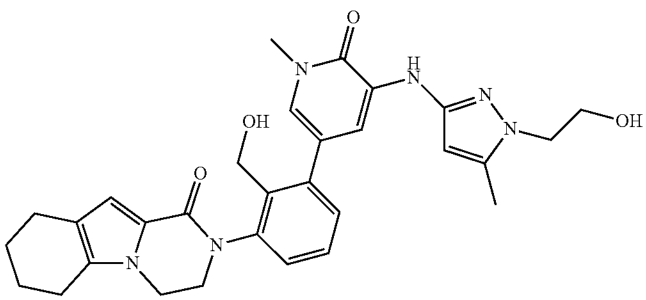 [SMILES: Cc1cc(Nc2cc(-c3cccc(N4CCn5c(cc6c5CCCC6)C4=O)c3CO)cn(C)c2=O)nn1CCO] | 3-{[1-(2-hydroxyethyl)-5-methyl-1H-pyrazol-3-yl]amino}-5-[2-(hydroxymethyl)-3-{1-oxo-1H,2H,3H,4H,6H,7H,8H,9H-pyrazino[1,2-a]indol-2-yl]phenyl]-1-methyl-1,2-dihydropyridin-2-one | 543 | |
| 162 | 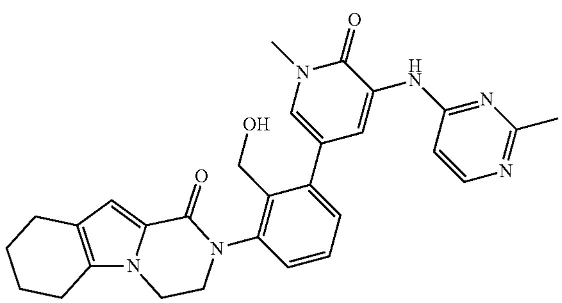 [SMILES: Cc1nccc(Nc2cc(-c3cccc(N4CCn5c(cc6c5CCCC6)C4=O)c3CO)cn(C)c2=O)n1] | 5-[2-(hydroxymethyl)-3-{1-oxo-1H,2H,3H,4H,6H,7H,8H,9H-pyrazino[1,2-a]indol-2-yl}phenyl]-1-methyl-3-[(2-methylpyrimidin-4-yl)amino]-1,2-dihydropyridin-2-one | 511 | |
| 163 | 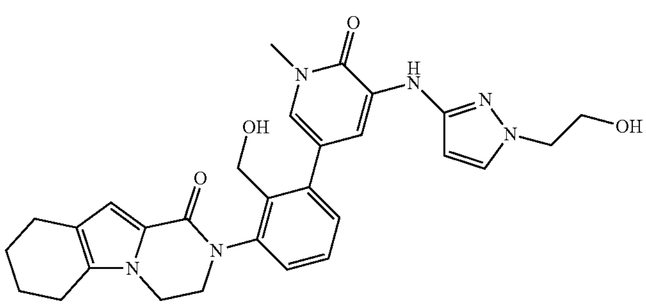 [SMILES: Cn1cc(-c2cccc(N3CCn4c(cc5c4CCCC5)C3=O)c2CO)cc(Nc2ccn(CCO)n2)c1=O] | 3-{[1-(2-hydroxyethyl)-1H-pyrazol-3-yl]amino}-5-[2-(hydroxymethyl)-3-{1-oxo-1H,2H,3H,4H,6H,7H,8H,9H-pyrazino[1,2-a]indol-2-yl}phenyl]-1-methyl-1,2-dihydropyridin-2-one | 529 | |
| 164 | 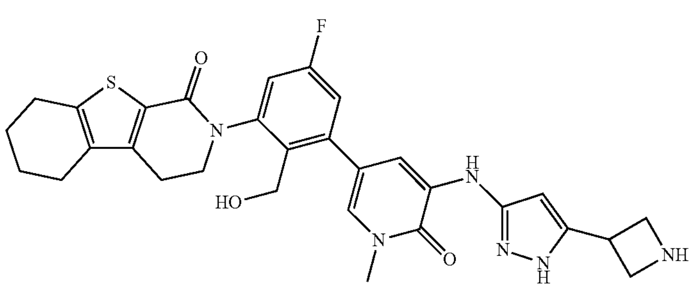 [SMILES: Cn1cc(-c2cc(F)cc(N3CCc4c(sc5c4CCCC5)C3=O)c2CO)cc(Nc2cc(C3CNC3)[nH]n2)c1=O] | 5-[3-(5-{[5-(azetidin-3-yl)-1H-pyrazol-3-yl]amino}-1-methyl-6-oxo-1,6-dihydropyridin-3-yl)-5-fluoro-2-(hydroxymethyl)phenyl]-8-thia-5-azatricyclo[7.4.0.0$^{2,7}$]trideca-1(9),2(7)-dien-6-one | 575 | |

TABLE 2-continued

| No. | Structure | Name | MH+ m/z | Btk IC$_{50}$ (μMol) |
|---|---|---|---|---|
| 165 | | 3-{[5-(azetidin-3-yl)-1H-pyrazol-3-yl]amino}-5-[5-fluoro-2-(hydroxymethyl)-3-{1-oxo-1H,2H,3H,4H,6H,7H,8H,9H-pyrazino[1,2-a]indol-2-yl}phenyl]-1-methyl-1,2-dihydropyridin-2-one | 558 | |
| 166 | | 5-[2-(hydroxymethyl)-3-{1-oxo-1H,2H,3H,4H,6H,7H,8H,9H-pyrazino[1,2-a]indol-2-yl}phenyl]-1-methyl-3-(5,6,7,8-tetrahydro-1,6-naphthyridin-2-ylamino)-1,2-dihydropyridin-2-one | 551.3 | |
| 167 | 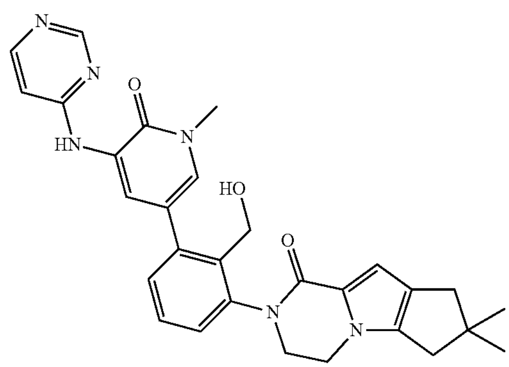 [SMILES: Cn1cc(-c2cccc(N3CCn4c(cc5c4CC(C)(C)C5)C3=O)c2CO)cc(Nc2ccncn2)c1=O] | 10-[2-(hydroxymethyl)-3-[1-methyl-6-oxo-5-(pyrimidin-4-ylamino)-1,6-dihydropyridin-3-yl]phenyl]-4,4-dimethyl-1,10-diazatricyclo[6.4.0.0$^{2,6}$]dodeca-2(6),7-dien-9-one | 511.8 | |
| 168 | 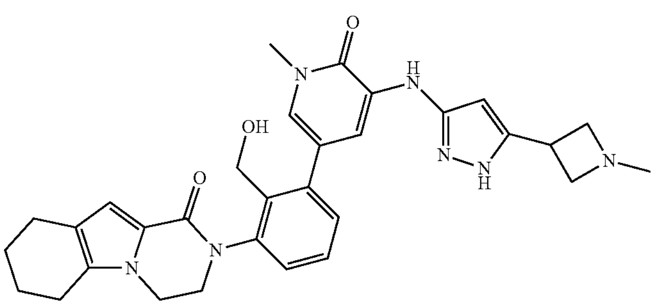 [SMILES: CN1CC(c2cc(Nc3cc(-c4cccc(N5CCn6c(cc7c6CCCC7)C5=O)c4CO)cn(C)c3=O)n[nH]2)C1] | 5-[2-(hydroxymethyl)-3-{1-oxo-1H,2H,3H,4H,6H,7H,8H,9H-pyrazino[1,2-a]indol-2-yl}phenyl]-1-methyl-3-{[5-(1-methylazetidin-3-yl)-1H-pyrazol-3-yl]amino}-1,2-dihydropyridin-2-one | 554 | |
| 169 | 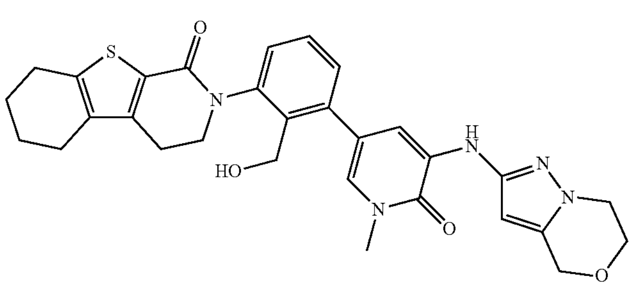 [SMILES: Cn1cc(-c2cccc(N3CCc4c(sc5c4CCCC5)C3=O)c2CO)cc(Nc2cc3n(n2)CCOC3)c1=O] | 5-[2-(hydroxymethyl)-3-(1-methyl-6-oxo-5-{4H,6H,7H-pyrazolo[3,2-c][1,4]oxazin-2-ylamino}-1,6-dihydropyridin-3-yl)phenyl]-8-thia-5-azatricyclo[7.4.0.0$^{2,7}$]trideca-1(9),2(7)-dien-6-one | 558 | |

TABLE 2-continued

| No. | Structure | Name | MH+ m/z | Btk IC$_{50}$ (μMol) |
|---|---|---|---|---|
| 170 | 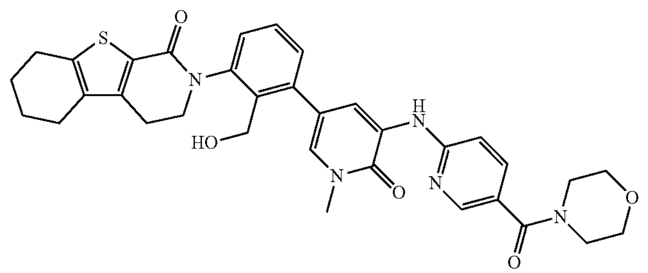 [SMILES: Cn1cc(-c2cccc(N3CCc4c(sc5c4CCCC5)C3=O)c2CO)cc(Nc2ccc(C(=O)N3CCOCC3)cn2)c1=O] | 5-[2-(hydroxymethyl)-3-(1-methyl-5-{[5-(morpholin-4-ylcarbonyl)pyridine-2-yl]amino}-6-oxo-1,6-dihydropyridin-3-yl)phenyl]-8-thia-5-azatricyclo[7.4.0.0$^{2,7}$]trideca-1(9),2(7)-dien-6-one | 626 | |
| 171 | 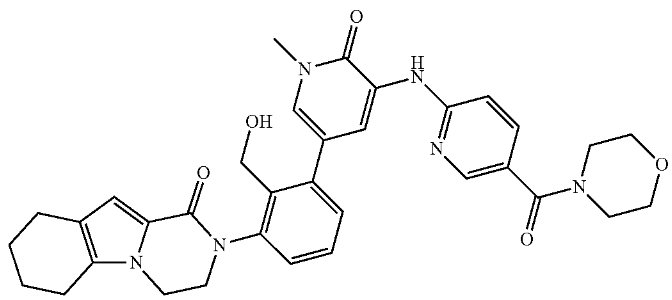 [SMILES: Cn1cc(-c2cccc(N3CCn4c(cc5c4CCCC5)C3=O)c2CO)cc(Nc2ccc(C(=O)N3CCOCC3)cn2)c1=O] | 5-[2-(hydroxymethyl)-3-{1-oxo-1H,2H,3H,4H,6H,7H,8H,9H-pyrazino[1,2-a]indol-2-yl}phenyl]-1-methyl-3-{[5-(morpholin-4-ylcarbonyl)pyridine-2-yl]amino}-1,2-dihydropyridin-2-one | 609 | |
| 172 | 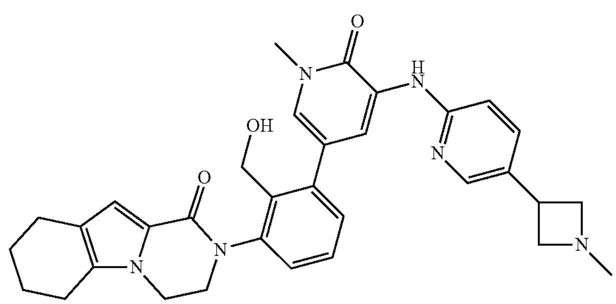 [SMILES: CN1CC(c2ccc(Nc3cc(-c4cccc(N5CCn6c(cc7c6CCCC7)C5=O)c4CO)cn(C)c3=O)nc2)C1] | 5-[2-(hydroxymethyl)-3-{1-oxo-1H,2H,3H,4H,6H,7H,8H,9H-pyrazino[1,2-a]indol-2-yl}phenyl]-1-methyl-3-{[5-(1-methylazetidin-3-yl)pyridine-2-yl]amino}-1,2-dihydropyridin-2-one | 565 | |
| 173 | 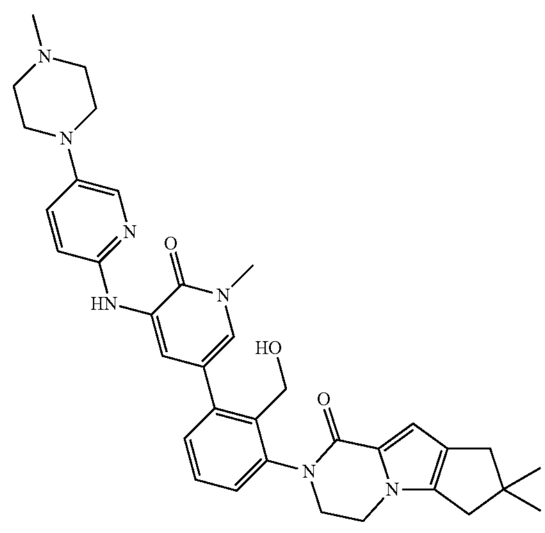 [SMILES: CN1CCN(c2ccc(Nc3cc(-c4cccc(N5CCn6c(cc7c6CC(C)(C)C7)C5=O)c4CO)cn(C)c3=O)nc2)CC1] | 10-[2-(hydroxymethyl)-3-(1-methyl-5-{[5-(4-methylpiperazin-1-yl)pyridine-2-yl]amino}-6-oxo-1,6-dihydropyridin-3-yl)phenyl]-4,4-dimethyl-1,10-diazatricyclo[6.4.0.0$^{2,6}$]dodeca-2(6),7-dien-9-one | 608.4 | |

TABLE 2-continued

| No. | Structure | Name | MH+ m/z | Btk IC$_{50}$ (μMol) |
|---|---|---|---|---|
| 174 | 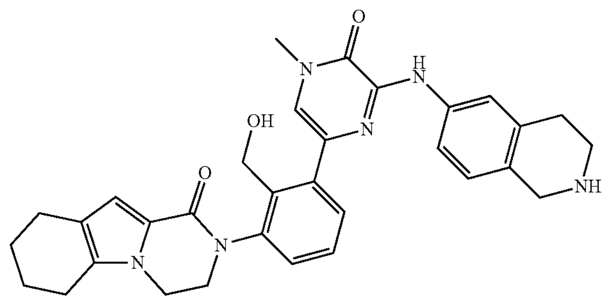 [SMILES: Cn1cc(-c2cccc(N3CCn4c(cc5c4CCCC5)C3=O)c2CO)nc(Nc2ccc3c(c2)CCNC3)c1=O] | 5-[2-(hydroxymethyl)-3-{1-oxo-1H,2H,3H,4H,6H,7H,8H,9H-pyrazino[1,2-a]indol-2-yl}phenyl]-1-methyl-3-(1,2,3,4-tetrahydroisoquinolin-6-ylamino)-1,2-dihydropyrazin-2-one | 551.4 | |
| 175 | 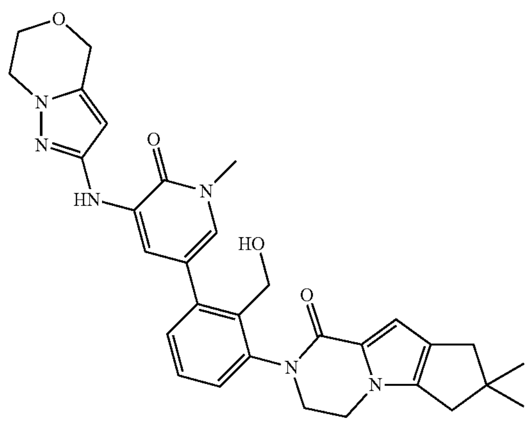 [SMILES: Cn1cc(-c2cccc(N3CCn4c(cc5c4CC(C)(C)C5)C3=O)c2CO)cc(Nc2cc3n(n2)CCOC3)c1=O] | 10-[2-(hydroxymethyl)-3-(1-methyl-6-oxo-5-{4H,6H,7H-pyrazolo[3,2-c][1,4]oxazin-2-ylamino}-1,6-dihydropyridin-3-yl)phenyl]-4,4-dimethyl-1,10-diazatricyclo[6.4.0.0$^{2,6}$]dodeca-2(6),7-dien-9-one | 555.3 | |
| 176 | 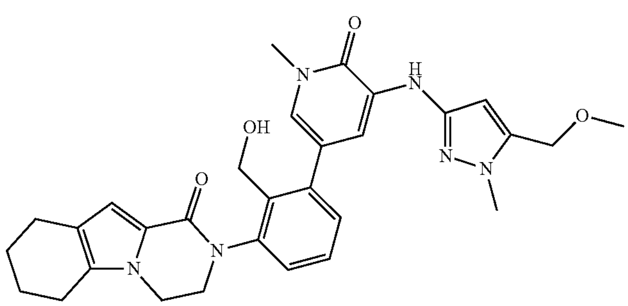 [SMILES: COCc1cc(Nc2cc(-c3cccc(N4CCn5c(cc6c5CCCC6)C4=O)c3CO)cn(C)c2=O)nn1C] | 5-[2-(hydroxymethyl)-3-{1-oxo-1H,2H,3H,4H,6H,7H,8H,9H-pyrazino[1,2-a]indol-2-yl}phenyl]-3-{[5-(methoxymethyl)-1-methyl-1H-pyrazol-3-yl]amino}-1-methyl-1,2-dihydropyridin-2-one | 543 | |
| 177 | | 5-[2-(hydroxymethyl)-3-{[5-(methoxymethyl)-1-methyl-1H-pyrazol-3-yl]amino}-1-methyl-6-oxo-1,6-dihydropyridin-3-yl)phenyl]-8-thia-5-azatricyclo[7.4.0.0$^{2,7}$]trideca-1(9),2(7)-dien-6-one | 560 | |

Replacement Sheet

TABLE 2-continued

| No. | Structure | Name | MH+ m/z | Btk IC$_{50}$ (μMol) |
|---|---|---|---|---|
| 178 | 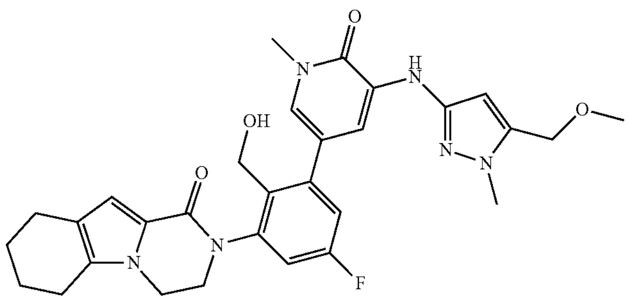 [SMILES: COCc1cc(Nc2cc(-c3cc(F)cc(N4CCn5c(cc6c5CCCC6)C4=O)c3CO)cn(C)c2=O)nn1C] | 5-[5-fluoro-2-(hydroxymethyl)-3-{1-oxo-1H,2H,3H,4H,6H,7H,8H,9H-pyrazino[1,2-a]indol-2-yl}phenyl]-3-{[5-(methoxymethyl)-1-methyl-1H-pyrazol-3-yl]amino}-1-methyl-1,2-dihydropyridin-2-one | 561 | |
| 179 | 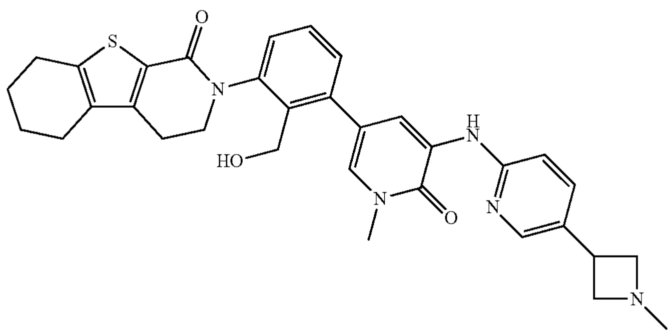 [SMILES: CN1CC(c2ccc(Nc3cc(-c4cccc(N5CCc6c(sc7c6CCCC7)C5=O)c4CO)cn(C)c3=O)nc2)C1] | 5-[2-(hydroxymethyl)-3-(1-methyl-5-{[5-(1-methylazetidin-3-yl)pyridine-2-yl]amino}-6-oxo-1,6-dihydropyridin-3-yl)phenyl]-8-thia-5-azatricyclo[7.4.0.0$^{2,7}$]trideca-1(9),2(7)-dien-6-one | 582 | |
| 180 | 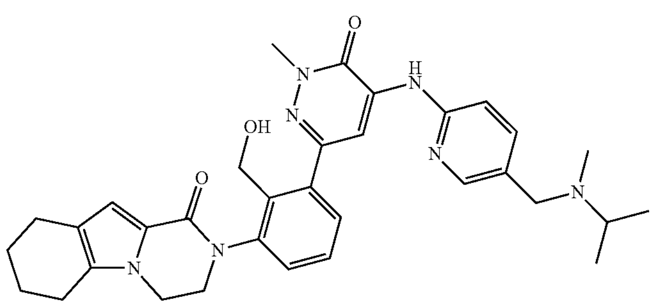 [SMILES: CC(C)N(C)Cc1ccc(Nc2cc(-c3cccc(N4CCn5c(cc6c5CCCC6)C4=O)c3CO)nn(C)c2=O)nc1] | 6-[2-(hydroxymethyl)-3-{1-oxo-1H,2H,3H,4H,6H,7H,8H,9H-pyrazino[1,2-a]indol-2-yl}phenyl]-2-methyl-4-[(5-{[methyl(propan-2-yl)amino]methyl}pyridine-2-yl)amino]-2,3-dihydropyridazin-3-one | 582.5 | |
| 181 | 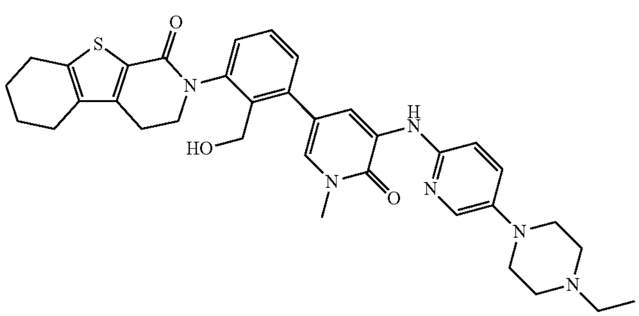 [SMILES: CCN1CCN(c2ccc(Nc3cc(-c4cccc(N5CCc6c(sc7c6CCCC7)C5=O)c4CO)cn(C)c3=O)nc2)CC1] | 5-[3-(5-{[5-(4-ethylpiperazin-1-yl)pyridine-2-yl]amino}-1-methyl-6-oxo-1,6-dihydropyridin-3-yl)-2-(hydroxymethyl)phenyl]-8-thia-5-azatricyclo[7.4.0.0$^{2,7}$]trideca-1(9),2(7)-dien-6-one | 625.4 | |

TABLE 2-continued

| No. | Structure | Name | MH+ m/z | Btk IC$_{50}$ (μMol) |
|---|---|---|---|---|
| 182 | 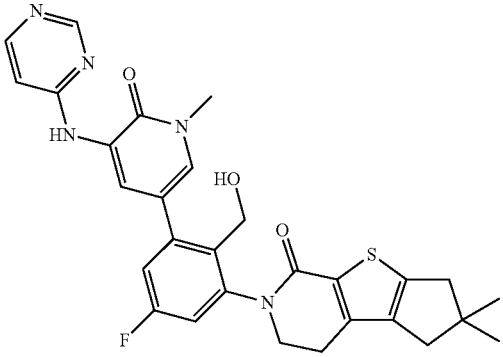 [SMILES: Cn1cc(-c2cc(F)cc(N3CCc4c(sc5c4CC(C)(C)C5)C3=O)c2CO)cc(Nc2ccncn2)c1=O] | 10-[5-fluoro-2-(hydroxymethyl)-3-[1-methyl-6-oxo-5-(pyrimidin-4-ylamino)-1,6-dihydropyridin-3-yl]phenyl]-4,4-dimethyl-7-thia-10-azatricyclo[6.4.0.0$^{2,6}$]dodeca-1(8),2(6)-dien-9-one | 546.2 | |
| 183 | 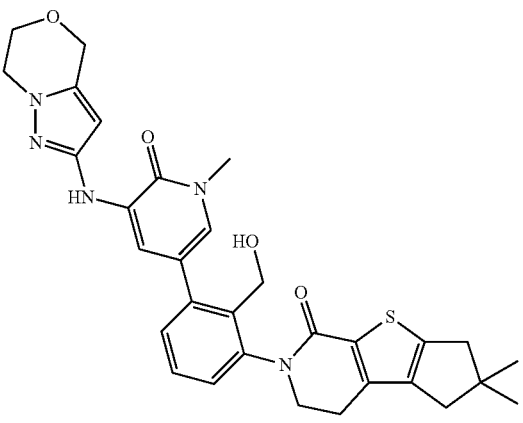 [SMILES: Cn1cc(-c2cccc(N3CCc4c(sc5c4CC(C)(C)C5)C3=O)c2CO)cc(Nc2cc3n(n2)CCOC3)c1=O] | 10-[2-(hydroxymethyl)-3-(1-methyl-6-oxo-5-{4H,6H,7H-pyrazolo[3,2-c][1,4]oxazin-2-ylamino}-1,6-dihydropyridin-3-yl)phenyl]-4,4-dimethyl-7-thia-10-azatricyclo[6.4.0.0$^{2,6}$]dodeca-1(8),2(6)-dien-9-one | 572.3 | |
| 184 | 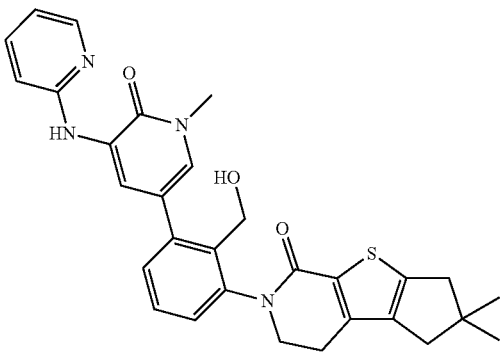 [SMILES: Cn1cc(-c2cccc(N3CCc4c(sc5c4CC(C)(C)C5)C3=O)c2CO)cc(Nc2ccccn2)c1=O] | 10-[2-(hydroxymethyl)-3-[1-methyl-6-oxo-5-(pyridine-2-ylamino)-1,6-dihydropyridin-3-yl]phenyl]-4,4-dimethyl-7-thia-10-azatricyclo[6.4.0.0$^{2,6}$]dodeca-1(8),2(6)-dien-9-one | 527.2 | |
| 185 | 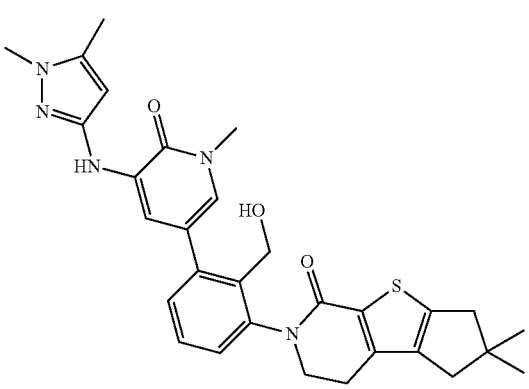 | 10-(3-{5-[(1,5-dimethyl-1H-pyrazol-3-yl)amino]-1-methyl-6-oxo-1,6-dihydropyridin-3-yl}-2-(hydroxymethyl)phenyl)-4,4-dimethyl-7-thia-10-azatricyclo[6.4.0.0$^{2,6}$]dodeca-1(8),2(6)-dien-9-one | 544.2 | |

TABLE 2-continued

| No. | Structure | Name | MH+ m/z | Btk IC$_{50}$ (μMol) |
|---|---|---|---|---|
| 186 | 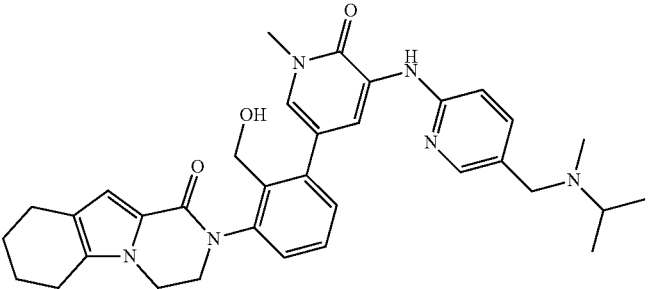 [SMILES: CC(C)N(C)Cc1ccc(Nc2cc(-c3cccc(N4CCn5c(cc6c5CCCC6)C4=O)c3CO)cn(C)c2=O)nc1] | 5-[2-(hydroxymethyl)-3-{1-oxo-1H,2H,3H,4H,6H,7H,8H,9H-pyrazino[1,2-a]indol-2-yl}phenyl]-1-methyl-3-[(5-{[methyl(propan-2-yl)amino]methyl}pyridine-2-yl)amino]-1,2-dihydropyridin-2-one | 581.4 | |
| 187 | 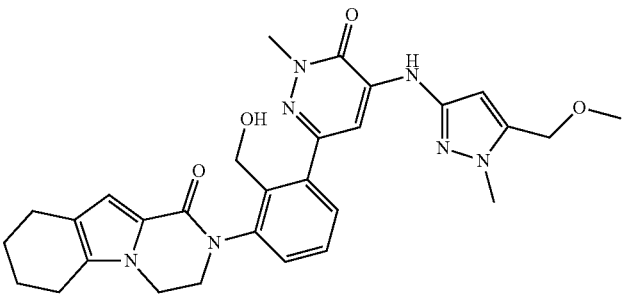 [SMILES: COCc1cc(Nc2cc(-c3cccc(N4CCn5c(cc6c5CCCC6)C4=O)c3CO)nn(C)c2=O)nn1C] | 6-[2-(hydroxymethyl)-3-{1-oxo-1H,2H,3H,4H,6H,7H,8H,9H-pyrazino[1,2-a]indol-2-yl}phenyl]-4-{[5-(methoxymethyl)-1-methyl-1H-pyrazol-3-yl]amino}-2-methyl-2,3-dihydropyridazin-3-one | 544 | |
| 188 | 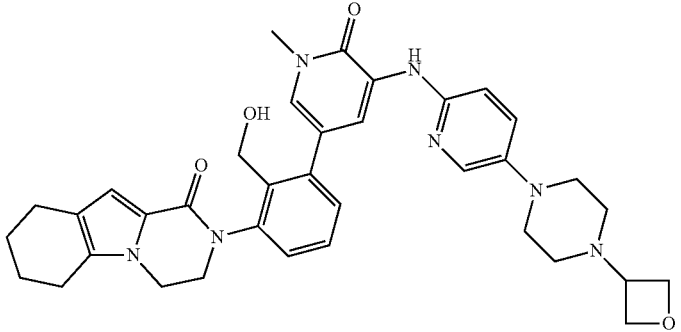 [SMILES: Cn1cc(-c2cccc(N3CCn4c(cc5c4CCCC5)C3=O)c2CO)cc(Nc2ccc(N3CCN(C4COC4)CC3)cn2)c1=O] | 5-[2-(hydroxymethyl)-3-{1-oxo-1H,2H,3H,4H,6H,7H,8H,9H-pyrazino[1,2-a]indol-2-yl}phenyl]-1-methyl-3-({5-[4-(oxetan-3-yl)piperazin-1-yl]pyridine-2-yl}amino)-1,2-dihydropyridin-2-one | 636 | |
| 189 | 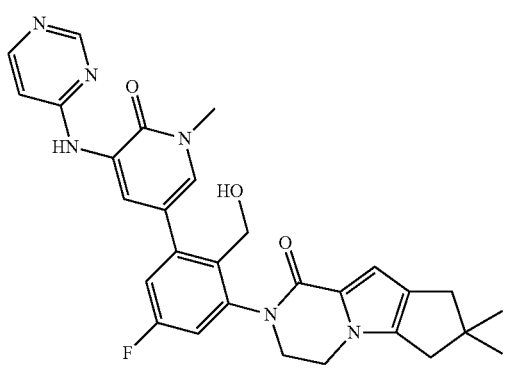 [SMILES: Cn1cc(-c2cc(F)cc(N3CCn4c(cc5c4CC(C)(C)C5)C3=O)c2CO)cc(Nc2ccncn2)c1=O] | 10-[5-fluoro-2-(hydroxymethyl)-3-[1-methyl-6-oxo-5-(pyrimidin-4-ylamino)-1,6-dihydropyridin-3-yl]phenyl]-4,4-dimethyl-1,10-diazatricyclo[6.4.0.0$^{2,6}$]dodeca-2(6),7-dien-9-one | 529.7 | |

TABLE 2-continued

| No. | Structure | Name | MH+ m/z | Btk IC$_{50}$ (μMol) |
|---|---|---|---|---|
| 190 | 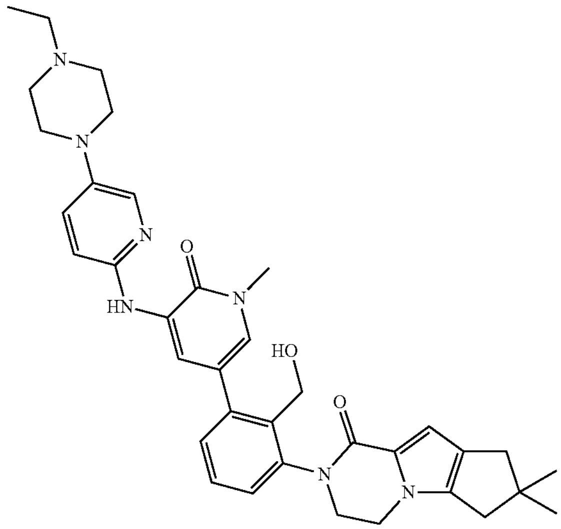 [SMILES: CCN1CCN(c2ccc(Nc3cc(-c4cccc(N5CCn6c(cc7c6CC(C)(C)C7)C5=O)c4CO)cn(C)c3=O)nc2)CC1] | 10-[3-(5-{[5-(4-ethylpiperazin-1-yl)pyridine-2-yl]amino}-1-methyl-6-oxo-1,6-dihydropyridin-3-yl)-2-(hydroxymethyl)phenyl]-4,4-dimethyl-1,10-diazatricyclo[6.4.0.0$^{2,6}$]dodeca-2(6),7-dien-9-one | 622.5 | |
| 191 | 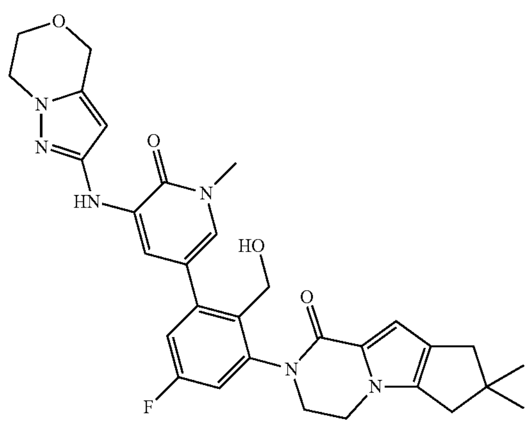 [SMILES: Cn1cc(-c2cc(F)cc(N3CCn4c(cc5c4CC(C)(C)C5)C3=O)c2CO)cc(Nc2cc3n(n2)CCOC3)c1=O] | 10-[5-fluoro-2-(hydroxymethyl)-3-(1-methyl-6-oxo-5-{4H,6H,7H-pyrazolo[3,2-c][1,4]oxazin-2-ylamino}-1,6-dihydropyridin-3-yl)phenyl]-4,4-dimethyl-1,10-diazatricyclo[6.4.0.0$^{2,6}$]dodeca-2(6),7-dien-9-one | 573.4 | |
| 192 | 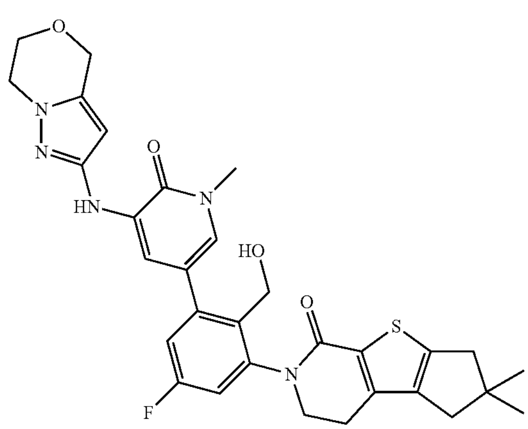 [SMILES: Cn1cc(-c2cc(F)cc(N3CCc4c(sc5c4CC(C)(C)C5)C3=O)c2CO)cc(Nc2cc3n(n2)CCOC3)c1=O] | 10-[5-fluoro-2-(hydroxymethyl)-3-(1-methyl-6-oxo-5-{4H,6H,7H-pyrazolo[3,2-c][1,4]oxazin-2-ylamino}-1,6-dihydropyridin-3-yl)phenyl]-4,4-dimethyl-7-thia-10-azatricyclo[6.4.0.0$^{2,6}$]dodeca-1(8),2(6)-dien-9-one | 590.2 | |

TABLE 2-continued

| No. | Structure | Name | MH+ m/z | Btk IC$_{50}$ (μMol) |
|---|---|---|---|---|
| 193 | 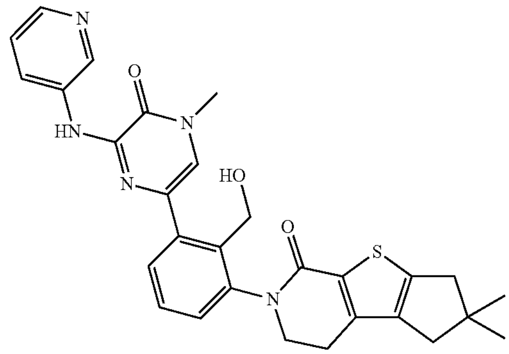 [SMILES: Cn1cc(-c2cccc(N3CCc4c(sc5c4CC(C)(C)C5)C3=O)c2CO)nc(Nc2cccnc2)c1=O] | 10-[2-(hydroxymethyl)-3-[4-methyl-5-oxo-6-(pyridine-3-ylamino)-4,5-dihydropyrazin-2-yl]phenyl]-4,4-dimethyl-7-thia-10-azatricyclo[6.4.0.0$^{2,6}$]dodeca-1(8),2(6)-dien-9-one | 528.2 | |
| 194 | 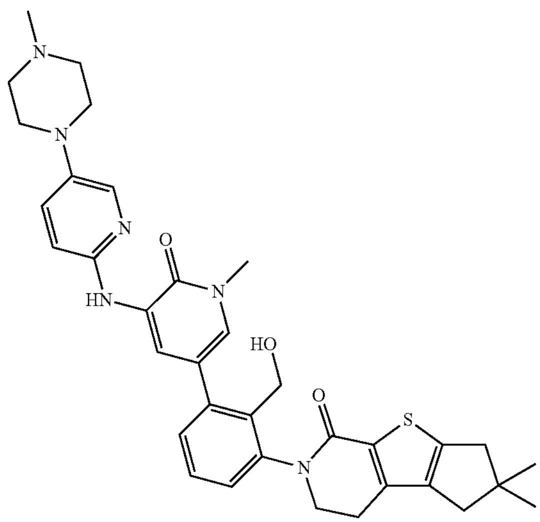 [SMILES: CN1CCN(c2ccc(Nc3cc(-c4cccc(N5CCc6c(sc7c6CC(C)(C)C7)C5=O)c4CO)cn(C)c3=O)nc2)CC1] | 10-[2-(hydroxymethyl)-3-(1-methyl-5-{[5-(4-methylpiperazin-1-yl)pyridine-2-yl]amino}-6-oxo-1,6-dihydropyridin-3-yl)phenyl]-4,4-dimethyl-7-thia-10-azatricyclo[6.4.0.0$^{2,6}$]dodeca-1(8),2(6)-dien-9-one | 625.3 | |
| 195 | 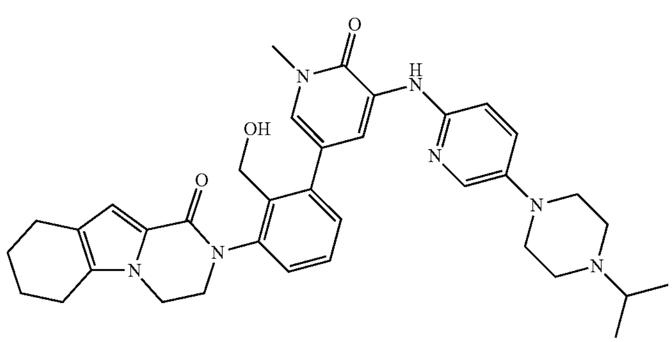 [SMILES: CC(C)N1CCN(c2ccc(Nc3cc(-c4cccc(N5CCn6c(cc7c6CCCC7)C5=O)c4CO)cn(C)c3=O)nc2)CC1] | 5-[2-(hydroxymethyl)-3-{1-oxo-1H,2H,3H,4H,6H,7H,8H,9H-pyrazino[1,2-a]indol-2-yl}phenyl]-1-methyl-3-({5-[4-(propan-2-yl)piperazin-1-yl]pyridine-2-yl}amino)-1,2-dihydropyridin-2-one | 622 | |

TABLE 2-continued

| No. | Structure | Name | MH+ m/z | Btk IC$_{50}$ (μMol) |
|---|---|---|---|---|
| 196 | 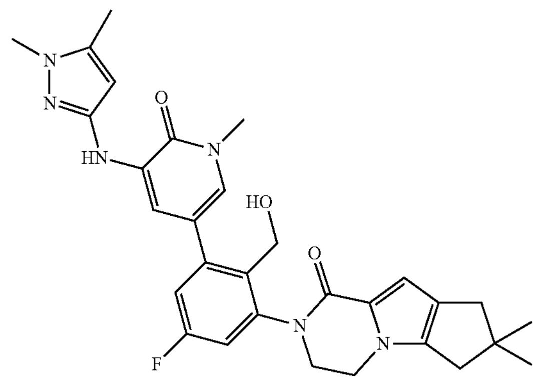 | 10-(3-{5-[(1,5-dimethyl-1H-pyrazol-3-yl)amino]-1-methyl-6-oxo-1,6-dihydropyridin-3-yl}-5-fluoro-2-(hydroxymethyl)phenyl)-4,4-dimethyl-1,10-diazatricyclo[6.4.0.0$^{2,6}$]dodeca-2(6),7-dien-9-one | 545.4 | |
| 197 | 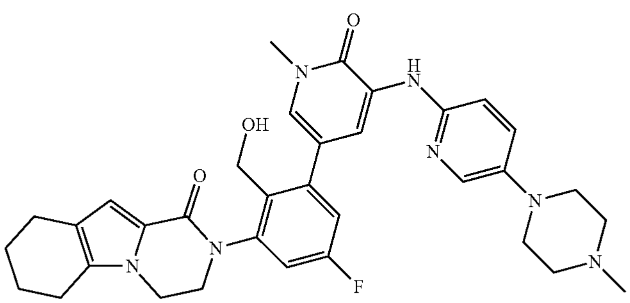 [SMILES: CN1CCN(c2ccc(Nc3cc(-c4cc(F)cc(N5CCn6c(cc7c6CCCC7)C5=O)c4CO)cn(C)c3=O)nc2)CC1] | 2-(5-fluoro-2-(hydroxymethyl)-3-(1-methyl-5-(4-methylpiperazin-1-yl)pyridine-2-ylamino)-6-oxo-1,6-dihydropyridin-3-yl)phenyl)-3,4,6,7,8,9-hexahydropyrazino[1,2-a]indol-1(2H)-one | 612.5 | 0.002 |
| 198 | 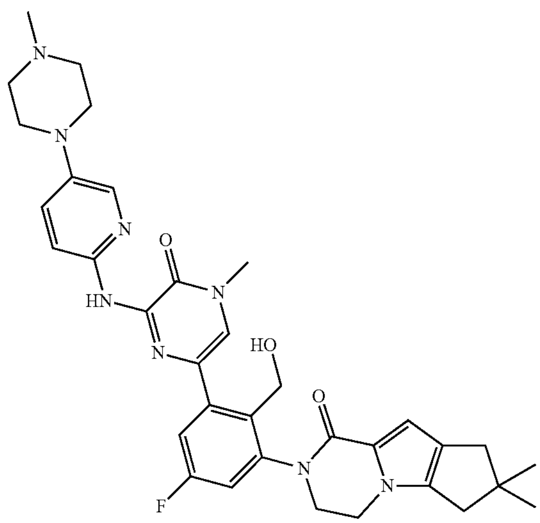 [SMILES: CN1CCN(c2ccc(Nc3nc(-c4cc(F)cc(N5CCn6c(cc7c6CC(C)(C)C7)C5=O)c4CO)cn(C)c3=O)nc2)CC1] | 10-[5-fluoro-2-(hydroxymethyl)-3-(1-methyl-5-{[5-(4-methylpiperazin-1-yl)pyridine-2-yl]amino}-6-oxo-1,6-dihydropyridin-3-yl)phenyl]-4,4-dimethyl-1,10-diazatricyclo[6.4.0.0$^{2,6}$]dodeca-2(6),7-dien-9-one | 626 | |
| 199 | 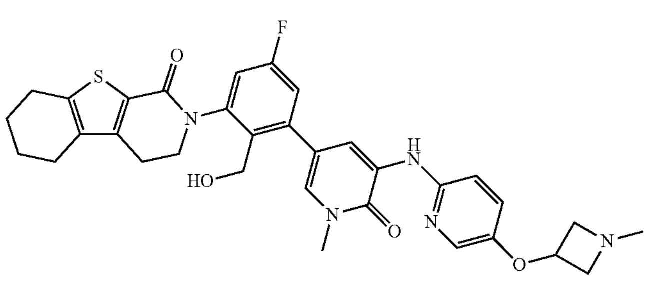 [SMILES: CN1CC(Oc2ccc(Nc3cc(-c4cc(F)cc(N5CCc6c(sc7c6CCCC7)C5=O)c4CO)cn(C)c3=O)nc2)C1] | 5-[5-fluoro-2-(hydroxymethyl)-3-[1-methyl-5-({5-[(1-methylazetidin-3-yl)oxy]pyridine-2-yl}amino)-6-oxo-1,6-dihydropyridin-3-yl]phenyl]-8-thia-5-azatricyclo[7.4.0.0$^{2,7}$]trideca-1(9),2(7)-dien-6-one | 616 | |

TABLE 2-continued

| No. | Structure | Name | MH+ m/z | Btk IC$_{50}$ (μMol) |
|---|---|---|---|---|
| 200 | 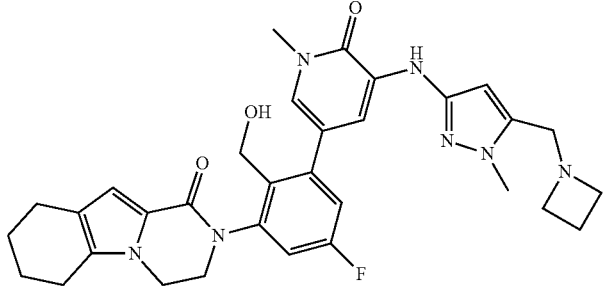 [SMILES: Cn1nc(Nc2cc(-c3cc(F)cc(N4CCn5c(cc6c5CCCC6)C4=O)c3CO)cn(C)c2=O)cc1CN1CCC1] | 3-{[5-(azetidin-1-ylmethyl)-1-methyl-1H-pyrazol-3-yl]amino}-5-[5-fluoro-2-(hydroxymethyl)-3-{1-oxo-1H,2H,3H,4H,6H,7H,8H,9H-pyrazino[1,2-a]indol-2-yl}phenyl]-1-methyl-1,2-dihydropyridin-2-one | 586.5 | |
| 201 | 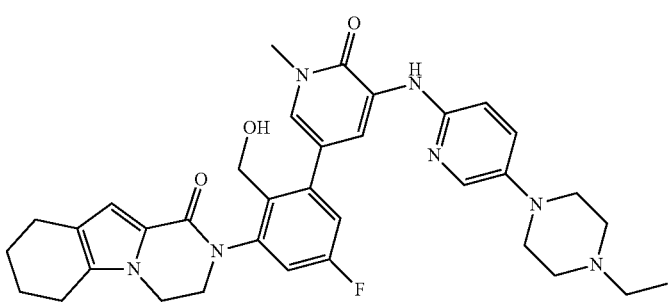 [SMILES: CCN1CCN(c2ccc(Nc3cc(-c4cc(F)cc(N5CCn6c(cc7c6CCCC7)C5=O)c4CO)cn(C)c3=O)nc2)CC1] | 3-{[5-(4-ethylpiperazin-1-yl)pyridine-2-yl]amino}-5-[5-fluoro-2-(hydroxymethyl)-3-{1-oxo-1H,2H,3H,4H,6H,7H,8H,9H-pyrazino[1,2-a]indol-2-yl}phenyl]-1-methyl-1,2-dihydropyridin-2-one | 626.4 | |
| 202 | 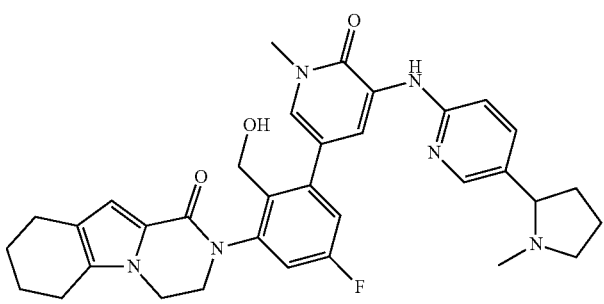 [SMILES: CN1CCCC1c1ccc(Nc2cc(-c3cc(F)cc(N4CCn5c(cc6c5CCCC6)C4=O)c3CO)cn(C)c2=O)nc1] | 5-[5-fluoro-2-(hydroxymethyl)-3-{1-oxo-1H,2H,3H,4H,6H,7H,8H,9H-pyrazino[1,2-a]indol-2-yl}phenyl]-1-methyl-3-{[5-(1-methylpyrrolidin-2-yl)pyridine-2-yl]amino}-1,2-dihydropyridin-2-one | 597.4 | |
| 203 | 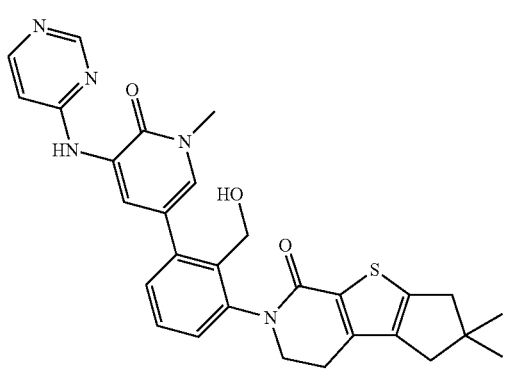 | 10-[2-(hydroxymethyl)-3-[1-methyl-6-oxo-5-(pyrimidin-4-ylamino)-1,6-dihydropyridin-3-yl]phenyl]-4,4-dimethyl-7-thia-10-azatricyclo[6.4.0.0$^{2,6}$]dodeca-1(8),2(6),11-trien-9-one | 526.2 | |

TABLE 2-continued

| No. | Structure | Name | MH+ m/z | Btk IC$_{50}$ (μMol) |
|---|---|---|---|---|
| 204 | 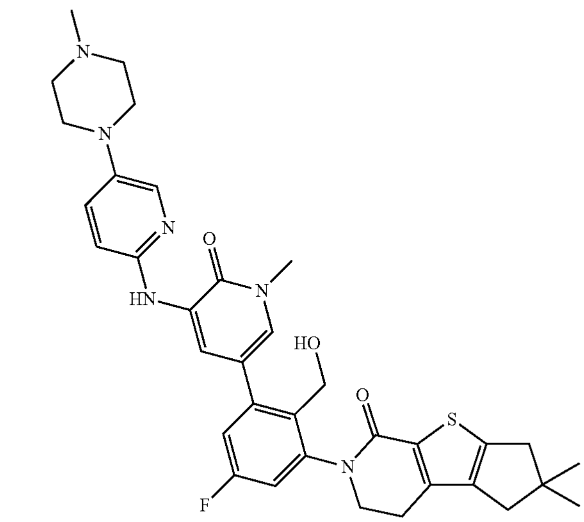 [SMILES: CN1CCN(c2ccc(Nc3cc(-c4cc(F)cc(N5CCc6c(sc7c6CC(C)(C)C7)C5=O)c4CO)cn(C)c3=O)nc2)CC1] | 10-[5-fluoro-2-(hydroxymethyl)-3-(1-methyl-5-{[5-(4-methylpiperazin-1-yl)pyridine-2-yl]amino}-6-oxo-1,6-dihydropyridin-3-yl)phenyl]-4,4-dimethyl-7-thia-10-azatricyclo[6.4.0.0$^{2,6}$]dodeca-1(8),2(6)-dien-9-one | 643.3 | |
| 205 | 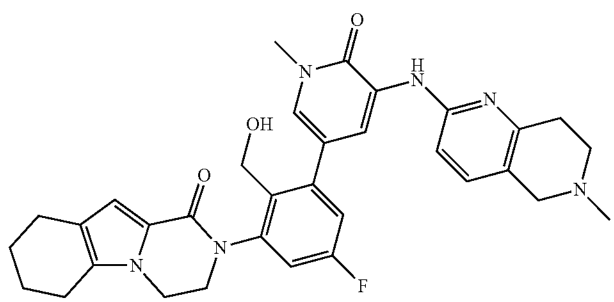 [SMILES: CN1CCc2nc(Nc3cc(-c4cc(F)cc(N5CCn6c(cc7c6CCCC7)C5=O)c4CO)cn(C)c3=O)ccc2C1] | 5-[5-fluoro-2-(hydroxymethyl)-3-{1-oxo-1H,2H,3H,4H,6H,7H,8H,9H-pyrazino[1,2-a]indol-2-yl}phenyl]-1-methyl-3-[(6-methyl-5,6,7,8-tetrahydro-1,6-naphthyridin-2-yl)amino]-1,2-dihydropyridin-2-one | 583 | |
| 206 | 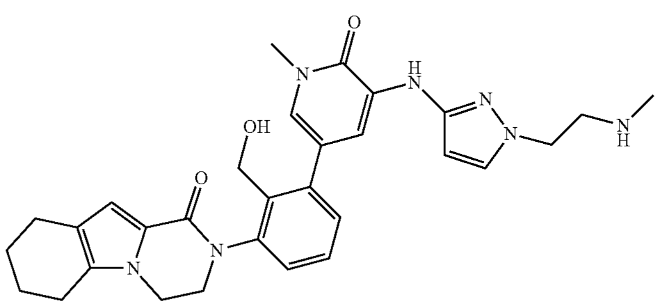 [SMILES: CNCCn1ccc(Nc2cc(-c3cccc(N4CCn5c(cc6c5CCCC6)C4=O)c3CO)cn(C)c2=O)n1] | 5-[2-(hydroxymethyl)-3-{1-oxo-1H,2H,3H,4H,6H,7H,8H,9H-pyrazino[1,2-a]indol-2-yl}phenyl]-1-methyl-3-({1-[2-(methylamino)ethyl]-1H-pyrazol-3-yl}amino)-1,2-dihydropyridin-2-one | 542 | |
| 207 | 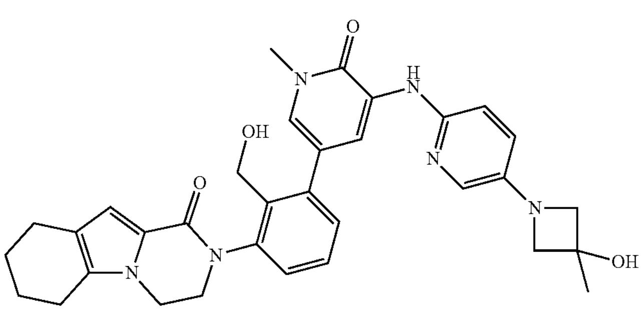 [SMILES: Cn1cc(-c2cccc(N3CCn4c(cc5c4CCCC5)C3=O)c2CO)cc(Nc2ccc(N3CC(C)(O)C3)cn2)c1=O] | 3-{[5-(3-hydroxy-3-methylazetidin-1-yl)pyridine-2-yl]amino}-5-[2-(hydroxymethyl)-3-{1-oxo-1H,2H,3H,4H,6H,7H,8H,9H-pyrazino[1,2-a]indol-2-yl}phenyl]-1-methyl-1,2-dihydropyridin-2-one | 581 | |

TABLE 2-continued

| No. | Structure | Name | MH+ m/z | Btk IC$_{50}$ (μMol) |
|---|---|---|---|---|
| 208 | 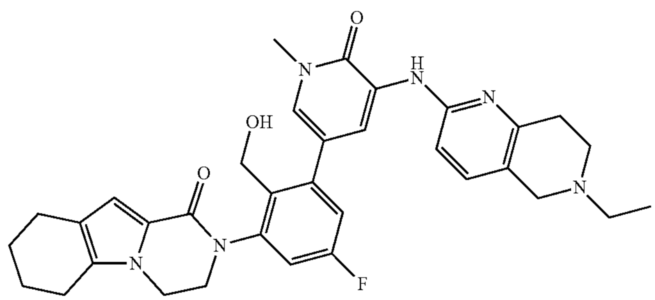 [SMILES: CCN1CCc2nc(Nc3cc(-c4cc(F)cc(N5CCn6c(cc7c6CCCC7)C5=O)c4CO)cn(C)c3=O)ccc2C1] | 3-[(6-ethyl-5,6,7,8-tetrahydro-1,6-naphthyridin-2-yl)amino]-5-[5-fluoro-2-(hydroxymethyl)-3-{1-oxo-1H,2H,3H,4H,6H,7H,8H,9H-pyrazino[1,2-a]indol-2-yl}phenyl]-1-methyl-1,2-dihydropyridin-2-one | 597 | |
| 209 | 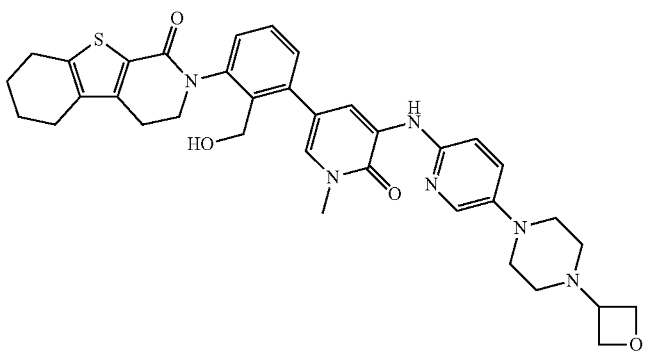 [SMILES: Cn1cc(-c2cccc(N3CCc4c(sc5c4CCCC5)C3=O)c2CO)cc(Nc2ccc(N3CCN(C4COC4)CC3)cn2)c1=O] | 5-[2-(hydroxymethyl)-3-[1-methyl-5-({5-[4-(oxetan-3-yl)piperazin-1-yl]pyridine-2-yl}amino)-6-oxo-1,6-dihydropyridin-3-yl]phenyl]-8-thia-5-azatricyclo[7.4.0.0$^{2,7}$]trideca-1(9),2(7)-dien-6-one | 653 | |
| 210 | 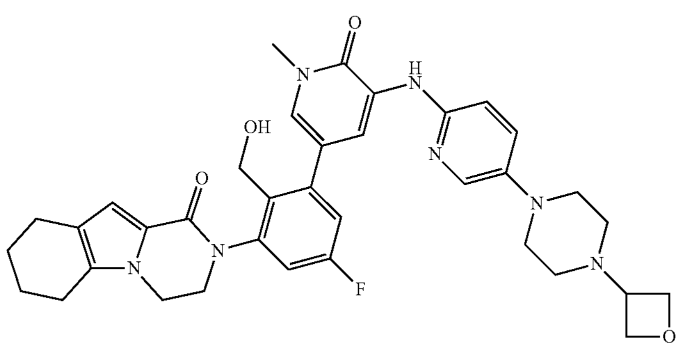 [SMILES: Cn1cc(-c2cc(F)cc(N3CCn4c(cc5c4CCCC5)C3=O)c2CO)cc(Nc2ccc(N3CCN(C4COC4)CC3)cn2)c1=O] | 2-(5-fluoro-2-(hydroxymethyl)-3-(1-methyl-5-(5-(4-(oxetan-3-yl)piperazin-1-yl)pyridine-2-ylamino)-6-oxo-1,6-dihydropyridin-3-yl)phenyl)-3,4,6,7,8,9-hexahydropyrazino[1,2-a]indol-1(2H)-one | 654 | 0.0039 |
| 211 | 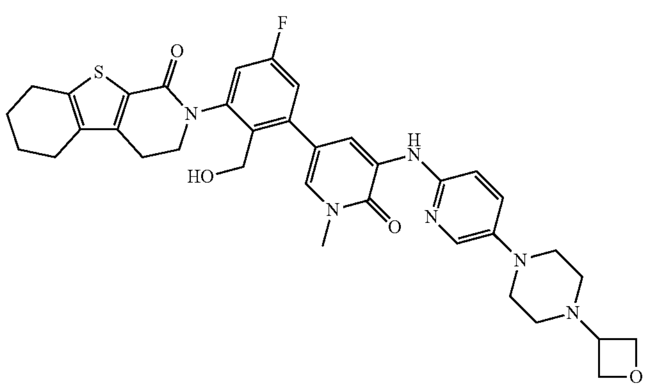 [SMILES: Cn1cc(-c2cc(F)cc(N3CCc4c(sc5c4CCCC5)C3=O)c2CO)cc(Nc2ccc(N3CCN(C4COC4)CC3)cn2)c1=O] | 5-[5-fluoro-2-(hydroxymethyl)-3-[1-methyl-5-({5-[4-(oxetan-3-yl)piperazin-1-yl]pyridine-2-yl}amino)-6-oxo-1,6-dihydropyridin-3-yl]phenyl]-8-thia-5-azatricyclo[7.4.0.0$^{2,7}$]trideca-1(9),2(7)-dien-6-one | 671 | |

TABLE 2-continued

| No. | Structure | Name | MH+ m/z | Btk IC$_{50}$ (µMol) |
|---|---|---|---|---|
| 212 | 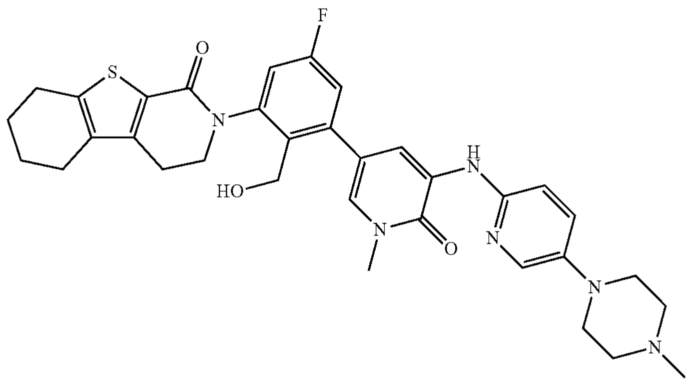 [SMILES: CN1CCN(c2ccc(Nc3cc(-c4cc(F)cc(N5CCc6c(sc7c6CCCC7)C5=O)c4CO)cn(C)c3=O)nc2)CC1] | 2-(5-Fluoro-2-hydroxymethyl-3-{1-methyl-5-[5-(4-methyl-piperazin-1-yl)-pyridin-2-ylamino]-6-oxo-1,6-dihydro-pyridin-3-yl}-phenyl)-3,4,5,6,7,8-hexahydro-2H-benzo[4,5]thieno[2,3-c]pyridine-1-one | 629 | 0.0010 |
| 213 | 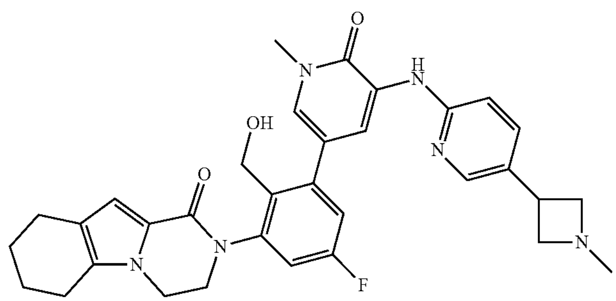 [SMILES: CN1CC(c2ccc(Nc3cc(-c4cc(F)cc(N5CCn6c(cc7c6CCCC7)C5=O)c4CO)cn(C)c3=O)nc2)C1] | 5-[5-fluoro-2-(hydroxymethyl)-3-{1-oxo-1H,2H,3H,4H,6H,7H,8H,9H-pyrazino[1,2-a]indol-2-yl}phenyl]-1-methyl-3-{[5-(1-methylazetidin-3-yl)pyridine-2-yl]amino)-1,2-dihydropyridin-2-one | 583 | |
| 214 | 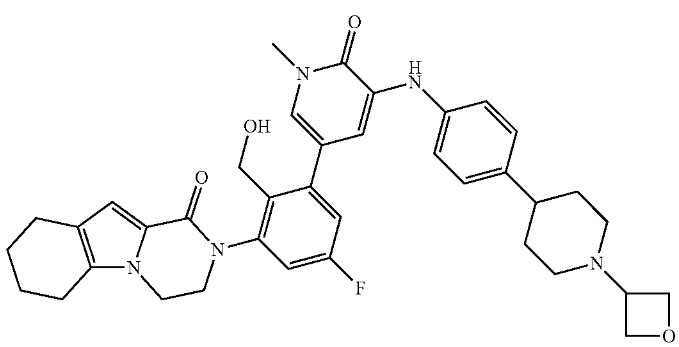 | 5-[5-fluoro-2-(hydroxymethyl)-3-{1-oxo-1H,2H,3H,4H,6H,7H,8H,9H-pyrazino[1,2-a]indol-2-yl}phenyl]-1-methyl-3-({4-[1-(oxetan-3-yl)piperidin-4-yl]phenyl}amino)-1,2-dihydropyrazin-2-one | 653.6 | |
| 215 | 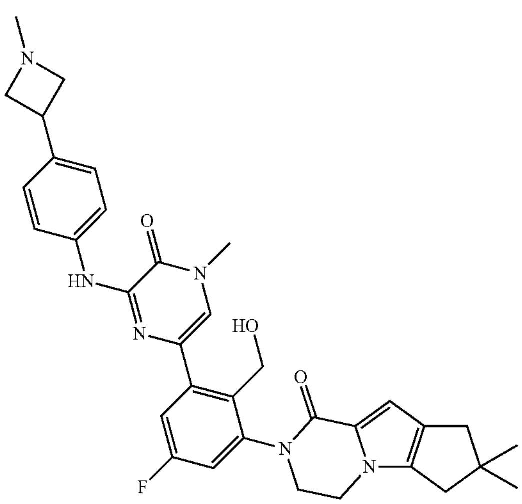 [SMILES: CN1CC(c2ccc(Nc3nc(-c4cc(F)cc(N5CCn6c(cc7c6CC(C)(C)C7)C5=O)c4CO)cn(C)c3=O)cc2)C1] | 10-[5-fluoro-2-(hydroxymethyl)-3-(4-methyl-6-{[4-(1-methylazetidin-3-yl)phenyl]amino}-5-oxo-4,5-dihydropyrazin-2-yl)phenyl]-4,4-dimethyl-1,10-diazatricyclo[6.4.0.0$^{2,6}$]dodeca-2(6),7-dien-9-one | 597.5 | |

TABLE 2-continued

| No. | Structure | Name | MH+ m/z | Btk IC$_{50}$ (μMol) |
|---|---|---|---|---|
| 216 | 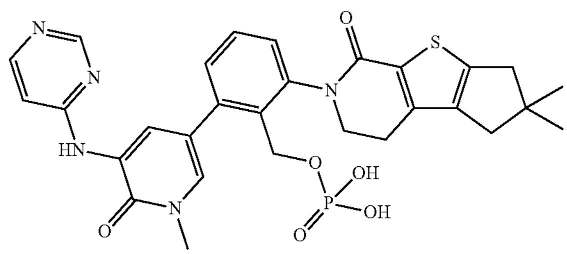 [SMILES: Cn1cc(-c2cccc(N3CCc4c(sc5c4CC(C)(C)C5)C3=O)c2COP(=O)(O)O)cc(Nc2ccncn2)c1=O] | [(2-{4,4-dimethyl-9-oxo-7-thia-10-azatricyclo[6.4.0.0$^{2,6}$]dodeca-1(8),2(6)-dien-10-yl}-6-[1-methyl-6-oxo-5-(pyrimidin-4-ylamino)-1,6-dihydropyridin-3-yl]phenyl)methoxy]phosphonic acid | 608.2 | |
| 217 | 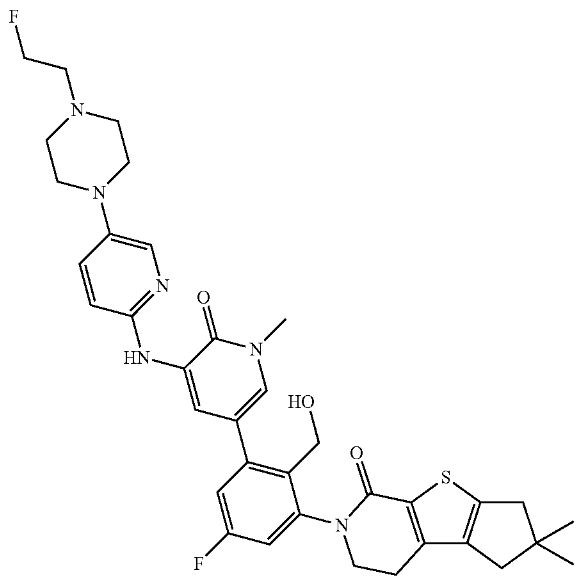 [SMILES: Cn1cc(-c2cc(F)cc(N3CCc4c(sc5c4CC(C)(C)C5)C3=O)c2CO)cc(Nc2ccc(N3CCN(CCF)CC3)cn2)c1=O] | 10-{5-fluoro-3-[5-({5-[4-(2-fluoroethyl)piperazin-1-yl]pyridine-2-yl}amino)-1-methyl-6-oxo-1,6-dihydropyridin-3-yl]-2-(hydroxymethyl)phenyl}-4,4-dimethyl-7-thia-10-azatricyclo[6.4.0.0$^{2,6}$]dodeca-1(8),2(6)-dien-9-one | 675.3 | |
| 218 | 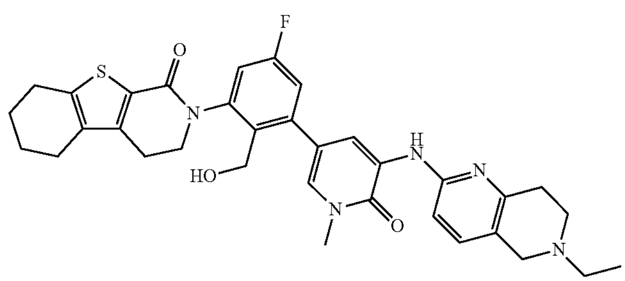 [SMILES: CCN1CCc2nc(Nc3cc(-c4cc(F)cc(N5CCc6c(sc7c6CCCC7)C5=O)c4CO)cn(C)c3=O)ccc2C1] | 5-(3-{5-[(6-ethyl-5,6,7,8-tetrahydro-1,6-naphthyridin-2-yl)amino]-1-methyl-6-oxo-1,6-dihydropyridin-3-yl}-5-fluoro-2-(hydroxymethyl)phenyl)-8-thia-5-azatricyclo[7.4.0.0$^{2,7}$]trideca-1(9),2(7)-dien-6-one | 614 | |
| 219 | 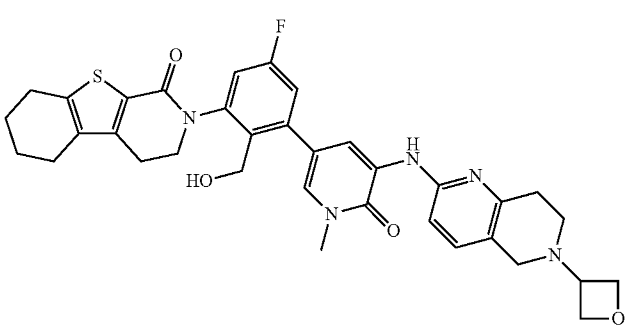 [SMILES: Cn1cc(-c2cc(F)cc(N3CCc4c(sc5c4CCCC5)C3=O)c2CO)cc(Nc2ccc3c(n2)CCN(C2COC2)C3)c1=O] | 5-[5-fluoro-2-(hydroxymethyl)-3-(1-methyl-5-{[6-(oxetan-3-yl)-5,6,7,8-tetrahydro-1,6-naphthyridin-2-yl]amino}-6-oxo-1,6-dihydropyridin-3-yl)phenyl]-8-thia-5-azatricyclo[7.4.0.0$^{2,7}$]trideca-1(9),2(7)-dien-6-one | 642 | |

TABLE 2-continued

| No. | Structure | Name | MH+ m/z | Btk IC$_{50}$ (μMol) |
|---|---|---|---|---|
| 220 | 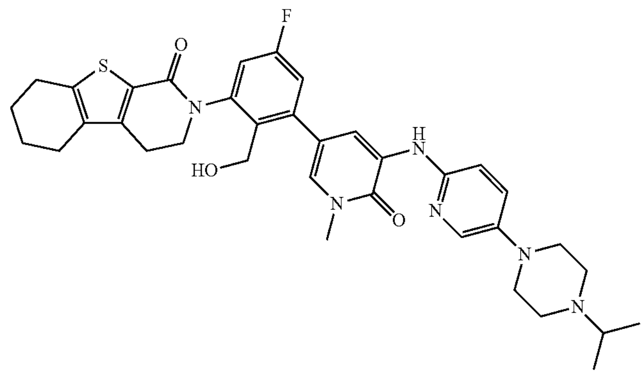 [SMILES: CC(C)N1CCN(c2ccc(Nc3cc(-c4cc(F)cc(N5CCc6c(sc7c6CCCC7)C5=O)c4CO)cn(C)c3=O)nc2)CC1] | 5-[5-fluoro-2-(hydroxymethyl)-3-[1-methyl-6-oxo-5-({5-[4-(propan-2-yl)piperazin-1-yl]pyridine-2-yl}amino)-1,6-dihydropyridin-3-yl]phenyl]-8-thia-5-azatricyclo[7.4.0.0$^{2,7}$]trideca-1(9),2(7)-dien-6-one | 657 | |
| 221 | 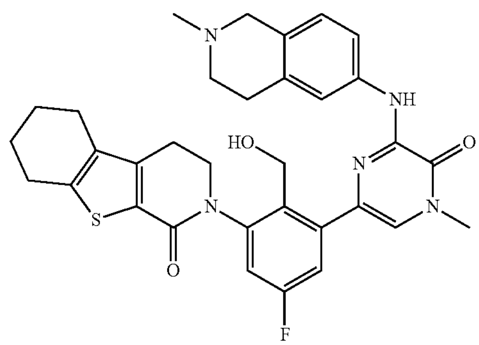 [SMILES: CN1CCc2cc(Nc3nc(-c4cc(F)cc(N5CCc6c(sc7c6CCCC7)C5=O)c4CO)cn(C)c3=O)ccc2C1] | 5-[5-Fluoro-2-(hydroxymethyl)-3-{4-methyl-6-[(2-methyl-1,2,3,4-tetrahydroisoquinolin-6-yl)amino]-5-oxo-4,5-dihydropyrazin-2-yl}phenyl]-8-thia-5-azatricyclo[7.4.0.0$^{2,7}$]trideca-1(9),2(7)-dien-6-one | 600 | |
| 222 | 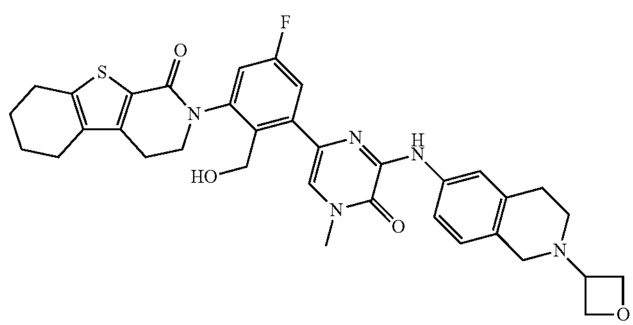 [SMILES: Cn1cc(-c2cc(F)cc(N3CCc4c(sc5c4CCCC5)C3=O)c2CO)nc(Nc2ccc3c(c2)CCN(C2COC2)C3)c1=O] | 5-[5-fluoro-2-(hydroxymethyl)-3-(4-methyl-6-{[2-(oxetan-3-yl)-1,2,3,4-tetrahydroisoquinolin-6-yl]amino}-5-oxo-4,5-dihydropyrazin-2-yl)phenyl]-8-thia-5-azatricyclo[7.4.0.0$^{2,7}$]trideca-1(9),2(7)-dien-6-one | 642 | |
| 223 | 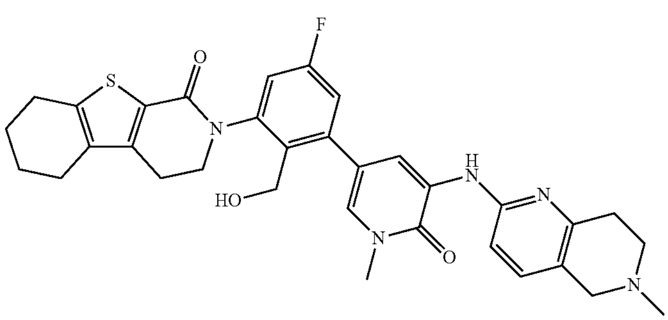 [SMILES: CN1CCc2nc(Nc3cc(-c4cc(F)cc(N5CCc6c(sc7c6CCCC7)C5=O)c4CO)cn(C)c3=O)ccc2C1] | 5-[5-fluoro-2-(hydroxymethyl)-3-{1-methyl-5-[(6-methyl-5,6,7,8-tetrahydro-1,6-naphthyridin-2-yl)amino]-6-oxo-1,6-dihydropyridin-3-yl}phenyl]-8-thia-5-azatricyclo[7.4.0.0$^{2,7}$]trideca-1(9),2(7)-dien-6-one | 600 | |

TABLE 2-continued

| No. | Structure | Name | MH+ m/z | Btk IC$_{50}$ (μMol) |
|---|---|---|---|---|
| 224 | 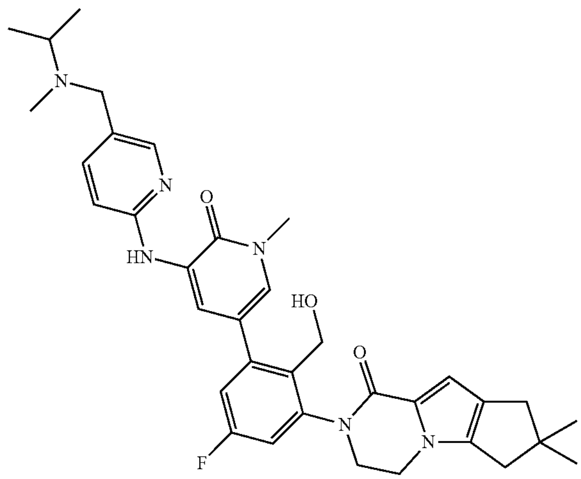 [SMILES: CC(C)N(C)Cc1ccc(Nc2cc(-c3cc(F)cc(N4CCn5c(cc6c5CC(C)(C)C6)C4=O)c3CO)cn(C)c2=O)nc1] | 10-[5-fluoro-2-(hydroxymethyl)-3-{1-methyl-5-[(5-{[methyl(propan-2-yl)amino]methyl}pyridine-2-yl)amino]-6-oxo-1,6-dihydropyridin-3-yl}phenyl]-4,4-dimethyl-1,10-diazatricyclo[6.4.0.0$^{2,6}$]dodeca-2(6),7-dien-9-one | 613.6 | |
| 225 | 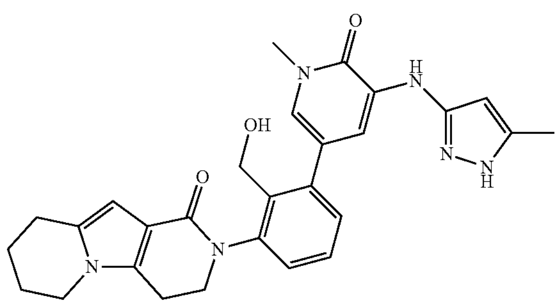 [SMILES: Cc1cc(Nc2cc(-c3cccc(N4CCc5c(cc6n5CCCC6)C4=O)c3CO)cn(C)c2=O)n[nH]1] | 5-[2-(hydroxymethyl)-3-{1-oxo-1H,2H,3H,4H,6H,7H,8H,9H-pyrido[3,4-b]indolizin-2-yl}phenyl]-1-methyl-3-[(5-methyl-1H-pyrazol-3-yl)amino]-1,2-dihydropyridin-2-one | 499.2 | |
| 226 | 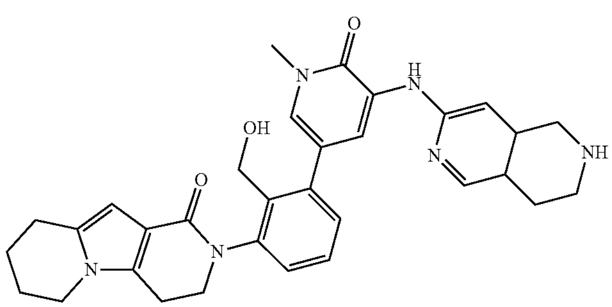 [SMILES: Cn1cc(-c2cccc(N3CCc4c(cc5n4CCCC5)C3=O)c2CO)cc(NC2=CC3CNCCC3C=N2)c1=O] | 5-[2-(hydroxymethyl)-3-{1-oxo-1H,2H,3H,4H,6H,7H,8H,9H-pyrido[3,4-b]indolizin-2-yl}phenyl]-1-methyl-3-(5,6,7,8-tetrahydro-2,6-naphthyridin-3-ylamino)-1,2-dihydropyridin-2-one | 551.2 | |
| 227 | 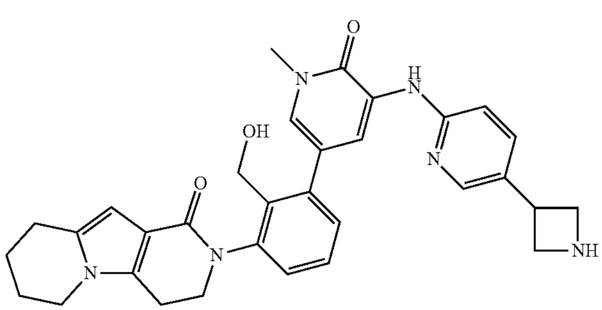 [SMILES: Cn1cc(-c2cccc(N3CCc4c(cc5n4CCCC5)C3=O)c2CO)cc(Nc2ccc(C3CNC3)cn2)c1=O] | 3-{[5-(azetidin-3-yl)pyridine-2-yl]amino}-5-[2-(hydroxymethyl)-3-{1-oxo-1H,2H,3H,4H,6H,7H,8H,9H-pyrido[3,4-b]indolizin-2-yl}phenyl]-1-methyl-1,2-dihydropyridin-2-one | 551.2 | |

TABLE 2-continued

| No. | Structure | Name | MH+ m/z | Btk IC$_{50}$ (μMol) |
|---|---|---|---|---|
| 228 | 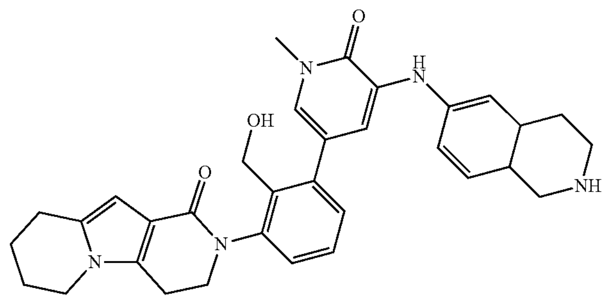 [SMILES: Cn1cc(-c2cccc(N3CCc4c(cc5n4CCCC5)C3=O)c2CO)cc(NC2=CC3CCNCC3C=C2)c1=O] | 5-[2-(hydroxymethyl)-3-{1-oxo-1H,2H,3H,4H,6H,7H,8H,9H-pyrido[3,4-b]indolizin-2-yl}phenyl]-1-methyl-3-(1,2,3,4-tetrahydroisoquinolin-6-ylamino)-1,2-dihydropyrazin-2-one | 551.2 | |
| 229 | 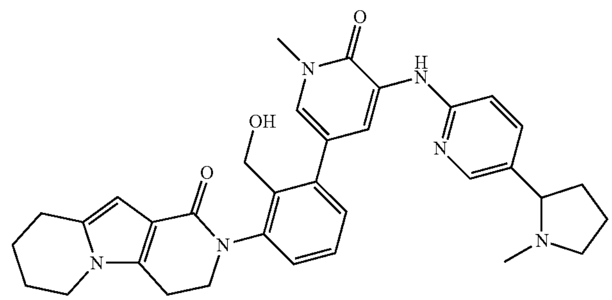 [SMILES: CN1CCCC1c1ccc(Nc2cc(-c3cccc(N4CCc5c(cc6n5CCCC6)C4=O)c3CO)cn(C)c2=O)nc1] | 5-[2-(hydroxymethyl)-3-{1-oxo-1H,2H,3H,4H,6H,7H,8H,9H-pyrido[3,4-b]indolizin-2-yl}phenyl]-1-methyl-3-{[5-(1-methylpyrrolidin-2-yl)pyridine-2-yl]amino}-1,2-dihydropyridin-2-one | 579.2 | |
| 230 | 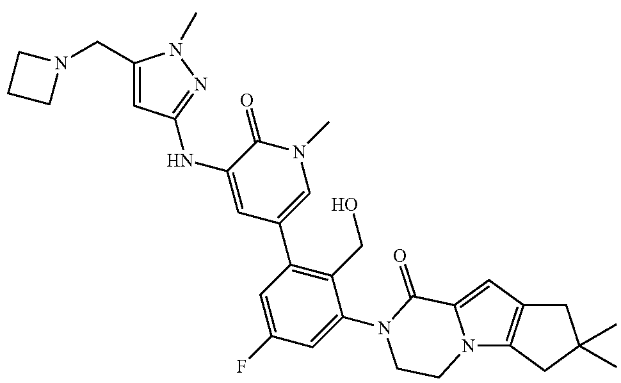 [SMILES: Cn1nc(Nc2cc(-c3cc(F)cc(N4CCn5c(cc6c5CC(C)(C)C6)C4=O)c3CO)cn(C)c2=O)cc1CN1CCC1] | 10-[3-(5-{[5-(azetidin-1-ylmethyl)-1-methyl-1H-pyrazol-3-yl]amino}-1-methyl-6-oxo-1,6-dihydropyridin-3-yl)-5-fluoro-2-(hydroxymethyl)phenyl]-4,4-dimethyl-1,10-diazatricyclo[6.4.0.0$^{2,6}$]dodeca-2(6),7-dien-9-one | 600.6 | |
| 231 | 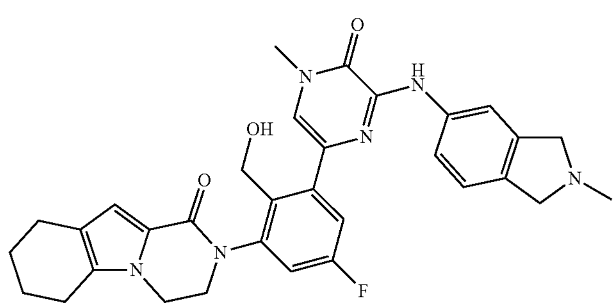 [SMILES: CN1Cc2ccc(Nc3nc(-c4cc(F)cc(N5CCn6c(cc7c6CCCC7)C5=O)c4CO)cn(C)c3=O)cc2C1] | 5-[5-fluoro-2-(hydroxymethyl)-3-{1-oxo-1H,2H,3H,4H,6H,7H,8H,9H-pyrazino[1,2-a]indol-2-yl}phenyl]-1-methyl-3-[(2-methyl-2,3-dihydro-1H-isoindol-5-yl)amino]-1,2-dihydropyrazin-2-one | 569 | |
| 232 | 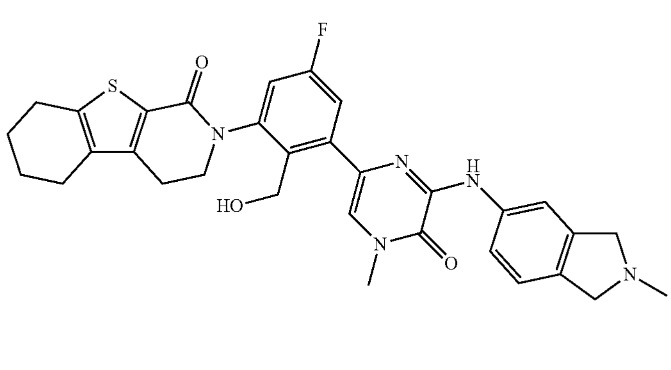 [SMILES: CN1Cc2ccc(Nc3nc(-c4cc(F)cc(N5CCc6c(sc7c6CCCC7)C5=O)c4CO)cn(C)c3=O)cc2C1] | 5-[5-fluoro-2-(hydroxymethyl)-3-{4-methyl-6-[(2-methyl-2,3-dihydro-1H-isoindol-5-yl)amino]-5-oxo-4,5-dihydropyrazin-2-yl}phenyl]-8-thia-5-azatricyclo[7.4.0.0$^{2,7}$]trideca-1(9),2(7)-dien-6-one | 586 | |

TABLE 2-continued

| No. | Structure | Name | MH+ m/z | Btk IC$_{50}$ (μMol) |
|---|---|---|---|---|
| 233 | 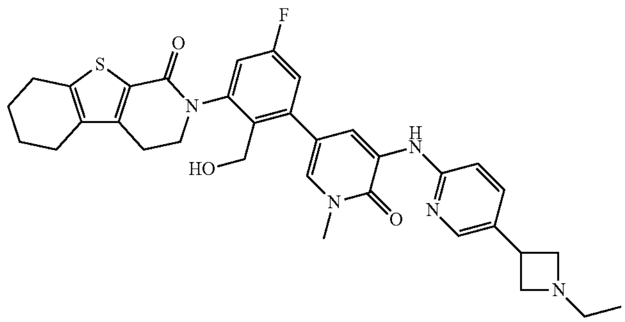 [SMILES: CCN1CC(c2ccc(Nc3cc(-c4cc(F)cc(N5CCc6c(sc7c6CCCC7)C5=O)c4CO)cn(C)c3=O)nc2)C1] | 5-[3-(5-{[5-(1-ethylazetidin-3-yl)pyridine-2-yl]amino}-1-methyl-6-oxo-1,6-dihydropyridin-3-yl)-5-fluoro-2-(hydroxymethyl)phenyl]-8-thia-5-azatricyclo[7.4.0.0$^{2,7}$]trideca-1(9),2(7)-dien-6-one | 614 | |
| 234 | 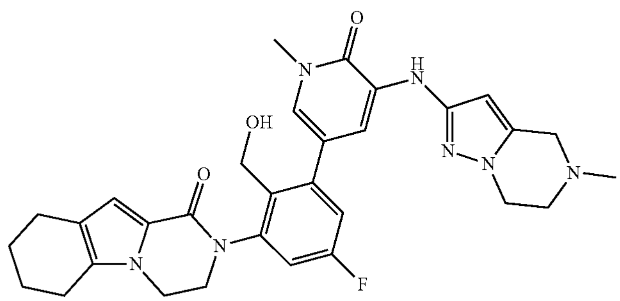 [SMILES: CN1CCn2nc(Nc3cc(-c4cc(F)cc(N5CCn6c(cc7c6CCCC7)C5=O)c4CO)cn(C)c3=O)cc2C1] | 5-[5-fluoro-2-(hydroxymethyl)-3-{1-oxo-1H,2H,3H,4H,6H,7H,8H,9H-pyrazino[1,2-a]indol-2-yl}phenyl]-1-methyl-3-({5-methyl-4H,5H,6H,7H-pyrazolo[1,5-a]pyrazin-2-yl}amino)-1,2-dihydropyridin-2-one | 572 | |
| 235 | 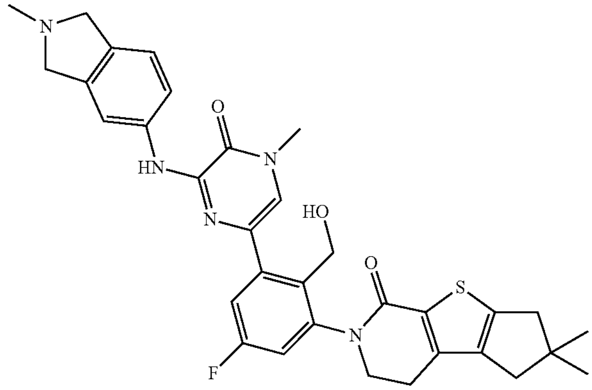 | 10-[5-fluoro-2-(hydroxymethyl)-3-{4-methyl-6-[(2-methyl-2,3-dihydro-1H-isoindol-5-yl)amino]-5-oxo-4,5-dihydropyrazin-2-yl}phenyl]-4,4-dimethyl-7-thia-10-azatricyclo[6.4.0.0$^{2,6}$]dodeca-1(8),2(6)-dien-9-one | 600.2 | |
| 236 | 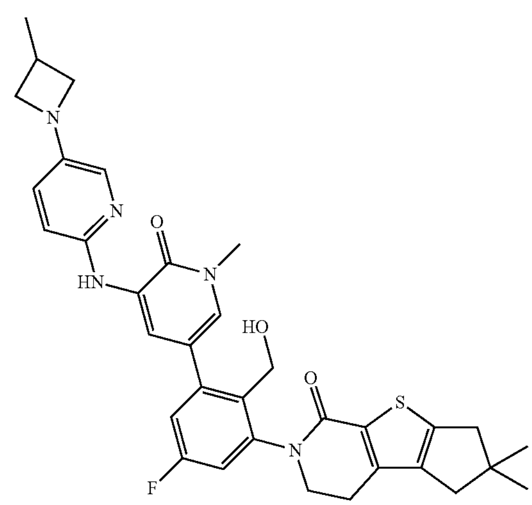 [SMILES: CC1CN(c2ccc(Nc3cc(-c4cc(F)cc(N5CCc6c(sc7c6CC(C)(C)C7)C5=O)c4CO)cn(C)c3=O)nc2)C1] | 10-[5-fluoro-2-(hydroxymethyl)-3-(1-methyl-5-{[5-(3-methylazetidin-1-yl)pyridine-2-yl]amino}-6-oxo-1,6-dihydropyridin-3-yl)phenyl]-4,4-dimethyl-7-thia-10-azatricyclo[6.4.0.0$^{2,6}$]dodeca-1(8),2(6)-dien-9-one | 614.3 | |

TABLE 2-continued
| No. | Structure | Name | MH+ m/z | Btk IC$_{50}$ (μMol) |
|---|---|---|---|---|
| 237 | 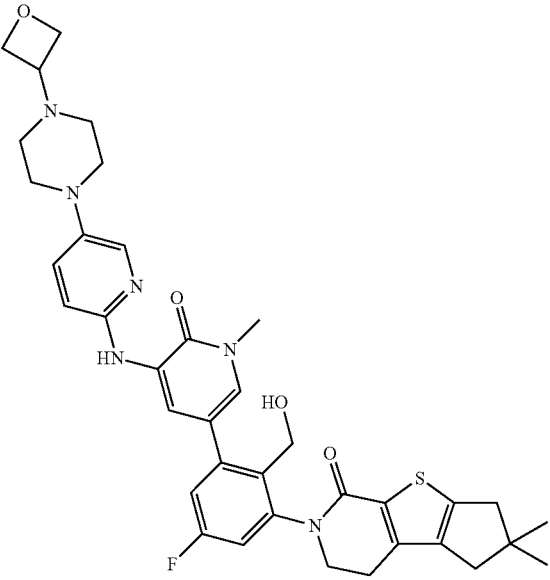 [SMILES: Cn1cc(-c2cc(F)cc(N3CCc4c(sc5c4CC(C)(C)C5)C3=O)c2CO)cc(Nc2ccc(N3CCN(C4COC4)CC3)cn2)c1=O] | 10-[5-fluoro-2-(hydroxymethyl)-3-[1-methyl-5-({5-[4-(oxetan-3-yl)piperazin-1-yl]pyridine-2-yl}amino)-6-oxo-1,6-dihydropyridin-3-yl]phenyl]-4,4-dimethyl-7-thia-10-azatricyclo[6.4.0.0$^{2,6}$]dodeca-1(8),2(6)-dien-9-one | 685.4 | |
| 238 | 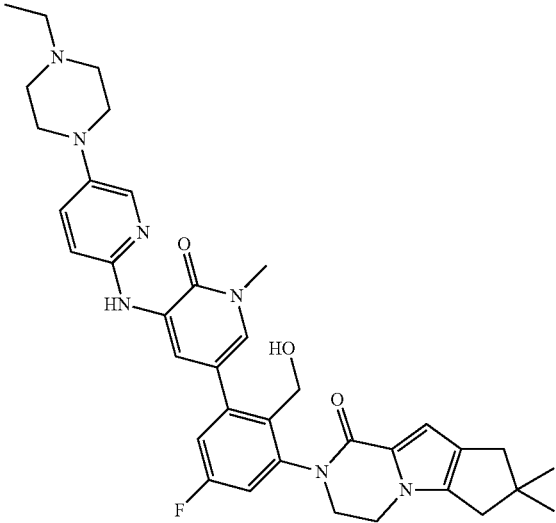 [SMILES: CCN1CCN(c2ccc(Nc3cc(-c4cc(F)cc(N5CCn6c(cc7c6CC(C)(C)C7)C5=O)c4CO)cn(C)c3=O)nc2)CC1] | 10-[3-(5-{[5-(4-ethylpiperazin-1-yl)pyridine-2-yl]amino}-1-methyl-6-oxo-1,6-dihydropyridin-3-yl)-5-fluoro-2-(hydroxymethyl)phenyl]-4,4-dimethyl-1,10-diazatricyclo[6.4.0.0$^{2,6}$]dodeca-2(6),7-dien-9-one | 640.6 | |

TABLE 2-continued

| No. | Structure | Name | MH+ m/z | Btk IC$_{50}$ (μMol) |
|---|---|---|---|---|
| 239 | 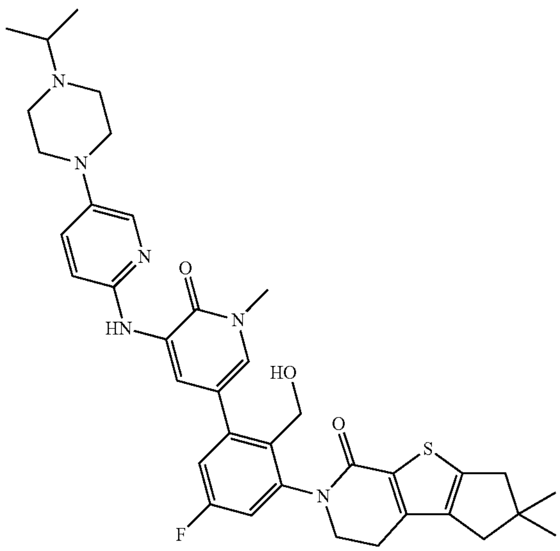 [SMILES: CC(C)N1CCN(c2ccc(Nc3cc(-c4cc(F)cc(N5CCc6c(sc7c6CC(C)(C)C7)C5=O)c4CO)cn(C)c3=O)nc2)CC1] | 10-[5-fluoro-2-(hydroxymethyl)-3-[1-methyl-6-oxo-5-({5-[4-(propan-2-yl)piperazin-1-yl]pyridine-2-yl}amino)-1,6-dihydropyridin-3-yl]phenyl]-4,4-dimethyl-7-thia-10-azatricyclo[6.4.0.0$^{2,6}$]dodeca-1(8),2(6)-dien-9-one | 671.3 | |
| 240 | 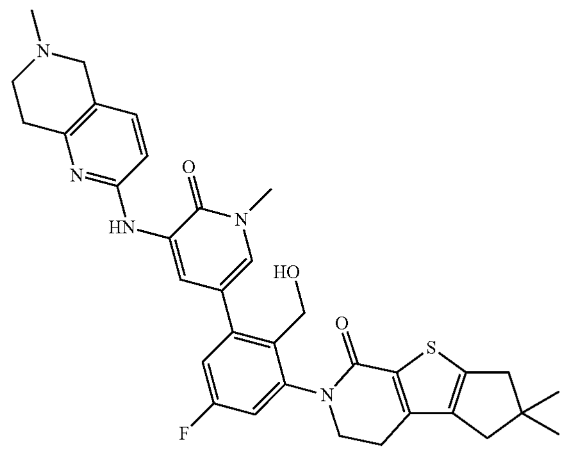 [SMILES: CN1CCc2nc(Nc3cc(-c4cc(F)cc(N5CCc6c(sc7c6CC(C)(C)C7)C5=O)c4CO)cn(C)c3=O)ccc2C1] | 10-[5-fluoro-2-(hydroxymethyl)-3-{1-methyl-5-[(6-methyl-5,6,7,8-tetrahydro-1,6-naphthyridin-2-yl)amino]-6-oxo-1,6-dihydropyridin-3-yl}phenyl]-4,4-dimethyl-7-thia-10-azatricyclo[6.4.0.0$^{2,6}$]dodeca-1(8),2(6)-dien-9-one | 614.3 | |
| 241 | 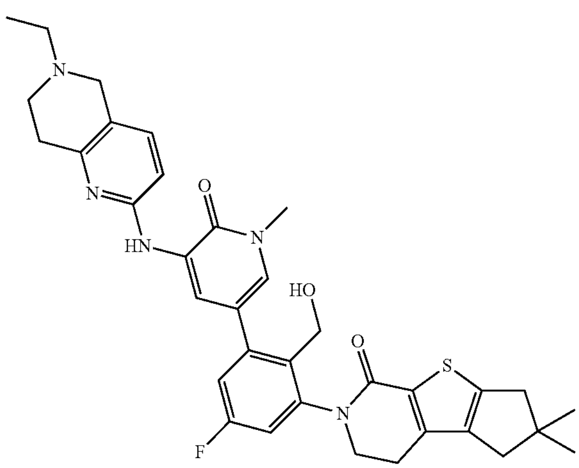 [SMILES: CCN1CCc2nc(Nc3cc(-c4cc(F)cc(N5CCc6c(sc7c6CC(C)(C)C7)C5=O)c4CO)cn(C)c3=O)ccc2C1] | 10-(3-{5-[(6-ethyl-5,6,7,8-tetrahydro-1,6-naphthyridin-2-yl)amino]-1-methyl-6-oxo-1,6-dihydropyridin-3-yl}-5-fluoro-2-(hydroxymethyl)phenyl)-4,4-dimethyl-7-thia-10-azatricyclo[6.4.0.0$^{2,6}$]dodeca-1(8),2(6)-dien-9-one | 628.3 | |

TABLE 2-continued

| No. | Structure | Name | MH+ m/z | Btk IC$_{50}$ (μMol) |
|---|---|---|---|---|
| 242 | 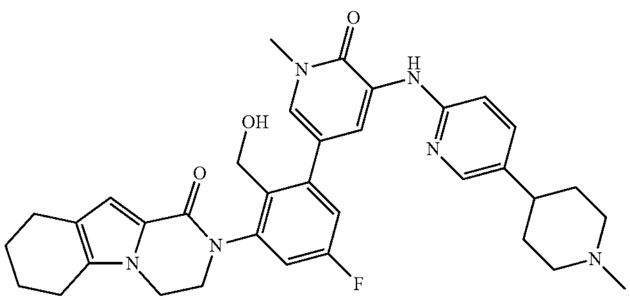 [SMILES: CN1CCC(c2ccc(Nc3cc(-c4cc(F)cc(N5CCn6c(cc7c6CCCC7)C5=O)c4CO)cn(C)c3=O)nc2)CC1] | 5-[5-fluoro-2-(hydroxymethyl)-3-{1-oxo-1H,2H,3H,4H,6H,7H,8H,9H-pyrazino[1,2-a]indol-2-yl}phenyl]-1-methyl-3-{[5-(1-methylpiperidin-4-yl)pyridine-2-yl]amino)-1,2-dihydropyridin-2-one | 611.5 | |
| 243 | 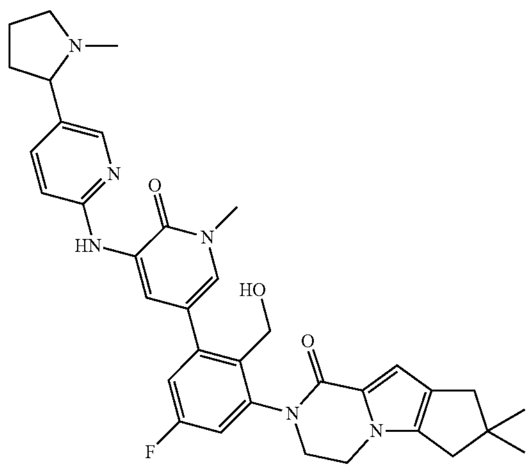 | 10-[5-fluoro-2-(hydroxymethyl)-3-(1-methyl-5-{[5-(1-methylpyrrolidin-2-yl)pyridine-2-yl]amino}-6-oxo-1,6-dihydropyridin-3-yl)phenyl]-4,4-dimethyl-1,10-diazatricyclo[6.4.0.0$^{2,6}$]dodeca-2(6),7-dien-9-one | 611.5 | |
| 244 | 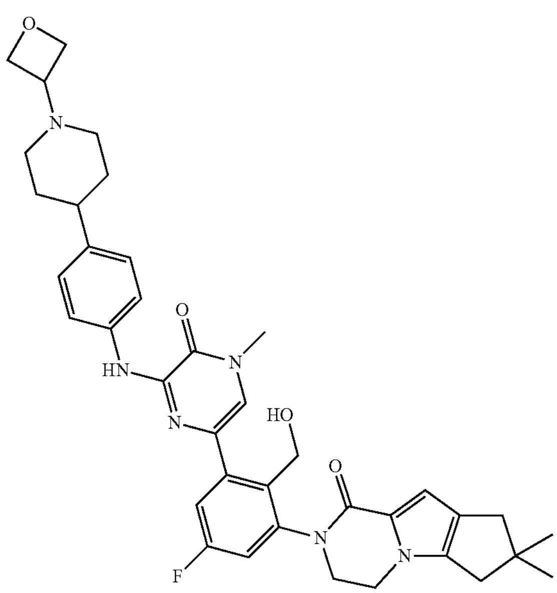 | 10-[5-fluoro-2-(hydroxymethyl)-3-[4-methyl-6-({4-[1-(oxetan-3-yl)piperidin-4-yl]phenyl}amino)-5-oxo-4,5-dihydropyrazin-2-yl]phenyl]-4,4-dimethyl-1,10-diazatricyclo[6.4.0.0$^{2,6}$]dodeca-2(6),7-dien-9-one | 667.6 | |

TABLE 2-continued

| No. | Structure | Name | MH+ m/z | Btk IC$_{50}$ (μMol) |
|---|---|---|---|---|
| 245 | 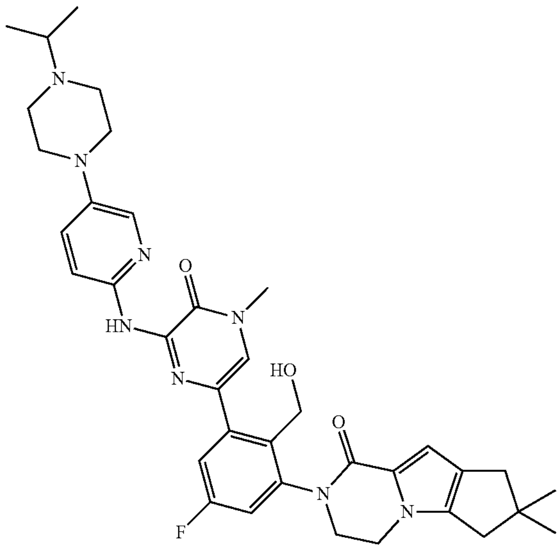 [SMILES: CC(C)N1CCN(c2ccc(Nc3nc(-c4cc(F)cc(N5CCn6c(cc7c6CC(C)(C)C7)C5=O)c4CO)cn(C)c3=O)nc2)CC1] | 10-[5-fluoro-2-(hydroxymethyl)-3-[1-methyl-6-oxo-5-({5-[4-(propan-2-yl)piperazin-1-yl]pyridine-2-yl}amino)-1,6-dihydropyridin-3-yl]phenyl]-4,4-dimethyl-1,10-diazatricyclo[6.4.0.0$^{2,6}$]dodeca-2(6),7-dien-9-one | 654.6 | |
| 246 | 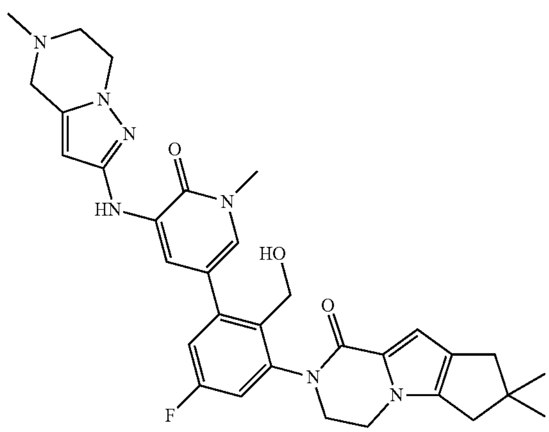 | 10-[5-fluoro-2-(hydroxymethyl)-3-[1-methyl-5-({5-methyl-4H,5H,6H,7H-pyrazolo[1,5-a]pyrazin-2-yl}amino)-6-oxo-1,6-dihydropyridin-3-yl]phenyl]-4,4-dimethyl-1,10-diazatricyclo[6.4.0.0$^{2,6}$]dodeca-2(6),7-dien-9-one | 586.6 | |
| 247 | 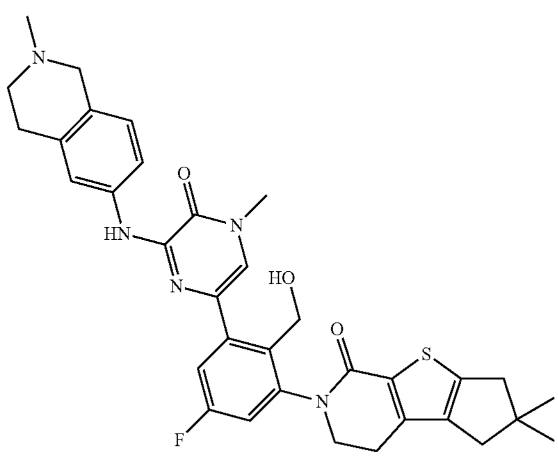 [SMILES: CN1CCc2cc(Nc3nc(-c4cc(F)cc(N5CCc6c(sc7c6CC(C)(C)C7)C5=O)c4CO)cn(C)c3=O)ccc2C1] | 10-[5-fluoro-2-(hydroxymethyl)-3-{4-methyl-6-[(2-methyl-1,2,3,4-tetrahydroisoquinolin-6-yl)amino]-5-oxo-4,5-dihydropyrazin-2-yl}phenyl]-4,4-dimethyl-7-thia-10-azatricyclo[6.4.0.0$^{2,6}$]dodeca-1(8),2(6)-dien-9-one | 614 | |

TABLE 2-continued

| No. | Structure | Name | MH+ m/z | Btk IC$_{50}$ (μMol) |
|---|---|---|---|---|
| 248 | 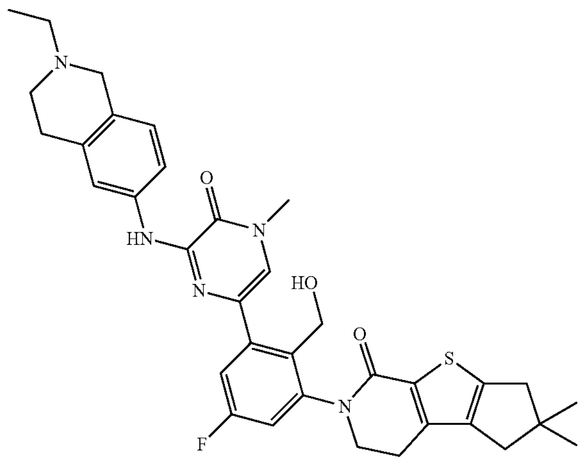 [SMILES: CCN1CCc2cc(Nc3nc(-c4cc(F)cc(N5CCc6c(sc7c6CC(C)(C)C7)C5=O)c4CO)cn(C)c3=O)ccc2C1] | 10-(3-{6-[(2-ethyl-1,2,3,4-tetrahydroisoquinolin-6-yl)amino]-4-methyl-5-oxo-4,5-dihydropyrazin-2-yl}-5-fluoro-2-(hydroxymethyl)phenyl)-4,4-dimethyl-7-thia-10-azatricyclo[6.4.0.0$^{2,6}$]dodeca-1(8),2(6)-dien-9-one | 628 | |
| 249 | 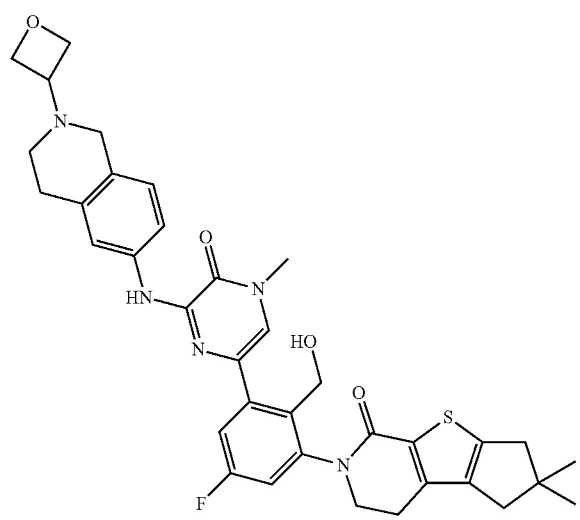 [SMILES: Cn1cc(-c2cc(F)cc(N3CCc4c(sc5c4CC(C)(C)C5)C3=O)c2CO)nc(Nc2ccc3c(c2)CCN(C2COC2)C3)c1=O] | 10-[5-fluoro-2-(hydroxymethyl)-3-(4-methyl-6-{[2-(oxetan-3-yl)-1,2,3,4-tetrahydroisoquinolin-6-yl]amino}-5-oxo-4,5-dihydropyrazin-2-yl)phenyl]-4,4-dimethyl-7-thia-10-azatricyclo[6.4.0.0$^{2,6}$]dodeca-1(8),2(6)-dien-9-one | 656 | |
| 250 | 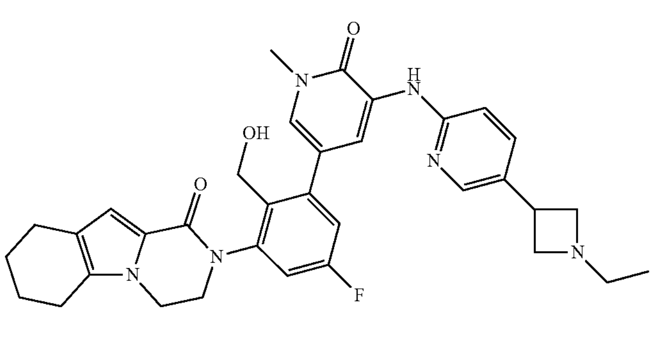 [SMILES: CCN1CC(c2ccc(Nc3cc(-c4cc(F)cc(N5CCn6c(cc7c6CCCC7)C5=O)c4CO)cn(C)c3=O)nc2)C1] | 3-{[5-(1-ethylazetidin-3-yl)pyridine-2-yl]amino}-5-[5-fluoro-2-(hydroxymethyl)-3-{1-oxo-1H,2H,3H,4H,6H,7H,8H,9H-pyrazino[1,2-a]indol-2-yl}phenyl]-1-methyl-1,2-dihydropyridin-2-one | 597 | |

TABLE 2-continued

| No. | Structure | Name | MH+ m/z | Btk IC50 (μMol) |
|---|---|---|---|---|
| 251 | 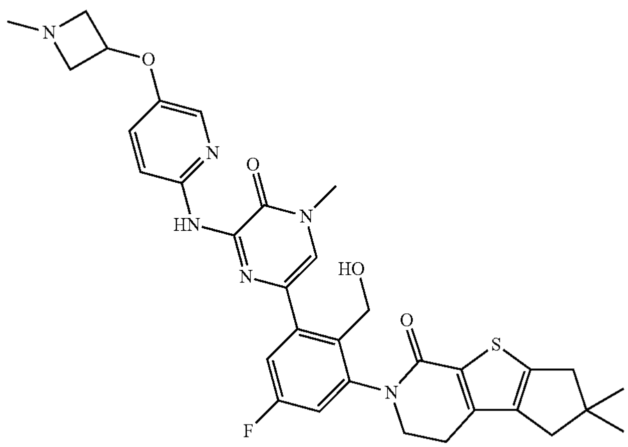 | 10-[5-fluoro-2-(hydroxymethyl)-3-[1-methyl-5-({5-[(1-methylazetidin-3-yl)oxy]pyridine-2-yl}amino)-6-oxo-1,6-dihydropyridin-3-yl]phenyl]-4,4-dimethyl-7-thia-10-azatricyclo[6.4.0.0$^{2,6}$]dodeca-1(8),2(6)-dien-9-one | 630.3 | |
| 252 | 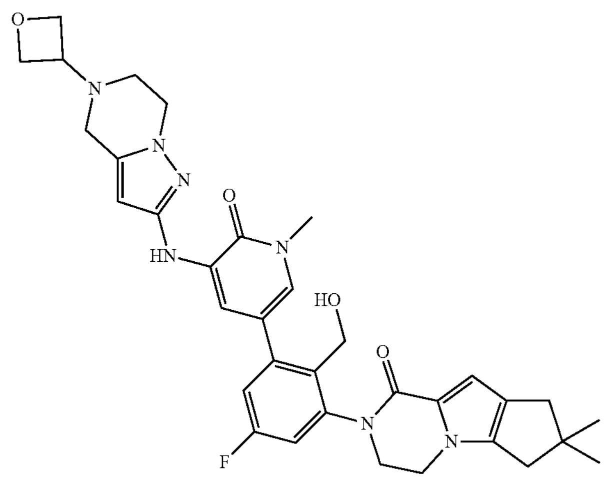 [SMILES: Cn1cc(-c2cc(F)cc(N3CCn4c(cc5c4CC(C)(C)C5)C3=O)c2CO)cc(Nc2cc3n(n2)CCN(C2COC2)C3)c1=O] | 10-[5-fluoro-2-(hydroxymethyl)-3-(1-methyl-5-{[5-(oxetan-3-yl)-4H,5H,6H,7H-pyrazolo[1,5-a]pyrazin-2-yl]amino}-6-oxo-1,6-dihydropyridin-3-yl)phenyl]-4,4-dimethyl-1,10-diazatricyclo[6.4.0.0$^{2,6}$]dodeca-2(6),7-dien-9-one | 628.5 | |
| 253 | 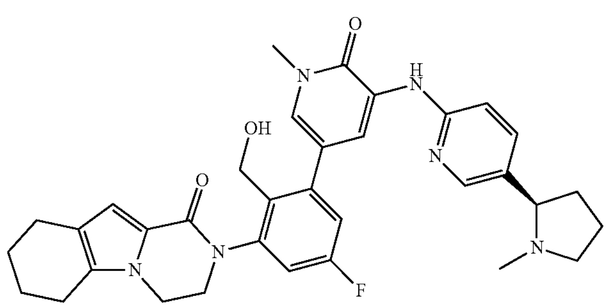 [SMILES: CN1CCC[C@@H]1c1ccc(Nc2cc(-c3cc(F)cc(N4CCn5c(cc6c5CCCC6)C4=O)c3CO)cn(C)c2=O)nc1] | 5-[5-fluoro-2-(hydroxymethyl)-3-{1-oxo-1H,2H,3H,4H,6H,7H,8H,9H-pyrazino[1,2-a]indol-2-yl}phenyl]-1-methyl-3-({5-[(2R)-1-methylpyrrolidin-2-yl]pyridine-2-yl}amino)-1,2-dihydropyridin-2-one | 597.4 | |
| 254 | 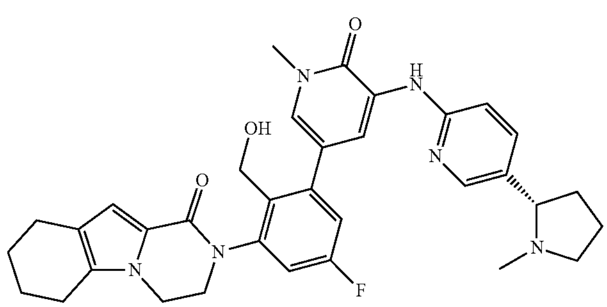 [SMILES: CN1CCC[C@H]1c1ccc(Nc2cc(-c3cc(F)cc(N4CCn5c(cc6c5CCCC6)C4=O)c3CO)cn(C)c2=O)nc1] | 5-[5-fluoro-2-(hydroxymethyl)-3-{1-oxo-1H,2H,3H,4H,6H,7H,8H,9H-pyrazino[1,2-a]indol-2-yl}phenyl]-1-methyl-3-({5-[(2S)-1-methylpyrrolidin-2-yl]pyridine-2-yl}amino)-1,2-dihydropyridin-2-one | 597.4 | |

TABLE 2-continued

| No. | Structure | Name | MH+ m/z | Btk IC$_{50}$ (µMol) |
|---|---|---|---|---|
| 255 | 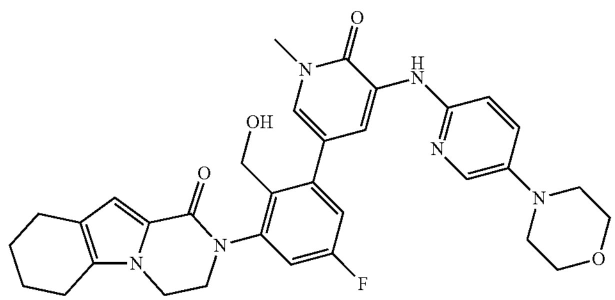 [SMILES: Cn1cc(-c2cc(F)cc(N3CCn4c(cc5c4CCCC5)C3=O)c2CO)cc(Nc2ccc(N3CCOCC3)cn2)c1=O] | 5-[5-fluoro-2-(hydroxymethyl)-3-{1-oxo-1H,2H,3H,4H,6H,7H,8H,9H-pyrazino[1,2-a]indol-2-yl}phenyl]-1-methyl-3-{[5-(morpholin-4-yl)pyridine-2-yl]amino}-1,2-dihydropyridin-2-one | 599 | |
| 256 | 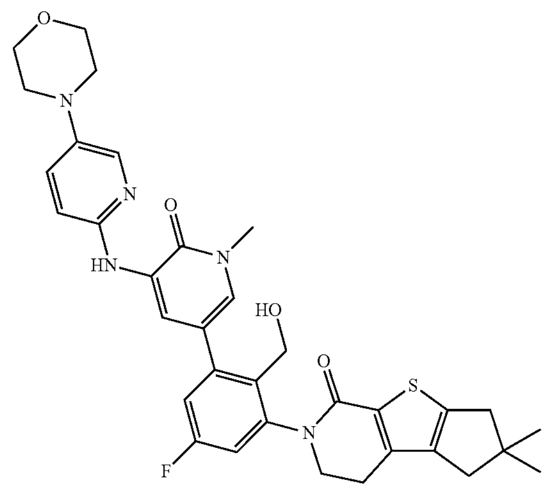 [SMILES: Cn1cc(-c2cc(F)cc(N3CCc4c(sc5c4CC(C)(C)C5)C3=O)c2CO)cc(Nc2ccc(N3CCOCC3)cn2)c1=O] | 10-[5-fluoro-2-(hydroxymethyl)-3-(1-methyl-5-{[5-(morpholin-4-yl)pyridine-2-yl]amino}-6-oxo-1,6-dihydropyridin-3-yl)phenyl]-4,4-dimethyl-7-thia-10-azatricyclo[6.4.0.0$^{2,6}$]dodeca-1(8),2(6)-dien-9-one | 630 | |
| 257 | 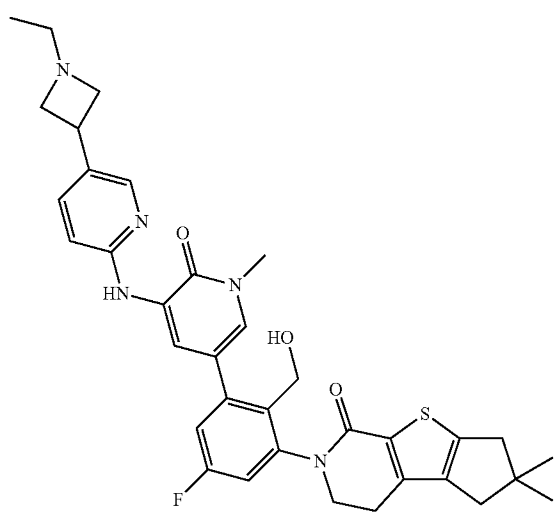 [SMILES: CCN1CC(c2ccc(Nc3cc(-c4cc(F)cc(N5CCc6c(sc7c6CC(C)(C)C7)C5=O)c4CO)cn(C)c3=O)nc2)C1] | 10-[3-(5-{[5-(1-ethylazetidin-3-yl)pyridine-2-yl]amino}-1-methyl-6-oxo-1,6-dihydropyridin-3-yl)-5-fluoro-2-(hydroxymethyl)phenyl]-4,4-dimethyl-7-thia-10-azatricyclo[6.4.0.0$^{2,6}$]dodeca-1(8),2(6)-dien-9-one | 628 | |

TABLE 2-continued

| No. | Structure | Name | MH+ m/z | Btk IC$_{50}$ (μMol) |
|---|---|---|---|---|
| 258 | 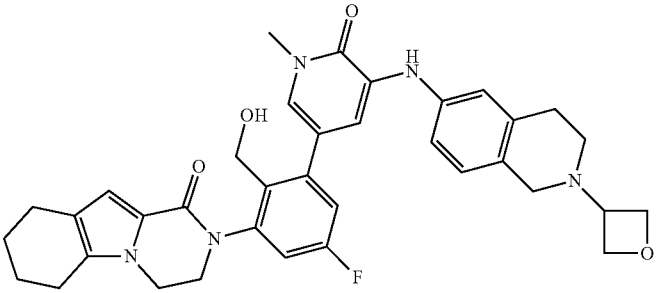 [SMILES: Cn1cc(-c2cc(F)cc(N3CCn4c(cc5c4CCCC5)C3=O)c2CO)cc(Nc2ccc3c(c2)CCN(C2COC2)C3)c1=O] | 5-[5-fluoro-2-(hydroxymethyl)-3-{1-oxo-1H,2H,3H,4H,6H,7H,8H,9H-pyrazino[1,2-a]indol-2-yl}phenyl]-1-methyl-3-{[2-(oxetan-3-yl)-1,2,3,4-tetrahydroisoquinolin-6-yl]amino}-1,2-dihydropyridin-2-one | 624 | |
| 259 | 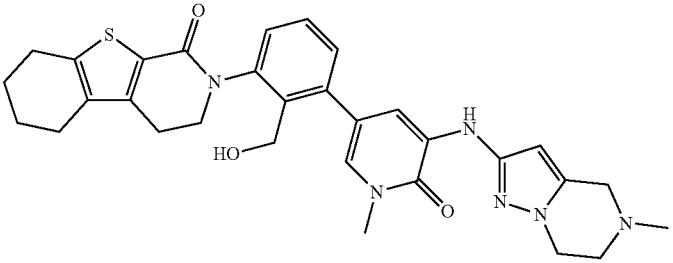 [SMILES: CN1CCn2nc(Nc3cc(-c4cccc(N5CCc6c(sc7c6CCCC7)C5=O)c4CO)cn(C)c3=O)cc2C1] | 5-[2-(hydroxymethyl)-3-[1-methyl-5-({5-methyl-4H,5H,6H,7H-pyrazolo[1,5-a]pyrazin-2-yl}amino)-6-oxo-1,6-dihydropyridin-3-yl]phenyl]-8-thia-5-azatricyclo[7.4.0.0$^{2,7}$]trideca-1(9),2(7)-dien-6-one | 571 | |
| 260 | 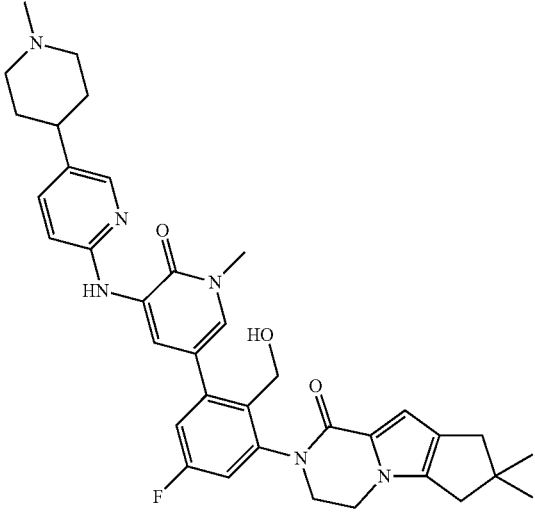 [SMILES: CN1CCC(c2ccc(Nc3cc(-c4cc(F)cc(N5CCn6c(cc7c6CC(C)(C)C7)C5=O)c4CO)cn(C)c3=O)nc2)CC1] | 10-[5-fluoro-2-(hydroxymethyl)-3-(1-methyl-5-{[5-(1-methylpiperidin-4-yl)pyridine-2-yl]amino}-6-oxo-1,6-dihydropyridin-3-yl)phenyl]-4,4-dimethyl-1,10-diazatricyclo[6.4.0.0$^{2,6}$]dodeca-2(6),7-dien-9-one | 625.5 | |
| 261 | 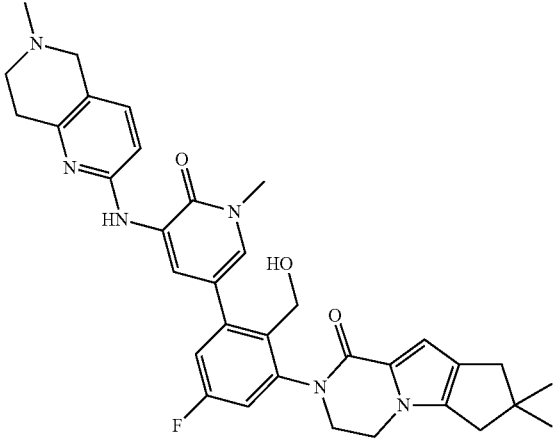 [SMILES: CN1CCc2nc(Nc3cc(-c4cc(F)cc(N5CCn6c(cc7c6CC(C)(C)C7)C5=O)c4CO)cn(C)c3=O)ccc2C1] | 10-[5-fluoro-2-(hydroxymethyl)-3-{1-methyl-5-[(6-methyl-5,6,7,8-tetrahydro-1,6-naphthyridin-2-yl)amino]-6-oxo-1,6-dihydropyridin-3-yl]phenyl]-4,4-dimethyl-1,10-diazatricyclo[6.4.0.0$^{2,6}$]dodeca-2(6),7-dien-9-one | 597.5 | |

TABLE 2-continued

| No. | Structure | Name | MH+ m/z | Btk IC$_{50}$ (μMol) |
|---|---|---|---|---|
| 262 | 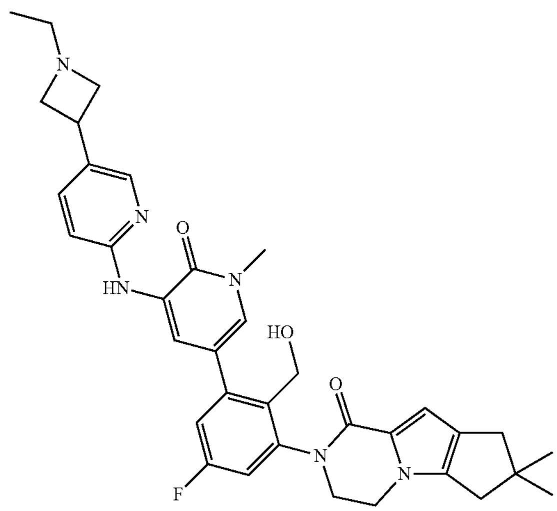 [SMILES: CCN1CC(c2ccc(Nc3cc(-c4cc(F)cc(N5CCn6c(cc7c6CC(C)(C)C7)C5=O)c4CO)cn(C)c3=O)nc2)C1] | 10-[3-(5-{[5-(1-ethylazetidin-3-yl)pyridine-2-yl]amino}-1-methyl-6-oxo-1,6-dihydropyridin-3-yl)-5-fluoro-2-(hydroxymethyl)phenyl]-4,4-dimethyl-1,10-diazatricyclo[6.4.0.0$^{2,6}$]dodeca-2(6),7-dien-9-one | 611.5 | |
| 263 | 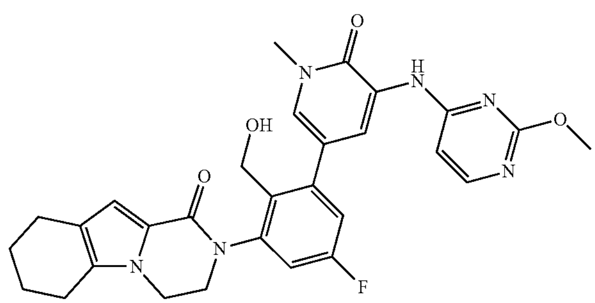 [SMILES: COc1nccc(Nc2cc(-c3cc(F)cc(N4CCn5c(cc6c5CCCC6)C4=O)c3CO)cn(C)c2=O)n1] | 5-[5-fluoro-2-(hydroxymethyl)-3-{1-oxo-1H,2H,3H,4H,6H,7H,8H,9H-pyrazino[1,2-a]indol-2-yl}phenyl]-3-[(2-methoxypyrimidin-4-yl)amino]-1-methyl-1,2-dihydropyridin-2-one | 545.5 | |
| 264 | 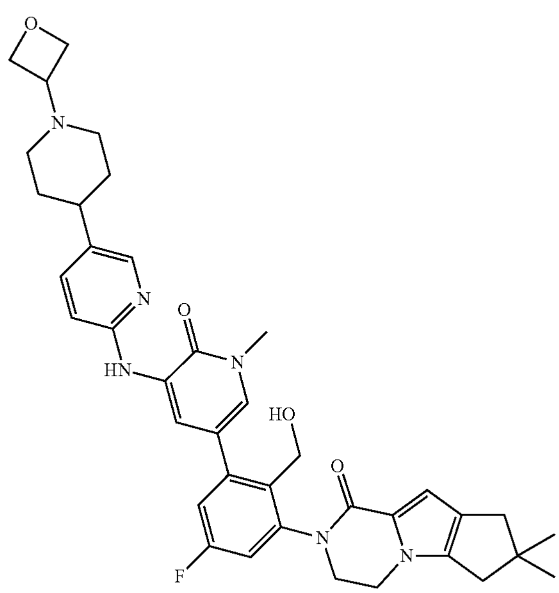 | 10-[5-fluoro-2-(hydroxymethyl)-3-[1-methyl-5-({5-[1-(oxetan-3-yl)piperidin-4-yl]pyridine-2-yl}amino)-6-oxo-1,6-dihydropyridin-3-yl]phenyl]-4,4-dimethyl-1,10-diazatricyclo[6.4.0.0$^{2,6}$]dodeca-2(6),7-dien-9-one | 667.6 | |

TABLE 2-continued

| No. | Structure | Name | MH+ m/z | Btk IC$_{50}$ (µMol) |
|---|---|---|---|---|
| 265 | 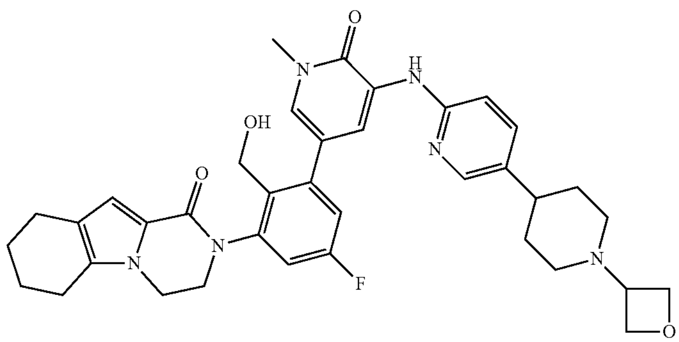 [SMILES: Cn1cc(-c2cc(F)cc(N3CCn4c(cc5c4CCCC5)C3=O)c2CO)cc(Nc2ccc(C3CCN(C4COC4)CC3)cn2)c1=O] | 5-[5-fluoro-2-(hydroxymethyl)-3-{1-oxo-1H,2H,3H,4H,6H,7H,8H,9H-pyrazino[1,2-a]indol-2-yl}phenyl]-1-methyl-3-({5-[1-(oxetan-3-yl)piperidin-4-yl]pyridine-2-yl]amino)-1,2-dihydropyridin-2-one | 653.6 | 0.0028 |
| 266 | 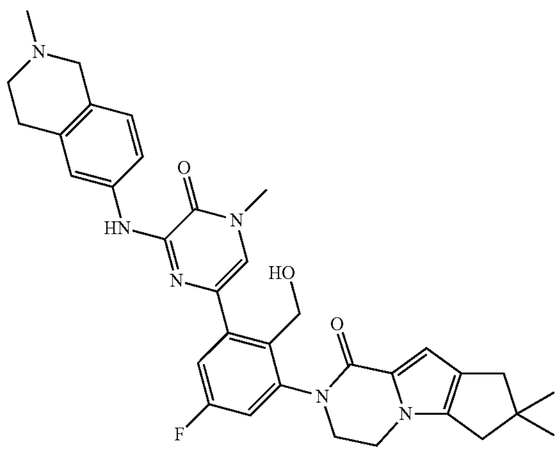 [SMILES: CN1CCc2cc(Nc3nc(-c4cc(F)cc(N5CCn6c(cc7c6CC(C)(C)C7)C5=O)c4CO)cn(C)c3=O)ccc2C1] | 10-[5-fluoro-2-(hydroxymethyl)-3-{4-methyl-6-[(2-methyl-1,2,3,4-tetrahydroisoquinolin-6-yl)amino]-5-oxo-4,5-dihydropyrazin-2-yl}phenyl]-4,4-dimethyl-1,10-diazatricyclo[6.4.0.0$^{2,6}$]dodeca-2(6),7-dien-9-one | 597.4 | |
| 267 | 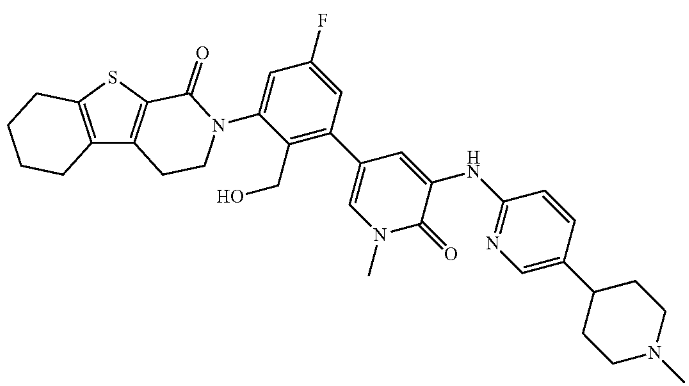 | 5-[5-fluoro-2-(hydroxymethyl)-3-(1-methyl-5-{[5-(1-methylpiperidin-4-yl)pyridine-2-yl]amino}-6-oxo-1,6-dihydropyridin-3-yl)phenyl]-8-thia-5-azatricyclo[7.4.0.0$^{2,7}$]trideca-1(9),2(7)-dien-6-one | 628 | 0.0038 |
| 268 | 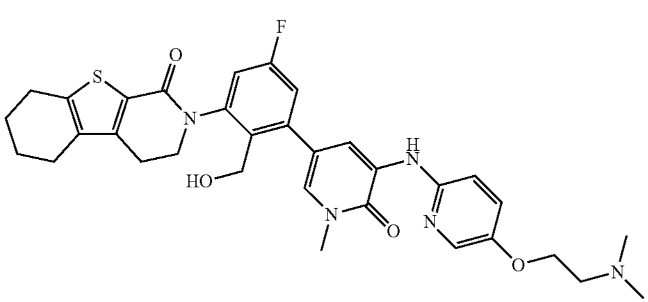 [SMILES: CN(C)CCOc1ccc(Nc2cc(-c3cc(F)cc(N4CCc5c(sc6c5CCCC6)C4=O)c3CO)cn(C)c2=O)nc1] | 5-{3-[5-({5-[2-(dimethylamino)ethoxy]pyridine-2-yl}amino)-1-methyl-6-oxo-1,6-dihydropyridin-3-yl]-5-fluoro-2-(hydroxymethyl)phenyl}-8-thia-5-azatricyclo[7.4.0.0$^{2,7}$]trideca-1(9),2(7)-dien-6-one | 618 | 0.0020 |

TABLE 2-continued

| No. | Structure | Name | MH+ m/z | Btk IC$_{50}$ (μMol) |
|---|---|---|---|---|
| 269 | 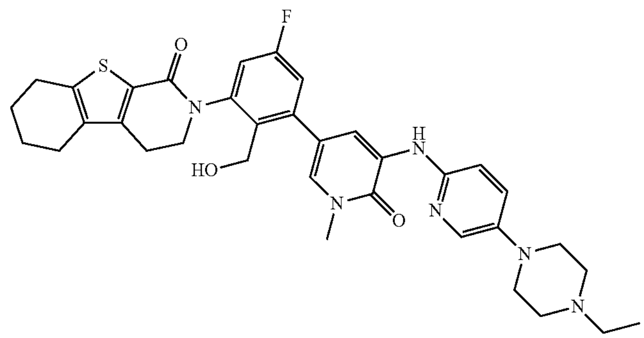 [SMILES: CCN1CCN(c2ccc(Nc3cc(-c4cc(F)cc(N5CCc6c(sc7c6CCCC7)C5=O)c4CO)cn(C)c3=O)nc2)CC1] | 5-[3-(5-{[5-(4-ethylpiperazin-1-yl)pyridine-2-yl]amino}-1-methyl-6-oxo-1,6-dihydropyridin-3-yl)-5-fluoro-2-(hydroxymethyl)phenyl]-8-thia-5-azatricyclo[7.4.0.0$^{2,7}$]trideca-1(9),2(7)-dien-6-one | 643.4 | 0.004 |
| 270 | 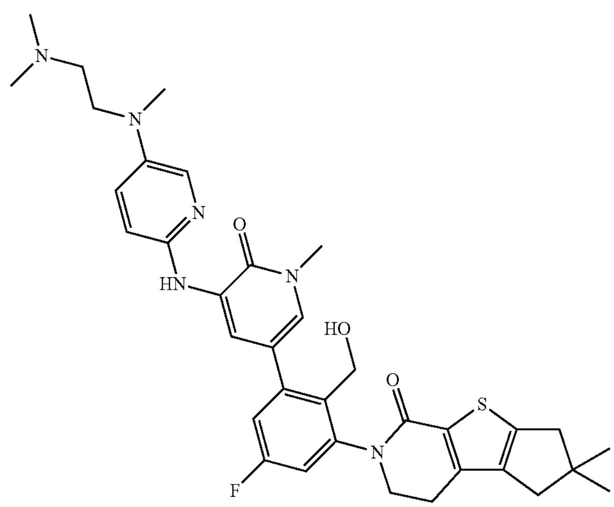 | 10-(3-{5-[(5-{[2-(dimethylamino)ethyl](methyl)amino}pyridine-2-yl)amino]-1-methyl-6-oxo-1,6-dihydropyridin-3-yl}-5-fluoro-2-(hydroxymethyl)phenyl)-4,4-dimethyl-7-thia-10-azatricyclo[6.4.0.0$^{2,6}$]dodeca-1(8),2(6)-dien-9-one | 645.3 | 0.0040 |
| 271 | 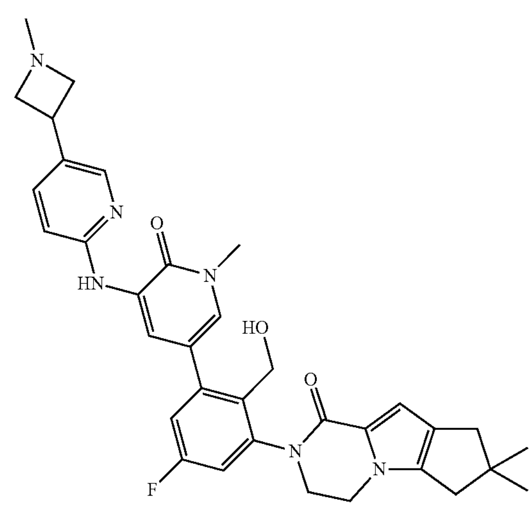 [SMILES: CN1CC(c2ccc(Nc3cc(-c4cc(F)cc(N5CCn6c(cc7c6CC(C)(C)C7)C5=O)c4CO)cn(C)c3=O)nc2)C1] | 10-[5-fluoro-2-(hydroxymethyl)-3-(1-methyl-5-{[5-(1-methylazetidin-3-yl)pyridine-2-yl]amino}-6-oxo-1,6-dihydropyridin-3-yl)phenyl]-4,4-dimethyl-1,10-diazatricyclo[6.4.0.0$^{2,6}$]dodeca-2(6),7-dien-9-one | 597.4 | 0.0047 |

TABLE 2-continued

| No. | Structure | Name | MH+ m/z | Btk IC$_{50}$ (μMol) |
|---|---|---|---|---|
| 272 | 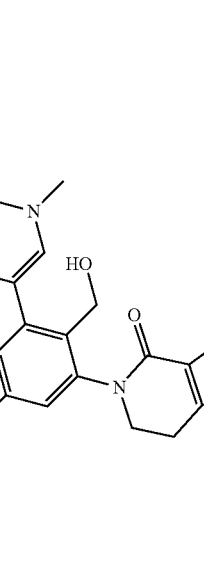 | 10-[3-(5-{[5-(4-ethylpiperazin-1-yl)pyridine-2-yl]amino}-1-methyl-6-oxo-1,6-dihydropyridin-3-yl)-5-fluoro-2-(hydroxymethyl)phenyl]-4,4-dimethyl-7-thia-10-azatricyclo[6.4.0.0$^{2,6}$]dodeca-1(8),2(6)-dien-9-one | 657.6 | 0.0064 |
| 273 | 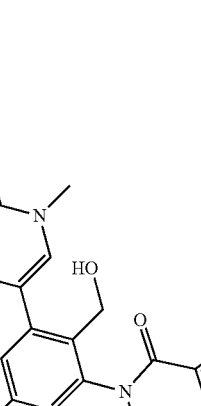 | 10-{5-fluoro-3-[5-({5-[4-(2-fluoroethyl)piperazin-1-yl]pyridine-2-yl}amino)-1-methyl-6-oxo-1,6-dihydropyridin-3-yl]-2-(hydroxymethyl)phenyl}-4,4-dimethyl-1,10-diazatricyclo[6.4.0.0$^{2,6}$]dodeca-2(6),7-dien-9-one | 658.5 | 0.00635 |
| 274 | 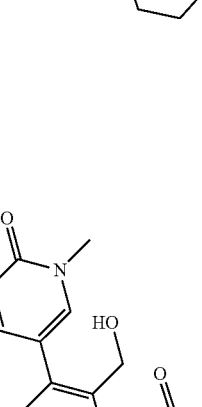 | 10-[5-fluoro-2-(hydroxymethyl)-3-(1-methyl-5-{[5-(morpholin-4-ylmethyl)pyridine-2-yl]amino}-6-oxo-1,6-dihydropyridin-3-yl)phenyl]-4,4-dimethyl-1,10-diazatricyclo[6.4.0.0$^{2,6}$]dodeca-2(6),7-dien-9-one | 627.5 | 0.00234 |

TABLE 2-continued

| No. | Structure | Name | MH+ m/z | Btk IC$_{50}$ (μMol) |
|---|---|---|---|---|
| 275 | 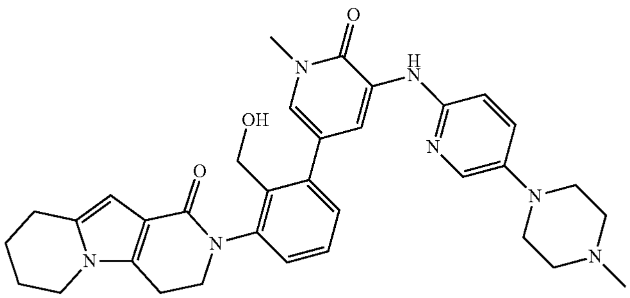 [SMILES: CN1CCN(c2ccc(Nc3cc(-c4cccc(N5CCc6c(cc7n6CCCC7)C5=O)c4CO)cn(C)c3=O)nc2)CC1] | 5-[2-(hydroxymethyl)-3-{1-oxo-1H,2H,3H,4H,6H,7H,8H,9H-pyrido[3,4-b]indolizin-2-yl}phenyl]-1-methyl-3-{[5-(4-methylpiperazin-1-yl)pyridine-2-yl]amino}-1,2-dihydropyridin-2-one | 594.3 | 0.0163 |
| 276 | 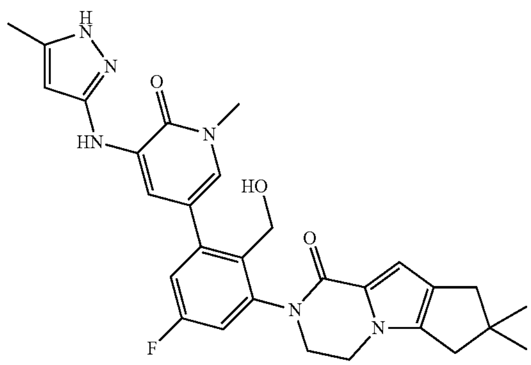 | 10-[5-fluoro-2-(hydroxymethyl)-3-{1-methyl-5-[(5-methyl-1H-pyrazol-3-yl)amino]-6-oxo-1,6-dihydropyridin-3-yl}phenyl]-4,4-dimethyl-1,10-diazatricyclo[6.4.0.0$^{2,6}$]dodeca-2(6),7-dien-9-one | 531.4 | 0.0022 |
| 277 | 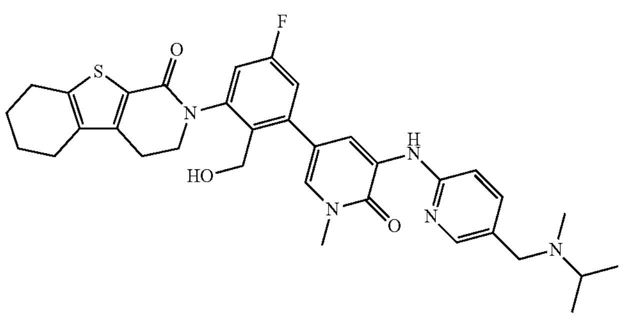 [SMILES: CC(C)N(C)Cc1ccc(Nc2cc(-c3cc(F)cc(N4CCc5c(sc6c5CCCC6)C4=O)c3CO)cn(C)c2=O)nc1] | 5-[5-fluoro-2-(hydroxymethyl)-3-{1-methyl-5-[(5-{[methyl(propan-2-yl)amino]methyl}pyridine-2-yl)amino]-6-oxo-1,6-dihydropyridin-3-yl}phenyl]-8-thia-5-azatricyclo[7.4.0.0$^{2,7}$]trideca-1(9),2(7)-dien-6-one | 616.4 | 0.0034 |
| 278 | 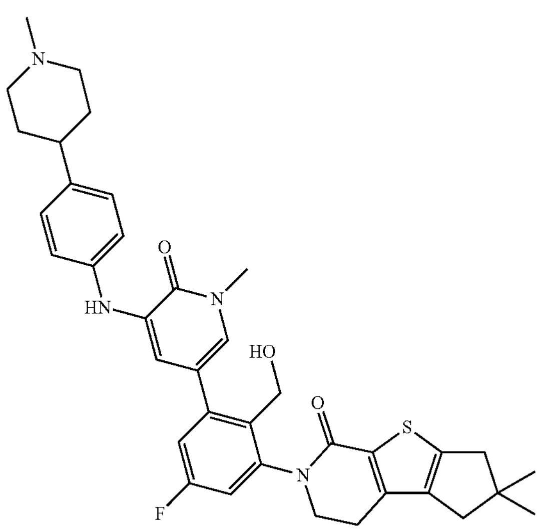 [SMILES: CN1CCC(c2ccc(Nc3cc(-c4cc(F)cc(N5CCc6c(sc7c6CC(C)(C)C7)C5=O)c4CO)cn(C)c3=O)cc2)CC1] | 10-[5-fluoro-2-(hydroxymethyl)-3-(4-methyl-6-{[4-(1-methylpiperidin-4-yl)phenyl]amino}-5-oxo-4,5-dihydropyrazin-2-yl)phenyl]-4,4-dimethyl-7-thia-10-azatricyclo[6.4.0.0$^{2,6}$]dodeca-1(8),2(6)-dien-9-one | 642 | 0.0026 |

US 10,053,469 B2

TABLE 2-continued

| No. | Structure | Name | MH+ m/z | Btk IC$_{50}$ (μMol) |
|---|---|---|---|---|
| 279 | 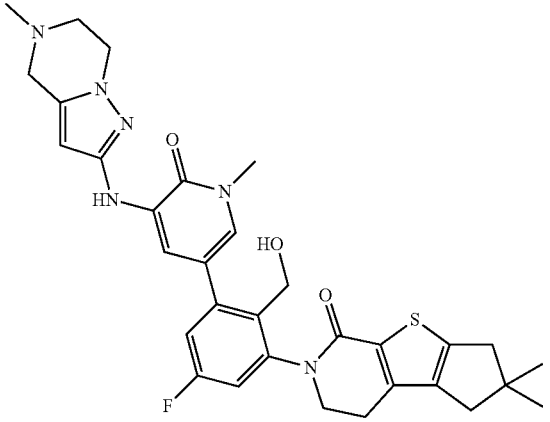 | 10-[5-fluoro-2-(hydroxymethyl)-3-[1-methyl-5-({5-methyl-4H,5H,6H,7H-pyrazolo[1,5-a]pyrazin-2-yl}amino)-6-oxo-1,6-dihydropyridin-3-yl]phenyl]-4,4-dimethyl-7-thia-10-azatricyclo[6.4.0.0$^{2,6}$]dodeca-1(8),2(6)-dien-9-one | 603 | 0.0049 |
| 280 | 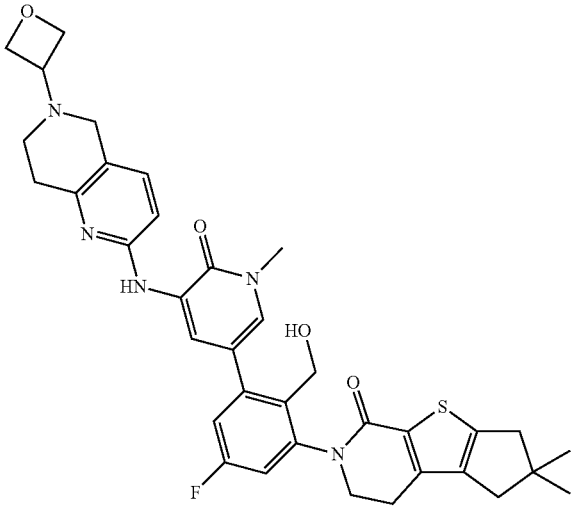 [SMILES: Cn1cc(-c2cc(F)cc(N3CCc4c(sc5c4CC(C)(C)C5)C3=O)c2CO)cc(Nc2ccc3c(n2)CCN(C2COC2)C3)c1=O] | 10-[5-fluoro-2-(hydroxymethyl)-3-(1-methyl-5-{[6-(oxetan-3-yl)-5,6,7,8-tetrahydro-1,6-naphthyridin-2-yl]amino}-6-oxo-1,6-dihydropyridin-3-yl)phenyl]-4,4-dimethyl-7-thia-10-azatricyclo[6.4.0.0$^{2,6}$]dodeca-1(8),2(6)-dien-9-one | 656 | 0.0042 |
| 281 | 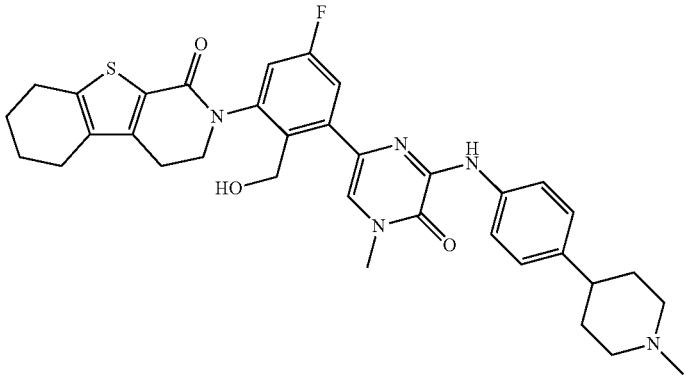 [SMILES: CN1CCC(c2ccc(Nc3nc(-c4cc(F)cc(N5CCc6c(sc7c6CCCC7)C5=O)c4CO)cn(C)c3=O)cc2)CC1] | 5-[5-fluoro-2-(hydroxymethyl)-3-(4-methyl-6-{[4-(1-methylpiperidin-4-yl)phenyl]amino}-5-oxo-4,5-dihydropyrazin-2-yl)phenyl]-8-thia-5-azatricyclo[7.4.0.0$^{2,7}$]trideca-1(9),2(7)-dien-6-one | 628 | 0.0052 |

TABLE 2-continued

| No. | Structure | Name | MH+ m/z | Btk IC$_{50}$ (µMol) |
|---|---|---|---|---|
| 282 | 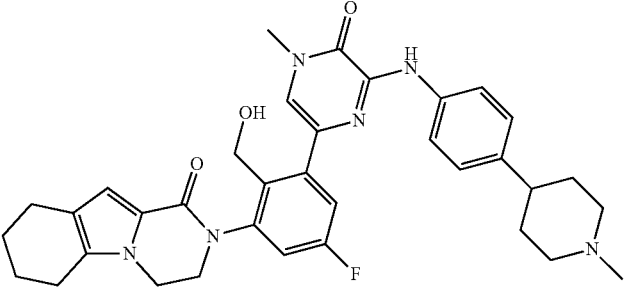 | 5-[5-fluoro-2-(hydroxymethyl)-3-{1-oxo-1H,2H,3H,4H,6H,7H,8H,9H-pyrazino[1,2-a]indol-2-yl}phenyl]-1-methyl-3-{[4-(1-methylpiperidin-4-yl)phenyl]amino}-1,2-dihydropyrazin-2-one | 611 | 0.004 |
| 283 | 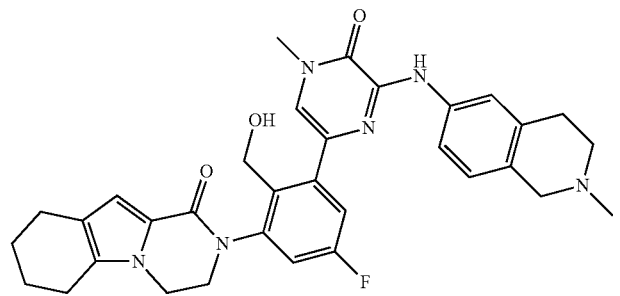 | 5-[5-fluoro-2-(hydroxymethyl)-3-{1-oxo-1H,2H,3H,4H,6H,7H,8H,9H-pyrazino[1,2-a]indol-2-yl}phenyl]-1-methyl-3-[(2-methyl-1,2,3,4-tetrahydroisoquinolin-6-yl)amino]-1,2-dihydropyrazin-2-one | 583 | 0.0081 |
| 284 | 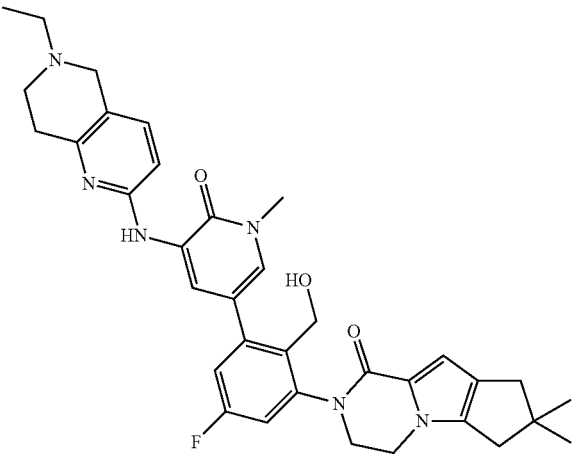 [SMILES: CCN1CCc2nc(Nc3cc(-c4cc(F)cc(N5CCn6c(cc7c6CC(C)(C)C7)C5=O)c4CO)cn(C)c3=O)ccc2C1] | 10-(3-{5-[(6-ethyl-5,6,7,8-tetrahydro-1,6-naphthyridin-2-yl)amino]-1-methyl-6-oxo-1,6-dihydropyridin-3-yl}-5-fluoro-2-(hydroxymethyl)phenyl)-4,4-dimethyl-1,10-diazatricyclo[6.4.0.0$^{2,6}$]dodeca-2(6),7-dien-9-one | 611.5 | 0.0028 |
| 285 | 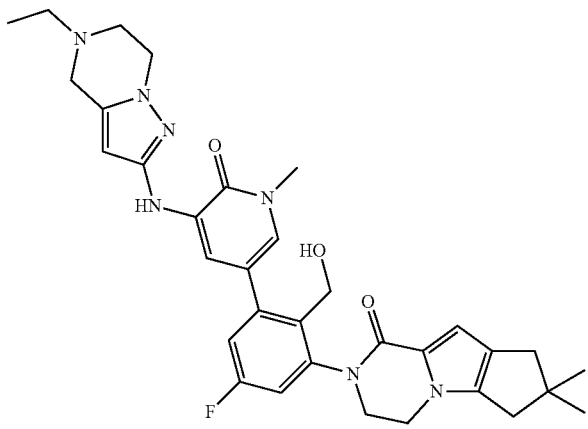 [SMILES: CCN1CCn2nc(Nc3cc(-c4cc(F)cc(N5CCn6c(cc7c6CC(C)(C)C7)C5=O)c4CO)cn(C)c3=O)cc2C1] | 10-{3-[5-({5-ethyl-4H,5H,6H,7H-pyrazolo[1,5-a]pyrazin-2-yl}amino)-1-methyl-6-oxo-1,6-dihydropyridin-3-yl]-5-fluoro-2-(hydroxymethyl)phenyl}-4,4-dimethyl-1,10-diazatricyclo[6.4.0.0$^{2,6}$]dodeca-2(6),7-dien-9-one | 600.6 | 0.0036 |

TABLE 2-continued

| No. | Name | MH+ m/z | Btk IC50 (μMol) |
|---|---|---|---|
| 286 | 5-(3-{5-[(5-{[2-(dimethylamino)ethyl](methyl)amino}pyridine-2-yl)amino]-1-methyl-6-oxo-1,6-dihydropyridin-3-yl}-5-fluoro-2-(hydroxymethyl)phenyl)-8-thia-5-azatricyclo[7.4.0.0²,⁷]trideca-1(9),2(7)-dien-6-one | 631.3 | 0.0034 |
| 287 | 10-[5-fluoro-2-(hydroxymethyl)-3-(1-methyl-5-{[5-(1-methylpyrrolidin-2-yl)pyridine-2-yl]amino}-6-oxo-1,6-dihydropyridin-3-yl)phenyl]-4,4-dimethyl-7-thia-10-azatricyclo[6.4.0.0²,⁶]dodeca-1(8),2(6)-dien-9-one | 628.3 | 0.0014 |
| 288 | 5-[5-fluoro-2-(hydroxymethyl)-3-(1-methyl-5-{[5-(1-methylpyrrolidin-2-yl)pyridine-2-yl]amino}-6-oxo-1,6-dihydropyridin-3-yl)phenyl]-8-thia-5-azatricyclo[7.4.0.0²,⁷]trideca-1(9),2(7)-dien-6-one | 614.3 | 0.0021 |
| 289 | 5-[5-fluoro-2-(hydroxymethyl)-3-(1-methyl-5-{[5-(morpholin-4-yl)pyridine-2-yl]amino}-6-oxo-1,6-dihydropyridin-3-yl)phenyl]-8-thia-5-azatricyclo[7.4.0.0²,⁷]trideca-1(9),2(7)-dien-6-one | 616.3 | 0.0050 |

TABLE 2-continued

| No. | Structure | Name | MH+ m/z | Btk IC$_{50}$ (μMol) |
|---|---|---|---|---|
| 290 | 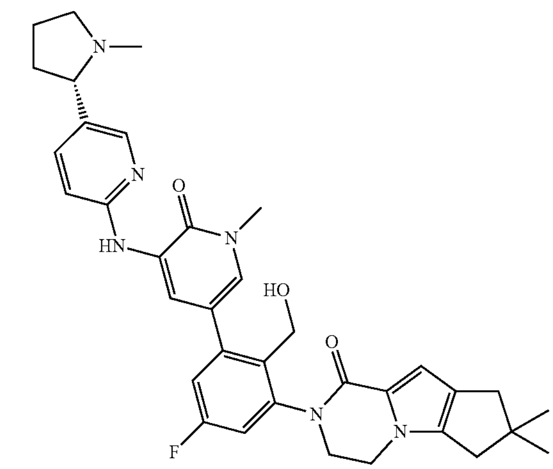 [SMILES: CN1CCC[C@H]1c1ccc(Nc2cc(-c3cc(F)cc(N4CCn5c(cc6c5CC(C)(C)C6)C4=O)c3CO)cn(C)c2=O)nc1] | 10-[5-fluoro-2-(hydroxymethyl)-3-[1-methyl-5-({5-[(2S)-1-methylpyrrolidin-2-yl]pyridin-2-yl}amino)-6-oxo-1,6-dihydropyridin-3-yl]phenyl]-4,4-dimethyl-1,10-diazatricyclo[6.4.0.0$^{2,6}$]dodeca-2(6),7-dien-9-one | 611.5 | |
| 291 | 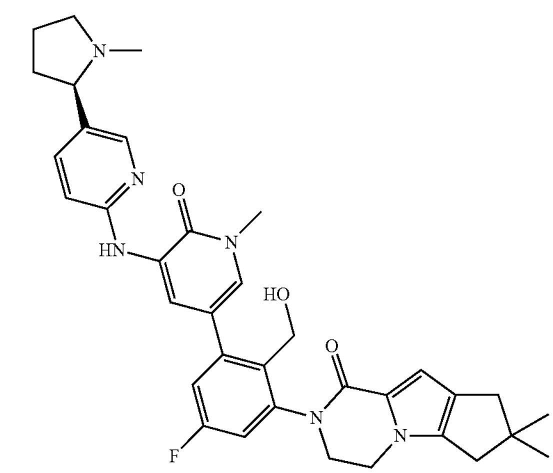 [SMILES: CN1CCC[C@@H]1c1ccc(Nc2cc(-c3cc(F)cc(N4CCn5c(cc6c5CC(C)(C)C6)C4=O)c3CO)cn(C)c2=O)nc1] | 10-[5-fluoro-2-(hydroxymethyl)-3-[1-methyl-5-({5-[(2R)-1-methylpyrrolidin-2-yl]pyridin-2-yl}amino)-6-oxo-1,6-dihydropyridin-3-yl]phenyl]-4,4-dimethyl-1,10-diazatricyclo[6.4.0.0$^{2,6}$]dodeca-2(6),7-dien-9-one | 611.5 | 0.00174 |
| 292 | 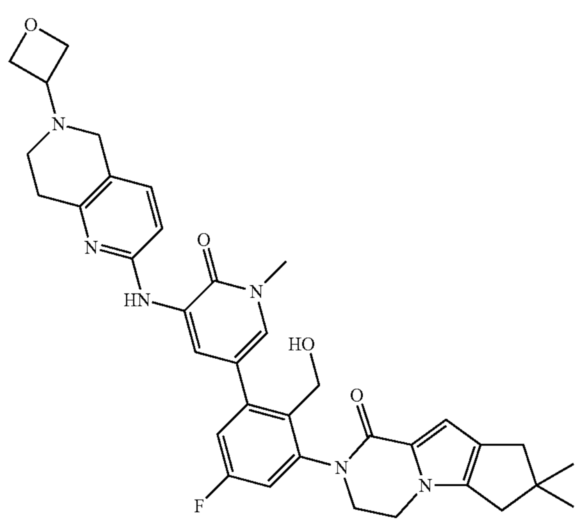 [SMILES: Cn1cc(-c2cc(F)cc(N3CCn4c(cc5c4CC(C)(C)C5)C3=O)c2CO)cc(Nc2ccc3c(n2)CCN(C2COC2)C3)c1=O] | 10-[5-fluoro-2-(hydroxymethyl)-3-(1-methyl-5-{[6-(oxetan-3-yl)-5,6,7,8-tetrahydro-1,6-naphthyridin-2-yl]amino}-6-oxo-1,6-dihydropyridin-3-yl)phenyl]-4,4-dimethyl-1,10-diazatricyclo[6.4.0.0$^{2,6}$]dodeca-2(6),7-dien-9-one | 639.5 | 0.0116 |

TABLE 2-continued

| No. | Structure | Name | MH+ m/z | Btk IC$_{50}$ (μMol) |
|---|---|---|---|---|
| 293 | 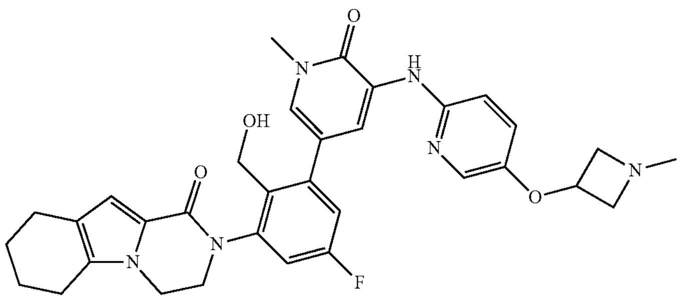 [SMILES: CN1CC(Oc2ccc(Nc3cc(-c4cc(F)cc(N5CCn6c(cc7c6CCCC7)C5=O)c4CO)cn(C)c3=O)nc2)C1] | 5-[5-fluoro-2-(hydroxymethyl)-3-{1-oxo-1H,2H,3H,4H,6H,7H,8H,9H-pyrazino[1,2-a]indol-2-yl}phenyl]-1-methyl-3-({5-[(1-methylazetidin-3-yl)oxy]pyridine-2-yl}amino)-1,2-dihydropyridin-2-one | 599 | 0.0098 |
| 294 | 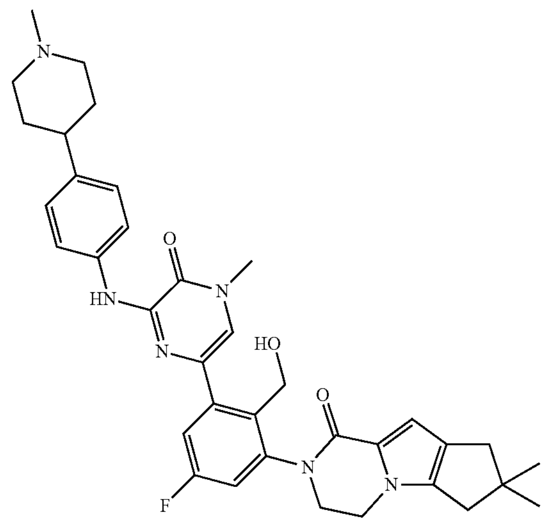 [SMILES: CN1CCC(c2ccc(Nc3nc(-c4cc(F)cc(N5CCn6c(cc7c6CC(C)(C)C7)C5=O)c4CO)cn(C)c3=O)cc2)CC1] | 10-[5-fluoro-2-(hydroxymethyl)-3-(4-methyl-6-{[4-(1-methylpiperidin-4-yl)phenyl]amino}-5-oxo-4,5-dihydropyrazin-2-yl)phenyl]-4,4-dimethyl-1,10-diazatricyclo[6.4.0.0$^{2,6}$]dodeca-2(6),7-dien-9-one | 625 | 0.016 |
| 295 | 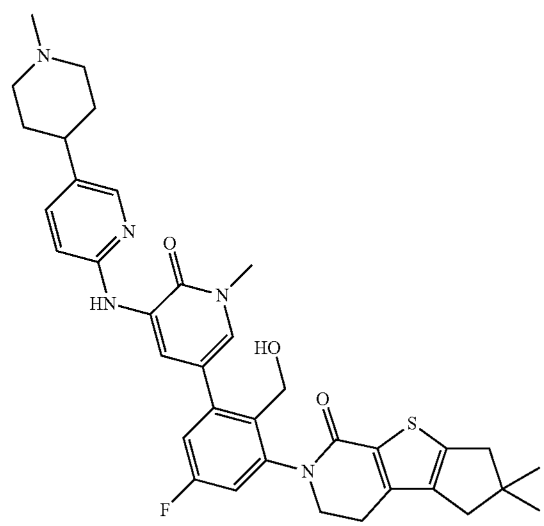 [SMILES: CN1CCC(c2ccc(Nc3cc(-c4cc(F)cc(N5CCc6c(sc7c6CC(C)(C)C7)C5=O)c4CO)cn(C)c3=O)nc2)CC1] | 10-[5-fluoro-2-(hydroxymethyl)-3-(1-methyl-5-{[5-(1-methylpiperidin-4-yl)pyridine-2-yl]amino}-6-oxo-1,6-dihydropyridin-3-yl)phenyl]-4,4-dimethyl-7-thia-10-azatricyclo[6.4.0.0$^{2,6}$]dodeca-1(8),2(6)-dien-9-one | 642 | 0.0022 |

TABLE 2-continued

| No. | Structure | Name | MH+ m/z | Btk IC$_{50}$ (μMol) |
|---|---|---|---|---|
| 296 | 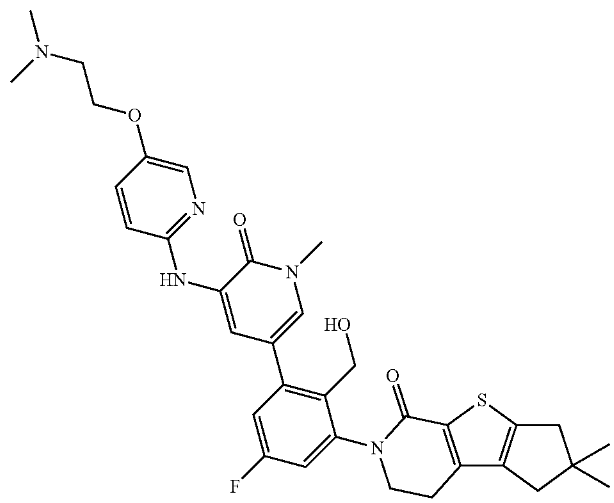 | 10-{3-[5-({5-[2-(dimethylamino)ethoxy]pyridine-2-yl}amino)-1-methyl-6-oxo-1,6-dihydropyridin-3-yl]-5-fluoro-2-(hydroxymethyl)phenyl}-4,4-dimethyl-7-thia-10-azatricyclo[6.4.0.0$^{2,6}$]dodeca-1(8),2(6)-dien-9-one | 632 | 0.0030 |
| 297 | 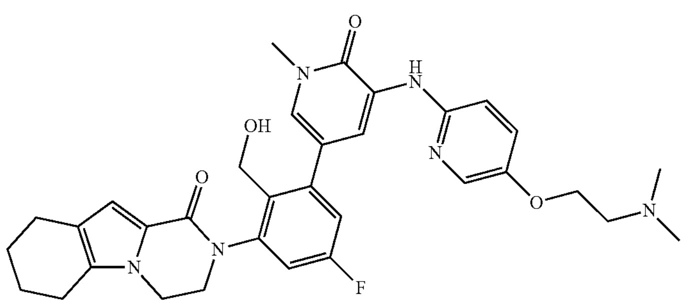 [SMILES: CN(C)CCOc1ccc(Nc2cc(-c3cc(F)cc(N4CCn5c(cc6c5CCCC6)C4=O)c3CO)cn(C)c2=O)nc1] | 3-({5-[2-(dimethylamino)ethoxy]pyridine-2-yl}amino)-5-[5-fluoro-2-(hydroxymethyl)-3-{1-oxo-1H,2H,3H,4H,6H,7H,8H,9H-pyrazino[1,2-a]indol-2-yl}phenyl]-1-methyl-1,2-dihydropyridin-2-one | 601 | 0.0042 |
| 298 | 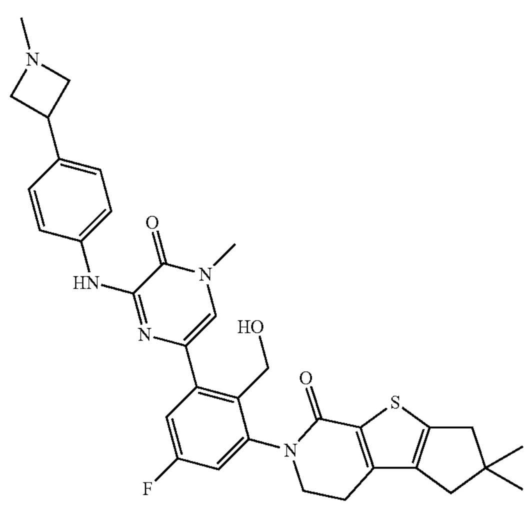 [SMILES: CN1CC(c2ccc(Nc3nc(-c4cc(F)cc(N5CCc6c(sc7c6CC(C)(C)C7)C5=O)c4CO)cn(C)c3=O)cc2)C1] | 10-[5-fluoro-2-(hydroxymethyl)-3-(4-methyl-6-{[4-(1-methylazetidin-3-yl)phenyl]amino}-5-oxo-4,5-dihydropyrazin-2-yl)phenyl]-4,4-dimethyl-7-thia-10-azatricyclo[6.4.0.0$^{2,6}$]dodeca-1(8),2(6)-dien-9-one | 614 | 0.0053 |

TABLE 2-continued

| No. | Structure | Name | MH+ m/z | Btk IC$_{50}$ (μMol) |
|---|---|---|---|---|
| 299 | 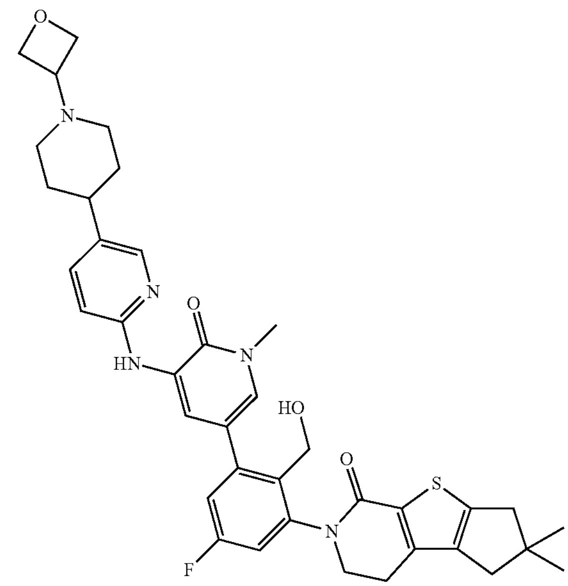 [SMILES: Cn1cc(-c2cc(F)cc(N3CCc4c(sc5c4CC(C)(C)C5)C3=O)c2CO)cc(Nc2ccc(C3CCN(C4COC4)CC3)cn2)c1=O] | 10-[5-fluoro-2-(hydroxymethyl)-3-[1-methyl-5-({5-[1-(oxetan-3-yl)piperidin-4-yl]pyridine-2-yl}amino)-6-oxo-1,6-dihydropyridin-3-yl]phenyl]-4,4-dimethyl-7-thia-10-azatricyclo[6.4.0.0$^{2,6}$]dodeca-1(8),2(6)-dien-9-one | 684.5 | 0.0087 |
| 300 | 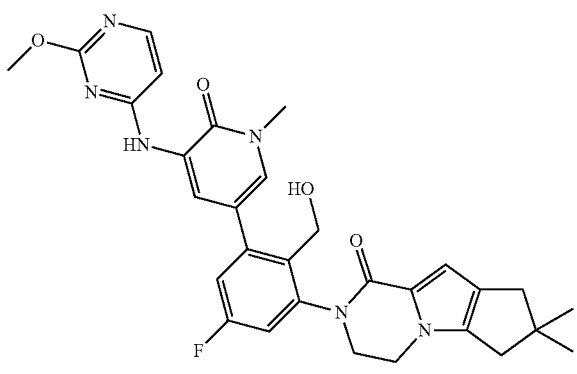 | 10-[5-fluoro-2-(hydroxymethyl)-3-{5-[(2-methoxypyrimidin-4-yl)amino]-1-methyl-6-oxo-1,6-dihydropyridin-3-yl}phenyl]-4,4-dimethyl-1,10-diazatricyclo[6.4.0.0$^{2,6}$]dodeca-2(6),7-dien-9-one | 559.4 | 0.0034 |
| 301 | 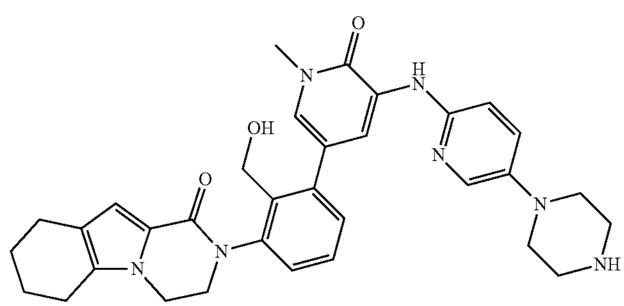 | 5-[2-(hydroxymethyl)-3-{1-oxo-1H,2H,3H,4H,6H,7H,8H,9H-pyrazino[1,2-a]indol-2-yl}phenyl]-1-methyl-3-{[5-(piperazin-1-yl)pyridine-2-yl]amino}-1,2-dihydropyridin-2-one | 580.4 | 0.0061 |

TABLE 2-continued

| No. | Structure | Name | MH+ m/z | Btk IC$_{50}$ (μMol) |
|---|---|---|---|---|
| 302 | 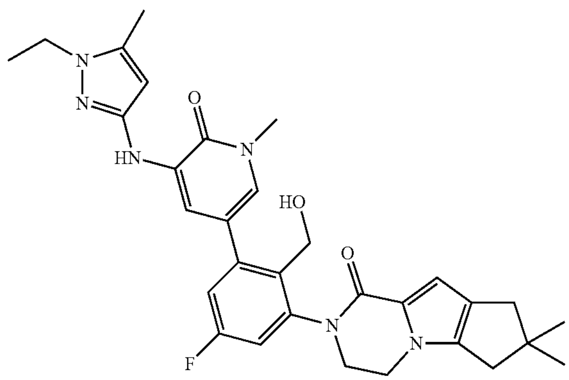 [SMILES: CCn1nc(Nc2cc(-c3cc(F)cc(N4CCn5c(cc6c5CC(C)(C)C6)C4=O)c3CO)cn(C)c2=O)cc1C] | 10-(3-{5-[(1-ethyl-5-methyl-1H-pyrazol-3-yl)amino]-1-methyl-6-oxo-1,6-dihydropyridin-3-yl}-5-fluoro-2-(hydroxymethyl)phenyl)-4,4-dimethyl-1,10-diazatricyclo[6.4.0.0$^{2,6}$]dodeca-2(6),7-dien-9-one | 559.4 | 0.0099 |
| 303 | 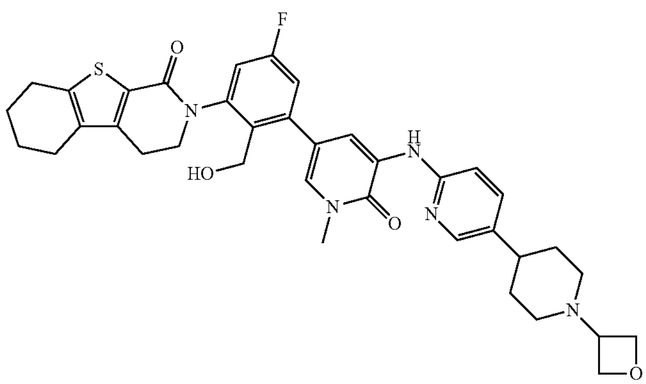 [SMILES: Cn1cc(-c2cc(F)cc(N3CCc4c(sc5c4CCCC5)C3=O)c2CO)cc(Nc2ccc(C3CCN(C4COC4)CC3)cn2)c1=O] | 5-[5-fluoro-2-(hydroxymethyl)-3-[1-methyl-5-({5-[1-(oxetan-3-yl)piperidin-4-yl]pyridine-2-yl}amino)-6-oxo-1,6-dihydropyridin-3-yl]phenyl]-8-thia-5-azatricyclo[7.4.0.0$^{2,7}$]trideca-1(9),2(7)-dien-6-one | 670.3 | 0.0049 |
| 304 | 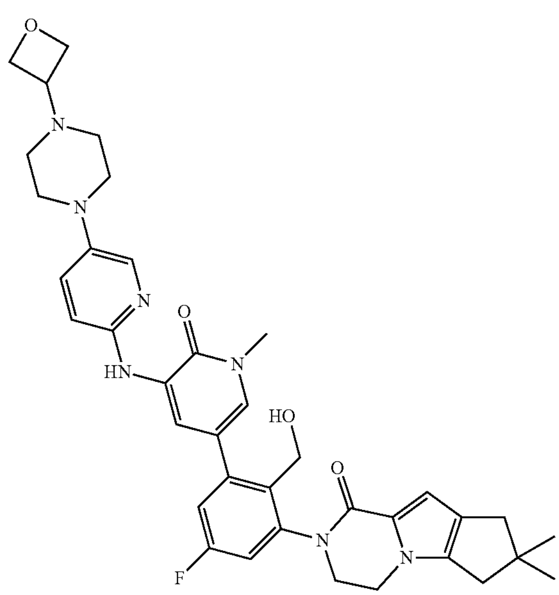 [SMILES: Cn1cc(-c2cc(F)cc(N3CCn4c(cc5c4CC(C)(C)C5)C3=O)c2CO)cc(Nc2ccc(N3CCN(C4COC4)CC3)cn2)c1=O] | 10-[5-fluoro-2-(hydroxymethyl)-3-[1-methyl-5-({5-[4-(oxetan-3-yl)piperazin-1-yl]pyridine-2-yl}amino)-6-oxo-1,6-dihydropyridin-3-yl]phenyl]-4,4-dimethyl-1,10-diazatricyclo[6.4.0.0$^{2,6}$]dodeca-2(6),7-dien-9-one | 668 | 0.0078 |

TABLE 2-continued

| No. | Structure | Name | MH+ m/z | Btk IC$_{50}$ (μMol) |
|---|---|---|---|---|
| 305 | 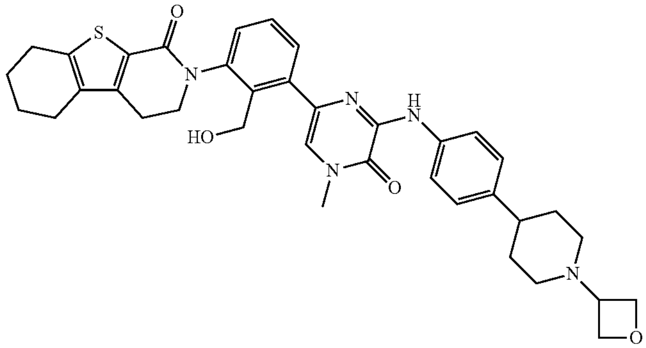 [SMILES: Cn1cc(-c2cccc(N3CCc4c(sc5c4CCCC5)C3=O)c2CO)nc(Nc2ccc(C3CCN(C4COC4)CC3)cc2)c1=O] | 5-[2-(hydroxymethyl)-3-[4-methyl-6-({4-[1-(oxetan-3-yl)piperidin-4-yl]phenyl}amino)-5-oxo-4,5-dihydropyrazin-2-yl]phenyl]-8-thia-5-azatricyclo[7.4.0.0$^{2,7}$]trideca-1(9),2(7)-dien-6-one | 652 | 0.0171 |
| 306 | 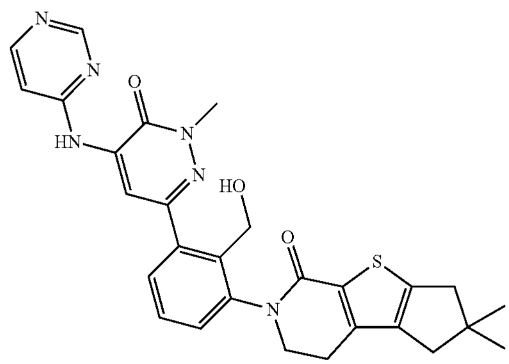 [SMILES: Cn1nc(-c2cccc(N3CCc4c(sc5c4CC(C)(C)C5)C3=O)c2CO)cc(Nc2ccncn2)c1=O] | 10-[2-(hydroxymethyl)-3-[1-methyl-6-oxo-5-(pyrimidin-4-ylamino)-1,6-dihydropyridazin-3-yl]phenyl]-4,4-dimethyl-7-thia-10-azatricyclo[6.4.0.0$^{2,6}$]dodeca-1(8),2(6)-dien-9-one | 529.3 | |
| 307 | 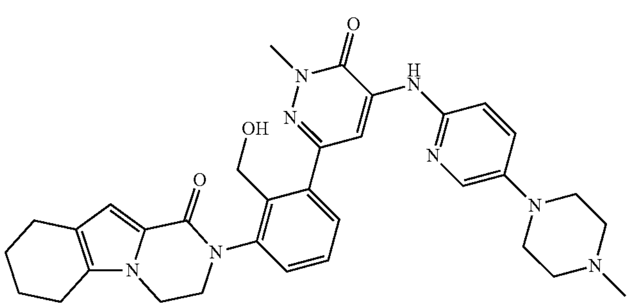 [SMILES: CN1CCN(c2ccc(Nc3cc(-c4cccc(N5CCn6c(cc7c6CCCC7)C5=O)c4CO)nn(C)c3=O)nc2)CC1] | 6-[2-(hydroxymethyl)-3-{1-oxo-1H,2H,3H,4H,6H,7H,8H,9H-pyrazino[1,2-a]indol-2-yl}phenyl]-2-methyl-4-{[5-(4-methylpiperazin-1-yl)pyridine-2-yl]amino}-2,3-dihydropyridazin-3-one | 595.6 | 0.0071 |
| 308 | 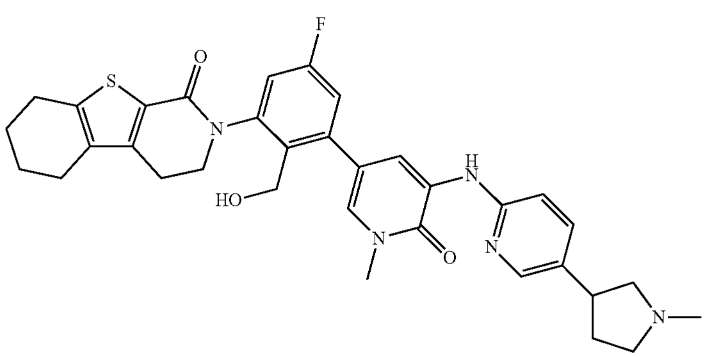 [SMILES: CN1CCC(c2ccc(Nc3cc(-c4cc(F)cc(N5CCc6c(sc7c6CCCC7)C5=O)c4CO)cn(C)c3=O)nc2)C1] | 5-[5-fluoro-2-(hydroxymethyl)-3-(1-methyl-5-{[5-(1-methylpyrrolidin-3-yl)pyridine-2-yl]amino}-6-oxo-1,6-dihydropyridin-3-yl)phenyl]-8-thia-5-azatricyclo[7.4.0.0$^{2,7}$]trideca-1(9),2(7)-dien-6-one | 614.3 | 0.0033 |

TABLE 2-continued

| No. | Structure | Name | MH+ m/z | Btk IC$_{50}$ (μMol) |
|---|---|---|---|---|
| 309 | 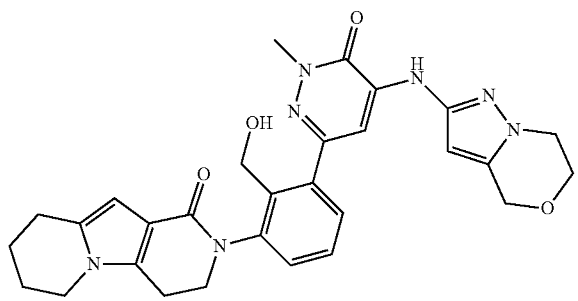 [SMILES: Cn1nc(-c2cccc(N3CCc4c(cc5n4CCCC5)C3=O)c2CO)cc(Nc2cc3n(n2)CCOC3)c1=O] | 5-[2-(hydroxymethyl)-3-{1-oxo-1H,2H,3H,4H,6H,7H,8H,9H-pyrido[3,4-b]indolizin-2-yl}phenyl]-1-methyl-3-{4H,6H,7H-pyrazolo[3,2-c][1,4]oxazin-2-ylamino}-1,2-dihydropyridin-2-one | 541.2 | 0.0165 |
| 310 | 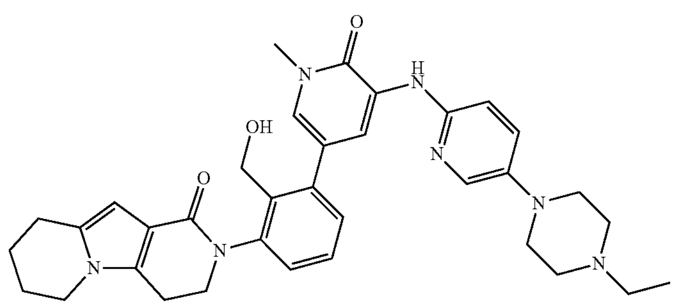 [SMILES: CCN1CCN(c2ccc(Nc3cc(-c4cccc(N5CCc6c(cc7n6CCCC7)C5=O)c4CO)cn(C)c3=O)nc2)CC1] | 3-{[5-(4-ethylpiperazin-1-yl)pyridine-2-yl]amino}-5-[2-(hydroxymethyl)-3-{1-oxo-1H,2H,3H,4H,6H,7H,8H,9H-pyrido[3,4-b]indolizin-2-yl}phenyl]-1-methyl-1,2-dihydropyridin-2-one | 608.3 | 0.0166 |
| 311 | 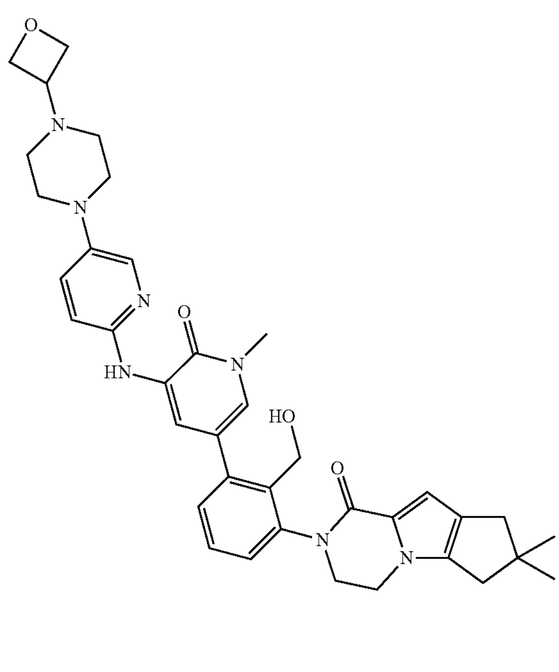 [SMILES: Cn1cc(-c2cccc(N3CCn4c(cc5c4CC(C)(C)C5)C3=O)c2CO)cc(Nc2ccc(N3CCN(C4COC4)CC3)cn2)c1=O] | 10-[2-(hydroxymethyl)-3-[1-methyl-5-({5-[4-(oxetan-3-yl)piperazin-1-yl]pyridine-2-yl}amino)-6-oxo-1,6-dihydropyridin-3-yl]phenyl]-4,4-dimethyl-1,10-diazatricyclo[6.4.0.0$^{2,6}$]dodeca-2(6),7-dien-9-one | 650 | 0.0052 |

TABLE 2-continued

| No. | Structure | Name | MH+ m/z | Btk IC$_{50}$ (μMol) |
|---|---|---|---|---|
| 312 | 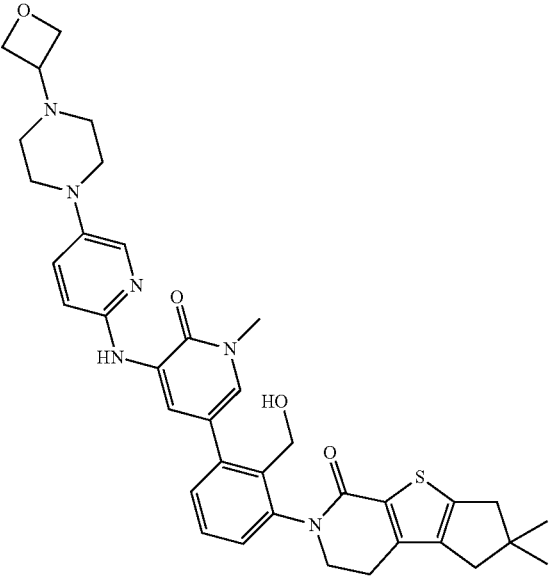 [SMILES: Cn1cc(-c2cccc(N3CCc4c(sc5c4CC(C)(C)C5)C3=O)c2CO)cc(Nc2ccc(N3CCN(C4COC4)CC3)cn2)c1=O] | 10-[2-(hydroxymethyl)-3-[1-methyl-5-({5-[4-(oxetan-3-yl)piperazin-1-yl]pyridine-2-yl}amino)-6-oxo-1,6-dihydropyridin-3-yl]phenyl]-4,4-dimethyl-7-thia-10-azatricyclo[6.4.0.0$^{2,6}$]dodeca-1(8),2(6)-dien-9-one | 667 | 0.043 |
| 313 | 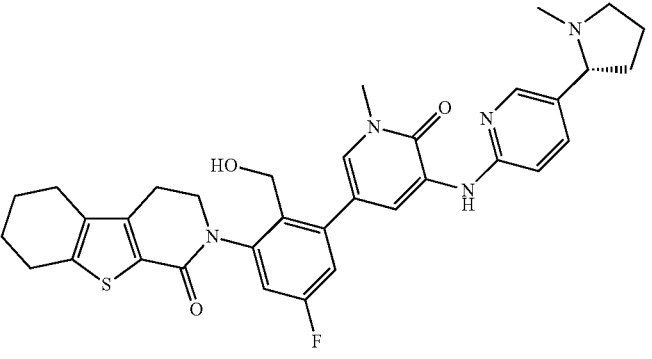 [SMILES: CN1CCC[C@@H]1c1ccc(Nc2cc(-c3cc(F)cc(N4CCc5c(sc6c5CCCC6)C4=O)c3CO)cn(C)c2=O)nc1] | 5-[5-fluoro-2-(hydroxymethyl)-3-(1-methyl-5-{[5-(2S)-(1-methylpyrrolidin-2-yl)pyridine-2-yl]amino}-6-oxo-1,6-dihydropyridin-3-yl)phenyl]-8-thia-5-azatricyclo[7.4.0.0$^{2,7}$]trideca-1(9),2(7)-dien-6-one | 614.2 | |
| 314 | 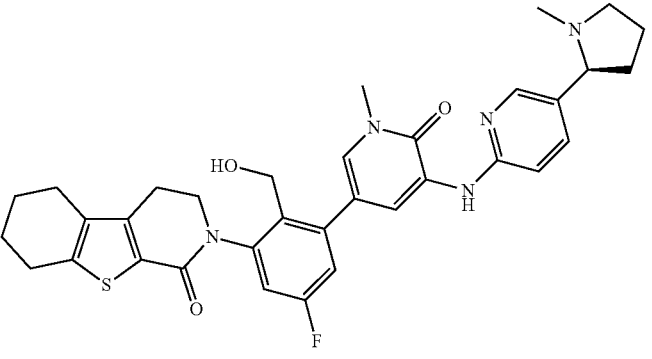 [SMILES: CN1CCC[C@H]1c1ccc(Nc2cc(-c3cc(F)cc(N4CCc5c(sc6c5CCCC6)C4=O)c3CO)cn(C)c2=O)nc1] | 5-[5-fluoro-2-(hydroxymethyl)-3-(1-methyl-5-{[5-(2R)-(1-methylpyrrolidin-2-yl)pyridine-2-yl]amino}-6-oxo-1,6-dihydropyridin-3-yl)phenyl]-8-thia-5-azatricyclo[7.4.0.0$^{2,7}$]trideca-1(9),2(7)-dien-6-one | 614.2 | |

Replacement Sheet

TABLE 2-continued

| No. | Structure | Name | MH+ m/z | Btk IC$_{50}$ (μMol) |
|---|---|---|---|---|
| 315 | 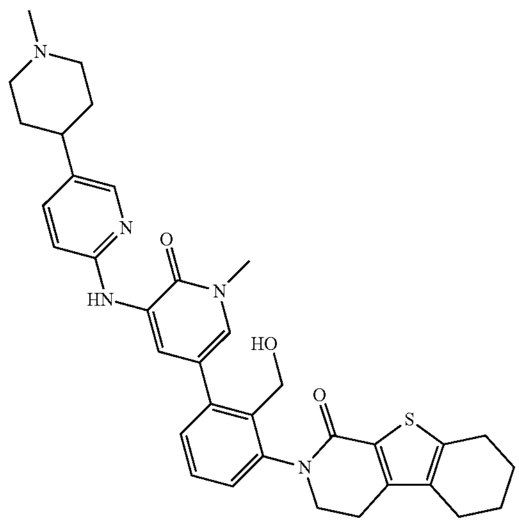 [SMILES: CN1CCC(c2ccc(Nc3cc(-c4cccc(N5CCc6c(sc7c6CCCC7)C5=O)c4CO)cn(C)c3=O)nc2)CC1] | 5-[2-(hydroxymethyl)-5-[1-methyl-5-({4-[1-methylpiperidin-4-yl]pyridine-2-yl}amino)-6-oxo-1,6-dihydropyridin-3-yl]phenyl]-8-thia-5-azatricyclo-[7.4.0.0$^{2,7}$]trideca-1(9),2(7)-dien-6-one | 610 | |
| 316 | 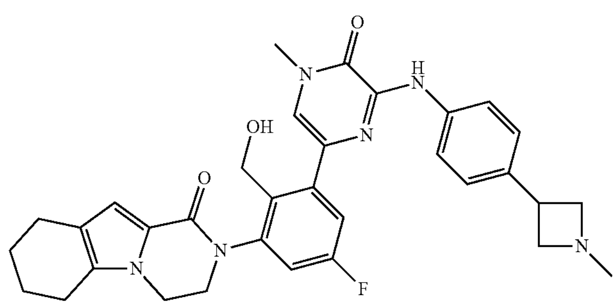 [SMILES: CN1CC(c2ccc(Nc3nc(-c4cc(F)cc(N5CCn6c(cc7c6CCCC7)C5=O)c4CO)cn(C)c3=O)cc2)C1] | 5-[5-fluoro-2-(hydroxymethyl)-3-{1-oxo-1H,2H,3H,4H,6H,7H,8H,9H-pyrazino[1,2-a]indol-2-yl}phenyl]-1-methyl-3-[(4-(1-methylazetidin-3-yl)phenyl)amino)-1,2-dihydropyrazin-2-one | 583 | |
| 317 | 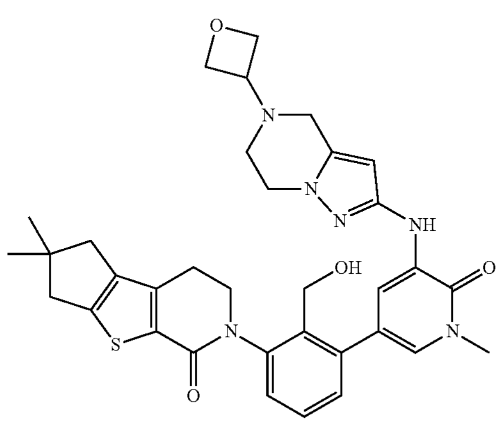 [SMILES: Cn1cc(-c2cccc(N3CCc4c(sc5c4CC(C)(C)C5)C3=O)c2CO)cc(Nc2cc3n(n2)CCN(C2COC2)C3)c1=O] | 10-[2-(hydroxymethyl)-3-[1-methyl-5-({5-(oxetan-3-yl)-4H,5H,6H,7H-pyrazolo[1,5-a]pyrazin-2-yl}amino)-6-oxo-1,6-dihydropyridin-3-yl]phenyl]-4,4-dimethyl-7-thia-10-azatricyclo-[6.4.0.0$^{2,6}$]dodeca-1(8),2(6)-dien-9-one | 627 | |

TABLE 2-continued

| No. | Structure | Name | MH+ m/z | Btk IC$_{50}$ (μMol) |
|---|---|---|---|---|
| 318 | 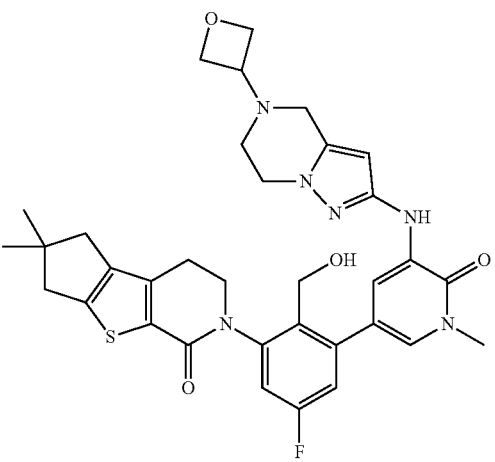 [SMILES: Cn1cc(-c2cc(F)cc(N3CCc4c(sc5c4CC(C)(C)C5)C3=O)c2CO)cc(Nc2cc3n(n2)CCN(C2COC2)C3)c1=O] | 10-[5-fluoro-2-(hydroxymethyl)-3-[1-methyl-5-({5-(oxetan-3-yl)-4H,5H,6H,7H-pyrazolo[1,5-a]pyrazin-2-yl}amino)-6-oxo-1,6-dihydropyridin-3-yl]phenyl]-4,4-dimethyl-7-thia-10-azatricyclo-[6.4.0.0$^{2,6}$]dodeca-1(8),2(6)-dien-9-one | 645.3 | |
| 319 | 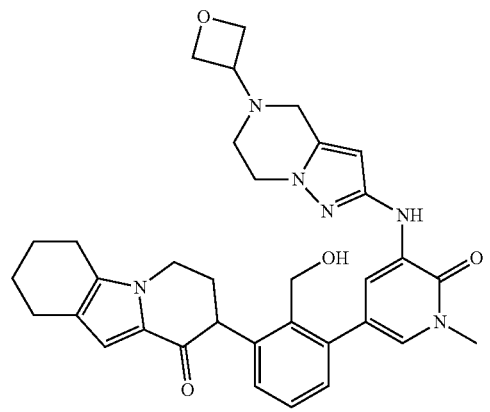 [SMILES: Cn1cc(-c2cccc(C3CCn4c(cc5c4CCCC5)C3=O)c2CO)cc(Nc2cc3n(n2)CCN(C2COC2)C3)c1=O] | 2-(2-(Hydroxymethyl)-3-(1-methyl-5-(5-(oxetan-3-yl)-4,5,6,7-tetrahydropyrazolo[1,5-a]pyrazin-2-ylamino)-6-oxo-1,6-dihydropyridin-3-yl)phenyl)-3,4,6,7,8,9-hexahydropyrazino[1,2-a]indol-1(2H)-one | 596 | |
| 320 | 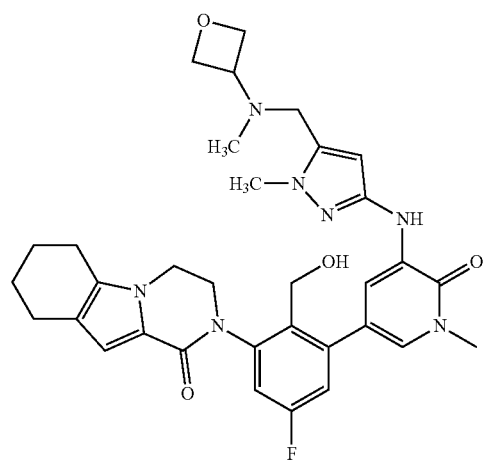 [SMILES: CN(Cc1cc(Nc2cc(-c3cc(F)cc(N4CCn5c(cc6c5CCCC6)C4=O)c3CO)cn(C)c2=O)nn1C)C1COC1] | 5-[5-fluoro-2-(hydroxymethyl)-3-{1-oxo-1H,2H,3H,4H,6H,7H,8H,9H-pyrido[3,4-b]indolizin-2-yl}phenyl]-3-{1-methyl-5-(N-methyl,N-oxetan-3-ylaminomethyl-1H-pyrazol-3-yl)amino}-1,2-dihydropyridin-2-one | 616 | |

Replacement Sheet

TABLE 2-continued

| No. | Structure | Name | MH+ m/z | Btk IC$_{50}$ (µMol) |
|---|---|---|---|---|
| 321 | 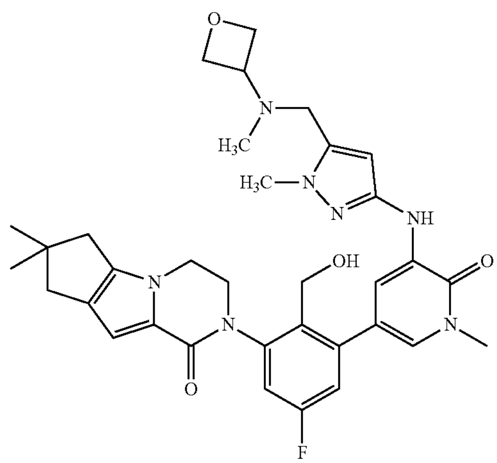 [SMILES: CN(Cc1cc(Nc2cc(-c3cc(F)cc(N4CCn5c(cc6c5CC(C)(C)C6)C4=O)c3CO)cn(C)c2=O)nn1C)C1COC1] | 10-[5-Fluoro-2-(Hydroxymethyl)-3-{1-methyl-5-[(1-methyl-5-{[methyl(oxetan-3-yl)amino]methyl}-1H-pyrazol-3-yl)amino]-6-oxo-1,6-dihydropyridin-3-yl}phenyl]-4,4-dimethyl-1,10-diazatricyclo[6.4.0.0$^{2,6}$]dodeca-2(6),7-dien-9-one | 630 | |
| 322 | 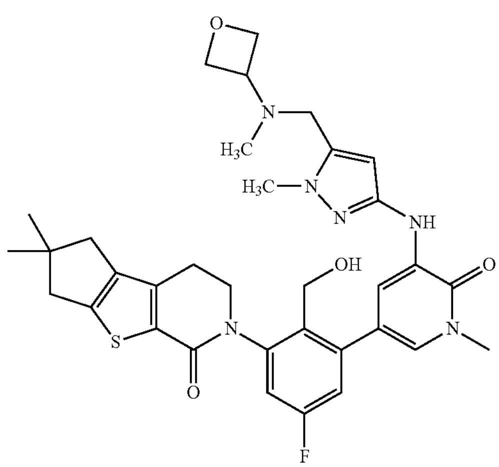 [SMILES: CN(Cc1cc(Nc2cc(-c3cc(F)cc(N4CCc5c(sc6c5CC(C)(C)C6)C4=O)c3CO)cn(C)c2=O)nn1C)C1COC1] | 10-[5-Fluoro-2-(hydroxymethyl)-3-{1-methyl-5-[(1-methyl-5-{[methyl(oxetan-3-yl)amino]methyl}-1H-pyrazol-3-yl)amino]-6-oxo-1,6-dihydropyridin-3-yl}phenyl]-4,4-dimethyl-7-thia-10-azatricyclo[6.4.0.0$^{2,6}$]dodeca-1(8),2(6)-dien-9-one | 647 | |
| 323 | 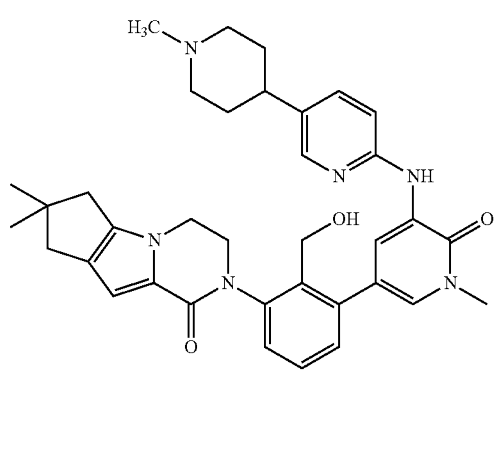 [SMILES: CN1CCC(c2ccc(Nc3cc(-c4cccc(N5CCn6c(cc7c6CC(C)(C)C7)C5=O)c4CO)cn(C)c3=O)nc2)CC1] | 10-[2-(Hydroxymethyl)-3-(1-methyl-5-{[5-(1-methylpiperidin-4-yl)pyridin-2-yl]amino}-6-oxopyridin-3-yl)phenyl]-4,4-dimethyl-1,10-diaza-tricyclo[6.4.0.0$^{2,6}$]dodeca-2(6),7-dien-9-one | 607 | |

TABLE 2-continued

| No. | Structure | Name | MH+ m/z | Btk IC$_{50}$ (μMol) |
|---|---|---|---|---|
| 324 | 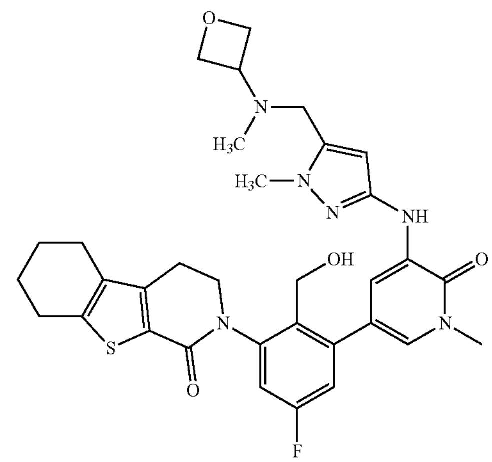 [SMILES: CN(Cc1cc(Nc2cc(-c3cc(F)cc(N4CCc5c(sc6c5CCCC6)C4=O)c3CO)cn(C)c2=O)nn1C)C1COC1] | 5-[5-fluoro-2-(hydroxymethyl)-5-[1-methyl-5-({1-methyl-5-(N-methyl, N-oxetan-3-ylaminomethyl)-1H-pyrazol-3-yl}amino)-6-oxo-1,6-dihydropyridin-3-yl]phenyl]-8-thia-5-azatricyclo-[7.4.0.0$^{2,7}$]trideca-1(9),2(7)-dien-6-one | 633 | |
| 325 | 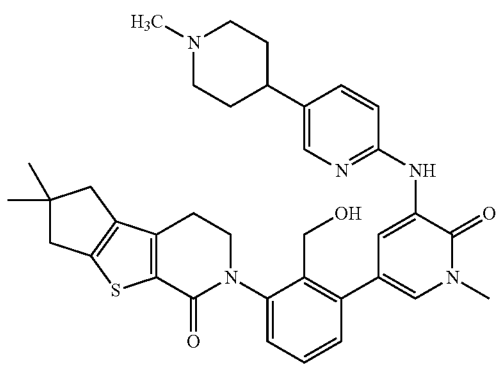 [SMILES: CN1CCC(c2ccc(Nc3cc(-c4cccc(N5CCc6c(sc7c6CC(C)(C)C7)C5=O)c4CO)cn(C)c3=O)nc2)CC1] | 10-[2-(hydroxymethyl)-3-[1-methyl-5-({5-[1-(methylpiperidin-4-yl)pyridine-2-yl]amino)-6-oxo-1,6-dihydropyridin-3-yl]phenyl)-4,4-dimethyl-7-thia-10-azatricyclo-[6.4.0.0$^{2,6}$]dodeca-1(8),2(6)-dien-9-one | 624 | |
| 326 | 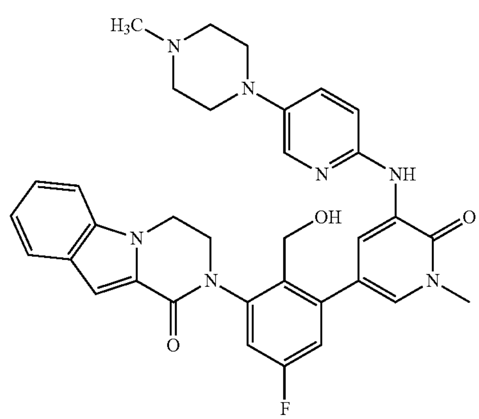 [SMILES: CN1CCN(c2ccc(Nc3cc(-c4cc(F)cc(N5CCn6c(cc7ccccc76)C5=O)c4CO)cn(C)c3=O)nc2)CC1] | 2-(5-fluoro-2-(hydroxymethyl)-3-(1-methyl-5-(5-(4-methylpiperazin-1-yl)pyridine-2-ylamino)-6-oxo-1,6-dihydropyridin-3-yl)phenyl)-3,4-dihydropyrazino[1,2-a]indol-1(2H)-one | 608 | |

TABLE 2-continued

| No. | Structure | Name | MH+ m/z | Btk IC$_{50}$ (µMol) |
|---|---|---|---|---|
| 327 | 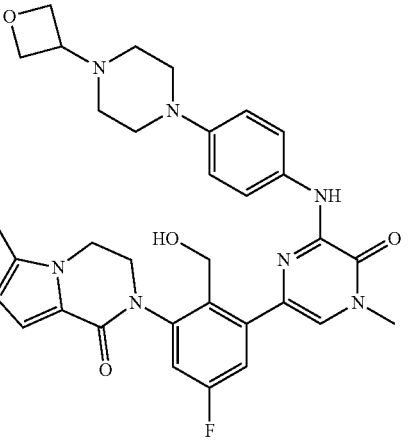 | 5-[5-fluoro-2-(hydroxymethyl)-3-{1-oxo-1H,2H,3H,4H,6H,7H,8H,9H-pyrazino[1,2-a]indol-2-yl}phenyl]-1-methyl-3-{[4-(oxetan-3-yl)piperazin-1-yl]}phenyl}amino}-1,2-dihydropyrazin-2-one | 654.8 | |
| 328 | 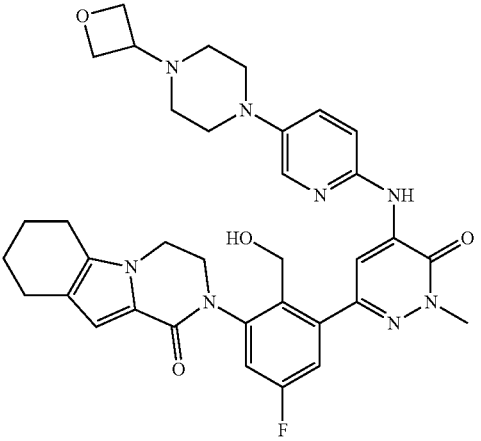 [SMILES: Cn1nc(-c2cc(F)cc(N3CCn4c(cc5c4CCCC5)C3=O)c2CO)cc(Nc2ccc(N3CCN(C4COC4)CC3)cn2)c1=O] | 5-[5-fluoro-2-(hydroxymethyl)-3-{1-oxo-1H,2H,3H,4H,6H,7H,8H,9H-pyrazino[1,2-a]indol-2-yl}phenyl]-2-methyl-4-{[4-(oxetan-3-yl)piperazin-1-yl]}phenyl}amino}-2,3-dihydropyrazin-3-one | 655.3 | |
| 329 | 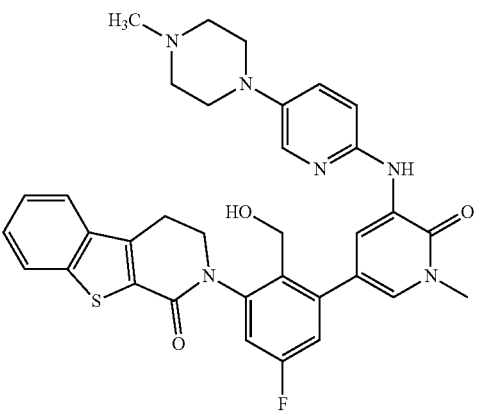 [SMILES: CN1CCN(c2ccc(Nc3cc(-c4cc(F)cc(N5CCc6c(sc7ccccc67)C5=O)c4CO)cn(C)c3=O)nc2)CC1] | 2-(5-fluoro-2-(hydroxymethyl)-3-(1-methyl-5-(5-(4-methylpiperazin-1-yl)pyridine-2-ylamino)-6-oxo-1,6-dihydropyridin-3-yl)phenyl)-3,4-dihydro-2H-[1]benzothiolo[2,3-c]pyridine-1-one | 625 | |

TABLE 2-continued

| No. | Structure | Name | MH+ m/z | Btk IC$_{50}$ (μMol) |
|---|---|---|---|---|
| 330 | 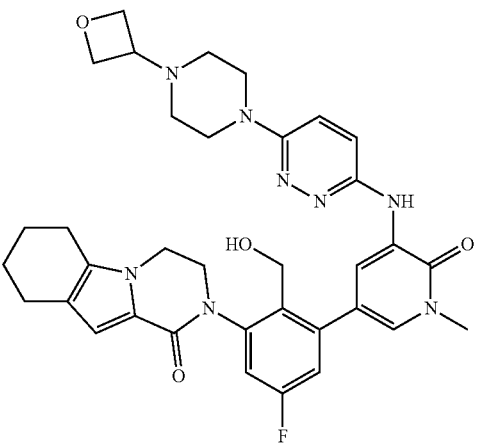 [SMILES: Cn1cc(-c2cc(F)cc(N3CCn4c(cc5c4CCCC5)C3=O)c2CO)cc(Nc2ccc(N3CCN(C4COC4)CC3)nn2)c1=O] | 5-[5-fluoro-2-(hydroxymethyl)-3-{1-oxo-1H,2H,3H,4H,6H,7H,8H,9H-pyrazino[1,2-a]indol-2-yl}phenyl]-1-methyl-3-({5-[4-(oxetan-3-yl)piperazin-1-yl]pyrazin-2-yl}amino)-1,2-dihydropyridin-2-one | 655 | |
| 331 | 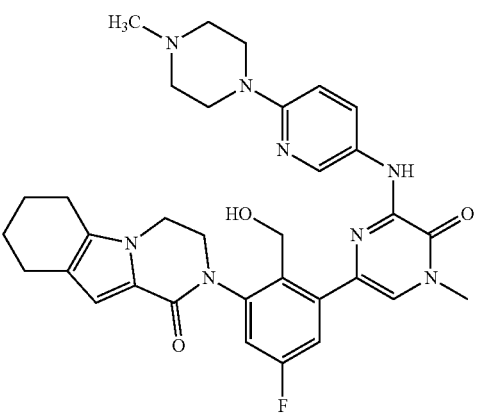 [SMILES: CN1CCN(c2ccc(Nc3nc(-c4cc(F)cc(N5CCn6c(cc7c6CCCC7)C5=O)c4CO)cn(C)c3=O)cn2)CC1] | 5-[5-fluoro-2-(hydroxymethyl)-3-{1-oxo-1H,2H,3H,4H,6H,7H,8H,9H-pyrazino[1,2-a]indol-2-yl}phenyl]-1-methyl-3-{[4-methylpiperazin-1-yl]phenyl]amino}-1,2-dihydropyrazin-2-one | 613 | |
| 332 | 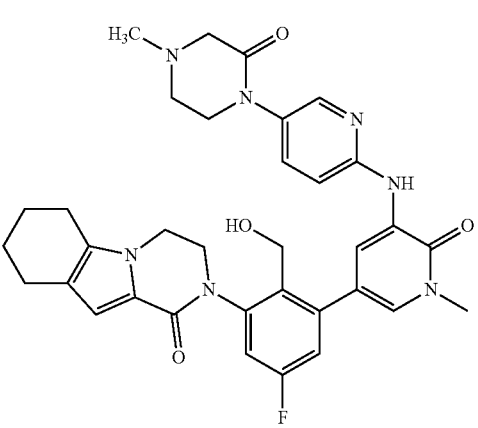 [SMILES: CN1CCN(c2ccc(Nc3cc(-c4cc(F)cc(N5CCn6c(cc7c6CCCC7)C5=O)c4CO)cn(C)c3=O)nc2)C(=O)C1] | 2-(5-fluoro-2-(hydroxymethyl)-3-(1-methyl-5-(5-(4-methyl-2-oxopiperazin-1-yl)pyridine-2-ylamino)-6-oxo-1,6-dihydropyridin-3-yl)phenyl)-3,4,6,7,8,9-hexahydropyrazino[1,2-a]indol-1(2H)-one | 626 | |

TABLE 2-continued

| No. | Structure | Name | MH+ m/z | Btk IC$_{50}$ (μMol) |
|---|---|---|---|---|
| 333 | 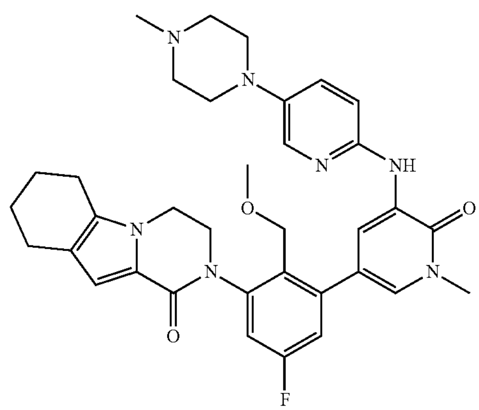 [SMILES: COCc1c(-c2cc(Nc3ccc(N4CCN(C)CC4)cn3)c(=O)n(C)c2)cc(F)cc1N1CCn2c(cc3c2CCCC3)C1=O] | 2-(5-fluoro-2-(methoxymethyl)-3-(1-methyl-5-(5-(4-methylpiperazin-1-yl)pyridine-2-ylamino)-6-oxo-1,6-dihydropyridin-3-yl)phenyl)-3,4,6,7,8,9-hexahydropyrazino[1,2-a]indol-1(2H)-one | 626 | |
| 334 | 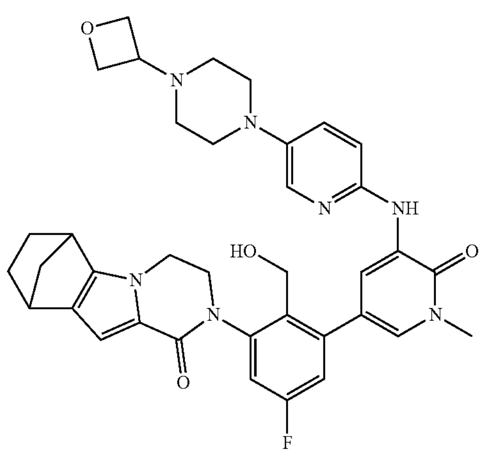 [SMILES: Cn1cc(-c2cc(F)cc(N3CCn4c(cc5c4C4CCC5C4)C3=O)c2CO)cc(Nc2ccc(N3CCN(C4COC4)CC3)cn2)c1=O] | 2-(5-fluoro-2-(hydroxymethyl)-3-(1-methyl-5-(5-(4-(oxetan-3-yl)-piperazin-1-yl)pyridine-2-ylamino)-6-oxo-1,6-dihydropyridin-3-yl)phenyl)-3,4,6,7,8,9-hexahydro-6,9-methanopyrazino[1,2-a]indol-1(2H)-one | 666 | |
| 335 | | 2-(5-fluoro-2-(hydroxymethyl)-3-(1-methyl-5-(5-(5-methylhexahydropyrrolo[3,4-c]pyrrol-2(1H)-yl)pyridin-2-ylamino)-6-oxo-1,6-dihydropyridin-3-yl)phenyl)-3,4,6,7,8,9-hexahydropyrazino[1,2-a]indol-1(2H)-one | 638.3 | |

TABLE 2-continued

| No. | Structure | Name | MH+ m/z | Btk IC$_{50}$ (μMol) |
|---|---|---|---|---|
| 336 | 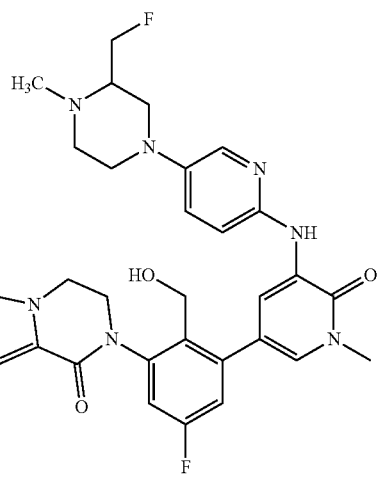 | 2-(5-fluoro-2-(hydroxymethyl)-3-(1-methyl-5-(5-(4-methyl-3-fluoromethyl-piperazin-1-yl)pyridine-2-ylamino)-6-oxo-1,6-dihydropyridin-3-yl)phenyl)-3,4,6,7,8,9-hexahydropyrazino[1,2-a]indol-1(2H)-one | 644 | |
| 337 | 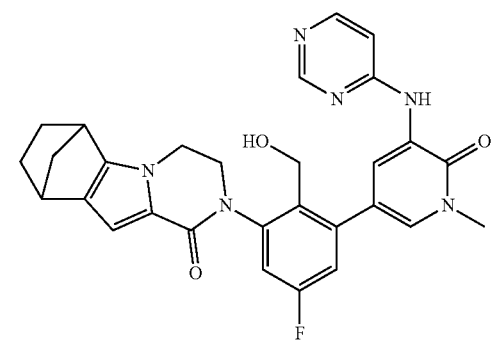 [SMILES: Cn1cc(-c2cc(F)cc(N3CCn4c(cc5c4C4CCC5C4)C3=O)c2CO)cc(Nc2ccncn2)c1=O] | 2-(5-fluoro-2-(hydroxymethyl)-3-(1-methyl-6-oxo-5-(pyrimidin-4-ylamino)-1,6-dihydropyridin-3-yl)phenyl)-3,4,6,7,8,9-hexahydro-6,9-methanopyrazino[1,2-a]indol-1(2H)-one | 527 | |
| 338 | 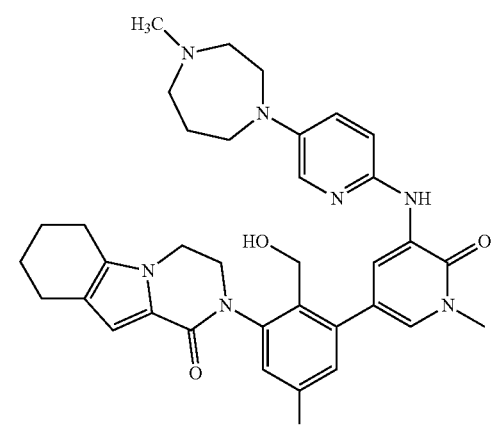 | 2-(5-fluoro-2-(hydroxymethyl)-3-(1-methyl-5-(5-(4-methyl-1,4-diazepan-1-yl)pyridin-2-ylamino)-6-oxo-1,6-dihydropyridin-3-yl)phenyl)-3,4,6,7,8,9-hexahydropyrazino[1,2-a]indol-1(2H)-one | 626 | |

163 164

TABLE 2-continued

| No. | Structure | Name | MH+ m/z | Btk IC$_{50}$ (μMol) |
|---|---|---|---|---|
| 339 | 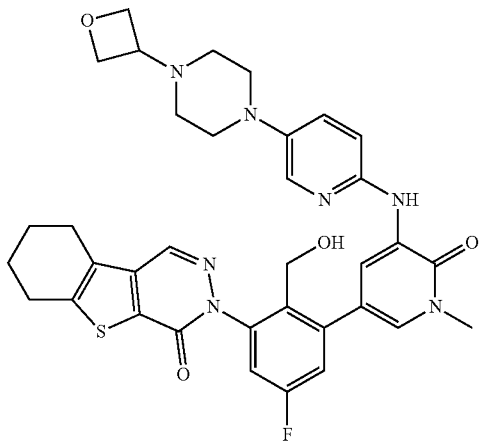 [SMILES: Cn1cc(-c2cc(F)cc(-n3ncc4c5c(sc4c3=O)CCCC5)c2CO)cc(Nc2ccc(N3CCN(C4COC4)CC3)cn2)c1=O] | 5-[5-fluoro-2-(hydroxymethyl)-3-[1-methyl-5-({5-[4-(oxetan-3-yl)piperazin-1-yl]pyridine-2-yl}amino)-6-oxo-1,6-dihydropyridin-3-yl]phenyl]-8-thia-4,5-diazatricyclo[7.4.0.0$^{2,7}$]-trideca-1(9),2(7),3(4)-trien-6-one | 670 | |
| 340 | 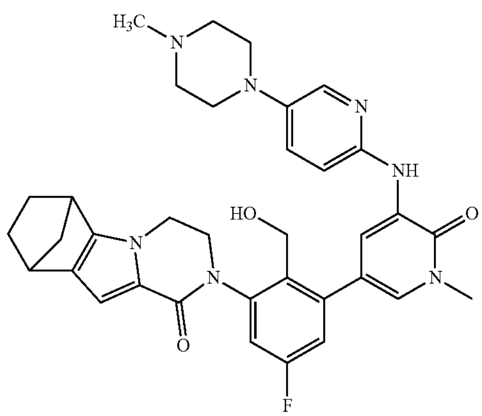 [SMILES: CN1CCN(c2ccc(Nc3cc(-c4cc(F)cc(N5CCn6c(cc7c6C6CCC7C6)C5=O)c4CO)cn(C)c3=O)nc2)CC1] | 2-(5-fluoro-2-(hydroxymethyl)-3-(1-methyl-5-(5-(4-methylpiperazin-1-ylpyridin-2-ylamino)-6-oxo-1,6-dihydropyridin-3-yl)phenyl)-3,4,6,7,8,9-hexahydro-6,9-methanopyrazino[1,2-a]indol-1(2H)-one | 624 | |
| 341 | 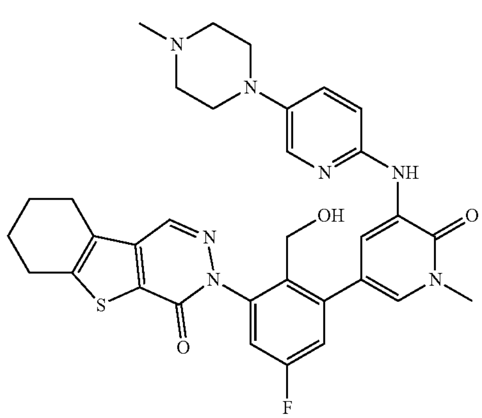 [SMILES: CN1CCN(c2ccc(Nc3cc(-c4cc(F)cc(-n5ncc6c7c(sc6c5=O)CCCC7)c4CO)cn(C)c3=O)nc2)CC1] | 5-[5-fluoro-2-(hydroxymethyl)-3-[1-methyl-5-({5-[4-methylpiperazin-1-yl]pyridine-2-yl}amino)-6-oxo-1,6-dihydropyridin-3-yl]phenyl]-8-thia-4,5-diazatricyclo[7.4.0.0$^{2,7}$]-trideca-1(9),2(7),3(4)-trien-6-one | 628 | |

TABLE 2-continued

| No. | Structure | Name | MH+ m/z | Btk IC$_{50}$ (μMol) |
|---|---|---|---|---|
| 342 | 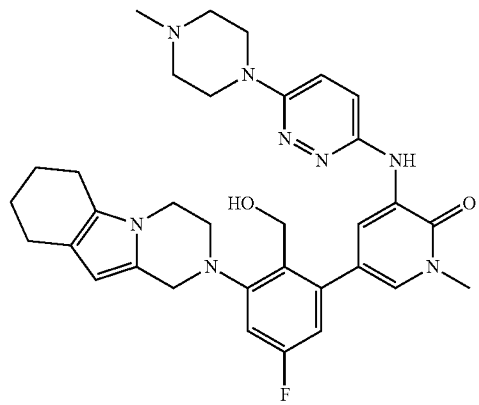 [SMILES: CN1CCN(c2ccc(Nc3cc(-c4cc(F)cc(N5CCn6c(cc7c6CCCC7)C5)c4CO)cn(C)c3=O)nn2)CC1] | 2-(5-fluoro-2-(hydroxymethyl)-3-(1-methyl-5-(6-(4-methylpiperazin-1-yl)pyridazin-3-ylamino)-6-oxo-1,6-dihydropyridin-3-yl)phenyl)-3,4,6,7,8,9-hexahydropyrazino[1,2-a]indol-1(2H)-one | 613 | |

TABLE 3

| No. | Structure | Name | MH+ m/z |
|---|---|---|---|
| 343 | 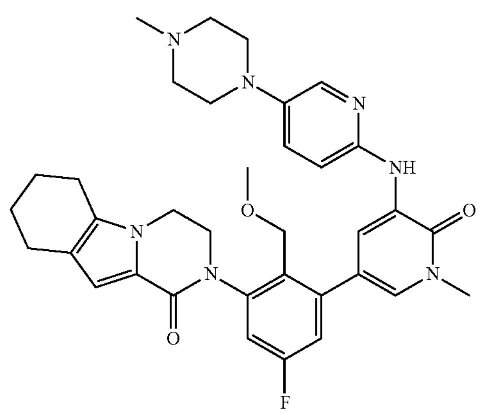 [SMILES: COCc1c(-c2cc(Nc3ccc(N4CCN(C)CC4)cn3)c(=O)n(C)c2)cc(F)cc1N1CCn2c(cc3c2CCCC3)C1=O] | 2-(5-fluoro-2-(methoxymethyl)-3-(1-methyl-5-(5-(4-methylpiperazin-1-yl)pyridin-2-ylamino)-6-oxo-1,6-dihydropyridin-3-yl)phenyl)-3,4,6,7,8,9-hexahydropyrazino[1,2-a]indol-1(2H)-one | 626.3 |
| 344 | 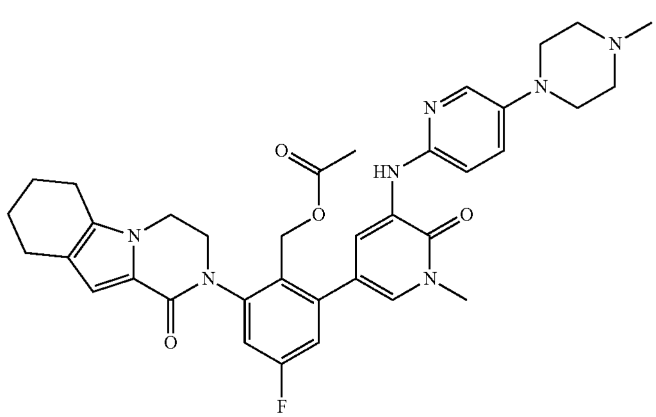 [SMILES: CC(=O)OCc1c(-c2cc(Nc3ccc(N4CCN(C)CC4)cn3)c(=O)n(C)c2)cc(F)cc1N1CCn2c(cc3c2CCCC3)C1=O] | 4-fluoro-2-(1-methyl-5-(5-(4-methylpiperazin-1-yl)pyridin-2-ylamino)-6-oxo-1,6-dihydropyridin-3-yl)-6-(1-oxo-3,4,6,7,8,9-hexahydropyrazino[1,2-a]indol-2(1H)-yl)benzyl acetate | 654.3 |

TABLE 3-continued

| No. | Structure | Name | MH+ m/z |
|---|---|---|---|
| 345 | 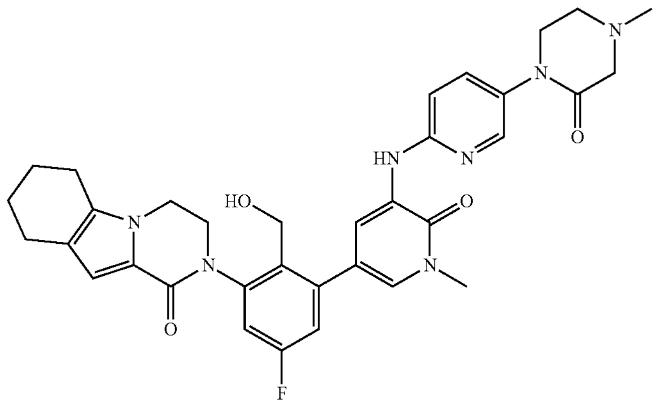 [SMILES: CN1CCN(c2ccc(Nc3cc(-c4cc(F)cc(N5CCn6c(cc7c6CCCC7)C5=O)c4CO)cn(C)c3=O)nc2)C(=O)C1] | 2-(5-fluoro-2-(hydroxymethyl)-3-(1-methyl-5-(5-(4-methyl-2-oxopiperazin-1-yl)pyridin-2-ylamino)-6-oxo-1,6-dihydropyridin-3-yl)phenyl)-3,4,6,7,8,9-hexahydropyrazino[1,2-a]indol-1(2H)-one | 626.3 |
| 346 | 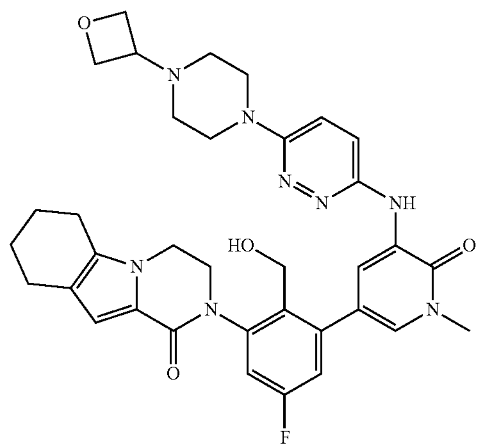 [SMILES: Cn1cc(-c2cc(F)cc(N3CCn4c(cc5c4CCCC5)C3=O)c2CO)cc(Nc2ccc(N3CCN(C4COC4)CC3)nn2)c1=O] | 2-(5-fluoro-2-(hydroxymethyl)-3-(1-methyl-5-(6-(4-(oxetan-3-yl)piperazin-1-yl)pyridazin-3-ylamino)-6-oxo-1,6-dihydropyridin-3-yl)phenyl)-3,4,6,7,8,9-hexahydropyrazino[1,2-a]indol-1(2H)-one | 655.3 |
| 347 | 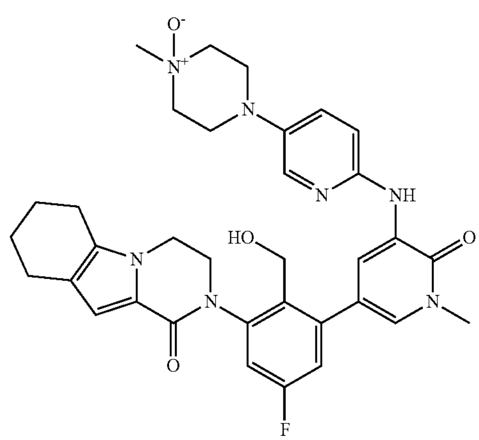 [SMILES: Cn1cc(-c2cc(F)cc(N3CCn4c(cc5c4CCCC5)C3=O)c2CO)cc(Nc2ccc(N3CC[N+](C)([O-])CC3)cn2)c1=O] | 4-(6-(5-(5-fluoro-2-(hydroxymethyl)-3-(1-oxo-3,4,6,7,8,9-hexahydropyrazino[1,2-a]indol-2(1H)-yl)phenyl)-1-methyl-2-oxo-1,2-dihydropyridin-3-ylamino)pyridin-3-yl)-1-methylpiperazine 1-oxide | 628.3 |

TABLE 3-continued

| No. | Structure | Name | MH+ m/z |
|---|---|---|---|
| 348 | 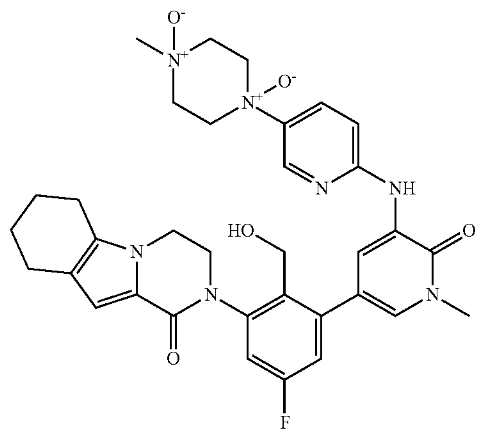 [SMILES: Cn1cc(-c2cc(F)cc(N3CCn4c(cc5c4CCCC5)C3=O)c2CO)cc(Nc2ccc([N+]3([O-])CC[N+](C)([O-])CC3)cn2)c1=O] | 1-(6-(5-(5-fluoro-2-(hydroxymethyl)-3-(1-oxo-3,4,6,7,8,9-hexahydropyrazino[1,2-a]indol-2(1H)-yl)phenyl)-1-methyl-2-oxo-1,2-dihydropyridin-3-ylamino)pyridin-3-yl)-4-methylpiperazine 1,4-dioxide | 644.3 |
| 349 | 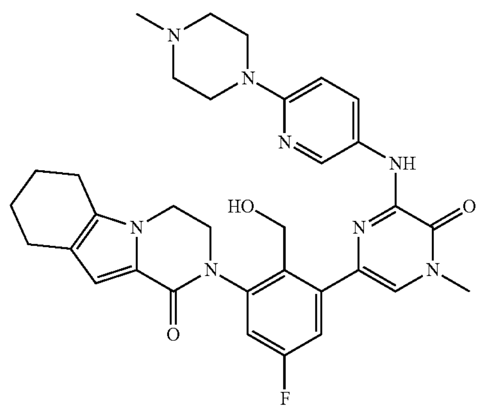 [SMILES: CN1CCN(c2ccc(Nc3nc(-c4cc(F)cc(N5CCn6c(cc7c6CCCC7)C5=O)c4CO)cn(C)c3=O)cn2)CC1] | 2-(5-fluoro-2-(hydroxymethyl)-3-(4-methyl-6-(6-(4-methylpiperazin-1-yl)pyridin-3-ylamino)-5-oxo-4,5-dihydropyrazin-2-yl)phenyl)-3,4,6,7,8,9-hexahydropyrazino[1,2-a]indol-1(2H)-one | 613.3 |
| 350 | 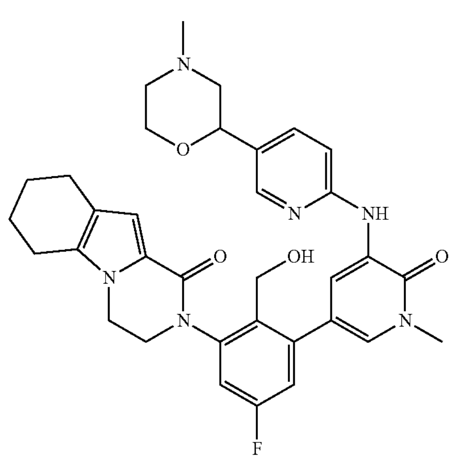 [SMILES: CN1CCOC(c2ccc(Nc3cc(-c4cc(F)cc(N5CCn6c(cc7c6CCCC7)C5=O)c4CO)cn(C)c3=O)nc2)C1] | 2-(5-fluoro-2-(hydroxymethyl)-3-(1-methyl-5-(5-(4-methylmorpholin-2-yl)pyridin-2-ylamino)-6-oxo-1,6-dihydropyridin-3-yl)phenyl)-3,4,6,7,8,9-hexahydropyrazino[1,2-a]indol-1(2H)-one | 613.3 |

| No. | Structure | Name | MH+ m/z |
|---|---|---|---|
| 351 | 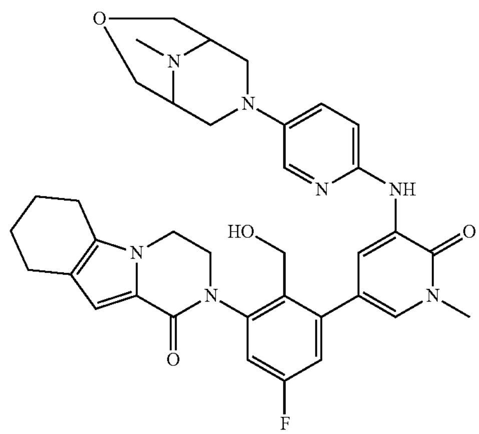 [SMILES: CN1C2COCC1CN(c1ccc(Nc3cc(-c4cc(F)cc(N5CCn6c(cc7c6CCCC7)C5=O)c4CO)cn(C)c3=O)nc1)C2] | 2-(5-fluoro-2-(hydroxymethyl)-3-(1-methyl-5-(5-(9-methyl-3-oxa-7,9-diazabicyclo[3.3.1]nonan-7-yl)pyridin-2-ylamino)-6-oxo-1,6-dihydropyridin-3-yl)phenyl)-3,4,6,7,8,9-hexahydropyrazino[1,2-a]indol-1(2H)-one | 654.3 |
| 352 | 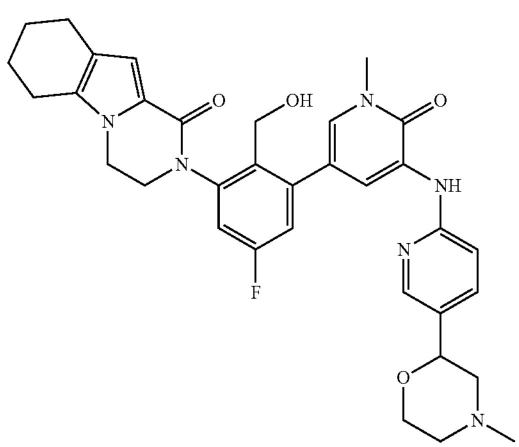 [SMILES: CN1CCOC(c2ccc(Nc3cc(-c4cc(F)cc(N5CCn6c(cc7c6CCCC7)C5=O)c4CO)cn(C)c3=O)nc2)C1] | 2-(5-fluoro-2-(hydroxymethyl)-3-(1-methyl-5-(5-(4-methylmorpholin-2-yl)pyridin-2-ylamino)-6-oxo-1,6-dihydropyridin-3-yl)phenyl)-3,4,6,7,8,9-hexahydropyrazino[1,2-a]indol-1(2H)-one | 613.3 |
| 353 | 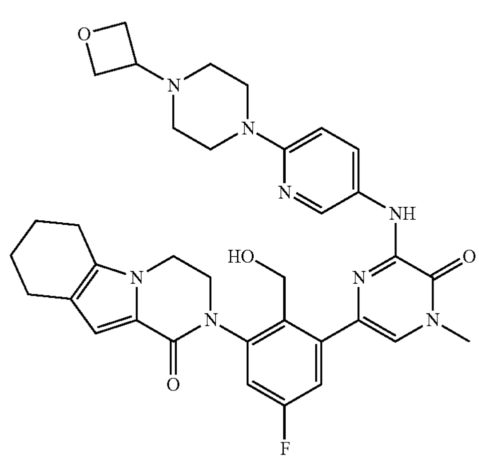 [SMILES: Cn1cc(-c2cc(F)cc(N3CCn4c(cc5c4CCCC5)C3=O)c2CO)nc(Nc2ccc(N3CCN(C4COC4)CC3)nc2)c1=O] | 2-(5-fluoro-2-(hydroxymethyl)-3-(4-methyl-6-(6-(4-(oxetan-3-yl)piperazin-1-yl)pyridin-3-ylamino)-5-oxo-4,5-dihydropyrazin-2-yl)phenyl)-3,4,6,7,8,9-hexahydropyrazino[1,2-a]indol-1(2H)-one | 655.3 |

TABLE 3-continued

| No. | Structure | Name | MH+ m/z |
|---|---|---|---|
| 354 | 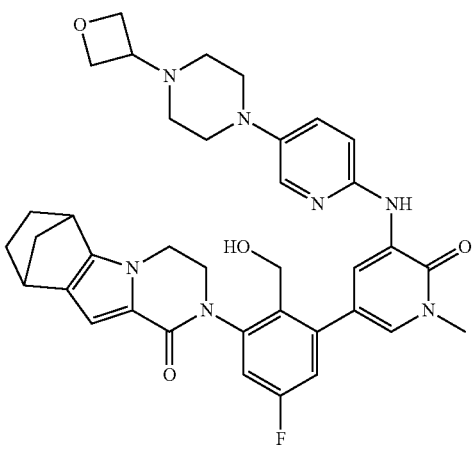 [SMILES: Cn1cc(-c2cc(F)cc(N3CCn4c(cc5c4C4CCC5C4)C3=O)c2CO)cc(Nc2ccc(N3CCN(C4COC4)CC3)cn2)c1=O] | 2-(5-fluoro-2-(hydroxymethyl)-3-(1-methyl-6-oxo-5-(3-(4-(oxetan-3-yl)piperazin-1-yl)pyrid-6-ylamino)-1,6-dihydropyridin-3-yl)phenyl)-3,4,6,7,8,9-hexahydro-6,9-methanopyrazino[1,2-a]indol-1(2H)-one | 666.3 |
| 355 | 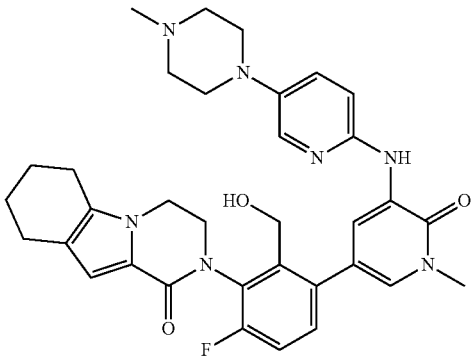 [SMILES: CN1CCN(c2ccc(Nc3cc(-c4ccc(F)c(N5CCn6c(cc7c6CCCC7)C5=O)c4CO)cn(C)c3=O)nc2)CC1] | 2-(6-fluoro-2-(hydroxymethyl)-3-(1-methyl-5-(5-(4-methylpiperazin-1-yl)pyridin-2-ylamino)-6-oxo-1,6-dihydropyridin-3-yl)phenyl)-3,4,6,7,8,9-hexahydropyrazino[1,2-a]indol-1(2H)-one | 612.3 |
| 356 | 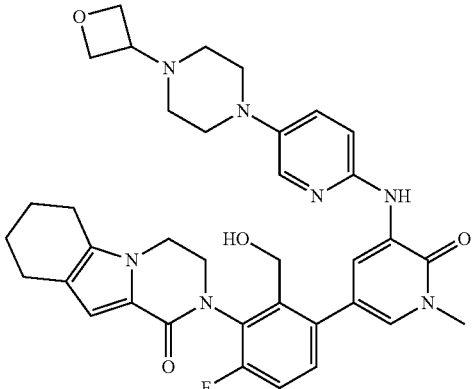 | 2-(6-fluoro-2-(hydroxymethyl)-3-(1-methyl-5-(5-(4-(oxetan-3-yl)piperazin-1-yl)pyridin-2-ylamino)-6-oxo-1,6-dihydropyridin-3-yl)phenyl)-3,4,6,7,8,9-hexahydropyrazino[1,2-a]indol-1(2H)-one | 654.3 |

TABLE 3-continued

| No. | Structure | Name | MH+ m/z |
|---|---|---|---|
| 357 | 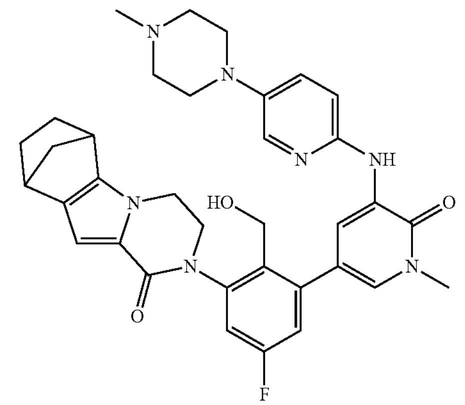 [SMILES: CN1CCN(c2ccc(Nc3cc(-c4cc(F)cc(N5CCn6c(cc7c6C6CCC7C6)C5=O)c4CO)cn(C)c3=O)nc2)CC1] | 2-(5-fluoro-2-(hydroxymethyl)-3-(1-methyl-6-oxo-5-(3-(4-methylpiperazin-1-yl)pyrid-6-ylamino)-1,6-dihydropyridin-3-yl)phenyl)-3,4,6,7,8,9-hexahydro-6,9-methanopyrazino[1,2-a]indol-1(2H)-one | 624.3 |
| 358 | 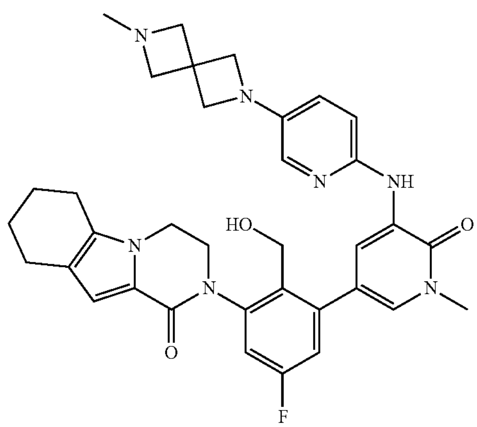 [SMILES: CN1CC2(C1)CN(c1ccc(Nc3cc(-c4cc(F)cc(N5CCn6c(cc7c6CCCC7)C5=O)c4CO)cn(C)c3=O)nc1)C2] | 2-(5-fluoro-2-(hydroxymethyl)-3-(1-methyl-5-(5-(6-methyl-2,6-diazaspiro[3.3]heptan-2-yl)pyridin-2-ylamino)-6-oxo-1,6-dihydropyridin-3-yl)phenyl)-3,4,6,7,8,9-hexahydropyrazino[1,2-a]indol-1(2H)-one | 624.3 |
| 359 | 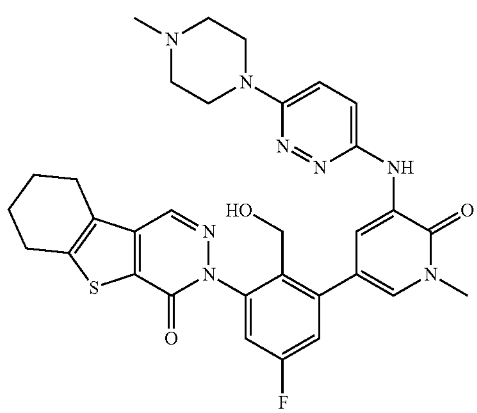 [SMILES: CN1CCN(c2ccc(Nc3cc(-c4cc(F)cc(-n5ncc6c7c(sc6c5=O)CCCC7)c4CO)cn(C)c3=O)nn2)CC1] | 3-(5-Fluoro-2-hydroxymethyl-3-{1-methyl-5-[6-(4-methyl-piperazin-1-yl)-pyridazin-3-ylamino]-6-oxo-1,6-dihydro-pyridin-3-yl}-phenyl)-6,7,8,9-tetrahydro-3H-benzo[4,5]thieno[2,3-d]pyridazin-4-one | 629.2 |

TABLE 3-continued

| No. | Structure | Name | MH+ m/z |
|---|---|---|---|
| 360 | 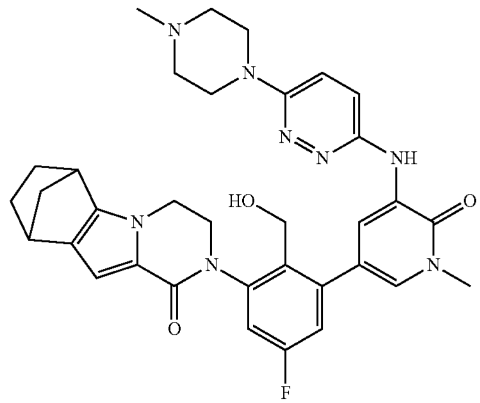 [SMILES: CN1CCN(c2ccc(Nc3cc(-c4cc(F)cc(N5CCn6c(cc7c6C6CCC7C6)C5=O)c4CO)cn(C)c3=O)nn2)CC1] | 2-(5-fluoro-2-(hydroxymethyl)-3-(1-methyl-6-oxo-5-(3-(4-methylpiperazin-1-yl)pyridazin-6-ylamino)-1,6-dihydropyridin-3-yl)phenyl)-3,4,6,7,8,9-hexahydro-6,9-methanopyrazino[1,2-a]indol-1(2H)-one | 625.3 |
| 361 | 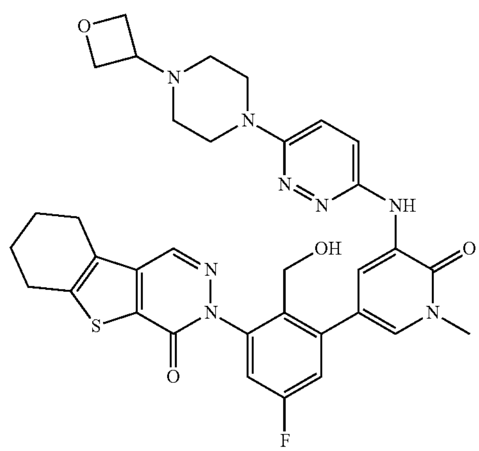 [SMILES: Cn1cc(-c2cc(F)cc(-n3ncc4c5c(sc4c3=O)CCCC5)c2CO)cc(Nc2ccc(N3CCN(C4COC4)CC3)nn2)c1=O] | 3-(5-Fluoro-2-hydroxymethyl-3-{1-methyl-5-[6-(4-oxetan-3-yl-piperazin-1-yl)-pyridazin-3-ylamino]-6-oxo-1,6-dihydro-pyridin-3-yl}-phenyl)-6,7,8,9-tetrahydro-3H-benzo[4,5]thieno[2,3-d]pyridazin-4-one | 671.2 |
| 362 | 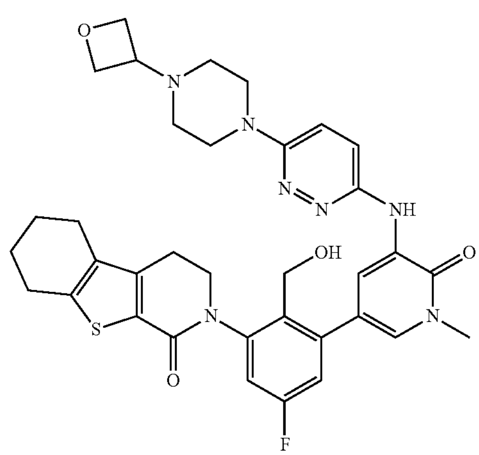 [SMILES: Cn1cc(-c2cc(F)cc(N3CCc4c(sc5c4CCCC5)C3=O)c2CO)cc(Nc2ccc(N3CCN(C4COC4)CC3)nn2)c1=O] | 2-(5-Fluoro-2-hydroxymethyl-3-{1-methyl-5-[6-(4-oxetan-3-yl-piperazin-1-yl)-pyridazin-3-ylamino]-6-oxo-1,6-dihydro-pyridin-3-yl}-phenyl)-3,4,5,6,7,8-hexahydro-2H-benzo[4,5]thieno[2,3-c]pyridin-1-one | 672.3 |

TABLE 3-continued

| No. | Structure | Name | MH+ m/z |
|---|---|---|---|
| 363 | 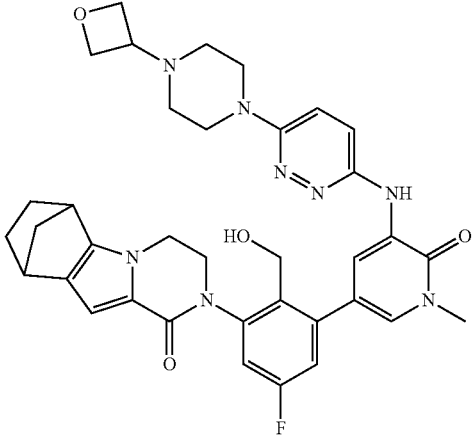 [SMILES: Cn1cc(-c2cc(F)cc(N3CCn4c(cc5c4C4CCC5C4)C3=O)c2CO)cc(Nc2ccc(N3CCN(C4COC4)CC3)nn2)c1=O] | 2-(5-fluoro-2-(hydroxymethyl)-3-(1-methyl-6-oxo-5-(3-(4-(oxetan-3-yl)piperazin-1-yl)pyridazin-6-ylamino)-1,6-dihydropyridin-3-yl)phenyl)-3,4,6,7,8,9-hexahydro-6,9-methanopyrazino[1,2-a]indol-1(2H)-one | 667.3 |
| 364 | 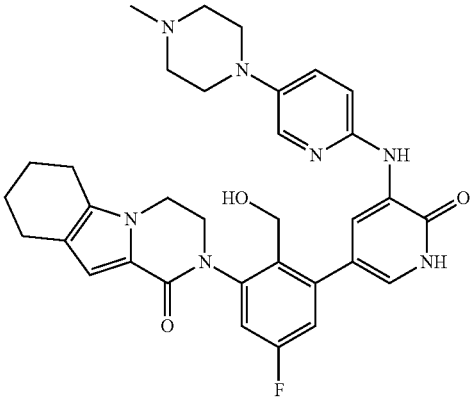 [SMILES: CN1CCN(c2ccc(Nc3cc(-c4cc(F)cc(N5CCn6c(cc7c6CCCC7)C5=O)c4CO)c[nH]c3=O)nc2)CC1] | 2-(5-fluoro-2-(hydroxymethyl)-3-(5-(5-(4-methylpiperazin-1-yl)pyridin-2-ylamino)-6-oxo-1,6-dihydropyridin-3-yl)phenyl)-3,4,6,7,8,9-hexahydropyrazino[1,2-a]indol-1(2H)-one | 598.3 |
| 365 | 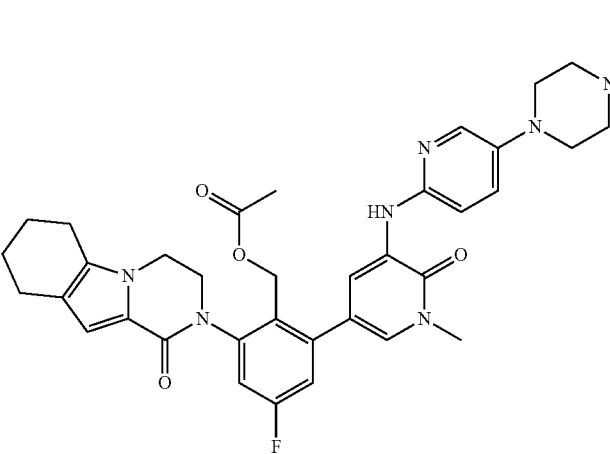 | 4-fluoro-2-(1-methyl-5-(5-(4-(oxetan-3-yl)piperazin-1-yl)pyridin-2-ylamino)-6-oxo-1,6-dihydropyridin-3-yl)-6-(1-oxo-3,4,6,7,8,9-hexahydropyrazino[1,2-a]indol-2(1H)-yl)benzyl acetate | 696.3 |

TABLE 3-continued

| No. | Structure | Name | MH+ m/z |
|---|---|---|---|
| 366 | 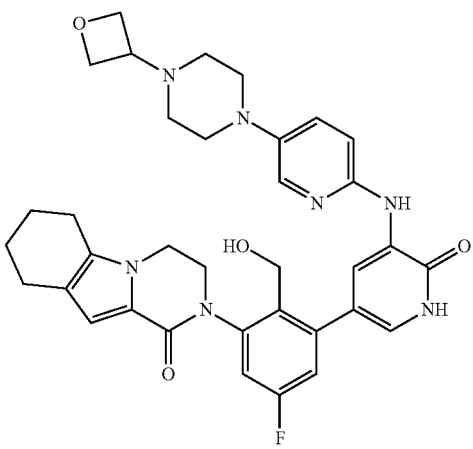 [SMILES: O=C1c2cc3c(n2CCN1c1cc(F)cc(-c2c[nH]c(=O)c(Nc4ccc(N5CCN(C6COC6)CC5)cn4)c2)c1CO)CCCC3] | 2-(5-fluoro-2-(hydroxymethyl)-3-(5-(5-(4-(oxetan-3-yl)piperazin-1-yl)pyridin-2-ylamino)-6-oxo-1,6-dihydropyridin-3-yl)phenyl)-3,4,6,7,8,9-hexahydropyrazino[1,2-a]indol-1(2H)-one | 640.3 |
| 367 | 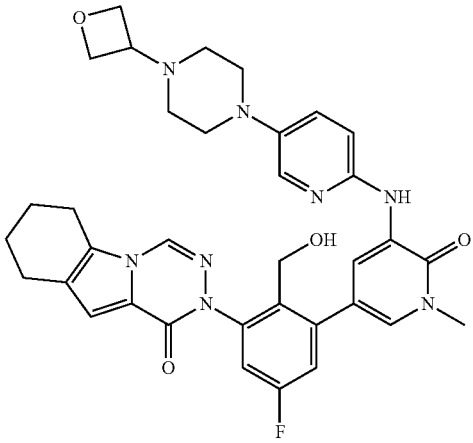 [SMILES: Cn1cc(-c2cc(F)cc(-n3ncn4c5c(cc4c3=O)CCCC5)c2CO)cc(Nc2ccc(N3CCN(C4COC4)CC3)cn2)c1=O] | 2-(5-fluoro-2-(hydroxymethyl)-3-(1-methyl-5-(5-(4-(oxetan-3-yl)piperazin-1-yl)pyridin-2-ylamino)-6-oxo-1,6-dihydropyridin-3-yl)phenyl)-6,7,8,9-tetrahydro-[1,2,4]triazino[4,5-a]indol-1(2H)-one | 653.3 |
| 368 | 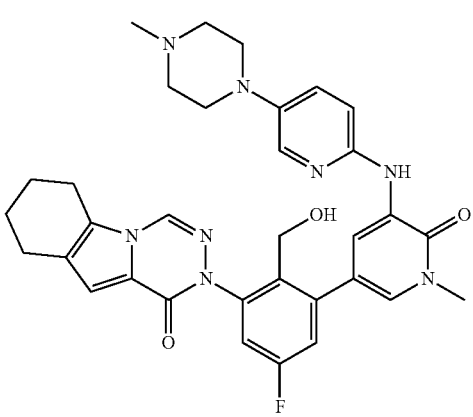 [SMILES: CN1CCN(c2ccc(Nc3cc(-c4cc(F)cc(-n5ncn6c7c(cc6c5=O)CCCC7)c4CO)cn(C)c3=O)nc2)CC1] | 2-(5-fluoro-2-(hydroxymethyl)-3-(1-methyl-5-(5-(4-methylpiperazin-1-yl)pyridin-2-ylamino)-6-oxo-1,6-dihydropyridin-3-yl)phenyl)-6,7,8,9-tetrahydro-[1,2,4]triazino[4,5-a]indol-1(2H)-one | 611.3 |

TABLE 3-continued

| No. | Structure | Name | MH+ m/z |
|---|---|---|---|
| 369 | 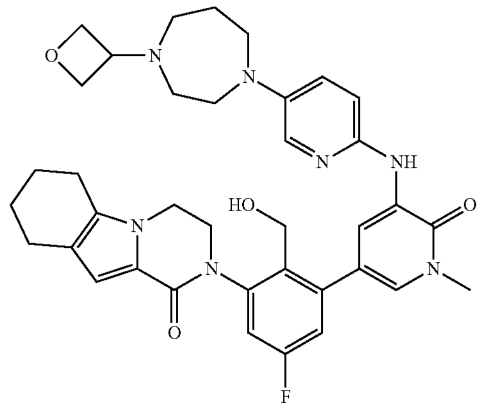 [SMILES: Cn1cc(-c2cc(F)cc(N3CCn4c(cc5c4CCCC5)C3=O)c2CO)cc(Nc2ccc(N3CCCN(C4COC4)CC3)cn2)c1=O] | 2-(5-fluoro-2-(hydroxymethyl)-3-(1-methyl-5-(5-(4-(oxetan-3-yl)-1,4-diazepan-1-yl)pyridin-2-ylamino)-6-oxo-1,6-dihydropyridin-3-yl)phenyl)-3,4,6,7,8,9-hexahydropyrazino[1,2-a]indol-1(2H)-one | 668.3 |
| 370 | 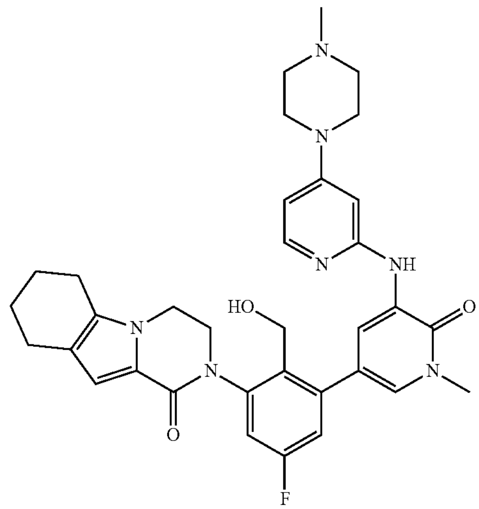 [SMILES: CN1CCN(c2ccnc(Nc3cc(-c4cc(F)cc(N5CCn6c(cc7c6CCCC7)C5=O)c4CO)cn(C)c3=O)c2)CC1] | 2-(5-fluoro-2-(hydroxymethyl)-3-(1-methyl-5-(4-(4-methylpiperazin-1-yl)pyridin-2-ylamino)-6-oxo-1,6-dihydropyridin-3-yl)phenyl)-3,4,6,7,8,9-hexahydropyrazino[1,2-a]indol-1(2H)-one | 612.3 |
| 371 | 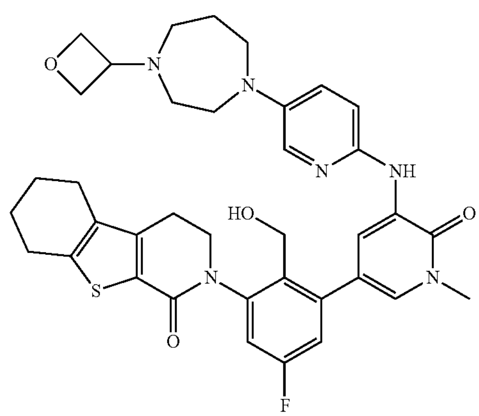 [SMILES: Cn1cc(-c2cc(F)cc(N3CCc4c(sc5c4CCCC5)C3=O)c2CO)cc(Nc2ccc(N3CCCN(C4COC4)CC3)cn2)c1=O] | 2-(5-Fluoro-2-hydroxymethyl-3-{1-methyl-5-[5-(4-oxetan-3-yl-[1,4]diazepan-1-yl)-pyridin-2-ylamino]-6-oxo-1,6-dihydro-pyridin-3-yl}-phenyl)-3,4,5,6,7,8-hexahydro-2H-benzo[4,5]thieno[2,3-c]pyridin-1-one | 685.3 |

Administration of Formula I Compounds

The compounds of the invention may be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

A dose to treat human patients may range from about 10 mg to about 1000 mg of Formula I compound. A typical dose may be about 100 mg to about 300 mg of the compound. A dose may be administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

Methods of Treatment with Formula I Compounds

Formula I compounds of the present invention are useful for treating a human or animal patient suffering from a disease or disorder arising from abnormal cell growth, function or behavior associated with Btk kinase such as an immune disorder, cardiovascular disease, viral infection, inflammation, a metabolism/endocrine disorder or a neurological disorder, may thus be treated by a method comprising the administration thereto of a compound of the present invention as defined above. A human or animal patient suffering from cancer may also be treated by a method comprising the administration thereto of a compound of the present invention as defined above. The condition of the patient may thereby be improved or ameliorated.

Formula I compounds may be useful for in vitro, in situ, and in vivo diagnosis or treatment of mammalian cells, organisms, or associated pathological conditions, such as systemic and local inflammation, immune-inflammatory diseases such as rheumatoid arthritis, immune suppression, organ transplant rejection, allergies, ulcerative colitis, Crohn's disease, dermatitis, asthma, systemic lupus erythematosus, Sjögren's Syndrome, multiple sclerosis, scleroderma/systemic sclerosis, idiopathic thrombocytopenic purpura (ITP), anti-neutrophil cytoplasmic antibodies (ANCA) vasculitis, chronic obstructive pulmonary disease (COPD), psoriasis, and for general joint protective effects.

Methods of the invention also include treating such diseases as arthritic diseases, such as rheumatoid arthritis, monoarticular arthritis, osteoarthritis, gouty arthritis, spondylitis; Behcet disease; sepsis, septic shock, endotoxic shock, gram negative sepsis, gram positive sepsis, and toxic shock syndrome; multiple organ injury syndrome secondary to septicemia, trauma, or hemorrhage; ophthalmic disorders such as allergic conjunctivitis, vernal conjunctivitis, uveitis, and thyroid-associated ophthalmopathy; eosinophilic granuloma; pulmonary or respiratory disorders such as asthma, chronic bronchitis, allergic rhinitis, ARDS, chronic pulmonary inflammatory disease (e.g., chronic obstructive pulmonary disease), silicosis, pulmonary sarcoidosis, pleurisy, alveolitis, vasculitis, emphysema, pneumonia, bronchiectasis, and pulmonary oxygen toxicity; reperfusion injury of the myocardium, brain, or extremities; fibrosis such as cystic fibrosis; keloid formation or scar tissue formation; atherosclerosis; autoimmune diseases, such as systemic lupus erythematosus (SLE), autoimmune thyroiditis, multiple sclerosis, some forms of diabetes, and Reynaud's syndrome; and transplant rejection disorders such as GVHD and allograft rejection; chronic glomerulonephritis; inflammatory bowel diseases such as chronic inflammatory bowel disease (CIBD), Crohn's disease, ulcerative colitis, and necrotizing enterocolitis; inflammatory dermatoses such as contact dermatitis, atopic dermatitis, psoriasis, or urticaria; fever and myalgias due to infection; central or peripheral nervous system inflammatory disorders such as meningitis, encephalitis, and brain or spinal cord injury due to minor trauma; Sjögren's syndrome; diseases involving leukocyte diapedesis; alcoholic hepatitis; bacterial pneumonia; antigen-antibody complex mediated diseases; hypovolemic shock; Type I diabetes mellitus; acute and delayed hypersensitivity; disease states due to leukocyte dyscrasia and metastasis; thermal injury; granulocyte transfusion-associated syndromes; and cytokine-induced toxicity.

The methods of the invention can have utility in treating subjects who are or can be subject to reperfusion injury, i.e., injury resulting from situations in which a tissue or organ experiences a period of ischemia followed by reperfusion. The term "ischemia" refers to localized tissue anemia due to obstruction of the inflow of arterial blood. Transient ischemia followed by reperfusion characteristically results in neutrophil activation and transmigration through the endothelium of the blood vessels in the affected area. Accumulation of activated neutrophils in turn results in generation of reactive oxygen metabolites, which damage components of the involved tissue or organ. This phenomenon of "reperfusion injury" is commonly associated with conditions such as vascular stroke (including global and focal ischemia), hemorrhagic shock, myocardial ischemia or infarction, organ transplantation, and cerebral vasospasm. To illustrate, reperfusion injury occurs at the termination of cardiac bypass procedures or during cardiac arrest when the heart, once prevented from receiving blood, begins to reperfuse. It is expected that inhibition of Btk activity may result in reduced amounts of reperfusion injury in such situations.

Pharmaceutical Formulations

In order to use a compound of this invention for the therapeutic treatment of mammals including humans, it is normally formulated in accordance with standard pharmaceutical practice as a pharmaceutical composition. According to this aspect of the invention there is provided a pharmaceutical composition comprising a compound of this invention in association with a pharmaceutically acceptable diluent or carrier.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration. For example, a compound of Formula I having the desired degree of purity may optionally be mixed with pharmaceutically acceptable diluents, carriers, excipients or stabilizers (Remington's Pharmaceutical Sciences (1980) 16th edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The compound ordinarily can be stored as a solid composition, a lyophilized formulation or as an aqueous solution.

The pharmaceutical compositions of the invention will be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to ameliorate, or treat the hyperproliferative disorder.

As a general proposition, the initial pharmaceutically effective amount of the inhibitor administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations of compounds of Formula I may be prepared. Suitable examples of sustained-release preparations include semipermeable matrices of solid hydrophobic polymers containing a compound of Formula I, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The formulations include those suitable for the administration routes detailed herein. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of Formula I suitable for oral administration may be prepared as discrete units such as pills, capsules, cachets or tablets each containing a predetermined amount of a compound of Formula I. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom. Tablets, troches, lozenges, aqueous or oil suspensions, dispersible powders or granules, emulsions, hard or soft capsules, e.g., gelatin capsules, syrups or elixirs may be prepared for oral use. Formulations of compounds of Formula I intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations are preferably applied as a topical ointment or cream containing the active ingredient (s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base. If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs. The oily phase of the emulsions of this invention may be constituted from known ingredients in a known manner. While the phase may comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of Formula I compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds of Formula I may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of Formula I may be employed alone or in combination with other therapeutic agents for the treatment of a disease or disorder described herein, such as inflammation or a hyperproliferative disorder (e.g., cancer). In certain embodiments, a compound of Formula I is combined in a pharmaceutical combination formulation, or dosing regimen as combination therapy, with a second therapeutic compound that has anti-inflammatory or anti-hyperproliferative properties or that is useful for treating an inflammation, immune-response disorder, or hyperproliferative disorder (e.g., cancer). The second therapeutic agent may be an NSAID anti-inflammatory agent. The second therapeutic agent may be a chemotherapeutic agent. The second compound of the pharmaceutical combination formulation or dosing regimen preferably has complementary activities to the compound of Formula I such that they do not adversely affect each other. Such compounds are suitably present in combination in amounts that are effective for the purpose intended. In one embodiment, a composition of this invention comprises a compound of Formula I, or a stereoisomer, tautomer, solvate, metabolite, or pharmaceutically acceptable salt or prodrug thereof, in combination with a therapeutic agent such as an NSAID.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other therapeutic agents or treatments.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes, separate pills or capsules, or separate infusions. In general, during alternation therapy, an effective dosage of each active ingredient is administered sequentially, i.e., serially, whereas in combination therapy, effective dosages of two or more active ingredients are administered together.

In a particular embodiment of therapy, a compound of Formula I, or a stereoisomer, tautomer, solvate, metabolite, or pharmaceutically acceptable salt or prodrug thereof, may be combined with other therapeutic, hormonal or antibody agents such as those described herein, as well as combined with surgical therapy and radiotherapy. Combination therapies according to the present invention thus comprise the administration of at least one compound of Formula I, or a stereoisomer, tautomer, solvate, metabolite, or pharmaceutically acceptable salt or prodrug thereof, and the use of at least one other cancer treatment method. The amounts of the compound(s) of Formula I and the other pharmaceutically active therapeutic agent(s) and the relative timings of administration will be selected in order to achieve the desired combined therapeutic effect.

Metabolites of Compounds of Formula I

Also falling within the scope of this invention are the in vivo metabolic products of Formula I described herein. Such products may result for example from the oxidation, reduction, hydrolysis, amidation, deamidation, esterification, deesterification, enzymatic cleavage, and the like, of the administered compound. Accordingly, the invention includes metabolites of compounds of Formula I, including compounds produced by a process comprising contacting a compound of this invention with a mammal for a period of time sufficient to yield a metabolic product thereof.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Articles of Manufacture

In another embodiment of the invention, an article of manufacture, or "kit", containing materials useful for the treatment of the diseases and disorders described above is provided. In one embodiment, the kit comprises a container comprising a compound of Formula I, or a stereoisomer, tautomer, solvate, metabolite, or pharmaceutically acceptable salt or prodrug thereof. The kit may further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of Formula I or a formulation thereof which is effective for treating the condition and may have a sterile access port (for example, the container may be an intravenous solution bag or a vial having a stopper pierceable by a hypodermic injection needle). At least one active agent in the composition is a compound of Formula I. The label or package insert indicates that the composition is used for treating the condition of choice, such as cancer. In addition, the label or package insert may indicate that the patient to be treated is one having a disorder such as a hyperproliferative disorder, neurodegeneration, cardiac hypertrophy, pain, migraine or a neurotraumatic disease or event. In one embodiment, the label or package inserts indicates that the composition comprising a compound of Formula I can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of Formula I and, if present, the second pharmaceutical formulation. For example, if the kit comprises a first composition comprising a compound of Formula I and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of Formula I, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a compound of Formula I contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a composition of Formula I and a second therapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

Preparation of Formula I Compounds

Compounds of Formula I may be synthesized by synthetic routes that include processes analogous to those well-known in the chemical arts, particularly in light of the description contained herein, and those for other heterocycles described in: Comprehensive Heterocyclic Chemistry II, Editors Katritzky and Rees, Elsevier, 1997, e.g. Volume 3; Liebigs Annalen der Chemie, (9):1910-16, (1985); Helvetica Chimica Acta, 41:1052-60, (1958); Arzneimittel-Forschung, 40(12):1328-31, (1990), each of which are expressly incorporated by reference. Starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-23, Wiley, N.Y. (1967-2006 ed.), or *Beilsteins Handbuch der organischen Chemie*, 4, Aufl. ed. Springer-Verlag, Berlin, including supplements (also available via the Beilstein online database).

Synthetic chemistry transformations and protecting group methodologies (protection and deprotection) useful in synthesizing Formula I compounds and necessary reagents and intermediates are known in the art and include, for example, those described in R. Larock, Comprehensive Organic Transformations, VCH Publishers (1989); T. W. Greene and P. G. M. Wuts, Protective Groups in Organic Synthesis, $3^{rd}$ Ed., John Wiley and Sons (1999); and L. Paquette, ed., Encyclopedia of Reagents for Organic Synthesis, John Wiley and Sons (1995) and subsequent editions thereof.

Compounds of Formula I may be prepared singly or as compound libraries comprising at least 2, for example 5 to 1,000 compounds, or 10 to 100 compounds. Libraries of compounds of Formula I may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds, or pharmaceutically acceptable salts thereof.

The Figures and Examples provide exemplary methods for preparing Formula I compounds. Those skilled in the art will appreciate that other synthetic routes may be used to synthesize the Formula I compounds. Although specific starting materials and reagents are depicted and discussed in the Figures and Examples, other starting materials and reagents can be easily substituted to provide a variety of derivatives and/or reaction conditions. In addition, many of the exemplary compounds prepared by the described methods can be further modified in light of this disclosure using conventional chemistry well known to those skilled in the art.

In preparing compounds of Formulas I, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

General Preparative Procedures

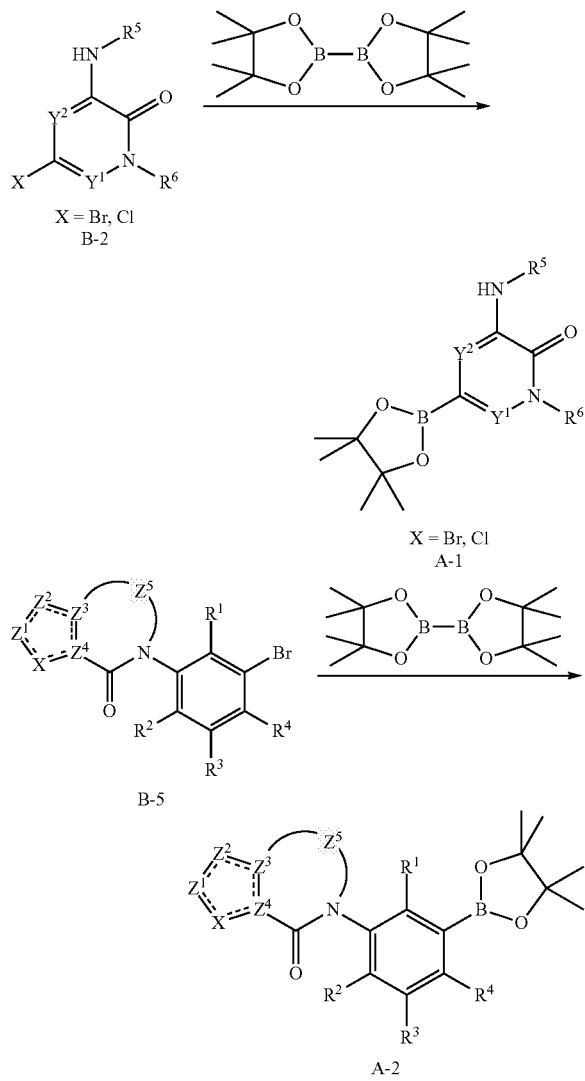

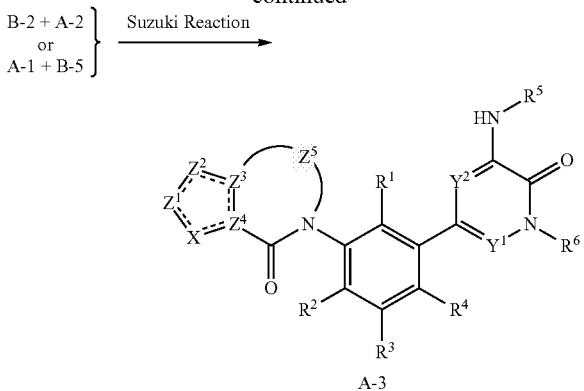

The Suzuki-type coupling reaction is useful to form carbon-carbon bonds to attach the rings of Formula I compounds and intermediates such as A-3 (Suzuki (1991) Pure Appl. Chem. 63:419-422; Miyaura and Suzuki (1979) Chem. Reviews 95(7):2457-2483; Suzuki (1999) J. Organometal. Chem. 576:147-168). Suzuki coupling is a palladium mediated cross coupling reaction of an arylhalide, such as B-2 or B-5, with a boronic acid such as A-1 or A-2. For example, B-2 may be combined with about 1.5 equivalents of 4,4,4',4',5,5,5',5'-octamethyl-2,2'-bi(1,3,2-dioxaborolane), and dissolved in about 3 equivalents of sodium carbonate as a 1 molar solution in water and an equal volume of acetonitrile. A catalytic amount, or more, of a low valent palladium reagent, such as bis(triphenylphosphine)palladium(II) dichloride, is added. In some cases potassium acetate is used in place of sodium carbonate to adjust the pH of the aqueous layer. The reaction is then heated to about 140-150° C. under pressure in a microwave reactor such as the Biotage Optimizer (Biotage, Inc.) for 10 to 30 minutes. The contents are extracted with ethyl acetate, or another organic solvent. After evaporation of the organic layer the boron ester A-1 may be purified on silica or by reverse phase HPLC. Substituents $Y^1$, $Y^2$, $R^5$ and $R^6$ are as defined, or protected forms or precursors thereof. Likewise, bromide intermediate B-5 can be boronylated to give A-2. Substituents $Y^1$, $Y^2$, $R^1$, $R^2$, $R^3$, $R^4$, $Z^1$, $Z^2$, $Z^3$, $Z^4$, and X are as defined, or protected forms or precursors thereof.

Suzuki coupling of B-2 and A-2, or of A-1 and B-5, gives Formula I compound or intermediate A-3. Boronic ester (or acid) (1.5 eq) A-1 or A-2, and a palladium catalyst such as bis(triphenylphosphine)palladium(II) chloride (0.05 eq) is added to a mixture of halo intermediate (1 eq) B-2 or B-5 in acetonitrile and 1 M of sodium carbonate aqueous solution (equal volume as acetonitrile). The reaction mixture is heated to about 150° C. in a microwave for about 15 min. LC/MS indicates when the reaction is complete. Water is added to the mixture, and the precipitated product is filtered and purified by HPLC to yield the product A-3. Substituents $R^{1'}$, $R^{2'}$, $R^{4'}$ may be $R^1$, $R^2$, $R^4$ as defined, or protected forms or precursors thereof.

A variety of palladium catalysts can be used during the Suzuki coupling step. Various low valent, Pd(II) and Pd(0) catalysts may be used in the Suzuki coupling reaction, including PdCl2(PPh$_3$)$_2$, Pd(t-Bu)$_3$, PdCl$_2$ dppf CH$_2$Cl$_2$, Pd(PPh$_3$)$_4$, Pd(OAc)/PPh$_3$, Cl$_2$Pd[(Pet$_3$)]$_2$, Pd(DIPHOS)$_2$, Cl$_2$Pd(Bipy), [PdCl(Ph$_2$PCH$_2$PPh$_2$)]$_2$, Cl$_2$Pd[P(o-tol)$_3$]$_2$, Pd$_2$(dba)$_3$/P(o-tol)$_3$, Pd$_2$(dba)/P(furyl)$_3$, Cl$_2$Pd[P(furyl)$_3$]$_2$, Cl$_2$Pd(PMePh$_2$)$_2$, Cl$_2$Pd[P(4-F-Ph)$_3$]$_2$, Cl$_2$Pd[P(C$_6$F$_6$)$_3$]$_2$, Cl$_2$Pd[P(2-COOH-Ph)(Ph)$_2$]$_2$, Cl$_2$Pd[P(4-COOH-Ph)(Ph)$_2$]

2, and encapsulated catalysts Pd EnCat™ 30, Pd EnCat™ TPP30, and Pd(II)EnCat™ BINAP30 (US 2004/0254066).

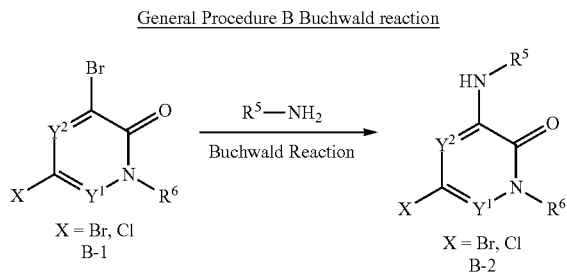

General Procedure B Buchwald reaction

The Buchwald reaction is useful to aminate 6-bromo intermediates B-1 (Wolf and Buchwald (2004) Org. Synth Coll. Vol. 10:423; Paul et al (1994) Jour. Amer. Chem. Soc. 116:5969-5970). To a solution of halo intermediate B-1 in DMF is added the appropriate amine $R^5$—$NH_2$ (200 mol %), $Cs_2CO_3$ (50 mol %), $Pd_2(dba)_3$ (5 mol %), and XANTPHOS (10 mol %). The reaction is heated to about 110° C. under pressure in a Biotage optimizer microwave reactor for about 30 min. The resulting solution is concentrated in vacuo to give B-2. Other palladium catalysts and phosphine ligands may be useful.

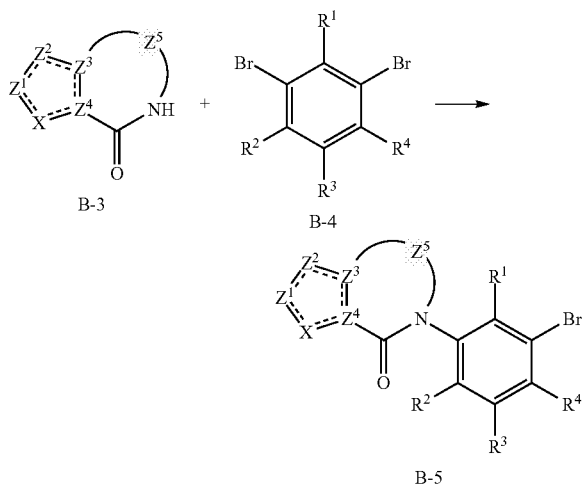

N-Aryl amide intermediates B-5 can also be prepared under Buchwald conditions with cyclic amide intermediates B-3 and aryl bromides B-4.

FIG. 1 shows an exemplary synthetic route to prepare 6-chloro,4-amino pyridazinone compounds, including 6-chloro-4-(5-methyl-4,5,6,7-tetrahydropyrazolo[1,5-a]pyrazin-2-ylamino)pyridazin-3(2H)-one 101f, from 3-nitropyrazole-5-carboxylic acid.

Figure 2:
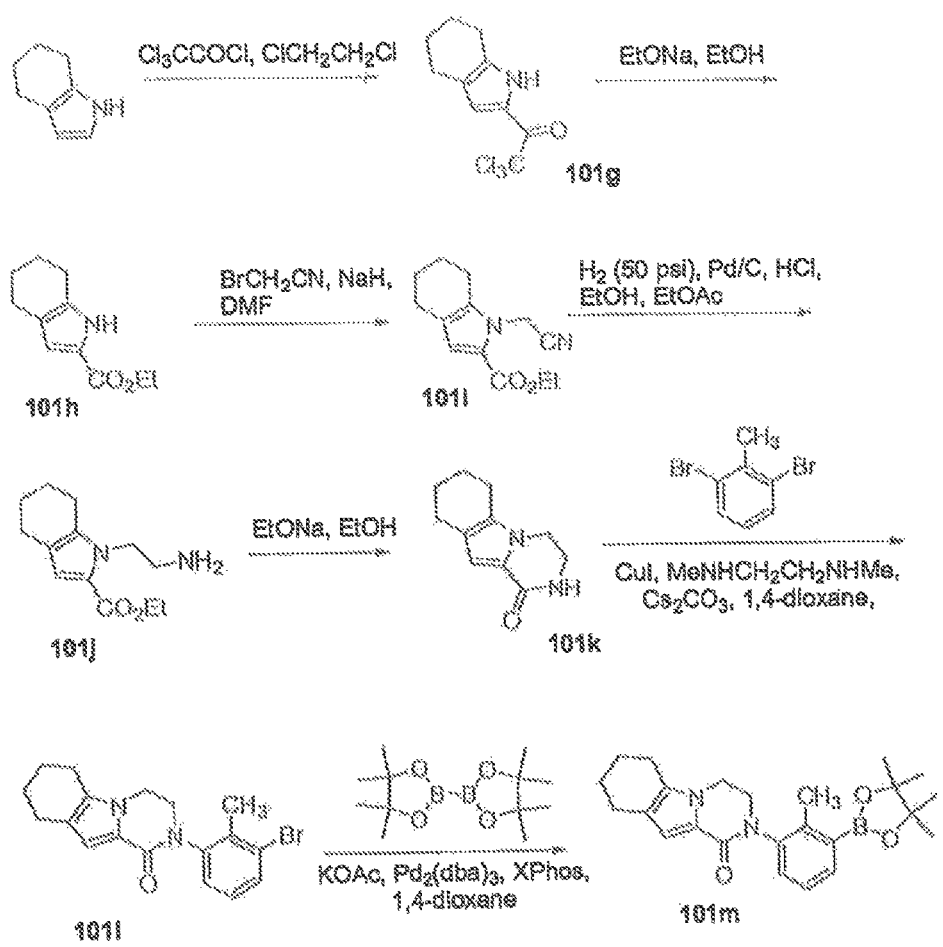
FIG. 2 shows an exemplary synthetic route to a tricyclic amide-phenyl boronate compounds, including 2-(2-methyl-3-(4,4,5,5-tetramethyl-1,3,2-dioxaborolan-2-yl)phenyl)-3,4,6,7,8,9-hexahydropyrazino[1,2-a]indol-1(2H)-one 101m, from 4,5,6,7-tetrahydro-1H-indole.

FIG. 2 shows an exemplary synthetic route to a tricyclic amide-phenyl boronate compounds, including 2-(2-methyl-3-(4,4,5,5-tetramethyl-1,3,2-dioxaborolan-2-yl)phenyl)-3,4,6,7,8,9-hexahydropyrazino[1,2-a]indol-1(2H)-one 101m, from 4,5,6,7-tetrahydro-1H-indole.

Figure 3:
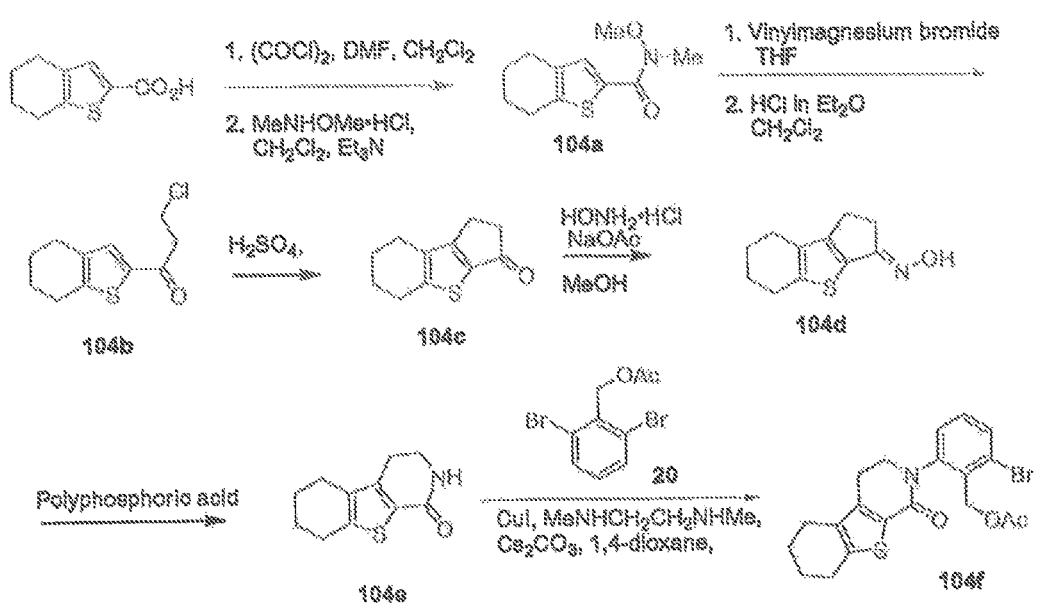
FIG. 3 shows an exemplary synthetic route to tricyclic amide-phenyl bromide compounds, including 2-bromo-6-(1-oxo-3,4,5,6,7,8-hexahydrobenzothieno[2,3-c]pyridin-2(1H)-yl)benzyl acetate 104h, from 4,5,6,7-tetrahydrobenzo[b]thiophene-2-carboxylic acid.

FIG. 3 shows an exemplary synthetic route to tricyclic amide-phenyl bromide compounds, including 2-bromo-6-(1-oxo-3,4,5,6,7,8-hexahydrobenzothieno[2,3-c]pyridin-2(1H)-yl)benzyl acetate 104h, from 4,5,6,7-tetrahydrobenzo[b]thiophene-2-carboxylic acid.

Figure 4:
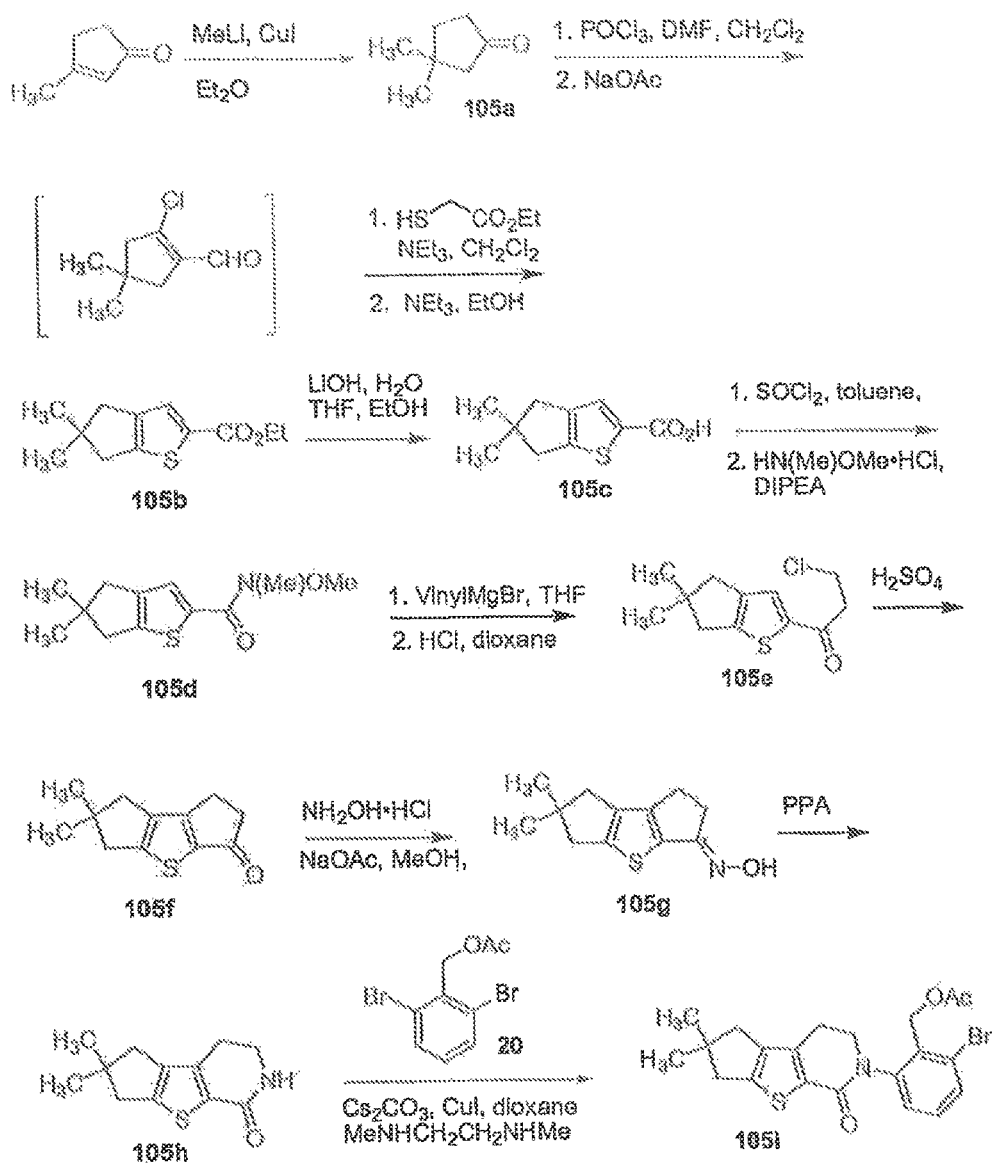
FIG. 4 shows another exemplary synthetic route to tricyclic amide-phenyl bromide compounds, including 6,6-dimethyl-3,4,6,7-tetrahydro-5H-cyclopenta[4,5]thieno[2,3-c]pyridine-1(2H)-one 105i, from 3-methylcyclopent-2-enone.

FIG. 4 shows another exemplary synthetic route to tricyclic amide-phenyl bromide compounds, including 6,6-dimethyl-3,4,6,7-tetrahydro-5H-cyclopenta[4,5]thieno[2,3-c]pyridine-1(2H)-one 105i, from 3-methylcyclopent-2-enone.

Figure 5:
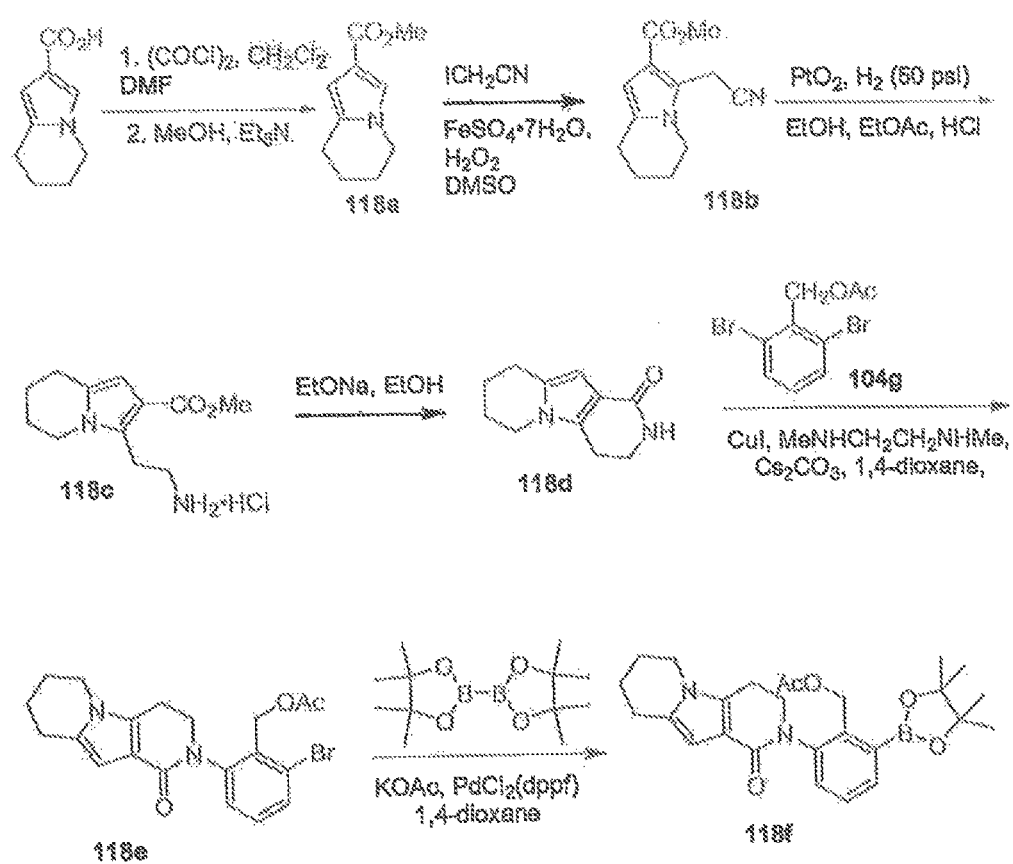
FIG. 5 shows an exemplary synthetic route to tricyclic 1,6-dihydropyridin-3-yl)phenyl)-3,4,6,7,8,9-hexahydropyrido[3,4-b]indolizin-1(2H)-one compounds as boronate esters, including 2-(1-Oxo-3,4,6,7,8,9-hexahydropyrido[3,4-b]indolizin-2(1H)-yl)-6-(4,4,5,5-tetramethyl-1,3,2-dioxaborolan-2-yl)benzyl Acetate 118f from 5,6,7,8-tetrahydroindolizine-2-carboxylic acid.

FIG. 5 shows an exemplary synthetic route to tricyclic 1,6-dihydropyridin-3-yl)phenyl)-3,4,6,7,8,9-hexahydropyrido[3,4-b]indolizin-1(2H)-one compounds as boronate esters, including 2-(1-oxo-3,4,6,7,8,9-hexahydropyrido[3,4-b]indolizin-2(1H)-yl)-6-(4,4,5,5-tetramethyl-1,3,2-dioxaborolan-2-yl)benzyl acetate 118f from 5,6,7,8-tetrahydroindolizine-2-carboxylic acid.

Figure 6:
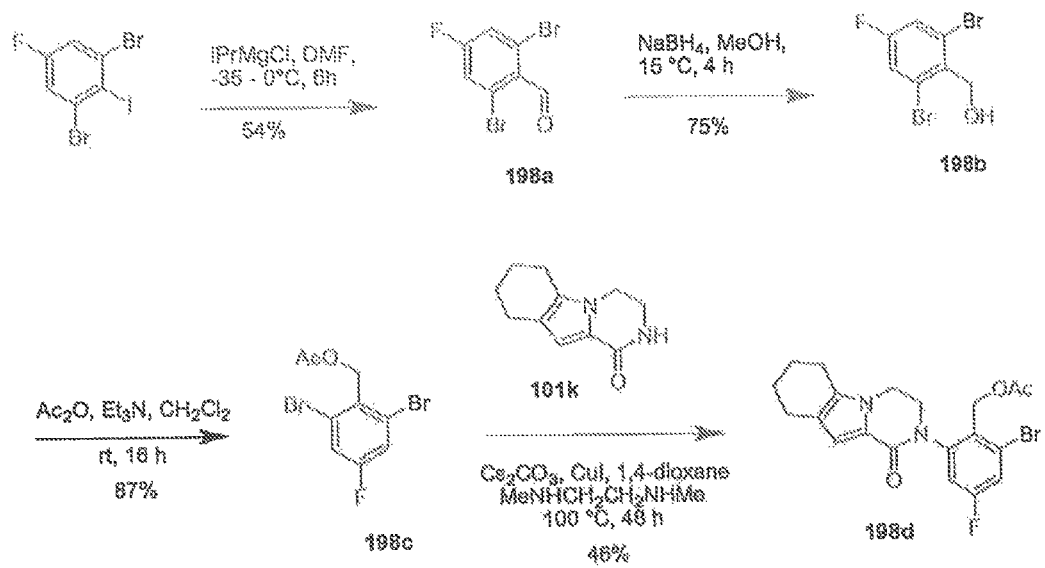
FIG. 6 shows an exemplary synthetic route to intermediate 2-Bromo-4-fluoro-6-(1-oxo-3,4,6,7,8,9-hexahydropyrazino[1,2-a]indol-2(1H)-yl)benzyl acetate 198d from 1,3-dibromo-5-fluoro-2-iodobenzene.

FIG. 6 shows an exemplary synthetic route to intermediate 2-Bromo-4-fluoro-6-(1-oxo-3,4,6,7,8,9-hexahydropyrazino[1,2-a]indol-2(1H)-yl)benzyl acetate 198d from 1,3-dibromo-5-fluoro-2-iodobenzene.

Figure 7:
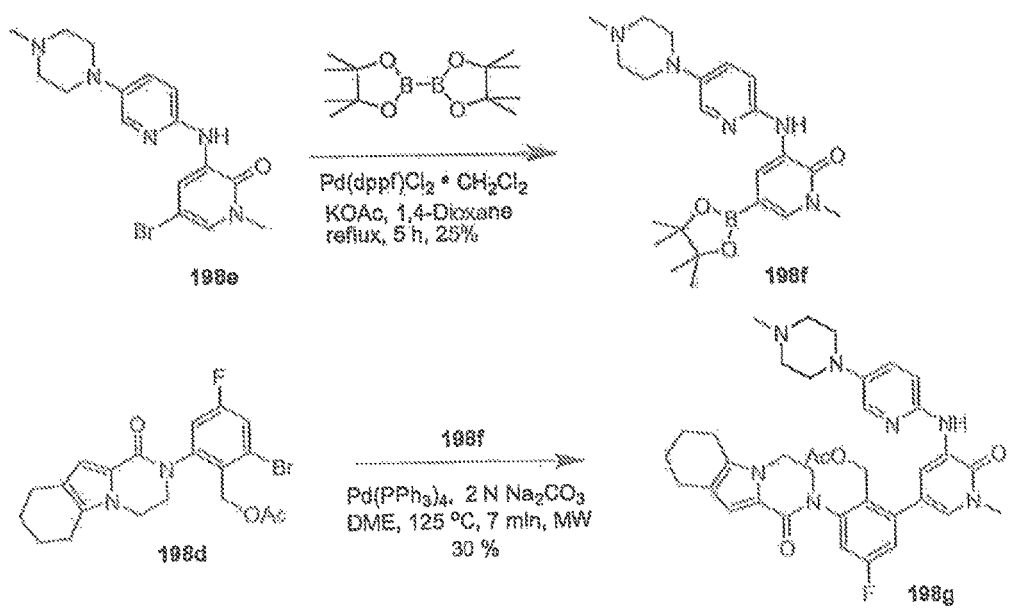
FIG. 7 shows an exemplary synthetic route to intermediate 4-Fluoro-2-(1-methyl-5-(5-(4-methylpiperazin-1-yl)pyridin-2-ylamino)-6-oxo-1,6-dihydropyridin-3-yl)-6-(1-oxo-3,4,6,7,8,9-hexahydropyrazino[1,2-a]indol-2(1H)-yl)benzyl acetate 198g.

FIG. 7 shows an exemplary synthetic route to intermediate 4-Fluoro-2-(1-methyl-5-(5-(4-methylpiperazin-1-yl)pyridin-2-ylamino)-6-oxo-1,6-dihydropyridin-3-yl)-6-(1-oxo-3,4,6,7,8,9-hexahydropyrazino[1,2-a]indol-2(1H)-yl)benzyl acetate 198g.

Figure 8:
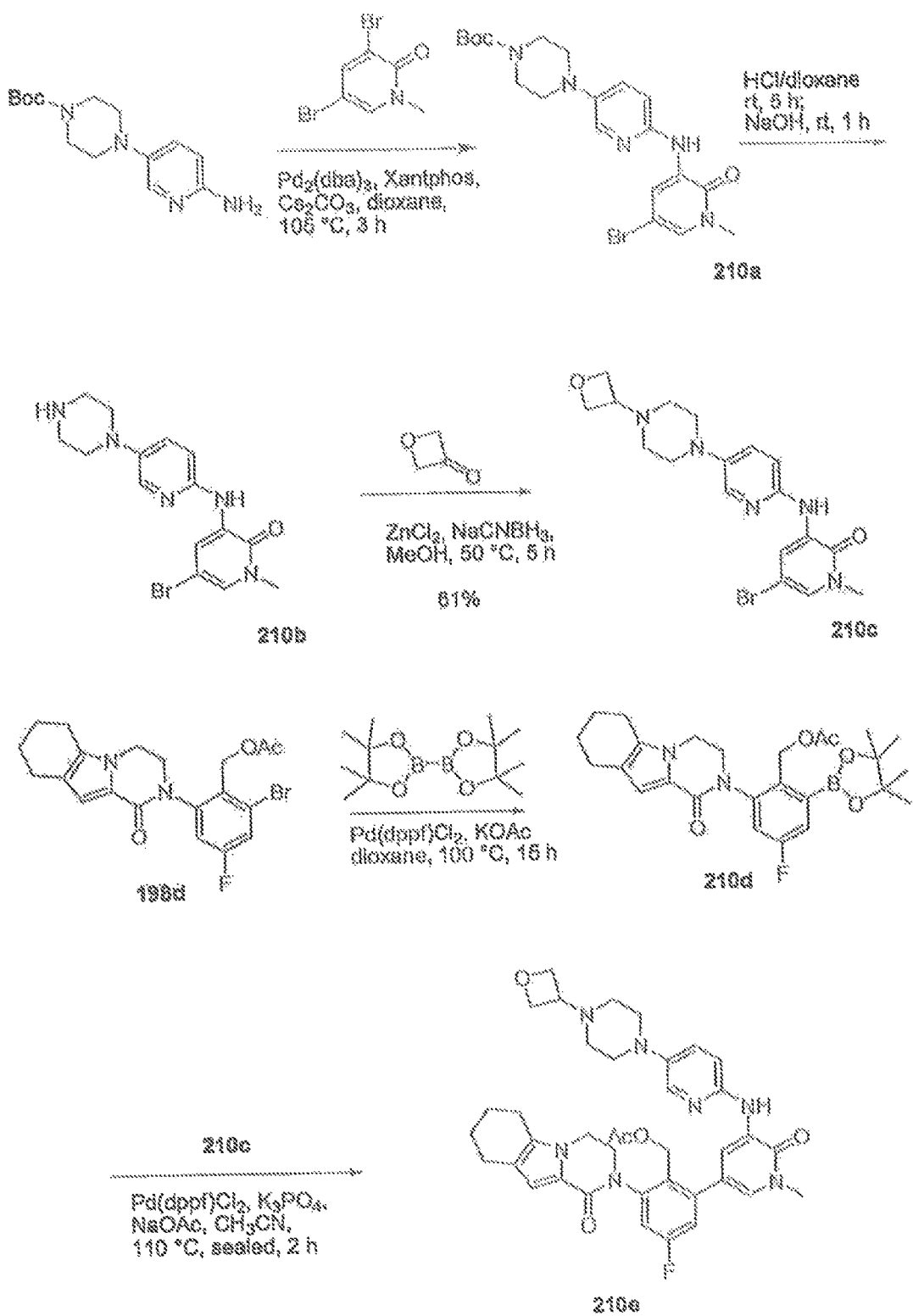
FIG. 8 shows an exemplary synthetic route to intermediate 5-Fluoro-2-(1-methyl-5-(5-(4-(oxetan-3-yl)piperazin-1-yl)pyridin-2-ylamino)-6-oxo-1,6-dihydropyridin-3-yl)-6-(1-oxo-3,4,6,7,8,9-hexahydropyrazino[1,2-a]indol-2(1H)-yl)benzyl acetate 210e.

FIG. 8 shows an exemplary synthetic route to intermediate 5-Fluoro-2-(1-methyl-5-(5-(4-(oxetan-3-yl)piperazin-1-yl)pyridin-2-ylamino)-6-oxo-1,6-dihydropyridin-3-yl)-6-(1-oxo-3,4,6,7,8,9-hexahydropyrazino[1,2-a]indol-2(1H)-yl) benzyl acetate 210e.

Figure 9:
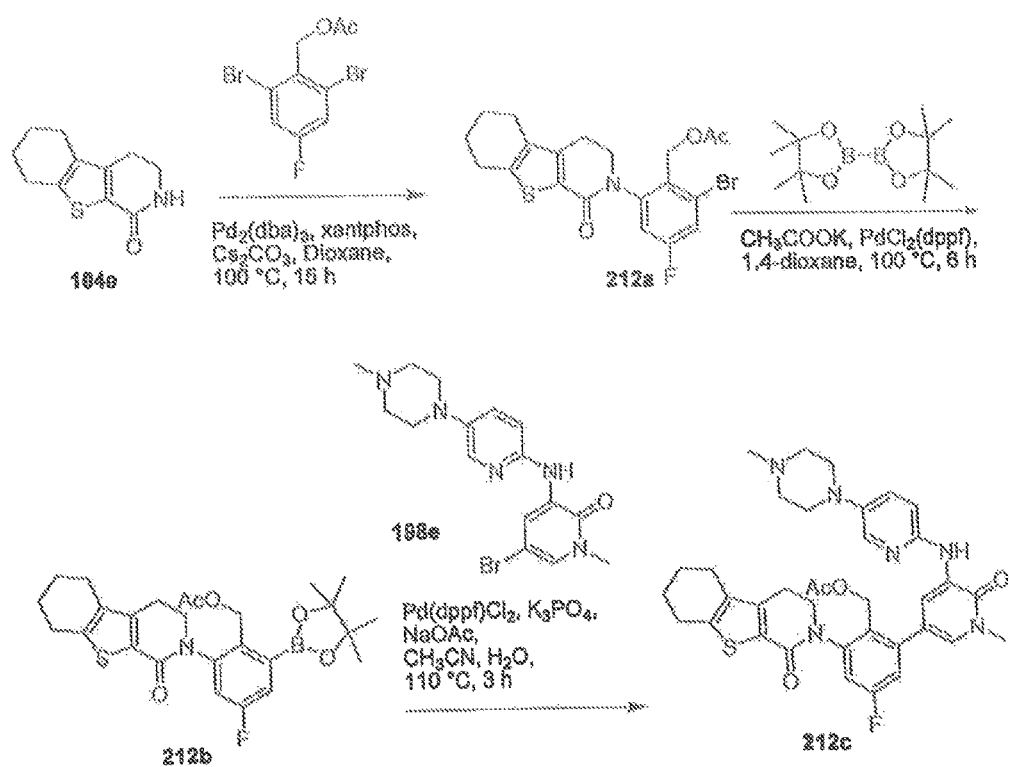
FIG. 9 shows an exemplary synthetic route to intermediate 5-[5-fluoro-2-(acetoxymethyl)-3-(1-methyl-5-{[5-(4-methylpiperazin-1-yl)pyridin-2-yl]amino}-6-oxo-1,6-dihydropyridin-3-yl)phenyl]-8-thia-5-azatricyclo[7.4.0.0$^{2,7}$]trideca-1(9),2(7)-dien-6-one 212c.

FIG. 9 shows an exemplary synthetic route to intermediate 5-[5-fluoro-2-(acetoxymethyl)-3-(1-methyl-5-{[5-(4-methylpiperazin-1-yl)pyridin-2-yl]amino}-6-oxo-1,6-dihydropyridin-3-yl)phenyl]-8-thia-5-azatricyclo[7.4.0.0$^{2,7}$]trideca-1(9),2(7)-dien-6-one 212c.

Methods of Separation

In the methods of preparing Formula I compounds, it may be advantageous to separate reaction products from one another and/or from starting materials. The desired products of each step or series of steps is separated and/or purified to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like. Selection of appropriate methods of separation depends on the nature of the materials involved, such as, boiling point and molecular weight in distillation and sublimation, presence or absence of polar functional groups in chromatography, stability of materials in acidic and basic media in multiphase extraction, and the like.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (-) menthyl chloroformate in the presence of base, or Mosher ester, α-methoxy-α-(trifluoromethyl)phenyl acetate (Jacob I I I. J. Org. Chem. (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. Chromatogr., (1990) 513:375-378). Enriched or purified enantiomers can be distinguished by methods used to distinguish other chiral molecules with asymmetric carbon atoms, such as optical rotation and circular dichroism.

EXAMPLES

Example 101 2-(2-methyl-3-(5-(5-methyl-4,5,6,7-tetrahydropyrazolo[1,5-a]pyrazin-2-ylamino)-6-oxo-1,6-dihydropyridazin-3-yl)phenyl)-3,4-dihydropyrazino[1,2-a]indol-1(2H)-one 101

Example 101a (3-Nitro-1H-pyrazol-5-yl)methanol 101a

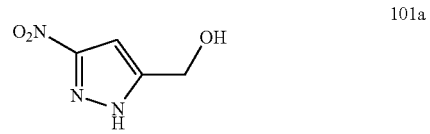

A 3-L three-neck round-bottomed flask equipped with a mechanical stirrer, addition funnel and nitrogen inlet was purged with nitrogen and charged with 3-nitropyrazole-5-carboxylic acid (28.0 g, 178 mmol) and THF (420 mL) and cooled to -5° C. using an ice/acetone bath. Borane-THF complex solution (1.0 M, 535 mL, 535 mmol) was added at a rate that maintained the internal reaction temperature below 5° C. After the addition was complete the cooling bath was removed and the reaction was stirred at room temperature for 18 h. After this time the reaction was cooled to -5° C. using an ice/acetone bath, water (70 mL) and 4N hydrochloric acid (70 mL) was added and the reaction was stirred at reflux for 1 h in order to destroy the borane complex with pyrazole. The reaction was cooled to room temperature and concentrated under reduced pressure to a volume of approximately 30 mL. Ethyl acetate (175 mL) was added and the mixture stirred for 15 min. The aqueous layer was separated and extracted with ethyl acetate (4×200 mL). The combined organic layers were washed with saturated aqueous sodium bicarbonate (2×50 mL), brine (50 mL) and dried over sodium sulfate, the drying agent was removed by filtration, and the filtrate concentrated under reduced pressure to afford 101a in a 94% yield (24.0 g) as a light yellow solid: $^1$H NMR (300 MHz, DMSO-d$_6$) δ 13.90 (br s, 1H), 6.87 (s, 1H), 5.58 (t, 1H, J=5.4 Hz), 4.53 (d, 2H, J=5.1 Hz); MS (ESI+) m/z 144.0 (M+H)

Example 101b (1-(2-Bromoethyl)-3-nitro-1H-pyrazol-5-yl)methanol 101b

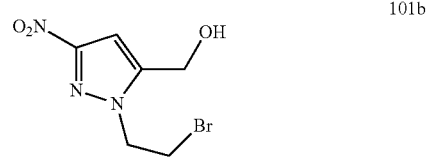 [SMILES: O=[N+]([O-])c1cc(CO)n(CCBr)n1]

A 1-L three-necked round-bottomed flask equipped with a mechanical stirrer and thermoregulator was purged with nitrogen and charged with (3-nitro-1H-pyrazol-5-yl)methanol 101a (25.0 g, 175 mmol), DMF (250 mL), and cesium carbonate (70.0 g, 215 mmol) was heated at 104° C. for 5 min. The reaction mixture was then cooled to 0° C. using an ice/acetone bath and dibromoethane (329 g, 1.75 mol) was added portionwise (no exotherm). The reaction was stirred at 0° C. for 1 then at room temperature for 4 h. After this time a solution of KH₂PO4 (40 g) in water (400 mL) was added slowly. The reaction mixture stirred at room temperature for 30 min. Ethyl acetate (450 mL) was added and the aqueous layer was separated and extracted with ethyl acetate (2×100 mL). The combined organic layers were washed with water (200 mL), brine (200 mL), dried over sodium sulfate, and the drying agent was removed by filtration. The filtrate was concentrated under reduced pressure to afford an 86% yield (37.5 g) of crude 101b as an orange oil: ¹H NMR (300 MHz, CDCl₃) δ 6.85 (s, 1H), 4.82 (d, 2H, J=5.4 Hz), 4.66 (t, 2H, J=6.3 Hz), 3.83 (t, 2H, J=6.3 Hz); MS (ESI+) m/z 249.9 (M+H).

Example 101c 1-(2-Bromoethyl)-5-(bromomethyl)-3-nitro-1H-pyrazole 101c

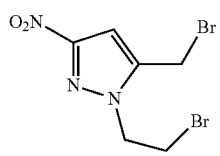

A 500-mL three-necked round-bottomed flask equipped with a magnetic stirrer, nitrogen inlet and reflux condenser was purged with nitrogen and charged with (1-(2-bromoethyl)-3-nitro-1H-pyrazol-5-yl)methanol 101b (37.0 g, 148 mmol) and chloroform (160 mL). The reaction was cooled to −5° C. using an ice/acetone bath and phosphorous tribromide (40.0 g, 148 mmol) was added portionwise. The cooling bath was removed and the reaction stirred at reflux for 2 h. After this time, the reaction was cooled to −5° C. and saturated aqueous sodium bicarbonate (250 mL) was added until a pH of 8.5 was reached. The mixture was extracted with ethyl acetate (3×150 mL) and the combined organic layers were washed with saturated aqueous sodium carbonate (2×50 mL), brine (75 mL), dried over sodium sulfate and the drying agent was removed by filtration. The filtrate was concentrated under reduced pressure to afford a yellow residue that was dissolved with gentle heating in methylene chloride (60 mL). Hexanes (approximately 20 mL) was added and the solution became cloudy. The mixture was heated until a solid precipitate formed, methylene chloride (9 mL) was added and the solution became clear. The solution was left to cool to room temperature and after 4 h the resulting crystals were collected by vacuum filtration. The filter cake was washed with a ice cold 1:2 mixture of methylene chloride:hexanes (2×20 mL) to afford 1-(2-bromoethyl)-5-(bromomethyl)-3-nitro-1H-pyrazole (19.7 g). The combined filtrates were evaporated and the procedure was performed again to afford an additional 9.70 g of 1-(2-bromoethyl)-5-(bromo-methyl)-3-nitro-1H-pyrazole. The solids were combined and dried under high vacuum for 18 h to afford a 57% yield (26.0 g) of 101c as white crystals: mp 95-97° C.; ¹H NMR (300 MHz, CDCl₃) δ 6.93 (s, 1H), 4.63 (t, 2H, J=6.0 Hz), 4.54 (s, 2H), 3.86 (t, 2H, J=6.0 Hz).

Example 101d 5-Methyl-2-nitro-4,5,6,7-tetrahydropyrazolo[1,5-a]pyrazine 101d

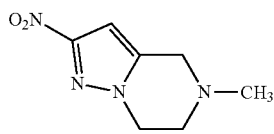

A 1-L single-neck round-bottomed flask equipped with a magnetic stirrer and nitrogen inlet was charged with THF (350 mL), 101c (10.0 g, 32.2 mmol), 2M methylamine solution in THF (113 mL, 225 mmol) and stirred at room temperature for 72 h. After this time the reaction was concentrated to dryness under reduced pressure, and the resulting solid was stirred with a mixture of ethyl acetate (75 mL) and 10% aqueous potassium carbonate (75 mL). The aqueous layer was separated and extracted with ethyl acetate (2×75 mL). The combined organic extracts were washed with 10% aqueous potassium carbonate (75 mL), followed by brine (50 mL) and dried over sodium sulfate. The drying agent was removed by filtration, and the filtrate concentrated under reduced pressure to afford 101d in 97% yield (5.70 g) as a yellow solid: ¹H NMR (300 MHz, CDCl₃) δ 6.62 (s, 1H), 4.28 (t, 2H, J=5.4 Hz), 3.67 (s, 2H), 2.95 (t, 2H, J=5.4 Hz), 2.52 (s, 3H); MS (ESI+) m/z 183.0 (M+H)

Example 101e 5-Methyl-4,5,6,7-tetrahydropyrazolo[1,5-a]pyrazin-2-amine 101e

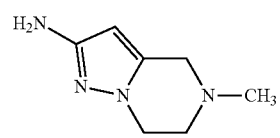

A 500-mL Parr reactor bottle was purged with nitrogen and charged with 10% palladium on carbon (50% wet, 800 mg dry weight) and a solution of 5-methyl-2-nitro-4,5,6,7-tetrahydropyrazolo[1,5-a]pyrazine 101d (4.00 g, 2.20 mmol) in ethanol (160 mL). The bottle was attached to Parr hydrogenator, evacuated, charged with hydrogen gas to a pressure of 45 psi and shaken for 2 h. After this time, the hydrogen was evacuated, and nitrogen was charged into the bottle. Celite 521 (1.0 g) was added, and the mixture was filtered through a pad of Celite 521. The filter cake was washed with ethanol (2×75 mL), and the combined filtrates were concentrated to dryness under reduced pressure to afford a 99% yield of 101e (3.31 g) as an orange solid: ¹H NMR (300 MHz, CDCl₃) δ 5.34 (s, 1H), 3.98 (t, 2H, J=5.4 Hz), 3.52 (s, 3H), 2.84 (t, 2H, J=5.7 Hz), 2.45 (s, 3H); MS (ESI+) m/z 153.1 (M+H)

Example 101f 6-Chloro-4-(5-methyl-4,5,6,7-tetrahydropyrazolo[1,5-a]pyrazin-2-ylamino)pyridazin-3(2H)-one 101f

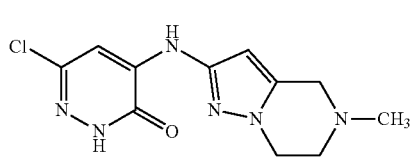

A 50-mL single-neck round-bottomed flask equipped with a magnetic stirrer, reflux condenser and nitrogen inlet was charged with 1,4-dioxane (5.0 mL), 101e (152 mg, 1.00 mmol), 4-bromo-6-chloropyridazin-3(2H)-one (209 mg, 1.00 mmol) and a 1 M THF solution of LiHMDS (5.0 mL, 5.00 mmol). After bubbling nitrogen through the resulting solution for 30 min, Xantphos (49 mg, 0.05 mmol) and tris(dibenzylideneacetone)dipalladium(0) (59 mg, 0.085 mmol) were added, and the reaction mixture was heated at reflux for 3 h. After this time, the reaction was cooled to room temperature, and water (10 mL) was added. The pH was adjusted to 6.5 with 2 N hydrochloric acid. The resulting precipitate was collected by vacuum filtration, washed with water (2×25 mL), absorbed on silica gel and purified by flash chromatography to afford a 74% yield (210 mg) of 101f as a light brown solid: $^1$H NMR (300 MHz, DMSO-$d_6$) δ 12.94 (s, 1H), 9.55 (s, 1H), 7.68 (s, 1H), 5.96 (s, 1H), 4.04 (t, 1H, J=5.7 Hz), 3.53 (s, 2H), 2.82 (t, 2H, J=5.7 Hz), 2.36 (s, 3H); MS (ESI+) m/z 281.1 (M+H)

Example 101g 2,2,2-Trichloro-1-(4,5,6,7-tetrahydro-1H-indol-2-yl)ethanone 101g

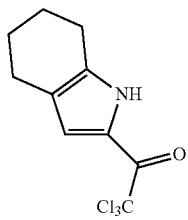

101g

A 100-mL single-neck round-bottomed flask equipped with a magnetic stirrer, condenser and nitrogen inlet was purged with nitrogen and charged with 4,5,6,7-tetrahydro-1H-indole (3.00 g, 24.8 mmol), trichloroacetyl chloride (13.5 g, 74.4 mmol) and 1,2-dichloroethane (50 mL). The solution was stirred at 85° C. for 2 h. After that time, the reaction mixture was concentrated under reduced pressure to afford a 100% yield (6.50 g) of 101g as a black semi-solid: $^1$H NMR (500 MHz, DMSO-$d_6$) δ 11.94 (s, 1H), 7.05 (s, 1H), 2.62 (t, 2H, J=6.0 Hz), 2.47 (t, 2H, J=6.0 Hz), 1.80 (m, 2H), 1.65 (m, 2H); MS (ESI+) m/z 266.0 (M+H)

Example 101h Ethyl 4,5,6,7-Tetrahydro-1H-indole-2-carboxylate 101h

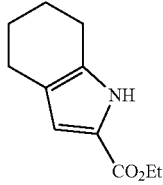

101h

A 100-mL single-neck round-bottomed flask equipped with a magnetic stirrer and nitrogen inlet was purged with nitrogen and charged with 101g (6.50 g, 24.8 mmol), sodium ethoxide (17.0 mg, 0.25 mmol) and ethanol (40 mL). The solution was stirred at room temperature for 1 h. After that time, the reaction mixture was concentrated under reduced pressure. The residue was purified by column chromatography to afford a 100% yield (4.80 g) of 101h as a brown solid: mp 70-72° C.; $^1$H NMR (300 MHz, CDCl$_3$) δ 9.08 (s, 1H), 6.75 (s, 1H), 4.25 (q, 2H, J=7.2 Hz), 2.65 (t, 2H, J=6.0 Hz), 2.56 (t, 2H, J=6.0 Hz), 1.85 (m, 4H), 1.28 (t, 3H, J=7.2 Hz); MS (ESI+) m/z 194.1 (M+H)

Example 101i Ethyl 1-(Cyanomethyl)-4,5,6,7-tetrahydro-1H-indole-2-carboxylate 101i

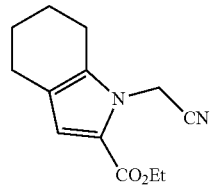

101i

A 125-mL single-neck round-bottomed flask equipped with a magnetic stirrer and nitrogen inlet was purged with nitrogen and charged with 101h (5.76 g, 29.8 mmol) and DMF (50 mL). The solution was cooled to 0° C. using an ice bath. NaH (60% dispersion in mineral oil, 1.43 g, 35.8 mmol) was added. The resulting mixture was stirred at room temperature for 1 h. After that time, bromoacetonitrile (1.43 g, 35.8 mmol) was added. The mixture was stirred at room temperature for 14 h. After that time, the reaction mixture was concentrated under reduced pressure and the residue was partitioned between ethyl acetate (150 mL) and water (450 mL). The organic layer was separated, and the aqueous layer was extracted with ethyl acetate (3×150 mL). The combined organic layers were washed with brine, dried over sodium sulfate and concentrated under reduced pressure. The residue was purified by column chromatography to afford a 55% yield (3.80 g) of ethyl 1-(cyanomethyl)-4,5,6,7-tetrahydro-1H-indole-2-carboxylate 101i as a yellow semi-solid: $^1$H NMR (300 MHz, CDCl$_3$) δ 6.66 (s, 1H), 5.29 (s, 2H), 4.28 (q, 2H, J=7.2 Hz), 2.62 (t, 2H, J=6.3 Hz), 2.49 (t, 2H, J=6.3 Hz), 1.92 (m, 2H), 1.75 (m, 2H), 1.33 (t, 3H, J=7.2 Hz); MS (ESI+) m/z 233.1 (M+H).

Example 101j Ethyl 1-(2-Aminoethyl)-4,5,6,7-tetrahydro-1H-indole-2-carboxylate 101j

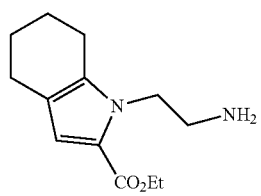

101j

A 200-mL Parr reactor bottle was purged with nitrogen and charged with 10% palladium on carbon (50% wet, 1.28 g dry weight), ethyl 1-(cyanomethyl)-4,5,6,7-tetrahydro-1H-indole-2-carboxylate 101i (3.00 g, 12.9 mmol), 12% hydrochloric acid (6.5 mL, 25 mmol), ethyl acetate (60 mL) and ethanol (40 mL). The bottle was attached to a Parr hydrogenator, evacuated, charged with hydrogen gas to a pressure of 50 psi and shaken for 6 h. After this time, the hydrogen was evacuated, and nitrogen was charged into the bottle. Celite 521 (4.0 g) was added, and the mixture was filtered through a pad of Celite 521. The filter cake was washed with ethanol (2×20 mL), and the combined filtrates were concentrated to dryness under reduced pressure. The residue was partitioned between ethyl acetate (150 mL) and 10% aqueous potassium carbonate (100 mL). The organic layer was separated, and the aqueous layer was extracted with ethyl acetate (3×75 mL). The combined organic layers were dried over sodium sulfate and concentrated under reduced pressure. The residue was triturated with ethanol (5 mL) to afford a 71% yield (1.71 g) of ethyl 1-(2-amino-ethyl)-4,5,6,7-tetrahydro-1H-indole-2-carboxylate 101j as a white solid: mp 102-104° C.; $^1$H NMR (500 MHz, DMSO-$d_6$) δ 6.61 (s, 1H), 6.22 (br, 2H), 4.15 (m, 4H), 2.77 (m, 2H), 2.59 (t, 2H, J=6.5 Hz), 2.42 (t, 2H, J=6.5 Hz), 1.70 (m, 2H), 1.62 (m, 2H), 1.23 (t, 3H, J=7.0 Hz); MS (APCI+) m/z 237.2 (M+H)

Example 101k Ethyl 1-(2-Aminoethyl)-4,5,6,7-tetrahydro-1H-indole-2-carboxylate 101k

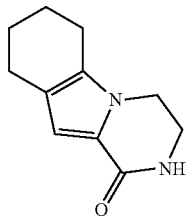

101k

A 100-mL single-neck round-bottomed flask equipped with a magnetic stirrer and nitrogen inlet was purged with nitrogen and charged with ethyl 1-(2-aminoethyl)-4,5,6,7-tetrahydro-1H-indole-2-carboxylate 101j (1.80 g, 7.63 mmol), sodium ethoxide (1.55 g, 22.8 mmol) and ethanol (50 mL). The mixture was stirred at 55° C. for 5 h. After that time, the reaction mixture was concentrated under reduced pressure and the residue was partitioned between ethyl acetate (200 mL) and water (100 mL). The organic layer was separated, and the aqueous layer was extracted with ethyl acetate (2×100 mL). The combined organic layers were washed with brine, dried over sodium sulfate and concentrated under reduced pressure. The residue was purified by column chromatography to afford a 42% yield (605 mg) of ethyl 1-(2-aminoethyl)-4,5,6,7-tetrahydro-1H-indole-2-carboxylate 101k as a white solid: mp 207-209° C.; $^1$H NMR (500 MHz, DMSO-$d_6$) δ 7.41 (s, 1H), 6.36 (s, 1H), 3.84 (t, 2H, J=6.0 Hz), 3.42 (m, 2H), 2.51 (t, 2H, J=6.0 Hz), 2.42 (t, 2H, J=6.0 Hz), 1.76 (m, 2H), 1.65 (m, 2H); (APCI+) m/z 191.3 (M+H)

Example 101l 2-(3-Bromo-2-methylphenyl)-3,4,6,7,8,9-hexahydropyrazino[1,2-a]indol-1(2H)-one 101l

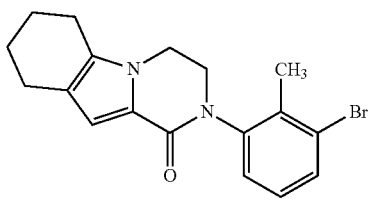

101l

A 50-mL three-neck round-bottomed flask equipped with a reflux condenser, magnetic stirrer and nitrogen inlet was charged with ethyl 1-(2-aminoethyl)-4,5,6,7-tetrahydro-1H-indole-2-carboxylate 101k (560 m g, 2.95 mmol), 2,6-dibromotoluene (1.47 g, cesium carbonate (1.92 g, 5.90 mmol), N,N'-dimethylethylenediamine (260 mg, 2.95 mmol) and 1,4-dioxane (25 mL). After bubbling nitrogen through the resulting suspension for 30 min, copper N,N'-dimethylethylenediamine (260 mg, 2.95 mmol) was added, and the reaction mixture was heated at 105° C. (oil bath temperature) for 14 h. After this time, the mixture was cooled to room temperature and filtered. The filtrate was diluted with ethyl acetate (100 mL) and water (20 mL). The organic layer was separated, and the aqueous layer was extracted with ethyl acetate (3×30 mL). The combined organic layers were dried over sodium sulfate and concentrated under reduced pressure. The residue was purified by column chromatography to afford a 57% yield (600 mg) of 2-(3-bromo-2-methylphenyl)-3,4,6,7,8,9-hexahydropyrazino[1,2-a]indol-1(2H)-one 101l as a white solid: mp 163-165° C.; $^1$H NMR (500 MHz, DMSO-$d_6$) δ 7.57 (dd, 1H, J=8.0, 0.5 Hz), 7.32 (d, 1H, J=7.5 Hz), 7.21 (t, 1H, J=8.0 Hz), 6.50 (s, 1H), 4.11 (m, 3H), 3.75 (m, 1H), 2.59 (m, 2H), 2.45 (m, 2H), 2.21 (s, 3H), 1.78 (m, 2H), 1.68 (m, 2H); (APCI+) m/z 358.6 (M+H)

Example 101m 2-(2-Methyl-3-(4,4,5,5-tetramethyl-1,3,2-dioxaborolan-2-yl)phenyl)-3,4,6,7,8,9-hexahydropyrazino[1,2-a]indol-1(2H)-one 101m

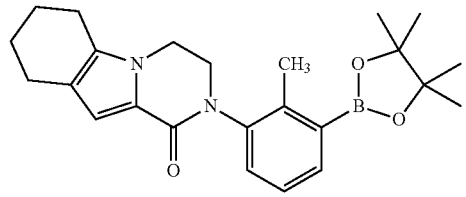

101m

A 50-mL three-neck round-bottomed flask equipped with a reflux condenser, magnetic stirrer and nitrogen inlet was charged with of 2-(3-bromo-2-methylphenyl)-3,4,6,7,8,9-hexahydropyrazino[1,2-a]indol-1(2H)-one 101l (600 mg, 1.67 mmol), 4,4,4',4',5,5,5',5'-octamethyl-2,2'-bi(1,3,2-dioxaborolane (1.70 g, 6.70 mmol), potassium acetate (656 mg, 6.68 mmol), and 1,4-dioxane (25 mL). After bubbling nitrogen through the resulting suspension for 30 min, XPhos (159 mg, 0.334 mmol) and tris(dibenzylideneacetone)dipalladium(0) (153 mg, 0.167 mmol) were added, and the reaction mixture was heated at 105° C. (oil bath temperature) for 14 h. After this time, the mixture was cooled to room temperature and filtered. The filtrate was diluted with ethyl acetate (75 mL) and water (20 mL). The organic layer was separated, and the aqueous layer was extracted with ethyl acetate (3×25 mL). The combined organic layers were dried over sodium sulfate and concentrated under reduced pressure. The residue was purified by column chromatography to afford a 109% crude yield (740 mg) of 2-(2-methyl-3-(4,4,5,5-tetramethyl-1,3,2-dioxaborolan-2-yl)phenyl)-3,4,6,7,8,9-hexahydropyrazino[1,2-a]indol-1(2H)-one 101m as a yellow oil: $^1$H NMR (300 MHz, CDCl$_3$) δ 7.75 (dd, 1H, J=6.6, 2.1 Hz), 7.26 (m, 2H), 6.80 (s, 1H), 4.10 (m, 3H), 3.75 (m, 1H), 2.54 (m, 4H), 2.45 (s, 3H), 1.87 (m, 2H), 1.75 (m, 2H), 1.25 (s, 12H); MS (APCI+) m/z 407.7 (M+H)

A 100-mL three-neck round-bottomed flask equipped with a reflux condenser, magnetic stirrer and nitrogen inlet was charged with 2-(2-methyl-3-(4,4,5,5-tetramethyl-1,3,2- dioxaborolan-2-yl)phenyl)-3,4,6,7,8,9-hexahydropyrazino[1,2-a]indol-1(2H)-one 101m (740 mg, 1.67 mmol), 6-chloro-4-(5-methyl-4,5,6,7-tetrahydropyrazolo[1,5-a]pyrazin-2-ylamino)pyridazin-3(2H)-one 101f (422 mg, 1.34 mmol), sodium carbonate (568 mg, 5.36 mmol), DMF (5 mL), water (5 mL) and 1,4-dioxane (20 mL). After bubbling nitrogen through the resulting suspension for 30 min, tetrakis(triphenylphosphine)palladium(0) (155 mg, 0.134 mmol) was added, and the reaction mixture was heated at 100° C. for 15 h. After this time, the mixture was cooled to room temperature and diluted with ethyl acetate (100 mL) and water (30 mL). The organic layer was separated, and the aqueous layer was extracted with ethyl acetate (3×25 mL). The combined organic layers were dried over sodium sulfate and concentrated under reduced pressure. The residue was purified by column chromatography on silica gel to afford a 17% yield (120 mg) of 101 as an off-white solid: mp 195-197° C.; $^1$H NMR (500 MHz, DMSO-$d_6$) d 12.95 (s, 1H), 9.19 (s, 1H), 7.75 (s, 1H), 7.34 (m, 2H), 7.29 (m, 1H), 6.50 (s, 1H), 5.96 (s, 1H), 4.14 (m, 1H), 4.08 (m, 2H), 3.95 (m, 2H), 3.77 (m, 1H), 3.51 (s, 2H), 2.78 (t, 2H, J=6.0 Hz), 2.60 (m, 2H), 2.46 (t, 2H, J=6.0 Hz), 2.35 (s, 3H), 2.07 (s, 3H), 1.78 (m, 2H), 1.68 (m, 2H); MS (ESI+) m/z 521 (M+H).

Example 102 2-(2-methyl-3-(5-(5-methyl-4,5,6,7-tetrahydropyrazolo[1,5-a]pyrazin-2-ylamino)-6-oxo-1,6-dihydropyridazin-3-yl)phenyl)-3,4,6,7,8,9-hexahydropyrazino[1,2-a]indol-1(2H)-one 102

Example 102a Ethyl 1-(Cyanomethyl)-1H-indole-2-carboxylate 102a

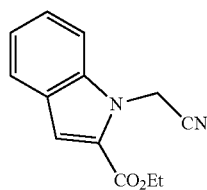

102a

A 250-mL single-neck round-bottomed flask equipped with a magnetic stirrer and nitrogen inlet was purged with nitrogen and charged with ethyl indole-2-carboxylate (10.0 g, 52.9 mmol) and DMF (100 mL). The solution was cooled to 0° C. using an ice bath. NaH (60% dispersion in mineral oil, 2.54 g, 63.5 mmol) was added. The resulting mixture was stirred at room temperature for 1 h. After that time, bromoacetonitrile (7.62 g, 63.5 mmol) was added. The mixture was stirred at room temperature for 14 h. After that time, the reaction mixture was concentrated under reduced pressure and the residue was partitioned between ethyl acetate (300 mL) and water (900 mL). The organic layer was separated, and the aqueous layer was extracted with ethyl acetate (3×300 mL). The combined organic layers were washed with brine, dried over sodium sulfate and concentrated under reduced pressure. The residue was purified by column chromatography to afford a 66% yield (8.00 g) of 102a as an off-white solid: mp 65-67° C.; $^1$H NMR (300 MHz, CDCl$_3$) δ 7.72 (d, 1H, J=8.1), 7.44 (m, 3H), 7.25 (m, 1H), 5.62 (s, 2H), 4.42 (q, 2H, J=7.2 Hz), 1.43 (t, 3H, J=7.2 Hz); MS (ESI+) m/z 229.1 (M+H).

Example 102b 3,4-Dihydropyrazino[1,2-a]indol-1(2H)-one 102b

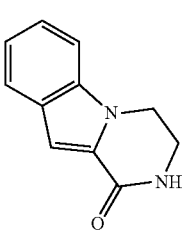

102b

A 500-mL Parr reactor bottle was purged with nitrogen and charged with 10% palladium on carbon (50% wet, 3.47 g dry weight), 102a (8.00 g, 35.0 mmol), 12% hydrochloric acid (17.5 mL, 70 mmol), ethyl acetate (150 mL) and ethanol (100 mL). The bottle was attached to a Parr hydrogenator, evacuated, charged with hydrogen gas to a pressure of 50 psi and shaken for 6 h. After this time, the hydrogen was evacuated, and nitrogen was charged into the bottle. Celite 521 (10.0 g) was added, and the mixture was filtered through a pad of Celite 521. The filter cake was washed with ethanol (2×50 mL), and the combined filtrates were concentrated to dryness under reduced pressure. The residue was partitioned between ethyl acetate (400 mL) and 10% aqueous potassium carbonate (300 mL). The organic layer was separated, and the aqueous layer was extracted with ethyl acetate (3×200 mL). The combined organic layers were dried over sodium sulfate and concentrated under reduced pressure. The residue was triturated with ethanol (5 mL) to afford a 70% yield (4.57 g) of 102b as an off-white solid: mp 228-230° C.; $^1$H NMR (300 MHz, CDCl$_3$) δ 7.73 (d, 1H, J=8.1 Hz), 7.34 (m, 3H), 7.18 (m, 1H), 6.75 (br s, 1H), 4.29 (t, 2H, J=5.4 Hz), 3.84 (m, 2H); MS (ESI+) m/z 187.1 (M+H).

Example 102c 2-(3-Bromo-2-methylphenyl)-3,4-dihydropyrazino[1,2-a]indol-1(2H)-one 102c

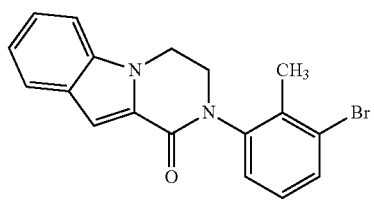

102c

A 100-mL three-neck round-bottomed flask equipped with a reflux condenser, magnetic stirrer and nitrogen inlet was charged with 102b (1.00 g, 5.37 mmol), (2.69 g, 10.7 mmol), cesium carbonate (3.49 g, 10.7 mmol), N,N'-dimethylethylenediamine (473 mg, 5.37 mmol) and 1,4-dioxane (45 mL). After bubbling nitrogen through the resulting suspension for 30 min, copper iodide (510 mg, 2.69 mmol) was added, and the reaction mixture was heated at 105° C. (oil bath temperature) for 14 h. After this time, the mixture was cooled to room temperature and filtered. The filtrate was diluted with ethyl acetate (200 mL) and water (40 mL). The organic layer was separated, and the aqueous layer was extracted with ethyl acetate (3×50 mL). The combined organic layers were dried over sodium sulfate and concentrated under reduced pressure. The residue was purified by column chromatography to afford a 62% yield (1.18 g) of 102c as an off-white solid: mp 178-180° C.; $^1$H NMR (300 MHz, CDCl$_3$) δ 7.74 (dt, 1H, J=8.2, 1.0 Hz), 7.58 (dd, 1H, J=7.8, 1.2 Hz), 7.37 (m, 3H), 7.19 (m, 3H), 4.45 (m, 2H), 4.21 (m, 1H), 3.95 (m, 1H), 2.38 (s, 3H); MS (ESI+) m/z 355.0 (M+H).

Example 102d 2-(2-Methyl-3-(4,4,5,5-tetramethyl-1,3,2-dioxaborolan-2-yl)phenyl)-3,4-dihydropyrazino[1,2-a]indol-1(2H)-one 102d

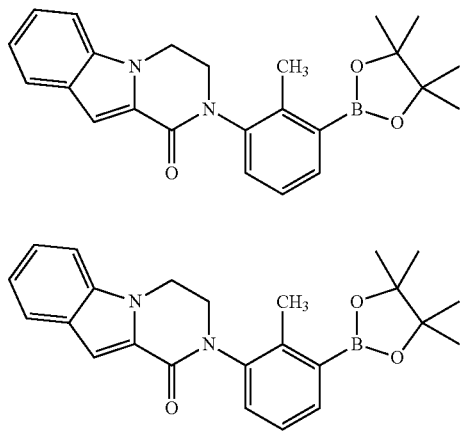

A 100-mL three-neck round-bottomed flask equipped with a reflux condenser, magnetic stirrer and nitrogen inlet was charged with 102c (1.18 g, 3.32 mmol), 4,4,4',4',5,5,5',5'-octamethyl-2,2'-bi(1,3,2-dioxaborolane) (929 mg, 3.65 mmol), potassium acetate (491 mg, 4.98 mmol) and 1,4-dioxane (25 mL). After bubbling nitrogen through the resulting suspension for 30 min, XPhos (317 mg, 0.664 mmol) and tris(dibenzylideneacetone)-dipalladium(0) (561 mg, 0.332 mmol) were added, and the reaction mixture was heated at 105° C. (oil bath temperature) for 14 h. After this time, the mixture was cooled to room temperature and filtered. The filtrate was diluted with ethyl acetate (150 mL) and water (40 mL). The organic layer was separated, and the aqueous layer was extracted with ethyl acetate (3×50 mL). The combined organic layers were dried over sodium sulfate and concentrated under reduced pressure. The residue was purified by column chroma-tography to afford a 57% yield (760 mg) of 102d as an off-white solid: mp 193-195° C.; $^1$H NMR (300 MHz, CDCl$_3$) δ 7.80 (dd, 1H, J=7.0, 1.7 Hz), 7.74 (d, 1H, J=8.2 Hz), 7.37 (m, 3H), 7.28 (m, 2H), 7.19 (m, 1H), 4.45 (m, 2H), 4.22 (m, 1H), 3.94 (m, 1H), 2.50 (s, 3H), 1.35 (s, 12H); MS (ESI+) m/z 403.2 (M+H).

A 25-mL three-neck round-bottomed flask equipped with a reflux condenser, magnetic stirrer and nitrogen inlet was charged with 102d (760 mg, 1.89 mmol), 101f (379 mg, 1.35 mmol), sodium carbonate (430 mg, 4.05 mmol), DMF (5 mL), water (2.5 mL) and 1,4-dioxane (8 mL). After bubbling nitrogen through the resulting suspension for 30 min, tetrakis(triphenylphosphine)palladium(0) (437 mg, 0.378 mmol) was added, and the reaction mixture was heated at reflux for 14 h. After this time, the mixture was cooled to room temperature and diluted with ethyl acetate (100 mL) and water (30 mL). The organic layer was separated, and the aqueous layer was extracted with ethyl acetate (3×25 mL). The combined organic layers were dried over sodium sulfate and concentrated under reduced pressure. The residue was purified by column chromatography on silica to afford a 26% yield (183 mg) of 102 as an off-white solid: mp 188-190° C. (dec); $^1$H NMR (300 MHz, DMSO-d$_6$) δ 12.99 (s, 1H), 9.23 (s, 1H), 7.79 (s, 1H), 7.71 (d, 1H, J=8.1 Hz), 7.61 (d, 1H, J=7.9 Hz), 7.38 (m, 4H), 7.14 (m, 2H), 5.97 (s, 1H), 4.63 (m, 1H), 4.49 (m, 1H), 4.27 (m, 1H), 4.12 (m, 3H), 3.51 (s, 2H), 2.79 (t, 2H, J=5.1 Hz), 2.35 (s, 3H), 2.18 (s, 3H); MS (ESI+) m/z 525 (M+H).

Example 103 4-{2-Methyl-3-[1-methyl-5-({5-methyl-4H,5H,6H,7H-pyrazolo[1,5-a]pyrazin-2-yl}amino)-6-oxo-1,6-dihydropyridazin-3-yl]phenyl}-7-thia-4-azatricyclo[6.4.0.0$^{2,6}$]dodeca-1(8),2(6),9,11-tetraen-5-one 103

Example 103a Methyl 3-(Bromomethyl)benzo[b]thiophene-2-carboxylate 103a

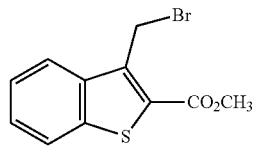

A 250-mL single-neck round-bottomed flask equipped with a magnetic stirrer, nitrogen inlet and reflux condenser was purged with nitrogen and charged with methyl 3-methylbenzo[b]thiophene-2-carboxylate (2.00 g, 9.70 mmol) and benzene (20 mL). N-bromosuccinimide (1.72 g, 9.70 mmol) and 2,2'-azobisisobutyronitrile (160 mg, 1.00 mmol) were added, and the mixture was refluxed for 2 h. After this time, the mixture was cooled to room temperature and filtered. The filter cake was rinsed with carbon tetrachloride (20 mL) and the filtrate was concentrated under reduced pressure. The resulting residue was purified by column chromatography to afford 103a in 82% yield (2.27 g) as a white solid: mp 101-102° C.; $^1$H NMR (500 MHz, CDCl$_3$) δ 7.97 (m, 1H), 7.86 (m, 1H), 7.51 (m, 2H), 5.22 (s, 2H), 3.97 (s, 3H).

Example 103b 3-((3-Bromo-2-methylphenylamino)methyl)benzo[b]thiophene-2-carboxylic Acid 103b

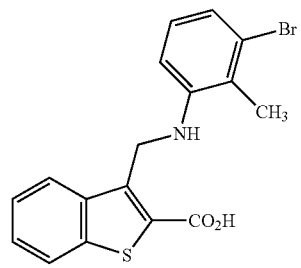

A 250-mL single-neck round-bottomed flask equipped with a magnetic stirrer and reflux condenser was purged with nitrogen and charged with 103a (2.26 g, 7.92 mmol), 3-bromo-2-methylaniline (1.77 g, 9.51 mmol) and acetonitrile (50 mL). Cesium carbonate (7.75 g, 23.8 mmol) was added, and the mixture was stirred at 50° C. for 14 h. After this time, the reaction mixture was concentrated under reduced pressure and the resulting residue was dissolved in THF (15 mL), methanol (15 mL) and water (15 mL) and treated with lithium hydroxide monohydrate (1.30 g, 31.0 mmol). After stirring at room temperature for 14 h, the solvent was removed under reduced pressure and the resulting residue was acidified with 2 M hydrochloric acid to pH 5. The resulting mixture was extracted with ethyl acetate (3×30 mL), and the organic extracts were combined and dried over sodium sulfate, filtered and concentrated under reduced pressure. The resulting residue was purified by flash chromatography to afford 103b in 59% yield (1.70 g) as a white solid: mp 120-121° C.; $^1$H NMR (500 MHz, DMSO-$d_6$) δ 8.30 (d, 1H, J=12.5 Hz), 7.98 (d, 1H, J=12.5 Hz), 7.46 (m, 2H), 6.77 (m, 3H), 4.97 (s, 2H), 2.15 (s, 3H); MS (ESI+) m/z 378.9 (M+H).

Example 103c 2-((3-Bromo-2-methylphenyl)-1Hbenzothieno[2,3-c]pyrrol-3(2H)-one 103c

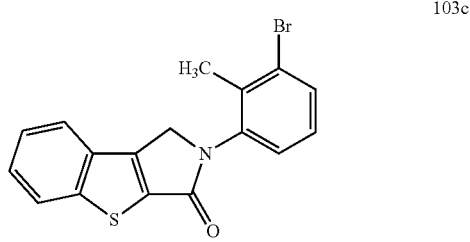 [SMILES: Cc1c(Br)cccc1N1Cc2c(sc3ccccc23)C1=O]

A 250-mL single-neck round-bottomed flask equipped with a magnetic stirrer was purged with nitrogen and charged with 103b (1.70 g, 4.51 mmol), triethylamine (914 mg, 9.00 mmol) and anhydrous DMF (25 mL). Benzotriazol-1-yl-oxy-tris(dimethylamino)-phosphonium hexafluorophosphate (BOP, 2.60 g, 5.90 mmol) was added, and the reaction was stirred at room temperature for 14 h. After this time, the reaction was diluted with water (20 mL), and the resulting suspension was filtered. The filter cake was dissolved in methylene chloride (40 mL), and the solution was washed with saturated aqueous sodium bicarbonate (10 mL), water (10 mL), and dried over sodium sulfate. The drying agent was removed by filtration, and the solvent was evaporated under reduced pressure. The resulting residue was purified by flash chromatography to afford a 78% yield of 103c (1.26 g) as a white semi-solid: $^1$H NMR (500 MHz, CDCl$_3$) δ 7.97 (m, 1H), 7.80 (m, 1H), 7.60 (d, 1H, J=8.0 Hz), 7.49 (m, 2H), 7.28 (d, 1H, J=8.0 Hz), 7.16 (t, 1H, J=8.0 Hz), 4.85 (s, 2H), 2.37 (s, 3H).

Example 103d 2-(2-Methyl-3-(4,4,5,5-tetramethyl-1,3,2-dioxaborolan-2-yl)phenyl)-1H-benzothieno[2,3-c]pyrrol-3(2H)-one 103d

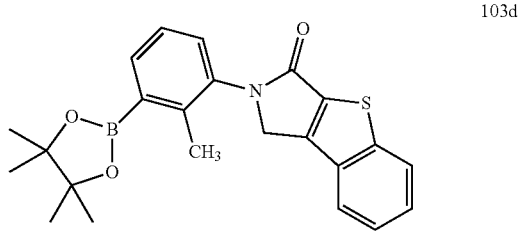 [SMILES: Cc1c(B2OC(C)(C)C(C)(C)O2)cccc1N1Cc2c(sc3ccccc23)C1=O]

A 250-mL single-neck round-bottomed flask equipped with a magnetic stirrer and reflux condenser was purged with nitrogen and charged with 103c (1.26 g, 3.51 mmol), 4,4,4',4'-5,5,5',5'-octamethyl-2,2'-bi(1,3,2-dioxaborolane (2.23 g, 8.80 mmol), potassium acetate (1.00 g, 10.20 mmol) and 1,4-dioxane (30 mL). A stream of nitrogen was passed through the resulting suspension for 30 min. [1,1'-Bis(diphenylphosphino)ferrocene]-dichloropalladium(II) (260 mg, 0.355 mmol) was added, and the reaction was stirred at reflux for 3 h. After this time, the mixture was cooled to ambient temperature, partitioned between water (25 mL) and ethyl acetate (50 mL) and filtered through a plug of Celite 521. The organic phase was separated, dried over sodium sulfate, filtered and concentrated under reduced pressure. The resulting residue was purified by flash chromatography to afford quantitative yield (1.84 g) of 103d as a yellow semi-solid: $^1$H NMR (500 MHz, CDCl$_3$) d 7.97 (m, 1H), 7.80 (m, 2H), 7.47 (m, 2H), 7.35 (d, 1H, J=7.5 Hz), 7.28 (d, 1H, J=7.5 Hz), 4.86 (s, 2H), 2.48 (s, 3H), 1.35 (s, 12H).

Example 103e 4-Bromo-6-chloro-2-methylpyridazin-3(2H)-one 103e

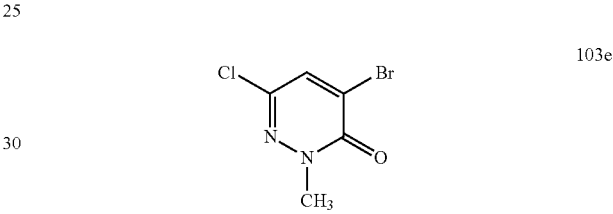

A 250-mL single-necked round bottomed flask equipped with a magnetic stirrer was purged with nitrogen and charged with 4-bromo-6-chloropyridazin-3(2H)-one (1.00 g, 4.77 mmol) and DMF (15 mL). Sodium hydride (60% by weight in oil, 229 mg, 5.73 mmol) was added in one portion. After stirring at room temperature for 10 minutes, iodomethane (1.02 g, 7.16 mmol) was added and the reaction stirred at room temperature for 1.5 h. The reaction was then quenched with aqueous saturated sodium bicarbonate (10 mL) and the resulting solution poured into water (150 mL). The mixture was then extracted with ethyl acetate (250 mL). The organic layer was dried over sodium sulfate. The drying agent was then removed by filtration, and the filtrate was concentrated under reduced pressure to residue. Purification by column chromatography afforded 103e in a 68% yield (722 mg) as a white solid: mp 107-108° C.; $^1$H NMR (300 MHz, CDCl$_3$) δ 7.62 (s, 1H), 3.81 (s, 3H).

Example 103f 6-Chloro-2-methyl-4-(5-methyl-4,5,6,7-tetrahydropyrazolo[1,5-a]pyrazin-2-ylamino)pyridazin-3(2H)-one 103f

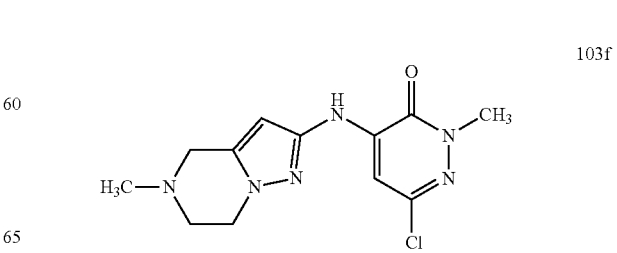

A 250-mL three-neck round-bottomed flask equipped with a reflux condenser, magnetic stirrer and nitrogen inlet was charged with 4-bromo-6-chloro-2-methylpyridazin-3 (2H)-one 103e (1.90 g, 8.53 mmol), 101e (1.18 g, 7.75 mmol) and 1,4-dioxane (40 mL). The flask was purged with nitrogen and cooled to 0° C. A 1 M solution of lithium hexamethyldisilazide in THF (39 mL, 39.0 mmol) was added. After bubbling nitrogen through the resulting suspension for 30 min, Xantphos (381 mg, 0.659 mmol) and tris(dibenzylideneacetone)-dipalladium(0) (355 mg, 0.388 mmol) were added, and the reaction mixture was heated at reflux for 2 h. After this time, the mixture was cooled to room temperature and diluted with water (10 mL). The pH of the solution was adjusted to 7.6 with 2 N hydrochloric acid. The organic layer was separated, and the aqueous layer was extracted with ethyl acetate (3×40 mL). The combined organic layers were dried over sodium sulfate and concentrated under reduced pressure. The residue was purified by column chromato-graphy on silica to afford a 76% yield (1.74 g) of 103f as an off-white solid: mp 184-186° C.; $^1$H NMR (300 MHz, DMSO-$d_6$) δ 9.62 (s, 1H), 7.72 (s, 1H), 6.00 (s, 1H), 4.04 (t, 2H, J=5.1 Hz), 3.65 (s, 3H), 3.53 (s, 2H), 2.82 (t, 2H, J=5.1 Hz), 2.37 (s, 3H); MS (ESI+) m/z 295.1 (M+H).

A 150-mL single-neck round-bottomed flask equipped with a magnetic stirrer and reflux condenser was purged with nitrogen and charged with 103d (580 mg, 1.43 mmol), 103f (300 mg, 1.00 mmol), sodium carbonate (320 mg, 3.00 mmol), 1,4-dioxane (8 mL), DMF (5 mL) and water (2.5 mL). This mixture was degassed with nitrogen for 30 min. Tetrakis(triphenylphosphine)palladium (120 mg, 0.103 mmol) was added. After heating at reflux for 14 h, the reaction mixture was cooled to room temperature and partitioned between water (40 mL) and methylene chloride (100 mL). The layers were separated, and the aqueous phase was extracted with methylene chloride (2×50 mL). The organic extracts were combined, dried over sodium sulfate, filtered and concentrated under reduced pressure. The resulting residue was purified by flash chromatography to afford 103 in 44% yield (240 mg) as an off-white solid: mp 175-176° C.; $^1$H NMR (500 MHz, DMSO-$d_6$) δ 9.28 (s, 1H), 8.20 (m, 1H), 8.04 (s, 1H), 7.81 (s, 1H), 7.56 (m, 3H), 7.40 (m, 2H), 5.99 (s, 1H), 5.12 (s, 1H), 3.97 (t, 2H, J=5.5 Hz), 3.76 (s, 3H), 3.51 (s, 2H), 2.79 (t, 2H, J=8.5 Hz), 2.35 (s, 3H), 2.17 (s, 3H); MS (ESI+) m/z 538.2 (M+H).

Example 104 5-[2-(Hydroxymethyl)-3-[1-methyl-6-oxo-5-(pyrimidin-4-ylamino)-1,6-dihydropyridin-3-yl]phenyl]-8-thia-5-azatricyclo[7.4.0.0$^{2,7}$]trideca-1(9),2(7)-dien-6-one 104

Example 104a N-Methoxy-N-methyl-4,5,6,7-tetrahydrobenzo[b]thiophene-2-carboxamide 104a

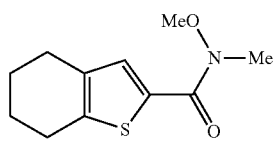

104a

A 250-mL single-neck round-bottomed flask equipped with a magnetic stirrer was purged with nitrogen, charged with 4,5,6,7-tetrahydrobenzo[b]thiophene-2-carboxylic acid (3.00 g, 16.5 mmol), methylene chloride (80 mL), and DMF (60 mg, 0.825 mmol) and cooled to 0° C. To the resulting solution, oxalyl chloride (2.31 g, 18.2 mmol) was added dropwise. After this addition was complete, the reaction was warmed to room temperature and stirred for 2 h. After this time, the reaction was concentrated to dryness under reduced pressure. The resulting white solid was dissolved in methylene chloride (80 mL) and the solution cooled to 0° C. Triethylamine (5.00 g, 49.5 mmol) and N,O-dimethylhydroxylamine (1.61 g, 16.5 mmol) were then added. After the addition was complete, the cooling bath was removed, and the reaction mixture was stirred at room temperature for 16 h. After this time, the reaction mixture was partitioned between water (100 mL) and ethyl acetate (200 mL). The layers were separated, and the aqueous phase was extracted with ethyl acetate (100 mL). The combined organic extracts were washed with water (100 mL), followed by brine (100 mL) and dried over sodium sulfate. The drying agent was removed by filtration, and the solvent was evaporated under reduced pressure. The resulting residue was purified by flash chromatography to afford an 88% yield of 104a (3.29 g) as a white solid: mp 36-37° C.; $^1$H NMR (500 MHz, CDCl$_3$) d 7.79 (s, 1H), 3.76 (s, 3H), 3.34 (s, 3H), 2.78 (t, 2H, J=6.0 Hz), 2.62 (t, 2H, J=6.0 Hz), 1.82 (m, 4H); MS (APCI+) m/z 226.3 (M+H)

Example 104b 3-Chloro-1-(4,5,6,7-tetrahydrobenzo[b]thiophen-2-yl)propan-1-one 104b

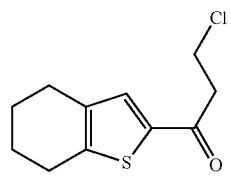

104b

A 100-mL single-necked round-bottomed flask equipped with a magnetic stirrer was purged with nitrogen and charged with 104a (2.70 g, 12.0 mmol) and anhydrous THF (45 mL), and the solution was cooled to −10° C. with acetone/ice bath. A 1.0 M solution of vinylmagnesium bromide in THF (13.2 mL, 13.2 mmol) was added dropwise, and the resulting reaction mixture was stirred at 0° C. for 4 h. After this time, the reaction mixture was partitioned between ethyl acetate (100 mL) and 2 M aqueous hydrochloric acid (40 mL). The layers were separated, and the aqueous phase was extracted with ethyl acetate (40 mL). The combined organic extracts were washed with water (100 mL), followed by brine (100 mL), dried over sodium sulfate, filtered and concentrated under reduced pressure. The resulting residue was dissolved in methylene chloride (30 mL), and a 2 M solution of hydrogen chloride in diethyl ether (15 mL) was added. After stirring at room temperature for 1 h, the solvents were removed under reduced pressure. Purification of the resulting residue by column chromatography afforded a 29% yield (804 mg) of 104b as an off-white solid: mp 57-58° C.; $^1$H NMR (500 MHz, CDCl$_3$) d 7.41 (s, 1H), 3.89 (t, 2H, J=7.0 Hz), 3.30 (t, 2H, J=7.0 Hz), 2.81 (t, 2H, J=6.0 Hz), 2.64 (t, 2H, J=6.0 Hz), 1.83 (m, 4H); MS (ECI+) m/z 229.1 (M+H)

Example 104c 5,6,7,8-Tetrahydro-1H-benzo[b]cyclopenta[d]thiophen-3(2H)-one 104c

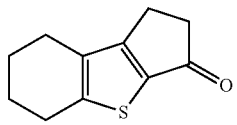

104c

A 50-mL single-necked round-bottomed flask equipped with a magnetic stirrer was charged with 104b (800 mg, 3.51 mmol) and 98% sulfuric acid (8 mL). After stirring at 95° C. for 16 h, the reaction mixture was poured into ice (50 g), and the resulting suspension was extracted with ethyl acetate (3×50 mL). The organic extracts were combined, dried over sodium sulfate, filtered and concentrated under reduced pressure. The resulting residue was purified by flash chromatography to afford 104c in 47% yield (320 mg) as an off-white solid: mp 75-76° C.; $^1$H NMR (500 MHz, CDCl$_3$) δ 2.89 (m, 2H), 2.87-2.83 (m, 4H), 2.56 (t, 2H, J=6.5 Hz), 1.84 (m, 4H)

Example 104d 5,6,7,8-Tetrahydro-1H-benzo[b]cyclopenta[d]thiophen-3(2H)-one oxime 104d

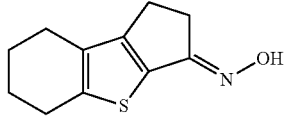

104d

A 100-mL single-neck round-bottomed flask equipped with a mechanical stirrer and nitrogen inlet was charged with hydroxylamine hydrochloride (573 mg, 8.25 mmol) and methanol (10 mL). The mixture was cooled to 0° C. using an ice bath. Sodium acetate (677 mg, 8.25 mmol) was added. The mixture was stirred at 0° C. for 30 min. After this time, 104c (319 mg, 1.65 mmol) was added, and the reaction was stirred at room temperature for 16 h.

After this time, the mixture was concentrated, and the resulting residue was triturated with water (10 mL). The resulting solid was collected and dried in a vacuum oven at 45° C. to afford an 84% yield (287 mg) of 104d as an off-white solid: mp 173-174° C.; $^1$H NMR (500 MHz, DMSO-d$_6$) δ 10.38 (s, 1H), 2.97 (m, 2H), 2.77-2.73 (m, 4H), 2.47 (m, 2H), 1.75 (m, 4H); MS (APCI+) m/z 208.3 (M+H).

Example 104e 3,4,5,6,7,8-Hexahydrobenzothieno[2,3-c]pyridin-1(2H)-one 104e

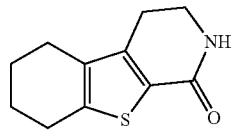

104e

A 50-mL single-neck round-bottomed flask equipped with a reflux condenser, magnetic stirrer and nitrogen inlet was charged with 104d (285 mg, 1.38 mmol) and polyphosphoric acid (15 g). After stirring at 80° C. for 16 h, the reaction mixture was cooled to room temperature, and water (30 mL) was added. The resulting mixture was stirred for 30 min and filtered. The filter cake was washed with water (20 mL) and dried in a vacuum oven at 45° C. to afford a 75% yield (215 mg) of 104e as an off-white solid: mp 203° C. dec; $^1$H NMR (500 MHz, CDCl$_3$) δ 5.62 (s, 1H), 3.59 (t, 2H, J=7.0 Hz), 2.81 (t, 2H, J=6.0 Hz), 2.72 (t, 2H, J=7.0 Hz), 2.48 (t, 2H, J=6.0 Hz), 1.84 (m, 4H). MS (APCI+) m/z 208.3 (M+H)

Example 104f 2-Bromo-6-(1-oxo-3,4,5,6,7,8-hexahydrobenzothieno[2,3-c]pyridin-2(1H)-yl)benzyl acetate 104f

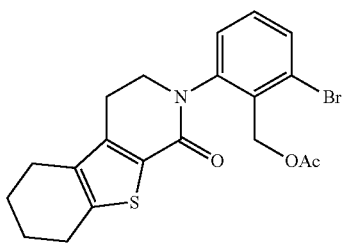

104f

A 100-mL three-neck round-bottomed flask equipped with a reflux condenser, magnetic stirrer and nitrogen inlet was charged with 104e (214 mg, 1.04 mmol), 2,6-dibromobenzyl acetate 104g (519 mg, 2.08 mmol), cesium carbonate (678 mg, 2.08 mmol), N,N'-dimethylethylenediamine (92 mg, 1.04 mmol) and 1,4-dioxane (10 mL). After bubbling nitrogen through the resulting suspension for 30 min, copper iodide (99 mg, 0.520 mmol) was added, and the reaction mixture was heated at 100° C. (oil bath temperature) for 16 h. After this time, the mixture was cooled to room temperature and filtered. The filtrate was diluted with ethyl acetate (100 mL) and water (50 mL). The organic layer was separated, and the aqueous layer was extracted with ethyl acetate (3×50 mL). The combined organic layers were dried over sodium sulfate and concentrated under reduced pressure. The residue was purified by column chromatography to afford a 30% yield (138 mg) of 2-Bromo-6-(1-oxo-3,4,5,6,7,8-hexahydrobenzothieno[2,3-c]pyridin-2(1H)-yl) benzyl acetate 104f as a yellow oil: $^1$H NMR (500 MHz, CDCl$_3$) δ 7.59 (dd, 1H, J=7.0, 1.5 Hz), 7.30-7.24 (m, 2H), 5.23 (m, 2H), 4.06 (m, 1H), 3.77 (m, 1H), 2.98 (m, 1H), 2.83-2.77 (m, 3H), 2.50 (m, 2H), 2.04 (s, 3H), 1.85 (m, 4H)

Example 104g 2,6-dibromobenzyl acetate 104g

A 250-mL single-neck round-bottomed flask equipped with a magnetic stirrer, reflux condenser and nitrogen inlet was purged with nitrogen and charged with 2,6-dibromotoluene (2.50 g, 10.0 mmol), N-bromosuccinimide (1.78 g, 10.0 mmol) and carbon tetrachloride (40 mL). The solution was heated to 80° C. (oil bath temperature), and 2,2'-azobisisobutyronitrile (164 mg, 1.00 mmol) was added. The resulting mixture was refluxed for 14 h. After that time, the mixture was cooled to room temperature and filtered. The filter cake was washed with carbon tetrachloride (2×20 mL). The filtrate was diluted with ethyl acetate (200 mL) and washed with water (40 mL), saturated aqueous sodium bicarbonate (40 mL) and brine (40 mL). The organic layer was dried over sodium sulfate and concentrated under reduced pressure to afford a quantative yield (3.28 g) of 1,3-dibromo-2-(bromomethyl)benzene as a yellow solid: mp 77-78° C.; $^1$H NMR (300 MHz, CDCl$_3$) d 7.55 (d, 2H, J=8.1 Hz), 7.07 (t, 1H, J=8.1 Hz), 4.83 (s, 2H)

A 250-mL single-neck round-bottomed flask equipped with a magnetic stirrer and nitrogen inlet was purged with nitrogen and charged with 1,3-dibromo-2-(bromomethyl) benzene (3.28 g, 10.0 mmol), potassium acetate (3.93 g, 40.0 mmol) and DMF (100 mL). The solution was stirred at room temperature for 14 h. After that time, the reaction mixture was diluted with water (900 mL) and extracted with ethyl acetate (3×200 mL). The combined organic layers were washed with brine (100 mL), dried over sodium sulfate and concentrated under reduced pressure. The residue was purified by column chromatography to afford an 88% yield (2.70 g) of 2,6-dibromobenzyl acetate 104g as an off-white solid: mp 62-65° C.; $^1$H NMR (300 MHz, CDCl$_3$) d 7.57 (d, 2H, J=8.0 Hz), 7.07 (t, 1H, J=7.9 Hz), 5.42 (s, 2H), 2.11 (s, 3H); MS (ESI+)

Example 104h 1-methyl-3-(pyrimidin-4-ylamino)-5-(4,4,5,5-tetramethyl-1,3,2-dioxaborolan-2-yl)pyridin-2(1H)-one 104h

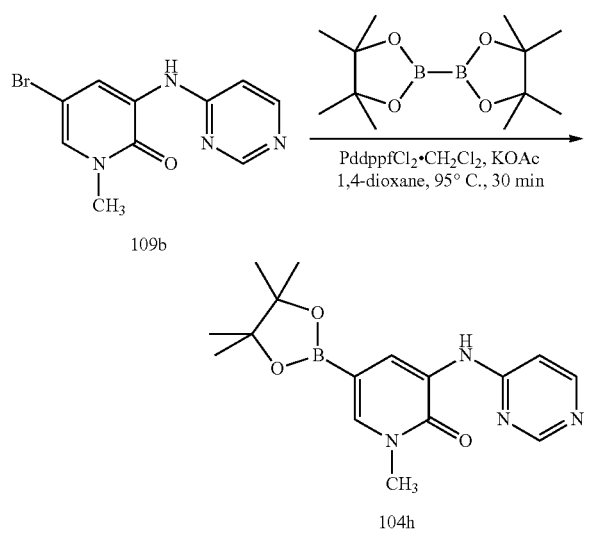

A 100-mL single-neck round-bottomed flask equipped with a magnetic stirrer and thermoregulator was purged with nitrogen and charged with 5-bromo-1-methyl-3-(pyrimidin-4-ylamino)pyridin-2(1H)-one 109b (300 mg, 1.07 mmol), 4,4,4',4',5,5,5',5'-octamethyl-2,2'-bi(1,3,2-dioxaborolane) (534 mg, 2.14 mmol), potassium acetate (210 mg, 2.14 mmol) and 1,4-dioxane (10 mL). A stream of nitrogen was passed through the resulting suspension for 30 min. [1,1'-Bis(diphenylphosphino)ferrocene]dichloro-palladium(II), complex with dichloromethane (PddppfCl$_2$.CH$_2$Cl$_2$, 39 mg, 0.054 mmol) was then added, and the reaction was stirred at 95° C. for 30 min. After this time, the mixture was cooled to ambient temperature, partitioned between water (40 mL) and ethyl acetate (60 mL) and filtered through a plug of Celite 521. The organic phase was separated, dried over sodium sulfate, filtered and concentrated under reduced pressure to afford crude 104h as a black oil which was used directly in the next step without further purification. MS (ESI+) m/z 329.1 (M+H)

A 100-mL single-neck round-bottomed flask equipped with a magnetic stirrer and reflux condenser was purged with nitrogen and charged with 104f (136 mg, 0.313 mmol), crude 104h (1.07 mmol, presumed quantitative yield), sodium carbonate (100 mg, 0.940 mmol), 1,4-dioxane (5 mL) and water (1 mL). This mixture was degassed with nitrogen for 30 min. Tetrakis(triphenyl-phosphine)palladium mixture (636 mg, 0.031 mmol) was added. After heating at 100° C. for 3 h, the reaction was cooled to room temperature and partitioned between water (40 mL) and methylene chloride (100 mL). The layers were separated, and the aqueous phase was extracted with methylene chloride (2×50 mL). The organic extracts were combined, dried over sodium sulfate, filtered and concentrated under reduced pressure. The resulting residue was dissolved in methanol (5 mL), and potassium carbonate (500 mg, 3.62 mmol) was added. After stirring at room temperature for 2 h, the reaction mixture was partitioned between water (20 mL) and methylene chloride (20 mL). The layers were separated, and the aqueous phase was extracted with methylene chloride (2×20 mL). The organic extracts were combined, dried over sodium sulfate, filtered and concentrated under reduced pressure. The resulting residue was purified by flash chromatography to afford 104 in 26% yield (42 mg) as a white solid: mp>250° C.; $^1$H NMR (500 MHz, DMSO-d$_6$) δ 9.17 (s, 1H), 8.71 (d, 1H, J=2.5 Hz), 8.64 (s, 1H), 8.29 (d, 1H, J=6.0 Hz), 7.52 (d, 1H, J=2.5 Hz), 7.45 (t, 1H, J=7.5 Hz), 7.36-7.30 (m, 3H), 4.84 (t, 1H, J=3.5 Hz), 4.36 (m, 2H), 4.03 (m, 1H), 3.87 (m, 1H), 3.60 (s, 3H), 2.96 (m, 1H), 2.85 (m, 1H), 2.77 (m, 2H), 2.58-2.46 (m, 2H), 1.79 (m, 4H); MS (APCI+) m/z 514.2 (M+H)

Example 105 10-[2-(Hydroxymethyl)-3-[1-methyl-6-oxo-5-(pyrimidin-4-ylamino)-1,6-dihydropyridin-3-yl]phenyl]-4,4-dimethyl-7-thia-10-azatricyclo[6.4.0.0$^{2,6}$]dodeca-1(8),2(6)-dien-9-one 105

Example 105a 3,3-Dimethylcyclopentanone 105a

A 1-L three-neck round-bottomed flask equipped with a magnetic stirrer, addition funnel and nitrogen inlet was purged with nitrogen and charged with ether (200 mL) and copper (I) iodide (54.46 g, 0.286 mol). The mixture was cooled to 0° C., methyllithium (1.6 M in ether, 357.5 mL, 0.572 mol) was added dropwise to the reaction mixture over 1.5 h and stirred at 0° C. for additional 2 h. After this time a solution of 3-methylcyclo-pent-2-enone (25 g, 0.260 mol) in ether (150 mL) was added dropwise over 1.5 h. The reaction mixture was then stirred at 0° C. for 2 h and poured into sodium sulfate deca-hydrate (300 g). The resulting mixture was stirred for 30 min. After this time the mixture was filtered and washed with ether (1000 mL). The filtrate was concentrated and distilled under reduced pressure to afford a 70% yield (20.5 g) of 3,3-dimethylcyclo-pentanone 105a as a colorless liquid: by 50-55° C. (at 10 mmHg); $^1$H NMR (300 MHz, CDCl$_3$) d 2.31 (t, 2H, J=7.8 Hz), 2.05 (s, 2H), 1.79 (t, 2H, J=7.8 Hz); MS (ESI+) m/z 113.3 (M+H)

Example 105b Ethyl 5,5-Dimethyl-5,6-dihydro-4H-cyclopenta[b]thiophene-2-carboxylate 105b

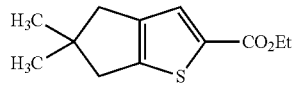

105b

A 500-mL three-neck round-bottomed flask equipped with a magnetic stirrer, reflux condenser, addition funnel and nitrogen inlet was purged with nitrogen and charged with DMF (9.49 g, 0.100 mol) and methylene chloride (100 mL). The reaction mixture was cooled to 0° C. and phosphorus oxychloride (14.1 g, 0.920 mol) was added dropwise to the reaction over 30 min. Once this addition was complete, the reaction was warmed to room temperature and stirred for 1 h. After this time a solution of 105a (11.2 g, 0.100 mol) in methylene chloride (100 mL) was added dropwise over 1 h. The reaction was then stirred at reflux for 18 h. The reaction mixture was cooled to room temperature and poured into a mixture of crushed ice (400 mL) and sodium acetate (100 g, 1.22 mol). The resulting mixture was stirred for 45 min. After this time the aqueous layer was separated and extracted with methylene chloride (2×500 mL). The combined organic layers were then washed with water (2×200 mL), followed by brine (200 mL) and dried over sodium sulfate. The drying agent was then removed by filtration, and the filtrate was concentrated to afford crude product 2-chloro-4,4-dimethylcyclopent-1-enecarbaldehyde which was placed in a 500-mL three-neck round bottomed flask equipped with a mechanical stirrer, reflux condenser and nitrogen inlet. Methylene chloride (200 mL), ethyl 2-mercaptoacetate (11.0 g, 0.092 mol) and triethylamine (30 g, 0.207 mol) were then added. The reaction mixture was then stirred at reflux for 6 h. After this time the reaction was cooled to room temperature and concentrated to a thick orange residue. Ethanol (200 mL) and triethylamine (30.0 g, 0.207 mol) were added and the reaction was heated at reflux for 12 h. The reaction was then cooled to room temperature and concentrated under reduced pressure and the resulting residue was diluted with ether (600 mL). The resulting mixture was washed with 1 M hydrochloric acid (150 mL), brine (100 mL), dried over sodium sulfate, filtered and concentrated under reduced pressure. The resulting residue was purified by flash chromatography to afford 105b in 34% yield (7.70 g) as a colorless liquid: $^1$H NMR (300 MHz, CDCl$_3$) d 7.48 (s, 1H), 4.33 (q, 2H, J=7.2 Hz), 2.72 (s, 2H), 2.56 (s, 2H), 1.38 (t, 3H, J=1.8 Hz), 1.17 (s, 6H); MS (ESI+) m/z 225.1

Example 105c 5,5-Dimethyl-5,6-dihydro-4H-cyclopenta[b]thiophene-2-carboxylic acid 105c

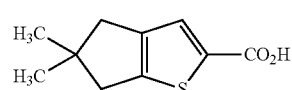

105c

In a 250-mL single-neck round-bottomed flask equipped with a magnetic stirrer and reflux condenser, 105b (4.00 g, 17.8 mmol) was dissolved in ethanol (50 mL). THF (50 mL), water (50 mL) and lithium hydroxide (854 mg, 35.6 mmol) were added, and the mixture was stirred at 60° C. for 4 h. After this time the reaction was cooled to room temperature and acidified with 2M hydrochloric acid to pH 1.5, and then extracted with ethyl acetate (2×200 mL). The organic layers were combined, washed with water (2×100 mL), followed by brine (100 ml) and dried over sodium sulfate. The drying agent was then separated by filtration. After evaporating the resulting filtrate, 105c was obtained in 91% yield (3.2 g) as a white solid: mp 170-172° C.; $^1$H NMR (300 MHz, CDCl$_3$) d 12.77 (s, 1H), 7.46 (s, 1H), 2.71 (s, 2H), 2.53 (s, 2H), 1.20 (s, 6H); MS (ESI−) m/z 195.0

Example 105d 5,5-Dimethyl-5,6-dihydro-4H-cyclopenta[b]thiophene-2-carboxylic acid 105d

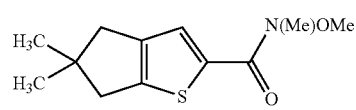

105d

A 100-mL single-neck round-bottomed flask equipped with a magnetic stirrer, reflux condenser and a bubbler placed on the condenser was charged with 105c (2.30 g, 11.6 mmol), toluene (25 mL), thionyl chloride (4.09 g, 34.9 mmol) and DMF (1 drop). The mixture was heated at reflux for 1 h and then evaporated under reduced pressure on a rotary evaporator at 45° C. The resulting acid chloride was diluted with methylene chloride (20 mL).

In a separate 250-mL three-neck round-bottomed flask equipped with a magnetic stirrer N,O-dimethylhydroxylamine hydrochloride (2.26 g, 23.2 mmol) and N,N-diisopropylethylamine (2.97 g, 23.0 mmol) were dissolved in anhydrous methylene chloride (20 mL) under nitrogen, and the solution was cooled to 0° C. in an ice/water bath. The solution of the acid chloride was added, and the reaction mixture was stirred at room temperature for 18 h. The reaction mixture was extracted with water (100 mL), 10% aqueous citric acid (50 mL) and a 1:1 mixture of saturated aqueous sodium bicarbonate and water (100 mL). The organic layer was dried over sodium sulfate and evaporated under reduced pressure on a rotary evaporator to afford a 93% yield (2.60 g) of 105d as a light yellow solid: $^1$H NMR (300 MHz, CDCl$_3$) d 7.66 (s, 1H), 3.77 (s, 3H), 3.35 (s, 3H), 2.74 (s, 2H), 2.58 (s, 2H), 1.23 (s, 6H)

Example 105e 3-Chloro-1-(5,5-dimethyl-5,6-dihydro-4H-cyclopenta[b]thiophen-2-yl)propan-1-one 105e

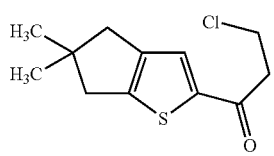

105e

A 100-mL single-neck round-bottomed flask equipped with a magnetic stirrer was purged with nitrogen and charged with 105d (2.41 g, 10.0 mmol) and anhydrous THF (20 mL). The solution was cooled to −70° C., and 1 M vinylmagnesium bromide in THF (11 mL, 11.0 mmol) was added with the reaction temperature maintained below −60° C. The reaction mixture was stirred at −13 to −7° C. for 2 h and then warmed to room temperature over 30 min. The reaction was again cooled to −70° C., and a 2 M solution of hydrogen chloride in ether (22.5 ml, 45 mmol) was added. The reaction was then stored in a freezer at −10° C. overnight. After this time the mixture was evaporated under reduced pressure on a rotary evaporator, and the resulting residue partitioned between water (100 mL) and ether (100 mL). The ether extract was dried over sodium sulfate and evaporated under reduced pressure on a rotary evaporator to afford crude 105e (2.86 g, 118%) as a brown oil with approximately 75% purity (by NMR): $^1$H NMR (300 MHz, CDCl$_3$) d 7.45 (s, 1H), 3.89 (t, 2H, J=6.9 Hz), 3.30 (t, 2H, J=6.9 Hz), 2.75 (s, 2H), 2.59 (s, 2H), 1.24 (s, 6H)

Example 105f 6,6-Dimethyl-1,2,6,7-tetrahydrodicyclopenta[b,d]thiophen-3 (5H)-one 105f

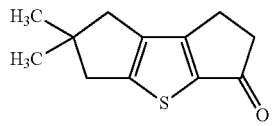

105f

A 100-mL single-neck round-bottomed flask equipped with a magnetic stirrer was charged with crude 105e (2.86 g, 10.0 mmol presuming quantitative yield) and 98% sulfuric acid. The reaction mixture was heated in a 90° C. oil bath overnight. The reaction mixture was placed into an ice/acetone bath, and a cold (5° C.) solution of dipotassium hydrogen phosphate (105 g, 0.603 mol) in water (300 mL) was added in one portion. The resulting mixture was shaken with ethyl acetate (300 mL) and filtered. The filter cake was washed with ethyl acetate (100 mL). The ethyl acetate layer of the filtrate was separated, dried over sodium sulfate and evaporated under reduced pressure on a rotary evaporator. the resulting residue was purified by flash column chromatography (silica, 80:20 hexanes/ethyl acetate) to afford 105f in 37% yield over two steps (683 mg) as an amorphous brown solid: mp 60-62° C.; $^1$H NMR (500 MHz, CDCl$_3$) d 2.92-2.87 (m, 4H), 2.79 (s, 2H), 2.53 (s, 2H), 1.26 (s, 6H); MS (ESI+) m/z 207.0 (M+H)

Example 105g 6,6-Dimethyl-1,2,6,7-tetrahydrodicyclopenta[b,d]thiophen-3(5H)-one 105g

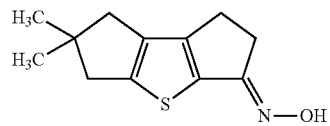

105g

A 250-mL single-neck round-bottomed flask equipped with a magnetic stirrer and nitrogen inlet was charged with hydroxylamine hydrochloride (688 mg, 9.90 mmol), sodium acetate (812 mg, 9.90 mmol) and methanol (10 mL), and the mixture at room temperature for 30 min. After this time, a solution of 105f (680 mg, 3.30 mmol) was added dropwise at room temperature, and the reaction was stirred at room temperature for 14 h under nitrogen atmosphere. Since the reaction was not complete, hydroxylamine hydrochloride (1.15 g, 16.5 mmol) and sodium acetate (1.35 g, 16.5 mmol) were added, and the stirring was continued at room temperature for 58 h. After this time, the mixture was diluted with methylene chloride (150 mL) and water (100 mL), and the layers were separated. The organic layer was washed with brine (50 mL) and dried over sodium sulfate. The drying agent was removed by filtration and the filtrate was concentrated to afford crude 105g in quantitative yield (730 mg) as a yellow semi-solid which was used in the next step without purification: mp 122-124° C.; $^1$H NMR for major isomer (500 MHz, CDCl$_3$) d 3.13-3.11 (m, 2H), 2.85-2.83 (m, 2H), 2.77 (s, 2H), 2.49 (s, 2H), 1.24 (s, 6H); MS (ESI+) m/z 222.0 (M+H).

Example 105h 6,6-Dimethyl-3,4,6,7-tetrahydro-5H-cyclopenta[4,5]thieno[2,3-c]pyridine-1(2H)-one 105h

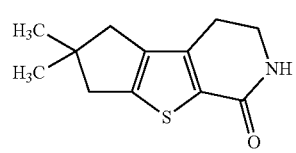

105h

A 100-mL three-neck round-bottomed flask equipped with a reflux condenser, mechanical stirrer and nitrogen inlet was charged with 105g (700 mg, 3.16 mmol) and polyphosphoric acid (25 g). The reaction mixture was stirred at 80° C. for 13 h under nitrogen atmosphere. After this time, the mixture was cooled to 0° C. and water (50 mL) was added dropwise carefully maintaining the internal temperature between 10-45° C. The mixture was diluted with 90:10 methylene chloride/methanol (100 mL) and the layers were separated. The aqueous layer was extracted with 90:10 methylene chloride/methanol (50 mL), and the combined organic layers were washed with saturated aqueous sodium bicarbonate (50 mL), brine (150 mL) and dried over sodium sulfate. The drying agent was removed by filtration. The filtrate was concentrated under reduced pressure, and the resulting residue was purified by flash column chromatography (silica, 95:5 methylene chloride/methanol) to afford 6,6-dimethyl-3,4,6,7-tetrahydro-5H-cyclopenta[4,5]thieno[2,3-c]pyridine-1(2H)-one 105h in 90% yield (630 mg) as an amorphous off-white solid: mp 205-207° C.; $^1$H NMR (500 MHz, CDCl$_3$) d 5.51 (s, 1H), 3.60-3.56 (m, 2H), 2.76-2.73 (m, 4H), 2.49 (s, 2H), 1.26 (s, 6H); MS (ESI+) m/z 222.0 (M+H)

Example 105i (2-Bromo-6-{4,4-dimethyl-9-oxo-7-thia-10-azatricyclo[6.4.0.0$^{2,6}$]dodeca-1(8),2(6)-dien-10-yl}phenyl)methyl Acetate 105i A 250-mL single-neck round-bottomed flask equipped with a magnetic stirrer and nitrogen inlet was charged with 105h (624 mg, 2.82 mmol), 2,6-dibromobenzyl acetate 104g (1.73 g, 5.65 mmol), cesium carbonate (1.84 g, 5.65 mmol), N,N'-dimethylethylenediamine (249 mg, 2.82 mmol) and 1,4-dioxane (15 mL). After bubbling nitrogen through the resulting suspension for 30 min, copper iodide (269 mg, 1.41 mmol) was added. A reflux condenser was attached to the flask, and the reaction mixture was heated at 90° C. for 14 h. After this time, the mixture was cooled to room temperature and filtered. The filtrate was diluted with ethyl acetate (100 mL) and water (50 mL), and the layers were separated. The aqueous layer was extracted with ethyl acetate (2×30 mL), and the combined organic layers were washed with brine (100 mL) and dried over sodium sulfate. The drying agent was removed by filtration. The filtrate was concentrated under reduced pressure, and the resulting residue was purified by flash column chromatography (silica, 70:30 hexanes/ethyl acetate) to afford 105i in 52% yield (660 mg) as a white solid: mp 126-128° C.; $^1$H NMR (500 MHz, CDCl$_3$) d 7.60 (dd, J=7.5, 1.5 Hz, 1H), 7.29-7.24 (m, 2H), 5.24 (s, 2H), 4.05-3.99 (m, 1H), 3.78-3.74 (m, 1H), 3.06-2.99 (m, 1H), 2.84-2.80 (m, 1H), 2.77 (s, 2H), 2.52 (s, 2H), 2.05 (s, 3H), 1.27 (s, 6H); MS (ESI+) m/z 448.0 (M+H)

A 100-mL single-neck round-bottomed flask equipped with a magnetic stirrer and nitrogen inlet was charged with 105i (250 mg, 0.558 mmol), crude 1-methyl-3-(pyrimidin-4-ylamino)-5-(4,4,5,5-tetramethyl-1,3,2-dioxaborolan-2-yl)pyridin-2(1H)-one 104h prepared above, 400 mg, 0.951 mmol, presuming quantitative yield in the previous step), sodium carbonate (177 mg, 1.67 mmol), DMF (2 mL), water (2 mL) and 1,4-dioxane (10 mL). After bubbling nitrogen through the resulting suspension for 30 min, tetrakis(triphenylphosphine)palladium(0) (129 mg, 0.112 mmol) was added. A reflux condenser was attached to the flask, and the reaction mixture was heated at 100° C. for 12 h. After this time, the mixture was diluted with 90:10 methylene chloride/methanol (100 mL) and water (75 mL), and the layers were separated. The aqueous layer was extracted with 90:10 methylene chloride/methanol (2×50 mL), and the combined organic layers were washed with brine (100 mL) and dried over sodium sulfate. The drying agent was removed by filtration. The filtrate was concentrated under reduced pressure, and the resulting residue was dissolved in THF (5 mL), water (5 mL) and methanol (5 mL). Lithium hydroxide monohydrate (117 mg, 2.79 mmol) was added, and the mixture was stirred at room temperature for 2 h. After this time, the mixture was diluted with 90:10 methylene chloride/methanol (100 mL) and water (50 mL), and the layers were separated. The aqueous layer was extracted with 90:10 methylene chloride/methanol (2×75 mL), and the combined organic layers were washed with brine (100 mL) and dried over sodium sulfate. The drying agent was removed by filtration. The filtrate was concentrated under reduced pressure, and the resulting residue was purified by flash column chromatography (silica, 90:10 methylene chloride/methanol) and preparative HPLC (70:30 water/acetonitrile) to afford 105 in 14% yield (42 mg) as an amorphous off-white solid: mp 252-254° C.; $^1$H NMR (500 MHz, DMSO-d$_6$) δ 9.18 (s, 1H), 8.71 (s, 1H), 8.64 (s, 1H), 8.30 (d, J=6.0 Hz, 1H), 7.53 (s, 1H), 7.47 (t, J=7.5 Hz, 1H), 7.37-7.31 (m, 3H), 4.86-4.85 (m, 1H), 4.40-4.32 (m, 2H), 4.05-4.00 (m, 1H), 3.88-3.84 (m, 1H), 3.60 (s, 3H), 3.05-2.99 (m, 1H), 2.91-2.88 (m, 1H), 2.75 (s, 2H), 2.57-2.53 (m, 2H), 1.23 (s, 6H); MS (ESI+) m/z 528.2 (M+H)

Example 106 2-(3-(5-(5-cyclopropyl-1H-pyrazol-3-ylamino)-1-methyl-6-oxo-1,6-dihydropyridin-3-yl)-2-(hydroxymethyl)phenyl)-3,4,6,7,8,9-hexahydropyrazino[1,2-a]indol-1(2H)-one 106

Example 106 was prepared using the same procedure as example 136e and Example 136 except using 113a and 136d to yield 20 mg of 106 as a white solid. MS (ESI+) m/z 525 (M+H).

Example 107 2-(2-(hydroxymethyl)-3-(1-methyl-5-(5-morpholinopyridin-2-ylamino)-6-oxo-1,6-dihydropyridin-3-yl)phenyl)-3,4,6,7,8,9-hexahydropyrazino[1,2-a]indol-1(2H)-one 107

Example 107 was prepared using the same procedure as example 301 using 255c and 114a as starting material to yield 122 mg of 107 as a white solid. MS (ESI+) m/z 581 (M+H).

Example 108 2-(3-(5-(5-acetyl-4,5,6,7-tetrahydropyrazolo[1,5-a]pyrazin-2-ylamino)-1-methyl-6-oxo-1,6-dihydropyridin-3-yl)-2-(hydroxymethyl)phenyl)-3,4,6,7,8,9-hexahydropyrazino[1,2-a]indol-1(2H)-one 108

Example 108a 2-nitro-4,5,6,7-tetrahydropyrazolo[1,5-a]pyrazine 108a

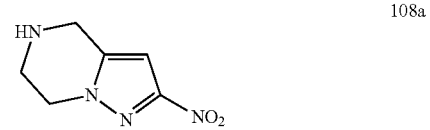 [SMILES: O=[N+]([O-])c1cc2n(n1)CCNC2]

A sealed tube equipped with a magnetic stirrer was charged with 1-(2-bromoethyl)-5-(bromomethyl)-3-nitro-1H-pyrazole 101c (4 g, 12.9 mmol) 0.5M ammonia solution in dioxane (200 mL). The resulting mixture was carefully heated to 50° C. overnight. After this time, the reaction mixture was concentrated under reduced pressure, and to the residue was added H$_2$O (50 mL) and EtOAc (50 mL). The aqueous layer was separated and extracted with EtOAc (2×50 mL). The combined organic extracts were washed with brine (100 mL) and dried over sodium sulfate. The resulting solution was concentrated under reduced pressure to afford a 100% yield (2.1 g) of crude 2-nitro-4,5,6,7-tetrahydropyrazolo[1,5-a]pyrazine 108a.

Example 108b 1-(2-nitro-6,7-dihydropyrazolo[1,5-a]pyrazin-5(4H)-yl)ethanone 108b

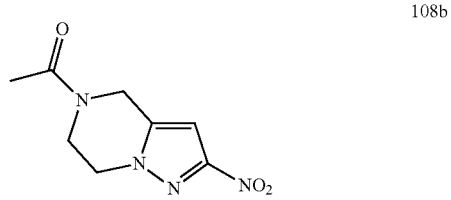

A 200 mL round bottom flask was charged with 2-nitro-4,5,6,7-tetrahydropyrazolo[1,5-a]pyrazine 108a (2.1 g, 12.9 mmol), triethylamine (5.5 mL, 38.7 mmol), acetyl chloride (1.1 mL, 15.5 mmol) and CH$_2$Cl$_2$ (100 mL). The mixture stirred at room temperature over night. After this time, the reaction mixture was concentrated under reduced pressure, and to the residue was added H$_2$O (50 mL) and EtOAc (50 mL). The aqueous layer was separated and extracted with EtOAc (2×50 mL). The combined organic extracts were washed with brine (100 mL). The combined aqueous extracts were back extracted with 9:1 CH$_2$Cl$_2$:MeOH (2×50 mL). The combined organics were dried over sodium sulfate. The resulting residue was purified by column chromatography eluting with a gradient of $CH_2Cl_2$—9:1 $CH_2Cl_2$:MeOH to afford a 84% yield (2.3 g) of 1-(2-nitro-6,7-dihydropyrazolo[1,5-a]pyrazin-5(4H)-yl)ethanone 108b.

Example 108c 1-(2-amino-6,7-dihydropyrazolo[1,5-a]pyrazin-5(4H)-yl)ethanone 108c

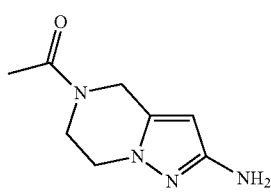

108c

A 500-mL Parr hydrogenation bottle was charged with 1-(2-nitro-6,7-dihydro-pyrazolo[1,5-a]pyrazin-5(4H)-yl)ethanone 108b (2.3 g, 10.9 mmol), 10% palladium on carbon (50% wet, 570 mg dry weight) and ethanol (100 mL). The bottle was evacuated, charged with hydrogen gas to a pressure of 50 psi and shaken for 2 h on a Parr hydrogenation apparatus. The catalyst was removed by filtration through a pad of Celite 521 washing with 1:1 $CH_2Cl_2$:MeOH (500 mL). The resulting solution was concentrated under reduced pressure to afford a 95% yield (1.9 g) of crude 1-(2-amino-6,7-dihydropyrazolo[1,5-a]pyrazin-5(4H)-yl)ethanone 108c.

Example 108d 3-(5-acetyl-4,5,6,7-tetrahydropyrazolo[1,5-a]pyrazin-2-ylamino)-5-bromo-1-methylpyridin-2(1H)-one 108d

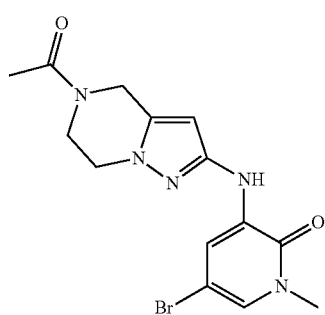

108d

A sealed tube was equipped with a magnetic stirrer and charged with 1-(2-amino-6,7-dihydropyrazolo[1,5-a]pyrazin-5(4H)-yl)ethanone 108c (860 mg, 4.8 mmol), 3,5-dibromo-1-methylpyridin-2(1H)-one (1.8 g, 6.7 mmol), and cesium carbonate (3.4 g, 10.5 mmol) in 1,4-dioxane (67 mL). After bubbling nitrogen through the solution for 30 min, Xantphos (330 mg, 0.6 mmol) and tris(dibenzylideneacetone)dipalladium(0) (300 mg, 0.3 mmol) were added, and the reaction mixture was heated to 100° C. for 16 h. After this time, $H_2O$ (50 mL) and EtOAc (50 mL) were added. The aqueous layer was separated and extracted with EtOAc (2×50 mL). The combined organic extracts were washed with brine (100 mL) and dried over sodium sulfate. The resulting residue was purified by column chromatography eluting with a gradient of $CH_2Cl_2$—60:35:5 $CH_2Cl_2$:$Et_2O$:MeOH to afford a 41% yield (720 mg) of 3-(5-acetyl-4,5,6,7-tetrahydropyrazolo[1,5-a]pyrazin-2-ylamino)-5-bromo-1-methylpyridin-2(1H)-one 108d.

Example 108e 2-(5-(5-acetyl-4,5,6,7-tetrahydropyrazolo[1,5-a]pyrazin-2-ylamino)-1-methyl-6-oxo-1,6-dihydropyridin-3-yl)-6-(1-oxo-3,4,6,7,8,9-hexahydropyrazino[1,2-a]indol-2(1H)-yl)benzyl acetate 108e

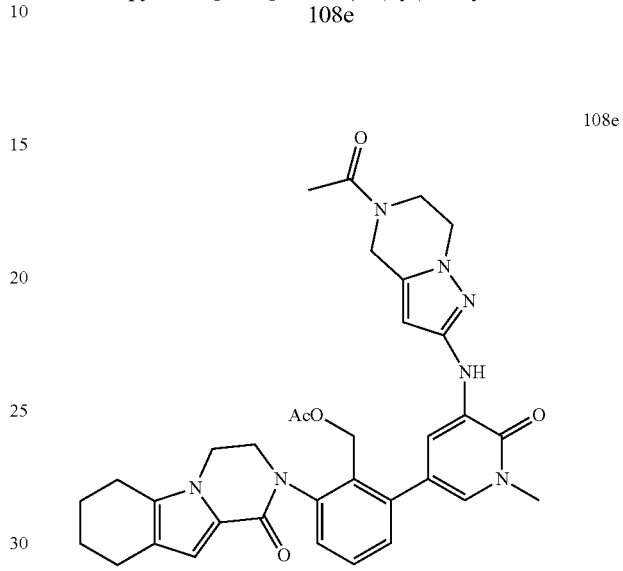

108e

A microwave tube equipped with a magnetic stirrer was charged with 3-(5-acetyl-4,5,6,7-tetrahydropyrazolo[1,5-a]pyrazin-2-ylamino)-5-bromo-1-methylpyridin-2(1H)-one 108d (120 mg, 0.3 mmol), 2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 114a (200 mg, 0.4 mmol), DME (4 mL) and 1M aqueous sodium carbonate (1 mL). After bubbling nitrogen for 15 min, $Pd(PPh_3)_4$ (19 mg, 0.02 mmol) was added. The mixture was heated in a microwave to 130° C. for 15 min. After this time, ethyl acetate (5 mL) and water (5 mL) were added. The separated aqueous layer was extracted with EtOAc (2×5 mL). The combined organics were washed with brine (10 mL), dried over sodium sulfate, filtered and concentrated under reduced pressure. The resulting residue was purified by column chromatography eluting with a gradient of $CH_2Cl_2$—60:35:5 $CH_2Cl_2$:$Et_2O$:MeOH to afford a 33% yield (69 mg) of 2-(5-(5-acetyl-4,5,6,7-tetrahydropyrazolo[1,5-a]pyrazin-2-ylamino)-1-methyl-6-oxo-1,6-dihydropyridin-3-yl)-6-(1-oxo-3,4,6,7,8,9-hexahydropyrazino[1,2-a]indol-2(1H)-yl)benzyl acetate 108e.

A 25 mL round bottom flask with a magnetic stirrer was charged with 2-(5-(5-acetyl-4,5,6,7-tetrahydropyrazolo[1,5-a]pyrazin-2-ylamino)-1-methyl-6-oxo-1,6-dihydropyridin-3-yl)-6-(1-oxo-3,4,6,7,8,9-hexahydropyrazino[1,2-a]indol-2(1H)-yl)benzyl acetate 108e (69 mg, 0.11 mmol), lithium hydroxide (8 mg, 0.3 mmol), THF (1 mL), i-PrOH (1 mL) and water (2 mL). The mixture stirred at rt for 2 h. After this time, EtOAc (3 mL) and water (3 mL) were added. The separated aqueous layer was extracted with EtOAc (2×5 mL). The combined organics were washed with brine (10 mL), dried over sodium sulfate, filtered and concentrated under reduced pressure. The resulting residue was purified by column chromatography eluting with a gradient of $CH_2Cl_2$—75:18:7 $CH_2Cl_2$:$Et_2O$:MeOH to afford a 63% yield (40 mg) of 2-(3-(5-(5-acetyl-4,5,6,7-tetrahydropyrazolo[1,5-a]pyrazin-2-ylamino)-1-methyl-6-oxo-1,6-dihydropyridin-3-yl)-2-(hydroxymethyl)phenyl)-3,4,6,7,8,9-hexahydropyrazino[1,2-a]indol-1(2H)-one 108. MS (ESI+) m/z 582.3 (M+H).

Example 109 2-(2-(hydroxymethyl)-3-(1-methyl-6-oxo-5-(pyrimidin-4-ylamino)-1,6-dihydropyridin-3-yl)phenyl)-3,4,6,7,8,9-hexahydropyrazino[1,2-a]indol-1(2H)-one 109

Example 109a 2-bromo-6-(1-oxo-3,4,6,7,8,9-hexahydropyrazino[1,2-a]indol-2(1H)-yl)benzyl acetate 109a

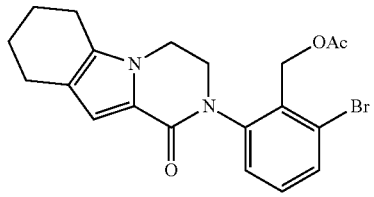

A 100-mL three-neck round-bottomed flask equipped with a reflux condenser, magnetic stirrer and nitrogen inlet was charged with 3,4,6,7,8,9-hexahydropyrazino[1,2-a]indol-1(2H)-one 101k (720 mg, 3.78 mmol), 2,6-dibromobenzyl acetate 104g (2.33 g, 7.57 mmol), cesium carbonate (2.47 g, 7.57 mmol), N,N'-dimethylethylenediamine (333 mg, 3.78 mmol) and 1,4-dioxane (31 mL). After bubbling nitrogen through the resulting suspension for 30 min, copper iodide (360 mg, 1.89 mmol) was added, and the reaction mixture was heated at 105° C. (oil bath temperature) for 3 days. After this time, the mixture was cooled to room temperature and filtered. The filtrate was diluted with ethyl acetate (200 mL) and water (40 mL). The organic layer was separated, and the aqueous layer was extracted with ethyl acetate (3×50 mL). The combined organic layers were dried over sodium sulfate and concentrated under reduced pressure. The residue was purified by column chromatography to afford a 31% yield (490 mg) of 2-bromo-6-(1-oxo-3,4,6,7,8,9-hexahydropyrazino[1,2-a]indol-2(1H)-yl)benzyl acetate 109a.

Example 109b 5-bromo-1-methyl-3-(pyrimidin-4-ylamino)pyridin-2(1H)-one 109b

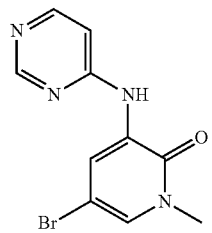 [SMILES: Cn1cc(Br)cc(Nc2ccncn2)c1=O]

A solution of pyrimidin-4-amine (2.0 g, 21 mmol), 3,5-dibromo-1-methylpyridin-2(1H)-one (6.2 g, 23.1 mmol), tris(dibenzylideneacetone)dipalladium(0) (0.96 g, 1.1 mmol), Xantphos (1.03 g, 1.79 mmol), and cesium carbonate (7.5 g, 23 mmol) in dioxane (25 mL) was heated in a sealed tube at 130° C. for 18 hours. The mixture was diluted with CH₂Cl₂ (100 mL) and filtered through a plug of celite. The solution was concentrated in vacuo on the rotary evaporator. The material was then dissolved in minimal CH₂Cl₂ (5 mL) and was triturated with Et₂O (80 mL). The product was then filtered and washed with Et₂O (100 mL) to afford 2.9 g (49%) of 109b.

Example 109c 1-Methyl-3-(pyrimidin-4-ylamino)-5-(4,4,5,5-tetramethyl-1,3,2-dioxaborolan-2-yl)pyridin-2(1H)-one 109c

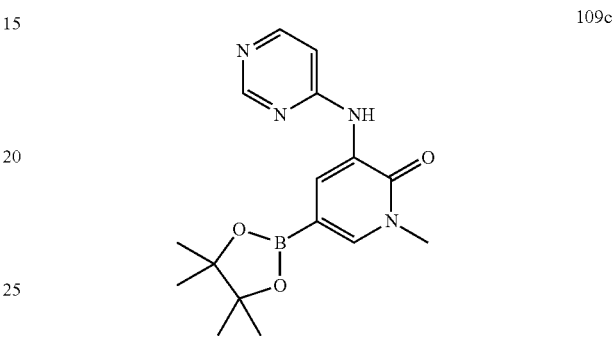

A solution of 5-bromo-1-methyl-3-(pyrimidin-4-ylamino)pyridin-2(1H)-one 109b (600 mg, 2.13 mmol), 4,4,4',4',5,5,5',5'-octamethyl-2,2'-bi(1,3,2-dioxaborolane) (596 mg, 2.35 mmol), [1,1'-Bis(diphenylphosphino)ferrocene]dichloropalladium(II), complex with dichloromethane (174 mg, 0.213 mmol), potassium acetate (628 mg, 6.40 mmol) in dioxane (4.5 mL) was sealed in a microwave tube and heated to 130° C. for 10 minutes. The solution was filtered through a plug of celite and concentrated. The crude 1-methyl-3-(pyrimidin-4-ylamino)-5-(4,4,5,5-tetramethyl-1,3,2-dioxaborolan-2-yl)pyridin-2(1H)-one 109c was carried on to the next step without purification.

A solution of 109c (crude, 2.13 mmol), 109a (300 mg, 0.719 mmol), tetrakis(triphenylphosphine)palladium(0) (83 mg, 0.0719 mmol), and sodium carbonate (229 mg, 2.16 mmol) in dioxane (4.5 mL) and water (2.3 mL) was sealed in a microwave tube and heated to 130° C. for 10 minutes. The organics layer was separated from the aqueous and filtered through a plug of celite. The material was then adsorbed to celite and was purified via silica chromatography using 0-100% ethyl acetate in hexanes followed by a switch to 0-15% methanol in dichloromethane to afford 105 mg (27%) of 109.

Example 110 2-(3-(5-(6,7-dihydro-4H-pyrazolo[5,1-c][1,4]oxazin-2-ylamino)-1-methyl-6-oxo-1,6-dihydropyridin-3-yl)-2-(hydroxymethyl)phenyl)-3,4,6,7,8,9-hexahydropyrazino[1,2-a]indol-1(2H)-one 110

Example 110a 2-Nitro-6,7-dihydro-4H-pyrazolo[5,1-c][1,4]oxazine 110a

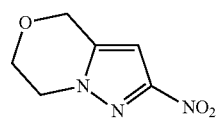

A 250-mL single-neck round-bottomed flask equipped with a magnetic stirrer and reflux condenser was charged with 101c (3.00 g, 9.59 mmol) and 4M aqueous hydrobromic acid (120 mL), and the resulting mixture was heated at reflux for 24 h. After this time, the reaction mixture was concentrated under reduced pressure to approximately 6 mL volume, and the residue was stirred in 2M aqueous sodium hydroxide (40 mL) for 2 h. After this time methylene chloride was added (40 mL) and the mixture was stirred for 15 min. The aqueous layer was separated and extracted with methylene chloride (2×50 mL). The combined organic extracts were washed with brine (100 mL) and dried over sodium sulfate. The drying agent was removed by filtration and the filtrate concentrated under reduced pressure to afford a 62% yield (1.01 g) of 110a as a white solid: mp 110-112° C.; $^1$H NMR (300 MHz, CDCl$_3$) 6.68 (s, 1H), 4.87 (s, 2H), 4.28 (t, 2H, J=5.4 Hz), 4.20 (t, 2H, J=5.1 Hz); MS (ESI+) m/z 170.0 (M+H).

Example 110b 6,7-Dihydro-4H-pyrazolo[5,1-c][1,4]oxazin-2-amine 110b

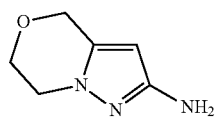

110b

A 500-mL Parr hydrogenation bottle was purged with nitrogen and charged with 110a (1.01 g, 5.92 mmol), 10% palladium on carbon (50% wet, 125 mg dry weight) and ethanol (50 mL). The bottle was evacuated, charged with hydrogen gas to a pressure of 25 psi and shaken for 2 h on a Parr hydrogenation apparatus. The hydrogen was then evacuated and nitrogen charged to the bottle. The catalyst was removed by filtration through a pad of Celite 521 and the filtrate concentrated under reduced pressure. The resulting residue was purified by column chromatography using 400 cc of silica gel and eluting with 3% methanol in methylene chloride. The fractions containing 110b were collected to afford, after concentrating under reduced pressure, a 73% yield (601 mg) of 110b as a yellow solid: mp 74-76° C. $^1$H NMR (300 MHz, CDCl$_3$) d 5.37 (s, 1H), 4.72 (s, 2H), 4.07 (t, 2H, J=5.1 Hz), 3.98 (t, 2H, J=5.1 Hz), 3.57 (br s, 2H); MS (ESI+) m/z 140.4 (M+H).

Example 110c 5-Bromo-3-(6,7-dihydro-4H-pyrazolo[5,1-c][1,4]oxazin-2-ylamino)-1-methylpyridin-2(1H)-one 110c

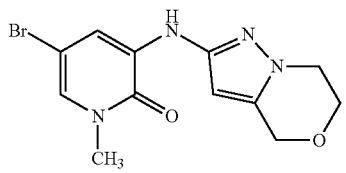

110c

A 50-mL three-neck round-bottomed flask equipped with a magnetic stirrer, reflux condenser and nitrogen inlet was charged with 1,4-dioxane (20 mL), 110b (600 mg, 4.31 mmol), 3,5-dibromo-1-methyl pyridine-2(1H)-one (1.44 g, 5.40 mmol) and cesium carbonate (3.08 g, 9.48 mmol). After bubbling nitrogen through the resulting solution for 30 min, Xantphos (300 mg, 0.52 mmol) and tris(dibenzylideneacetone)-dipalladium(0) (320 mg, 0.35 mmol) were added, and the reaction mixture was heated at reflux for 2 h. After this time the reaction was cooled to room temperature, partitioned between ethyl acetate (75 mL) and water (75 mL) and filtered. The aqueous layer was separated and extracted with ethyl acetate (2×25 mL). The organic layers were combined and washed with brine (50 mL) and dried over sodium sulfate. The drying agent was removed by filtration and the filtrate concentrated under reduced pressure. The resulting residue was purified by column chromatography using 500 cc of silica gel and eluting with 1% methanol in methylene chloride. The fractions containing 110c were collected to afford, after concentrating under reduced pressure, a 31% yield (433 mg) of 110c as a green solid: mp 195-197° C.; $^1$H NMR (300 MHz, CDCl$_3$) 7.92 (d, 1H, J=2.4 Hz), 7.44 (s, 1H), 6.90 (d, 1H, J=2.4 Hz), 5.65 (s, 1H), 4.80 (s, 2H), 4.13 (s, 2H), 3.61 (s, 5H); MS (ESI+) m/z 324.9 (M+H).

Example 110d 2-(5-(6,7-Dihydro-4H-pyrazolo[5,1-c][1,4]oxazin-2-ylamino)-1-methyl-6-oxo-1,6-dihydropyridin-3-yl)-6-(1-oxo-3,4,6,7,8,9-hexahydropyrazino[1,2-a]indol-2(1H)-yl)benzyl acetate 110d

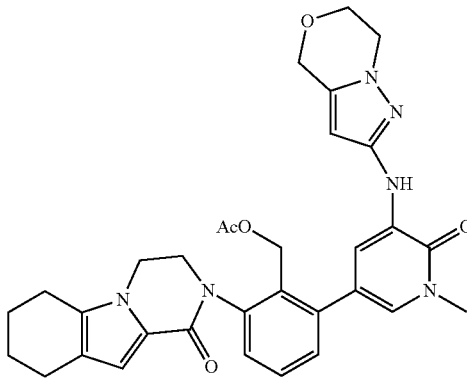

110d

A microwave tube equipped with a magnetic stirrer was charged with 5-bromo-3-(6,7-dihydro-4H-pyrazolo[5,1-c][1,4]oxazin-2-ylamino)-1-methylpyridin-2(1H)-one 110c (130 mg, 0.4 mmol), 2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 114a (220 mg, 0.5 mmol), DME (4 mL) and 1M aqueous sodium carbonate (1.2 mL). After bubbling N2 for 15 min, Pd(PPh$_3$)$_4$ (23 mg, 0.02 mmol) was added. The mixture was heated in microwave to 130° C. for 20 min. After this time, EtOAc (5 mL) and water (5 mL) were added. The separated aqueous layer was extracted with EtOAc (2×5 mL). The combined organics were washed with brine (10 mL), dried over sodium sulfate, filtered and concentrated under reduced pressure. The resulting residue was purified by column chromatography eluting with a gradient of CH$_2$Cl$_2$—60:35:5 CH$_2$Cl$_2$:Et$_2$O:MeOH to afford a 89% yield (210 mg) of 110d.

A 25 mL round bottom flask with a magnetic stirrer was charged with 110d (210 mg, 0.4 mmol), lithium hydroxide (45 mg, 1.1 mmol), THF (3.6 mL), i-PrOH (3.6 mL) and water (7.2 mL). The mixture stirred at rt for 3 h. After this time, EtOAc (10 mL) and water (10 mL) were added. The separated aqueous layer was extracted with EtOAc (2×10 mL). The combined organics were washed with brine (20 mL), dried over sodium sulfate, filtered and concentrated under reduced pressure. The resulting residue was purified by column chromatography eluting with a gradient of $CH_2Cl_2$—60:35:5 $CH_2Cl_2$:$Et_2O$:MeOH to afford a 57% yield (110 mg) of 110. MS (ESI+) m/z 541.3 (M+H).

Example 111 5-[2-(Hydroxymethyl)-3-[4-methyl-5-oxo-6-(pyridine-3-ylamino)-4,5-dihydropyrazin-2-yl]phenyl]-8-thia-5-azatricyclo[7.4.0.02,7]trideca-1(9),2(7)-dien-6-one 111

Example 111a 2-(1-Oxo-3,4,5,6,7,8-hexahydrobenzothieno[2,3-c]pyridin-2(1H)-yl)-6-(4,4,5,5-tetramethyl-1,3,2-dioxaborolan-2-yl)benzyl Acetate 111a

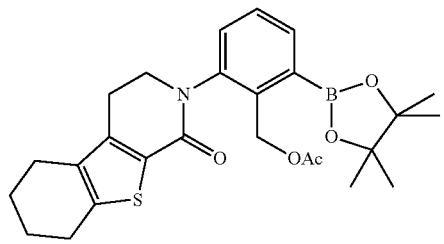

111a

A 100-mL single-neck round-bottomed flask equipped with a magnetic stirrer and reflux condenser was purged with nitrogen and charged with 104f (1.18 g, 2.72 mmol), 4,4,4',4',5,5,5',5'-octamethyl-2,2'-bi(1,3,2-dioxaborolane (2.04 g, 8.16 mmol), potassium acetate (800 mg, 8.16 mmol) and 1,4-dioxane (20 mL). A stream of nitrogen was passed through the resulting suspension for 30 min. [1,1'-Bis(diphenylphosphino)ferrocene]-dichloropalladium(II) (398 mg, 0.544 mmol) was then added, and the reaction was stirred at 90° C. for 8 h. After this time, the mixture was cooled to ambient temperature, partitioned between water (25 mL) and ethyl acetate (50 mL) and filtered through a plug of Celite 521. The organic phase was separated, dried over sodium sulfate, filtered and concentrated under reduced pressure. the resulting residue was purified by flash chromatography to afford a 77% yield (1.01 g) of 111a as a brown solid: $^1$H NMR (500 MHz, CDCl$_3$) d 7.81 (d, 1H, J=7.0 Hz), 7.41 (t, 1H, J=7.0 Hz), 7.37 (d, 1H, J=7.0 Hz), 5.49 (d, 1H, J=11.5 Hz), 5.23 (d, 1H, J=11.5 Hz), 4.01 (m, 1H), 3.76 (m, 1H), 2.96 (m, 1H), 2.81-2.75 (m, 3H), 2.50 (m, 2H), 1.99 (s, 3H), 1.86 (m, 4H), 1.33 (s, 12H); MS (ESI+) m/z 482.2 (M+H).

Example 111b 5-Bromo-1-methyl-3-(pyridin-3-ylamino)pyrazin-2(1H)-one 111b 8.21 mmol). After bubbling nitrogen through the resulting solution for 30 min, di-μ-bromobis(tri-t-butylphosphino)dipalladium(I) (29 mg, 0.037 mmol) was added, and the reaction mixture was stirred at room temperature for 2.5 h. After this time the reaction was partitioned between ethyl acetate (50 mL) and water (50 mL) and filtered. The aqueous layer was separated and extracted with ethyl acetate (2×25 mL). The organic layers were combined, washed with brine (50 mL) and dried over sodium sulfate. The drying agent was removed by filtration and the filtrate concentrated under reduced pressure. The resulting residue was purified by column chromatography to afford a 35% yield (370 mg) of 111b as a brown solid: mp>250° C.; $^1$H NMR (500 MHz, DMSO-d$_6$) δ 9.75 (s, 1H), 9.08 (d, 1H, J=2.5 Hz), 8.32 (m, 1H), 8.24 (dd, 1H, J=5.0, 1.5 Hz), 7.40 (s, 1H), 7.36 (dd, 1H, J=8.5, 4.5 Hz), 3.45 (s, 3H); MS (APCI+) m/z 281.0 (M+H).

A 100-mL single-neck round-bottomed flask equipped with a magnetic stirrer and reflux condenser was purged with nitrogen and charged with 111a (134 mg, 0.279 mmol), 111b (71 mg, 0.253 mmol), sodium carbonate (80 mg, 0.759 mmol), 1,4-dioxane (5 mL) and water (1 mL). This mixture was degassed with nitrogen for 30 min. Tetrakis(triphenylphosphine)palladium (29 mg, 0.025 mmol) was added. After heating at 100° C. for 3 h, the reaction mixture was cooled to room temperature and partitioned between water (40 mL) and methylene chloride (100 mL). The layers were separated, and the aqueous phase was extracted with methylene chloride (2×50 mL). The organic extracts were combined, dried over sodium sulfate, filtered and concentrated under reduced pressure. The resulting residue was dissolved in methanol (5 mL), and potassium carbonate (500 mg, 3.62 mmol) was added. After stirring at room temperature for 2 h, the reaction mixture was partitioned between water (20 mL) and methylene chloride (20 mL). The layers were separated, and the aqueous phase was extracted with methylene chloride (2×20 mL). The organic extracts were combined, dried over sodium sulfate, filtered and concentrated under reduced pressure. The resulting residue was purified by flash chromatography to afford 111 in 38% yield (49 mg) as a white solid: mp 164-165° C.; $^1$H NMR (500 MHz, DMSO-d$_6$) δ 9.54 (s, 1H), 9.14 (d, 1H, J=2.5 Hz), 8.42 (m, 1H), 8.18 (dd, 1H, J=4.5, 1.5 Hz), 7.54 (d, 1H, J=8.0 Hz), 7.49-7.46 (m, 2H), 7.34 (d, 1H, J=8.0 Hz), 7.30 (dd, 1H, J=8.0, 4.5 Hz), 4.81 (m, 1H), 4.49 (dd, 1H, J=11.0, 3.5 Hz), 4.43 (dd, 1H, J=11.0, 6.5 Hz), 4.02 (m, 1H), 3.86 (m, 1H), 3.56 (s, 3H), 2.95 (m, 1H), 2.86 (m, 1H), 2.77 (m, 2H), 2.58-2.46 (m, 2H), 1.79 (m, 4H); MS (APCI+) m/z 514.2 (M+H).

Example 112 2-(2-(hydroxymethyl)-3-(1-methyl-5-(5-methyl-1H-pyrazol-3-ylamino)-6-oxo-1,6-dihydropyridin-3-yl)phenyl)-3,4,6,7,8,9-hexahydropyrazino[1,2-a]indol-1(2H)-one 112

Example 112a 5-Bromo-1-methyl-3-(5-methyl-1H-pyrazol-3-ylamino)pyridin-2(1H)-one 112a

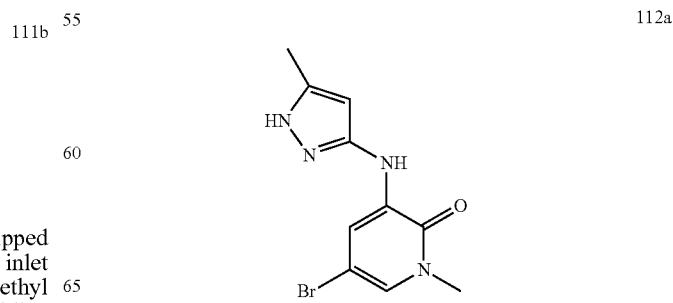

112a

A 100-mL single-neck round-bottomed flask equipped with a magnetic stirrer, reflux condenser and nitrogen inlet was charged with THF (15 mL), 3,5-dibromo-1-methyl pyrazin-2(1H)-one (1.00 g, 3.73 mmol), 3-aminopyridine (351 mg, 3.73 mmol) and sodium tert-butoxide (789 mg, A 250 ml sealed tube with a magnetic stirrer was charged with 5-methyl-1H-pyrazol-3-amine (0.91 g, 9.36 mmol), 3,5-dibromo-1-methyl-1H-pyridin-2-one (2.1 g, 7.87 mmol), cesium carbonate (7.6 g, 23.56 mmol) and 1,4-dioxane (78 mL). After degassing for 10 minutes, tris(dibenzylideneacetone)dipalladium(0) (0.72 g, 0.8 mmol) and Xantphos (0.91 g, 1.57 mmol) were added. The reaction mixture was heated at 115° C. for 48 hours. Then the mixture was cooled to room temperature and partitioned between dichloro-methane (50 mL) and water (30 mL). The organic phase was separated, and the aqueous layer was extracted with dichloromethane (3×30 mL). The combined organic phases were dried over sodium sulfate and concentrated under reduced pressure. The residue was purified by flash column chromatography (silica, 9:1 methylene chloride/methanol) to give 85% yield (1.88 g) of 112a as a solid: MS (ESI+) m/z 285.0 (M+H).

A 10 mL microwave vial with a magnetic stirrer was charged with 2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 114a (181 mg, 0.39 mmol), 112a (85 mg, 0.3 mmol), 1M sodium carbonate solution (1.2 mL, 1.2 mmol) and 1,2-dimethoxyethane (3 mL). After bubbling nitrogen through the resulting suspension for 10 min, tetrakis(triphenylphosphine)-palladium(0) (18 mg, 0.015 mmol) was added. The reaction mixture was heated at 130° C. for 10 minutes in a microwave reactor. Then ethyl acetate (10 mL) and water (5 mL) were added, and the layers were separated. The aqueous layer was extracted with ethyl acetate (2×10 mL), and the combined organic layers were washed with brine and dried over sodium sulfate. The drying agent was removed by filtration. The filtrate was concentrated under reduced pressure, and the resulting residue was purified by flash column chromatography (silica, 60:35:5 methylene chloride/diethyl ether/methanol) to give 100 mg mixture of 112b and 112 as a yellow residue. The residue was dissolved in a mixture of THF (1 mL), water (0.5 mL) and isopropanol (1 mL). Lithium hydroxide monohydrate (31 mg, 0.74 mmol) was added, and the mixture was stirred at room temperature for 2 h. After this time, the mixture was diluted with 90:10 methylene chloride/methanol (10 mL) and water (5 mL), and the layers were separated. The aqueous layer was extracted with 90:10 methylene chloride/methanol (2×10 mL), and the combined organic layers were washed with brine and dried over sodium sulfate. The drying agent was removed by filtration. The filtrate was concentrated under reduced pressure, and the resulting residue was purified by flash column chromatography (silica, 60:35:5 methylene chloride/ether/methanol) to afford a 18% yield (two steps, 28 mg) of 2-(2-(hydroxymethyl)-3-(1-methyl-5-(5-methyl-1H-pyrazol-3-ylamino)-6-oxo-1,6-dihydropyridin-3-yl)phenyl)-3,4,6,7,8,9-hexahydropyrazino[1,2-a]indol-1(2H)-one 112 as a white solid: MS (ESI+) m/z 499.3 (M+H).

Example 113 2-(2-(hydroxymethyl)-3-(1-methyl-5-(5-(4-methylpiperazin-1-yl)pyridine-2-ylamino)-6-oxo-1,6-dihydropyridin-3-yl)phenyl)-3,4,6,7,8,9-hexahydropyrazino[1,2-a]indol-1(2H)-one 113

Example 113a Acetic Acid 2-Bromo-6-(1-oxo-3,4,6,7,8,9-hexahydro-1H-pyrazino[1,2-a]indol-2-yl)-benzyl Ester 113a

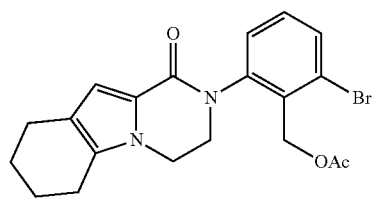

113a

A 350-mL sealed tube equipped with a magnetic stirring bar was charged with 3,4,6,7,8,9-hexahydro-2H-pyrazino[1,2-a]indol-1-one 101k (5.0 g, 0.026 mol), 2,6-dibromobenzyl acetate 104g (16.2 g, 0.052 mol) N,N'-dimethylethylenediamine (2.6 mL, 0.026 mol), Cs₂CO₃ (17.0 g, 0.052 mol), and 1,4-dioxane (80 mL). After a stream of nitrogen was passed through the resulting suspension for 30 min., CuI (2.5 g, 0.013 mol) was added and the resulting reaction mixture was stirred at 95° C. for 16 h. Then the mixture was cooled to room temperature, partitioned between EtOAc (50 mL) and water (50 mL), and the organic phase was extracted with EtOAc (30 mL×3). The combined organic phases were washed with water (20 mL×2) and brine (20 mL×1), dried (Na₂SO₄), and concentrated. The crude product was purified by flash chromatography (dichloromethane:MeOH, 97:3) to give 35% yield (4.5 g) of 113a as white solids.

Example 113b Acetic Acid 2-{1-Methyl-5-[5-(4-methyl-piperazin-1-yl)-pyridin-2-ylamino]-6-oxo-1,6-dihydro-pyridin-3-yl}-6-(1-oxo-3,4,6,7,8,9-hexahydro-1H-pyrazino[1,2-a]indol-2-yl)-benzyl Ester 113b

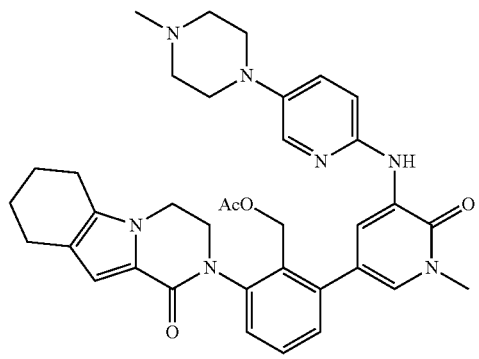

113b

In a 10-mL glass vessel equipped with a magnetic stirring bar were placed 1-methyl-3-[5-(4-methyl-piperazin-1-yl)-pyridin-2-ylamino]-5-(4,4,5,5-tetramethyl-[1,3,2]dioxaborolan-2-yl)-1H-pyridin-2-one 197f (210 mg, 0.49 mmol), 113a (250 mg, 0.60 mmol), Pd(PPh₃)₄ (50 mg, 0.043 mmol) in 2 N Na₂CO₃ (2 mL) and 1,2-dimethoxyethane (5 mL). The vessel was sealed with a septum and placed into the microwave cavity. After the reaction mixture was stirred at 125° C. for 7 min., it was purified by flash chromatography (dichloromethane:methanol, 85:15) to give 34% (105 mg) of acetic acid 2-{1-methyl-5-[5-(4-methyl-piperazin-1-yl)-pyridin-2-ylamino]-6-oxo-1,6-dihydro-pyridin-3-yl}-6-(1-oxo-3,4,6,7,8,9-hexahydro-1H-pyrazino[1,2-a]indol-2-yl)-benzyl ester 113b as solids.

A 100-mL, single-necked, round-bottomed flask equipped with a magnetic stirring bar was charged with 113b (105 mg, 0.17 mmol), LiOH.H₂O (35 mg, 0.83 mmol), THF (2 mL), isopropanol (2 mL), and water (1 mL). After the reaction mixture was stirred at room temperature for 3 h, it was partitioned between dichloromethane (5 mL) and water (5 mL), and the organic phase was extracted with dichloromethane (5 mL×3). The combined organic phases were washed with water (5 mL×2) and brine (5 mL×1), dried (Na₂SO₄), and concentrated. The crude product was redissolved in dichloromethane (3 mL). To this solution was added hexane (10 mL) and the resulting precipitates were filtered to give 80% yield (79 mg) of 2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-3,4,6,7,8,9-hexahydro-2H-pyrazino[1,2-a]indol-1-one 113; MS(ESI+) m/z 594.3 (M+H).

Example 114 2-(3-(6-(1-cyclopropyl-1H-pyrazol-4-ylamino)-4-methyl-5-oxo-4,5-dihydropyrazin-2-yl)-2-(hydroxymethyl)phenyl)-3,4,6,7,8,9-hexahydropyrazino[1,2-a]indol-1(2H)-one 114

Example 114a 2-(2-(Acetoxymethyl)-3-(4,4,5,5-tetramethyl-1,3,2-dioxaborolan-2-yl)phenyl)-3,4,6,7,8,9-hexahydropyrazino[1,2-a]indol-1(2H)-one 114a

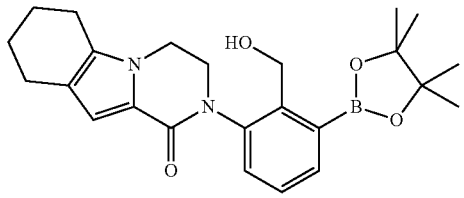 [SMILES: CC1(C)OB(c2cccc(N3CCn4c(cc5c4CCCC5)C3=O)c2CO)OC1(C)C]

To a round-bottomed flask equipped with a stirring bar, 2-(3-bromo-2-(hydroxymethyl)phenyl)-3,4,6,7,8,9-hexahydropyrazino[1,2-a]indol-1(2H)-one 113a (1.96 g, 4.70 mmol), 4,4,4',4',5,5,5',5'-octamethyl-2,2'-bi(1,3,2-dioxaborolane) (1.79 g, 7.05 mmol), Cl$_2$Pd(dppf)$_2$·CH$_2$Cl$_2$ (306.9 mg, 0.376 mmol), KOAc (4.77 g, 18.79 mmol), and dioxane (33.6 mL) were added. The mixture was heated at 95° C. overnight. The resulting mixture was filtered through Celite, washed with ethyl acetate (200 mL). The organic phase was washed with water (50 mL), dried over MgSO$_4$, and the solvent removed in vacuo to yield the crude product 114a, which was directly used as starting material other syntheses.

Example 114b 5-Bromo-3-(1-cyclopropyl-1H-pyrazol-4-ylamino)-1-methylpyrazin-2(1H)-one 114b

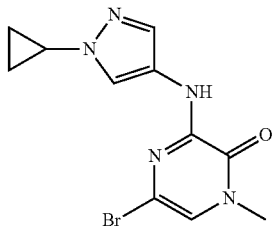 [SMILES: Cn1cc(Br)nc(Nc2cnn(C3CC3)c2)c1=O]

To a seal tube equipped with a stirring bar, 1-cyclopropyl-1H-pyrazol-4-amine (600 mg, 4.87 mmol), 3,5-dibromo-1-methylpyrazin-2(1H)-one (1.96 g, 7.31 mmol), Pd$_2$(dba)$_3$ (223.1 mg, 0.244 mmol), XantPhos (225.5 mg, 0.390 mmol), Cs$_2$CO$_3$ (5.25 g, 16.08 mmol) and dioxane (12 mL) were added. The tube was sealed and heated at 100° C. overnight. CH$_2$Cl$_2$ (200 mL) was added to the resulting mixture, and the CH$_2$Cl$_2$ solution was washed with water (30 mL×3). The precipitate in the aqueous phase was filtered as pure product 114b. The organic phase was dried over MgSO$_4$, filtered and solvent removed in vacuo. CH$_2$Cl$_2$/ether (1:2, 3 mL) were added to the residue and the mixture was sonicated. The precipitate was filtered, combined with the filtered solids from the aqueous phase, and dried. 5-Bromo-3-(1-cyclopropyl-1H-pyrazol-4-ylamino)-1-methylpyrazin-2(1H)-one 114b was obtained as a yellow solid.

Example 114c 2-(6-(1-Cyclopropyl-1H-pyrazol-4-ylamino)-4-methyl-5-oxo-4,5-dihydropyrazin-2-yl)-6-(1-oxo-3,4,6,7,8,9-hexahydropyrazino[1,2-a]indol-2(1H)-yl)benzyl Acetate 114c

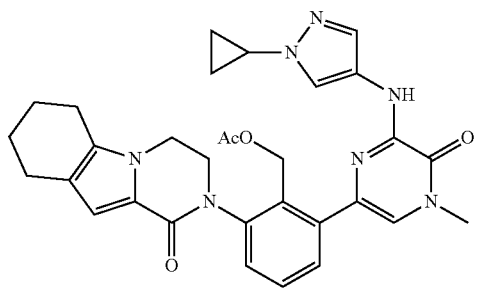 [SMILES: CC(=O)OCc1c(-c2cn(C)c(=O)c(Nc3cnn(C4CC4)c3)n2)cccc1N1CCn2c(cc3c2CCCC3)C1=O]

To a microwave tube equipped with a stirring bar, 114b (200 mg, 0.645 mmol), 114a (0.903 mmol), Pd(PPh$_3$)$_4$, Na$_2$CO$_3$ aqueous solution (1.0 N, 2.13 mL, 2.13 mmol), DME (2.0 mL) were added. The mixture was reacted in microwave at 135° C. for 15 min. DCM (200 mL) was added and the resulting mixture was washed with water (30 mL×3), brine (30 mL×1), dried over MgSO$_4$, filtered, and removed solvent in vacuo. Silica gel column chromatography (MeOH:DCM=5:95) gave 2-(6-(1-cyclopropyl-1H-pyrazol-4-ylamino)-4-methyl-5-oxo-4,5-dihydropyrazin-2-yl)-6-(1-oxo-3,4,6,7,8,9-hexahydropyrazino[1,2-a]indol-2(1H)-yl) benzyl acetate 114c, it was directly used in the next step.

To a round-bottomed flask equipped with a stirring bar, 114c THF (1.25 mL), i-PrOH (1.25 mL), H$_2$O (1.25 mL), LiOH H$_2$O (135 mg) were added. The resulting mixture was stirred at RT for 1 hr. Removed all the solvent in vacuo and silica gel column chromatography (MeOH:DCM=10:90) gave 38.6 mg 2-(3-(6-(1-cyclopropyl-1H-pyrazol-4-ylamino)-4-methyl-5-oxo-4,5-dihydropyrazin-2-yl)-2-(hydroxymethyl)-phenyl)-3,4,6,7,8,9-hexahydro-pyrazino[1,2-a]indol-1(2H)-one 114 as a yellow solid. MS (ESI+) m/z 526.3 (M+H).

Example 115 5-[5-Fluoro-2-(hydroxymethyl)-3-[1-methyl-6-oxo-5-(pyrimidin-4-ylamino)-1,6-dihydro-pyridin-3-yl]phenyl]-8-thia-5-azatricyclo[7.4.0.02,7]trideca-1(9),2(7)-dien-6-one 115

Example 115b tert-Butyl(2-bromo-4-fluoro-6-(1-oxo-3,4,5,6,7,8-hexahydrobenzothieno[2,3-c]pyridin-2(1H)-yl)benzyloxy)dimethylsilane 115b

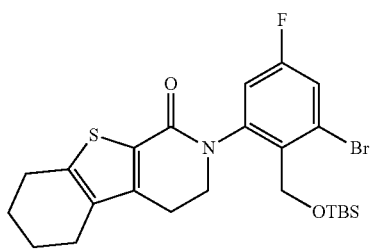

A sealed tube with a magnetic stirrer was charged with 104e (1.11 g, 5.37 mmol), 115a (4.24 g, 10.7 mmol), cesium carbonate (3.49 g, 10.7 mmol), N,N'-dimethylethylenediamine (0.47 g, 5.37 mmol) and 1,4-dioxane (45 mL). After degassed for 10 minutes, copper iodide (0.51 g, 2.68 mmol) was added, and the reaction mixture was heated at 105° C. for 2 days. Another portion of N,N'-dimethylethylenediamine (0.47 g, 5.37 mmol) and copper iodide (0.51 g, 2.68 mmol) was added, and the reaction mixture was heated at 105° C. for another 5 hours. After this time, the mixture was cooled to room temperature and filtered. The filtrate was diluted with ethyl acetate (50 mL) and water (40 mL). The combined organic layers were dried over sodium sulfate and concentrated under reduced pressure. The residue was purified by column chromatography (silica, Ethyl Acetate/Hexanes) to afford a 40% yield (1.14 g) of compound 115b as a yellow solid: MS (ESI+) m/z 524.1 (M+H).

A 10 mL microwave vial with a magnetic stirrer was charged with 115b (157 mg, 0.3 mmol), 1-methyl-3-(pyrimidin-4-ylamino)-5-(4,4,5,5-tetramethyl-1,3,2-dioxaborolan-2-yl)pyridin-2(1H)-one 109c (148 mg, 0.45 mmol), 1M sodium carbonate solution (1.2 mL, 1.2 mmol) and 1,2-Dimethoxyethane (3 mL). After bubbling nitrogen through the resulting suspension for 10 min, tetrakis(triphenylphosphine)palladium(0) (18 mg, 0.015 mmol) was added. The reaction mixture was heated at 130° C. for 15 minutes in the microwave reactor. The reaction was repeated at the same scale, and the reaction mixture was combined. Ethyl Acetate (20 mL) and water (10 mL) were added, and the layers were separated. The aqueous layer was extracted with Ethyl acetate (2×10 mL), and the combined organic layers were washed with brine and dried over sodium sulfate. The drying agent was removed by filtration. The filtrate was concentrated under reduced pressure, and the resulting residue was purified by flash column chromatography (silica, 60:35:5 methylene chloride/ether/methanol) to give 400 mg mixture of compounds 115c and 115 as a yellow residue. The above residue was dissolved in methanol (5 mL). 10-Camphorsulfonic acid (350 mg, 1.5 mmol) was added, and the mixture was stirred at room temperature for 1 h. After this time, the mixture was basified with saturated sodium bicarbonate. The aqueous layer was extracted with methylene chloride (2×10 mL), and the combined organic layers were washed with brine and dried over sodium sulfate. The drying agent was removed by filtration. The filtrate was concentrated under reduced pressure, and the resulting residue was purified by flash column chromatography (NH-silica, Ethyl acetate/Hexanes) to afford a 33% yield (88 mg) of compound 115 as a pale yellow solid: MS (ESI+) m/z 532.2 (M+H)

Example 116 5-[3-(6-{[1-(2-Hydroxyethyl)-1H-pyrazol-4-yl]amino}-4-methyl-5-oxo-4,5-dihydropyrazin-2-yl)-2-(hydroxymethyl)phenyl]-8-thia-5-azatricyclo[7.4.0.02,7]trideca-1(9),2(7)-dien-6-one 116

Example 116a 1-(2-(tert-Butyldimethylsilyloxy)ethyl)-4-nitro-1H-pyrazole 116a

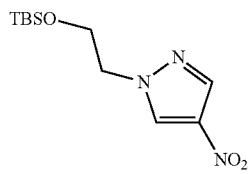

116a

A 100-mL single-neck round-bottomed flask equipped with a reflux condenser and magnetic stirrer was purged with nitrogen and charged with 4-nitro-1H-pyrazole (500 mg, 4.42 mmol), (2-bromoethoxy)(tert-butyl)dimethylsilane (2.12 g, 8.85 mmol), cesium carbonate (5.76 g, 17.7 mmol) and anhydrous DMF (5 mL). After heating at 70° C. for 1 h, the mixture was cooled to room temperature and diluted with methylene chloride (50 mL) and water (30 mL). The organic layer was separated, and the aqueous layer was extracted with methylene chloride (2×30 mL). The combined organic layers were dried over sodium sulfate and concentrated under reduced pressure. The residue was purified by column chromatography to afford a 92% yield (1.11 g) of 116a as a white solid: mp 63-64° C.; $^1$H NMR (500 MHz, CDCl$_3$) d 8.20 (s, 1H), 8.08 (s, 1H), 4.24 (t, 2H, J=4.5 Hz), 3.95 (t, 2H, J=4.5 Hz), 0.84 (s, 9H), −0.04 (s, 6H).

Example 116b 1-(2-(tert-Butyldimethylsilyloxy)ethyl)-1H-pyrazol-4-amine 116b

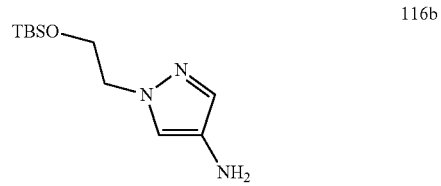 [SMILES: CC(C)(C)[Si](C)(C)OCCn1cc(N)cn1]

116b

A 250-mL Parr reactor bottle was purged with nitrogen and charged with 10% palladium on carbon (50% wet, 150 mg dry weight) and a solution of 116a (1.11 g, 4.10 mmol) in ethanol (20 mL). The bottle was attached to a Parr hydrogenator, evacuated, charged with hydrogen gas to a pressure of 50 psi and shaken for 3 h. After this time, the hydrogen was evacuated, and nitrogen was charged into the bottle. Celite 521 (1.00 g) was added, and the mixture was filtered through a pad of Celite 521. The filter cake was washed with ethanol (2×25 mL), and the combined filtrates were concentrated to dryness under reduced pressure to afford a 100% yield of 116b (985 mg) as an orange oil: $^1$H NMR (500 MHz, CDCl$_3$) d 7.18 (s, 1H), 7.11 (s, 1H), 4.09 (t, 2H, J=5.5 Hz), 3.89 (t, 2H, J=5.5 Hz), 3.25 (br s, 2H), 0.86 (s, 9H), −0.32 (s, 6H). MS (ESI+) m/z 242.2 (M+H).

Example 116c 5-Bromo-3-(1-(2-(tert-butyldimethylsilyloxy)ethyl)-1H-pyrazol-4-ylamino)-1-methylpyrazin-2(1H)-one 116c

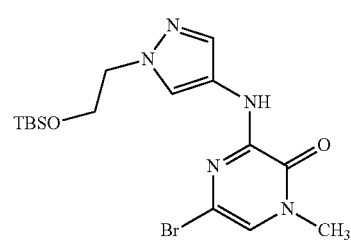

116c

A 100-mL three-neck round-bottomed flask equipped with a reflux condenser, magnetic stirrer and nitrogen inlet was charged with 116b (400 mg, 1.66 mmol), 3,5-dibromo- 1-methyl pyrazin-2(1H)-one (443 mg, 1.66 mmol), cesium carbonate (1.19 g, 3.65 mmol), and 1,4-dioxane (20 mL). After bubbling nitrogen through the resulting suspension for 30 min, Xantphos (144 mg, 0.249 mmol) and tris(dibenzylideneacetone)-dipalladium(0) (152 mg, 0.166 mmol) were added, and the reaction mixture was heated at reflux for 4 h. After this time, the mixture was cooled to room temperature and filtered, and the filter cake was washed with methylene chloride (2×20 mL). The filtrates were combined and concentrated under reduced pressure, and the resulting residue was purified by column chromatography to afford a 51% yield (353 mg) of 116c as a yellow solid: mp 172-173° C.; $^1$H NMR (500 MHz, CDCl$_3$) d 8.17 (s, 1H), 8.06 (s, 1H), 7.65 (s, 1H), 6.70 (s, 1H), 4.28 (t, 2H, J=5.0 Hz), 3.97 (t, 2H, J=5.5 Hz), 3.51 (s, 3H), 0.85 (s, 9H), −0.79 (s, 6H); MS (APCI+) m/z 428.3 (M+H).

A 100-mL single-neck round-bottomed flask equipped with a magnetic stirrer and reflux condenser was purged with nitrogen and charged with 116c (150 mg, 0.312 mmol), 111a (133 mg, 0.312 mmol), sodium carbonate (99 mg, 0.936 mmol), 1,4-dioxane (5 mL) and water (1 mL). This mixture was degassed with nitrogen for 30 min. Tetrakis-(triphenylphosphine)palladium (36 mg, 0.031 mmol) was added. After heating at 100° C. for 3 h, the reaction mixture was cooled to room temperature and partitioned between water (40 mL) and methylene chloride (100 mL). The layers were separated, and the aqueous phase was extracted with methylene chloride (2×50 mL). The organic extracts were combined, dried over sodium sulfate, filtered and concentrated under reduced pressure. The resulting residue was dissolved in methanol (5 mL), and potassium carbonate (500 mg, 3.62 mmol) was added. After stirring at room temperature for 2 h, the reaction mixture was partitioned between water (20 mL) and methylene chloride (20 mL). The layers were separated, and the aqueous phase was extracted with methylene chloride (2×20 mL). The organic extracts were combined, dried over sodium sulfate, filtered and concentrated under reduced pressure. The resulting residue was redissolved in THF (5 mL), and tetrabutylammonium fluoride trihydrate (500 mg, 1.58 mmol) was added. After stirring at room temperature for 3 h, the solvent was removed under reduced pressure, and the resulting residue was washed with water (10 mL). The resulting solid was purified by flash chromatography to afford 116 in 27% yield (47 mg) as an off-white solid: mp 171-172° C.; $^1$H NMR (500 MHz, DMSO-d$_6$) δ 9.56 (s, 1H), 8.16 (s, 1H), 7.75 (s, 1H), 7.58 (d, 1H, J=8.0 Hz), 7.44 (t, 1H, J=8.0 Hz), 7.33-7.32 (m, 2H), 4.86 (m, 1H), 4.81 (t, 1H, J=5.5 Hz), 4.51 (dd, 1H, J=11.0, 6.5 Hz), 4.44 (dd, 1H, J=11.0, 6.5 Hz), 4.06 (t, 2H, J=5.5 Hz), 4.02 (m, 1H), 3.68 (t, 2H, J=5.5 Hz), 3.88 (m, 1H), 3.68 (q, 2H, J=5.5 Hz), 3.52 (s, 3H), 2.98 (m, 1H), 2.86 (m, 1H), 2.77 (m, 2H), 2.58-2.46 (m, 2H), 1.79 (m, 4H); MS (APCI+) m/z 547.2 (M+H)

Example 117 2-(2-methyl-3-(5-(5-methyl-4,5,6,7-tetrahydropyrazolo[1,5-a]pyrazin-2-ylamino)-6-oxo-1,6-dihydropyridazin-3-yl)phenyl)-2,3,4,9-tetrahydro-1H-pyrido[3,4-b]indol-1-one 117

Example 117a 9-((2-(Trimethylsilyl)ethoxy)methyl)-2,3,4,9-tetrahydro-1H-pyrido[3,4-b]indol-1-one 117a

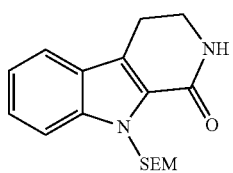

117a

A 25-mL single-neck round-bottomed flask equipped with a magnetic stirrer was purged with nitrogen and charged with anhydrous DMF (4 mL) and a 60% dispersion of sodium hydride in mineral oil (181 mg, 4.52 mmol) and the reaction mixture was cooled to 0° C. 1,2,3,4-tetrahydro-1-oxo-beta-carboline (841 mg, 4.52 mmol) was added, and the reaction was stirred at 0° C. for 15 min. After this time, 2-(trimethylsilyl)ethoxymethyl chloride (829 mg, 4.97 mmol) was added, and the reaction was stirred at 0° C. for 1 h. The reaction mixture was then partitioned between water (10 mL) and ethyl acetate (20 mL). The layers were separated, and the aqueous phase was extracted with ethyl acetate (2×10 mL). The organic extracts were combined, dried over sodium sulfate, filtered and concentrated under reduced pressure. The resulting residue was purified by flash chromatography to afford 117a in 57% yield (818 mg) as a colorless oil: $^1$H NMR (500 MHz, CDCl$_3$) d 7.67 (d, 1H, J=8.0 Hz), 7.65 (d, 1H, J=8.0 Hz), 7.46 (t, 1H, J=8.0 Hz), 7.27 (t, 1H, J=8.0 Hz), 6.14 (s, 2H), 5.72 (br s, 1H), 3.75 (t, 2H, J=7.0 Hz), 3.66 (t, 2H, J=8.0 Hz), 3.14 (t, 2H, J=7.0 Hz), 0.96 (t, 2H, J=8.0 Hz), −0.25 (s, 9H).

Example 117b 2-(3-Bromo-2-methylphenyl)-9-((2-(trimethylsilyl)ethoxy)methyl)-2,3,4,9-tetrahydro-1H-pyrido[3,4-b]indol-1-one 117b

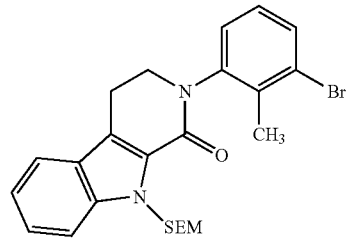

117b

A 100-mL single-neck round-bottomed flask equipped with a magnetic stirrer and nitrogen inlet was charged with 117a (400 mg, 1.27 mmol), 2,6-dibromotoluene (633 mg, 2.53 mmol), cesium carbonate (828 mg, 2.54 mmol), N-methylethylenediamine (112 mg, 1.27 mmol) and 1,4-dioxane (20 mL). After bubbling nitrogen through the resulting suspension for 30 min, copper iodide (121 mg, 2.54 mmol) was added. A reflux condenser was attached to the flask, and the reaction mixture was heated at 100° C. for 16 h. After this time, the mixture was cooled to room temperature and filtered. The filtrate was concentrated under reduced pressure, and the resulting residue was purified by flash column to afford 117b in 41% yield (251 mg) as a yellow oil: $^1$H NMR (500 MHz, CDCl$_3$) d 7.71 (d, 1H, J=8.0 Hz), 7.68 (d, 1H, J=8.0 Hz), 7.63 (d, 1H, J=8.0 Hz), 7.47 (t, 1H, J=8.0 Hz), 7.32-7.28 (m, 2H), 7.21 (t, 1H, J=8.0 Hz), 6.13 (s, 2H), 4.15 (m, 1H), 3.93 (m, 1H), 3.69 (m, 2H), 3.29 (m, 2H), 2.45 (s, 3H), 0.95 (t, 2H, J=8.0 Hz), −0.07 (s, 9H).

Example 117c 2-(2-Methyl-3-(4,4,5,5-tetramethyl-1,3,2-dioxaborolan-2-yl)phenyl)-9-((2-(trimethylsilyl)ethoxy)methyl)-2,3,4,9-tetrahydro-1H-pyrido[3,4-b]indol-1-one 117c

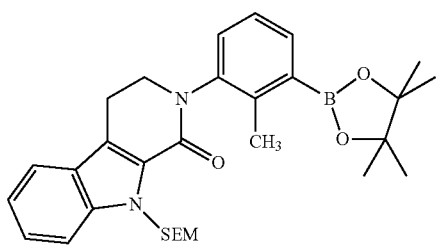

A 100-mL single-neck round-bottomed flask equipped with a magnetic stirrer, reflux condenser and nitrogen inlet was charged with 117b (250 mg, 0.515 mmol), 4,4,4',4',-5,5,5',5'-octamethyl-2,2'-bi(1,3,2-dioxaborolane (157 mg, 0.619 mmol), potassium acetate (152 mg, 1.55 mmol) and 1,4-dioxane (5 mL). After bubbling nitrogen through the resulting suspension for 30 min, [1,1-Bis(diphenylphosphino)ferrocene]-dichloro-palladium(II)/CH$_2$Cl$_2$ (38 mg, 0.052 mmol) was added, and the reaction mixture was heated at 95° C. for 5 h. After this time, the mixture was diluted with ethyl acetate (20 mL) and water (20 mL), and the layers were separated. The aqueous layer was extracted with ethyl acetate (50 mL), and the combined organic layers were washed with brine (50 mL) and dried over sodium sulfate. The drying agent was removed by filtration. The filtrate was concentrated under reduced pressure, and the resulting residue was purified by flash column chromatography to afford 117c in 97% yield (242 mg) as a colorless oil: $^1$H NMR (500 MHz, CDCl$_3$) d 7.85 (d, 1H, J=8.0 Hz), 7.72 (d, 1H, J=8.0 Hz), 7.68 (d, 1H, J=8.0 Hz), 7.46 (t, 1H, J=8.0 Hz), 7.39-7.28 (m, 2H), 7.21 (t, 1H, J=8.0 Hz), 6.19 (d, 1H, J=10.5 Hz), 6.15 (d, 1H, J=10.5 Hz), 4.16 (m, 1H), 3.97 (m, 1H), 3.68 (m, 2H), 3.29 (m, 2H), 2.45 (s, 3H), 0.95 (t, 2H, J=8.0 Hz), 1.34 (s, 12H), −0.07 (s, 9H).

Example 117d 4-Bromo-6-chloro-2-((2-(trimethylsilyl)ethoxy)methyl)pyridazin-3(2H)-one 117d

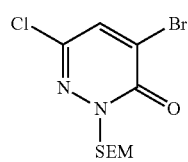

A 500-mL single-neck round-bottomed flask equipped with a magnetic stirrer was purged with nitrogen and charged with anhydrous DMF (150 mL) and 4-bromo-6-chloro-pyridazin-3(2H)-one (10.0 g, 47.8 mmol). The reaction mixture was cooled to 0° C. and sodium hydride was added. The reaction was stirred at 0° C. for 20 min. After this time, 2-(Trimethylsilyl)ethoxymethyl chloride (11.9 g, 71.6 mmol) was added and the cooling bath was removed, and the reaction was stirred at room temperature for 3 h. The reaction was then quenched with saturated aqueous sodium bicarbonate (30 mL). The mixture was extracted with ethyl acetate (2×300 mL). The extracts were dried over sodium sulfate, filtered and concentrated under reduced pressure. The resulting residue was purified by flash chromatography to afford 117d in a 56% yield (9.00 g) as a yellow oil: $^1$H NMR (300 MHz, CDCl$_3$) d 8.02 (s, 1H), 5.42 (s, 2H), 3.79 (t, 2H, J=5.4 Hz), 0.96 (t, 2H, J=5.4 Hz), 0.01 (s, 9H).

Example 117e 6-Chloro-4-(5-methyl-4,5,6,7-tetrahydropyrazolo[1,5-a]pyrazin-2-ylamino)-2-((2-(trimethylsilyl)ethoxy)methyl)pyridazin-3(2H)-one 117e

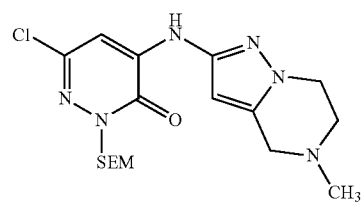

A 100-mL single-neck round-bottomed flask equipped with a magnetic stirrer and reflux condenser was charged with 117d (1.12 g, 3.29 mmol), 103e (500 mg, 3.29 mmol), cesium carbonate (3.22 g, 9.87 mmol) and 1,4-dioxane (25 mL). After bubbling nitrogen through the resulting solution for 30 min, Xantphos (286 mg, 0.494 mmol) and tris(dibenzylideneacetone)dipalladium(0) (301 mg, 0.329 mmol) were added and the reaction mixture was heated at reflux for 3 h. After this time, the reaction mixture was cooled to room temperature and partitioned between water (30 mL) and methylene chloride (60 mL). The layers were separated, and the aqueous phase was extracted with methylene chloride (60 mL). The organic extracts were combined, dried over sodium sulfate and filtered, and the solvent was removed from the filtrate under reduced pressure. The resulting residue was purified by column chromatography to afford a 72% yield (977 mg) of 117e as a yellow solid: mp 68-69° C.; $^1$H NMR (500 MHz, CDCl$_3$) d 7.85 (s, 1H), 7.56 (s, 1H), 5.70 (s, 1H), 5.47 (s, 2H), 4.16 (t, 2H, J=5.5 Hz), 3.73 (m, 2H), 3.63 (s, 2H), 2.94 (t, 2H, J=5.5 Hz), 2.51 (s, 3H), 0.98 (m, 2H), 0.12 (s, 9H); MS (ESI+) m/z 411.2 (M+H).

Example 117f 2-(2-Methyl-3-(5-(5-methyl-4,5,6,7-tetrahydropyrazolo[1,5-a]pyrazin-2-ylamino)-6-oxo-1-((2-(trimethylsilyl)ethoxy)methyl)-1,6-dihydropyridazin-3-yl)phenyl)-9-((2-(trimethylsilyl)ethoxy)methyl)-2,3,4,9-tetrahydro-1H-pyrido[3,4-b]indol-1-one 117f

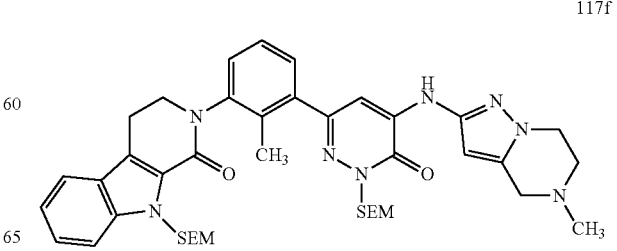

A 50-mL single-neck round-bottomed flask equipped with a magnetic stirrer, reflux condenser and nitrogen inlet was charged with 1,4-dioxane (5 mL), water (1 mL) and sodium carbonate (143 mg, 1.35 mmol). After bubbling nitrogen through the resulting mixture for 30 min, 117c (240 mg, 0.451 mmol), 117e (185 mg, 0.451 mmol) and tetrakis (triphenylphosphine)palladium(0) (52 mg, 0.045 mmol) were added, and the reaction mixture was heated at 100° C. for 3 h. After this time, the reaction was cooled to room temperature and partitioned between water (25 mL) and methylene chloride (50 mL). The organic layer was separated, washed with brine (75 mL) and dried over sodium sulfate. The drying agent was removed by filtration, and the filtrate was concentrated under reduced pressure to a dark oil, which was purified by flash chromatography to afford an 89% yield (315 mg) of 117f as a yellow oil: $^1$H NMR (500 MHz, CDCl$_3$) δ 7.88 (s, 1H), 7.66 (d, 1H, J=8.0 Hz), 7.45 (m, 3H), 7.39 (t, 1H, J=8.0 Hz), 7.34 (d, 1H, J=8.0 Hz), 7.24 (t, 2H, J=8.0 Hz), 6.12 (d, 1H, J=10.5 Hz), 6.05 (d, 1H, J=10.5 Hz), 5.69 (s, 1H), 5.63 (d, 1H, J=10.5 Hz), 5.52 (d, 1H, J=10.5 Hz), 4.09 (m, 2H), 3.88 (m, 2H), 3.75 (m, 2H), 3.68 (s, 3H), 3.59 (m, 2H), 3.26-3.17 (m, 4H), 2.61 (m, 2H), 2.29 (s, 3H), 0.98 (t, 2H, J=8.0 Hz), 0.85 (t, 2H, J=8.0 Hz), −0.01 (s, 9H), −0.07 (s, 9H); MS (ESI+) m/z 781.4 (M+H).

A 50-mL single-neck round-bottomed flask equipped with a magnetic stirrer was purged with nitrogen and charged with 117f (315 mg, 0.404 mmol), anisole (438 mg, 4.04 mmol), methylene chloride (3 mL) and trifluoroacetic acid (3 mL). After stirring at room temperature for 2 h, the reaction mixture was concentrated, and the resulting residue was partitioned between 1 M aqueous potassium dihydrogen phosphate (10 mL) and methylene chloride (20 mL). The layers were separated, and the aqueous phase was extracted with methylene chloride (2×10 mL). The organic extracts were combined and dried over sodium sulfate, filtered and concentrated under reduced pressure. The resulting residue was purified by flash chromatography to afford 117 in 23% yield (49 mg) as a white solid: mp 254° C. dec; $^1$H NMR (500 MHz, DMSO-d$_6$) δ 12.97 (s, 1H), 11.74 (s, 1H), 9.21 (s, 1H), 7.79 (s, 1H), 7.65 (d, 1H, J=8.0 Hz), 7.44-7.37 (m, 3H), 7.34 (d, 1H, J=8.0 Hz), 7.26 (t, 1H, J=8.0 Hz), 7.08 (t, 1H, J=8.0 Hz), 5.75 (s, 1H), 4.17 (m, 1H), 3.97 (t, 2H, J=5.0 Hz), 3.84 (m, 1H), 3.51 (s, 2H), 3.17 (m, 2H), 2.79 (t, 2H, J=5.0 Hz), 2.35 (s, 3H), 2.18 (s, 3H); MS (ESI+) m/z 521.2 (M+H)

Example 118 2-(2-(hydroxymethyl)-3-(1-methyl-6-oxo-5-(pyrimidin-4-ylamino)-1,6-dihydropyridin-3-yl)phenyl)-3,4,6,7,8,9-hexahydropyrido[3,4-b]indolizin-1(2H)-one 118

Example 118a Methyl 5,6,7,8-Tetrahydroindolizine-2-carboxylate 118a

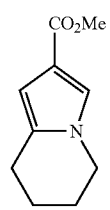
118a

A 500-mL round-bottomed flask equipped with a magnetic stirrer and nitrogen inlet was purged with nitrogen and charged with 5,6,7,8-tetrahydroindolizine-2-carboxylic acid (30.4 g, 184 mmol), DMF (1.00 g, 13.6 mmol) and methylene chloride (300 mL). The solution was cooled to 0° C. using an ice bath. Oxalyl chloride (28.0 g, 221 mmol) was added dropwise, and the reaction mixture was warmed to room temperature over 30 min and stirred for 5 h. After this time, the resulting solution was concentrated to afford a brown solid. This solid was dissolved in anhydrous methanol (400 mL), and the solution was cooled to 0° C. Triethylamine (57 g, 552 mmol) was added to the reaction mixture, and it was stirred for a further 2 h at room temperature. After this time, the reaction mixture was concentrated to dryness under reduced pressure. The residue was diluted with methylene chloride (300 mL) and washed with water (200 mL) and saturated aqueous sodium bicarbonate (200 mL). The organic layer was dried over sodium sulfate, filtered and concentrated under reduced pressure. The resulting residue was titrated with hexane (200 mL) to afford 118a in 58% yield (19.1 g) as a white solid: mp 72-74° C.; $^1$H NMR (300 MHz, DMSO-d$_6$) δ 7.13 (s, 1H), 6.23 (s, 1H), 3.93 (t, 2H, J=6.0 Hz), 3.77 (s, 3H), 2.75 (t, 2H, J=6.0 Hz), 1.93 (m, 2H), 1.80 (m, 2H); (APCI+) m/z 180.1 (M+H)

Example 118b Methyl 3-(Cyanomethyl)-5,6,7,8-tetrahydroindolizine-2-carboxylate 118b

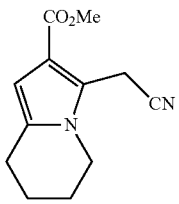
118b

A 500-mL three-neck round-bottomed flask equipped with an addition funnel, thermometer and charged with 118a (6.70 g, 37.4 mmol), Iodoacetonitrile (12.5 g, 74.9 mmol), iron (II) sulfate heptahydrate (5.20 g, 18.7 mmol) and dimethyl sulfoxide (250 mL). Hydrogen peroxide (35%, 18.2 g, 187 mmol) was added dropwise to the mixture in 1 h through a syringe pump at room temperature using a water bath. Iron (II) sulfate heptahydrate (2 to 3 equivalent) was added to the reaction mixture in portions to keep the temperature between 25° C. to 35° C., until the color of the reaction mixture is deep red. If TLC show the reaction not completed, then more hydrogen peroxide (2-3 equivalent) and more iron (II) sulfate heptahydrate (1-2 equivalent) were added in the same manner until the reaction is completed. After that time, the reaction mixture was partitioned between saturated sodium bicarbonate solution (200 mL) and ethyl acetate (400 mL). The organic layer was separated, and the aqueous layer was extracted with ethyl acetate (2×100 mL). The combined organic layers were washed with saturated Sodium thiosulfate solution (50 mL), dried over sodium sulfate and concentrated under reduced pressure. The residue was purified by column chromatography to afford a 78% yield (6.40 g) of 118b as a yellow oil: $^1$H NMR (500 MHz, CDCl$_3$) δ 6.23 (s, 1H), 4.23 (s, 2H), 3.94 (t, 2H, J=6.5 Hz), 3.81 (s, 3H), 2.74 (t, 2H, J=6.5 Hz), 2.00 (m, 2H), 1.83 (m, 2H); (APCI+) m/z 219.3 (M+H)

Example 118c Methyl 3-(2-Aminoethyl)-5,6,7,8-tetrahydroindolizine-2-carboxylate Hydrogen Chloride Salt 118c

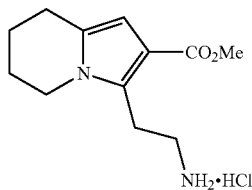

118c

Intermediate 118b was hydrogenated with platinum oxide catalyst under 50 psi of hydrogen in ethanol and ethyl acetate in the presence of hydrogen chloride overnight at room temperature to give 118c (380 mg, 1.74 mmol) which was used in directly in the next step.

Example 118d 3,4,6,7,8,9-Hexahydropyrido[3,4-b]indolizin-1(2H)-one 118d

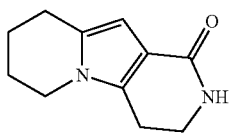

118d

A 100-mL single-neck round-bottomed flask equipped with a magnetic stirrer and nitrogen inlet was purged with nitrogen and charged with methyl 3-(2-aminoethyl)-5,6,7,8-tetrahydroindolizine-2-carboxylate hydrogen chloride salt 118c (estimated 1.74 mmol, presuming quantitative yield), sodium ethoxide (354 mg, 5.22 mmol) and ethanol (20 mL). The mixture was stirred at 55° C. for 5 h. After that time, the reaction mixture was concentrated under reduced pressure and the residue was partitioned between ethyl acetate (200 mL) and water (100 mL). The organic layer was separated, and the aqueous layer was extracted with ethyl acetate (2×100 mL). The combined organic layers were washed with brine, dried over sodium sulfate and concentrated under reduced pressure. The residue was purified by column chromatography to afford a 67% yield (220 mg) of 118d as a white solid: mp 195-197° C.; $^1$H NMR (500 MHz, DMSO-$d_6$) δ 6.76 (s, 1H), 5.89 (s, 1H), 3.78 (t, 2H, J=6.5 Hz), 3.35 (m, 2H), 2.66 (m, 4H), 1.87 (m, 2H), 1.72 (m, 2H); (APCI+) m/z 191.3 (M+H)

Example 118e 2-Bromo-6-(1-oxo-3,4,6,7,8,9-hexahydropyrido[3,4-b]indolizin-2(1H)-yl)benzyl Acetate 118e

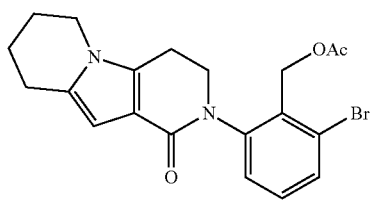

118e

A 250-mL three-neck round-bottomed flask equipped with a reflux condenser, magnetic stirrer was purged with nitrogen and charged with 118d (1.50 g, 7.89 mmol), 2,6-dibromobenzyl acetate 104g (4.80 g, 15.7 mmol), cesium carbonate (5.11 g, 15.7 mmol), N,N'-dimethylethylenediamine (695 mg, 7.89 mmol), and 1,4-dioxane (100 mL). After bubbling nitrogen through the resulting suspension for 20 min, copper iodide (752 mg, 3.95 mmol) was added, and the reaction mixture was heated at 95° C. (oil bath temperature) for 12 h. And then N,N'-dimethylethylenediamine (695 mg, 7.89 mmol) and copper iodide (752 mg, 3.95 mmol) were added and heated at 95° C. for another 12 h, repeated this until most of 118d was converted to 118e, about 48 h. After this time, the mixture was cooled to room temperature and filtered. The filtrate was diluted with ethyl acetate (300 mL) and water (100 mL). The organic layer was separated, and the aqueous layer was extracted with ethyl acetate (3×100 mL). The combined organic layers were dried over sodium sulfate and concentrated under reduced pressure. The residue was purified by flash chromatography to afford a 27% yield (905 mg) of 118e as an off-white solid: mp 176-178° C.; $^1$H NMR (300 MHz, DMSO-$d_6$) δ 7.64 (dd, 1H, J=7.5, 1.8 Hz), 7.37 (m, 2H), 5.99 (s, 1H), 5.00 (d, 2H, J=6.0 Hz), 4.00 (m, 1H), 3.85 (m, 2H), 3.62 (m, 1H), 2.93 (t, 2H, J=6.1 Hz), 2.67 (t, 2H, J=6.1 Hz), 2.00 (d, 3H, J=6.0 Hz), 1.90 (m, 2H), 1.75 (m, 2H); MS (ESI+) m/z 417.0 (M+H)

Example 118f 2-(1-Oxo-3,4,6,7,8,9-hexahydropyrido[3,4-b]indolizin-2(1H)-yl)-6-(4,4,5,5-tetramethyl-1,3,2-dioxaborolan-2-yl)benzyl Acetate 118f

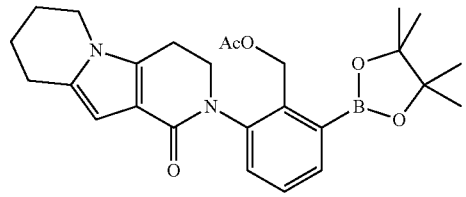

118f

A 100-mL three-neck round-bottomed flask equipped with a reflux condenser, magnetic stirrer and nitrogen inlet was charged with 118e (1.20 g, 2.88 mmol), 4,4,4',4',5,5,5',5'-octamethyl-2,2'-bi(1,3,2-dioxaborolane) (2.20 g, 8.65 mmol), potassium acetate (1.13 g, 11.5 mmol) and 1,4-dioxane (50 mL). After bubbling nitrogen through the resulting suspension for 20 min, [1,1-Bis(diphenylphosphino)ferrocene]dichloro-palladium(II) (210 mg, 0.288 mmol) was added, and the reaction mixture was heated at 95° C. for 8 h. After this time, the mixture was cooled to room temperature and filtered. The filter cake was washed with ethyl acetate (40 mL). The filtrate was diluted with ethyl acetate (150 mL) and water (40 mL). The organic layer was separated, and the aqueous layer was extracted with ethyl acetate (3×50 mL). The combined organic layers were dried over sodium sulfate and concentrated under reduced pressure to afford a 100% yield (1.35 g) of crude 118f as a yellow oil.

A 100-mL three-neck round-bottomed flask equipped with a magnetic stirrer and reflux condenser was charged with 118f (400 mg, 0.862 mmol), 5-bromo-1-methyl-3-(pyrimidin-4-ylamino)pyridin-2(1H)-one 109b (241 mg, 0.862 mmol), sodium carbonate (365 mg, 3.45 mmol), water (4 mL) and 1,4-dioxane (20 mL). After bubbling nitrogen through the resulting suspension for 20 min, tetrakis(triphenylphosphine)-palladium(0) (100 mg, 0.086 mmol) was added, and the reaction mixture was heated at 100° C. for 2 h. After this time, the reaction mixture was cooled to room temperature and filtered, and the filter cake was washed with a 1:10 mixture of methanol and methylene chloride (30 mL). The filtrate was concentrated under reduced pressure to afford a brown residue. Another 50-mL single-neck round-bottomed flask equipped with a magnetic stirrer and reflux condenser was charged with residue obtained above, THF (5 mL), ethanol (5 mL), water (5 mL) and lithium hydroxide (83.0 mg, 3.45 mmol). The mixture was stirred at 50° C. for 2 h. After this time, the reaction mixture was concentrated under reduced pressure. The resulting residue was purified by flash chromatography to afford a 23% (106 mg) yield of 118 as an off-white solid: mp 173-175° C.; $^1$H NMR (500 MHz, DMSO-$d_6$) δ 7.16 (s, 1H), 8.72 (s, 1H), 8.64 (s, 1H), 8.29 (d, 1H, J=6.0 Hz), 7.55 (s, 1H), 7.45 (t, 1H, J=7.5 Hz), 7.29 (m, 3H), 6.00 (s, 1H), 4.75 (t, 1H, J=5.0 Hz), 4.31 (d, 2H, J=5.0 Hz), 4.00 (m, 1H), 3.96 (m, 1H), 3.81 (m, 2H), 3.60 (s, 3H), 3.00 (m, 1H), 2.91 (m, 1H), 2.71 (t, 2H, J=5.5 Hz), 1.92 (m, 2H), 1.75 (m, 2H); MS (ESI+) m/z 497.2 (M+H)

Example 119 5-[2-(Hydroxymethyl)-3-(5-{[5-(2-hydroxypropan-2-yl)-1-methyl-1H-pyrazol-3-yl]amino}-1-methyl-6-oxo-1,6-dihydropyridazin-3-yl)phenyl]-8-thia-5-azatricyclo[7.4.0.0$^{2,7}$]trideca-1(9),2(7)-dien-6-one 119

Example 119a Methyl 3-Amino-1-methyl-1H-pyrazole-5-carboxylate 119a

In a 250 mL Parr hydrogenation flask was placed methyl 1-methyl-3-nitro-1H-pyrazole-5-carboxylate, (530 mg, 2.9 mmol) dissolved in ethyl acetate (15 mL) and ethanol (15 mL), to which was added 10% Pd/C (Degussa type) (100 mg). The mixture was placed on the Parr apparatus and pressurized with hydrogen to 50 PSI and shaken for 2.5 hrs. The reaction was filtered through a pad of celite which was washed with ethyl acetate. The solvent was removed under vacuum to give 119a as a white solid (450 mg, 2.9 mmol, quantitative yield).

Example 119b Methyl 3-(6-Chloro-2-methyl-3-oxo-2,3-dihydropyridazin-4-ylamino)-1-methyl-1H-pyrazole-5-carboxylate 119b

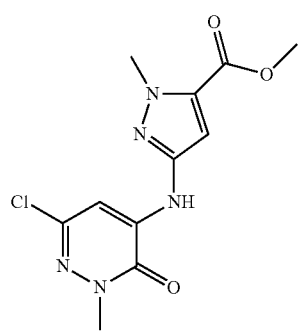

In a 3-neck RBF was placed 119a (500 mg, 3.2 mmol), 4-bromo-6-chloro-2-methylpyridazin-3(2H)-one (725 mg, 3.2 mmol), cesium carbonate (2.3 g, 7.0 mmol), and Xantphos (160 mg, 8.5 mol %). The flask was evacuated and filled with nitrogen 3×. Dioxane (20 ml) was added and the mixture degassed for 25 min with bubbling nitrogen. Tris(dibenzylideneacetone)dipalladium(0) (150 mg, 5 mol %) was then added and the reaction heated to 100° C. for 6 hrs. The reaction was cooled and diluted with EtOAc (125 mL) and saturated aqueous NaHCO3 (50 mL), the layers were separated and extracted EtOAc (2×100 mL). The organics were washed with brine 3×, dried over Na2SO4, filtered, and concentrated under reduced pressure. The residue was purified by chromatography: ISCO 40 g silica, EtOAc/hexanes, to give 119b.

Example 119c 6-Chloro-4-(5-(2-hydroxypropan-2-yl)-1-methyl-1H-pyrazol-3-ylamino)-2-methyl-pyridazin-3(2H)-one 119c

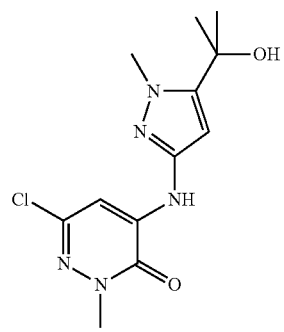

In a 100 mL round bottom flask containing 119b (500 mg, 1.7 mmol) under nitrogen was added anh. THF (20 mL) and anh.toluene (5 mL) and the mixture stirred and cooled to −20 to −30° C. 3.0M methylmagnesium bromide in diethylether (1.6 mL, 4.75 mmol) was then slowly added. After the addition the reaction was allowed to slowly warm to room temp. and stir for about 3 hrs after which the reaction was quenched with 1N HCl. Concentrated to remove THF, diluted with ethyl acetate and water then adjusted the pH to ~6-7 with 1M NaOH. Separated and extracted 2× with ethyl acetate washed with brine, dried over Na$_2$SO$_4$, filtered, and concentrated under reduced pressure. The residue was purified by chromatography: ISCO 24 g silica, ethyl acetate/hexanes, to give 119c.

Example 119d 2-(5-(5-(2-Hydroxypropan-2-yl)-1-methyl-1H-pyrazol-3-ylamino)-1-methyl-6-oxo-1,6-dihydropyridazin-3-yl)-6-(1-oxo-3,4,6,7,8,9-hexahydropyrazino[1,2-a]indol-2(1H)-yl)benzyl Acetate 119d

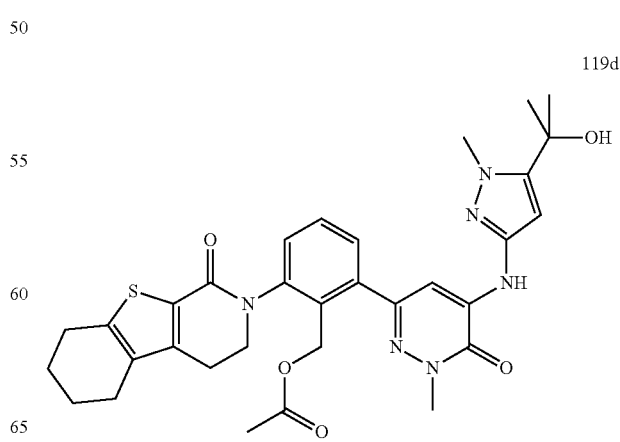

In a microwave vial was placed 119c (150 mg, 0.50 mmol) and 111a (240 mg, 0.50 mmol) and DME (4 mL) was added followed by 1N Na$_2$CO$_3$ (1.1 mL). After degassing with bubbling argon for 5 min, tetrakis(triphenylphosphine) palladium(0) (29 mg, 5 mol %) was added and the mixture was heated in a microwave reactor at 130° C. for 15 min. An additional 40 mg 111a was added and the mixture heated an additional 10 min. The reaction was diluted with ethyl acetate and water, the ethyl acetate layer separated, washed with brine, dried over Na$_2$SO$_4$, filtered, and concentrated under reduced pressure. The residue was purified by chromatography: ISCO 12 g silica, eluting with methanol and CH$_2$Cl$_2$, to give 119d (170 mg, 56% yield).

To a vial containing 119d (170 mg, 0.28 mmol) dissolved in THF (1.5 mL) and I-propanol (1.5 ml) was added 1N LiOH/water (1.4 mL, 1.4 mmol) and the mixture stirred overnight after with the reaction was judged complete by LC-MS. The mixture was concentrated then diluted with ethyl acetate and water and 1N HCl and 1N NaOH were added to adjust the pH to 7. The ethyl acetate layer was separated, washed with brine, dried over Na$_2$SO$_4$, filtered, and concentrated under reduced pressure. The residue was triturated with ethyl acetate and the solids collected by filtration to give 119 (98 mg, 61% yield). MS (ESI+) m/z 575.2 (M+H).

Example 120 5-[5-Fluoro-2-(hydroxymethyl)-3-[4-methyl-5-oxo-6-(1,2,3,4-tetrahydroisoquinolin-6-ylamino)pyrazin-2-yl]phenyl]-8-thia-5-azatricyclo[7.4.0.0$^{2,7}$]trideca-1(9),2(7)-dien-6-one 120

Example 120a tert-Butyl 6-(6-bromo-4-methyl-3-oxo-3,4-dihydropyrazin-2-ylamino)-3,4-dihydroisoquinoline-2(1H)-carboxylate 120a

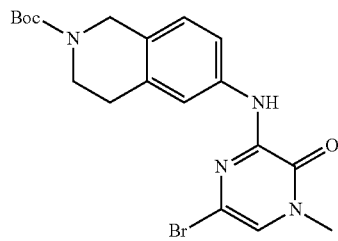

A mixture of tert-butyl 6-amino-3,4-dihydroisoquinoline-2(1H)-carboxylate (3 g, 12 mmol), 3,5-dibromo-1-methylpyrazin-2(1H)-one (2.68 g, 10 mmol), and triethylamine (1.5 g, 15 mmol) in IPA (50 mL) was heated at 70° C. for 15 h. The mixture was cooled to room temperature. The resulting yellow solids were collected by filtration and dried in vacuum to afford 120a as a yellow solid (2.83 g, 65%). MS: [M+H]$^+$ 435.

Example 120b 4-Fluoro-2-[4-methyl-5-oxo-6-(1,2,3,4-tetrahydroisoquinolin-6-ylamino)pyrazin-2-yl]-6-{6-oxo-8-thia-5-azatricyclo[7.4.0.0$^{2,7}$]trideca-1(9),2(7)-dien-5-yl}phenyl}methyl acetate 120b

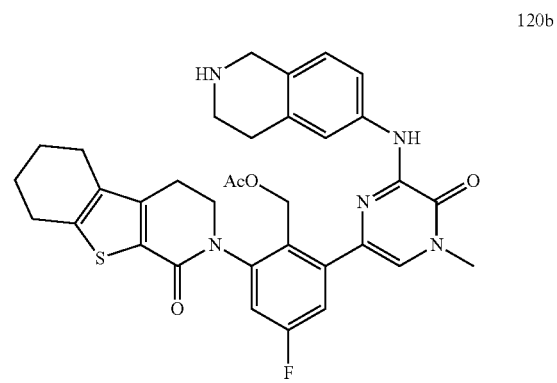 [SMILES: CC(=O)OCc1c(-c2cn(C)c(=O)c(Nc3ccc4c(c3)CCNC4)n2)cc(F)cc1N1CCc2c(sc3c2CCCC3)C1=O]

Following Example 150b, 482 mg of 218b and 435 mg of 120a were reacted to give 362 mg (51%) of 120b as a yellow solid MS: [M+H]$^+$ 711.

Following Example 149, 200 mg of 120b was converted to 120 as a white solid (78 mg, 42%). $^1$H NMR (500 MHz, MeOD) δ 7.72 (s, 1H), 7.58 (d, J=8.0, 1H), 7.39 (m, 2H), 7.21 (ss, J=9.5, 1H), 7.10 (d, J=8.5, 1H), 4.62 (d, J=12, 1H), 4.50 (d, J=12, 1H), 4.11 (m, 3H), 3.98 (m, 1H), 3.64 (s, 3H), 3.28 (s, 2H), 2.95 (m, 4H), 2.85 (s, 2H), 2.60 (m, 2H), 1.9 (m, 4H).

Example 121 5-[2-(Hydroxymethyl)-3-(4-methyl-5-oxo-6-{[4-(piperidin-4-yl)phenyl]-amino}-4,5-dihydropyrazin-2-yl)phenyl]-8-thia-5-azatricyclo[7.4.0.0$^{2,7}$]trideca-1(9),2(7)-dien-6-one 121

Example 121a tert-Butyl 4-(4-(6-bromo-4-methyl-3-oxo-3,4-dihydropyrazin-2-ylamino)phenyl)-piperidine-1-carboxylate 121a Compound 121a was synthesized using the same procedure as example 112a, except using tert-butyl 4-(4-aminophenyl)piperidine-1-carboxylate (0.83 g, 3.0 mmol), 3,5-dibromo-1-methylpyrazin-2(1H)-one (0.88 g, 3.3 mmol), cesium carbonate (1.27 g, 3.9 mmol), tris(dibenzylideneacetone)dipalladium(0) (0.275 g, 0.3 mmol), Xantphos (0.26 g, 0.45 mmol) and 1,4-dioxane (30 mL). The reaction mixture was heated at 100° C. overnight. Work-up and purified by flash column chromatography (silica, ethyl acetate/hexanes) to give a 80% yield (1.1 g) of 121a as a solid: MS (ESI+) m/z 465.0 (M+H).

Example 121b 5-[2-(Acetoxymethyl)-3-(4-methyl-5-oxo-6-{[4-(piperidin-4-yl)phenyl]-amino}-4,5-dihydropyrazin-2-yl)phenyl]-8-thia-5-azatricyclo[7.4.0.0$^{2,7}$]trideca-1(9),2(7)-dien-6-one 121b A 10 mL microwave vial with a magnetic stirrer was charged with 111a (173 mg, 0.36 mmol), 121a (139 mg, 0.3 mmol), 1M sodium carbonate solution (1.2 mL, 1.2 mmol) and 1,2-dimethoxyethane (3 mL). After bubbling nitrogen through the resulting suspension for 10 min, tetrakis(triphenylphosphine)-palladium(0) (18 mg, 0.015 mmol) was added. The reaction mixture was heated at 130° C. for 15 minutes in the microwave reactor. After this time, ethyl acetate (15 mL) and water (10 mL) were added, and the layers were separated. The aqueous layer was extracted with Ethyl acetate (2×20 mL), and the combined organic layers were washed with brine and dried over sodium sulfate. The drying agent was removed by filtration. The filtrate was concentrated under reduced pressure, and the resulting residue was purified by flash column chromatography (silica, ethyl acetate/hexanes) to afford compound 121b as yellow oil (240 mg).

Compound 121b was dissolved in methylene chloride (10 mL). Trifluoroacetic acid (0.3 mL, 3.9 mmol) was added, and the mixture was stirred at room temperature for 4 h. After this time, the mixture was basified by saturated sodium bicarbonate, and the aqueous layer was extracted with methylene chloride (2×15 mL). The combined organic layers were washed with brine and dried over sodium sulfate. The drying agent was removed by filtration. The filtrate was concentrated, and the resulting residue 121c was dissolved in a mixture of THF (1.5 mL), water (0.8 mL) and isopropanol (1.5 mL). Lithium hydroxide monohydrate (56 mg, 1.32 mmol) was added, and the mixture was stirred at room temperature for 3 h. After this time, the mixture was diluted with 90:10 methylene chloride/methanol (10 mL) and water (5 mL), and the layers were separated. The aqueous layer was extracted with 90:10 methylene chloride/methanol (2×10 mL), and the combined organic layers were washed with brine and dried over sodium sulfate. The drying agent was removed by filtration. The filtrate was purified by flash column chromatography (silica, methylene chloride/methanol) to afford a 35% yield (3 steps, 63 mg) of compound 121 as a light pink solid: MS (ESI+) m/z 596.3 (M+H).

Example 122 5-[5-Fluoro-2-(hydroxymethyl)-3-(4-methyl-6-{[4-(morpholin-4-yl)phenyl]amino}-5-oxo-4,5-dihydropyrazin-2-yl)phenyl]-8-thia-5-azatricyclo[7.4.0.0$^{2,7}$]trideca-1(9),2(7)-dien-6-one 122

Example 122a 5-Bromo-1-methyl-3-(4-morpholinophenylamino) pyrazin-2(1H)-one (3-3) 122a A microwave vial equipped with a magnetic stirrer was charged with 3,5-dibromo-1-methylpyrazin-2(1H)-one (1.97 g, 7.4 mmol), 4-morpholinobenzenamine (1.97 g, 11.1 mmol), and isopropanol (25 mL). The system was evacuated and then refilled with $N_2$. It was heated at 90° C. for 16 h. Then, the mixture was cooled to room temperature and concentrated under reduced pressure. The residue was purified by flash column chromatography eluting with 5:1 petroleum ether/ethyl acetate to afford 122a (2.3 g, 85%). LCMS: [M+H]$^+$ 365.

Example 122b 4-Methyl-6-(4-morpholinophenylamino)-5-oxo-4,5-dihydropyrazin-2-ylboronic Acid 122b A microwave vial equipped with a magnetic stirrer was charged with 122a (764 mg, 2.1 mmol), (PinB)$_2$ (2.75 g, 10 mmol), Pd(dppf)Cl$_2$ (0.1 g, 0.13 mmol), KOAc (0.6 g, 6 mmol), and DMF (5 mL). The system was evacuated and then refilled with $N_2$. The reaction mixture was then heated at 105° C. for 1 h, then cooled to room temperature and filtered. The filtrate was concentrated under reduced pressure to give the crude 122b, which was used without further purification. LCMS: [M+H]$^+$ 331.

Example 122c [4-Fluoro-2-(4-methyl-6-{[4-(morpholin-4-yl)phenyl]amino}-5-oxopyrazin-2-yl)-6-{6-oxo-8-thia-5-azatricyclo[7.4.0.0$^{2,7}$]trideca-1(9),2(7)-dien-5-yl}phenyl]methyl Acetate 122c

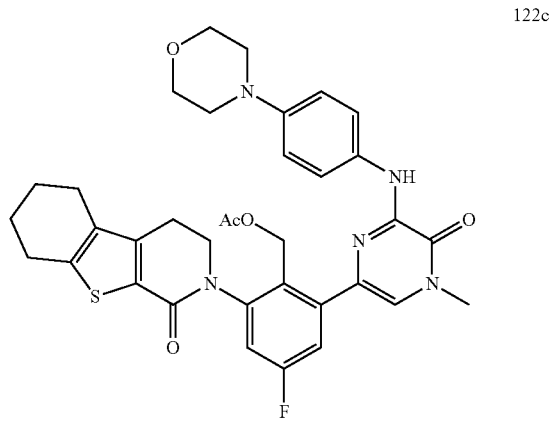 [SMILES: CC(=O)OCc1c(-c2cn(C)c(=O)c(Nc3ccc(N4CCOCC4)cc3)n2)cc(F)cc1N1CCc2c(sc3c2CCCC3)C1=O]

A 25 mL vial was charged with (2-bromo-4-fluoro-6-{6-oxo-8-thia-5-azatricyclo-[7.4.0.0$^{2,7}$]trideca-1(9),2(7)-dien-5-yl}phenyl)methyl acetate 212a (300 mg, 0.67 mmol), 122b (440 mg, 1.33 mmol) suspended in 1,2-dimethoxyethane (15 mL) and water (1 mL). The resulting orange solution was heated for 30 minutes in a Biotage microwave reactor held at a constant temperature of 130° C. After reaction the residue was purified by reverse phase Combiflash eluting with 0.3% NH$_4$HCO$_3$ in 1:6 water/CH$_3$CN to 122c as a brown solid (200 mg, 46%). MS: (M+H)$^+$ 658.

To a solution of 122c (220 mg, 0.33 mmol) in propan-2-ol (7 mL), tetrahydrofuran (7 mL), and water (2 mL) was added LiOH (804 mg, 33 mmol). The mixture was stirred at 30° C. for 2 h. It was then evaporated under reduced pressure and the residue was purified by prep-HPLC to afford 122 as a yellow solid (82 mg, 40%). MS: (M+H)$^+$ 616. $^1$H NMR (500 MHz, MeOD) δ 1.89 (s, 5H), 2.55-2.63 (m, 2H), 2.94 (s, 2H), 3.11-3.13 (t, 5H), 3.64 (s, 3H), 3.82-3.84 (t, 4H), 3.93-3.98 (m, 1H), 4.07-4.14 (m, 1H), 4.43-4.53 (m, 2H), 6.97-6.99 (d, 2H), 7.18-7.20 (d, 1H), 7.29 (s, 1H), 7.36-7.38 (d, 1H), 7.62-7.64 (d, 2H).

Example 123 5-(3-{5-[(5-cyclopropyl-1H-pyrazol-3-yl)amino]-1-methyl-6-oxo-1,6-dihydropyridin-3-yl}-2-(hydroxymethyl)phenyl)-8-thia-5-azatricyclo[7.4.0.0$^{2,7}$]trideca-1(9),2(7)-dien-6-one 123

Example 123a 1-Cyclopropyl-3-nitro-1H-pyrazole 123a

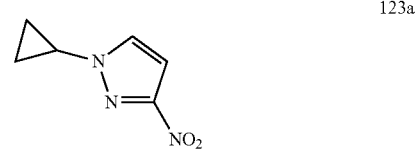

A 250-mL three-neck round-bottomed flask equipped with a reflux condenser and magnetic stirrer was purged with nitrogen and charged with 3-nitro-(1H)pyrazole (1.30 g, 11.5 mmol), cyclopropylboronic acid (1.98 g, 23.0 mmol), sodium carbonate (3.66 g, 34.5 mmol), 2,2'-bipyridyl (3.58 g, 23.0 mmol), dichloroethane (60 mL) and copper(II) acetate (2.08 g, 11.5 mmol). The reaction mixture was heated at 70° C. (oil bath temperature) for 3 h. After this time, another portion of cyclopropyl boronic acid (1.98 g, 23.0 mmol) was added, and the mixture was heated for 3 h. After this time, the mixture was cooled to room temperature and filtered. The filtrate was diluted with ethyl acetate (350 mL) and water (40 mL). The organic layer was separated, and the aqueous layer was extracted with ethyl acetate (3×150 mL). The combined organic layers were dried over sodium sulfate and concentrated under reduced pressure. The residue was purified by column chromatography (silica, 0% to 100% ethyl acetate/hexanes) to afford an 85% yield (1.49 g) of 123a as a colorless oil: $^1$H NMR (500 MHz, CDCl$_3$) d 7.53 (d, 1H, J=2.4 Hz), 6.87 (d, 1H, J=2.5 Hz), 3.71 (m, 1H), 1.25 (m, 2H), 1.12 (m, 2H); MS (APCI+) m/z 154.1 (M+H).

Example 123b 1-Cyclopropyl-1H-pyrazol-3-amine 123b

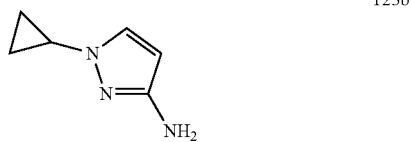

A 250-mL Parr reactor bottle was purged with nitrogen and charged with 10% palladium on carbon (50% wet, 137 mg dry weight) and a solution of 123a (600 mg, 3.92 mmol) in ethanol (70 mL). The bottle was attached to a Parr hydrogenator, evacuated, charged with hydrogen gas to a pressure of 50 psi and shaken for 3 h. After this time, the hydrogen was evacuated, and nitrogen was charged into the bottle. Celite 521 (1.00 g) was added, and the mixture was filtered through a pad of Celite 521. The filter cake was washed with ethanol (2×25 mL), and the combined filtrates were concentrated to dryness under reduced pressure to afford a 93% yield of 123b (450 mg) as a purple oil: $^1$H NMR (300 MHz, CDCl$_3$) d 7.17 (d, 1H, J=2.4 Hz), 5.55 (d, 1H, J=2.4 Hz), 3.43 (m, 1H), 2.92 (br s, 2H), 1.01 (m, 2H), 0.93 (m, 2H); MS (ESI+) m/z 124.1 (M+H).

Example 123c 5-Bromo-3-(1-cyclopropyl-1H-pyrazol-3-ylamino)-1-methylpyridin-2(1H)-one 123c

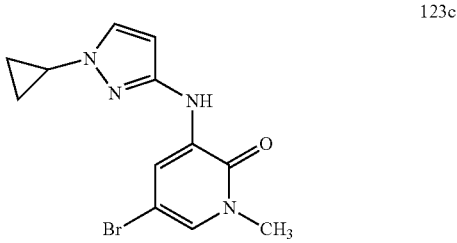 [SMILES: Cn1cc(Br)cc(Nc2ccn(C3CC3)n2)c1=O]

A 250-mL three-neck round-bottomed flask equipped with a reflux condenser, magnetic stirrer and nitrogen inlet was charged with 123b (444 mg, 3.61 mmol), 2,5-dibromo-1-methylpyrazin-6-one (1.06 g, 3.97 mmol), cesium carbonate (3.52 g, 10.8 mmol), and 1,4-dioxane (45 mL). After bubbling nitrogen through the resulting suspension for 30 min, Xantphos (177 mg, 0.306 mmol) and tris(dibenzylideneacetone)-dipalladium(0) (165 mg, 0.180 mmol) were added, and the reaction mixture was heated at reflux for 3 h. After this time, the mixture was cooled to room temperature and diluted with ethyl acetate (150 mL) and water (30 mL). The organic layer was separated, and the aqueous layer was extracted with ethyl acetate (3×150 mL). The combined organic layers were dried over sodium sulfate and concentrated under reduced pressure. The residue was triturated with methanol (20 mL) to afford a 63% yield (700 mg) of 123c as an off-white solid: mp 161-163° C.; $^1$H NMR (300 MHz, DMSO-d$_6$) δ 8.42 (s, 1H), 8.00 (d, 1H, J=2.5 Hz), 7.57 (d, 1H, J=2.4 Hz), 7.38 (d, 1H, J=2.5 Hz), 6.05 (d, 1H, J=2.4 Hz), 3.61 (m, 1H), 3.49 (s, 1H), 0.95 (m, 4H); MS (ESI+) m/z 309.0 (M+H).

A 150-mL single-neck round-bottomed flask equipped with a reflux condenser, magnetic stirrer and nitrogen inlet was charged with 123c (247 mg, 0.800 mmol), 111a (770 mg, 1.60 mmol), sodium carbonate (254 mg, 2.40 mmol), DMF (5 mL), water (2.5 mL) and 1,4-dioxane (8 mL). After bubbling nitrogen through the resulting suspension for 30 min, tetrakis(triphenylphosphine)palladium(0) (93 mg, 0.080 mmol) was added, and the reaction mixture was heated at reflux for 14 h. After this time, the mixture was cooled to room temperature and diluted with ethyl acetate (150 mL) and water (30 mL). The organic layer was separated, and the aqueous layer was extracted with ethyl acetate (3×150 mL). The combined organic layers were dried over sodium sulfate and concentrated under reduced pressure. The residue was dissolved in a mixture of THF (8 mL), methanol (4 mL) and water (4 mL). To the resulting solution was added lithium hydroxide monohydrate (167 mg, 3.40 mmol). The mixture was stirred for 2 h at room temperature and then concentrated in vacuo. The residue was partitioned between ethyl acetate (150 mL) and water (30 mL). The organic layer was separated, and the aqueous layer was extracted with a 20% (v/v) solution of methanol in methylene chloride (3×150 mL). The combined organic layers were dried over sodium sulfate and concentrated under reduced pressure. The residue was purified by column chromatography (silica, 0% to 10% methanol/methylene chloride) to afford a 19% yield (84 mg) of 123 as an off-white solid: mp 200-201° C.; $^1$H NMR (500 MHz, DMSO-d$_6$) δ 11.75 (s, 1H), 7.98 (s, 1H), 7.92 (s, 1H), 7.418 (t, 1H, J=8.0 Hz), 7.31 (d, 1H, J=7.5 Hz), 7.27 (d, 1H, J=7.5 Hz), 7.21 (s, 1H), 5.78 (s, 1H), 4.79 (m, 1H), 4.36 (m, 2H), 4.12 (m, 1H), 3.80 (m, 1H), 3.56 (s, 3H), 2.95 (m, 1H), 2.80 (m, 1H), 2.78 (s, 2H), 1.80 (m, 5H), 0.87 (m, 2H), 0.62 (m, 2H); MS (ESI+) m/z 542.1 (M+H).

Example 124 5-[5-fluoro-2-(hydroxymethyl)-3-{1-oxo-1H,2H,3H,4H,6H,7H,8H,9H-pyrazino[1,2-a]indol-2-yl}phenyl]-1-methyl-3-[(5-methyl-1H-pyrazol-3-yl)amino]-1,2-dihydropyridin-2-one 124

Example 124a 1-Methyl-3-(5-methyl-1H-pyrazol-3-ylamino)-5-(4,4,5,5-tetramethyl-1,3,2-dioxaborolan-2-yl)pyridin-2(1H)-one 124a A microwave vial equipped with a magnetic stirrer was charged with 5-bromo-1-methyl-3-(5-methyl-1H-pyrazol-3-ylamino)pyridine-2(1H)-one 112a (2.3 g, 8.3 mmol), (PinB)$_2$ (11 g, 41 mmol), Pd(dppf)Cl$_2$ (0.4 g, 0.5 mmol), KOAc (2.4 g, 25 mmol), and 1,4-dioxane (150 mL). The system was evacuated and then refilled with $N_2$. The reaction mixture was heated at 100° C. for 0.5 h under microwave irradiation. Then, the mixture was cooled to room temperature and filtered. The filtrate was concentrated under reduced pressure and the residue was purified by flash column chromatography eluting with 5:1 petroleum ether/ethyl acetate to afford 124a (0.57 g, 21%). LCMS: $[M+H]^+$ 331.

Example 124b 4-Fluoro-2-(1-methyl-5-(5-methyl-1H-pyrazol-3-ylamino)-6-oxo-1,6-dihydropyridin-3-yl)-6-(1-oxo-3,4,6,7,8,9-hexahydropyrazino[1,2-a]indol-2(1H)-yl)-benzyl acetate 124b A mixture of 124a (330 mg, 1 mmol), 2-bromo-4-fluoro-6-(1-oxo-3,4,6,7,8,9-hexahydropyrazino[1,2-a]indol-2(1H)-yl)benzyl acetate 197d (434 mg, 1 mmol), $PdCl_2(dppf)$ (82 mg, 0.1 mmol), 2.0M $Na_2CO_3$ (2.0 equiv) in DME (10 mL) was heated at 120° C. under microwave irradiation for 0.5 h. The solvent was evaporated in vacuo. The residue was purified on reverse phase Combi-flash to give the title compound (160 mg, 29%). LCMS: $[M+H]^+$ 559

A mixture of 124b (150 mg, 0.27 mmol) and LiOH (324 mg, 14 mmol) in isopropanol/THF (1:1, 10 mL) and water (3 mL) was stirred at 30° C. for 2 h. The mixture was evaporated in vacuo and the residue was extracted with ethyl acetate (10 mL×2). The combined ethyl acetate extract was concentrated under reduced pressure and the residue was purified with prep-HPLC to give 124 (60 mg, 43%). LCMS: $[M+H]^+$ 517. $^1H$ NMR (500 MHz, DMSO) δ 11.74 (s, 1H), 8.00 (m, 2H), 7.30 (m, 2H), 7.16 (dd, J=9.5, 1H), 6.52 (s, 1H), 5.87 (s, 1H), 4.87 (m, 1H), 4.33 (m, 2H), 4.12 (m, 3H), 3.87 (m, 1H), 3.56 (s, 3H), 2.59 (m, 2H), 2.47 (m, 2H), 2.45 (s, 3H), 1.70 (m, 4H).

Example 125 3-[(5-ethyl-1H-pyrazol-3-yl)amino]-5-[2-(hydroxymethyl)-3-{1-oxo-1H,2H,3H,4H,6H,7H,8H,9H-pyrazino[1,2-a]indol-2-yl}phenyl]-1-methyl-1,2-dihydropyridin-2-one 125

Experiment 125a

5-Bromo-3-(5-ethyl-1H-pyrazol-3-ylamino)-1-methylpyridin-2(1H)-one 125a

A 350-mL sealed tube equipped with a magnetic stirring bar was charged with 3,5-dibromo-1-methyl-1H-pyridin-2-one (3.2 g, 0.012 mol), 5-ethyl-1H-pyrazol-3-amine (2.0 g, 0.018 mol), $Pd_2(dba)_3$ (0.55 g, 0.60 mmol), 9,9-dimethyl-4,5-bis(diphenyl-phosphino)xanthene (0.49 g, 0.00084 mol), $Cs_2CO_3$ (7.8 g, 0.024 mol), and 1,4-dioxane (80 mL). After the reaction mixture was stirred at 105° C. for 16 h, it was cooled to room temperature, partitioned between dichloromethane (50 mL) and water (30 mL), and the organic phases were extracted with dichloromethane (30 mL×3). The combined organic phases were washed with water (30 mL×2) and brine (20 mL×1), dried ($Na_2SO_4$), and filtered through a pad of Celite, and the resulting filtrated was concentrated. To the crude product were added dichloromethane (20 mL) and ether (100 mL). The mixture was sonicated for 10 min., and the resulting precipitates were filtered to give 42% yield (1.5 g) of 5-bromo-3-(5-ethyl-1H-pyrazol-3-ylamino)-1-methylpyridin-2(1H)-one (125a) as a solid.

Example 125b 2-(5-(5-Ethyl-1H-pyrazol-3-ylamino)-1-methyl-6-oxo-1,6-dihydropyridin-3-yl)-6-(1-oxo-3,4,6,7,8,9-hexahydropyrazino[1,2-a]indol-2(1H)-yl)benzyl acetate 125b In a 10-mL glass vessel equipped with a magnetic stirring bar were placed 125a (116 mg, 0.39 mmol), 2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 114a (200 mg, 0.43 mmol), $Pd(PPh_3)_4$ (30 mg, 0.0.26 mmol) in 2 N $Na_2CO_3$ (2 mL) and 1,2-dimethoxyethane (5 mL). The vessel was sealed with a septum and placed into the microwave cavity. After the reaction mixture was stirred at 125° C. for 7 min., it was purified by flash chromatography (dichloromethane:methanol, 85:15) to give 23% (50 mg) of 125b as a solid.

A 25-mL, single-necked, round-bottomed flask equipped with a magnetic stirring bar was charged with 125b (50 mg, 0.090 mmol), $LiOH.H_2O$ (20 mg, 0.83 mmol), THF (2 mL), isopropanol (2 mL), and water (2 mL). After the reaction mixture was stirred at room temperature for 3 h, it was partitioned between dichloromethane (5 mL) and water (5 mL), and the organic phase was extracted with dichloromethane (5 mL×3). The combined organic phases were washed with water (5 mL×2) and brine (5 mL×1), dried ($Na_2SO_4$), and concentrated. The crude product was re-dissolved in dichloromethane (3 mL). To this solution was added hexane (10 mL) and the resulting precipitates were filtered to give 50% yield (23 mg) of 2-(3-(5-(5-ethyl-1H-pyrazol-3-ylamino)-1-methyl-6-oxo-1,6-dihydropyridin-3-yl)-2-(hydroxymethyl)phenyl)-3,4,6,7,8,9-hexahydropyrazino[1,2-a]indol-1(2H)-one 125 MS($ESI^+$) m/z 513.3 (M+H).

Example 126 2-(2-(Hydroxymethyl)-3-(1-methyl-6-oxo-5-(4,5,6,7-tetrahydropyrazolo[1,5-a]pyrazin-2-ylamino)-1,6-dihydropyridin-3-yl)phenyl)-3,4,6,7,8,9-hexahydropyrazino[1,2-a]indol-1(2H)-one 126

Experiment 126a

5-Bromo-1-methyl-3-(4,5,6,7-tetrahydropyrazolo[1,5-a]pyrazin-2-ylamino)pyridin-2(1H)-one 126a

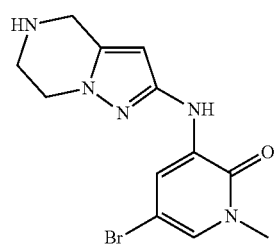

126a

A 50 mL round bottom flask with a magnetic stirrer and reflux condenser was charged with 3-(5-acetyl-4,5,6,7-tetrahydropyrazolo[1,5-a]pyrazin-2-ylamino)-5-bromo-1-methylpyridin-2(1H)-one 108d (250 mg, 0.7 mmol), aqueous NaOH (5N, 6 mL), ethanol (6 mL). The mixture stirred at reflux for 30 min. After this time, ethyl acetate (5 mL) and water (5 mL) were added. The separated aqueous layer was extracted with ethyl acetate (2×5 mL). The combined organics were washed with brine (10 mL), dried over sodium sulfate, filtered and concentrated under reduced pressure to afford a 91% yield (200 mg) of crude 5-bromo-1-methyl-3-(4,5,6,7-tetrahydropyrazolo[1,5-a]pyrazin-2-ylamino)pyridin-2(1H)-one (126a).

Example 126b 2-(1-Methyl-6-oxo-5-(4,5,6,7-tetrahydropyrazolo[1,5-a]pyrazin-2-ylamino)-1,6-dihydropyridin-3-yl)-6-(1-oxo-3,4,6,7,8,9-hexahydropyrazino[1,2-a]indol-2(1H)-yl)benzyl acetate 126b

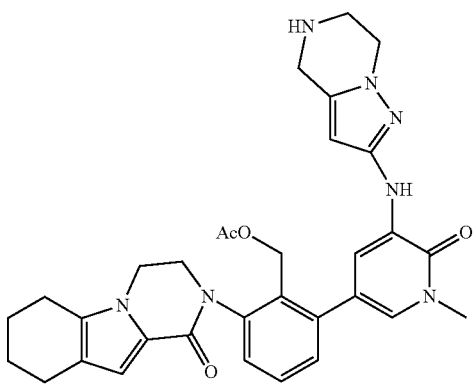

126b

A microwave tube equipped with a magnetic stirrer was charged with 126a (210 mg, 0.65 mmol), 2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 114a (330 mg, 0.7 mmol), DME (6 mL) and 1M aqueous sodium carbonate (1.9 mL). After bubbling N2 for 15 min, Pd(PPh$_3$)$_4$ (38 mg, 0.03 mmol) was added. The mixture was heated in microwave to 135° C. for 15 min. After this time, ethyl acetate (10 mL) and water (10 mL) were added. The separated aqueous layer was extracted with ethyl acetate (2×10 mL). The combined organics were washed with brine (20 mL), dried over sodium sulfate, filtered and concentrated under reduced pressure. The resulting residue was purified by column chromatography eluting with a gradient of CH$_2$Cl$_2$—9:1 CH$_2$Cl$_2$:MeOH to afford a 36% yield (140 mg) of 126b.

A 25 mL round bottom flask with a magnetic stirrer was charged with 126b (140 mg, 0.24 mmol), lithium hydroxide (50 mg, 1.2 mmol), THF (1.2 mL), i-propanol (1.2 mL) and water (2.4 mL). The mixture stirred at rt for 1 h. After this time ethyl acetate (5 mL) and water (5 mL) were added. The separated aqueous layer was extracted with ethyl acetate (2×5 mL). The combined organics were washed with brine (10 mL), dried over sodium sulfate, filtered and concentrated under reduced pressure. The resulting residue was purified by column chromatography eluting with a gradient of CH$_2$Cl$_2$-60:35:5 CH$_2$Cl$_2$:Et$_2$O:MeOH to afford a 33% yield (42 mg) of 126. MS (ESI+) m/z 540.3 (M+H).

Example 127 2-(5-fluoro-2-(hydroxymethyl)-3-(4-methyl-6-(4-morpholinophenylamino)-5-oxo-4,5-dihydropyrazin-2-yl)phenyl)-3,4,6,7,8,9-hexahydropyrazino[1,2-a]indol-1(2H)-one 127

Example 127a 4-Fluoro-2-(4-methyl-6-(4-morpholinophenylamino)-5-oxo-4,5-dihydropyrazin-2-yl)-6-(1-oxo-3,4,6,7,8,9-hexahydropyrazino[1,2-a]indol-2(1H)-yl)benzyl acetate 127a A mixture of 4-methyl-6-(4-morpholinophenylamino)-5-oxo-4,5-dihydropyrazin-2-yl boronic acid 122b (330 mg, 1 mmol), 2-bromo-4-fluoro-6-(1-oxo-3,4,6,7,8,9-hexahydropyrazino[1,2-a]indol-2(1H)-yl)benzyl acetate 197d (434 mg, 1 mmol), PdCl$_2$(dppf) (82 mg, 0.1 mmol), 2.0M Na$_2$CO$_3$ (1 mL, 2.0 equiv) in DME (10 mL) was heated at 130° C. under microwave irradiation for 0.5 h. The solvent was evaporated in vacuo and the residue was purified on reverse phase Combi-flash to give 127a (200 mg, 45%). LCMS: [M+H]$^+$ 641.

A mixture of 127a (200 mg, 0.31 mmol) and LiOH (372 mg, 16 mmol) in $^i$PrOH/THF (1:1, 10 mL) and H$_2$O (3 mL) was stirred at 30° C. for 2 h. The mixture was then evaporated in vacuo and the residue was extracted with ethyl acetate (10 mL×2). The combined extract was concentrated under reduced pressure and the residue was purified with prep-HPLC to give 127 (58 mg, 33%). LCMS: [M+H]$^+$ 599 $^1$H NMR (500 MHz, DMSO) δ 9.13 (s, 1H), 7.81 (m, 2H), 7.43 (s, 1H), 7.34 (m, 2H), 6.89 (m, 2H), 6.52 (s, 1H), 4.85 (s, 1H), 4.14 (m, 1H), 3.72 (m, 3H), 3.56 (m, 3H), 3.07 (m, 4H), 2.63 (m, 3H), 2.47 (m, 2H), 1.75 (m, 4H).

Example 128 2-(3-(5-(5-(3-hydroxyazetidin-1-yl)pyridin-2-ylamino)-1-methyl-6-oxo-1,6-dihydropyridin-3-yl)-2-(hydroxymethyl)phenyl)-3,4,6,7,8,9-hexahydropyrazino[1,2-a]indol-1(2H)-one 128

Example 128a 1-(6-Nitropyridin-3-yl)azetidin-3-ol 128a

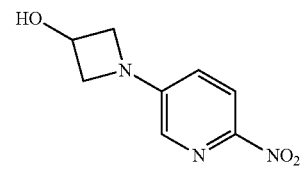

128a

A 50 mL round bottom flask with a magnetic stirrer and reflux condenser was charged with 3-hydroxyazetidine-HCl (2 g, 18.4 mmol), 5-bromo-2-nitropyridine (2.1 g, 10.2 mmol), diisopropylethylamine (5.4 mL, 30.7 mmol), tetrabutylammonium iodide (5.7 g, 15.4 mmol) and N,N-dimethylacetamide (10 mL). The mixture stirred at 120° C. for 16 h. After this time the mixture was cooled and ethyl acetate (25 mL) and water (25 mL) were added. The separated aqueous layer was extracted with ethyl acetate (2×10 mL). The combined organics were washed with brine (20 mL), dried over sodium sulfate, filtered and concentrated under reduced pressure. The resulting residue was purified by column chromatography eluting with a gradient of 4:1 hexanes:ethyl acetate c—100 ethyl acetate to afford a 52% yield (1.9 g) of 128a.

Example 128b 1-(6-Aminopyridin-3-yl)azetidin-3-ol 128b

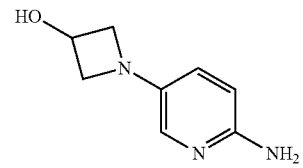

128b

A 500-mL Parr hydrogenation bottle was charged with 128a (1.9 g, 9.6 mmol), 10% palladium on carbon (50% wet, 570 mg dry weight) and ethanol (100 mL). The bottle was evacuated, charged with hydrogen gas to a pressure of 50 psi and shaken for 24 h on a Parr hydrogenation apparatus. The catalyst was removed by filtration through a pad of Celite 521 washing with 1:1 $CH_2Cl_2$:MeOH (500 mL). The resulting residue was purified by column chromatography eluting with a gradient of 100% DCM—100% 3:1 DCM:MeOH to afford a 70% yield (1.1 g) of 128b.

Example 128c 5-Bromo-3-(5-(3-hydroxyazetidin-1-yl)pyridin-2-ylamino)-1-methylpyridin-2(1H)-one 128c

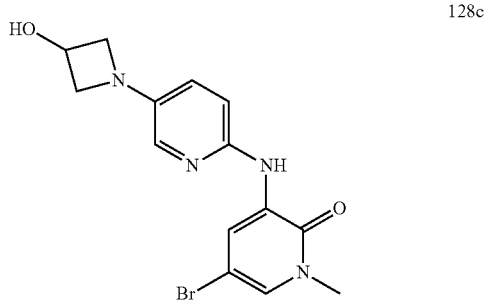 [SMILES: Cn1cc(Br)cc(Nc2ccc(N3CC(O)C3)cn2)c1=O]

128c

A sealed tube was equipped with a magnetic stirrer and charged with 128b (375 mg, 2.3 mmol), 3,5-dibromo-1-methylpyridin-2(1H)-one (848 g, 3.2 mmol) and cesium carbonate (1.7 g, 5 mmol) in 1,4-dioxane (24 mL). After bubbling nitrogen through the solution for 30 min, Xantphos (160 mg, 0.3 mmol) and tris(dibenzylideneacetone)dipalladium(0) (150 mg, 0.2 mmol) were added, and the reaction mixture was heated to 100° C. for 5 days. After this time, $H_2O$ (20 mL) and EtOAc (20 mL) were added. The aqueous layer was separated and extracted with ethyl acetate (2×20 mL). The combined organic extracts were washed with brine (50 mL) and dried over sodium sulfate. The resulting residue was purified by column chromatography eluting with a gradient of $CH_2Cl_2$—9:1 $CH_2Cl_2$:MeOH to afford a 39% yield (430 mg) of 128c.

Example 128d 2-(5-(5-(3-Hydroxyazetidin-1-yl)pyridin-2-ylamino)-1-methyl-6-oxo-1,6-dihydropyridin-3-yl)-6-(1-oxo-3,4,6,7,8,9-hexahydropyrazino[1,2-a]indol-2(1H)-yl)benzyl Acetate 128d 128d

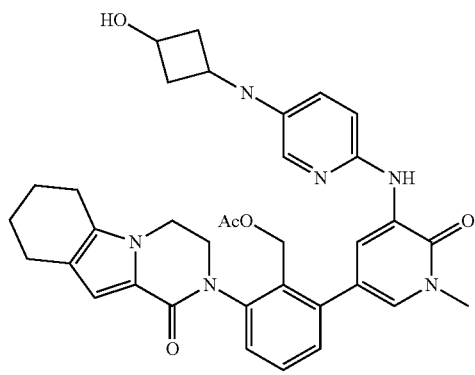

A microwave tube equipped with a magnetic stirrer was charged with 128c (220 mg, 0.6 mmol), 2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 114a (350 mg, 0.8 mmol), DME (7 mL) and 1M aqueous sodium carbonate (1.9 mL). After bubbling N2 for 15 min, $Pd(PPh_3)_4$ (36 mg, 0.03 mmol) was added. The mixture was heated in microwave to 135° C. for 15 min. After this time, ethyl acetate (10 mL) and water (10 mL) were added. The separated aqueous layer was extracted with ethyl acetate (2×10 mL). The combined organics were washed with brine (20 mL), dried over sodium sulfate, filtered and concentrated under reduced pressure. The resulting residue was purified by column chromatography eluting with a gradient of $CH_2Cl_2$—60:35:5 $CH_2Cl_2$:diethyl ether:MeOH to afford a 30% yield (110 mg) of 128d.

A 25 mL round bottom flask with a magnetic stirrer was charged with 128d (110 mg, 0.2 mmol), lithium hydroxide (38 mg, 0.9 mmol), THF (0.9 mL), i-propanol (0.9 mL) and water (1.8 mL). The mixture stirred at room temperature (rt) for 1 hr. After this time, ethyl acetate (5 mL) and water (5 mL) were added. The separated aqueous layer was extracted with ethyl acetate (2×5 mL). The combined organics were washed with brine (10 mL), dried over sodium sulfate, filtered and concentrated under reduced pressure. The resulting residue was purified by column chromatography eluting with a gradient of $CH_2Cl_2$—60:35:5 $CH_2Cl_2$:diethyl ether: MeOH to afford a 12% yield (12 mg) of 128. MS (ESI+) m/z 567.2 (M+H).

Example 129 2-(5-fluoro-2-(hydroxymethyl)-3-(4-methyl-5-oxo-6-(1,2,3,4-tetrahydroisoquinolin-6-ylamino)-4,5-dihydropyrazin-2-yl)phenyl)-3,4,6,7,8,9-hexahydropyrazino[1,2-a]indol-1(2H)-one 129

Example 129a tert-Butyl-6-(6-(2-(acetoxymethyl)-5-fluoro-3-(1-oxo-3,4,6,7,8,9-hexahydropyrazino[1,2-a]indol-2(1H)-yl)phenyl)-4-methyl-3-oxo-3,4-dihydropyrazin-2-ylamino)-3,4-dihydroisoquinoline-2(1H)-carboxylate 129a

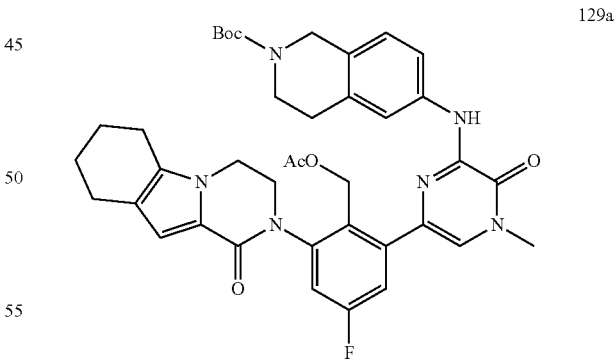

129a

A mixture of 482 mg of 4-fluoro-2-(1-oxo-3,4,6,7,8,9-hexahydropyrazino[1,2-a]indol-2(1H)-yl)-6-(1-oxo-3,4,6,7,8,9-hexahydropyrazino[1,2-a]indol-2(1H)-yl)benzyl acetate 210d and 435 mg of tert-butyl-6-(6-bromo-4-methyl-3-oxo-3,4-dihydropyrazin-2-ylamino)-3,4-dihydro-isoquinoline-2(1H)-carboxylate 120a, $PdCl_2$(dppf) (1110 mg, 0.015 mmol), 2 M $Na_2CO_3$ solution (3 mL) in DME (16 mL) was heated at 120° C. under microwave irradiation for 0.5 h. The solvent was evaporated in vacuo and the residue was purified on reverse phase Combi-flash to give 129a as a yellow solid (362 mg, 51%). MS: [M+H]+ 711.

Example 129b 4-Fluoro-2-(4-methyl-5-oxo-6-(1,2,3, 4-tetrahydroisoquinolin-6-ylamino)-4,5-dihydropyrazin-2-yl)-6-(1-oxo-3,4,6,7,8,9-hexahydropyrazino [1,2-a]indol-2(1H)-yl)benzyl Acetate 129b

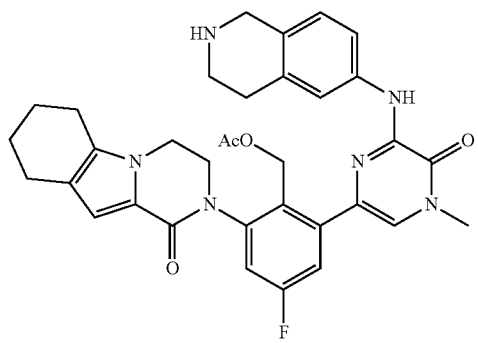

129b

To the solution of 129a (360 mg 0.51 mmol) in DCM (30 mL) was added 3M HCl in dioxane (8 mL) at room temperature. The mixture was stirred at room temperature for 5 h. After the reaction was completed, the solvent was removed at reduced pressure to afford 129b as a yellow solid (310 mg, 99%).

Following Example 149, 250 mg of 129b was converted to 129 as a white solid (98 mg, 42%). $^1$H NMR (500 MHz, MeOD) δ 7.62 (s, 1H), 7.55 (dd, J=7.0, 1H), 7.41 (dd, J=9.5, 1H), 7.38 (s, 1H), 7.20 (dd, J=9.5, 1H), 7.04 (d, J=8.5, 1H), 6.71 (s, 1H), 4.59 (d, J=12, 1H), 4.8 (d, J=11.5, 1H), 4.20 (m, 3H), 4.00 (m, 3H), 3.64 (s, 3H), 3.13 (m, 2H), 2.86 (m, 2H), 2.64 (m, 2H), 2.54 (m, 2H), 1.88 (m, 2H), 1.78 (m, 2H).

Example 130 2-(2-(hydroxymethyl)-3-(1-methyl-5-(5-(1-methylpiperidin-4-yl)pyridin-2-ylamino)-6-oxo-1,6-dihydropyridin-3-yl)phenyl)-3,4,6,7,8,9-hexahydropyrazino[1,2-a]indol-1(2H)-one 130

Example 130a 5-(1-Methyl-1,2,3,6-tetrahydropyridin-4-yl)-2-nitropyridine 130a

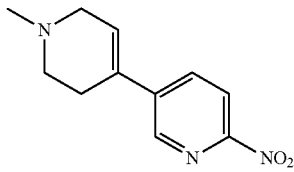 [SMILES: CN1CC=C(c2ccc([N+](=O)[O-])nc2)CC1]

To a round-bottomed flask equipped with a stirring bar, 1-methyl-4-(4,4,5,5-tetramethyl-1,3,2-dioxaborolan-2-yl)-1,2,3,6-tetrahydropyridine (1.50 g, 6.72 mmol), 5-bromo-2-nitropyridine (1.64 g, 8.07 mmol), Pd(PPh$_3$)$_4$ (388 mg, 0.336 mmol), Na$_2$CO$_3$ aqueous solution (1.0 N, 20.2 mL, 20.2 mmol), dioxane (60.6 mL) were added. The reaction mixture was heated at 100° C. for 10 hrs. CH$_2$Cl$_2$ (200 mL) was added to the resulting mixture was washed with water (30 mL×3). CH$_2$Cl$_2$ (200 mL) was added and the resulting mixture was washed with water (30 mL×3), brine (30 mL×1), dried over MgSO$_4$, filtered, and removed solvent in vacuo. Silica gel column chromatography (MeOH:DCM=5: 95) gave 5-(1-methyl-1,2,3,6-tetrahydropyridin-4-yl)-2-nitropyridine (130a) as a yellow solid.

Example 130b 5-(1-Methylpiperidin-4-yl)pyridin-2-amine 130b

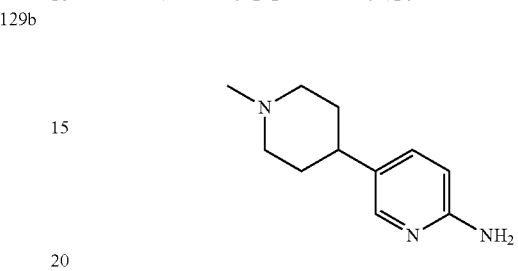

In a hydrogenation bottle, 130a (1.25 g, 5.73 mmol), EtOH (100 mL), 10% Pd/C (304 mmol, 0.286 mmol) were added. The mixture was hydrogenated at 55 psi for 2 hrs, filtered through celite, and washed with MeOH (20 mL). The solvent was removed in vacuo and off-white solids were obtained as 5-(1-methylpiperidin-4-yl)pyridin-2-amine 130b (1.13 g, 100%).

Example 130c 5-Bromo-1-methyl-3-(5-(1-methylpiperidin-4-yl)pyridin-2-ylamino)pyridin-2(1H)-one 130c

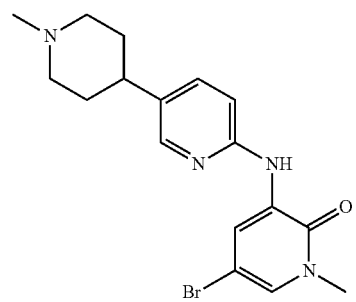

To a round-bottomed flask equipped with a stirring bar, 130b (1.08 g, 5.65 mmol), 3,5-dibromo-1-methylpyridin-2 (1H)-one (2.26 g, 8.47 mmol), Pd$_2$(dba)$_3$ (517 mg, 0.565 mmol), XantPhos (523 mg, 0.903 mmol), Cs$_2$CO$_3$ (6.07 g, 18.6 mmol) and dioxane (28.3 mL) were added. The reaction mixture was heated at 100° C. overnight. CH$_2$Cl$_2$ (200 mL) was added to the resulting mixture was washed with water (30 mL×3). CH$_2$Cl$_2$ (200 mL) was added and the resulting mixture was washed with water (30 mL×3), brine (30 mL×1), dried over MgSO$_4$, filtered, and removed solvent in vacuo. CH$_2$Cl$_2$/ether (1:2, 5 mL) were added followed by sonication, the precipitation was filtered and dried. Compound 130c was obtained as a green solid, 784 mg (37%).

Example 130d 2-(1-Methyl-5-(5-(1-methylpiperidin-4-yl)pyridin-2-ylamino)-6-oxo-1,6-dihydropyridin-3-yl)-6-(1-oxo-3,4,6,7,8,9-hexahydropyrazino[1,2-a]indol-2(1H)-yl)benzyl Acetate 130d

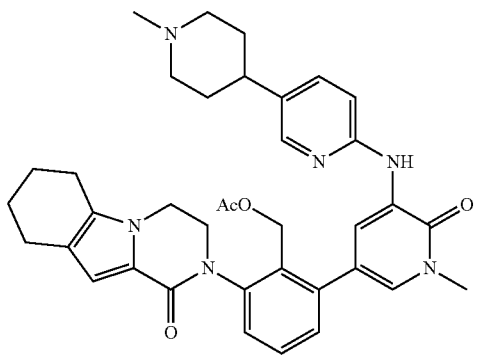 [SMILES: CC(=O)OCc1c(-c2cc(Nc3ccc(C4CCN(C)CC4)cn3)c(=O)n(C)c2)cccc1N1CCn2c(cc3c2CCCC3)C1=O]

To a microwave tube equipped with a stirring bar, 130c (250 mg, 0.663 mmol), 2-(2-(hydroxymethyl)-3-(4,4,5,5-tetramethyl-1,3,2-dioxaborolan-2-yl)phenyl)-3,4,6,7,8,9-hexahydropyrazino[1,2-a]indol-1(2H)-one 114a (338 mg, 0.729 mmol), Pd(PPh$_3$)$_4$ (38.3 mg, 0.033 mmol), Na$_2$CO$_3$ aqueous solution (1.0 N, 2.19 mL, 2.19 mmol), DME (2 mL) were added. The mixture was reacted in microwave at 135° C. for 15 min. CH$_2$Cl$_2$ (200 mL) was added and the resulting mixture was washed with water (30 mL×3), brine (30 mL×1), dried over MgSO$_4$, filtered, and removed solvent in vacuo. Silica gel column chromatography (MeOH:DCM=5:95) gave 130d.

To a round-bottomed flask equipped with a stirring bar, 130d THF (1.25 mL), i-PrOH (1.25 mL), H$_2$O (1.25 mL), LiOH H$_2$O (135 mg) were added. The resulting mixture was stirred at RT for 1 hr. The solvent was removed in vacuo and the resulting residue was added to CH$_2$Cl$_2$ (200 mL), the solution was washed with water (30 mL×3), brine (30 mL×1), dried over MgSO$_4$, filtered, and removed solvent in vacuo. Silica gel column chromatography (MeOH:CH$_2$Cl$_2$=10:90) gave 130 as an off-white solid, 39 mg. MS (ESI+) m/z 593.4 (M+H).

Example 131 5-(3-(6,6-Dimethyl-3,4,6,7-tetrahydro-5H-cyclopenta[4,5]thieno[2,3-c]pyridine-1 (2H)-yl)-2-(hydroxymethyl)phenyl)-1-methyl-3-(1-ethyl-1H-pyrazol-4-ylamino) pyrazin-2(1H)-one 131

Example 131a 2-(6,6-Dimethyl-3,4,6,7-tetrahydro-5H-cyclopenta[4,5]thieno[2,3-c]pyridine-1(2H)-yl)-6-(4,4,5,5-tetramethyl-1,3,2-dioxaborolan-2-yl)benzyl Acetate 131a

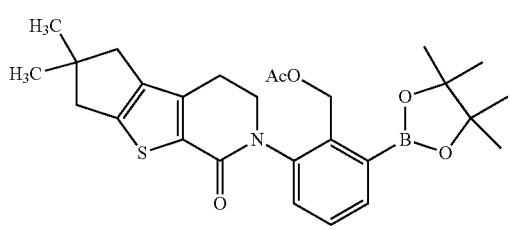

A 250-mL single-neck round-bottomed flask equipped with a magnetic stirrer and nitrogen inlet was charged with 105i (411 mg, 0.917 mmol), 4,4,4',4',5,5,5',5'-octamethyl-2,2'-bi(1,3,2-dioxaborolane) (698 mg, 2.75 mmol), potassium acetate (360 mg, 3.66 mmol) and 1,4-dioxane (15 mL). After bubbling nitrogen through the resulting suspension for 30 min, Pd(dppf)Cl$_2$.CH$_2$Cl$_2$ (35 mg, 0.047 mmol) was added. A reflux condenser was attached to the flask, and the reaction mixture was heated at 90° C. for 14 h. After this time, more Pd(dppf)Cl$_2$.CH$_2$Cl$_2$ (70 mg, 0.094 mmol) was added, and the reaction was stirred for 4 h at 90° C. After this time, the mixture was diluted with ethyl acetate (100 mL) and water (75 mL), and the layers were separated. The aqueous layer was extracted with ethyl acetate (50 mL), and the combined organic layers were washed with brine (50 mL) and dried over sodium sulfate. The drying agent was removed by filtration. The filtrate was concentrated under reduced pressure, and the resulting residue was purified by flash column chromatography (silica, 70:30 hexanes/ethyl acetate) to afford 131a in 82% yield (373 mg) as an amorphous off-white solid: $^1$H NMR (500 MHz, CDCl$_3$) δ 7.81 (dd, J=7.5, 1.5 Hz, 1H), 7.41 (t, J=7.5 Hz, 1H), 7.35 (dd, J=7.0, 1.5 Hz, 1H), 5.51 (d, J=11.5 Hz, 1H), 5.26 (d, J=11.5 Hz, 1H), 4.03-3.98 (m, 1H), 3.77-3.72 (m, 1H), 3.05-2.98 (m, 1H), 2.82-2.76 (m, 1H), 2.76 (s, 2H), 2.52 (s, 2H), 1.99 (s, 3H), 1.33 (s, 12H), 1.27 (s, 3H), 1.26 (s, 3H); MS (ESI+) m/z 496.2 (M+H).

Example 131b 5-Bromo-3-(1-ethyl-1H-pyrazol-4-ylamino)-1-methylpyrazin-2(1H)-one 131b

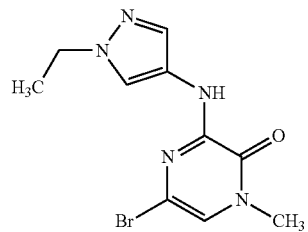

Following Example 111b, reaction of 1-ethyl-1H-pyrazol-4-amine (500 mg, 4.50 mmol) and 3,5-dibromo-1-methyl pyrazin-2(1H)-one (1.33 g, 4.95 mmol) afforded a 75% yield (1.01 g) of 131b as an off-white solid: mp 237-239° C.; $^1$H NMR (300 MHz, DMSO-d$_6$) δ 9.90 (s, 1H), 8.02 (s, 1H), 7.73 (s, 1H), 7.20 (s, 1H), 4.11 (q, 2H, J=7.5 Hz), 3.41 (s, 3H), 1.34 (t, 3H, J=7.3 Hz); MS (ESI+) m/z 298.0 (M+H).

A 100-mL single-neck round-bottomed flask equipped with a magnetic stirrer and nitrogen inlet was charged with 131b (200 mg, 0.670 mmol), boronate 131a (365 mg, 0.737 mmol), sodium carbonate (184 mg, 1.73 mmol), DMF (2 mL), water (2 mL) and 1,4-dioxane (10 mL). After bubbling nitrogen through the resulting suspension for 30 min, tetrakis(triphenylphosphine)palladium(0) (134 mg, 0.116 mmol) was added. A reflux condenser was attached to the flask, and the reaction mixture was heated at 100° C. for 14 h. After this time, the mixture was diluted with 90:10 methylene chloride/methanol (100 mL) and water (75 mL), and the layers were separated. The aqueous layer was extracted with 90:10 methylene chloride/methanol (2×50 mL), and the combined organic layers were washed with brine (100 mL) and dried over sodium sulfate. The drying agent was removed by filtration. The filtrate was concentrated under reduced pressure, and the resulting residue was dissolved in a mixture of THF (5 mL), water (5 mL) and methanol (5 mL). Lithium hydroxide monohydrate (121 mg, 2.89 mmol) was added, and the mixture was stirred at room temperature for 2 h. After this time, the mixture was diluted with 90:10 methylene chloride/methanol (100 mL) and water (50 mL), and the layers were separated. The aqueous layer was extracted with 90:10 methylene chloride/methanol (2×75 mL), and the combined organic layers were washed with brine (100 mL) and dried over sodium sulfate. The drying agent was removed by filtration. The filtrate was concentrated under reduced pressure, and the resulting residue was purified by flash column chromatography (silica, 90:10 methylene chloride/methanol) to afford 131 in 26% yield (96 mg) as an amorphous yellow solid: mp 138-140° C.; $^1$H NMR (500 MHz, DMSO-d$_6$) δ 9.56 (s, 1H), 8.16 (s, 1H), 7.73 (s, 1H), 7.56 (dd, J=7.5, 1.0 Hz, 1H), 7.46 (t, J=8.0 Hz, 1H), 7.34 (dd, J=7.5, 1.0 Hz, 1H), 7.31 (s, 1H), 4.85-4.82 (m, 1H), 4.56-4.53 (m, 1H), 4.47-4.44 (m, 1H), 4.08-4.02 (m, 3H), 3.90-3.86 (m, 1H), 3.52 (s, 3H), 3.03-3.00 (m, 1H), 2.92-2.87 (m, 1H), 2.75 (s, 2H), 2.54 (d, J=5.0 Hz, 2H), 1.32 (t, J=7.5 Hz, 3H), 1.23 (s, 6H); MS (ESI+) m/z 545.1 (M+H).

Example 132 2-(2-(hydroxymethyl)-3-(5-(5-(2-hydroxypropan-2-yl)-1-methyl-1H-pyrazol-3-ylamino)-1-methyl-6-oxo-1,6-dihydropyridazin-3-yl)phenyl)-3,4,6,7,8,9-hexahydropyrazino[1,2-a]indol-1(2H)-one 132

Example 132a 2-(2-(Acetydroxymethyl)-3-(5-(5-(2-hydroxypropan-2-yl)-1-methyl-1H-pyrazol-3-ylamino)-1-methyl-6-oxo-1,6-dihydropyridazin-3-yl)phenyl)-3,4,6,7,8,9-hexahydropyrazino[1,2-a]indol-1(2H)-one 132a

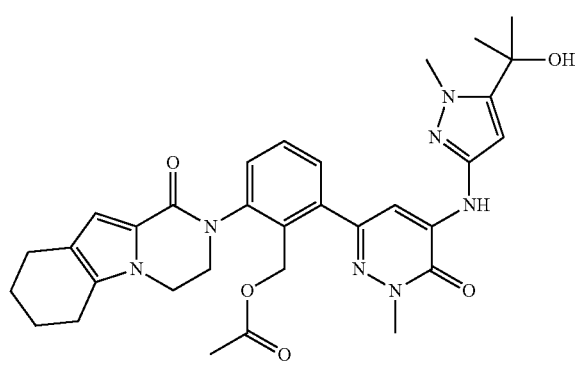

Following Example 119d, 119c (150 mg, 0.50 mmol), 113a (257 mg, 0.55 mmol), 1N Na$_2$CO$_3$ (1.1 mL) and tetrakis(tripheny-phosphine)-palladium(0) (29 mg, 5 mol %) were reacted to give 132a (160 mg, 53% yield).

Following Example 132, 132a (160 mg, 0.27 mmol), 1N LiOH (1.3 mL), THF (2 mL) and isopropanol (2 mL) were reacted to give 132 (118 mg, 78% yield) as a white solid. MS (ESI+) m/z 558.3 (M+H).

Example 133 2-(2-(Hydroxymethyl)-3-(6-oxo-5-(pyrimidin-4-ylamino)-1,6-dihydropyridazin-3-yl)phenyl)-3,4,5,6,7,8-hexahydrobenzothieno[2,3-c]pyridin-1(2H)-one 133

Example 133a 6-Chloro-4-(pyrimidin-4-ylamino)pyridazin-3(2H)-one 133a

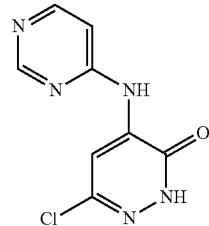

A 1-L three-neck round-bottomed flask equipped with a mechanical stirrer, nitrogen inlet and reflux condenser was charged with 4-bromo-6-chloropyridazin-3(2H)-one (7.30 g, 35.0 mmol), 2-aminopyrimidine (3.33 g, 35.0 mmol), cesium carbonate (25.0 g, 76.8 mmol) and 1,4-dioxane (345 mL). After bubbling nitrogen through the resulting solution for 30 minutes, Xantphos (1.71 g, 2.96 mmol) and tris (dibenzylideneacetone)di-palladium(0) (1.60 g, 1.74 mmol) were added and the reaction mixture was heated at reflux for 3 h. After this time the reaction was cooled to room temperature and filtered. The filter cake was washed with methylene chloride (3×50 mL) and water (3×20 mL) and dried in a vacuum oven overnight at 45° C. to afford 133a (5.54 g, 71%) as a tan solid: mp>300° C.; $^1$H NMR (500 MHz, DMSO-d$_6$) d 13.28 (br s, 1H), 9.90 (br s, 1H), 8.91 (s, 1H), 8.51 (d, 1H, J=6.0 Hz), 8.39 (s, 1H), 7.53 (dd, 1H, J=1.5, 6.0 Hz); MS (ESI+) m/z 224.1 (M+H).

Following Example 119d, 133a (145 mg, 0.650 mmol) and 111a (313 mg, 0.650 mmol) afforded a 18% yield (60 mg) of 133 as a pink solid: mp 150-151° C.; $^1$H NMR (500 MHz, DMSO-d$_6$) δ 13.30 (s, 1H), 9.81 (s, 1H), 8.79 (s, 1H), 8.66 (s, 1H), 8.47 (s, 1H), 7.48 (m, 2H), 7.43 (m, 2H), 4.66 (m, 1H), 4.44 (m, 1H), 4.38 (m, 1H), 4.04 (m, 1H), 3.85 (m, 1H), 2.94 (m, 1H), 2.87 (m, 1H), 2.77 (m, 2H), 2.53 (m, 1H), 1.79 (m, 4H); MS (ESI+) m/z 501.1 (M+H).

Example 134 2-(2-(Hydroxymethyl)-3-(5-(5-(2-hydroxypropan-2-yl)-1-methyl-1H-pyrazol-3-ylamino)-1-methyl-6-oxo-1,6-dihydropyridin-3-yl)phenyl)-3,4,6,7,8,9-hexahydropyrazino[1,2-a]indol-1(2H)-one 134

Example 134a Methyl 3-(5-Bromo-1-methyl-2-oxo-1,2-dihydropyridin-3-ylamino)-1-methyl-1H-pyrazole-5-carboxylate 134a

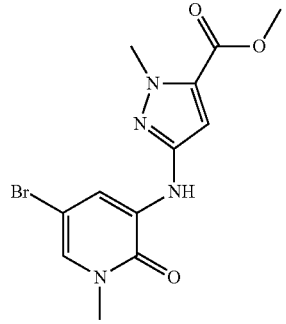

Following Example 119a, 3,5-dibromo-1-methylpyridin-2(1H)-one (2.0 g, 7.5 mmol) was converted to 134a.

Example 134b 5-Bromo-3-(5-(2-hydroxypropan-2-yl)-1-methyl-1H-pyrazol-3-ylamino)-1-methylpyridin-2(1H)-one 134b

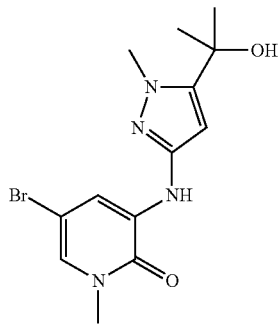

134b

Following Example 119b, 132a (330 mg, 0.97 mmol) and 3.0M in ether MeMgBr (5.8 mmol, 1.9 mL) in THF (10 mL) were reacted to give 134b (270 mg, 82% yield).

Example 134c 2-(5-(5-(2-hydroxypropan-2-yl)-1-methyl-1H-pyrazol-3-ylamino)-1-methyl-6-oxo-1,6-dihydropyridin-3-yl)-6-(1-oxo-3,4,6,7,8,9-hexahydropyrazino[1,2-a]indol-2(1H)-yl)benzyl acetate 134c Following Example 119, 113b (120 mg, 0.35 mmol), 113a (180 mg, 0.39 mmol), 1N $Na_2CO_3$ (0.8 mL) and Palladium tetrakis (20 mg, 5 mol %) were reacted to give 134c (85 mg, 40% yield).
Following Example 119, 134c (80 mg, 0.13 mmol), 1N LiOH (0.7 mL), THF (1.5 mL) and isopropanol (1.5 mL) were reacted. The product was purified via column chromatography, silica, MeOH/CH2Cl2 then triturated with EtOAc to give 134 (18 mg, 25% yield). MS (ESI+) m/z 557.3 (M+H).

Example 135 2-(3-(5-(5-cyclopropyl-4,5,6,7-tetrahydropyrazolo[1,5-a]pyrazin-2-ylamino)-1-methyl-6-oxo-1,6-dihydropyridin-3-yl)-5-fluoro-2-(hydroxymethyl)phenyl)-3,4,6,7,8,9-hexahydropyrazino[1,2-a]indol-1(2H)-one 135

Example 135a 5-Cyclopropyl-2-nitro-4,5,6,7-tetrahydropyrazolo[1,5-a]pyrazine 135a

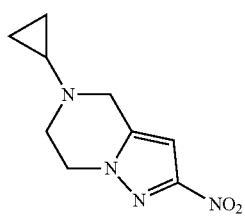 [SMILES: O=[N+]([O-])c1cc2n(n1)CCN(C1CC1)C2]

A mixture of 1-(2-bromoethyl)-5-(bromomethyl)-3-nitro-1H-pyrazole 101c (4 g, 12.9 mmol) and cyclopropanamine (7.35 g, 129 mmol) in THF (40 mL) was stirred at 30° C. overnight. After the completion of the reaction, the mixture was filtered off and the solid was washed with THF (100 mL). The filtrate was concentrated under reduced pressure to give 135a (2.68 g, 99%). MS: [M+H]$^+$ 209.

Example 135b 5-Cyclopropyl-4,5,6,7-tetrahydropyrazolo[1,5-a]pyrazin-2-amine 135b

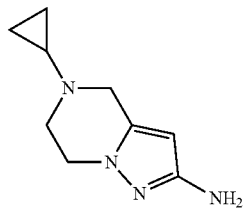

A mixture of 5-cyclopropyl-2-nitro-4,5,6,7-tetrahydropyrazolo[1,5-a]pyrazine 135a (2.68 g, 12.9 mmol), Fe (3.6 g, 64.4 mmol) and $NH_4Cl$ (4.1 g, 77.4 mmol) in ethanol (30 mL) and water (5 mL) was heated at reflux for 2 h. After the completion of the reaction, the mixture was filtered off. And the solid was washed with ethanol (150 mL). The filtrate was evaporated in vacuo and the residue was extracted with methanol/methylene chloride (1/7). The combined extracts were dried over $Na_2SO_4$ and evaporated. The residue was purified on reverse phase Combi-flash to give 135b (1.8 g, 75%). MS: [M+H]$^+$ 179.

Example 135c 5-Bromo-3-(5-cyclopropyl-4,5,6,7-tetrahydropyrazolo[1,5-a]pyrazin-2-ylamino)-1-methylpyridin-2(1H)-one 135c

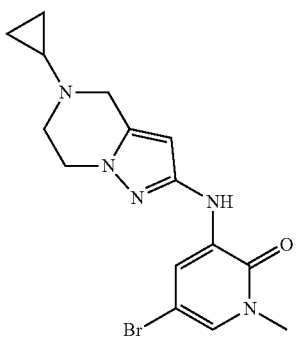 [SMILES: Cn1cc(Br)cc(Nc2cc3n(n2)CCN(C2CC2)C3)c1=O]

A mixture of 5-cyclopropyl-4,5,6,7-tetrahydropyrazolo[1,5-a]pyrazin-2-amine 135b (1.39 g, 7.8 mmol), XantPhos (450 mg, 0.78 mmol), $Pd_2dba_3$ (476 mg, 0.52 mmol), 3,5-dibromo-1-methylpyridin-2(1H)-one (1.72 g, 6.5 mmol) and $Cs_2CO_3$ (6.3 mg. 19.5 mmol) in 1,4-dioxane (30 mL) was heated at reflux for 1 h. After the completion of the reaction the mixture was filtered off and the solid was washed with methanol (60 mL). The filtrate was evaporated in vacuo and the residue was purified on reverse phase Combi-flash to give 135c (0.84 g, 30%). MS: [M+H]$^+$ 364.

Example 135d 2-(5-(5-Cyclopropyl-4,5,6,7-tetrahy-
dropyrazolo[1,5-a]pyrazin-2-ylamino)-1-methyl-6-
oxo-1,6-dihydropyridin-3-yl)-4-fluoro-6-(1-oxo-3,4,
6,7,8,9-hexahydropyrazino[1,2-a]indol-2(1H)-yl)
benzyl acetate 135d

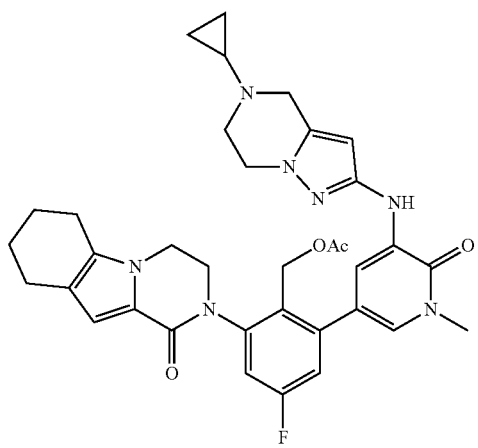 [SMILES: CC(=O)OCc1c(-c2cc(Nc3cc4n(n3)CCN(C3CC3)C4)c(=O)n(C)c2)cc(F)cc1N1CCn2c(cc3c2CCCC3)C1=O]

A mixture of 4-fluoro-2-(1-oxo-3,4,6,7,8,9-hexahydropy-razino[1,2-a]indol-2(1H)-yl)-6-(4,4,5,5-tetramethyl-1,3,2-dioxaborolan-2-yl)benzyl acetate 210d (105 mg, 0.26 mmol), 135c (100 mg, 0.28 mmol), PdCl$_2$(dppf) (29 mg, 0.039 mmol), K$_3$PO$_4$ (100 mg), and NaOAc (50 mg) in MeCN (10 mL) and water (3 mL) was heated at 110° C. for 2 h. The solvent was evaporated in vacuo. The residue was purified on reverse phase Combi-flash to give 135d (100 mg, 60%). MS: [M+H]$^+$ 640.

A mixture of 135d (100 mg, 0.16 mmol) and LiOH hydrate (100 mg. 2.3 mmol) in isopropanol (10 mL) and water (3 mL) was stirred at 30° C. for 2 h. The mixture was evaporated in vacuo and the residue was extracted with ethyl acetate (10 mL×2). The combined extracts were concentrated under reduced pressure and the residue was purified with prep-HPLC to give 135 (40 mg, 42%). MS: [M+H]$^+$ 598. $^1$H NMR (500 MHz, MeOD) δ 7.89 (s, 1H), 7.26 (s, 1H), 7.20 (d, J=9.0, 2H), 6.72 (s, 1H), 5.88 (s, 1H), 4.52-4.44 (m, 2H), 4.22-4.18 (m, 3H), 4.03-3.97 (m, 3H), 3.81 (s, 2H), 3.69 (s, 3H), 3.15-3.13 (m, 2H), 2.67-2.61 (m, 2H), 2.57-2.51 (m, 2H), 1.96-1.87 (m, 3H), 1.81-1.75 (m, 2H), 0.62-0.58 (m, 2H), 0.53-0.49 (m, 2H).

Example 136 5-(3-{5-[(5-Cyclopropyl-1H-pyrazol-
3-yl)amino]-1-methyl-6-oxo-1,6-dihydropyridin-3-
yl}-5-fluoro-2-(hydroxymethyl)phenyl)-8-thia-5-
azatricyclo-[7.4.0.0$^{2,7}$]trideca-1(9),2(7)-dien-6-one
136

Example 136a 3-Cyclopropyl-3-oxopropanenitrile
136a

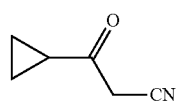

To a solution of CH$_3$CN (0.34 mL, 6.58 mmol) in THF (3 mL) at −78° C. under N$_2$ protection was added LDA (3.3 mL, 6.58 mmol) dropwise. The reaction mixture was stirred at −78° C. for 3 h. Then ethyl cyclopropanecarboxylate (0.5 g, 4.38 mmol) in THF (2 mL) was added and the mixture was allowed to warm to room temperature in a period of 1 h. Water (2 mL) was added and the solvents were removed under reduced pressure. CH$_2$Cl$_2$ (2 mL) was added and the pH of the mixture was adjusted to 5 with 2N HCl. It was then extracted with CH$_2$Cl$_2$ (5 mL×2), dried over Na$_2$SO$_4$, and concentrated to afford 136a as a yellow oil, which was used in the next step without further purification.

Example 136b 3-Cyclopropyl-1H-pyrazol-5-amine
136b

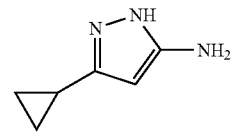

To a solution of 136a (477 mg, 4.38 mmol) in MeOH (5 mL) was added N$_2$H$_4$.H$_2$O (80%) (5 mL). The reaction mixture was heated at 75° C. for 15 h. MeOH was removed under reduced pressure. The residue was extracted with CH$_2$Cl$_2$ (2×8 mL), dried over Na$_2$SO$_4$, and concentrated. The residue was purified by flash column eluting with 100:1 CH$_2$Cl$_2$/MeOH to afford 136b as a yellow oil (37%, for two steps). LCMS: (M+H)$^+$ 124.

Example 136c tert-Butyl
5-Amino-3-cyclopropyl-1H-pyrazole-1-carboxylate
136c

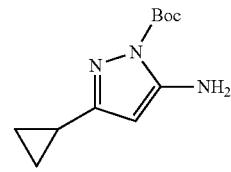 [SMILES: CC(C)(C)OC(=O)n1nc(C2CC2)cc1N]

To a mixture of 136b (0.25 g, 2 mmol) and K$_2$CO$_3$ (0.828 g, 6 mmol) in THF (5 mL) was added (Boc)$_2$O (0.436 g, 2 mmol) in THF (5 mL). The reaction mixture was stirred at room temperature for 15 h. It was then filtered and concentrated. The residue was purified by flash column eluting with 6:1 petroleum ether/ethyl acetate to afford 136c as a white solid (240 mg, 54%). LCMS: (M-Boc)$^+$ 124.

Example 136d 5-Bromo-3-(3-cyclopropyl-1H-pyra-
zol-5-ylamino)-1-methylpyridin-2(1H)-one 136d

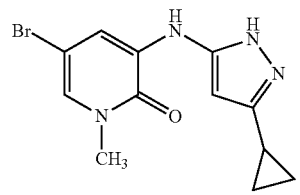 [SMILES: Cn1cc(Br)cc(Nc2cc(C3CC3)n[nH]2)c1=O]

A 100-mL single-neck round-bottomed flask equipped with a magnetic stirrer and reflux condenser was charged with 1,4-dioxane (15 mL), 136c (455 mg, 1.95 mmol), 3,5-dibromo-1-methylpyridin-2(1H)-one (0.40 g, 1.5 mmol) and cesium carbonate (1.22 g, 3.75 mmol). After bubbling nitrogen through the resulting mixture for 30 minutes, XantPhos (87 mg, 0.15 mmol) and tris(dibenzylideneacetone)dipalladium(0) (70 mg, 0.075 mmol) were added, and the reaction mixture was heated at reflux for 15 h. After this time the reaction was cooled to room temperature, partitioned between ethyl acetate (30 mL) and water (30 mL) and filtered. The aqueous layer was separated and extracted with ethyl acetate 2×50 mL). The organic layers were combined, washed with brine (50 mL) and dried over $Na_2SO_4$. The drying agent was removed by filtration and the filtrate was concentrated under reduced pressure. The residue was purified on flash column eluting with 50:1 $CH_2Cl_2$/MeOH to afford 136d as a yellow solid (320 mg, 50%). LCMS: $(M+H)^+$ 309. $^1$H NMR (500 MHz, DMSO) δ 11.85 (s, 1H), 8.23 (s, 1H), 8.02 (d, J=2.5, 1H), 7.35 (d, J=2.5, 1H), 5.77 (d, J=2, 1H), 3.46 (s, 3H), 1.83 (m, 1H), 0.90 (m, 2H), 0.64 (m, 2H)

Example 136e (2-{5-[(5-Cyclopropyl-1H-pyrazol-3-yl)amino]-1-methyl-6-oxopyridin-3-yl}-4-fluoro-6-{6-oxo-8-thia-5-azatricyclo[7.4.0.0$^{2,7}$]trideca-1(9),2(7)-dien-5-yl}phenyl)methyl acetate 136e A 25 mL sealed vial was charged with (4-fluoro-6-{6-oxo-8-thia-5-azatricyclo[7.4.0.0$^{2,7}$]trideca-1(9),2(7)-dien-5-yl}-6-(4,4,5,5-tetramethyl-1,3,2-dioxaborolan-2-yl)phenyl)-methyl acetate 212b (580 mg, 1.16 mmol), 136d (300 mg, 0.97 mmol), $CH_3COONa$ (160 mg, 1.94 mmol), $K_3PO_4$ (410 mg, 1.94 mmol), $PdCl_2(dppf)$ (100 mg, 0.12 mmol), $CH_3CN$ (12 mL), and $H_2O$ (1 mL). The mixture was heated at 110° C. for 2 hours. The reaction mixture was evaporated and the residue was purified by flash column eluting with 50:1 methylene chloride/methanol containing 0.5% triethylamine to give 136e as a black solid (300 mg, 52%).

To a solution of 136e (300 mg, 0.50 mmol) in propan-2-ol (3 mL), tetrahydrofuran (3 mL), and water (3 mL) was added LiOH (1.0 g, 25 mmol). The mixture was stirred at 30° C. for 2 h. Then, 20 mL $H_2O$ was added and extracted with EA (30 mL×3). The combined organic layer was dried with $Na_2SO_4$ and concentrated to give yellow solid, which was further purified by prep-HPLC to give 136 as a white solid (200 mg, 70%). LCMS: $(M+H)^+$ 560 $^1$H NMR (500 MHz, DMSO) δ 7.78 (s, 1H), 7.25 (d, J=2.5, 1H), 7.21 (m, 2H), 5.79 (s, 1H), 4.48 (m, 2H), 4.15 (m, 1H), 4.00 (m, 1H), 3.69 (s, 3H), 3.07 (m, 1H), 2.95 (m, 1H), 2.85 (m, 2H), 2.61 (m, 2H), 1.89 (m, 5H), 0.96 (m, 2H), 0.73 (m, 2H).

Example 137 5-[5-Fluoro-2-(hydroxymethyl)-3-[1-methyl-5-(5-(oxetan-3-yl)-4,5,6,7-tetrahydropyrazolo[1,5-a]pyrazin-2-ylamino)-6-oxopyridin-3-yl]phenyl]-8-thia-5-azatricyclo[7.4.0.0$^{2,7}$]trideca-1(9),2(7)-dien-6-one 137

Example 137a 5-[5-Fluoro-3-[1-methyl-5-(5-(oxetan-3-yl)-4,5,6,7-tetrahydropyrazolo-[1,5-a]pyrazin-2-ylamino)-6-oxopyridin-3-yl]benzyl acetate]-8-thia-5-azatricyclo-[7.4.0.0$^{2,7}$]trideca-1(9),2(7)-dien-6-one 137a

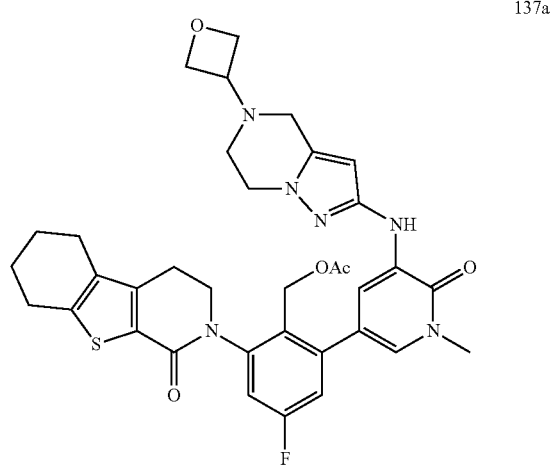 [SMILES: CC(=O)OCc1c(-c2cc(Nc3cc4n(n3)CCN(C3COC3)C4)c(=O)n(C)c2)cc(F)cc1N1CCc2c(sc3c2CCCC3)C1=O]

137a

A 25 mL sealed tube was charged with (4-fluoro-2-{6-oxo-8-thia-5-azatricyclo[7.4.0.0$^{2,7}$]trideca-1(9),2(7)-dien-5-yl}-6-(4,4,5,5-tetramethyl-1,3,2-dioxaborolan-2-yl)phenyl) methyl acetate 212b (990 mg, 2 mmol), 5-bromo-1-methyl-3-(5-(oxetan-3-yl)-4,5,6,7-tetrahydropyrazolo[1,5-a] pyrazin-2-ylamino)pyridin-2(1H)-one 252a (500 mg, 1.3 mmol), $CH_3COONa$ (220 mg, 2.6 mmol), $K_3PO_4$ (700 mg, 2.6 mmol), and $PdCl_2(dppf)$ (110 mg, 0.13 mmol) suspended in $CH_3CN$ (25 mL) and $H_2O$ (1 mL). The mixture was stirred at 110° C. for 2 hours. The solvent was then evaporated and the residue was purified by silical-gel column eluting with 20:1 $CH_2Cl_2$/methanol to give 137a as a brown solid (300 mg, 35%). MS: $(M+H)^+$ 673.

To a solution of 137a (270 mg, 0.4 mmol) in propan-2-ol (8 mL), tetrahydrofuran (8 mL), and water (1.5 mL) was added LiOH (964 mg, 40 mmol). The mixture was stirred at 30° C. for 2 h. It was then evaporated under reduced pressure and the residue was purified by prep-HPLC to afford 137 as a yellow solid (84 mg, 33%). MS: $(M+H)^+$ 631. 1H NMR (500 MHz, MeOD) δ 1.87 (s, 4H), 2.52-2.56 (d, 2H), 2.83-2.90 (d, 5H), 3.01 (s, 1H), 3.56-3.74 (t, 6H), 3.96-4.01 (t, 4H), 4.44-4.48 (t, 2H), 4.63 (s, 2H), 4.74 (s, 2H), 5.87 (s, 1H), 7.16-7.18 (d, 2H), 7.25 (s, 1H), 7.89 (s, 1H).

Example 138 2-(3-(5-(5-(4-Ethylpiperazin-1-yl)pyridin-2-ylamino)-1-methyl-6-oxo-1,6-dihydropyridin-3-yl)-2-(hydroxymethyl)phenyl)-3,4,6,7,8,9-hexahydropyrazino[1,2-a]indol-1(2H)-one 138

Example 138a
1-Ethyl-4-(6-nitropyridin-3-yl)piperazine 138a

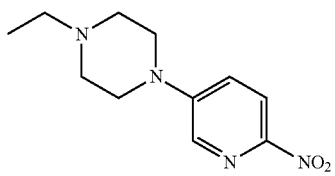 [SMILES: CCN1CCN(c2ccc([N+](=O)[O-])nc2)CC1]

To a sealed tube equipped with a stirring bar, 5-bromo-2-nitropyridine (3.00 g, 14.78 mmol), 1-ethylpiperazine (5.06 g, 44.34 mmol), tetrabutylammonium iodide (273 mmol, 0.739 mmol), $K_2CO_3$ (6.128 g, 44.34 mmol), and DMSO (30 mL) were added. The tube was sealed and heated at 90° C. overnight. Water (200 mL) was added and the precipitation was filtered to afford 138a as a yellow solid, 1.24 g.

Example 138b
5-(4-Ethylpiperazin-1-yl)pyridin-2-amine 138b

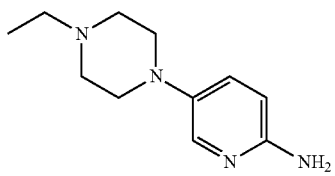

In a hydrogenation bottle, 138a (2.59 g, 10.96 mmol), EtOH (100 mL), 10% Pd/C (580 mg, 0.55 mmol) were added. The mixture was hydrogenated at 55 psi for 2 hrs, and then filtered through celite and washed with MeOH (20 mL). The solvent was removed in vacuo and pink solids were obtained as 138b (2.51 g, 82%).

Example 138c 5-Bromo-3-(5-(4-Ethylpiperazin-1-yl)pyridin-2-ylamino)-1-methylpyridin-2(1H)-one 138c

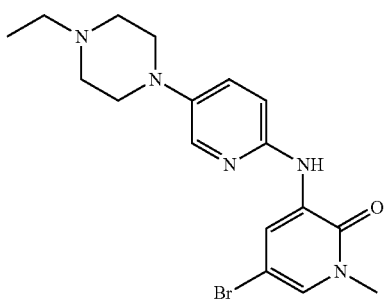 [SMILES: CCN1CCN(c2ccc(Nc3cc(Br)cn(C)c3=O)nc2)CC1]

To a round-bottomed flask equipped with a stirring bar, 138b (2.52 g, 12.22 mmol), 3,5-dibromo-1-methylpyridin-2(1H)-one (4.89 g, 18.32 mmol), $Pd_2(dba)_3$ (1.12 g, 1.22 mmol), XantPhos (1.13 mg, 1.96 mmol), $Cs_2CO_3$ (13.14 g, 40.33 mmol) and dioxane (50 mL) were added. The reaction mixture was heated at 100° C. overnight. $CH_2Cl_2$ (200 mL) was added to the resulting mixture was washed with water (30 mL×3). $CH_2Cl_2$ (200 mL) was added and the resulting mixture was washed with water (30 mL×3), brine (30 mL×1), dried over $MgSO_4$, filtered, and removed solvent in vacuo. $CH_2Cl_2$/ether (1:2, 5 mL) was added followed by sonication, the precipitation was filtered as 138c, a yellow solid, 2.718 g (57%).

Example 138d 2-(5-(5-(4-Ethylpiperazin-1-yl)pyridin-2-ylamino)-1-methyl-6-oxo-1,6-dihydropyridin-3-yl)-6-(1-oxo-3,4,6,7,8,9-hexahydropyrazino[1,2-a]indol-2(1H)-yl)benzyl acetate 138d

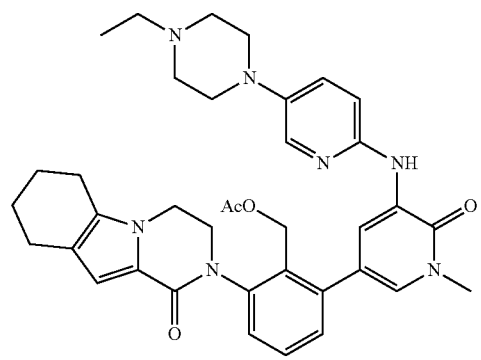 [SMILES: CCN1CCN(c2ccc(Nc3cc(-c4cccc(N5CCn6c(cc7c6CCCC7)C5=O)c4COC(C)=O)cn(C)c3=O)nc2)CC1]

To a microwave tube equipped with a stirring bar, 138c (250 mg, 0.637 mmol), 2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 114a (325.5 mg, 0.701 mmol), $Pd(PPh_3)_4$ (36.8 mg, 0.0319 mmol), $Na_2CO_3$ aqueous solution (1.0 N, 2.10 mL, 2.10 mmol), DME (2.0 mL) were added. The mixture was reacted in microwave at 135° C. for 15 min. $CH_2Cl_2$ (200 mL) was added and the resulting mixture was washed with water (30 mL×3), brine (30 mL×1), dried over $MgSO_4$, filtered, and removed solvent in vacuo. Silica gel column chromatography (MeOH:$CH_2Cl_2$=5:95) gave 2-(5-(5-(4-ethylpiperazin-1-yl)pyridin-2-ylamino)-1-methyl-6-oxo-1,6-dihydropyridin-3-yl)-6-(1-oxo-3,4,6,7,8,9-hexahydropyrazino[1,2-a]indol-2(1H)-yl)benzyl acetate 138d.

To a round-bottomed flask equipped with a stirring bar, 138d, THF (5.0 mL), i-PrOH (5.0 mL), $H_2O$ (5.0 mL), LiOH $H_2O$ (200 mg) were added. The resulting mixture was stirred at RT for 2 hrs. Removed all the solvent in vacuo and the resulting residue was added to $CH_2Cl_2$ (200 mL), the solution was washed with water (30 mL×3), brine (30 mL×1), dried over $MgSO_4$, filtered, and removed solvent in vacuo. Silica gel column chromatography (MeOH: $CH_2Cl_2$=10:90) gave 138 as a gray solid, 60 mg. MS (ESI+) m/z 608.3 (M+H).

Example 139 3-{[4-(3-Hydroxy-3-methylazetidin-1-yl)phenyl]amino}-5-[2-(hydroxymethyl)-3-{1-oxo-1H,2H,3H,4H,6H,7H,8H,9H-pyrazino[1,2-a]indol-2-yl}phenyl]-1-methyl-1,2-dihydropyrazin-2-one 139

Following Example 301, 1-(4-aminophenyl)-3-methyl-azetidin-3-ol was converted to 99 mg of 139 as a white solid. MS (ESI+) m/z 581 (M+H).

Example 140 2-(3-(6-(1-(2-Hydroxyethyl)-1H-pyrazol-4-ylamino)-4-methyl-5-oxo-4,5-dihydropyrazin-2-yl)-2-(hydroxymethyl)phenyl)-3,4,6,7,8,9-hexahydropyrazino[1,2-a]indol-1(2H)-one 140

Example 140a 5-Bromo-3-(1-(2-hydroxyethyl)-1H-pyrazol-4-ylamino)-1-methylpyrazin-2(1H)-one 140a A flask equipped with a magnetic stirrer was charged with 1-(2-(tert-butyldimethylsilyloxy)ethyl)-1H-pyrazol-4-amine 116b (1.7 g, 7.1 mmol), 3,5-dibromo-1-methylpyrazin-2(1H)-one (1.25 g, 4.7 mmol), and IPA (25 mL). The system was evacuated and then refilled with $N_2$. The reaction mixture was heated at 90° C. for 6 h. Then, the mixture was cooled to room temperature and concentrated under reduced pressure. The residue was purified by flash column chromatography eluting with petroleum ether/ethyl acetate to afford 140a (1.7 g, 78%). LCMS: [M+H]$^+$ 314.

Example 140b 2-(6-(1-(2-Hydroxyethyl)-1H-pyrazol-4-ylamino)-4-methyl-5-oxo-4,5-dihydropyrazin-2-yl)-6-(1-oxo-3,4,6,7,8,9-hexahydropyrazino[1,2-a]indol-2(1H)-yl)benzyl acetate 140b A mixture of 140a (595 mg, 1.9 mmol), 2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 114a (882 mg, 1.9 mmol), $CH_3COONa$ (309 mg, 3.8 mmol), $PdCl_2(dppf)$ (153 mg, 0.19 mmol) and $K_3PO_4$ (1 g, 3.8 mmol) suspended in $CH_3CN$ (30 mL) and $H_2O$ (2 mL) was heated at 110° C. for 15 h under argon atmosphere. After reaction $CH_3CN$ was evaporated and the residue was purified by reverse phase Combi-flash eluting with 0.3% $NH_4HCO_3$ in 1:4 water/$CH_3CN$ to give 140b as a brown solid (477 mg, 44%). LCMS: [M+H]$^+$ 572.

A mixture of 140b (410 mg, 0.72 mmol) and LiOH (372 mg, 16 mmol) in $^i$PrOH/THF (1:1, 10 mL) and $H_2O$ (3 mL) was stirred at 30° C. for 2 h. The mixture was evaporated in vacuo and the residue was extracted with EtOAc (10 mL×2). The combined extract was concentrated under reduced pressure and the residue was purified on pre-HPLC to give 140 (200 mg, 54%). LCMS: [M+H]$^+$ 530 $^1$H NMR (500 MHz, CDCl3) δ 7.71 (s, 1H), 7.68 (s, 1H), 7.49 (s, 1H), 7.36 (m, 2H), 7.27 (m, 1H), 6.92 (s, 1H), 6.78 (s, 1H), 5.29 (s, 1H), 4.43 (d, J=12, 1H), 4.21 (m, 4H), 4.04 (m, 2H), 4.01 (m, 3H), 3.63 (s, 3H), 2.55 (dt, J=14.5, 4H), 1.78 (m, 4H).

Example 141 2-(2-(Hydroxymethyl)-3-(1-methyl-5-(5-methyl-4,5,6,7-tetrahydrothiazolo[5,4-c]pyridin-2-ylamino)-6-oxo-1,6-dihydropyridin-3-yl)phenyl)-3,4,6,7,8,9-hexahydropyrazino[1,2-a]indol-1(2H)-one 141

Example 141a 5-Methyl-4,5,6,7-tetrahydrothiazolo[5,4-c]pyridin-2-amine 141a

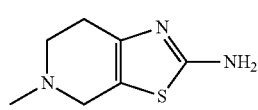

A solution of 1-methyl-4-piperidone (11.3 g, 100 mmol) in 2-propanol (80 mL) was heated to 50° C. To the solution was sequentially added a solution of cyanamide (4.2 g, 100 mmol) in 2-propanol (25 mL) and sulfur powder (3.2 g). After a catalytic amount of pyrrolidine (1.3 mL) was added thereto, the resultant mixture was stirred at or above 50° C. for 2 hours. The reaction mixture was allowed to cool to room temperature, followed by stirring for overnight. The resultant mixture was cooled to or below 10° C. in an ice-water bath, and was stirred for 1 hour at the same temperature. The precipitated crystals were collected by filtration, and washed with 2-propanol (20 mL). The wet crystals were dried under reduced pressure, to give 141a (10 g, 60%). LCMS: [M+H]$^+$ 170 $^1$H NMR (500 MHz, DMSO) δ 6.70 (s, 2H), 3.31 (s, 2H), 2.61 (t, J=5.5, 2H), 2.45 (m, 2H), 2.33 (s, 3H).

Example 141b 5-Bromo-1-methyl-3-(5-methyl-4,5,6,7-tetrahydrothiazolo[5,4-c]pyridin-2-ylamino)pyridin-2(1H)-one 141b

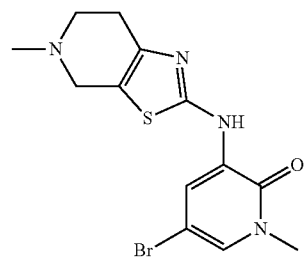

Following Example 110c, 3 g of 141a and 4 g of 3,5-dibromo-1-methylpyridin-2(1H)-one were reacted to give 141b as a yellow solid (2.8 g, 52%). LCMS: [M+H]$^+$ 357

Example 141c 2-(1-Methyl-5-(5-methyl-4,5,6,7-tetrahydrothiazolo[5,4-c]pyridin-2-ylamino)-6-oxo-1,6-dihydropyridin-3-yl)-6-(1-oxo-3,4,6,7,8,9-hexahydropyrazino[1,2-a]indol-2(1H)-yl)benzyl Acetate 141c

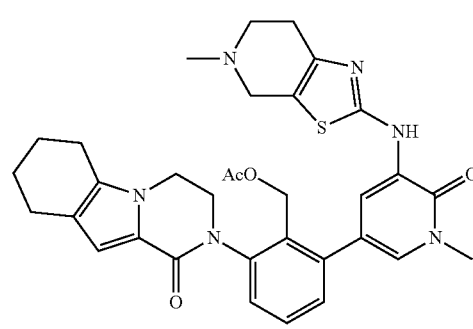

Following Example 147b, 232 mg of 114a and 178 mg of 141b were reacted to give 141c as a yellow solid (240 mg, 80%). LCMS: [M+H]$^+$ 613

Following Example 148, 240 mg of 141c was converted to 141 as a white solid (112 mg, 50%). LCMS: [M+H]$^+$ 571.

Example 142 2-(3-(5-(1,5-Dimethyl-1H-pyrazol-3-ylamino)-1-methyl-6-oxo-1,6-dihydropyridin-3-yl)-2-(hydroxymethyl)phenyl)-3,4,6,7,8,9-hexahydropyrazino[1,2-a]indol-1(2H)-one 142

Example 142a 5-Bromo-3-(1,5-dimethyl-1H-pyrazol-3-ylamino)-1-methylpyridin-2(1H)-one 142a A solution of 5-bromo-1-methyl-3-(5-methyl-1H-pyrazol-3-ylamino)pyridin-2(1H)-one 112a (2.8 g, 9.9 mmol) in anhydrous DMF (10 mL) was treated with 60% dispersion of NaH in mineral oil (0.5 g, 13 mmol) while stirring under nitrogen. After effervescence the reaction was stirred for an additional 30 minutes. At this time the reaction was treated with MeI (0.98 g, 7 mmol) and continued to stir under nitrogen for 2 hours. Water (50 mL) was added slowly and the mixture was filtered and then concentrated. The residue was purified by flash column chromatography eluting with petroleum ether/ethyl acetate to afford 142a (0.7 g, 24%), which was used directly without further purification. LCMS: (M+H)+297.

Example 142b 2-(5-(1,5-Dimethyl-1H-pyrazol-3-ylamino)-1-methyl-6-oxo-1,6-dihydropyridin-3-yl)-6-(1-oxo-3,4,6,7,8,9-hexahydropyrazino[1,2-a]indol-2(1H)-yl)benzyl Acetate 142b A mixture of 142a (510 mg, 1.7 mmol), 2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 114a (882 mg, 1.9 mmol), $CH_3COONa$ (309 mg, 3.8 mmol), $PdCl_2$(dppf) (153 mg, 0.19 mmol), and $K_3PO_4$ (1 g, 3.8 mmol) suspended in $CH_3CN$ (30 mL) and $H_2O$ (2 mL) was heated at 110° C. for 15 h under argon atmosphere. It was then evaporated and the residue was purified by reverse phase Combi-flash eluting with 0.3% $NH_4HCO_3$ 1:4 water/$CH_3CN$ to give 142b as a brown solid (200 mg, 21%). LCMS: [M+H]+ 555.

A mixture of 142b (210 mg, 0.38 mmol) and LiOH (372 mg, 16 mmol) in $^iPrOH$/THF (1:1, 10 mL) and water (3 mL) was stirred at 30° C. for 2 h. The mixture was evaporated in vacuo, and the residue was extracted with EtOAc (10 mL×2). The combined extract was concentrated under reduced pressure and the residue was purified on prep-HPLC to give 142 (95 mg, 50%). LCMS: [M+H]+ 513. $^1$H NMR (500 MHz, CDCl3) δ 7.88 (s, 1H), 7.43 (m, 2H), 7.38 (s, 1H), 7.30 (m, 1H), 7.21 (m, 1H), 6.84 (s, 1H), 5.71 (s, 1H), 4.58 (d, J=11.5, 1H), 4.38 (d, J=11.5, 1H), 4.13 (m, 3H), 3.94 (m, 1H), 3.67 (s, 3H), 3.64 (s, 3H), 2.57 (m, 4H), 2.21 (s, 3H), 1.78 (m, 4H).

Example 143 2-(5-Fluoro-2-(hydroxymethyl)-3-(1-methyl-5-(5-(oxetan-3-yl)-4,5,6,7-tetrahydropyrazolo[1,5-a]pyrazin-2-ylamino)-6-oxo-1,6-dihydropyridin-3-yl)phenyl)-3,4,6,7,8,9-hexahydropyrazino[1,2-a]indol-1(2H)-one 143

Example 143a 1-Methyl-5-(5-(oxetan-3-yl)-4,5,6,7-tetrahydropyrazolo[1,5-a]pyrazin-2-ylamino)-6-oxo-1,6-dihydropyridin-3-ylboronic acid 143a

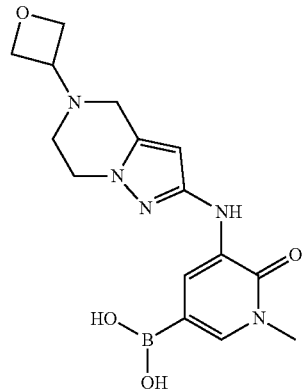

143a

To a solution of 5-bromo-1-methyl-3-(5-(oxetan-3-yl)-4,5,6,7-tetrahydro-pyrazolo[1,5-a]pyrazin-2-ylamino)pyridin-2(1H)-one 252a (1 g, 2.64 mmol), 4,4,4',4',5,5,5',5'-octam- ethyl-2,2'-bi(1,3,2-dioxaborolane) (2 g, 7.92 mmol) in dioxane (40 mL) was added $PdCl_2$(dppf) (215 mg, 0.26 mmol) and $CH_3COOK$ (776 mg, 7.92 mmol). The mixture was stirred at 100° C. for 6 h under argon atmosphere. After reaction the mixture was filtered and evaporated in vacuo. The residue was purified by reverse phase combiflash eluting with 0.3% $NH_4HCO_3$ in 1:3 water/$CH_3CN$ to give 143a as a white solid (300 mg, 33%). MS: (M+H)+ 346.

Example 143b 4-Fluoro-2-(1-methyl-5-(5-(oxetan-3-yl)-4,5,6,7-tetrahydropyrazolo[1,5-a]pyrazin-2-ylamino)-6-oxo-1,6-dihydropyridin-3-yl)-6-(1-oxo-3,4,6,7,8,9-hexahydropyrazino[1,2-a]indol-2(1H)-yl) benzyl Acetate 143b

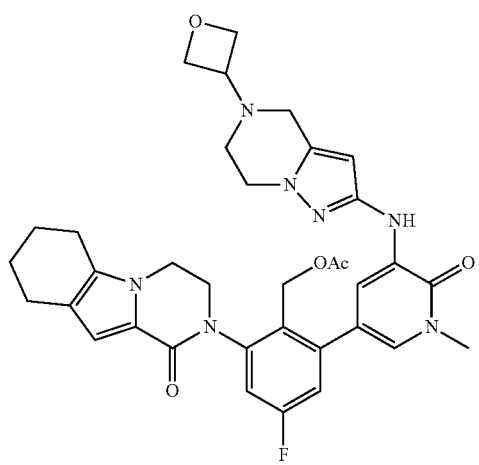

143b

A 25 mL vial was charged with 143a (238 mg, 0.7 mmol), 2-bromo-4-fluoro-6-(1-oxo-3,4,6,7,8,9-hexahydro-pyrazino [1,2-a]indol-2(1H)-yl)benzyl acetate 197d (300 mg, 0.7 mmol), $Na_2CO_3$ (147 mg, 1.4 mmol), $PdCl_2$(dppf) (56 mg, 0.07 mmol) suspended in DME (15 mL), and $H_2O$ (1 mL). The resulting orange mixture was heated for 30 minutes in a Biotage microwave reactor at 130° C. After reaction the residue was purified by reverse phase Combi-flash eluting with 0.3% $NH_4HCO_3$ in 1:7 water/$CH_3CN$ to give 143b as a brown solid (150 mg, 33%). MS: (M+H)+ 656.

To a solution of 4-fluoro-2-(1-methyl-5-(5-(oxetan-3-yl)-4,5,6,7-tetrahydropyrazolo[1,5-a]pyrazin-2-ylamino)-6-oxo-1,6-dihydropyridin-3-yl)-6-(1-oxo-3,4,6,7,8,9-hexa- hydro-pyrazino[1,2-a]indol-2(1H)-yl)benzyl acetate 143b (120 mg, 0.18 mmol) in propan-2-ol (5 mL), tetrahydrofuran (5 mL) and water (1.5 mL) was added LiOH (440 mg, 18 mmol). The mixture was stirred at 30° C. for 2 h. The reaction mixture was then evaporated and the residue was purified by prep-HPLC to afford 143 as a yellow solid (50 mg, 45%). MS: (M+H)+ 614. $^1$H NMR (500 MHz, MeOD) δ 1.79 (s, 2H), 1.90 (s, 2H), 2.54-2.56 (t, J=6.5 Hz, 2H), 2.63-2.67 (m, 2H), 2.86-2.88 (t, J=6 Hz, 2H), 3.59 (s, 2H), 3.70 (s, 3H), 3.76-3.79 (m, 1H), 4.00-4.07 (m, 3H), 4.21 (s, 3H), 4.48-4.53 (m, 2H), 4.64-4.67 (t, J=6.5 Hz, 2H), 4.75-4.78 (t, J=7 Hz, 2H), 5.90 (s, 1H), 6.72 (s, 1H), 7.20-7.27 (m, 3H), 7.91-7.92 (d, 1H).

Example 144 5-[5-Fluoro-2-(hydroxymethyl)-3-[1-methyl-5-(5-cyclopropyl-4,5,6,7-tetrahydropyrazolo[1,5-a]pyrazin-2-ylamino)-6-oxopyridin-3-yl]phenyl]-8-thia-5-azatricyclo[7.4.0.0$^{2,7}$]trideca-1(9),2(7)-dien-6-one 144

Example 144a 3-(5-Cyclopropyl-4,5,6,7-tetrahydropyrazolo[1,5-a]pyrazin-2-ylamino)-1-methyl-5-(4,4,5,5-tetramethyl-1,3,2-dioxaborolan-2-yl)pyridin-2(1H)-one 144a

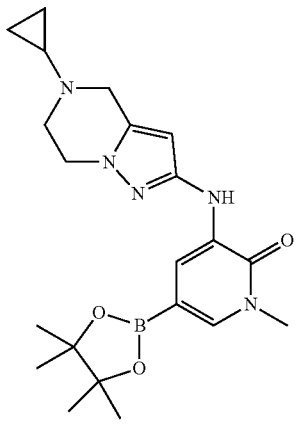 [SMILES: Cn1cc(B2OC(C)(C)C(C)(C)O2)cc(Nc2cc3n(n2)CCN(C2CC2)C3)c1=O]

A mixture of 5-bromo-3-(5-cyclopropyl-4,5,6,7-tetrahydropyrazolo[1,5-a]-pyrazin-2-ylamino)-1-methylpyridin-2(1H)-one 135c (0.9 g, 2.48 mmol), bis(pinacolato)diboron (1.26 g, 4.96 mmol), PdCl$_2$(dppf) (272 mg, 0.37 mmol) and KOAc (486 mg, 4.96 mmol) in 1,4-dioxane (40 mL) was heated at reflux for 15 h. After the completion of the reaction, the mixture was filtered off, and washed with ethyl acetate (100 mL). The filtrate was evaporated in vacuo and the residue was purified on silica gel column to give 144a (407 mg, 40%). MS: [M+H]$^+$ 412.

Example 144b 5-[5-Fluoro-3-[1-methyl-5-(5-cyclopropyl-4,5,6,7-tetrahydropyrazolo[1,5-a]pyrazin-2-ylamino)-6-oxopyridin-3-yl]benzylacetate]-8-thia-5-azatricyclo[7.4.0.0$^{2,7}$]trideca-1(9),2(7)-dien-6-one 144b

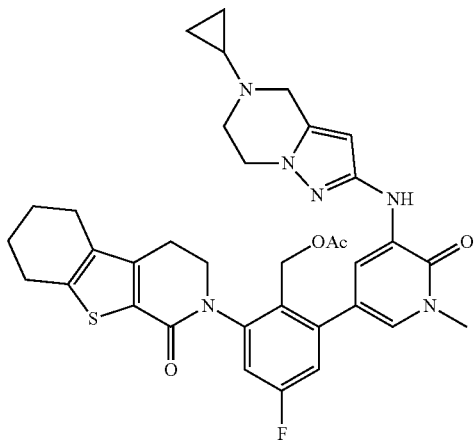 [SMILES: CC(=O)OCc1c(-c2cc(Nc3cc4n(n3)CCN(C3CC3)C4)c(=O)n(C)c2)cc(F)cc1N1CCc2c(sc3c2CCCC3)C1=O]

A mixture of 144a (300 mg, 0.73 mmol), (2-bromo-4-fluoro-6-{6-oxo-8-thia-5-azatricyclo-[7.4.0.0$^{2,7}$]trideca-1(9),2(7)-dien-5-yl}phenyl)methyl acetate (212a) (297 mg, 0.66 mmol), PdCl$_2$(dppf) (73 mg, 0.1 mmol), and 2M Na$_2$CO$_3$ solution (2 mL) in DME (8 mL) was heated at 120° C. under microwave irradiation for 0.5 h. The solvent was evaporated in vacuo and the residue was purified on reverse phase Combi-flash to give 144b (173 mg, 40%). MS: [M+H]$^+$ 657.

A mixture of 144b (170 mg, 0.26 mmol) and LiOH hydrate (104 mg, 2.6 mmol) in $^i$PrOH (15 mL) and H$_2$O (3 mL) was stirred at 30° C. for 2 h. The mixture was evaporated in vacuo and the residue was extracted with EtOAc (20 mL×2). The combined extracts were concentrated under reduced pressure. The residue was purified on prep-HPLC to give 144 (50 mg, 31%). MS: [M+H]$^+$ 615. $^1$H NMR (500 MHz, MEOD) δ 7.89 (d, J=2.0, 1H), 7.26 (d, J=2.0, 1H), 7.22-7.18 (m, 2H), 5.89 (s, 1H), 4.52-4.46 (m, 2H), 4.17-4.11 (m, 1H), 4.02-3.97 (m, 3H), 3.82 (s, 2H), 3.69 (s, 3H), 3.16-3.14 (m, 2H), 3.10-3.03 (m, 1H), 2.96-2.90 (m, 1H), 2.87-2.85 (m, 2H), 2.65-2.53 (m, 2H), 1.97-1.85 (m, 5H), 0.62-0.58 (m, 2H), 0.53-0.50 (m, 2H)

Example 145 2-(2-(Hydroxymethyl)-3-(4-methyl-5-oxo-6-(4-(piperidin-4-yl)phenyl-amino)-4,5-dihydropyrazin-2-yl)phenyl)-3,4,6,7,8,9-hexahydropyrazino[1,2-a]indol-1(2H)-one 145

Example 145a tert-Butyl 4-(4-(6-bromo-4-methyl-3-oxo-3,4-dihydropyrazin-2-ylamino)phenyl)-piperidine-1-carboxylate 145a

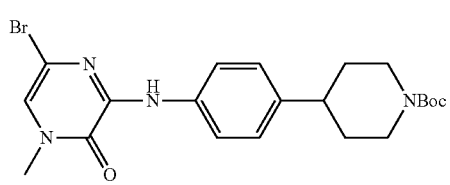

Compound 145a was synthesized using the same procedure as Example 112a, except using tert-butyl 4-(4-aminophenyl)piperidine-1-carboxylate (0.83 g, 3.0 mmol), 3,5-dibromo-1-methylpyrazin-2(1H)-one (0.88 g, 3.3 mmol), cesium carbonate (1.27 g, 3.9 mmol), tris(dibenzylideneacetone)dipalladium(0) (0.275 g, 0.3 mmol), Xantphos (0.26 g, 0.45 mmol) and 1,4-dioxane (30 mL). The reaction mixture was heated at 100° C. overnight. Work-up and purified by flash column chromatography (silica, ethyl acetate/hexanes) to give a 80% yield (1.1 g) of tert-butyl 4-(4-(6-bromo-4-methyl-3-oxo-3,4-dihydropyrazin-2-ylamino)phenyl)-piperidine-1-carboxylate 145a as a solid: MS (ESI+) m/z 465.0 (M+H).

Example 145b

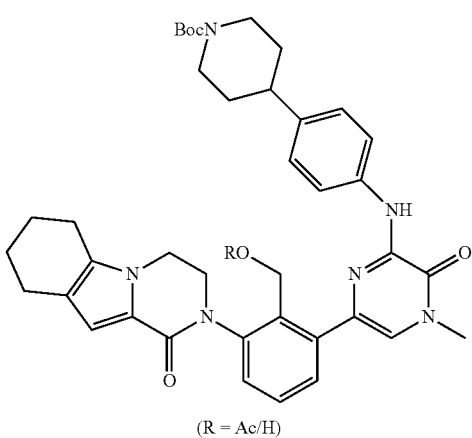

(R = Ac/H)

The compound mixture 145b was synthesized using the same procedure as Example 121b, except using 2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 114a (162 mg, 0.35 mmol), tert-butyl 4-(4-(6-bromo-4-methyl-3-oxo-3,4-dihydropyrazin-2-ylamino)phenyl)-piperidine-1-carboxylate 145a (135 mg, 0.3 mmol), 1M sodium carbonate solution (1.2 mL, 1.2 mmol), tetrakis(triphenylphosphine)palladium(0) (18 mg, 0.015 mmol) and 1,2-dimethoxyethane (3 mL). Work-up and flash column chromatography (silica, ethyl acetate/hexanes) afford 145b (120 mg) as yellow oil.

Example 145c

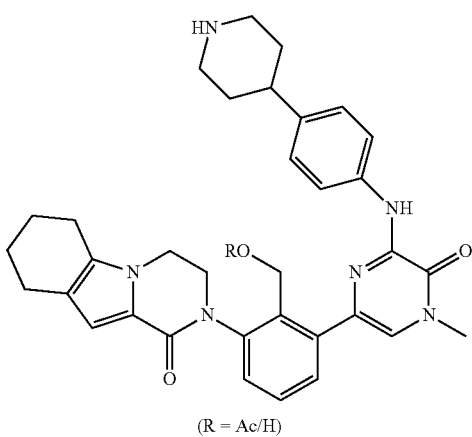

(R = Ac/H)

The compound mixture was synthesized using the same procedure as Example 121c, except using 145b (120 mg), Trifluoroacetic acid (0.5 mL, 6.5 mmol) in methylene chloride (7 mL). Workup and concentrated to dryness to gave compound 145c as yellow oil, which was used without purification in the next step.

Compound 145 was synthesized using the same procedure as for Example 121, except using a mixture of THF (1 mL), water (0.5 mL) and isopropanol (1 mL), compound 145c and lithium hydroxide monohydrate (50 mg, 1.30 mmol). Workup and flash column chromatography (silica, methylene chloride/20% TEA in methanol) give a yellow solid (68 mg), which was flushed out from a basic aluminum column (ethyl acetate) again to afford a 15% yield (3 steps, 25 mg) of 145 as a white solid: MS (ESI+) m/z 579.4 (M+H).

Example 146 2-(2-(Hydroxymethyl)-3-(1-methyl-5-(5-methyl-4,5,6,7-tetrahydropyrazolo[1,5-a]pyrazin-2-ylamino)-6-oxo-1,6-dihydropyridin-3-yl)phenyl)-3,4,6,7,8,9-hexahydropyrazino[1,2-a]indol-1(2H)-one 146

Example 146a 5-Bromo-1-methyl-3-(5-methyl-4,5,6,7-tetrahydropyrazolo[1,5-a]pyrazin-2-ylamino)pyridin-2(1H)-one 146a

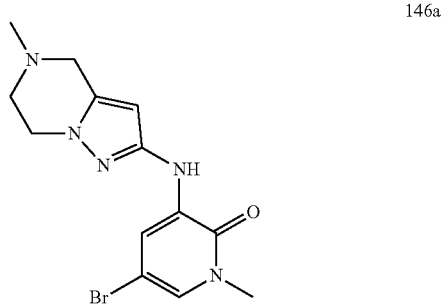 [SMILES: CN1CCn2nc(Nc3cc(Br)cn(C)c3=O)cc2C1]

A suspension of 5-methyl-4,5,6,7-tetrahydropyrazolo[1,5-a]pyrazin-2-amine 101e (1 g, 6.6 mmol), 3,5-dibromo-1-methylpyridin-2(1H)-one (1.7 g, 6.6 mmol), XantPhos (380 mg, 0.66 mmol), $Pd_2(dba)_3$ (602 mg, 0.66 mmol) and $Cs_2CO_3$ (4 g, 13.2 mmol) in dioxane (30 mL) was heated in a sealed tube at 120° C. for 2 h under nitrogen. After reaction the solvent was filtered and the filtrate was evaporated in vacuo to give a yellow solid. The yellow solid was washed with EtOAc (10 mL×3) to give 146a as a yellow solid (1 g, 45%), which was used without further purification. MS: (M+H)$^+$ 338.

Example 146b 2-(1-Methyl-5-(5-methyl-4,5,6,7-tetrahydropyrazolo[1,5-a]pyrazin-2-ylamino)-6-oxo-1,6-dihydropyridin-3-yl)-6-(1-oxo-3,4,6,7,8,9-hexahydropyrazino[1,2-a]indol-2(1H)-yl)benzyl Acetate 146b

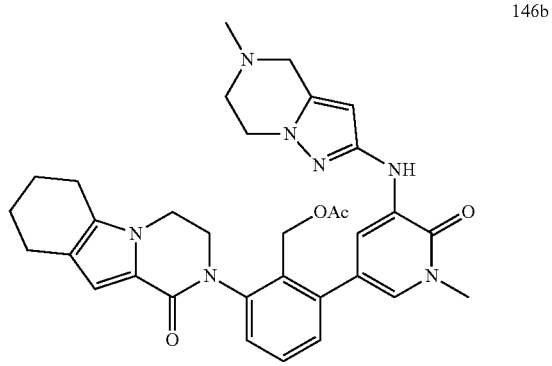 [SMILES: CC(=O)OCc1c(-c2cc(Nc3cc4n(n3)CCN(C)C4)c(=O)n(C)c2)cccc1N1CCn2c(cc3c2CCCC3)C1=O]

A 25 mL vial was charged with 5-bromo-1-methyl-3-(5-methyl-4,5,6,7-tetrahydropyrazolo[1,5-a]pyrazin-2-ylamino)pyridin-2(1H)-one 145a (500 mg, 1.48 mmol), 2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 114a (664 mg, 1.48 mmol), CH₃COONa (243 mg, 2.96 mmol), PdCl₂(dppf) (121 mg, 0.148 mmol), and K₃PO₄ (790 mg, 2.96 mmol) suspended in CH₃CN (50 mL) and H₂O (3 mL). It was then heated at 110° C. for 12 h under argon atmosphere. After reaction the mixture was evaporated and the residue was purified by reverse phase Combi-flash eluting with 0.3% NH₄HCO₃ in 1:5 water/CH₃CN to give 146b as a brown solid (200 mg, 23%). MS: (M+H)⁺ 596.

To a solution of 2-(1-methyl-5-(5-methyl-4,5,6,7-tetrahydropyrazolo[1,5-a]pyrazin-2-ylamino)-6-oxo-1,6-dihydropyridin-3-yl)-6-(1-oxo-3,4,6,7,8,9-hexa-hydropyrazino[1,2-a]indol-2(1H)-yl)benzyl acetate 146b (180 mg, 0.3 mmol) in propan-2-ol (9 mL), tetrahydrofuran (9 mL), and water (3 mL) was added LiOH (726 mg, 30 mmol). The mixture was stirred at 30° C. for 2 h. After reaction the mixture was evaporated and the residue was purified by prep-HPLC to afford 146 as a white solid (67 mg, 41%). MS: (M+H)⁺ 554. ¹H NMR (500 MHz, MeOD) δ 1.80 (s, 2H), 1.90 (s, 2H), 2.49 (s, 3H), 2.54-2.57 (t, 2H), 2.63-2.67 (m, 2H), 2.93-2.96 (t, J=5.5 Hz, 2H), 3.64 (s, 2H), 3.70 (s, 3H), 4.02-4.06 (m, 3H), 4.18-4.23 (m, 3H), 4.49-4.57 (m, 2H), 5.89 (s, 1H), 6.72 (s, 1H), 7.23 (s, 1H), 7.36-7.38 (d, 1H), 7.41-7.42 (d, 1H), 7.49-7.52 (t, 1H), 7.1 (s, 1H).

Example 147 2-(3-(5-(6,7-Dihydro-4H-pyrazolo[5,1-c][1,4]oxazin-2-ylamino)-1-methyl-6-oxo-1,6-dihydropyridazin-3-yl)-2-(hydroxymethyl)phenyl)-3,4,6,7,8,9-hexahydropyrazino[1,2-a]indol-1(2H)-one 147

Example 147a 6-Chloro-4-(6,7-dihydro-4H-pyrazolo[5,1-c][1,4]oxazin-2-ylamino)-2-methylpyridazin-3(2H)-one 147a

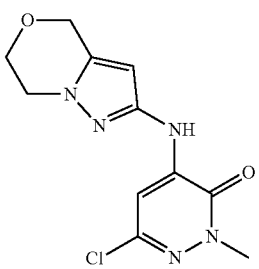 [SMILES: Cn1nc(Cl)cc(Nc2cc3n(n2)CCOC3)c1=O]

A mixture of 6,7-dihydro-4H-pyrazolo[5,1-c][1,4]oxazin-2-amine 110b (0.8 g, 5.76 mmol), xantophos (360 mg, 0.623 mmol), Pd₂dba₃ (384 mg, 0.42 mmol), 4-bromo-6-chloro-2-methylpyridazin-3(2H)-one 103e (1.28 g, 5.76 mmol) and Cs₂CO₃ (5.05 g. 17.3 mmol) in 1,4-dioxane (40 mL) was heated at reflux for 2 h. After the completion of the reaction, the mixture was filtered off, and washed with MeOH (60 mL). The filtrate was evaporated in vacuo. The residue was purified on reverse phase Combi-flash to give 147a (1.3 g, 81%). MS: [M+H]⁺ 282.

Example 147b 2-(5-(6,7-Dihydro-4H-pyrazolo[5,1-c][1,4]oxazin-2-ylamino)-1-methyl-6-oxo-1,6-dihydropyridazin-3-yl)-6-(1-oxo-3,4,6,7,8,9-hexahydropyrazino[1,2-a]indol-2(1H)-yl)benzyl Acetate 147b

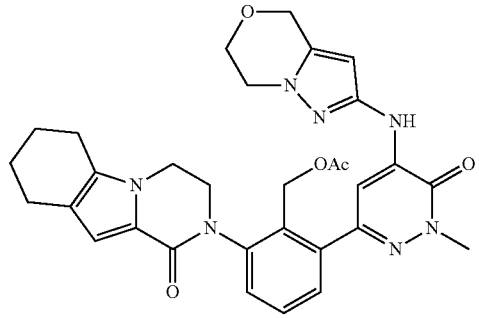 [SMILES: CC(=O)OCc1c(-c2cc(Nc3cc4n(n3)CCOC4)c(=O)n(C)n2)cccc1N1CCn2c(cc3c2CCCC3)C1=O]

A mixture of 6-chloro-4-(6,7-dihydro-4H-pyrazolo[5,1-c][1,4]oxazin-2-ylamino)-2-methylpyridazin-3(2H)-one 147a (400 mg, 1.42 mmol), 2-(1-oxo-3,4,6,7,8,9-hexa-hydropyrazino[1,2-a]indol-2(1H)-yl)-6-(4,4,5,5-tetramethyl-1,3,2-dioxaborolan-2-yl)-benzyl acetate 114a (660 mg, 1.42 mmol), PdCl₂(dppf) (155 mg, 0.21 mmol), K₃PO₄ (150 mg), and NaOAc (50 mg) in MeCN (20 mL) and H₂O (4 mL) was heated at 110° C. in sealed tube for 2 h. The solvent was evaporated in vacuo and the residue was purified on reverse phase Combi-flash to give 147b (273 mg, 33%). MS: [M+H]⁺ 584.

A mixture of 2-(5-(6,7-dihydro-4H-pyrazolo[5,1-c][1,4]oxazin-2-ylamino)-1-methyl-6-oxo-1,6-dihydropyridazin-3-yl)-6-(1-oxo-3,4,6,7,8,9-hexahydropyrazino[1,2-a]indol-2(1H)-yl)benzyl acetate 147b (410 mg, 0.7 mmol) and LiOH hydrate (590 mg, 14 mmol) in ⁱPrOH (20 mL) and H₂O (4 mL) was stirred at 30° C. for 2 h. The mixture was evaporated in vacuo and the residue was extracted with ethyl acetate (20 mL×2). The combined extracts were concentrated under reduced pressure. The residue was purified on prep-HPLC to give 147 (120 mg, 32%). MS: [M+H]⁺ 542. ¹H NMR (500 MHz, DMSO) δ 9.30 (s, 1H), 7.90 (s, 1H), 7.49-7.46 (m, 1H), 7.41-7.37 (m, 2H), 6.51 (s, 1H), 6.04 (s, 1H), 4.74 (s, 2H), 4.62-4.60 (m, 1H), 4.48-4.45 (m, 1H), 4.39-4.35 (m, 1H), 4.18-4.06 (m, 3H), 4.04-3.95 (m, 4H), 3.90-3.85 (m, 1H), 3.75 (s, 3H), 2.60-2.56 (m, 2H), 2.51-2.45 (m, 2H), 1.82-1.74 (m, 2H), 1.73-1.64 (m, 2H).

Example 148 2-(3-(5-(5-Fluoropyridin-2-ylamino)-1-methyl-6-oxo-1,6-dihydropyridin-3-yl)-2-(hydroxymethyl)phenyl)-3,4,6,7,8,9-hexahydropyrazino[1,2-a]indol-1(2H)-one 148

Example 148a 5-Bromo-3-(5-fluoropyridin-2-ylamino)-1-methylpyridin-2(1H)-one 148a

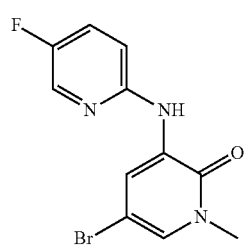

A 100-mL single-neck round-bottomed flask equipped with a magnetic stirrer and reflux condenser was charged with 1,4-dioxane (50 mL), 5-fluoropyridin-2-amine (0.67 g, 6 mmol), 3,5-dibromo-1-methylpyridin-2(1H)-one (1.34 g, 5 mmol) and cesium carbonate (4.89 g, 15 mmol). After bubbling nitrogen through the resulting solution for 30 minutes, XantPhos (576 mg, 1 mmol) and tris(dibenzylideneacetone)dipalladium(0) (460 mg, 0.5 mmol) were added, and the reaction mixture was heated at reflux for 15 h. After this time the reaction was cooled to room temperature, partitioned between ethyl acetate (100 mL) and water (100 mL) and filtered. The aqueous layer was separated and extracted with ethyl acetate (50 mL×2). The organic layers were combined and washed with brine (50 mL) and dried over sodium sulfate. The drying agent was removed by filtration and the filtrate was concentrated under reduced pressure. The residue was washed with acetonitrile (30 mL) and filtered to afford 148a (900 mg, 61%). MS: [M+H]+ 298.

Example 148b 2-(5-(5-Fluoropyridin-2-ylamino)-1-methyl-6-oxo-1,6-dihydropyridin-3-yl)-6-(1-oxo-3,4,6,7,8,9-hexahydropyrazino[1,2-a]indol-2(1H)-yl)benzyl Acetate 148b

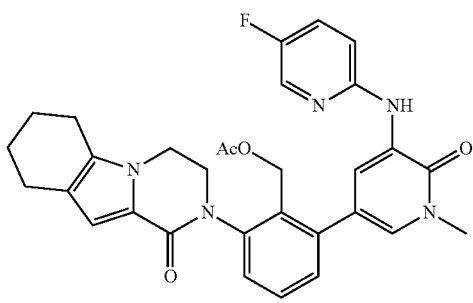

A sealed tube was charged with the mixture of 2-(1-oxo-3,4,6,7,8,9-hexa-hydropyrazino[1,2-a]indol-2(1H)-yl)-6-(4,4,5,5-tetramethyl-1,3,2-dioxaborolan-2-yl)benzyl acetate 114a (232 mg, 0.5 mmol), 148a (148 mg, 0.50 mmol), Pd(dppf)Cl₂ (25 mg, 0.03 mmol), K₃PO₄·3H₂O (266 mg, 1.0 mmol), and NaOAc (82 mg, 1.0 mmol) in CH₃CN (18 mL). The system was evacuated and refilled with N₂. The reaction mixture was heated at 110° C. for 2 h. It was then cooled to room temperature and filtered. The filtrate was concentrated under reduced pressure and the resulting residue was purified by flash column chromatography eluting with 30:1 DCM/MeOH to afford 148b as a yellow solid (200 mg, 72%). MS: [M+H]+ 556.

At room temperature, to the solution of 148b (200 mg, 0.36 mmol) in THF/iPA/H₂O (6 mL/6 mL/2 mL) was added LiOH (87 mg, 3.6 mmol) while stirring. This mixture was stirred for 0.5 h. Then, 20 mL H₂O was added and extracted with ethyl acetate (30 mL×3). The combined organic layer was dried with Na₂SO₄ and concentrated to get a yellow solid, which was further purified by prep-HPLC to afford 148 as a white solid (110 mg, 59%). LCMS: [M+H]+ 514. ¹H NMR (500 MHz, DMSO) δ 8.77 (s, 1H), 8.62 (d, J=2.0, 1H), 8.16 (d, J=2.5, 1H), 7.59 (m, 1H), 7.47 (t, J=7.5, 1H), 7.39-7.14 (m, 2H), 7.34 (m, 2H), 6.52 (s, 1H), 4.85 (s, 1H), 4.35 (d, J=4.0, 2H), 4.17 (m, 2H), 4.10 (m, 1H), 3.90 (m, 1H), 3.61 (s, 3H), 2.60 (m, 2H), 2.48 (m, 2H), 1.80 (t, J=5.5, 2H), 1.70 (m, 2H).

Example 149 2-(3-(5-(6,7-Dihydro-4H-pyrazolo[5,1-c][1,4]oxazin-2-ylamino)-1-methyl-6-oxo-1,6-dihydropyridin-3-yl)-5-fluoro-2-(hydroxymethyl)phenyl)-3,4,6,7,8,9-hexahydropyrazino[1,2-a]indol-1(2H)-one 149

Example 149a 2-(5-(6,7-Dihydro-4H-pyrazolo[5,1-c][1,4]oxazin-2-ylamino)-1-methyl-6-oxo-1,6-dihydropyridin-3-yl)-4-fluoro-6-(1-oxo-3,4,6,7,8,9-hexahydropyrazino[1,2-a]indol-2(1H)-yl)benzyl Acetate 149a

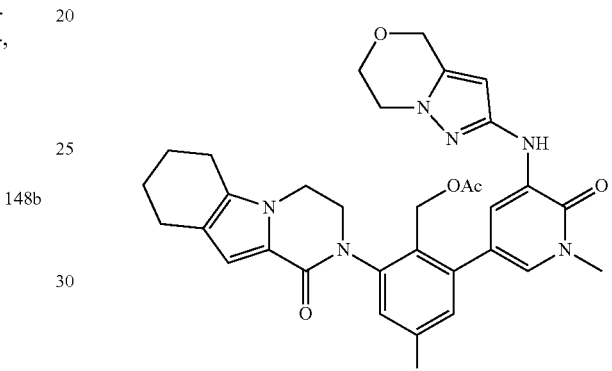

A mixture of 2-(acetoxymethyl)-5-fluoro-3-(1-oxo-3,4,6,7,8,9-hexahydro-pyrazino[1,2-a]indol-2(1H)-yl)phenylboronic acid 210d (150 mg, 0.38 mmol), 5-bromo-3-(6,7-dihydro-4H-pyrazolo[5,1-c][1,4]oxazin-2-ylamino)-1-methylpyridin-2(1H)-one 110c (122 mg, 0.38 mmol), PdCl₂(dppf) (41 mg, 0.056 mmol), K₃PO₄ (100 mg), and NaOAc (50 mg) in MeCN (10 mL) and H₂O (3 mL) was heated at 110° C. in a sealed tube for 2 h. The solvent was evaporated in vacuo and the residue was purified on reverse phase Combi-flash to give 149a (120 mg, 53%). MS: [M+H]+ 601.

A mixture of 149a (120 mg, 0.2 mmol) and LiOH hydrate (84 mg, 2 mmol) in ⁱPrOH (10 mL) and H₂O (3 mL) was stirred at 30° C. for 2 h. The mixture was evaporated in vacuo and the residue was extracted with ethyl acetate (10 mL×2). The combined extracts were concentrated under reduced pressure and the residue was purified on prep-HPLC to give 149 (60 mg, 54%). MS: [M+H]+ 559. ¹H NMR (500 MHz, MeOD) δ 7.82 (s, 1H), 7.16 (s, 1H), 7.10 (d, J=9.0, 2H), 6.62 (s, 1H), 5.77 (s, 1H), 4.67 (s, 2H), 4.43-4.35 (m, 2H), 4.11-4.07 (m, 3H), 4.00-3.99 (m, 2H), 3.93-3.90 (m, 3H), 3.60 (s, 3H), 2.55-2.52 (m, 2H), 2.46-2.43 (m, 2H), 1.82-1.78 (m, 2H), 1.71-1.67 (m, 2H).

Example 150 5-[5-Fluoro-2-(hydroxymethyl)-3-(1-methyl-6-oxo-5-{4H,6H,7H-pyrazolo[3,2-c][1,4]oxazin-2-ylamino}pyridin-3-yl)phenyl]-8-thia-5-azatricyclo-[7.4.0.0²,⁷]trideca-1(9),2(7)-dien-6-one 150

Example 150a 3-(6,7-Dihydro-4H-pyrazolo[5,1-c][1,4]oxazin-2-ylamino)-1-methyl-5-(4,4,5,5-tetramethyl-1,3,2-dioxaborolan-2-yl)pyridin-2(1H)-one 150a

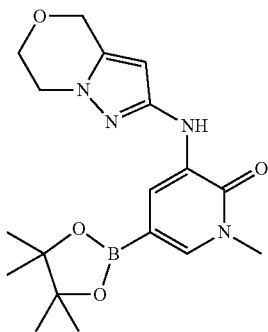 [SMILES: Cn1cc(B2OC(C)(C)C(C)(C)O2)cc(Nc2cc3n(n2)CCOC3)c1=O]

A mixture of 5-bromo-3-(6,7-dihydro-4H-pyrazolo[5,1-c][1,4]oxazin-2-ylamino)-1-methylpyridin-2(1H)-one 110c (1.3 g, 4.0 mmol), bis(pinacolato)diboron (2.03 g, 8 mmol), PdCl$_2$(dppf) (439 mg, 0.6 mmol) and KOAc (784 mg, 8.0 mmol) in 1,4-dioxane (60 mL) was heated at reflux for 15 h. After the completion of the reaction, the mixture was filtered off and washed with EtOAc (100 mL). The filtrate was evaporated in vacuo and the residue was purified on silica gel column to give 150a (446 mg, 30%). MS: [M+H]$^+$ 373.

Example 150b [4-Fluoro-2-(1-methyl-6-oxo-5-{4H,6H,7H-pyrazolo[3,2-c][1,4]oxazin-2-ylamino}pyridin-3-yl)-6-{6-oxo-8-thia-5-azatricyclo[7.4.0.0²,⁷]trideca-1(9),2(7)-dien-5-yl}phenyl]methyl Acetate 150b

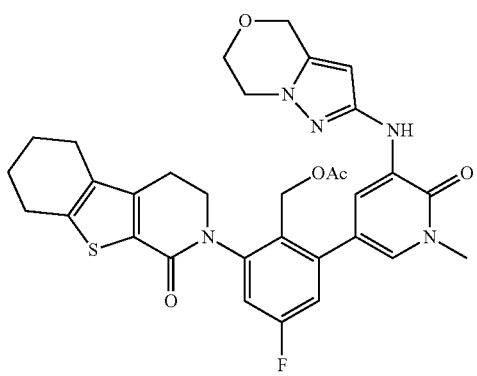 [SMILES: CC(=O)OCc1c(-c2cc(Nc3cc4n(n3)CCOC4)c(=O)n(C)c2)cc(F)cc1N1CCc2c(sc3c2CCCC3)C1=O]

A mixture of 150a (260 mg, 0.70 mmol), (2-bromo-4-fluoro-6-{6-oxo-8-thia-5-azatricyclo[7.4.0.0²,⁷]trideca-1(9),2(7)-dien-5-yl}phenyl)methyl acetate 218a (225 mg, 0.50 mmol), PdCl$_2$(dppf) (55 mg, 0.075 mmol), 2 M Na$_2$CO$_3$ solution (1.5 mL) in DME (8 mL) was heated at 120° C. under microwave irradiation for 0.5 h. The solvent was evaporated in vacuo and the residue was purified on reverse phase Combi-flash to give 150b (154 mg, 50%). MS: [M+H]$^+$ 618.

A mixture of 150b (150 mg, 0.24 mmol) and LiOH hydrate (96 mg, 2.4 mmol) in $^i$PrOH (15 mL) and H$_2$O (3 mL) was stirred at 30° C. for 2 h. The mixture was evaporated in vacuo and the residue was extracted with ethyl acetate (20 mL×2). The combined extracts were concentrated under reduced pressure. The residue was purified on prep-HPLC to give 150 (70 mg, 51%). MS: [M+H]$^+$ 576. $^1$H NMR (500 MHz, DMSO) δ 8.22 (s, 1H), 8.00 (s, 1H), 7.32-7.29 (m, 2H), 7.17-7.15 (m, 1H), 5.93 (s, 1H), 4.86-4.85 (m, 1H), 4.71 (s, 2H), 4.36-4.28 (m, 2H), 4.10-3.84 (m, 7H), 3.57 (s, 3H), 3.02-2.92 (m, 1H), 2.90-2.76 (m, 3H), 1.86-1.74 (m, 4H).

Example 151 2-(3-(5-(5-(Azetidin-3-yl)pyridin-2-ylamino)-1-methyl-6-oxo-1,6-dihydropyridin-3-yl)-2-(hydroxymethyl)phenyl)-3,4,6,7,8,9-hexahydropyrazino[1,2-a]indol-1(2H)-one 151

Example 151a 2-(5-(5-(Azetidin-3-yl)pyridin-2-ylamino)-1-methyl-6-oxo-1,6-dihydropyridin-3-yl)-6-(1-oxo-3,4,6,7,8,9-hexahydropyrazino[1,2-a]indol-2(1H)-yl)benzyl Acetate 151a In a 44-mL sealed tube equipped with a magnetic stirring bar were placed 3-(5-(azetidin-3-yl)pyridin-2-ylamino)-5-bromo-1-methylpyridin-2(1H)-one 155n (60 mg, 0.18 mmol), 2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 114a (110 mg, 0.23 mmol), Pd(PPh$_3$)$_4$ (21 mg, 0.0.18 mmol) in 2 N Na$_2$CO$_3$ (3 mL), DME (2 mL), and dioxane (3 mL). After the reaction mixture was stirred at 100° C. for 14 h., it was partitioned between dichloromethane (5 mL) and water (5 mL), and the organic phase was extracted with dichloromethane (5 mL×3). The combined organic phases were washed with water (5 mL×2) and brine (5 mL×1), dried (Na$_2$SO$_4$), and concentrated. The crude product was purified by flash chromatography (dichloromethane:MeOH, 85:15) to give 40% (40 mg) of 2-(5-(5-(azetidin-3-yl)pyridin-2-ylamino)-1-methyl-6-oxo-1,6-dihydropyridin-3-yl)-6-(1-oxo-3,4,6,7,8,9-hexahydropyrazino[1,2-a]indol-2(1H)-yl)benzyl acetate 151a as a solid.

A 25-mL, single-necked, round-bottomed flask equipped with a magnetic stirring bar was charged with 151a (40 mg, 0.068 mmol), LiOH.H$_2$O (20 mg, 0.48 mmol), THF (2 mL), i-PrOH (2 mL), and water (2 mL). After the reaction mixture was stirred at room temperature for 3 h, it was partitioned between dichloromethane (5 mL) and water (5 mL), and the organic phase was extracted with dichloromethane (5 mL×3). The combined organic phases were washed with water (5 mL×2) and brine (5 mL×1), dried (Na$_2$SO$_4$), and concentrated. The crude product was re-dissolved in dichloromethane (3 mL). To this solution was added hexane (10 mL) and the resulting precipitates were filtered to give 88% yield (33 mg) of 151; MS(ESI$^+$) m/z 551.3 (M+H).

Example 152 2-(2-(Hydroxymethyl)-3-(1-methyl-6-oxo-5-(pyrimidin-4-ylamino)-1,6-dihydropyridin-3-yl)phenyl)-3,4,6,7,8,9-hexahydropyrazino[1,2-a]benzoimidazole-1-one 152

Example 152a N-(2-Hydroxyethyl)-1H-benzo[d]imidazole-2-carboxamide 152a

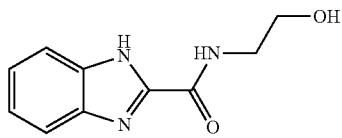

152a

A 100-mL single-neck round-bottomed flask equipped with a magnetic stirrer and reflux condenser was purged with nitrogen and charged with 1H-benzo[d]imidazole-2-carboxylic acid (1.50 g, 9.26 mmol) and thionyl chloride (10 mL). After heating at reflux for 16 h, the suspension was cooled to room temperature and filtered. The filter cake was washed with toluene (10 mL) and dried under vacuum at room temperature for 5 h. The resulting solid was charged into a 100-mL single-neck round-bottomed flask equipped with a magnetic stirrer and reflux condenser, followed by chloroform (10 mL) and 2-hydroxyethylamine (559 mg, 9.17 mmol). After stirring at reflux for 16 h, the reaction mixture was concentrated under reduced pressure, and the resulting residue was triturated with water (20 mL) and dried in a vacuum oven at 45° C. to afford a 73% yield (1.41 g) of 152a as a white solid: mp 194-195° C.; $^1$H NMR (500 MHz, DMSO-$d_6$) δ 13.13 (s, 1H), 8.74 (s, 1H), 7.71-7.29 (m, 4H), 4.80 (s, 1H), 3.55 (dd, 2H, J=10.5, 5.5 Hz), 3.38 (dd, 2H, J=10.5, 5.5 Hz); MS (APCI+) m/z 206.6 (M+H).

Example 152b 3,4-Dihydropyrazino[1,2-a]benzoimidazole-1-one 152b

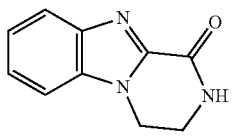

152b

A 100-mL single-neck round-bottomed flask equipped with a magnetic stirrer and reflux condenser was purged with nitrogen and charged with 152a (1.41 g, 6.84 mmol) and DMF (10 mL), and the reaction mixture was cooled to 0° C. A solution of thionyl chloride (896 mg, 7.53 mmol) in DMF (5 mL) was added dropwise. The reaction was heated at 150° C. for 2 h. After this time, the solvent was removed under reduced pressure. The resulting residue was partitioned between water (20 mL) and methylene chloride (20 mL). The layers were separated, and the aqueous phase was extracted with methylene chloride (2×20 mL). The organic extracts were combined, dried over sodium sulfate, filtered and concentrated under reduced pressure. The resulting residue was purified by flash chromatography to afford a 52% yield (672 mg) of 152b as a brown solid: mp>250° C.; $^1$H NMR (500 MHz, DMSO-$d_6$) δ 8.53 (s, 1H), 7.76 (d, 1H, J=9.0 Hz), 7.66 (d, 1H, J=9.0 Hz), 7.40 (t, 1H, J=9.0 Hz), 7.31 (t, 1H, J=9.0 Hz), 4.41 (t, 2H, J=6.0 Hz), 3.71 (m, 2H); MS (APCI+) m/z 188.4 (M+H).

Example 152c 3,4,6,7,8,9-Hexahydropyrazino[1,2-a]benzoimidazole-1-one 152c

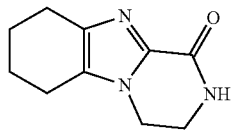

152c

A 250-mL stainless steel pressure reactor was charged with 10% palladium on carbon (50% wet, 150 mg dry weight) and a solution of 152b (670 mg, 3.58 mmol) in acetic acid (25 mL). The reactor was evacuated, charged with hydrogen gas to a pressure of 350 psi and stirred at 95° C. for 16 h. After this time, the hydrogen was evacuated, and nitrogen was charged into the reactor. Celite 521 (1.00 g) was added, and the mixture was filtered through a pad of Celite 521. The filter cake was washed with ethanol (2×25 mL), and the combined filtrates were concentrated to dryness under reduced pressure. To the resulting residue was added water (10 mL), and followed by potassium carbonate to adjust pH to 9. The mixture was extracted with methylene chloride (4×20 mL), and the organic extracts were combined, dried over sodium sulfate, filtered and concentrated under reduced pressure to afford a 71% yield 152c (487 mg) as a white solid: mp>250° C.; $^1$H NMR (500 MHz, DMSO-$d_6$) δ 7.86 (s, 1H), 3.98 (t, 2H, J=6.5 Hz), 3.51 (m, 2H), 2.50 (m, 4H), 1.75 (m, 4H); MS (APCI+) m/z 192.6 (M+H).

Example 152d 2-Bromo-6-(1-oxo-3,4,6,7,8,9-hexahydropyrazino[1,2-a]benzoimidazole-2-yl)benzyl Acetate 152d

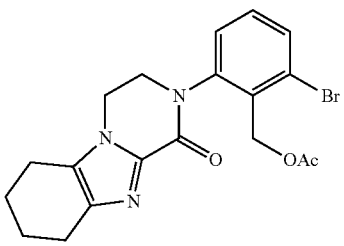

152d

A 100-mL three-neck round-bottomed flask equipped with a reflux condenser, magnetic stirrer and nitrogen inlet was charged with 152c (485 mg, 2.54 mmol), 104g (1.56 g, 5.08 mmol), cesium carbonate (1.66 g, 5.08 mmol), N,N'-dimethylethylene-diamine (447 mg, 5.08 mmol) and 1,4-dioxane (20 mL). After bubbling nitrogen through the resulting suspension for 30 min, copper iodide (484 mg, 2.54 mmol) was added, and the reaction mixture was heated at 100° C. (oil bath temperature) for 16 h. After this time, the mixture was cooled to room temperature and filtered. The filtrate was diluted with ethyl acetate (100 mL) and water (50 mL). The organic layer was separated, and the aqueous layer was extracted with ethyl acetate (3×50 mL). The combined organic layers were dried over sodium sulfate and concentrated under reduced pressure. The residue was purified by column chromatography to afford a yellow oil, which was dissolved in methylene chloride (5 mL). Acetyl chloride (506 mg, 2.54 mmol) and triethylamine (1.28 g, 12.7 mmol) were added, and the reaction mixture was stirred at room temperature for 2 h. After this time, the reaction mixture was diluted with methylene chloride (50 mL) and saturated aqueous sodium bicarbonate (20 mL). The organic layer was separated, and the aqueous layer was extracted with methylene chloride (3×50 mL). The combined organic layers were dried over sodium sulfate and concentrated under reduced pressure to afford a 13% yield (140 mg) of 152d as a yellow oil: $^1$H NMR (500 MHz, CDCl$_3$) δ 7.60 (d, 1H, J=8.0 Hz), 7.27 (t, 1H, J=8.0 Hz), 7.18 (d, 1H, J=8.0 Hz), 5.26 (d, 1H, J=12.0 Hz), 5.14 (d, 1H, J=12.0 Hz), 4.32 (m, 1H), 4.24 (m, 1H), 4.14 (m, 1H), 3.87 (m, 1H), 2.75 (m, 2H), 2.56 (m, 2H), 2.07 (s, 3H), 1.83 (m, 4H); MS (APCI+) m/z 418.8 (M+H).

A 100-mL single-neck round-bottomed flask equipped with a magnetic stirrer and reflux condenser was purged with nitrogen and charged with 152d (140 mg, 0.335 mmol), 104h (140 mg, 0.426 mmol), sodium carbonate (106 mg, 1.00 mmol), 1,4-dioxane (5 mL) and water (1 mL). This mixture was degassed with nitrogen for 30 min. Tetrakis (triphenylphosphine)palladium (39 mg, 0.033 mmol) was added. After heating at 100° C. for 5 h, the reaction mixture was cooled to room temperature and partitioned between water (40 mL) and methylene chloride (100 mL). The layers were separated, and the aqueous phase was extracted with methylene chloride (2×50 mL). The organic extracts were combined, dried over sodium sulfate, filtered and concentrated under reduced pressure. The resulting residue was dissolved in methanol (5 mL), and potassium carbonate (500 mg, 3.62 mmol) was added. After stirring at room temperature for 2 h, the reaction mixture was partitioned between water (20 mL) and methylene chloride (20 mL). The layers were separated, and the aqueous phase was extracted with methylene chloride (2×20 mL). The organic extracts were combined, dried over sodium sulfate, filtered and concentrated under reduced pressure. The resulting residue was purified by flash chromatography to afford 152 in 9% yield (15 mg) as a yellow solid: mp 205-206° C.; $^1$H NMR (500 MHz, DMSO-d$_6$) δ 9.18 (s, 1H), 8.70 (d, 1H, J=2.5 Hz), 8.64 (m, 1H), 8.30 (d, 1H, J=6.0 Hz), 7.51-7.47 (m, 2H), 7.39 (d, 1H, J=8.0 Hz), 7.35 (d, 1H, J=8.0 Hz), 7.31 (d, 1H, J=6.0 Hz), 4.92 (t, 1H, J=4.5 Hz), 4.36 (m, 2H), 4.27 (m, 2H), 4.19 (m, 1H), 3.97 (m, 1H), 3.61 (s, 3H), 2.63 (m, 2H), 2.52 (m, 2H), 1.87 (m, 4H); MS (ESI+) m/z 498.2 (M+H).

Example 153 2-(2-(Hydroxymethyl)-3-(4-methyl-5-oxo-6-(1,2,3,4-tetrahydroisoquinolin-6-ylamino)-4,5-dihydropyrazin-2-yl)phenyl)-3,4,5,6,7,8-hexahydrobenzothieno[2,3-c]pyridin-1(2H)-one 153

Example 153a 5-Bromo-1-methyl-3-(1,2,3,4-tetrahydroisoquinolin-6-ylamino)pyrazin-2(1H)-one 153a

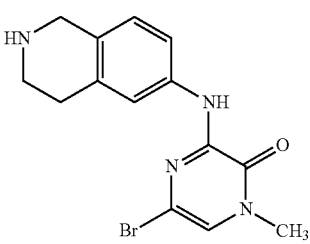

153a

A 100-mL single-neck round-bottomed flask equipped with a magnetic stirrer and nitrogen inlet was purged with nitrogen and charged with 120a (1.14 g, 2.62 mmol), methylene chloride (10 mL) and trifluoroacetic acid (10 mL). The solution was stirred for 2 h at room temperature. After this time, the solution was concentrated under reduced pressure. The residue was partitioned between methylene chloride (100 mL) and 1 M aqueous dibasic potassium phosphate (30 mL). The aqueous layer was extracted with a 20% (v/v) solution of methanol in methylene chloride (3×100 mL). The organic extracts were combined, washed with brine (20 mL) and dried over sodium sulfate. The drying agent was removed by filtration, and the filtrate was concentrated under reduced pressure to afford a 68% yield (600 mg) of 153a as an off-white solid: mp 170-171° C.; $^1$H NMR (300 MHz, DMSO-d$_6$) δ 9.30 (s, 1H), 7.62 (m, 2H), 7.31 (s, 1H), 6.97 (d, 1H, J=7.8 Hz), 4.10 (br s, 1H), 3.83 (s, 2H), 3.43 (s, 3H), 2.96 (t, 2H, J=5.7 Hz), 2.68 (t, 2H, J=5.7 Hz); MS (ESI+) m/z 334.0 (M+H).

A 50-mL three-neck round-bottomed flask equipped with a reflux condenser, magnetic stirrer and nitrogen inlet was charged with 153a (168 mg, 0.500 mmol), 111a (289 mg, 0.600 mmol), sodium carbonate (159 mg, 1.50 mmol), DMF (5 mL), water (2.5 mL) and 1,4-dioxane (8 mL). After bubbling nitrogen through the resulting suspension for 30 min, tetrakis(triphenylphosphine)palladium(0) (58 mg, 0.050 mmol) was added, and the reaction mixture was heated at reflux for 14 h. After this time, the mixture was cooled to room temperature, and methanol (2 mL), water (2 mL) and lithium hydroxide monohydrate (42 mg, 1.00 mmol) were added. The mixture was stirred for 4 h at room temperature and then concentrated in vacuo. The residue was partitioned between ethyl acetate (150 mL) and water (30 mL). The organic layer was separated, and the aqueous layer was extracted with a 20% (v/v) solution of methanol in methylene chloride (3×150 mL). The combined organic layers were dried over sodium sulfate and concentrated under reduced pressure. The residue was purified by column chromatography (silica, 0% to 10% methanol/methylene chloride) to afford a 4% yield (12 mg) of 153 as an off-white solid: 209-210° C. dec; $^1$H NMR (500 MHz, DMSO-d$_6$) δ 9.04 (s, 1H), 7.74 (s, 1H), 7.61 (d, 1H, J=7.4 Hz), 7.53 (d, 1H, J=8.0 Hz), 7.46 (t, 1H, J=8.0 Hz), 7.40 (s, 1H), 7.32 (d, 1H, J=7.4 Hz), 6.90 (d, 1H, J=8.3 Hz), 4.77 (m, 1H), 4.53 (m, 1H), 4.43 (m, 1H), 4.02 (m, 1H), 3.87 (m, 1H), 3.77 (s, 2H), 3.58 (s, 3H), 2.91 (m, 4H), 2.79 (s, 2H), 2.63 (m, 2H), 1.78 (m, 4H); MS (ESI+) m/z 568.1 (M+H).

Example 154 2-(2-(Hydroxymethyl)-3-(6-oxo-5-(pyrimidin-4-ylamino)-1,6-dihydropyridin-3-yl)phenyl)-3,4,5,6,7,8-hexahydrobenzothieno[2,3-c]pyridin-1(2H)-one 154

Example 154a 5-Bromo-3-(pyrimidin-4-ylamino)pyridin-2(1H)-one 154a

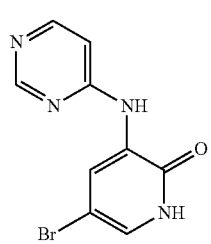

154a le;.3qA 250-mL three-neck round-bottomed flask equipped with a reflux condenser, magnetic stirrer and nitrogen inlet was charged with 2-aminopyrimidine (376 mg, 3.95 mmol), 3,5-dibromo pyridin-2(1H)-one (1.00 g, 3.95 mmol), 1 M THF solution of lithium hexamethyldisilazide (20 mL, 20.0 mmol), and 1,4-dioxane (25 mL). After bubbling nitrogen through the resulting suspension for 30 min, Xantphos (194 mg, 0.211 mmol) and tris(dibenzylideneacetone)dipalladium(0) (165 mg, 0.197 mmol) were added, and the reaction mixture was heated at reflux for 3 h. After this time, the mixture was cooled to room temperature and diluted with ethyl acetate (150 mL) and water (30 mL). The organic layer was separated, and the aqueous layer was extracted with ethyl acetate (3×150 mL). The combined organic extracts were dried over sodium sulfate and concentrated under reduced pressure. The residue was purified by flash chromatography followed by trituration with ethyl acetate (20 mL) to afford a 24% yield (250 mg) of 154a as an off-white solid: mp 150-151° C.; $^1$H NMR (500 MHz, DMSO-$d_6$) d 12.03 (s, 1H), 9.27 (s, 1H), 8.54 (s, 1H), 8.20 (d, 1H, J=6.0 Hz), 7.85 (s, 1H), 6.64 (d, 1H, J=6.0 Hz); MS (ESI+) m/z 268.2 (M+H).

A 50-mL three-neck round-bottomed flask equipped with a reflux condenser, magnetic stirrer and nitrogen inlet was charged with 154a (175 mg, 0.655 mmol), 111a (315 mg, 0.655 mmol), sodium carbonate (208 mg, 2.00 mmol), DMF (2.5 mL), water (1.2 mL) and 1,4-dioxane (4 mL). After bubbling nitrogen through the resulting suspension for 30 min, tetrakis(triphenylphosphine)palladium(0) (76 mg, 0.065 mmol) was added, and the reaction mixture was heated at reflux for 14 h. After this time, the mixture was cooled to room temperature, and methanol (2 mL), water (2 mL) and lithium hydroxide monohydrate (82 mg, 1.95 mmol) were added. The mixture was stirred for 2 h at room temperature and then concentrated in vacuo. The residue was partitioned between ethyl acetate (150 mL) and water (30 mL). The organic layer was separated, and the aqueous layer was extracted with a 20% (v/v) solution of methanol in methylene chloride (3×150 mL). The combined organic extracts were dried over sodium sulfate and concentrated under reduced pressure. The residue was purified by column chromatography (silica, 0% to 10% methanol/methylene chloride) to afford a 5% yield (15 mg) of 154 as an off-white solid: mp 200-201° C.; $^1$H NMR (500 MHz, DMSO-$d_6$) δ 11.99 (s, 1H), 9.34 (s, 1H), 8.57 (s, 1H), 8.21 (d, 1H, J=6.0 Hz), 8.00 (s, 1H), 7.62 (s, 1H), 7.44 (t, 1H, J=7.5 Hz), 7.35 (d, 1H, J=7.0 Hz), 6.70 (d, 1H, J=5.5 Hz), 5.05 (br s, 1H), 4.28 (t, 1H, J=11.0 Hz), 4.18 (d, 1H, J=10.0 Hz), 3.96 (m, 1H), 3.90 (m, 1H), 2.94 (m, 1H), 2.84 (m, 1H), 2.77 (m, 2H), 1.76 (m, 4H); MS (ESI+) m/z 500.1 (M+H).

Example 155 5,5,6,6,7,7-Hexadeutero-2-(2-(hydroxymethyl)-3-(1-methyl-5-(5-(1-methylazetidin-3-yl)pyridin-2-ylamino)-6-oxo-1,6-dihydropyridin-3-yl)phenyl)-3,4,5,6,7,8-hexahydrobenzothieno[2,3-c]pyridin-1(2H)-one 155

Example 155c Ethyl 4,4,5,5,6,6-Hexadeutero-4,5,6,7-tetrahydrobenzo[b]thiophene-2-carboxylate 155c

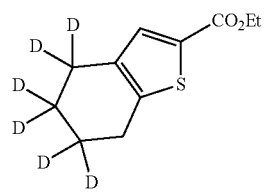

Intermediate 155a (1.53 g) was reacted with ethyl 2-mercaptoacetate (1.57 g) using the same general procedure as described in Example 105b. Intermediate 155c was obtained as a clear oil in 51% yield (1.46 g): $^1$H NMR (500 MHz, CDCl$_3$) δ 7.46 (s, 1H), 4.31 (q, 2H, J=7.5 Hz), 2.77 (s, 2H), 1.35 (t, 3H, J=7.5 Hz); MS (ESI+) m/z 217 (M+H).

Example 155d 4,4,5,5,6,6-Hexadeutero-4,5,6,7-tetrahydrobenzo[b]thiophene-2-carboxylic Acid 155d

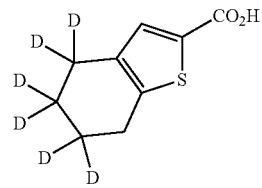

Intermediate 155d (1.34 g) was saponified using the same general procedure as described in Example 105c. Intermediate 155d was obtained as a white solid in 94% yield (1.10 g): mp 192-193° C.; $^1$H NMR (500 MHz, DMSO-$d_6$) δ 12.75 (br s, 1H), 7.40 (s, 1H), 2.73 (s, 2H).

Example 155e 4,4,5,5,6,6-Hexadeutero-N-methoxy-N-methyl-4,5,6,7-tetrahydrobenzo[b]thiophene-2-carboxamide 155e

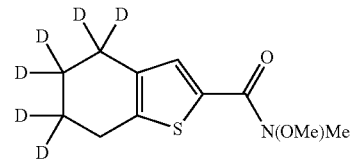

A 250-mL single-neck round-bottomed flask equipped with a magnetic stirrer was purged with nitrogen, charged with 155d (5.67 g, 30.1 mmol), methylene chloride (100 mL), and DMF (110 mg, 1.50 mmol) and cooled to 0° C. To the resulting solution, oxalyl chloride (4.21 g, 33.1 mmol) was added dropwise. After this addition was complete, the reaction was warmed to room temperature and stirred for 3 h. After this time, the reaction was concentrated to dryness under reduced pressure. The residue was dissolved in methylene chloride (100 mL), and the resulting solution was cooled to 0° C. Triethylamine (9.15 g, 90.3 mmol) and N,O-dimethylhydroxylamine hydrochloride (3.23 g, 33.1 mmol) were added. After the addition was complete, the cooling bath was removed, and the reaction mixture was stirred at room temperature for 14 h. After this time, the reaction mixture was partitioned between water (100 mL) and ethyl acetate (200 mL). The layers were separated, and the aqueous phase was extracted with ethyl acetate (100 mL). The combined organic extracts were washed with water (100 mL), followed by brine (100 mL) and dried over sodium sulfate. The drying agent was removed by filtration, and the solvent was evaporated under reduced pressure. The resulting residue was purified by flash chromatography (silica, 0% to 100% ethyl acetate/hexanes) to afford a 90% yield of 155e (6.29 g) as a white solid: mp 47-48° C.; $^1$H NMR (500 MHz, CDCl$_3$) δ 7.62 (s, 1H), 3.76 (s, 3H), 3.31 (s, 3H), 2.77 (s, 2H); MS (ESI+) m/z 232.1 (M+H).

Example 155f 1-(4,4,5,5,6,6-Hexadeutero-4,5,6,7-tetrahydrobenzo[b]thiophen-2-yl)prop-2-en-1-one 155f

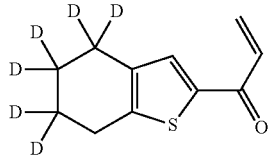

A 250-mL single-necked round-bottomed flask equipped with a magnetic stirrer was purged with nitrogen and charged with 155e (6.29 g, 27.2 mmol) and anhydrous THF (60 mL), and the resulting solution was cooled to −25° C. with acetone/ice bath. A 1.0 M solution of vinylmagnesium bromide in THF (32.3 mL, 32.6 mmol) was added dropwise, and the resulting reaction mixture was stirred at 0° C. for 1 h. After this time, the reaction mixture was partitioned between ethyl acetate (250 mL) and 2 M hydrochloric acid (50 mL). The layers were separated, and the aqueous phase was extracted with ethyl acetate (40 mL). The combined organic extracts were washed with water (100 mL), followed by brine (100 mL), dried over sodium sulfate, filtered and concentrated under reduced pressure to afford a crude quantitative yield of 155f (5.39 g) as a semi-solid. The material was used in the next step without further purification.

Example 155g 3-Chloro-1-(4,4,5,5,6,6-hexadeutero-4,5,6,7-tetrahydrobenzo[b]thiophen-2-yl)propan-1-one 155g

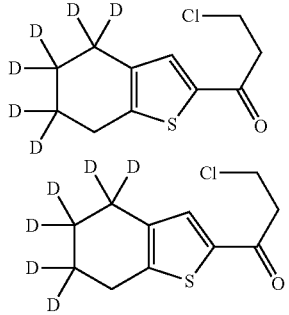

A 250-mL single-necked round-bottomed flask equipped with a magnetic stirrer was purged with nitrogen and charged with 155f (5.39 g, 27.2 mmol), methylene chloride (60 mL), and the resulting solution was cooled to 0° C. A 2 M solution of hydrogen chloride in diethyl ether (34 mL) was added. After stirring at room temperature for 3 h, the solvents were removed under reduced pressure. Purification of the resulting residue by column chromatography (silica, 0% to 50% ethyl acetate/hexanes) afforded a quantitative yield (6.38 g) of 155g as an off-white solid: mp 51-53° C.; $^1$H NMR (300 MHz, CDCl$_3$) δ 7.41 (s, 1H), 3.89 (t, 2H, J=7.0 Hz), 3.30 (t, 2H, J=7.0 Hz), 2.79 (s, 2H); MS (ESI+) m/z 235.1 (M+H).

Example 155h 6,6,7,7,8,8-Hexadeutero-5,6,7,8-tetrahydro-1H-benzo[b]cyclopenta[d]thiophen-3(2H)-one 155h

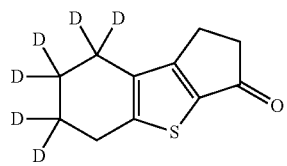

A 250-mL single-necked round-bottomed flask equipped with a magnetic stirrer was charged with 155g (6.38 g, 27.2 mmol) and 98% sulfuric acid (50 mL). After stirring at 95° C. for 14 h, the reaction mixture was poured into ice (50 g), and the resulting suspension was extracted with ethyl acetate (3×50 mL). The organic extracts were combined, dried over sodium sulfate, filtered and concentrated under reduced pressure. The resulting residue was purified by flash chromatography (silica, 0% to 50% ethyl acetate/hexanes) to afford 155h in a 56% yield (3.03 g) as an off-white solid: mp 43-44° C.; $^1$H NMR (300 MHz, CDCl$_3$) δ 2.91 (m, 6H).

Example 155i 6,6,7,7,8,8-Hexadeutero-5,6,7,8-tetrahydro-1H-benzo[b]cyclopenta[d]thiophen-3(2H)-one Oxime 155i

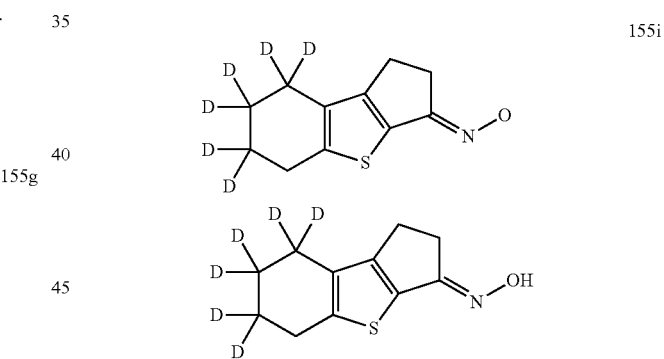

A 250-mL single-neck round-bottomed flask equipped with a mechanical stirrer and nitrogen inlet was charged with hydroxylamine hydrochloride (1.59 g, 22.9 mmol) and methanol (40 mL). The mixture was cooled to 0° C. using an ice bath. Sodium acetate trihydrate (3.19 g, 22.9 mmol) was added. The mixture was stirred at 0° C. for 30 min. After this time, 155h (3.03 g, 15.3 mmol) was added, and the reaction was stirred at room temperature for 14 h. After this time, the mixture was concentrated, redissolved in methylene chloride (200 mL) with water (30 mL). The organic layer was separated, and the aqueous layer was extracted with methylene chloride (3×150 mL). The combined organic layers were dried over sodium sulfate and concentrated under reduced pressure to afford a 84% yield (2.72 g) of 155i as an off-white solid: mp 174-176° C.; $^1$H NMR (300 MHz, CDCl$_3$) δ 3.12 (m, 2H), 2.82 (m, 4H); MS (ESI+) m/z 214.1 (M+H).

Example 155j 5,5,6,6,7,7-Hexadeutero-3,4,5,6,7,8-hexahydrobenzothieno[2,3-c]pyridin-1(2H)-one 155j

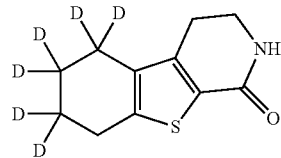

A 50-mL single-neck round-bottomed flask equipped with a reflux condenser, magnetic stirrer and nitrogen inlet was charged with 155i (2.72 g, 12.8 mmol) and polyphosphoric acid (150 g). After stirring at 80° C. for 14 h, the reaction mixture was cooled to room temperature, and water (300 mL) was added. The resulting mixture was stirred for 30 min and filtered. The filter cake was washed with water (20 mL) and dried in a vacuum oven at 45° C. to afford a 74% yield (2.00 g) of 155j as an off-white solid: mp 204-205° C.; $^1$H NMR (300 MHz, CDCl$_3$) δ 5.58 (s, 1H), 3.58 (m, 2H), 2.79 (s, 2H), 2.71 (t, 2H, J=7.0 Hz); MS (ESI+) m/z 214.1 (M+H).

Example 155k 2-Bromo-6-(5,5,6,6,7,7-hexadeutero-1-oxo-3,4,5,6,7,8-hexahydrobenzothieno[2,3-c]pyridin-2(1H)-yl)benzyl Acetate 155k

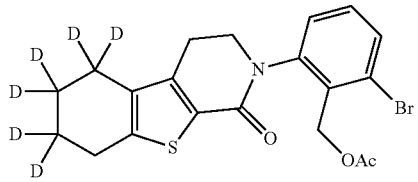

A 250-mL three-neck round-bottomed flask equipped with a reflux condenser, magnetic stirrer and nitrogen inlet was charged with 155j (1.00 g, 4.69 mmol), 104g (2.89 g, 9.38 mmol), cesium carbonate (4.59 g, 14.1 mmol), N,N'-dimethylethylene-diamine (412 mg, 4.69 mmol) and 1,4-dioxane (35 mL). After bubbling nitrogen through the resulting suspension for 30 min, copper iodide (447 mg, 2.35 mmol) was added, and the reaction mixture was heated at 80° C. (oil bath temperature) for 20 h. After this time, the mixture was cooled to room temperature and filtered. The filtrate was diluted with ethyl acetate (150 mL) and water (30 mL). The organic layer was separated, and the aqueous layer was extracted with ethyl acetate (3×100 mL). The combined organic layers were dried over sodium sulfate and concentrated under reduced pressure. The residue was purified by column chromatography (silica, 0% to 40% ethyl acetate/hexanes) to afford a 35% yield (715 mg) of 155k as an off-white solid: mp 74-75° C.; $^1$H NMR (500 MHz, CDCl$_3$) δ 7.59 (m, 1H), 7.31 (m, 2H), 5.15 (d, 1H, J=12.0 Hz), 5.04 (d, 1H, J=12.0 Hz), 3.99 (m, 1H), 3.65 (m, 1H), 2.81 (m, 1H), 2.74 (s, 2H), 2.06 (s, 3H); MS (ESI+) m/z 440.1 (M+H).

Example 155l 2-(5,5,6,6,7,7-Hexadeutero-1-oxo-3,4,5,6,7,8-hexahydrobenzothieno[2,3-c]pyridin-2(1H)-yl)-6-(4,4,5,5-tetramethyl-1,3,2-dioxaborolan-2-yl)benzyl Acetate 155l

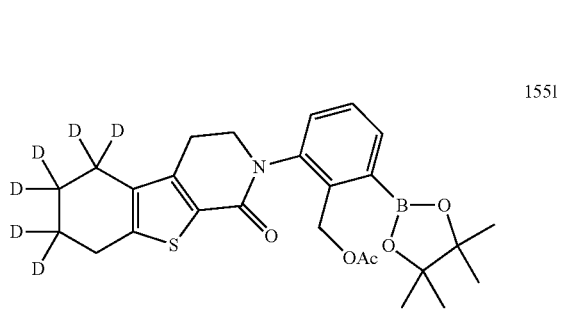 [SMILES: [2H]C1([2H])Cc2sc3c(c2C([2H])([2H])C1([2H])[2H])CCN(c1cccc(B2OC(C)(C)C(C)(C)O2)c1COC(C)=O)C3=O]

A 100-mL single-neck round-bottomed flask equipped with a magnetic stirrer and reflux condenser was purged with nitrogen and charged with 155k (710 mg, 1.61 mmol), 4,4,4',4',5,5,5',5'-octamethyl-2,2'-bi(1,3,2-dioxaborolane) (819 mg, 3.22 mmol), potassium acetate (474 mg, 4.83 mmol) and 1,4-dioxane (12 mL). After bubbling nitrogen through the resulting suspension for 30 min, [1,1'-bis(diphenylphosphino)-ferrocene]dichloropalladium(II) (118 mg, 0.161 mmol) was added, and the reaction mixture was heated at reflux for 2 h. After this time, the mixture was cooled to room temperature and diluted with ethyl acetate (150 mL) and water (30 mL). The organic layer was separated, and the aqueous layer was extracted with ethyl acetate (3×150 mL). The combined organic layers were dried over sodium sulfate and concentrated under reduced pressure to afford a crude 155l (785 mg) in a quantitative yield. The material was used in the next step without further purification.

Example 155m tert-Butyl 3-(6-(6-Bromo-2-methyl-3-oxo-2,3-dihydropyrin-4-ylamino)pyridin-3-yl)azetidine-1-carboxylate 155m

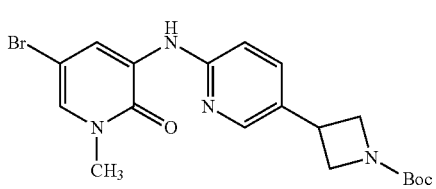

A 250-mL single-neck round-bottomed flask equipped with a magnetic stirrer and reflux condenser was charged with tert-butyl 3-(6-aminopyridin-3-yl)azetidine-1-carboxylate (333 mg, 1.33 mmol), 3,5-dibromo-1-methylpyridin-2(1H)-one (350 mg, 1.33 mmol), cesium carbonate (870 mg, 2.70 mmol) and 1,4-dioxane (10 mL). After bubbling nitrogen through the resulting solution for 30 min, Xantphos (66 mg, 0.114 mmol) and tris(dibenzylideneacetone)dipalladium(0) (61 mg, 0.066 mmol) were added and the reaction mixture was heated at 105° C. for 3 h. After this time, the mixture was cooled to room temperature and filtered. The filter cake was washed with methylene chloride (2×10 mL), and the combined filtrates were concentrated under reduced pressure. The resulting residue was purified by column chromatography on silica to afford a 79% yield (460 mg) of 155m as a green solid: mp 134-136° C.; $^1$H NMR (500 MHz, DMSO-d$_6$) δ 8.75 (s, 1H), 8.65 (s, 1H), 8.19 (s, 1H), 7.66 (dd, 1H, J=8.5, 2.0 Hz), 7.51 (s, 1H), 7.35 (d, 1H, J=8.5 Hz), 4.21 (t, 2H, J=8.0 Hz), 3.81 (m, 2H), 3.51 (s, 3H), 1.40 (s, 9H); MS (ESI+) m/z 436.1 (M+H).

Example 155n 3-(5-(Azetidin-3-yl)pyridin-2-ylamino)-5-bromo-1-methylpyridin-2(1H)-one 155n

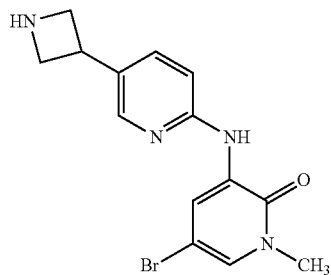

A 100-mL single-neck round-bottomed flask equipped with a magnetic stirrer and nitrogen inlet was purged with nitrogen and charged with 155m (1.20 g, 2.76 mmol), methylene chloride (10 mL) and trifluoroacetic acid (10 mL). The solution was stirred for 2 h at room temperature. After this time, the solution was concentrated under reduced pressure. The residue was partitioned between methylene chloride (100 mL) and 1 M aqueous dibasic potassium phosphate (30 mL). The aqueous layer was extracted with a 20% (v/v) solution of methanol in methylene chloride (3×100 mL). The organic extracts were combined, washed with brine (20 mL) and dried over sodium sulfate. The drying agent was removed by filtration, and the filtrate was concentrated under reduced pressure to afford a quantitative yield (920 mg) of 155n as an off-white solid: mp 123-124° C.; $^1$H NMR (300 MHz, DMSO-d$_6$) δ 8.72 (s, 1H), 8.65 (d, 1H, J=2.3 Hz), 8.19 (d, 1H, J=2.1 Hz), 7.71 (dd, 1H, J=8.6, 2.2 Hz), 7.51 (d, 1H, J=2.3 Hz), 7.33 (d, 1H, J=8.2 Hz), 3.74 (m, 3H), 3.58 (m, 2H), 3.52 (s, 3H); MS (ESI+) m/z 335.1 (M+H).

Example 155o 2-(5-(5-(Azetidin-3-yl)pyridin-2-ylamino)-1-methyl-6-oxo-1,6-dihydropyridin-3-yl)-6-(5,5,6,6,7,7-hexadeutero-1-oxo-3,4,5,6,7,8-hexahydrobenzothieno[2,3-c]pyridin-2(1H)-yl)benzyl Acetate 155o

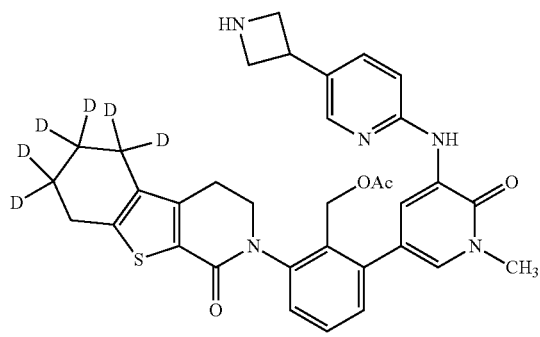

A 100-mL three-neck round-bottomed flask equipped with a reflux condenser, magnetic stirrer and nitrogen inlet was charged with crude 155l (785 mg, presumed 1.61 mmol), 155n (450 mg, 1.34 mmol), sodium carbonate (426 mg, 4.02 mmol), DMF (10 mL), water (5 mL) and 1,4-dioxane (16 mL). After bubbling nitrogen through the resulting suspension for 30 min, tetrakis(triphenylphosphine)palladium(0) (155 mg, 0.134 mmol) was added, and the reaction mixture was heated at reflux for 14 h. The residue was partitioned between ethyl acetate (150 mL) and water (30 mL). The organic layer was separated, and the aqueous layer was extracted with a 20% (v/v) solution of methanol in methylene chloride (3×150 mL). The combined organic layers were dried over sodium sulfate and concentrated under reduced pressure to afford crude 155o. The material was used in the next step without further purification.

Example 155p 2-(3-(5-(5-(Azetidin-3-yl)pyridin-2-ylamino)-1-methyl-6-oxo-1,6-dihydropyridin-3-yl)-2-(hydroxymethyl)phenyl)-5,5,6,6,7,7-hexadeutero-3,4,5,6,7,8-hexahydrobenzothieno[2,3-c]pyridin-1(2H)-one 155p

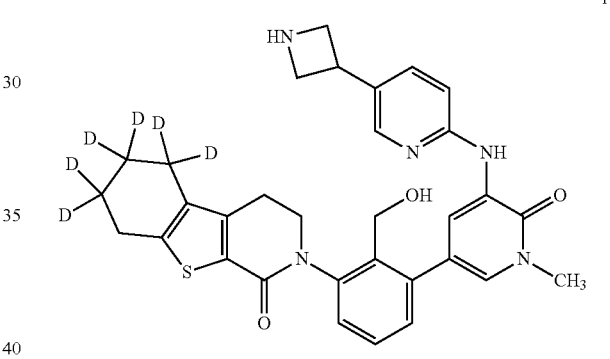

A 100-mL single-neck round-bottomed flask equipped with a was charged with crude 155o from the previous step, THF (8 mL), methanol (4 mL), water (4 mL) and lithium hydroxide monohydrate (420 mg, 10.0 mmol) were added. The mixture was stirred for 4 h at room temperature and then concentrated in vacuo. The residue was partitioned between ethyl acetate (150 mL) and water (30 mL). The organic layer was separated, and the aqueous layer was extracted with a 20% (v/v) solution of methanol in methylene chloride (3×150 mL). The combined organic layers were dried over sodium sulfate and concentrated under reduced pressure. The residue was purified by column chromatography (silica, 0% to 10% methanol/methylene chloride) to afford a 15% yield (140 mg) of 155p as an off-white solid: mp 140-142° C.; $^1$H NMR (500 MHz, DMSO-d$_6$) δ 8.65 (d, 1H, J=2.0 Hz), 8.53 (s, 1H), 8.10 (d, 1H, J=2.4 Hz), 7.67 (m, 1H), 7.45 (t, 1H, J=8.0 Hz), 7.31 (m, 4H), 4.81 (t, 1H, J=5.0 Hz), 4.35 (m, 2H), 4.04 (m, 1H), 3.88 (m, 1H), 3.71 (m, 3H), 3.59 (s, 3H), 3.55 (m, 2H), 2.96 (m, 1H), 2.86 (m, 1H), 2.77 (s, 2H); MS (ESI+) m/z 574.3 (M+H).

A 150-mL single-neck round-bottomed flask equipped with a magnetic stirrer was purged with nitrogen, charged with 155p (140 mg, 0.244 mmol), 37% solution of formaldehyde in water (26 mg, 0.317 mmol) and methanol (10 mL). A suspension of sodium cyanoborohydride (48 mg, 0.732 mmol) and zinc chloride (50 mg, 0.366 mmol) in methanol (4 mL) was added, and the reaction was stirred at room temperature for 16 h. After this time, the reaction mixture was concentrated in vacuo. The residue was partitioned between ethyl acetate (150 mL) and water (30 mL). The organic layer was separated, and the aqueous layer was extracted with a 20% (v/v) solution of methanol in methylene chloride (3×150 mL). The combined organic layers were dried over sodium sulfate and concentrated under reduced pressure. The residue was purified by column chromatography (silica, 0% to 10% methanol/methylene chloride) to afford a 45% yield (65 mg) of 155 as a white solid: mp 190-192° C.; $^1$H NMR (500 MHz, DMSO-$d_6$) δ 8.65 (d, 1H, J=2.5 Hz), 8.58 (s, 1H), 8.15 (d, 1H, J=2.5 Hz), 7.67 (dd, 1H, J=8.5, 2.5 Hz), 7.46 (t, 1H, J=8.0 Hz), 7.33 (m, 4H), 4.81 (t, 1H, J=4.0 Hz), 4.35 (m, 2H), 4.02 (m, 1H), 3.85 (m, 3H), 3.64 (m, 1H), 3.59 (s, 3H), 3.42 (m, 2H), 2.98 (m, 1H), 2.87 (m, 1H), 2.76 (s, 2H), 2.47 (s, 3H); MS (ESI+) m/z 588.2 (M+H).

Example 156 2-(3-(5-(5-((3,3-Difluoroazetidin-1-yl) methyl)-1-methyl-1H-pyrazol-3-ylamino)-1-methyl-6-oxo-1,6-dihydropyridin-3-yl)-2-(hydroxymethyl) phenyl)-3,4,6,7,8,9-hexahydropyrazino[1,2-a]indol-1 (2H)-one 156

Example 156a Methyl 5-Nitro-1H-pyrazole-3-carboxylate 156a

A 50-mL single-neck round-bottomed flask equipped with a magnetic stirrer and reflux condenser was purged with nitrogen and charged with 5-nitro-1H-pyrazole-3-carboxylic acid (0.86 g, 5.5 mmol) and anhydrous methanol (10 mL), and the reaction mixture was cooled to 0° C. in an ice/water cooling bath. To the resulting solution thionyl chloride (1.7 g, 14.4 mmol) was added dropwise. After the addition was complete, the bath was removed, and the reaction was heated at reflux for 3 h. After this time, the reaction was concentrated to dryness under reduced pressure to afford a quantitative yield of 156a (0.94 g) as a white solid: MS (ESI−) m/z 170 (M−H).

Example 156b Methyl 1-Methyl-3-nitro-1H-pyrazole-5-carboxylate 156b

A 50-mL single-neck round-bottomed flask equipped with a magnetic stirrer was purged with nitrogen and charged with methyl 5-nitro-1H-pyrazole-3-carboxylate (156a) (0.94 g, 5.5 mmol), anhydrous N,N-dimethylformamide (11 mL), methyl iodide (0.85 g, 6 mmol) and potassium carbonate (0.83 g, 6.1 mmol). The reaction was stirred at room temperature for 16 h. After this time the reaction was diluted with water (40 mL) and extracted with methylene chloride (3×25 mL). The combined organic extracts were dried over sodium sulfate, filtered and concentrated under reduced pressure. The resulting residue was subjected to flash chromatography (silica, ethyl acetate/hexanes) to afford methyl 1-methyl-3-nitro-1H-pyrazole-5-carboxylate 156b in 66% yield (0.67 g) as a white solid: MS (ESI+) m/z 186.0 (M+H). Also isolated was the regioisomer methyl 1-methyl-5-nitro-1H-pyrazole-3-carboxylate in 15% yield (0.15 g) as a white solid: MS (ESI−) m/z 186.0 (M+H).

Example 156c (1-Methyl-3-nitro-1H-pyrazol-5-yl)methanol 156c

A 100-mL three-neck round-bottomed flask equipped with a magnetic stirrer, addition funnel and nitrogen inlet was purged with nitrogen and charged with 156b (0.67 g, 3.6 mmol), THF (20 mL) and cooled to 0° C. using an ice bath. 2 M lithium borohydride solution (3.6 mL, 7.2 mmol) was added dropwise at a rate that maintained the internal reaction temperature below 5° C. After the addition was complete, the cooling bath was removed and the reaction was stirred at room temperature for 3 h. The reaction was cooled to 0° C. using an ice bath, and saturated aqueous sodium bicarbonate (30 mL) was added dropwise. The layers were separated, and aqueous layer was extracted with ethyl acetate (3×30 mL). The combined organic layers were washed with brine (30 mL), dried over sodium sulfate and concentrated under reduced pressure. The residue was purified by column chromatography (silica, ethyl acetate/hexanes) to afford a quant. yield (0.56 g) of (1-methyl-3-nitro-1H-pyrazol-5-yl) methanol (156c) as an off-white solid: MS (ESI+) m/z 158.1 (M+H).

Example 156d 5-(Bromomethyl)-1-methyl-3-nitro-1H-pyrazole 156d

A 25-mL round-bottomed flask equipped with a magnetic stirrer and reflux condenser was purged with nitrogen and charged with 156c (0.56 g, 3.6 mmol) and chloroform (10 mL). The reaction was cooled to 0° C. using an ice bath and phosphorous tribromide (0.98 g, 3.6 mmol) was added dropwise. The cooling bath was removed and the reaction stirred at reflux for 3 h. After this time, the reaction was cooled to 0° C. and diluted with methylene chloride (25 mL). Saturated aqueous sodium bicarbonate was added until a pH of 8.5 was reached. The layers were separated, and the aqueous layer was extracted with methylene chloride (3×25 mL). The combined organic layers were washed with brine (30 mL), dried over sodium sulfate and concentrated under reduced pressure to afford a quantitative yield (0.79 g) of 156d as an off-white solid: MS (ESI+) m/z 222.1 (M+H).

Example 156e 5-((3,3-Difluoroazetidin-1-yl) methyl)-1-methyl-3-nitro-1H-pyrazole 156e A sealed tube with a magnetic stirrer was charged with DMF (5 mL), 5-(Bromomethyl)-1-methyl-3-nitro-1H-pyrazole 156d (0.39 g, 1.78 mmol), 3,3-difluoroazetidine hydrochloride (276 mg, 2.13 mmol) and DIPEA (0.8 mL, 4.45 mmol). The reaction mixture was heated at 65° C. for 3-5 h. After this time the reaction was concentrated to dryness under reduced pressure, and the resulting residue was diluted with a mixture of Ethyl Acetate (15 mL) and water (15 mL). The aqueous layer was separated and extracted with Ethyl Acetate (2×15 mL). The combined organic extracts were dried over sodium sulfate and concentrated under reduced pressure to afford a quantitative yield of 156e as yellow oil, which was used without further purification for the next step. MS (ESI+) m/z 233.0 (M+H).

Example 156f 5-((3,3-Difluoroazetidin-1-yl) methyl)-1-methyl-1H-pyrazol-3-amine 156f A Parr reactor bottle was purged with nitrogen and charged with 10% palladium on carbon (30% wet, 150 mg dry weight) and a solution of 156e (1.78 mmol) in ethanol (25 mL). The bottle was attached to a Parr hydrogenator, evacuated, charged with hydrogen gas to a pressure of 40 psi and shaken for 2 h. After this time, the hydrogen was evacuated, and the reaction mixture was filtered through a pad of Celite 521. The filter cake was washed with ethanol (2×25 mL), and the combined filtrates were concentrated to dryness under reduced pressure to afford a quantitative yield of 156f (360 mg) as yellow oil: MS (ESI+) m/z 203.1 (M+H).

Example 156g 5-Bromo-3-(5-((3,3-difluoroazetidin-1-yl)methyl)-1-methyl-1H-pyrazol-3-ylamino)-1-methylpyridin-2(1H)-one 156g Intermediate 156g was synthesized using the same procedure as Example 112a, except using 156f (360 mg, 1.78 mmol), 3,5-dibromo-1-methyl-1H-pyridin-2-one (0.43 g, 1.6 mmol), cesium carbonate (1.56 g, 4.8 mmol), tris(dibenzylideneacetone)dipalladium(0) (0.15 g, 0.16 mmol), Xantphos (0.18 g, 0.32 mmol) and 1,4-dioxane (18 mL). The reaction mixture was heated at 115° C. for 24 hours. Work-up and flash column chromatography (silica, 60:35:5 methylene chloride/diethyl ether/methanol) give 38% yield (0.23 g) of 156g as a green solid: MS (ESI+) m/z 390.1 (M+H).

Following Example 121c, except using 2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 114a (165 mg, 0.35 mmol), 156g (115 mg, 0.3 mmol), 1M sodium carbonate solution (1.2 mL, 1.2 mmol), tetrakis(triphenylphosphine)palladium(0) (18 mg, 0.015 mmol) and 1,2-Dimethoxyethane (3 mL). Work-up and flash column chromatography (silica, 60:35:5 methylene chloride/diethyl ether/methanol) afford 156h (a mixture of compound 156 and its acetate) as yellow oil (190 mg). The mixture (0.3 mmol) was deprotected using a mixture of THF (2 mL), water (1 mL) and isopropanol (2 mL), and Lithium hydroxide monohydrate (80 mg, 1.90 mmol). Work-up and flash column chromatography (silica, 60:35:5 methylene chloride/diethyl ether/methanol) afford a 12% yield (2 steps, 22 mg) of 156 as a white solid: MS (ESI+) m/z 604.4 (M+H).

Example 157 2-(2-(Hydroxymethyl)-3-(5-(5-methoxy-1H-pyrazol-3-ylamino)-1-methyl-6-oxo-1,6-dihydropyridin-3-yl)phenyl)-3,4,6,7,8,9-hexahydropyrazino[1,2-a]indol-1(2H)-one 157

Example 157a 5-Bromo-3-(5-methoxy-1H-pyrazol-3-ylamino)-1-methylpyridin-2(1H)-one 157a

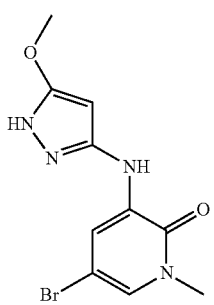

157a

A sealed tube was equipped with a magnetic stirrer and charged with 5-methoxy-1H-pyrazol-3-amine (1.9 g, 17 mmol), 3,5-dibromo-1-methylpyridin-2(1H)-one (4.9 g, 18 mmol) and cesium carbonate (12 g, 37 mmol) in 1,4-dioxane (160 mL). After bubbling nitrogen through the solution for 30 min, Xantphos (1.1 g, 2 mmol) and tris(dibenzylideneacetone)dipalladium(0) (1.1 g, 1.2 mmol) were added, and the reaction mixture was heated to 100° C. for 16 hours. After this time, H$_2$O (50 mL) and EtOAc (50 mL) were added. The aqueous layer was separated and extracted with EtOAc (2×50 mL). The combined organic extracts were washed with brine (100 mL) and dried over sodium sulfate. The resulting solution was concentrated under reduced pressure to near dryness and the desired product fell out of solution. Filtering and washing with Et$_2$O (10 mL) afforded 12% yield (590 mg) of crude 157a.

Example 157b 2-(5-(5-Methoxy-1H-pyrazol-3-ylamino)-1-methyl-6-oxo-1,6-dihydropyridin-3-yl)-6-(1-oxo-3,4,6,7,8,9-hexahydropyrazino[1,2-a]indol-2(1H)-yl)benzyl Acetate 157b

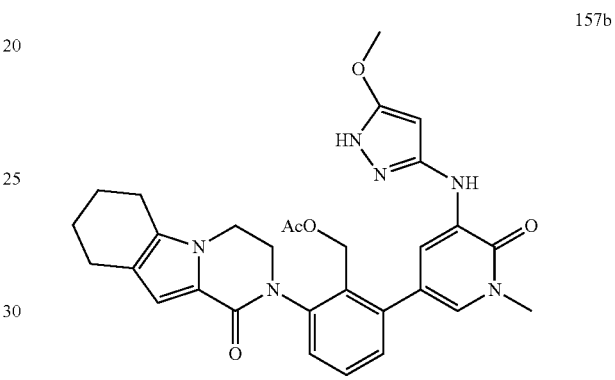

157b

A microwave tube equipped with a magnetic stirrer was charged with 157a (94 mg, 0.3 mmol), 2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 114a (180 mg, 0.4 mmol), DME (4 mL) and 1M aqueous sodium carbonate (0.9 mL). After bubbling N$_2$ for 15 min, Pd(PPh$_3$)$_4$ (18 mg, 0.02 mmol) was added. The mixture was heated in microwave to 130° C. for 25 min. After this time, EtOAc (5 mL) and water (5 mL) were added. The separated aqueous layer was extracted with EtOAc (2×5 mL). The combined organics were washed with brine (10 mL), dried over sodium sulfate, filtered and concentrated under reduced pressure. The resulting residue was purified by column chromatography eluting with a gradient of CH$_2$Cl$_2$—60:35:5 CH$_2$Cl$_2$:Et$_2$O:MeOH to afford a 19% yield (33 mg) of 157b.

A 25 mL round bottom flask with a magnetic stirrer was charged with 157b (33 mg, 0.06 mmol), lithium hydroxide (10 mg, 1.2 mmol), THF (0.3 mL), i-PrOH (0.3 mL) and water (0.6 mL). The mixture stirred at rt for 1 h. After this time, EtOAc (5 mL) and water (5 mL) were added. The separated aqueous layer was extracted with EtOAc (2×5 mL). The combined organics were washed with brine (10 mL), dried over sodium sulfate, filtered and concentrated under reduced pressure. The resulting residue was purified by column chromatography eluting with a gradient of CH$_2$Cl$_2$—60:35:5 CH$_2$Cl$_2$:Et$_2$O:MeOH to afford a 76% yield (23 mg) of 157. MS (ESI+) m/z 515.4 (M+H).

Example 158 5-[2-(Hydroxymethyl)-3-[1-methyl-6-oxo-5-(5,6,7,8-tetrahydro-1,6-naphthyridin-2-ylamino)-1,6-dihydropyridin-3-yl]phenyl]-8-thia-5-azatricyclo[7.4.0.0²,⁷]trideca-1(9),2(7)-dien-6-one 158

Example 158a tert-Butyl 2-(Diphenylmethyl-eneamino)-7,8-dihydro-1,6-naphthyridine-6(5H)-carboxylate 158a

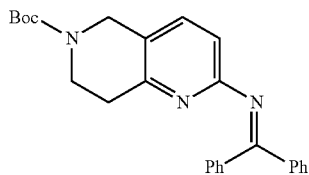 [SMILES: CC(C)(C)OC(=O)N1CCc2nc(N=C(c3ccccc3)c3ccccc3)ccc2C1]

To a round-bottomed flask equipped with a stirring bar, tert-butyl 2-chloro-7,8-dihydro-1,6-naphthyridine-6(5H)-carboxylate (1.09 g, 4.05 mmol), diphenyl-methanimine 26 (2.20 g, 12.14 mmol), Pd(OAc)2 (181.6 mg, 0.809 mmol), BINAP (503.8 mg, 0.809 mmol), $Cs_2CO_3$ (6.59 g, 20.23 mmol) and toluene (16 mL) were added. The reaction mixture was heated at 110° C. for 2 days. The reaction mixture was filtered and removed solvent in vacuo. The residue 158a was directly used in the next step.

Example 158b tert-Butyl 2-Amino-7,8-dihydro-1,6-naphthyridine-6(5H)-carboxylate 158b

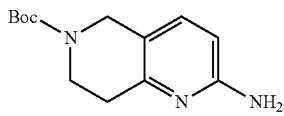 [SMILES: CC(C)(C)OC(=O)N1CCc2nc(N)ccc2C1]

Intermediate 158a was added to a round-bottomed flask. MeOH (50 mL) and $NH_2OH$ HCl (1.76 g, 25.3 mmol) was added. The resulting mixture was stirred at RT for 5 hrs. The solvents were removed in vacuo and silica gel column (MeOH:DCM=10:90) gave 158b as dark oil, 851 mg (84%, 2 steps).

Example 158c tert-Butyl 2-(5-Bromo-1-methyl-2-oxo-1,2-dihydropyridin-3-ylamino)-7,8-dihydro-1,6-naphthyridine-6(5H)-carboxylate 158c

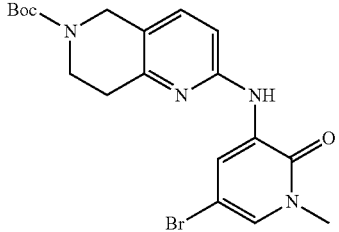 [SMILES: Cn1cc(Br)cc(Nc2ccc3c(n2)CCN(C(=O)OC(C)(C)C)C3)c1=O]

To a round-bottomed flask equipped with a stirring bar, 158b (851 mg, 3.41 mmol), 3,5-dibromo-1-methylpyridin-2(1H)-one (1.37 g, 5.12 mmol), $Pd_2(dba)_3$ (312.5 mg, 0.341 mmol), XantPhos (316 mg, 0.546 mmol), $Cs_2CO_3$ (3.67 g, 11.3 mmol) and dioxane (17 mL) were added. The reaction mixture was heated at 100° C. overnight. DCM (200 mL) was added to the resulting mixture was washed with water (30 mL×3). DCM (200 mL) was added and the resulting mixture was washed with water (30 mL×3), brine (30 mL×1), dried over $MgSO_4$, filtered, and removed solvent in vacuo. DCM/ether (1:2, 5 mL) was added followed by sonication, the precipitation was filtered as 158c, green solids, 865 mg (58%).

Example 158d 5-[2-(Acetoxymethyl)-3-[1-methyl-6-oxo-5-(5,6,7,8-tetrahydro-1,6-naphthyridin-2-ylamino)-1,6-dihydropyridin-3-yl]phenyl]-8-thia-5-azatricyclo[7.4.0.0²,⁷]trideca-1(9),2(7)-dien-6-one 158d

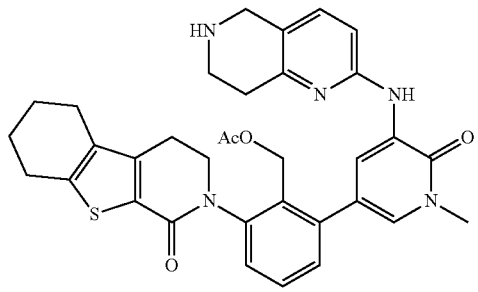 [SMILES: CC(=O)OCc1c(-c2cc(Nc3ccc4c(n3)CCNC4)c(=O)n(C)c2)cccc1N1CCc2c(sc3c2CCCC3)C1=O]

To a microwave tube equipped with a stirring bar, 158c (300 mg, 0.689 mmol), boronic ester 111a (365 mg, 0.758 mmol), $Pd(PPh_3)_4$ (39.8 mg, 0.034 mmol), $Na_2CO_3$ aqueous solution (1.0 N, 2.27 mL. 2.27 mmol), 1,2-dimethoxyethane (3.0 mL) were added. The mixture was reacted in microwave at 130° C. for 10 min. methylene chloride (200 mL) was added and the resulting mixture was washed with water (30 mL×3), brine (30 mL×1), dried over $MgSO_4$, filtered, and removed solvent in vacuo. Silica gel column chromatography (MeOH:methylene chloride=5:95) gave 158d.

To a round-bottomed flask equipped with a stirring bar, 158d, THF (5 mL), i-propanol (5 mL), water (5 mL), LiOH monohydrate (278 mg) were added. The resulting mixture was stirred at room temperature for 1 hr. The solvent was removed in vacuo and the resulting residue was added to methylene chloride (200 mL), the solution was washed with water (30 mL×3), brine (30 mL×1), dried over $MgSO_4$, filtered, and removed solvent in vacuo. Silica gel column chromatography (methanol:methylene chloride=10:90) gave 158 as a yellow solid (145 mg). MS (ESI+) m/z 568.3 (M+H).

Example 159 2-(2-(Hydroxymethyl)-3-(1-methyl-6-oxo-5-(pyrimidin-4-ylamino)-1,6-dihydropyridin-3-yl)phenyl)-3,4,6,7,8,9-hexahydropyrido[3,4-b]imidazo[4,5-c]pyridine-1-one 159

Example 159a 3-Nitro-4-(piperidin-1-yl)pyridine 159a

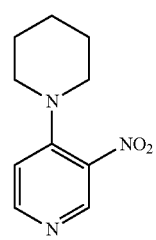

A 500-mL single-neck round-bottomed flask equipped with a reflux condenser and magnetic stirrer was purged with nitrogen and charged with 3-nitro-4-chloro-pyridine (10.0 g, 63.3 mmol), piperidine (16.2 g, 190 mmol) and ethanol (200 mL). After heating at 70° C. for 2 h, the solvent was removed under reduced pressure, and the residue was partitioned between ethyl acetate (200 mL) and 10% aqueous potassium carbonate (100 mL). The organic layer was separated, and the aqueous layer was extracted with ethyl acetate (2×100 mL). The combined organic layers were dried over sodium sulfate and concentrated under reduced pressure. The residue was purified by column chromatography to afford a 100% yield (15.2 g) of 159a as a yellow oil: $^1$H NMR (500 MHz, CDCl$_3$) δ 8.81 (s, 1H), 8.31 (d, 1H, J=6.0 Hz), 6.86 (d, 1H, J=6.0 Hz), 3.22 (t, 4H, J=4.5 Hz), 1.72 (m, 6H); MS (APCI+) m/z 208.4 (M+H).

Example 159b 6,7,8,9-Tetrahydropyrido[3,4-b]imidazo[4,5-c]pyridine 159b

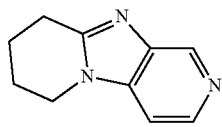

159b

A 500-mL single-neck round-bottomed flask equipped with a reflux condenser and magnetic stirrer was purged with nitrogen and charged with 159a (6.00 g, 29.0 mmol) and triethyl phosphite (200 mL). After heating at 110° C. for 24 h, the triethyl phosphite was removed under reduced pressure, and the residue was partitioned between methylene chloride (200 mL) and water (100 mL). The organic layer was separated, and the aqueous layer was extracted with methylene chloride (2×100 mL). The combined organic layers were dried over sodium sulfate and concentrated under reduced pressure. The residue was purified by column chromatography to afford a 53% yield (2.66 g) of 159b as a yellow solid: mp 94-95° C.; $^1$H NMR (500 MHz, CDCl$_3$) δ 8.98 (s, 1H), 8.37 (d, 1H, J=6.0 Hz), 7.22 (d, 1H, J=6.0 Hz), 4.09 (t, 2H, J=6.0 Hz), 3.11 (t, 2H, J=6.0 Hz), 2.15 (m, 2H), 2.05 (m, 2H); MS (APCI+) m/z 174.1 (M+H).

Example 159c 6,7,8,9-Tetrahydropyrido[3,4-b]imidazo[4,5-c]pyridine 2-Oxide 159c

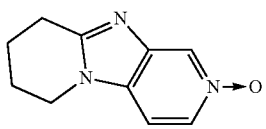

159c

A 100-mL single-neck round-bottomed flask equipped with a reflux condenser and magnetic stirrer was charged with 159b (2.50 g, 14.4 mmol) and methylene chloride (50 mL), and the reaction mixture was cooled to 0° C. 3-chloroperbenzoic acid (4.99 g, 28.9 mmol) was added, and the mixture was stirred at room temperature for 1.5 h. After this time, the solvent was removed under reduced pressure, and the residue was purified by column chromatography to afford an 83% yield (2.26 g) of 159c as a yellow solid: mp 178-179° C.; $^1$H NMR (500 MHz, CDCl$_3$) δ 8.71 (s, 1H), 8.15 (d, 1H, J=6.0 Hz), 7.19 (d, 1H, J=6.0 Hz), 4.12 (t, 2H, J=6.0 Hz), 3.12 (t, 2H, J=6.0 Hz), 2.18 (m, 2H), 2.05 (m, 2H); MS (APCI+) m/z 190.4 (M+H).

Example 159d 6,7,8,9-Tetrahydropyrido[3,4-b]imidazo[4,5-c]pyridine-1-one 159d

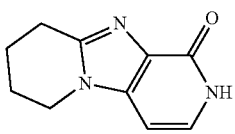

159d

A 250-mL single-neck round-bottomed flask equipped with a reflux condenser and magnetic stirrer was purged with nitrogen and charged with 159c (2.26 g, 12.0 mmol) and acetic anhydride (90 mL). After heating at 140° C. for 1.5 h, the solvent was removed under reduced pressure, and the residue was purified by column chromatography to afford a 62% yield (1.40 g) of 159d as a yellow solid: mp>250° C.; $^1$H NMR (500 MHz, CDCl$_3$) δ 11.3 (s, 1H), 7.24 (d, 1H, J=7.0 Hz), 6.39 (d, 1H, J=6.0 Hz), 4.07 (t, 2H, J=6.0 Hz), 3.11 (t, 2H, J=6.0 Hz), 2.13 (m, 2H), 2.02 (m, 2H); MS (APCI+) m/z 190.7 (M+H).

Example 159e 3,4,6,7,8,9-hexahydropyrido[3,4-b]imidazo[4,5-c]pyridine-1-one 159e

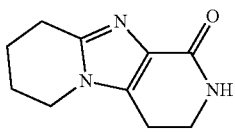

159e

A 250-mL stainless steel pressure reactor was charged with 10% palladium on carbon (50% wet, 250 mg dry weight) and a solution of 159d (1.07 g, 5.66 mmol) in acetic acid (50 mL). The reactor was evacuated, charged with hydrogen gas to a pressure of 350 psi and stirred at 85° C. for 48 h. After this time, the hydrogen was evacuated, and nitrogen was charged into the reactor. Celite 521 (1.00 g) was added, and the mixture was filtered through a pad of Celite 521. The filter cake was washed with ethanol (2×25 mL), and the combined filtrates were concentrated to dryness under reduced pressure. To the resulting residue was added water (10 mL), followed by potassium carbonate to adjust pH to 9. The mixture was extracted with methylene chloride (4×20 mL), and the organic extracts were combined, dried over sodium sulfate, filtered and concentrated under reduced pressure to afford a 69% yield of 159e (749 mg) as a white solid: mp>250° C.; $^1$H NMR (500 MHz, CDCl$_3$) δ 5.28 (s, 1H), 3.85 (t, 2H, J=6.0 Hz), 3.62 (m, 2H), 2.92 (t, 2H, J=6.0 Hz), 2.81 (t, 2H, J=6.0 Hz), 2.03 (m, 2H), 1.94 (m, 2H); MS (APCI+) m/z 192.7 (M+H).

Example 159f 2-Bromo-6-(1-oxo-3,4,6,7,8,9-hexahydropyrido[3,4-b]imidazo[4,5-c]pyridine-2-yl)benzyl Acetate 159f

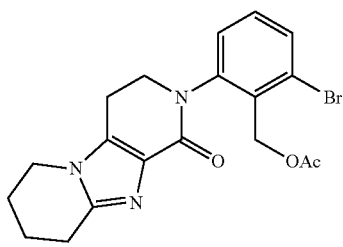

159f

A 100-mL three-neck round-bottomed flask equipped with a reflux condenser, magnetic stirrer and nitrogen inlet was charged with 159e (745 mg, 3.90 mmol), 104g (2.40 g, 7.80 mmol), cesium carbonate (2.54 g, 7.80 mmol), copper iodide (743 mg, 3.90 mmol), and 1-methyl-2-pyrrolidinone (7 mL). After heating at 120° C. (oil bath temperature) for 16 h, the mixture was cooled to room temperature and partitioned between methylene chloride (100 mL) and water (50 mL). The organic layer was separated, and the aqueous layer was extracted with methylene chloride (3×50 mL). The combined organic layers were dried over sodium sulfate and concentrated under reduced pressure. The residue was purified by column chromatography to afford a yellow oil, which was dissolved in methylene chloride (5 mL). Acetyl chloride (306 mg, 3.90 mmol) and triethylamine (1.97 g, 19.5 mmol) was added, and the reaction mixture was stirred at room temperature for 2 h. After this time, the reaction mixture was diluted with methylene chloride (50 mL) and saturated aqueous sodium bicarbonate (20 mL). The organic layer was separated, and the aqueous layer was extracted with methylene chloride (3×50 mL). The combined organic layers were dried over sodium sulfate and concentrated under reduced pressure to afford a 6% yield (100 mg) of 159f as a pink oil: $^1$H NMR (500 MHz, CDCl$_3$) δ 7.60 (d, 1H, J=8.0 Hz), 7.34 (t, 1H, J=8.0 Hz), 7.16 (d, 1H, J=8.0 Hz), 5.18 (m, 2H), 4.18 (m, 1H), 4.04 (m, 1H), 3.87 (m, 1H), 3.79 (m, 1H), 3.16 (m, 1H), 3.05 (m, 1H), 2.95 (m, 2H), 2.09-1.99 (m, 7H); MS (APCI+) m/z 418.9 (M+H).

A 100-mL single-neck round-bottomed flask equipped with a magnetic stirrer and reflux condenser was purged with nitrogen and charged with 159f (100 mg, 0.239 mmol), 104h (350 mg, 1.07 mmol), sodium carbonate (183 mg, 1.72 mmol), 1,4-dioxane (8 mL) and water (2 mL). This mixture was degassed with nitrogen for 30 min. Tetrakis(tri-phenylphosphine)palladium (66 mg, 0.057 mmol) was added. After heating at 100° C. for 5 h, the reaction mixture was cooled to room temperature and partitioned between water (40 mL) and methylene chloride (100 mL). The layers were separated, and the aqueous phase was extracted with methylene chloride (2×50 mL). The organic extracts were combined, dried over sodium sulfate, filtered and concentrated under reduced pressure. The resulting residue was dissolved in methanol (5 mL), and potassium carbonate (500 mg, 3.62 mmol) was added. After stirring at room temperature for 2 h, the reaction mixture was partitioned between water (20 mL) and methylene chloride (20 mL). The layers were separated, and the aqueous phase was extracted with methylene chloride (2×20 mL). The organic extracts were combined, dried over sodium sulfate, filtered and concentrated under reduced pressure. The resulting residue was purified by flash chromatography to afford 159 in 10% yield (12 mg) as a light brown solid: mp>250° C.; $^1$H NMR (500 MHz, DMSO-d$_6$) δ 9.16 (s, 1H), 8.71 (d, 1H, J=2.0 Hz), 8.64 (s, 1H), 8.29 (dd, 1H, J=6.0, 1.5 Hz), 7.53 (s, 1H), 7.45 (td, 1H, J=6.0, 1.5 Hz), 7.31 (m, 3H), 4.75 (m, 1H), 4.32 (m, 2H), 4.02 (m, 2H), 3.88 (m, 2H), 3.60 (s, 3H), 3.05 (m, 1H), 2.96 (m, 1H), 2.76 (t, 2H, J=5.5 Hz), 1.95 (m, 2H), 1.86 (m, 2H); MS (ESI+) m/z 498.2 (M+H).

Example 160 3-({4-[(2R)-1,4-Dimethyl-3-oxopiperazin-2-yl]phenyl}amino)-5-[2-(hydroxymethyl)-3-{1-oxo-1H,2H,3H,4H,6H,7H,8H,9H-pyrazino[1,2-a]indol-2-yl}phenyl]-1-methyl-1,2-dihydropyrazin-2-one 160

Following Example 121b, 2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 114a (167 mg, 0.36 mmol), 5-bromo-3-(4-(1,4-dimethyl-3-oxopiperazin-2-yl)phenylamino)-1-methylpyrazin-2(1H)-one 160a (WO 2009/039397; 122 mg, 0.3 mmol), 1M sodium carbonate solution (0.9 mL, 0.9 mmol), tetrakis(triphenylphosphine)-palladium (0) (18 mg, 0.015 mmol) and 1,2-dimethoxyethane (3 mL). Work-up and flash column chromatography (silica, 60:35:5 methylene chloride/diethyl ether/methanol) afford a mixture of 2-(5-(4-(1,4-dimethyl-3-oxopiperazin-2-yl)phenylamino)-1-methyl-6-oxo-1,6-dihydropyridin-3-yl)-6-(2-oxo-3,4,6,7,8,9-hexahydropyrazino[1,2-a]indol-2(1H)-yl) benzyl acetate 160b and 160 as yellow oil. The mixture (0.3 mmol) was deprotected using a mixture of THF (1 mL), water (0.5 mL) and isopropanol (1 mL), and Lithium hydroxide monohydrate (80 mg, 1.90 mmol). Work-up and flash column chromatography (silica, 60:35:5 methylene chloride/diethylether/methanol) afford a 37% yield of compound 160 (2 steps, 70 mg) as a white solid: MS (ESI+) m/z 622.4 (M+H).

Example 161 2-(3-(5-(1-(2-Hydroxyethyl)-5-methyl-1H-pyrazol-3-ylamino)-1-methyl-6-oxo-1,6-dihydropyridin-3-yl)-2-(hydroxymethyl)phenyl)-3,4,6,7,8,9-hexahydropyrazino[1,2-a]indol-1(2H)-one 161

Example 161a 5-Bromo-3-(1-(2-(tert-butyldimethylsilyloxy)ethyl)-5-methyl-1H-pyrazol-3-ylamino)-1-methylpyridin-2(1H)-one 161a A solution of 5-bromo-1-methyl-3-(5-methyl-1H-pyrazol-3-ylamino)pyridin-2(1H)-one 112a (1.08 g, 3.8 mmol) in anhydrous DMF (10 mL) was treated with 60% dispersion of NaH in mineral oil (0.17 g, 4.3 mmol) while stirring under nitrogen. After effervescence the reaction was stirred for an additional 30 min. At this time the reaction was treated with (2-bromoethoxy)(tert-butyl)dimethylsilane (15-1) (0.908 g, 3.8 mmol) and continued to stir under nitrogen for 10 hours. After reaction water (50 mL) was added slowly and the mixture was filtered. The filtrate was concentrated under reduced pressure and the residue was purified by flash column chromatography eluting with petroleum ether/ethyl acetate to afford 161a (1 g, 35%), which was used directly without further purification. LCMS: (M+H)+443.

Example 161b 2-(5-(1-(2-(tert-Butyldimethylsilyloxy)ethyl)-5-methyl-1H-pyrazol-3-ylamino)-1-methyl-6-oxo-1,6-dihydropyridin-3-yl)-6-(1-oxo-3,4,6,7,8,9-hexahydro-pyrazino[1,2-a]indol-2(1H)-yl) benzyl acetate 161b A mixture of 161a (750 mg, 1.7 mmol), 2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 114a (882 mg, 1.9 mmol), CH$_3$COONa (309 mg, 3.8 mmol), PdCl₂(dppf) (153 mg, 0.19 mmol) and K₃PO₄ (1 g, 3.8 mmol) suspended in CH₃CN (30 mL) and H₂O (2 mL) was heated at 110° C. for 12 h under argon atmosphere. After reaction the mixture was evaporated and the residue was purified by reverse phase Combi-flash eluting with 0.3% NH₄HCO₃ in 1:4 water/CH₃CN to give 161b as a brown solid (210 mg, 18%). LCMS: [M+H]⁺ 699.

Example 161c 2-(3-(5-(1-(2-(tert-Butyldimethylsilyloxy)ethyl)-5-methyl-1H-pyrazol-3-ylamino)-1-methyl-6-oxo-1,6-dihydropyridin-3-yl)-2-(hydroxymethyl)phenyl)-3,4,6,7,8,9-hexahydropyrazino[1,2-a]indol-1(2H)-one 161c A mixture of 161b (210 mg, 0.4 mmol) and LiOH (372 mg, 16 mmol) in isopropanol/THF (1:1, 10 mL) and water (3 mL) was stirred at 30° C. for 2 h. The mixture was evaporated in vacuo and the residue was extracted with ethyl acetate (2×10 mL). The combined extract was concentrated under reduced pressure and the residue was purified on prep-HPLC to 161c. LCMS: [M+H]⁺ 657

A solution of 161c, camphorsulfonic acid (330 mg, 1.5 mmol) in methanol (30 mL) was stirred at room temperature for 3 h. After reaction methanol was evaporated and the residue was purified by prep-HPLC to afford 161 as a brown solid (63 mg, 29%, two steps). LCMS: [M+H]⁺543. ¹H NMR (500 MHz, DMSO) δ 7.96 (m, 1H), 7.45 (m, 1H), 7.33 (m, 2H), 7.24 (m, 1H), 6.51 (s, 1H), 5.87 (s, 1H), 4.86 (m, 1H), 4.77 (m, 1H), 4.36 (m, 2H), 4.15 (m, 3H), 3.90 (m, 3H), 3.64 (m, 2H), 3.57 (s, 3H), 2.51 (m, 2H), 2.46 (m, 2H), 2.19 (s, 3H), 1.79 (m, 4H).

Example 162 2-(2-(Hydroxymethyl)-3-(1-methyl-5-(2-methylpyrimidin-4-ylamino)-6-oxo-1,6-dihydropyridin-3-yl)phenyl)-3,4,6,7,8,9-hexahydropyrazino[1,2-a]indol-1(2H)-one 162

Example 162a 2-Methylpyrimidin-4-amine 162a

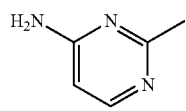

In a pressure-resistant vessel made of stainless steel having an inner volume of 500 mL was charged with 3-methoxypropanenitrile (10 g, 120 mmol), 1,1,1-trimethoxy-ethane (39 g, 324 mmol) and 40.0 g (560 mmol, 24% by weight ammonia-methanol solution). The mixture was stirred at 130° C. for 8 hours. After completion of the reaction, it was filtered and concentrated to give a yellow solid. The solid was washed with ethyl acetate (50 mL), dried in vacuo to afford 162a (7.8 g, 60%). LCMS: [M+H]⁺ 110

Example 162b 5-Bromo-1-methyl-3-(2-methylpyrimidin-4-ylamino)pyridin-2(1H)-one 162b

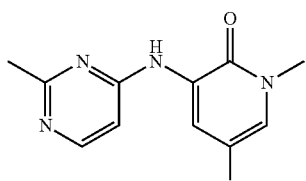

Following Example 148a, 2.0 g of 162a and 4.0 g of 3,5-dibromo-1-methyl-pyridin-2(1H)-one were reacted to give 162b as a yellow solid (2.3 g, 50%). LCMS: [M+H]⁺ 357 ¹H NMR (500 MHz, DMSO) δ 9.20 (s, 1H), 8.78 (s, 1H), 8.26 (d, J=4.5, 1H), 7.68 (s, 1H), 7.18 (d, J=4.5, 1H), 3.59 (s, 3H), 2.52 (s, 3H).

Example 162c 2-(1-Methyl-5-(2-methylpyrimidin-4-ylamino)-6-oxo-1,6-dihydropyridin-3-yl)-6-(1-oxo-3,4,6,7,8,9-hexahydropyrazino[1,2-a]indol-2(1H)-yl) benzyl Acetate 162c

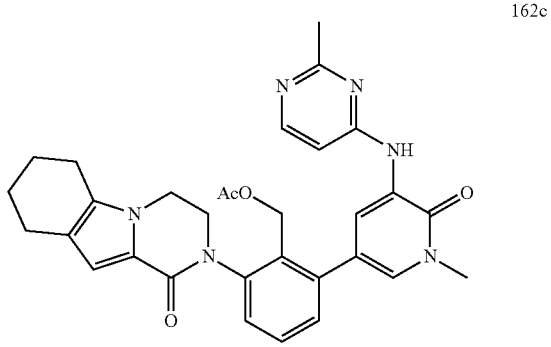 [SMILES: CC(=O)OCc1c(-c2cc(Nc3ccnc(C)n3)c(=O)n(C)c2)cccc1N1CCn2c(cc3c2CCCC3)C1=O]

Following Example 148b, 464 mg of 2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 114a and 443 mg of 162b were reacted to give 162c as a yellow solid (386 mg, 70%). LCMS: [M+H]⁺ 553

Following Example 148 160 mg of 162c was hydrolyzed to give 162 as a white solid (90 mg, 60%). LCMS: [M+H]⁺ 511. ¹H NMR (500 MHz, DMSO) δ 9.04 (s, 1H), 8.87 (s, 1H), 8.21 (s, 1H), 7.55 (s, 1H), 7.48 (s, 1H), 7.36 (0=6.5, 1H),7.12 (s, 1H), 6.52 (s, H), 4.85 (s, 1H), 4.40 (s, 1H), 4.17-4.10 (m, 3H), 3.92 (m, 1H), 3.61 (s, 3H), 2.60 (m, 2H), 2.47 (m, 2H), 2.42 (S, 3H), 1.80 (m, 2H), 1.69 (m, 2H).

Example 163 2-(3-(5-(1-(2-Hydroxyethyl)-1H-pyrazol-3-ylamino)-1-methyl-6-oxo-1,6-dihydropyridin-3-yl)-2-(hydroxymethyl)phenyl)-3,4,6,7,8,9-hexahydropyrazino[1,2-a]indol-1(2H)-one 163

Example 163a 5-Bromo-3-(1-(2-(tert-butyldimethylsilyloxy)ethyl)-1H-pyrazol-3-ylamino)-1-methyl-pyridin-2(1H)-one 163a

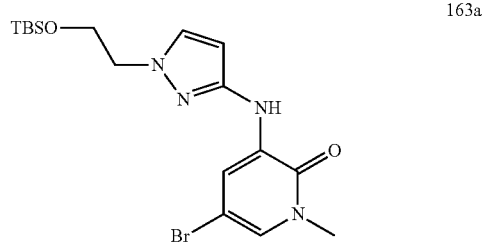 [SMILES: Cn1cc(Br)cc(Nc2ccn(CCO[Si](C)(C)C(C)(C)C)n2)c1=O]

A mixture of 1-(2-(tert-butyldimethylsilyloxy)ethyl)-1H-pyrazol-3-amine 116b (1.2 g, 5 mmol), 3,5-dibromo-1-methylpyridin-2(1H)-one (1.3 g, 5 mmol), XantPhos (300 mg, 0.5 mmol), Pd$_2$(dba)$_3$ (460 mg, 0.5 mmol) and Cs$_2$CO$_3$ (4 g, 2.5 mmol) in dioxane (30 mL) was heated in a sealed tube at 120° C. for 2 h under nitrogen. After reaction the mixture was filtered and the filtrated was evaporated in vacuo to give a yellow solid, which was then washed with ethyl acetate (6 mL×3) to give 163a as a yellow solid (0.80 g, 38%) and used without further purification. MS: (M+H)$^+$ 427.

Example 163b 2-(5-(1-(2-(tert-Butyldimethylsilyloxy)ethyl)-1H-pyrazol-3-ylamino)-1-methyl-6-oxo-1,6-dihydropyridin-3-yl)-6-(1-oxo-3,4,6,7,8,9-hexahydropyrazino[1,2-a]indol-2(1H)-yl)benzyl Acetate 163b

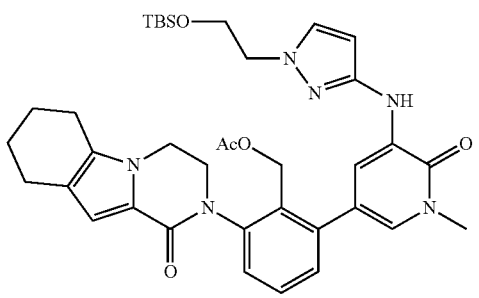

A mixture of 163a (800 mg, 1.88 mmol), 2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 114a (1.3 g, 2.82 mmol), sodium acetate (308 mg, 3.76 mmol), PdCl$_2$(dppf) (153 mg, 0.188 mmol) and K$_3$PO$_4$ (1 g, 3.76 mmol) suspended in CH$_3$CN (50 mL) and water (3 mL) was heated at 110° C. for 12 h under argon atmosphere. The mixture was then evaporated and the residue was purified by reverse phase Combi-flash eluting with 0.3% NH$_4$HCO$_3$ in 1:5 water/CH$_3$CN to give 163b as a brown solid (350 mg, 29%). MS: (M+H)$^+$ 685

Example 163c 2-(3-(5-(1-(2-(tert-Butyldimethylsilyloxy)ethyl)-1H-pyrazol-3-ylamino)-1-methyl-6-oxo-1,6-dihydropyridin-3-yl)-2-(hydroxymethyl)phenyl)-3,4,6,7,8,9-hexahydropyrazino[1,2-a]indol-1(2H)- 163c

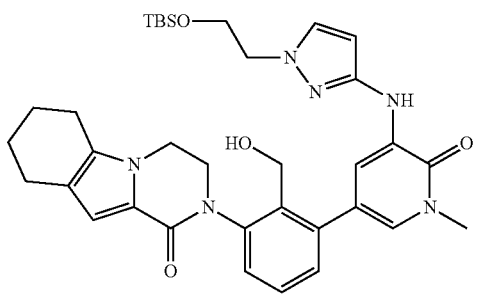

To a solution of 163b (460 mg, 0.67 mmol) in propan-2-ol (15 mL), tetrahydrofuran (15 mL), and water (5 mL) was added LiOH monohydrate (1.6 g, 67 mmol). The mixture was stirred at 30° C. for 2 h. It was then evaporated and the residue was purified by reverse phase Combi-flash eluting with 0.3% NH$_4$HCO$_3$ in 1:4 water/CH$_3$CN to give 163c as a brown solid (300 mg, 70%). MS: (M+H)$^+$ 643

A solution of 163c (300 mg, 0.50 mmol), camphorsulfonic acid (330 mg, 1.5 mmol) in methanol (30 mL) was stirred at room temperature for 3 h. It was then evaporated and the residue was purified by prep-HPLC to afford 163 as a brown solid (140 mg, 57%). MS: (M+H)$^+$ 529. $^1$H NMR (500 MHz, MeOD) δ 1.79 (s, 2H), 1.89 (s, 2H), 2.54-2.56 (t, J=5.5 Hz, 2H), 2.62-2.66 (m, 2H), 3.70 (s, 3H), 3.84-3.86 (t, J=5.5 Hz, 2H), 4.01-4.02 (m, 1H), 4.09-4.11 (t, J=5.5 Hz, 2H), 4.17-4.22 (m, 3H), 4.49-4.57 (m, 2H), 6.05-6.06 (d, 1H), 6.71 (s, 1H), 7.22-7.23 (d, 1H), 7.35-7.37 (d, 1H), 7.40-7.42 (d, 1H), 7.48-7.51 (m, 2H), 7.94-7.95 (d, 1H).

Example 164 5-[3-(5-{[5-(Azetidin-3-yl)-1H-pyrazol-3-yl]amino}-1-methyl-6-oxopyridin-3-yl)-5-fluoro-2-(hydroxymethyl)phenyl]-8-thia-5-azatricyclo-[7.4.0.0$^{2,7}$]trideca-1(9),2(7)-dien-6-one 164

Example 164b tert-Butyl 3-(2-Cyanoacetyl)azetidine-1-carboxylate 164b

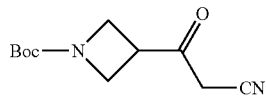

Following Example 136a, 1-tert-butyl 3-ethyl azetidine-1,3-dicarboxylate 164a was converted to 164b as a yellow oil (crude). LCMS: (M+H)$^+$ 424. $^1$H NMR (500 MHz, DMSO) δ 12.1 (dd, J=2, 1H), 8.38 (s, 1H), 8.04 (d, J=2.5, 1H), 7.36 (s, J=2.5, 1H), 6.06 (d, J=2.5, 1H), 4.18 (s, 2H), 3.80 (m, 1H), 3.49 (s, 3H), 1.39 (s, 9H).

Example 164c tert-Butyl 3-(5-Amino-1H-pyrazol-3-yl)azetidine-1-carboxylate 164c

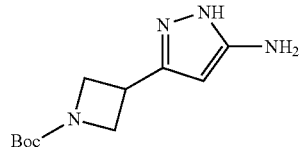

Following Example 136b, 164b was converted to 164c which was used directly in the next step without further purification.

Example 164d tert-Butyl 5-Amino-3-(1-(tert-butoxycarbonyl)azetidin-3-yl)-1H-pyrazole-1-carboxylate 164d

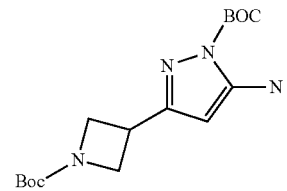

-continued

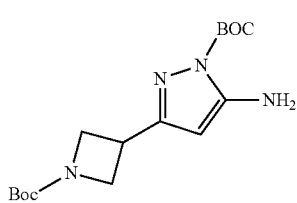

164d

Following Example 136c, 164c was converted to 164d in 26% yield.

Example 164e tert-Butyl 3-(5-(5-Bromo-1-methyl-2-oxo-1,2-dihydropyridin-3-ylamino)-1H-pyrazol-3-yl)azetidine-1-carboxylate 164e

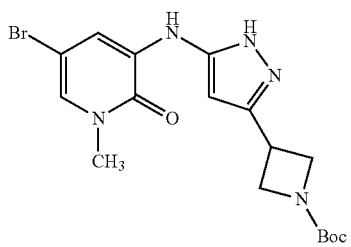

164c

Following Example 136d, 164d was converted to 164e in 50% yield.

Example 164e [2-(5-{[5-(Azetidin-3-yl)-1H-pyrazol-3-yl]tert-butoxycarbonylamino}-1-methyl-6-oxopyridin-3-yl)-4-fluoro-6-{6-oxo-8-thia-5-azatricyclo[7.4.0.0$^{2,7}$]trideca-1(9),2(7)-dien-5-yl}phenyl]methyl Acetate 164e

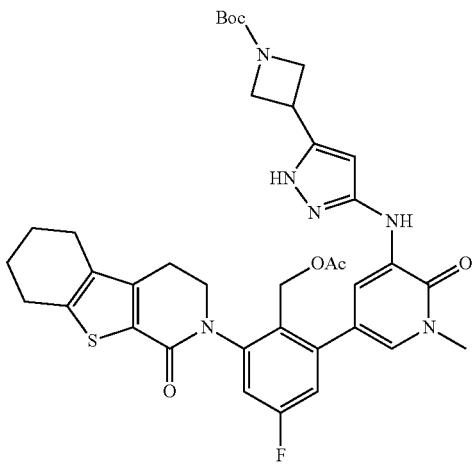

164e

Following Example 136e, 164d and (4-fluoro-2-{6-oxo-8-thia-5-azatricyclo[7.4.0.0$^{2,7}$]trideca-1(9),2(7)-dien-5-yl}-6-(4,4,5,5-tetramethyl-1,3,2-dioxaborolan-2-yl)phenyl) methyl acetate 112b were reacted to give 164e in 39% of yield.

Example 164f [2-(5-{[5-(Azetidin-3-yl)-1H-pyrazol-3-yl]amino}-1-methyl-6-oxopyridin-3-yl)-4-fluoro-6-{6-oxo-8-thia-5-azatricyclo[7.4.0.0$^{2,7}$]trideca-1(9),2(7)-dien-5-yl}phenyl]methyl Acetate 164f

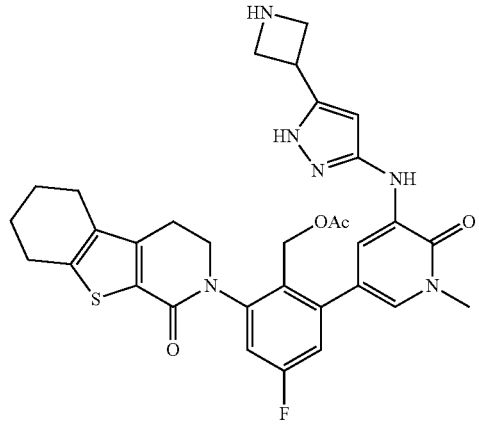

164f

To a solution of 164e (300 mg, 0.42 mmol) in dioxane (2 mL) at room temperature was added HCl/dioxane (4M, 6 mL) dropwise. The reaction mixture was stirred for 1 h. After the reaction was finished, it was concentrated to afford 164f (crude product) as a black solid, which was used in the next step without purification. LCMS: (M+H)$^+$ 617

Following Example 136, 164f was converted to 164 in 20% yield. LCMS: (M+H)$^+$ 575. $^1$H NMR (500 MHz, DMSO) δ 7.78 (s, 1H), 7.28 (d, J=1.5, 1H), 7.223 (s, 1H), 7.21 (s, 1H), 6.21 (s, 1H), 4.50 (m, 2H), 4.14 (m, 1H), 4.00 (m, 3H), 3.90 (m, 2H), 3.71 (s, 3H), 3.09 (m, 1H), 2.96 (m, 1H), 2.86 (m, 2H), 2.60 (m, 2H), 1.88 (m, 4H).

Example 165 2-(3-(5-(5-(Azetidin-3-yl)-1H-pyrazol-3-ylamino)-1-methyl-6-oxo-1,6-dihydropyridin-3-yl)-5-fluoro-2-(hydroxymethyl)phenyl)-3,4,6,7,8,9-hexahydropyrazino[1,2-a]indol-1(2H)-one 165

Example 165a tert-Butyl 3-(3-(5-(2-(Acetoxymethyl)-5-fluoro-3-(1-oxo-3,4,6,7,8,9-hexahydropyrazino[1,2-a]indol-2(1H)-yl)phenyl)-1-methyl-2-oxo-1,2-dihydropyridin-3-ylamino)-1H-pyrazol-5-yl)azetidine-1-carboxylate 165a

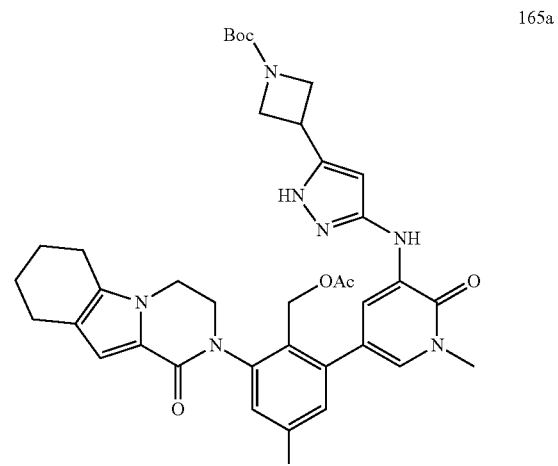

165a

Following Example 164f, 164e and 4-fluoro-2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 210d were reacted to give 165a in 20% yield. LCMS: (M+H)+ 700

Example 165b 2-(5-(5-(Azetidin-3-yl)-1H-pyrazol-3-ylamino)-1-methyl-6-oxo-1,6-dihydropyridin-3-yl)-4-fluoro-6-(1-oxo-3,4,6,7,8,9-hexahydropyrazino[1,2-a]indol-2(1H)-yl)benzyl Acetate 165b

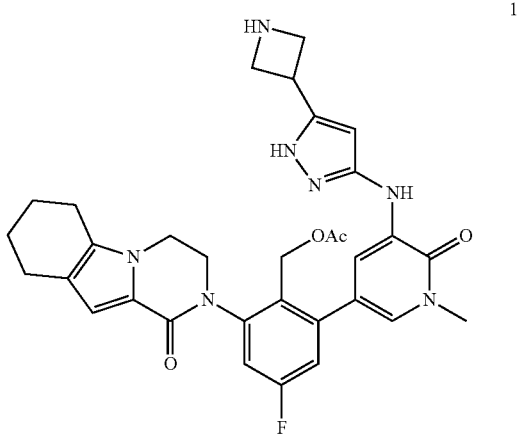

165b

Following Example 164g, 165a was converted to crude 165b which was used directly in the next step without further purification. LCMS: (M+H)+ 600

Following Example 164, 165b was converted to 165 in 40% (two steps). LCMS: (M+H)+ 558. $^1$H NMR (500 MHz, DMSO) δ 7.78 (s, 1H), 7.28 (d, J=1.5, 1H), 7.22 (s, 1H), 7.21 (s, 1H), 6.21 (s, 1H), 4.50 (m, 2H), 4.14 (m, 1H), 4.00 (m, 3H), 3.90 (m, 2H), 3.71 (s, 3H), 3.09 (m, 1H), 2.96 (m, 1H), 2.86 (m, 2H), 2.60 (m, 2H), 1.88 (m, 4H).

Example 166 2-(2-(Hydroxymethyl)-3-(1-methyl-6-oxo-5-(5,6,7,8-tetrahydro-1,6-naphthyridin-2-ylamino)-1,6-dihydropyridin-3-yl)phenyl)-3,4,6,7,8,9-hexahydropyrazino[1,2-a]indol-1(2H)-one 166

Example 166a tert-Butyl 2-(5-(2-(Acetoxymethyl)-3-(1-oxo-3,4,6,7,8,9-hexahydro-pyrazino[1,2-a]indol-2(1H)-yl)phenyl)-1-methyl-2-oxo-1,2-dihydropyridin-3-ylamino)-7,8-dihydro-1,6-naphthyridine-6(5H)-carboxylate 166a

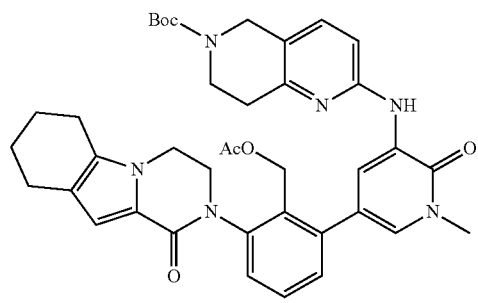 [SMILES: CC(=O)OCc1c(-c2cc(Nc3ccc4c(n3)CCN(C(=O)OC(C)(C)C)C4)c(=O)n(C)c2)cccc1N1CCn2c(cc3c2CCCC3)C1=O]

To a microwave tube equipped with a stirring bar, tert-butyl 2-(5-bromo-1-methyl-2-oxo-1,2-dihydropyridin-3-ylamino)-7,8-dihydro-1,6-naphthyridine-6(5H)-carboxylate 158c (300 mg, mmol), 2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 114a (352 mg, 0.758 mmol), Pd(PPh$_3$)$_4$ (39.8 mg, 0.035 mmol), Na$_2$CO$_3$ aqueous solution (1.0 N, 2.27 mL, 2.27 mmol), and 1,2-dimethoxyethane (3.5 mL) were added. The mixture was reacted in microwave at 130° C. for 10 min. methylene chloride (200 mL) was added and the resulting mixture was washed with water (30 mL×3), brine (30 mL×1), dried over MgSO$_4$, filtered, and removed solvent in vacuo. Silica gel column chromatography (methanol:methylene chloride=5:95) gave 166a.

To a round-bottomed flask equipped with a stirring bar, 166a and methylene chloride (10 mL) were added. The solution was cooled to 0° C. in an ice-water bath. TFA (1 mL) was added and the resulting solution was stirred overnight. All the volatiles were removed in vacuo, and to the bottle THF (10 mL), i-PrOH (10 mL), H$_2$O (10 mL), LiOH H$_2$O (1.00 g) were added. The resulting mixture was stirred at RT for 1 hr. All the solvent were removed in vacuo and the resulting residue was added to methylene chloride (200 mL), the solution was washed with water (×30 mL), brine (30 mL), dried over MgSO$_4$, filtered, and removed solvent in vacuo. Silica gel column chromatography (methanol:methylene chloride=10:90) gave 166 as a light brown solid, 53 mg. MS (ESI+) m/z 551.3 (M+H).

Example 167 10-[2-(Hydroxymethyl)-3-[1-methyl-6-oxo-5-(pyrimidin-4-ylamino)-1,6-dihydropyridin-3-yl]phenyl]-4,4-dimethyl-1,10-diazatricyclo[6.4.0.0$^{2,6}$]dodeca-2(6),7-dien-9-one 167

Example 167a (E)-Ethyl 3-(2-Chloro-4,4-dimethylcyclopent-1-enyl)acrylate 167a

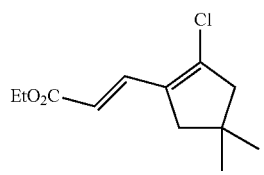

167a

The following two procedures were adapted from *Organic Preparations and Procedures Int.,* 29(4):471-498. A 500-mL single neck round bottomed flask equipped with a magnetic stirrer and nitrogen inlet was charged with 2-chloro-4,4-dimethylcyclopent-1-enecarbaldehyde (38 g, 240 mmol) in benzene (240 mL). To the solution was added ethoxycarbonylmethylene triphenylphosphorane (84 g, 240 mmol). The mixture was stirred for 14 h. After that time, the solvent was evaporated and the residue was triturated with hexanes (2 L) to extract the product away from the PPh$_3$ by-products. The organic layer was dried over sodium sulfate and concentrated in vacuo. The residue was purified by column chromatography using a 100% hexane—1:1 hexane/ethyl acetate gradient to afford a 37% yield (20 g) of 167a.

Example 167b Ethyl 5,5-Dimethyl-1,4,5,6-tetrahydrocyclopenta[b]pyrrole-2-carboxylate 167b

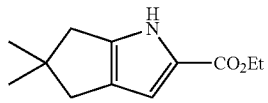

167b

A 250-mL single neck round bottomed flask equipped with a magnetic stirrer and nitrogen inlet was charged with 167a (17 g, 74 mmol) in DMSO (100 mL). To the solution was added sodium azide (9.6 g, 150 mmol). The mixture was then heated to 75° C. and stirred for 8 h. After cooling to rt, $H_2O$ (100 mL) and $CH_2Cl_2$ (200 mL) were added and the organic layer was separated. The aqueous layer was extracted with $CH_2Cl_2$ (50 mL). The combined organic layers were washed with brine, dried over sodium sulfate and concentrated in vacuo. The residue was purified by column chromatography using a 100% hexane—1:1 hexane/ethyl acetate gradient to afford a 37% yield (5.7 g) of 167b.

Example 167c Ethyl 1-(Cyanomethyl)-5,5-dimethyl-1,4,5,6-tetrahydrocyclopenta[b]pyrrole-2-carboxylate 167c

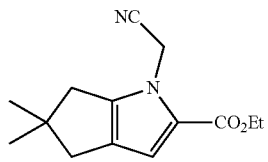

167c

A 250-mL single neck round bottomed flask equipped with a magnetic stirrer and nitrogen inlet was charged with 167b (6.2 g, 30 mmol) in DMF (57 mL). To the solution was added NaH (80% dispersion in mineral oil, 1.26 g, 42.1 mmol). The resulting mixture was stirred at rt for 90 min. After that time, bromoacetonitrile (2.94 mL, 42 mmol) was added. The mixture was stirred for 14 h. After that time, water (100 mL) and ethyl acetate (200 mL) were added and the organic layer was separated. The aqueous layer was extracted with ethyl acetate (2×50 mL). The combined organic layers were washed with brine, dried over sodium sulfate and concentrated in vacuo. The residue was purified by column chromatography to afford a 95% yield (7 g) of 167c.

Example 167d Ethyl 1-(2-Aminoethyl)-5,5-dimethyl-1,4,5,6-tetrahydrocyclopenta[b]pyrrole-2-carboxylate hydrochloride 167d

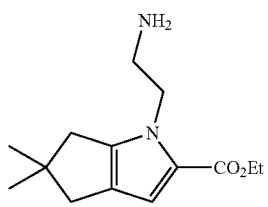

167d

A 500-mL Parr reactor bottle was purged with nitrogen and charged with 10% palladium on carbon (50% wet, 2.0 g dry weight), 167c (4.5 g, 18 mmol), 12% hydrochloric acid (9.2 mL, 37 mmol), ethyl acetate (80 mL) and ethanol (52 mL). The bottle was attached to a Parr hydrogenator, evacuated, charged with hydrogen gas to a pressure of 50 psi and shaken for 6 h. After this time, the hydrogen was evacuated, and nitrogen was charged into the bottle. Celite 521 (10.0 g) was added, and the mixture was filtered through a pad of Celite 521. The filter cake was washed with ethanol (2×50 mL), and the combined filtrates were concentrated to dryness under reduced pressure. The crude residue 167d was carried onto the next step without further purification.

Example 167e 4,4-Dimethyl-1,10-diazatricyclo[6.4.0.0$^{2,6}$]dodeca-2(6),7-dien-9-one 167e

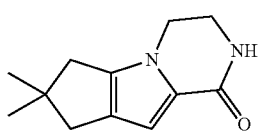

167e

A 100-mL single-neck round-bottomed flask equipped with a magnetic stirrer and nitrogen inlet was purged with nitrogen and charged with crude 167d (~18 mmol), sodium ethoxide (6.2 g, 92 mmol) and ethanol (120 mL). The mixture was stirred at 55° C. over night. After that time, the reaction mixture was concentrated under reduced pressure and the residue was partitioned between ethyl acetate (200 mL) and water (100 mL). The solution was filtered. The solid was washed with ethyl acetate (15 mL) to give 850 mg of 167e. The organic layer was separated, and the aqueous layer was extracted with ethyl acetate (2×100 mL). The combined organic layers were dried over sodium sulfate and concentrated under reduced pressure to near dryness. The solution was filtered and the solid (1.44 g) was washed with ethyl acetate (15 mL). The combined solids were dried under vacuum a afford 61% yield (2.3 g) of 167e.

Example 167f 2-Bromo-6-(9-oxo-4,4-dimethyl-1,10-diazatricyclo[6.4.0.0$^{2,6}$]dodeca-2(6),7-dien-10-yl)benzyl Acetate 167f

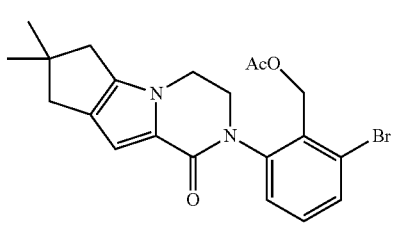

167f

A microwave tube equipped with a magnetic stirrer was charged with 167e (301 mg, 1.47 mmol), 2,6-dibromobenzyl acetate 104g (1.1 g, 3.0 mmol), CuI (140 mg, 0.7 mmol) $Cs_2CO_3$ (961 mg, 3.0 mmol), N',N',N',N'-tetramethylethylenediamine (0.22 mL, 1.5 mmol) and 1,2-dimethoxyethane (4.1 mL). The mixture was heated in microwave to 150° C. for 3 h. After this time, the mixture was filtered and the resulting solid was washed with 9:1 $CH_2Cl_2$/MeOH (50 mL). The combined organics were washed with brine (20 mL), dried over sodium sulfate, filtered and concentrated under reduced pressure. The resulting residue was purified by column chromatography eluting with a gradient of hexanes—ethyl acetate to afford a 32% yield (200 mg) of 167f.

Example 167g 10-[2-(Acetoxymethyl)-3-[1-methyl-6-oxo-5-(pyrimidin-4-ylamino)-1,6-dihydropyridin-3-yl]phenyl]-4,4-dimethyl-1,10-diazatricyclo[6.4.0.0²,⁶]dodeca-2(6),7-dien-9-one 167g

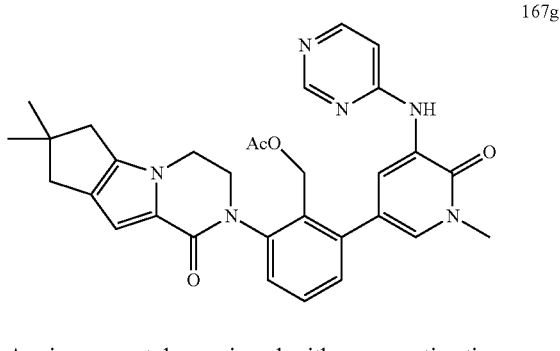

A microwave tube equipped with a magnetic stirrer was charged with 1-methyl-3-(pyrimidin-4-ylamino)-5-(4,4,5,5-tetramethyl-1,3,2-dioxaborolan-2-yl)pyridin-2(1H)-one 109c (210 mg, 0.64 mmol), 167f (140 mg, 0.3 mmol), 1,2-dimethoxyethane (4 mL) and 1M aqueous sodium carbonate (1 mL). After bubbling $N_2$ for 15 min, Pd(PPh₃)₄ (18 mg, 0.02 mmol) was added. The mixture was heated in microwave to 130° C. for 25 min. After this time, ethyl acetate (5 mL) and water (5 mL) were added. The separated aqueous layer was extracted with ethyl acetate (2×5 mL). The combined organics were washed with brine (10 mL), dried over sodium sulfate, filtered and concentrated under reduced pressure. The resulting residue was purified by column chromatography eluting with a gradient of CH₂Cl₂—60:35:5 CH₂Cl₂:diethyl ether:methanol to afford a 53% yield (93 mg) of 167g.

A 25 mL round bottom flask with a magnetic stirrer was charged with 167g (93 mg, 0.17 mmol), lithium hydroxide (35 mg, 0.8 mmol), THF (0.8 mL), isopropanol (0.8 mL) and water (1.7 mL). The mixture stirred at rt for 1 h. After this time, ethyl acetate (5 mL) and water (5 mL) were added. The separated aqueous layer was extracted with ethyl acetate (2×5 mL). The combined organics were washed with brine (10 mL), dried over sodium sulfate, filtered and concentrated under reduced pressure. The resulting residue was purified by column chromatography eluting with a gradient of CH₂Cl₂—60:35:5 CH₂Cl₂:diethyl ether:methanol to afford a 76% yield (23 mg) of 167. MS (ESI+) m/z 511.8 (M+H).

Example 168 2-(2-(Hydroxymethyl)-3-(1-methyl-5-(5-(1-methylazetidin-3-yl)-1H-pyrazol-3-ylamino)-6-oxo-1,6-dihydropyridin-3-yl)phenyl)-3,4,6,7,8,9-hexahydropyrazino[1,2-a]indol-1(2H)-one 168

Example 168a 3-(5-(Azetidin-3-yl)-1H-pyrazol-3-ylamino)-5-bromo-1-methylpyridin-2(1H)-one 168a

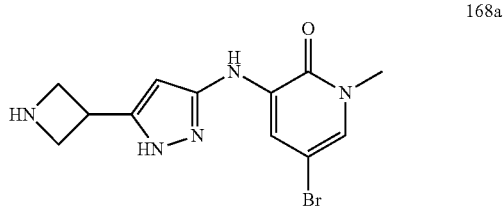 [SMILES: Cn1cc(Br)cc(Nc2cc(C3CNC3)[nH]n2)c1=O]

To solution of tert-butyl 3-(3-(5-bromo-1-methyl-2-oxo-1,2-dihydropyridin-3-ylamino)-1H-pyrazol-5-yl)azetidine-1-carboxylate 164e (1 g, 2.36 mmol) in dioxane (10 ml) at room temperature, was added HCl/dioxane (4M, 20 mL) dropwise. Then the reaction mixture was stirred for 1 h at room temperature. After the reaction was finished, it was concentrated to afford 168a as a yellow solid, which was used in the next step without purification. LCMS: (M+H)⁺ 325

Example 168b 5-Bromo-1-methyl-3-(5-(1-methylazetidin-3-yl)-1H-pyrazol-3-ylamino)pyridine-2(1H)-one 168b

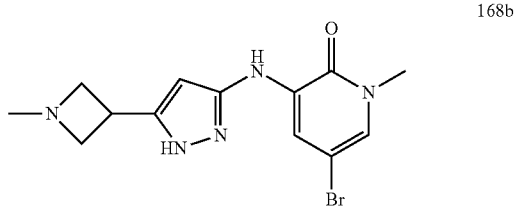

To a solution of 3-(5-(azetidin-3-yl)-1H-pyrazol-3-ylamino)-5-bromo-1-methylpyridin-2(1H)-one 168a (crude, 2.36 mmol) in methanol (30 mL) and acetic acid (5 mL) at 0° C., was added CH₂O (30% wt in H₂O) (12 g, 120 mmol), followed by the addition of NaBH₄ (1.8 g, 47.2 mmol) in small portions over the period of 1 h at 0° C. After the reaction was finished, the mixture was adjusted to pH>7 with 2N aq. NaOH. It was then extracted with methylene chloride (60 mL×3), dried over Na₂SO₄ and, concentrated to give a yellow solid, which was further purified on flash column eluting with 50:1 methylene chloride/methanol containing 0.5% triethylamine to afford 168b as a yellow solid (50%, two steps).

Example 168c 2-(1-Methyl-5-(5-(1-methylazetidin-3-yl)-1H-pyrazol-3-ylamino)-6-oxo-1,6-dihydropyridin-3-yl)-6-(1-oxo-3,4,6,7,8,9-hexahydropyrazino[1,2-a]indol-2(1H)-yl)benzyl Acetate 168c

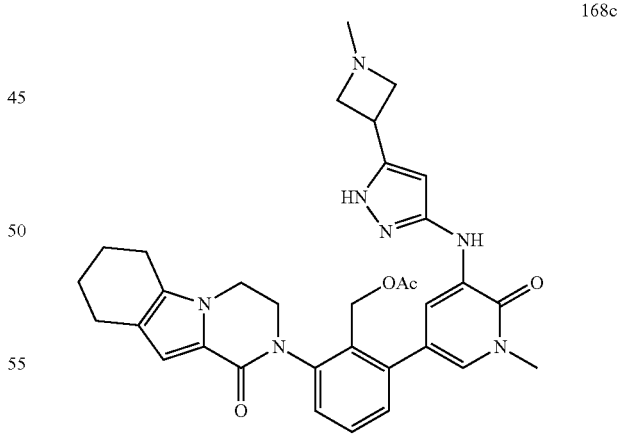

Following Example 136e, 168b and 2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 114a were reacted to give 168c in 20% yield.

Following Example 136, 168c was converted to 168 in 54% yield. LCMS: (M+H)⁺ 554. ¹H NMR (500 MHz, DMSO) δ 8.05 (s, 1H), 8.01 (s, 1H), 7.45 (t, J=8, 1H), 7.31 (m, 2H), 7.24 (d, J=2.5, 1H), 6.50 (s, 1H), 6.02 (s, 1H), 4.37 (m, 2H), 4.14 (m, 3H), 3.88 (m, 1H), 3.57 (s, 3H), 3.53 (m, 2H), 3.50 (m, 2H), 3.03 (m, 2H), 2.61 (m, 2H), 2.47 (m, 3H), 2.23 (s, 3H), 1.78 (m, 2H), 1.69 (m, 2H).

Example 169 5-[2-(Hydroxymethyl)-3-[1-methyl-6-oxo-5-({4H,6H,7H-pyrazolo[3,2-c][1,4]oxazin-2-yl}amino)-1,6-dihydropyridin-3-yl]phenyl]-8-thia-5-azatricyclo-[7.4.0.0²,⁷]trideca-1(9),2(7)-dien-6-one 169

Example 169a {2-[1-Ethyl-6-oxo-5-({4H,6H,7H-pyrazolo[3,2-c][1,4]oxazin-2-yl}amino)1,6-dihydropyridin-3-yl]-6-{6-oxo-8-thia-5-azatricyclo[7.4.0.0²,⁷]trideca-1(9),2(7)-dien-5-yl}phenyl}methyl Acetate 169a

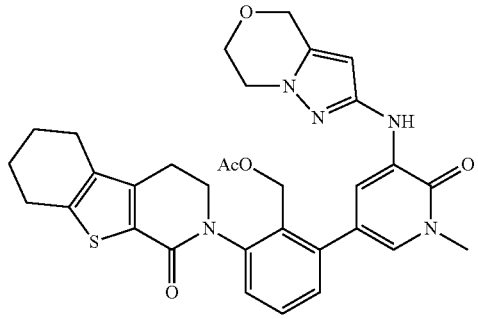 [SMILES: CC(=O)OCc1c(-c2cc(Nc3cc4n(n3)CCOC4)c(=O)n(C)c2)cccc1N1CCc2c(sc3c2CCCC3)C1=O]

A mixture of 5-bromo-3-(6,7-dihydro-4H-pyrazolo[5,1-c][1,4]oxazin-2-ylamino)-1-methylpyridin-2(1H)-one 110c (500 mg, 1.54 mmol), (2-{6-oxo-8-thia-5-azatricyclo-[7.4.0.0²,⁷]trideca-1(9),2(7)-dien-5-yl}-6-(4,4,5,5-tetramethyl-1,3,2-dioxaborolan-2-yl)phenyl)methyl acetate 111a (750 mg, 1.56 mmol), PdCl₂(dppf) (170 mg, 0.23 mmol), K₃PO₄ (150 mg) and sodium acetate (60 mg) in MeCN (25 mL) and water (5 mL) was heated at reflux for 2 h. The solvent was evaporated in vacuo and the residue was purified on reverse phase Combi-flash to give 169a (369 mg, 40%). MS: [M+H]⁺ 600.

A mixture of 169a (440 mg, 0.73 mmol) and LiOH hydrate (308 mg, 7.3 mmol) in isopropanol (20 mL) and H₂O (4 mL) was stirred at 30° C. for 2 h. The mixture was evaporated in vacuo and the residue was extracted with ethyl acetate (20 mL×2). The combined extracts were concentrated under reduced pressure. And the residue was purified on pre-HPLC to give 169 (104 mg, 26%). MS: [M+H]⁺ 558. ¹H NMR (500 MHz, CDCl3) δ 7.93 (s, 1H), 7.46-7.39 (m, 3H), 7.31-7.24 (m, 3H), 5.73 (s, 1H), 4.78 (s, 2H), 4.61 (d, J=11.5, 1H), 4.42-4.20 (m, 2H), 4.14-3.98 (m, 4H), 3.90-3.82 (m, 1H), 3.69 (s, 3H), 3.04-2.80 (m, 4H), 2.60-2.46 (m, 2H), 1.94-1.82 (m, 4H).

Example 170 5-[2-(Hydroxymethyl)-3-[1-methyl-5-({5-[(morpholin-4-yl)carbonyl]pyridine-2-yl}amino)-6-oxo-1,6-dihydropyridin-3-yl]phenyl]-8-thia-5-azatricyclo[7.4.0.0²,⁷]trideca-1(9),2(7)-dien-6-one 170

Example 170a (6-Aminopyridin-3-yl)(morpholino)methanone 170a

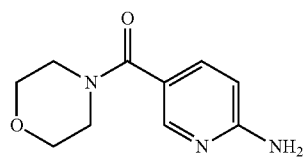

To a solution of morpholine (9.00 g, 103 mmol) in EtOH (400 mL) was added EDCI (10.0 g, 52.2 mmol), HOBt (7.00 g 51.8 mmol), and 6-aminonicotinic acid (6.00 g, 43.4 mmol). After stirring for 18 h, the resulting suspension was filtered. The solid was triturated with a mixture of MeOH (100 mL) and methylene chloride (100 mL) to afford 170a as a white solid (2.7 g, 30%). LCMS: (M+H)⁺ 208

Example 170b 5-Bromo-1-methyl-3-(5-(morpholine-4-carbonyl)pyridin-2-ylamino)pyridine-2(1H)-one 170b

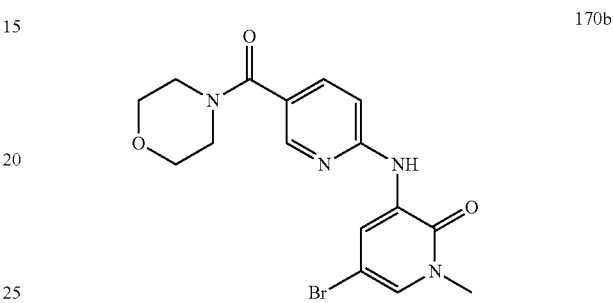

Following Example 136e, 170a and 3,5-dibromo-1-methylpyridin-2(1H)-one were reacted to give 170b in 21% yield. LCMS: (M+H)⁺ 394. ¹H NMR (500 MHz, MeOD) δ 8.84 (d, J=2.5, 1H), 8.42 (d, J=2, 1H), 7.72 (m, 1H), 7.42 (d, J=2, 1H), 7.11 (d, J=8.5, 1H), 3.72 (m, 8H), 3.63 (s, 3H).

Example 170c {2-[1-Methyl-5-({5-[(morpholin-4-yl)carbonyl]pyridin-2-yl}amino)-6-oxo-1,6-dihydropyridin-3-yl]-6-{6-oxo-8-thia-5-azatricyclo[7.4.0.0²,⁷]trideca-1(9),2(7)-dien-5-yl}phenyl}methyl Acetate 170c

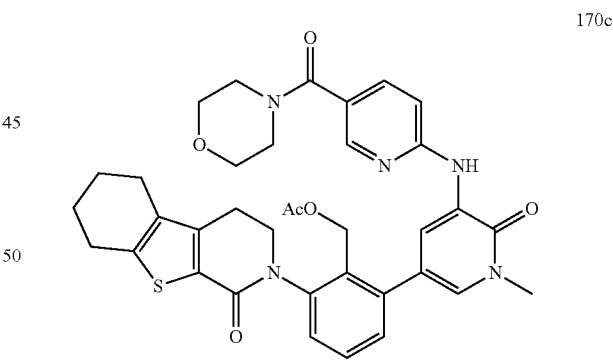

Following Example 136e, 170b and (2-{6-oxo-8-thia-5-azatricyclo[7.4.0.0²,⁷]trideca-1(9),2(7)-dien-5-yl}-6-(4,4,5,5-tetramethyl-1,3,2-dioxaborolan-2-yl)phenyl)methyl acetate 111a were reacted to give 170c in 65% yield. LCMS: (M+H)⁺ 668

Following Example 148, 170c was converted to 170 in 71% yield. LCMS: (M+H)⁺ 626. ¹H NMR (500 MHz, DMSO) δ 8.95 (s, 1H), 8.72 (d, J=2, 1H), 8.25 (d, J=2, 1H), 7.64 (dd, J=8.5, 1H), 7.45 (m, 2H), 7.35 (m, 3H), 4.85 (t, J=4, 1H), 4.35 (m, 2H), 4.03 (m, 1H), 3.88 (m, 1H), 3.59 (m, 7H), 3.49 (m, 4H), 2.98 (m, 1H), 2.85 (m, 1H), 2.77 (m, 2H), 2.54 (m, 2H), 1.79 (m, 4H).

Example 171 2-(2-(Hydroxymethyl)-3-(1-methyl-5-(5-(morpholine-4-carbonyl)pyridin-2-ylamino)-6-oxo-1,6-dihydropyridin-3-yl)phenyl)-3,4,6,7,8,9-hexahydropyrazino[1,2-a]indol-1(2H)-one 171

Example 171a 2-(1-Methyl-5-(5-(morpholine-4-carbonyl)pyridin-2-ylamino)-6-oxo-1,6-dihydropyridin-3-yl)-6-(1-oxo-3,4,6,7,8,9-hexahydropyrazino[1,2-a]indol-2(1H)-yl)benzyl acetate 171a

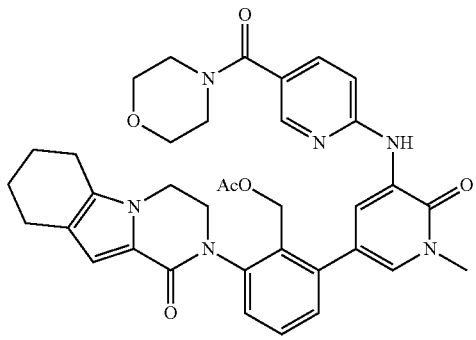

171a

Following Example 136d, 5-bromo-1-methyl-3-(5-(morpholine-4-carbonyl)pyridin-2-ylamino)pyridin-2(1H)-one 170a and 2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 114a were reacted to give 171a in 27% yield. LCMS: (M+H)+ 651

Following Example 170, 171a was converted to 171 in 60% yield. LCMS: (M+H)+ 609. ¹H NMR (500 MHz, DMSO) δ 8.85 (d, J=2, 1H), 8.32 (d, J=1.5, 1H), 7.71 (dd, J=8.5, 1H), 7.53 (m, 1H), 7.43 (m, 3H), 7.35 (m, 3H), 7.11 (d, J=8, 1H), 6.72 (s, 1H), 4.56 (m, 2H), 4.21 (s, 3H), 4.03 (m, 1H), 3.71 (m, 11H), 2.65 (m, 2H), 2.55 (m, 2H), 1.89 (m, 2H), 1.80 (m, 1H).

Example 172 2-(2-(Hydroxymethyl)-3-(1-methyl-5-(5-(1-methylazetidin-3-yl)pyridin-2-ylamino)-6-oxo-1,6-dihydropyridin-3-yl)phenyl)-3,4,6,7,8,9-hexahydropyrazino[1,2-a]indol-1(2H)-one 172

Example 172a 5-Bromo-1-methyl-3-(5-(1-methylazetidin-3-yl)pyridin-2-ylamino)pyridine-2(1H)-one 172a

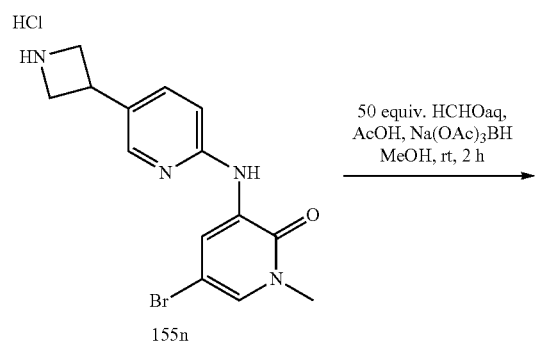

155n 50 equiv. HCHOaq,
AcOH, Na(OAc)₃BH
MeOH, rt, 2 h

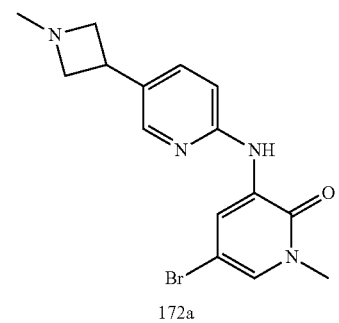

172a

A mixture of 3-(5-(azetidin-3-yl)pyridin-2-ylamino)-5-bromo-1-methylpyridin-2(1H)-one 155n (469 mg, 1.4 mmol), 37% aqueous formaldehyde solution (4 g, 50 mmol), NaBH₃CN (261 mg, 4.2 mmol), and 1M zinc chloride in 1,2-diethoxyethane (4 mL, 4.2 mmol) and methanol (40 mL) was stirred for 2 hours at room temperature. The mixture was added to water (20 mL) and extracted with methylene chloride (50 mL×3). The organic layers were concentrated under reduced pressure. The residue was purified by column chromatography eluting with 10:1 methylene chloride/methanol to give 172a as a yellow solid (0.3 g, 83%). MS: [M+H]+ 348.

Example 172b 2-(1-Methyl-5-(5-(1-methylazetidin-3-yl)pyridin-2-ylamino)-6-oxo-1,6-dihydropyridin-3-yl)-6-(1-oxo-3,4,6,7,8,9-hexahydropyrazino[1,2-a]indol-2(1H)-yl)benzyl Acetate 172b A sealed tube was charged with the mixture of 172a (167 mg, 0.48 mmol), 2-(2-(hydroxymethyl)-3-(4,4,5,5-tetramethyl-1,3,2-dioxaborolan-2-yl)phenyl)-3,4,6,7,8,9-hexahydropyrazino[1,2-a]indol-1(2H)-one 114a (231 mg, 0.48 mmol), Pd(dppf)Cl₂ (39 mg, 0.048 mmol), and Na₂CO₃ (101 mg, 0.96 mmol) in N,N-dimethylformamide (18 mL). The system was evacuated and then refilled with N₂. And the reaction mixture was heated at 150° C. under microwave irradiation for 1 h. Then, the mixture was cooled to room temperature and filtered. The filtrate was concentrated under reduced pressure and the resulting residue was purified by column chromatography eluting with 15:1 methylene chloride/methanol to give 172b as a brown solid (140 mg, 50%). MS: [M+H]+ 606.

To a solution of 172b (150 mg, 0.25 mol) in THF/isopropyl acetate/H₂O (6 mL/6 mL/2 mL) was added LiOH (346 mg, 14 mmol) while stirring at room temperature. This mixture was stirred for 2 h. Then, 20 mL of water was added and the mixture was extracted with ethyl acetate (60 mL×3). The combined organic layer was dried with Na₂SO₄ and concentrated to give a yellow solid, which was further purified by prep-HPLC to afford 172 as a white solid (50 mg, 35%). MS: [M+H]+ 565. ¹H NMR (500 MHz, DMSO) δ 8.66 (s, 1H), 8.54 (s, 1H), 8.10 (s, 1H), 7.65 (d, J=8, 1H), 7.46 (m, 1H), 7.31 (m, 4H), 6.51 (s, 1H), 4.84 (s, 1H), 4.33 (m, 2H), 4.13 (m, 3H), 3.85 (m, 1H), 3.59 (s, 3H), 3.53 (m, 2H), 3.35 (m, 1H), 3.02 (m, 2H), 2.60 (m, 2H), 2.46 (m, 2H), 2.23 (s, 3H), 1.77 (m, 4H).

Example 173 10-[2-(hydroxymethyl)-3-(1-methyl-5-{[5-(4-methylpiperazin-1-yl)pyridin-2-yl]amino}-6-oxo-1,6-dihydropyridin-3-yl)phenyl]-4,4-dimethyl-1,10-diazatricyclo[6.4.0.0$^{2,6}$]dodeca-2(6),7-dien-9-one 173

Example 173a 10-[2-(Acetoxymethyl)-3-(1-methyl-5-{[5-(4-methylpiperazin-1-yl)pyridin-2-yl]amino}-6-oxo-1,6-dihydropyridin-3-yl)phenyl]-4,4-dimethyl-1,10-diazatricyclo[6.4.0.0$^{2,6}$]dodeca-2(6),7-dien-9-one 173a In a 10-mL glass vessel equipped with a magnetic stirring bar were placed 1-methyl-3-[5-(4-methyl-piperazin-1-yl)-pyridin-2-ylamino]-5-(4,4,5,5-tetramethyl-[1,3,2]dioxaborolan-2-yl)-1H-pyridin-2-one 197e (210 mg, 0.49 mmol), 10-[2-(acetoxymethyl)-3-bromophenyl]-4,4-dimethyl-1,10-diazatricyclo[6.4.0.0$^{2,6}$]dodeca-2(6),7-dien-9-one 167f (143 mg, 0.33 mmol), Pd(PPh$_3$)$_4$ (30 mg, 0.0.26 mmol) in 2 N Na$_2$CO$_3$ (2 mL) and 1,2-dimethoxyethane (5 mL). The vessel was sealed with a septum and placed into the microwave cavity. After the reaction mixture was stirred at 125° C. for 7 min., it was purified by flash chromatography (dichloromethane:methanol, 85:15) to give 26% (50 mg) of 173a as a solid.

A 100-mL, single-necked, round-bottomed flask equipped with a magnetic stirring bar was charged with 173a (50 mg, 0.077 mmol), LiOH.H$_2$O (20 mg, 0.83 mmol), THF (2 mL), isopropanol (2 mL), and water (2 mL). After the reaction mixture was stirred at room temperature for 3 h, it was partitioned between dichloromethane (5 mL) and water (5 mL), and the organic phase was extracted with dichloromethane (3×5 mL). The combined organic phases were washed with water (5 mL×2) and brine (5 mL×1), dried (Na$_2$SO$_4$), and concentrated. The crude product was re-dissolved in dichloromethane (3 mL). To this solution was added hexane (10 mL) and the resulting precipitates were filtered to give 75% yield (35 mg) of 173. MS(ESI$^+$) m/z 608.4 (M+H).

Example 174 2-(2-(hydroxymethyl)-3-(4-methyl-5-oxo-6-(1,2,3,4-tetrahydroisoquinolin-6-ylamino)-4,5-dihydropyrazin-2-yl)phenyl)-3,4,6,7,8,9-hexahydropyrazino[1,2-a]indol-1(2H)-one 174

Example 174a tert-Butyl 6-(6-(2-(Acetoxymethyl)-3-(1-oxo-3,4,6,7,8,9-hexahydropyrazino[1,2-a]indol-2(1H)-yl)phenyl)-4-methyl-3-oxo-3,4-dihydropyrazin-2-ylamino)-3,4-dihydroisoquinoline-2(1H)-carboxylate 174a

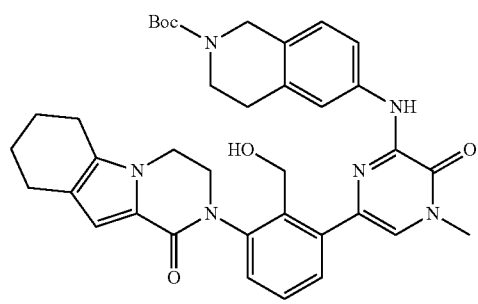 [SMILES: Cn1cc(-c2cccc(N3CCn4c(cc5c4CCCC5)C3=O)c2CO)nc(Nc2ccc3c(c2)CCN(C(=O)OC(C)(C)C)C3)c1=O]

To a microwave tube equipped with a stirring bar, tert-butyl 6-(6-bromo-4-methyl-3-oxo-3,4-dihydropyrazin-2-ylamino)-3,4-dihydroisoquinoline-2(1H)-carboxylate 120a (300 mg, 0.689 mmol), 114a (352 mg, 0.758 mmol), Pd(PPh$_3$)$_4$ (39.8 mg, 0.0345 mmol), Na$_2$CO$_3$ aqueous solution (1.0 N, 2.27 mL, 2.27 mmol), 1,2-dimethoxyethane (3.5 mL) were added. The mixture was reacted in microwave at 130° C. for 10 min. methylene chloride (200 mL) was added and the resulting mixture was washed with water (30 mL×3), brine (30 mL×1), dried over MgSO$_4$, filtered, and removed solvent in vacuo. Silica gel column chromatography (methanol:methylene chloride=5:95) gave 174a.

To a round-bottomed flask equipped with a stirring bar, 174a and methylene chloride (50 mL) were added. The solution was cooled to 0° C. in an ice-water bath. TFA (1 mL) was added and the resulting solution was stirred overnight. Removed all the volatiles in vacuo, and to the bottle THF (10 mL), isopropanol (10 mL), water (10 mL), LiOH monohydrate (1.00 g) were added. The resulting mixture was stirred at RT for 1 hr. The solvent was removed in vacuo and the resulting residue was added to methylene chloride (200 mL), the solution was washed with water (3 30 mL), brine (30 mL), dried over MgSO$_4$, filtered, and removed solvent in vacuo. Silica gel column chromatography (methanol:methylene chloride=10:90) gave 174 as a yellow solid, 28 mg. MS (ESI+) m/z 551.4 (M+H).

Example 175 10-[2-(Hydroxymethyl)-3-(1-methyl-6-oxo-5-{4H,6H,7H-pyrazolo[3,2-c][1,4]oxazin-2-ylamino}-1,6-dihydropyridin-3-yl)phenyl]-4,4-dimethyl-1,10-diazatricyclo[6.4.0.0$^{2,6}$]dodeca-2(6),7-dien-9-one 175

Example 175a 3-(6,7-Dihydro-4H-pyrazolo[5,1-c][1,4]oxazin-2-ylamino)-1-methyl-5-(4,4,5,5-tetramethyl-1,3,2-dioxaborolan-2-yl)pyridin-2(1H)-one 175a

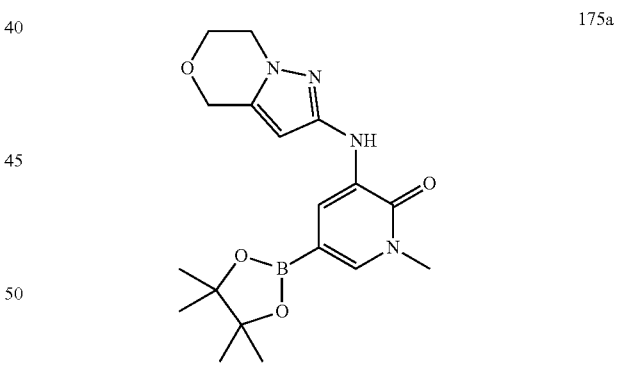

A sealed tube equipped with a magnetic stirrer was charged with 5-bromo-3-(6,7-dihydro-4H-pyrazolo[5,1-c][1,4]oxazin-2-ylamino)-1-methylpyridin-2(1H)-one (110c) (250 mg, 0.77 mmol), 4,4,4',4',5,5,5',5'-octamethyl-2,2'-bi(1,3,2-dioxaborolane) (290 mg, 1.2 mmol), potassium acetate (230 mg, 2.3 mmol) and 1,4-dioxane (5.5 mL). After bubbling nitrogen through the resulting suspension for 30 min, [1,1'-bis(diphenyl-phosphino)ferrocene]dichloropalladium(II) complex with CH$_2$Cl$_2$ (Pd Cl$_2$dppf:CH$_2$Cl$_2$ (1:1), 63 mg, 0.08 mmol) was then added, and the reaction was stirred at 105° C. for 90 min. After this time, the mixture was cooled to ambient temperature, partition between water (20 mL) and ethyl acetate (20 mL). The separated aqueous layer was extracted with yl acetate (2×10 mL). The combined organics were washed with brine (30 mL), dried over sodium sulfate, filtered and concentrated under reduced pressure. The resulting crude 175a was used in the next step without further purification.

Example 175b 10-[2-(Acetoxymethyl)-3-(1-methyl-6-oxo-5-{4H,6H,7H-pyrazolo[3,2-c][1,4]oxazin-2-ylamino}-1,6-dihydropyridin-3-yl)phenyl]-4,4-dimethyl-1,10-diazatricyclo[6.4.0.0²,⁶]dodeca-2(6),7-dien-9-one 175b

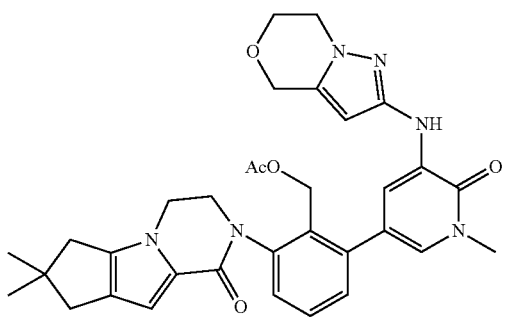

A microwave tube equipped with a magnetic stirrer was charged with 175a (120 mg, 0.31 mmol), 167f (130 mg, 0.3 mmol), 1,2-dimethoxyethane (4 mL) and 1M aqueous sodium carbonate (1 mL). After bubbling $N_2$ for 15 min, Pd(PPh$_3$)$_4$ (18 mg, 0.02 mmol) was added. The mixture was heated in microwave to 130° C. for 10 min. After this time, 1 acetate (5 mL) and water (5 mL) were added. The separated aqueous layer was extracted with 1 acetate (2×5 mL). The combined organics were washed with brine (10 mL), dried over sodium sulfate, filtered and concentrated under reduced pressure. The resulting residue was purified by column chromatography eluting with a gradient of CH$_2$Cl$_2$—60:35:5 CH$_2$Cl$_2$:diethyl ether:methanol to afford a 74% yield (140 mg) of 175b A 25 mL round bottom flask with a magnetic stirrer was charged with 175b (140 mg, 0.23 mmol), lithium hydroxide (49 mg, 1.2 mmol), THF (1.2 mL), i-PrOH (1.2 mL) and water (2.4 mL). The mixture stirred at rt for 90 min. After this time, ethyl acetate (5 mL) and water (5 mL) were added. The separated aqueous layer was extracted with ethyl acetate (2×5 mL). The combined organics were washed with brine (10 mL), dried over sodium sulfate, filtered and concentrated under reduced pressure. The resulting residue was purified by column chromatography eluting with a gradient of CH$_2$Cl$_2$—60:35:5 CH$_2$Cl$_2$:diethyl ether:methanol to afford a 79% yield (100 mg) of 175. MS (ESI+) m/z 555.3 (M+H).

Example 176 2-(2-(Hydroxymethyl)-3-(5-(5-(methoxymethyl)-1-methyl-1H-pyrazol-3-ylamino)-1-methyl-6-oxo-1,6-dihydropyridin-3-yl)phenyl)-3,4,6,7,8,9-hexahydropyrazino[1,2-a]indol-1(2H)-one 176

Example 176a
5-(Methoxymethyl)-1-methyl-3-nitro-1H-pyrazole 176a

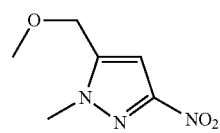

A 250-mL single-neck round-bottomed flask equipped with a magnetic stirrer and reflux condenser was charged with CH$_3$OH (50 mL), 5-(bromomethyl)-1-methyl-3-nitro-1H-pyrazole 156d (8.8 g, 40 mmol) and CH$_3$ONa (4.3 g, 80 mmol). The reaction mixture was heated at reflux for 2 h. After this time the reaction was cooled to room temperature and concentrated. The residue was partitioned between ethyl acetate (60 mL) and water (60 mL). The aqueous layer was separated and extracted with ethyl acetate (50 mL×2). The organic layers were combined, washed with brine (50 mL), and dried over sodium sulfate. The drying agent was removed by filtration and the filtrate was concentrated under reduced pressure to afford 176a as a yellow oil (6.1 g, 90%). LCMS: [M+H]⁺ 172.

Example 176b
5-(Methoxymethyl)-1-methyl-1H-pyrazol-3-amine 176b

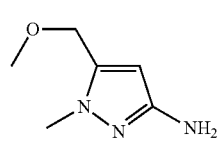

A 250-mL single-neck round-bottomed flask equipped with a magnetic stirrer was charged with 176a (4 g, 23 mmol), Pd/C (1 g) and C$_2$H$_5$OH (100 mL). The mixture was hydrogenated at room temperature for 15 h. It was then filtered and the filtrate was concentrated under reduced pressure to afford 176b as a yellow oil (3.3 g, 99%), which was used in the next step without further purification. MS: [M+H]⁺ 142.

Example 176c 5-Bromo-3-(5-(methoxymethyl)-1-methyl-1H-pyrazol-3-ylamino)-1-methylpyridin-2(1H)-one 176c

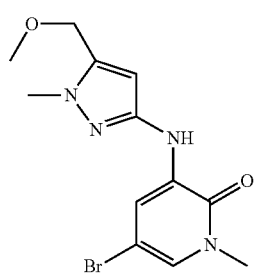

Following Example 148a, 1.7 g of 176b and 3.2 g of 3,5-dibromo-1-methylpyridin-2(1H)-one were reacted to give 176c as a yellow solid (2.8 g, 70%). MS: [M+H]⁺ 327. ¹H NMR (500 MHz, CDCl3) δ 7.86 (d, J=2.5, 1H), 7.38 (s, 1H), 6.88 (d, J=2.5, 1H), 5.86 (s, 1H), 4.41 (s, 2H), 3.82 (s, 3H), 3.58 (s, 3H), 3.36 (s, 3H).

Example 176d 2-(5-(5-(Methoxymethyl)-1-methyl-1H-pyrazol-3-ylamino)-1-methyl-6-oxo-1,6-dihydropyridin-3-yl)-6-(1-oxo-3,4,6,7,8,9-hexahydropyrazino[1,2-a]indol-2(1H)-yl)benzyl Acetate 176d

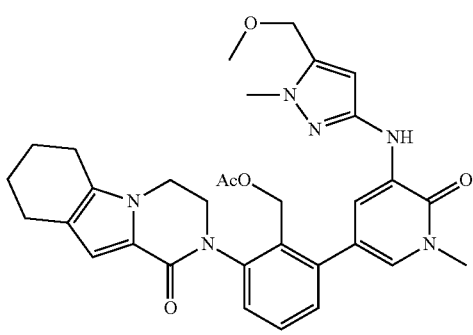

Following Example 148b, 557 mg of 2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 114a and 327 mg of 5-bromo-3-(5-(methoxymethyl)-1-methyl-1H-pyrazol-3-ylamino)-1-methylpyridin-2(1H)-one 176c were reacted to give 176d as a yellow solid (420 mg, 72%). LCMS: [M+H]$^+$ 585

Following Example 148, 240 mg of 176d was converted to 176 as a white solid (133 mg, 60%). LCMS: [M+H]$^+$ 542. $^1$H NMR (500 MHz, CDCl3) δ 7.91 (d, J=2, 1H), 7.43 (m, 3H), 7.30 (d, J=2, 1H), 7.23 (s, 1H), 6.85 (s, 1H), 5.96 (s, 1H), 4.60 (d, J=6, 1H), 4.40 (m, 3H), 4.16 (m, 3H), 3.94 (m, 1H), 3.76 (s, 3H), 3.69 (s, 3H), 3.34 (s, 3H), 2.60 (m, 4H), 1.89 (m, 2H), 1.78 (m, 2H).

Example 177 5-[2-(Hydroxymethyl)-3-(5-{[5-(methoxymethyl)-1-methyl-1H-pyrazol-3-yl]amino}-1-methyl-6-oxo-1,6-dihydropyridin-3-yl)phenyl]-8-thia-5-azatricyclo[7.4.0.0$^{2,7}$]trideca-1(9),2(7)-dien-6-one 177

Example 177a [2-(5-{[5-(Methoxymethyl)-1-methyl-1H-pyrazol-3-yl]amino}-1-methyl-6-oxo-1,6-dihydropyridin-3-yl)-6-{6-oxo-8-thia-5-azatricyclo[7.4.0.0$^{2,7}$]-trideca-1(9),2(7)-dien-5-yl}phenyl]methyl Acetate 177a

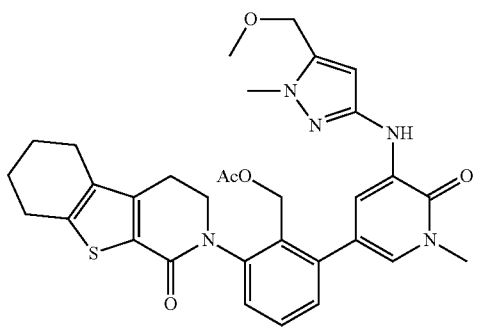

Following Example 176d, 327 mg of 5-bromo-3-(5-(methoxymethyl)-1-methyl-1H-pyrazol-3-ylamino)-1-methylpyridin-2(1H)-one 176b and 481 mg of 111a were reacted to give 177a as a yellow solid (420 mg, 70%). LCMS: [M+H]$^+$ 602

Following Example 176, 240 mg of 177a was converted to 177 as a white solid (112 mg, 50%). LCMS: [M+H]$^+$ 560. $^1$H NMR (500 MHz, CDCl3) δ 7.90 (s, 1H), 7.44-7.38 (m, 3H), 7.30-7.24 (m, 2H), 5.94 (s, 1H), 4.62 (d, J=11.5, 1H), 4.37 (m, 3H), 4.26 (d, J=10.5, 1H), 4.05 (m, 1H), 3.87 (m, 1H), 3.75 (s, 3H), 3.68 (s, 3H), 3.34 (s, 3H), 2.85 (m, 4H), 2.54 (s, 2H), 1.89 (s, 5H).

Example 178 2-(5-fluoro-2-(hydroxymethyl)-3-(5-(5-(methoxymethyl)-1-methyl-1H-pyrazol-3-ylamino)-1-methyl-6-oxo-1,6-dihydropyridin-3-yl)phenyl)-3,4,6,7,8,9-hexahydropyrazino[1,2-a]indol-1(2H)-one 178

Example 178a 4-Fluoro-2-(5-(5-(methoxymethyl)-1-methyl-1H-pyrazol-3-ylamino)-1-methyl-6-oxo-1,6-dihydropyridin-3-yl)-6-(1-oxo-3,4,6,7,8,9-hexahydropyrazino[1,2-a]indol-2(1H)-yl)benzyl Acetate 178a A sealed tube was charged with the mixture of 4-fluoro-2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 210d (230 mg, 0.48 mmol), 5-bromo-3-(5-(methoxymethyl)-1-methyl-1H-pyrazol-3-ylamino)-1-methylpyridin-2(1H)-one 176c (156 mg, 0.48 mmol), Pd(dppf)Cl$_2$ (39 mg, 0.048 mmol), Na$_2$CO$_3$ (101 mg, 0.96 mmol) in DMF (18 mL). The system was evacuated and then refilled with N$_2$. And the reaction mixture was heated at 110° C. for 2 h. Then, the mixture was cooled to room temperature and filtered. The filtrate was concentrated under reduced pressure and the resulting residue was purified by column chromatography eluting with 15:1 methylene chloride/methanol to give 178a as a brown solid (160 mg, 53%). MS: [M+H]$^+$ 603.

To a solution of 178a (160 mg, 0.27 mol) in THF/iPA/H$_2$O (6 mL/6 mL/2 mL) was added LiOH (346 mg, 14 mmol) while stirring at room temperature. This mixture was stirred for 2 h. Then, 20 mL water was added and the mixture was extracted with ethyl acetate (60 mL×3). The combined organic layer was dried with Na$_2$SO$_4$ and concentrated to give a yellow solid, which was further purified by prep-HPLC to afford 178 as a white solid (60 mg, 40%). LCMS: [M+H]$^+$ 561. $^1$H NMR (500 MHz, DMSO) δ 8.16 (s, 1H), 7.99 (m, 1H), 7.32 (m, 2H), 7.18 (m, 1H), 6.52 (s, 1H), 6.11 (s, 1H), 4.89 (m, 1H), 4.38 (m, 2H), 4.31 (m, 2H), 4.17 (m, 3H), 3.90 (m, 1H), 3.64 (s, 3H), 3.57 (s, 3H), 3.26 (s, 3H), 2.63 (m, 2H), 2.51 (m, 2H), 1.70 (m, 4H).

Example 179 5-[2-(Hydroxymethyl)-3-(1-methyl-5-{[5-(1-methylazetidin-3-yl)pyridin-2-yl]amino}-6-oxo-1,6-dihydropyridin-3-yl)phenyl]-8-thia-5-azatricyclo[7.4.0.0²,⁷]-trideca-1(9),2(7)-dien-6-one 179

Example 179a [2-(1-Methyl-5-{[5-(1-methylazetidin-3-yl)pyridin-2-yl]amino}-6-oxo-1,6-dihydropyridin-3-yl)-6-{6-oxo-8-thia-5-azatricyclo[7.4.0.0²,⁷]tridec-1(9),2(7)-dien-5-yl}phenyl]methyl Acetate 179a

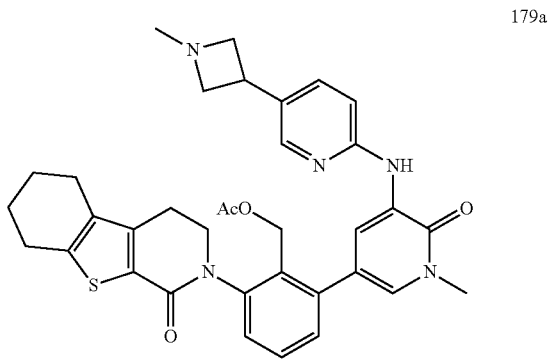 [SMILES: CC(=O)OCc1c(-c2cc(Nc3ccc(C4CN(C)C4)cn3)c(=O)n(C)c2)cccc1N1CCc2c(sc3c2CCCC3)C1=O]

Following Example 176d, 5-bromo-1-methyl-3-(5-(1-methylazetidin-3-yl)pyridin-2-ylamino)pyridin-2(1H)-one 172a and (2-{6-oxo-8-thia-5-azatricyclo[7.4.0.0²,⁷]tridec-1(9),2(7)-dien-5-yl}-6-(4,4,5,5-tetramethyl-1,3,2-dioxaborolan-2-yl)phenyl)methyl acetate 111a were reacted to give 179a in 55% yield. LCMS: (M+H)⁺ 624

Following Example 176, 179a was converted to 179 in 42% yield. LCMS: (M+H)⁺ 582. ¹H NMR (500 MHz, MEOD) δ 8.73 (s, 1H), 8.17 (s, 1H), 7.74 (m, 1H), 7.51 (m, 1H), 7.40 (m, 3H), 7.10 (d, J=3.5, 1H), 4.55 (m, 2H), 4.31 (m, 2H), 4.13 (m, 1H), 4.06 (s, 3H), 3.99 (m, 1H), 3.71 (s, 3H), 3.05 (m, 1H), 2.94 (m, 6H), 2.59 (m, 2H), 1.89 (m, 4H).

Example 180 6-[2-(hydroxymethyl)-3-{1-oxo-1H,2H,3H,4H,6H,7H,8H,9H-pyrazino[1,2-a]indol-2-yl}phenyl]-2-methyl-4-[(5-{[methyl(propan-2-yl)amino]methyl}pyridine-2-yl)amino]-2,3-dihydropyridazin-3-one 180

Example 180a Methyl 6-(6-Chloro-2-methyl-3-oxo-2,3-dihydropyridazin-4-ylamino)nicotinate 180a

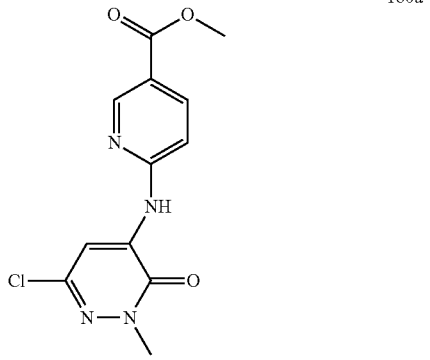

Following Example 186b, 4-bromo-6-chloro-2-methylpyridazin-3(2H)-one 103e (4.0 g, 17.9 mmol), 186a (2.7 g, 17.9 mmol), cesium carbonate (12.8 g, 39.4 mmol), and Xantphos (880 mg, 8.5 mol %), dioxane (120 ml) and tris(dibenzylideneacetone)dipalladium(0) (820 mg, 5 mol %) were reacted to give 180a (3.0 g, 57% yield).

Example 180b 6-Chloro-4-(5-(hydroxymethyl)pyridin-2-ylamino)-2-methylpyridazin-3(2H)-one 180b

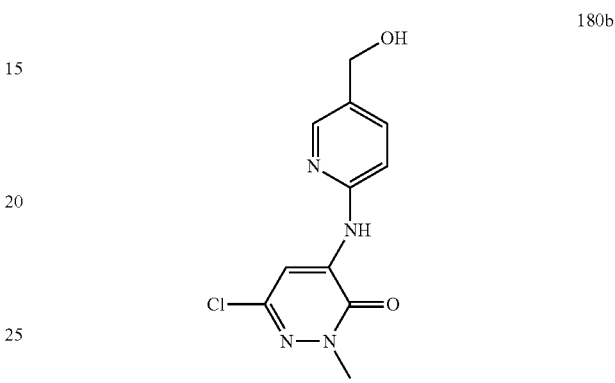

Following Example 186c, 180a (3.0 g, 10.2 mmol), methylene chloride (100 mL) and 1.0M DIBAL-H in methylene chloride (30.5 mL, 30.5 mmol) were reacted to give 180b (2.3 g, 86% yield).

Example 180c (6-(6-chloro-2-methyl-3-oxo-2,3-dihydropyridazin-4-ylamino)pyridin-3-yl)methyl methanesulfonate 180c

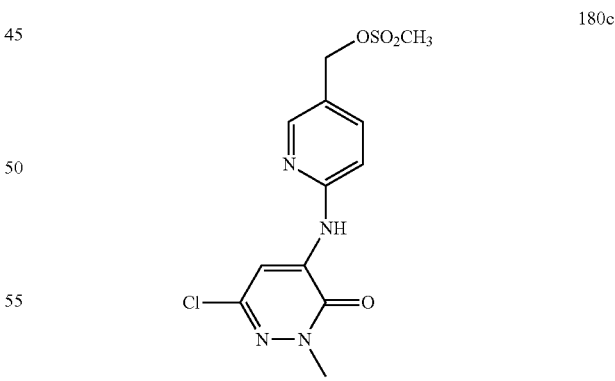

Intermediate 180b was treated with methanesulfonyl chloride and diisopropylethylamine in methylene chloride at 0° C. to give 180c.

Example 180d 6-Chloro-4-(5-((isopropyl(methyl)amino)methyl)pyridin-2-ylamino)-2-methylpyridazin-3(2H)-one 180d

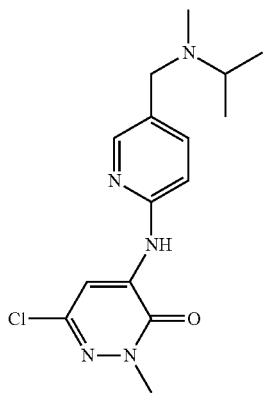 [SMILES: CC(C)N(C)Cc1ccc(Nc2cc(Cl)nn(C)c2=O)nc1]

Following Example 186c, 180c and methylisopropylamine were reacted to give 180d.

Example 180e 2-(5-(5-((isopropyl(methyl)amino)methyl)pyridin-2-yl amino)-1-methyl-6-oxo-1,6-dihydropyridazin-3-yl)-6-(1-oxo-3,4,6,7,8,9-hexahydropyrazino[1,2-a]indol-2(1H)-yl)benzyl Acetate 180e

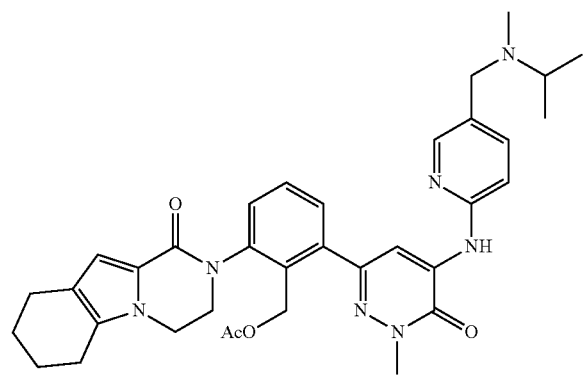

Following Example 179a, 180d (125 mg, 0.39 mmol), 114a (215 mg, 0.47 mmol), 1N Na$_2$CO$_3$ (0.86 mL) and tetrakis(triphenyl-phosphine)palladium(0) (23 mg, 5 mol %) were reacted to give 180e (150 mg, 61% yield).

Following Example 179, 180e (150 mg, 0.24 mmol), 1N LiOH (1.2 mL), THF (2 mL) and isopropanol (2 mL) were reacted and the mixture was purified via column chromatography, silica, methanol/methylene chloride to give 180 (105 mg, 75% yield). MS (ESI+) m/z 582.5 (M+H).

Example 181 5-[3-(5-{[5-(4-Ethylpiperazin-1-yl)pyridine-2-yl]amino}-1-methyl-6-oxo-1,6-dihydropyridin-3-yl)-2-(hydroxymethyl)phenyl]-8-thia-5-azatricyclo[7.4.0.0$^{2,7}$]trideca-1(9),2(7)-dien-6-one 181

Example 181a 5-[3-(5-{[5-(4-Ethylpiperazin-1-yl)pyridine-2-yl]amino}-1-methyl-6-oxo-1,6-dihydropyridin-3-yl)-2-(acetoxymethyl)phenyl]-8-thia-5-azatricyclo[7.4.0.0$^{2,7}$]trideca-1(9),2(7)-dien-6-one 181a

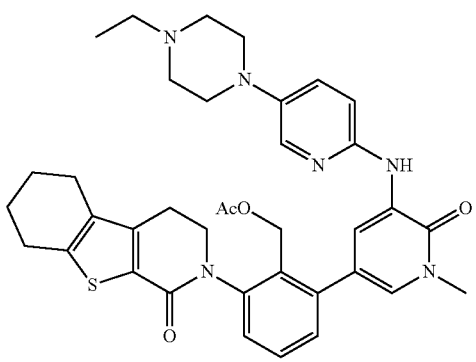 [SMILES: CCN1CCN(c2ccc(Nc3cc(-c4cccc(N5CCc6c(sc7c6CCCC7)C5=O)c4COC(C)=O)cn(C)c3=O)nc2)CC1]

To a microwave tube equipped with a stirring bar, 5-bromo-3-(5-(4-ethyl-piperazin-1-yl)pyridin-2-ylamino)-1-methylpyridin-2(1H)-one 138c (250 mg, 0.637 mmol), boronic ester 111a (308 mg, 0.701 mmol), Pd(PPh$_3$)$_4$ (36.8 mg, 0.0319 mmol), Na$_2$CO$_3$ aqueous solution (1.0 N, 2.10 mL, 2.10 mmol), 1,2-dimethoxyethane (3.0 mL) were added. The mixture was reacted in microwave at 130° C. for 10 min. methylene chloride (200 mL) was added and the resulting mixture was washed with water (3×30 mL), brine (30 mL×1), dried over MgSO$_4$, filtered, and removed solvent in vacuo. Silica gel column chromatography (methanol:methylene chloride=5:95) gave 181a.

To a round-bottomed flask equipped with a stirring bar, 181a, THF (5 mL), isopropanol (5 mL), water (5 mL), LiOH monohydrate (300 mg) were added. The resulting mixture was stirred at RT for 1 hr. Removed all the solvent in vacuo and the resulting residue was added to methylene chloride (200 mL), the solution was washed with water (30 mL×3), brine (30 mL×1), dried over MgSO$_4$, filtered, and removed solvent in vacuo. Silica gel column chromatography (methanol:methylene chloride=10:90) gave 181 as a brick red solid, 101 mg, MS (ESI+) m/z 625.4 (M+H).

Example 182 5-(3-(6,6-Dimethyl-3,4,6,7-tetrahydro-5H-cyclopenta[4,5]thieno[2,3-c]pyridine-1(2H)-yl)-5-fluoro-2-(hydroxymethyl)phenyl)-1-methyl-3-(pyrimidin-4-ylamino)pyridin-2(1H)-one 182

Example 182a tert-Butyl(2,6-dibromo-4-fluorobenzyloxy)dimethylsilane 182a

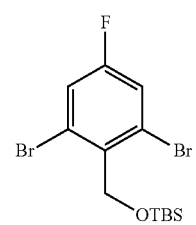

A 250-mL single-neck round-bottomed flask equipped with a magnetic stirrer was purged with nitrogen and charged with 197b (5.00 g, 17.6 mmol), imidazole (6.00 g, 88.0 mmol) and methylene chloride (125 mL). tert-butyldimethylsilyl chloride (7.96 g, 52.8 mmol) was added, and the reaction mixture was stirred at room temperature for 16 h. After this time, the reaction was diluted with water (100 mL) and methylene chloride (100 mL). The layers were separated, and the aqueous phase was extracted with methylene chloride (100 mL). The organic extracts were combined and dried over sodium sulfate. The drying agent was removed by filtration, and the solvent was evaporated under reduced pressure. The resulting residue was purified by flash chromatography to afford a 96% yield (6.75 g) of 182a as a colorless oil: $^1$H NMR (500 MHz, CDCl$_3$) δ 7.30 (d, 2H, J=8.0 Hz), 4.93 (s, 2H), 0.93 (s, 9H), 0.15 (s, 6H).

Example 182b 2-(3-Bromo-2-((tert-butyldimethylsilyloxy)methyl)-5-fluorophenyl)-6-(6,6-dimethyl-3,4,6,7-tetrahydro-5H-cyclopenta[4,5]thieno[2,3-c]pyridin-1(2H)-one 182b

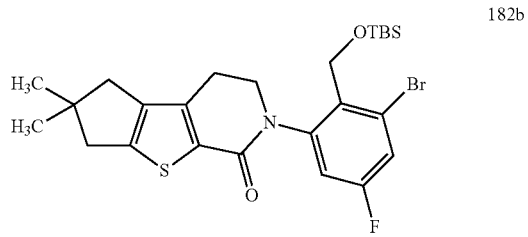 [SMILES: CC1(C)Cc2sc3c(c2C1)CCN(c1cc(F)cc(Br)c1CO[Si](C)(C)C(C)(C)C)C3=O]

A 250-mL single-neck round-bottomed flask equipped with a magnetic stirrer and nitrogen inlet was charged with 105h (400 mg, 1.81 mmol), 182a (1.44 g, 3.62 mmol), cesium carbonate (1.18 g, 3.62 mmol), N,N'-dimethylethylenediamine (159 mg, 1.81 mmol) and 1,4-dioxane (15 mL). After bubbling nitrogen through the resulting suspension for 30 min, copper iodide (174 mg, 0.905 mmol) was added. A reflux condenser was attached to the flask, and the reaction mixture was heated at 100° C. for 16 h. After this time, the mixture was cooled to room temperature and filtered. The filtrate was diluted with ethyl acetate (100 mL) and water (50 mL), and the layers were separated. The aqueous layer was extracted with ethyl acetate (2×30 mL), and the combined organic layers were washed with brine (100 mL) and dried over sodium sulfate. The drying agent was removed by filtration. The filtrate was concentrated under reduced pressure, and the resulting residue was purified by flash column chromatography to afford 182b in 57% yield (554 mg) as a white solid: mp 38-39° C.; $^1$H NMR (500 MHz, CDCl$_3$) δ 7.32 (dd, 1H, J=8.0, 2.5 Hz), 7.00 (dd, 1H, J=8.0, 2.5 Hz), 4.74 (s, 2H), 3.93 (m, 2H), 2.98 (m, 1H), 2.80 (m, 1H), 2.77 (s, 2H), 2.52 (s, 2H), 1.28 (s, 3H), 1.27 (s, 3H), 0.89 (s, 9H), 0.11 (s, 6H).

Example 182c 2-((tert-Butyldimethylsilyloxy)methyl)-5-fluorophenyl-6-(6,6-dimethyl-3,4,6,7-tetrahydro-5H-cyclopenta[4,5]thieno[2,3-c]pyridin-1(2H)-yl-6-(4,4,5,5-tetramethyl-1,3,2-dioxaborolan-2-yl)-one 182c

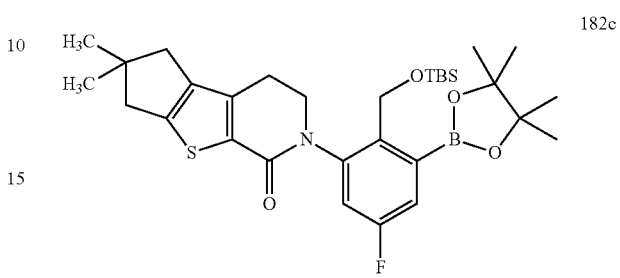

A 100-mL single-neck round-bottomed flask equipped with a magnetic stirrer and nitrogen inlet was charged with 182b (554 mg, 1.03 mmol), 4,4,4',4',5,5,5',5'-octamethyl-2,2'-bi(1,3,2-dioxaborolane) (785 mg, 3.09 mmol), potassium acetate (404 mg, 4.12 mmol) and 1,4-dioxane (8 mL). After bubbling nitrogen through the resulting suspension for 30 min, Pd(dppf)Cl$_2$.CH$_2$Cl$_2$ (75 mg, 0.103 mmol) was added. A reflux condenser was attached to the flask, and the reaction mixture was heated at reflux for 8 h. After this time, the mixture was diluted with ethyl acetate (100 mL) and water (75 mL), and the layers were separated. The aqueous layer was extracted with ethyl acetate (2×50 mL), and the combined organic layers were washed with brine (100 mL) and dried over sodium sulfate. The drying agent was removed by filtration. The filtrate was concentrated under reduced pressure, and the resulting residue was purified by flash column chromatography to afford 182c in 91% yield (600 mg) as a white solid: mp 41-42° C.; $^1$H NMR (500 MHz, CDCl$_3$) δ 7.52 (dd, 1H, J=8.0, 2.5 Hz), 7.02 (dd, 1H, J=8.0, 2.5 Hz), 5.14 (d, 1H, J=10.5 Hz), 5.70 (d, 1H, J=10.5 Hz), 3.93 (m, 2H), 2.98 (m, 1H), 2.80 (m, 1H), 2.77 (s, 2H), 2.52 (s, 2H), 1.34 (s, 3H), 1.33 (s, 3H), 1.26 (s, 12H), 0.84 (s, 9H), 0.04 (s, 6H).

A 100-mL single-neck round-bottomed flask equipped with a magnetic stirrer and reflux condenser was purged with nitrogen and charged with 182c (300 mg, 0.513 mmol), 109b (111 mg, 0.394 mmol), sodium carbonate (125 mg, 1.18 mmol), 1,4-dioxane (8 mL) and water (2 mL). This mixture was degassed with nitrogen for 30 min. Tetrakis-(triphenylphosphine)palladium(0) (46 mg, 0.039 mmol) was added. After heating at reflux for 2 h, the reaction mixture was cooled to room temperature and partitioned between water (40 mL) and methylene chloride (100 mL). The layers were separated, and the aqueous phase was extracted with methylene chloride (2×50 mL). The organic extracts were combined, dried over sodium sulfate, filtered and concentrated under reduced pressure. The resulting residue was dissolved in THF (3 mL), and tetrabutyl-ammonium fluoride trihydrate (372 mg, 1.18 mmol) was added. After stirring at room temperature for 2 h, the reaction mixture was partitioned between water (20 mL) and methylene chloride (20 mL). The layers were separated, and the aqueous phase was extracted with methylene chloride (2×20 mL). The organic extracts were combined, dried over sodium sulfate, filtered and concentrated under reduced pressure. The resulting residue was purified by flash chromatography to afford 182 in 41% yield (88 mg) as an off-white solid: mp>250° C.; $^1$H NMR (500 MHz, DMSO-d$_6$) δ 9.22 (s, 1H), 8.72 (d, 1H, J=2.0 Hz), 8.65 (s, 1H), 8.29 (d, 1H, J=6.0 Hz), 7.57 (d, 1H, J=2.0 Hz), 7.34 (dd, 1H, J=8.5, 3.0 Hz), 7.31 (d, 1H, J=6.0 Hz), 7.29 (dd, 1H, J=8.5, 3.0 Hz), 4.87 (m, 1H), 4.31 (m, 2H), 4.04 (m, 1H), 3.84 (m, 1H), 3.60 (s, 3H), 3.03 (m, 1H), 2.89 (m, 1H), 2.75 (s, 2H), 2.53 (m, 2H), 1.23 (s, 6H); MS (ESI+) m/z 546.2 (M+H).

Example 183 5-(3-(6,6-Dimethyl-3,4,6,7-tetrahydro-5H-cyclopenta[4,5]thieno[2,3-c]pyridine-1 (2H)-yl)-2-(hydroxymethyl)phenyl)-1-methyl-3-(6,7-dihydro-4H-pyrazolo[5,1-c][1,4]oxazin-3-ylamino)pyridin-2 (1H)-one 183

Following Example 184, reaction of 131a (300 mg, 0.606 mmol) with 110c (151 mg, 0.466 mmol) gave a 51% yield (129 mg) of 183 as an off-white solid: mp 167-168° C.; $^1$H NMR (500 MHz, DMSO-d$_6$) δ 8.18 (s, 1H), 7.95 (d, 1H, J=2.0 Hz), 7.44 (t, 1H, J=8.0 Hz), 7.33 (dd, 1H, J=8.0, 1.0 Hz), 7.29 (dd, 1H, J=8.0, 1.0 Hz), 7.23 (d, 1H, J=2.0 Hz), 5.92 (s, 1H), 4.81 (m, 1H), 4.71 (s, 2H), 4.36 (m, 2H), 4.01 (m, 3H), 3.94 (m, 2H), 3.85 (m, 1H), 3.57 (s, 3H), 3.02 (m, 1H), 2.86 (m, 1H), 2.75 (m, 2H), 2.53 (m, 2H), 1.23 (s, 6H); MS (ESI+) m/z 572.3 (M+H).

Example 184 5-(3-(6,6-Dimethyl-3,4,6,7-tetrahydro-5H-cyclopenta[4,5]thieno[2,3-c]pyridine-1 (2H)-yl)-2-(hydroxymethyl)phenyl)-1-methyl-3-(pyridin-2-ylamino)pyridin-2(1H)-one 184

Example 184a 5-Bromo-1-methyl-3-(pyridin-2-ylamino)pyridin-2(1H)-one 184a

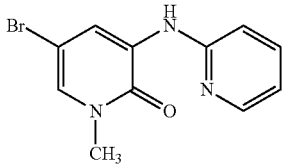

184a

A 100-mL single-neck round-bottomed flask equipped with a magnetic stirrer, nitrogen inlet and reflux condenser was charged with 3,5-dibromo-1-methylpyridin-2(1H)-one (936 mg, 3.51 mmol), 2-aminopyridine (300 mg, 3.19 mmol), cesium carbonate (3.11 g, 9.57 mmol) and 1,4-dioxane (20 mL). After bubbling nitrogen through the resulting solution for 20 minutes, Xantphos (184 mg, 0.319 mmol) and tris(dibenzylideneacetone)dipalladium(0) (146 mg, 0.160 mmol) were added, and the reaction mixture was heated at 100° C. for 3 h. After this time, the reaction was cooled to room temperature, filtered and concentrated under reduced pressure. The resulting residue was purified by flash chromatography to afford a 42% yield (376 mg) of 184a as an off-white solid: mp 153-154° C.; $^1$H NMR (300 MHz, DMSO-d$_6$) δ 8.75 (s, 1H), 8.69 (d, 1H, J=2.4 Hz), 8.26 (dd, 1H, J=5.4, 1.5 Hz), 7.61 (m, 1H), 7.54 (d, 1H, J=2.4 Hz), 7.33 (d, 1H, J=5.4 Hz), 6.86 (m, 1H), 3.45 (s, 3H).

A 100-mL single-neck round-bottomed flask equipped with a magnetic stirrer and reflux condenser was purged with nitrogen and charged with 131a (300 mg, 0.606 mmol), 184a (131 mg, 0.466 mmol), sodium carbonate (148 mg, 1.40 mmol), 1,4-dioxane (8 mL) and water (2 mL). This mixture was degassed with nitrogen for 30 min. Tetrakis(triphenylphosphine)palladium (54 mg, 0.047 mmol) was added. After heating at 100° C. for 3 h, the reaction mixture was cooled to room temperature and partitioned between water (40 mL) and methylene chloride (100 mL). The layers were separated, and the aqueous phase was extracted with methylene chloride (2×50 mL). The organic extracts were combined, dried over sodium sulfate, filtered and concentrated under reduced pressure. The resulting residue was dissolved in methanol (5 mL), and potassium carbonate (500 mg, 3.62 mmol) was added. After stirring at room temperature for 2 h, the reaction mixture was partitioned between water (20 mL) and methylene chloride (20 mL). The layers were separated, and the aqueous phase was extracted with methylene chloride (2×20 mL). The organic extracts were combined, dried over sodium sulfate, filtered and concentrated under reduced pressure. The resulting residue was purified by flash chromatography to afford 184 in 49% yield (118 mg) as a white solid: mp 150-151° C.; $^1$H NMR (500 MHz, DMSO-d$_6$) δ 8.66 (d, 1H, J=2.0 Hz), 8.57 (m, 1H), 8.16 (dd, 1H, J=5.0, 1.0 Hz), 7.57 (m, 1H), 7.45 (t, 1H, J=8.0 Hz), 7.38 (d, 1H, J=2.0 Hz), 7.36-7.31 (m, 2H), 7.28 (d, 1H, J=8.0 Hz), 6.78 (dd, 1H, J=11.0, 5.0 Hz), 4.82 (m, 1H), 4.35 (m, 2H), 4.02 (m, 1H), 3.86 (m, 1H), 3.59 (s, 3H), 3.01 (m, 1H), 2.87 (m, 1H), 2.75 (s, 2H), 2.53 (m, 2H), 1.23 (s, 6H); MS (ESI+) m/z 527.2 (M+H).

Example 185 5-(3-(6,6-Dimethyl-3,4,6,7-tetrahydro-5H-cyclopenta[4,5]thieno[2,3-c]pyridine-1 (2H)-yl)-2-(hydroxymethyl)phenyl)-1-methyl-3-(1,5-dimethyl-1H-pyrazol-4-ylamino)pyridin-2(1H)-one 185

Using the same general procedure as described for the preparation of 184, reaction of 131a (300 mg, 0.606 mmol) with 142a (138 mg, 0.466 mmol) gave a 41% yield (104 mg) of 185 as a yellow solid: mp 164-165° C.; $^1$H NMR (500 MHz, DMSO-d$_6$) δ 7.93-7.92 (m, 2H), 7.44 (t, 1H, J=7.5 Hz), 7.33 (dd, 1H, J=7.5, 1.0 Hz), 7.29 (dd, 1H, J=7.5, 1.0 Hz), 7.21 (d, 1H, J=2.0 Hz), 5.88 (s, 1H), 4.83 (m, 1H), 4.36 (m, 2H), 4.02 (m, 1H), 3.87 (m, 1H), 3.57 (s, 3H), 3.56 (s, 3H), 3.03 (m, 1H), 2.86 (m, 1H), 2.75 (m, 2H), 2.53 (m, 2H), 2.17 (s, 3H), 1.23 (s, 6H); MS (ESI+) m/z 544.2 (M+H).

Example 186 2-(2-(Hydroxymethyl)-3-(5-(5-((isopropyl(methyl)amino)methyl)pyridin-2-ylamino)-1-methyl-6-oxo-1,6-dihydropyridin-3-yl)phenyl)-3,4,6,7,8,9-hexahydropyrazino[1,2-a]indol-1(2H)-one 186

Example 186a Methyl 6-(5-Bromo-1-methyl-2-oxo-1,2-dihydropyridin-3-ylamino)nicotinate 186a

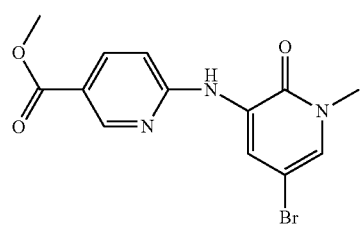

186a

In a 300 mL sealed tube was placed 3,5-dibromo-1-methylpyridin-2(1H)-one (4.0 g, 15.0 mmol), methyl 6-aminonicotinate (2.3 g, 15.0 mmol), cesium carbonate (10.7 g, 33 mmol), and Xantphos (740 mg, 8.5 mol %). The flask was evacuated and filled with nitrogen 3×. Dioxane (100 ml) was added and the mixture degassed for 25 min with bubbling nitrogen. Tris(dibenzylideneacetone)dipalladium(0) (690 mg, 5 mol %) was then added, the vessel sealed and the reaction heated to 120° C. overnight. The reaction was cooled and diluted with Ethyl acetate (500 mL) and saturated aqueous NaHCO₃ (150 mL), the layers were separated and extracted ethyl acetate 2×. The organics were washed with brine 3×, dried over Na₂SO₄, filtered, and concentrated under reduced pressure. The residue was purified by chromatography: ISCO 80 g silica, ethyl acetate/hexanes, to give 186a.

Example 186b 5-bromo-3-(5-(hydroxymethyl)pyridin-2-ylamino)-1-methylpyridin-2(1H)-one 186b

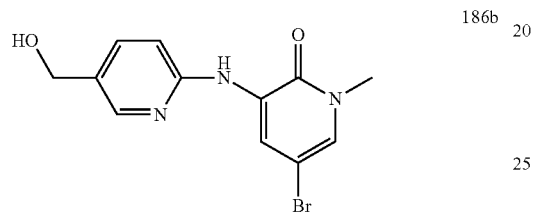

186b

In a flask under N₂, 186a (500 mg, 1.5 mmol) was suspended in methylene chloride and cooled to −78° C. in a dry ice/acetone bath. 1.0M DIBAL-H in methylene chloride (4.4 mL, 4.4 mmol) was slowly added via syringe. After the addition was complete the reaction was allowed to warm to −20° C. at which time the dry ice/acetone bath was exchanged for a ice/water bath and the reaction stirred an additional 0.5 hr at which time it was slowly quenched with 1N HCl (~5 mL). The reaction was then diluted with ethyl acetate and allowed to stir and warm to room temp over ~1 hr. The pH was adjusted to ~7 with 1N NaOH and 50 mL of saturated aqueous Rochelle's salt was added and the mixture heated and stirred at 40° C. for 1 hr during which time the mixture cleared. The layers were separated, the organics washed with brine, dried over Na₂SO₄, filtered and concentrated to give 186b as a white solid (420 mg, 90% yield).

Example 186d 5-Bromo-3-(5-((isopropyl(methyl)amino)methyl)pyridin-2-ylamino)-1-methylpyridin-2(1H)-one 186d

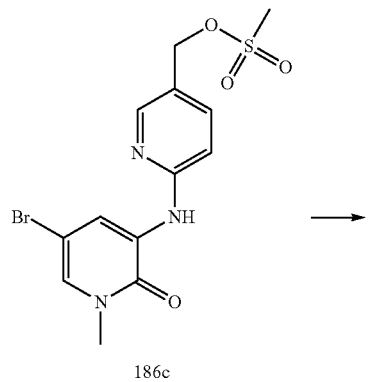

186c

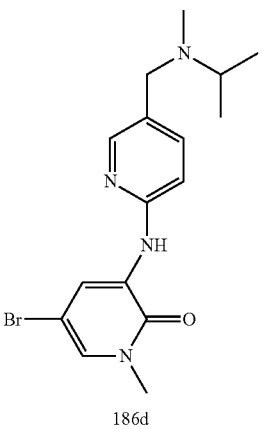

186d

In a flask under N₂, 186b (350 mg, 1.13 mmol) was suspended in methylene chloride (20 mL) then di-isopropylethylamine (0.89 mL, 5.09 mmol) was added and the reaction cooled to 0° C. in an ice/water bath. Methanesulfonyl chloride (518 mg, 0.35 mL, 4.52 mmol) was added and the reaction allowed to warm to room temp and stir for ~1 hr. The reaction was diluted with methylene chloride and saturated aqueous sodium bicarbonate was added. The layers were separated and the organics again washed with bicarb then dried over anh. magnesium sulfate, filtered and concentrated to give the mesylate 186c which was used directly to produce 186d by dissolving 186c in DMF (10 mL) and transferring the solution to a pressure flask whereupon N-methylpropan-2-amine (1.2 mL, 830 mg, 11.3 mmol) was added, the flask sealed, and heated to 80° C. overnight. The reaction was allowed to cool then diluted with ethyl acetate and water and the layers separated. The organics were washed with brine 4×, dried over Na₂SO₄, filtered and concentrated to give 186d.

Example 186f 2-(5-(5-((Isopropyl(methyl)amino)methyl)pyridin-2-ylamino)-1-methyl-6-oxo-1,6-dihydropyridin-3-yl)-6-(1-oxo-3,4,6,7,8,9-hexahydropyrazino[1,2-a]indol-2(1H)-yl)benzyl Acetate 186f

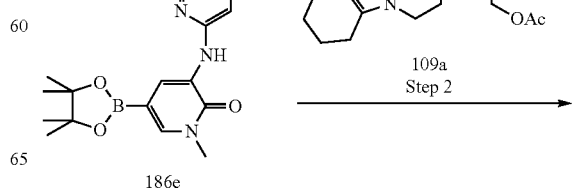

186e    109a Step 2

-continued

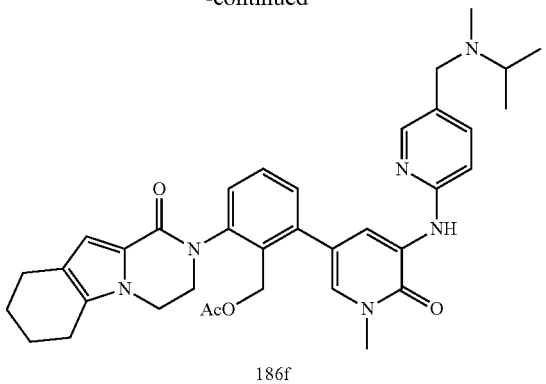

186f

Step 1

In a pressure flask was placed 186d (205 mg, 0.56 mmol), 4,4,4',4',5,5,5',5'-octamethyl-2,2'-bi(1,3,2-dioxaborolane) (213 mg, 0.84 mmol), potassium acetate (220 mg, 2.24 mmol) and 1,1'-bis(diphenylphosphino)ferrocene-palladium (II) dichloride dichloromethane complex (817 mg, 0.1 mol %). The flask was evacuated and filled with $N_2$ 3×, dioxane (5 mL) was added, the vessel sealed and heated to 90° C. for ~3 hrs. The reaction was allowed to cool then diluted with ethyl acetate, and filtered through a pad of celite and concentrated under reduced pressure to give 186e which was used directly in the next step.

Step 2

186e was dissolved in DME (5 mL) and transferred to a pressure flask containing 109a (187 mg, 0.45 mmol), 1N $Na_2CO_3$ (1.2 ml) and tetrakis(tripheny-phosphine)palladium (0) (32 mg, 5 mol %). The flask was sealed and heated to 100° C. overnight. The reaction was then diluted with ethyl acetate and water, separated, washed with brine, dried over $Na_2SO_4$, filtered, and concentrated under reduced pressure. The residue was purified by chromatography: ISCO 12 g silica, eluting with methanol and $CH_2Cl_2$, to give 186f (110 mg, 32% yield over 2 steps).

Following Example 119, 186f (110 mg, 0.18 mmol), 1N LiOH (0.88 mL), THF (2 mL) and isopropanol (2 mL) were reacted and purified via column chromatography, ISCO 12 g silica, methanol/methylene chloride to give 186 (80 mg, 77% yield). MS (ESI+) m/z 581.4 (M+H).

Example 187 2-(2-(Hydroxymethyl)-3-(5-(5-(methoxymethyl)-1-methyl-1H-pyrazol-3-ylamino)-1-methyl-6-oxo-1,6-dihydropyridazin-3-yl)phenyl)-3,4,6,7,8,9-hexahydropyrazino[1,2-a]indol-1(2H)-one 187

Example 187a 6-Chloro-4-(5-(methoxymethyl)-1-methyl-1H-pyrazol-3-ylamino)-2-methylpyridazin-3(2H)-one 187a

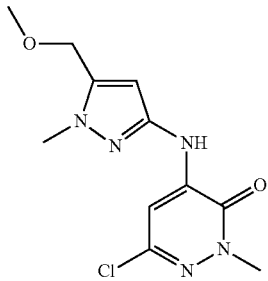

A mixture of 5-(methoxymethyl)-1-methyl-1H-pyrazol-3-amine 176b (600 mg, 4.26 mmol), XantPhos (300 mg, 0.51 mmol), $Pd_2dba_3$ (310 mg, 0.34 mmol), 4-bromo-6-chloro-2-methylpyridazin-3(2H)-one (103e) (1.22 g, 5.53 mmol) and $Cs_2CO_3$ (4.2 g. 12.8 mmol) in 1,4-dioxane (40 mL) was heated at reflux for 2 h. After the completion of the reaction, the mixture was filtered off and washed with methanol (100 mL). The filtrate was evaporated in vacuo and the residue was purified on reverse phase Combi-flash to give 187a (1.13 g, 94%). MS: [M+H]$^+$ 284.

Example 187b 2-(5-(5-(Methoxymethyl)-1-methyl-1H-pyrazol-3-ylamino)-1-methyl-6-oxo-1,6-dihydropyridazin-3-yl)-6-(1-oxo-3,4,6,7,8,9-hexahydropyrazino[1,2-a]indol-2(1H)-yl)benzyl Acetate 187b

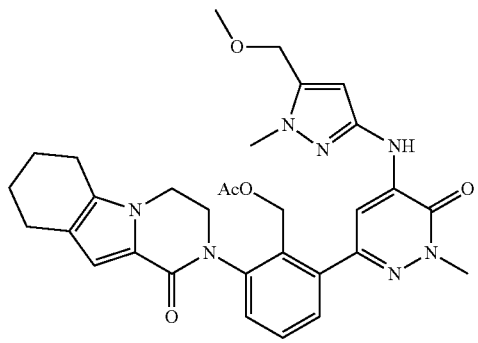 [SMILES: COCc1cc(Nc2cc(-c3cccc(N4CCn5c(cc6c5CCCC6)C4=O)c3COC(C)=O)nn(C)c2=O)nn1C]

A mixture of 6-chloro-4-(5-(methoxymethyl)-1-methyl-1H-pyrazol-3-ylamino)-2-methylpyridazin-3(2H)-one 187a (300 mg, 1.06 mmol), 2-(acetoxy-methyl)-3-(1-oxo-3,4,6,7,8,9-hexahydropyrazino[1,2-a]indol-2(1H)-yl)phenylboronic acid 114a (500 mg, 1.3 mmol), $PdCl_2(dppf)$ (116 mg, 0.16 mmol), $K_3PO_4$ (100 mg), and NaOAc (50 mg) in MeCN (15 mL) and water (3 mL) was heated at reflux for 2 h. The solvent was evaporated in vacuo and the residue was purified on reverse phase Combi-flash to 187b (310 mg, 50%). MS: [M+H]$^+$ 586.

A mixture of 187b (310 mg, 0.53 mmol) and LiOH hydrate (222 mg, 5.3 mmol) in isopropanol (20 mL) and water (4 mL) was stirred at 30° C. for 2 h. The mixture was evaporated in vacuo and the residue was extracted with ethyl acetate (20 mL×2). The combined extracts were concentrated under reduced pressure. The residue was purified on prep-HPLC to give 187 (103 mg, 36%). MS: [M+H]$^+$ 544. $^1$H NMR (500 MHz, DMSO) δ 9.25 (s, 1H), 7.89 (s, 1H), 7.50-7.47 (m, 1H), 7.42-7.38 (m, 2H), 6.51 (s, 1H), 6.22 (s, 1H), 4.63-4.60 (m, 1H), 4.48-4.45 (m, 1H), 4.40-4.35 (m, 3H), 4.20-4.05 (m, 3H), 3.90-3.86 (m, 1H), 3.75 (s, 3H), 3.67 (s, 3H), 3.26 (s, 3H), 2.65-2.54 (m, 2H), 2.48-2.42 (m, 2H), 1.84-1.74 (m, 2H), 1.74-1.64 (m, 2H).

Example 188 2-(2-(Hydroxymethyl)-3-(1-methyl-5-(5-(4-(oxetan-3-yl)piperazin-1-yl)pyridine-2-ylamino)-6-oxo-1,6-dihydropyridin-3-yl)phenyl)-3,4,6,7,8,9-hexahydropyrazino[1,2-a]indol-1(2H)-one 188

Example 188a tert-Butyl 4-(6-Nitropyridin-3-yl)piperazine-1-carboxylate 188a

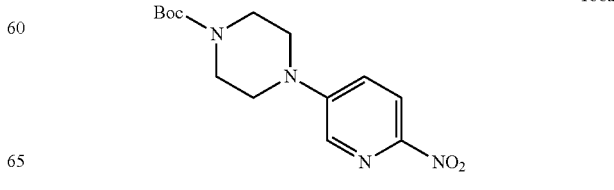

Into a solution of 5-bromo-2-nitropyridine (30 g, 148 mmol) in DMSO (1 L) were added K$_2$CO$_3$ (40 g, 296 mmol) and tert-butyl piperazine-1-carboxylate (28 g, 148 mmol). The mixture was stirred at 65 degree for overnight. After cooling down, it was poured into water (2 L). The solid precipitated was collected and dried under vacuum. It was then further purified by flash column eluting with 20:1 petroleum ether/ethyl acetate and then with methylene chloride to give 188a as a yellow solid (17 g, 37%). MS: [M+H]$^+$ 309.

Example 188b tert-Butyl 4-(6-Aminopyridin-3-yl)piperazine-1-carboxylate 188b

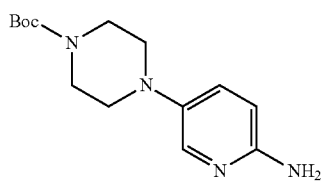

A 500-mL bottle was purged with nitrogen and charged with 188a (3.1 g, 10 mmol), 10% palladium on carbon (50% wet, 1.0 g) and ethanol (100 mL). It was evacuated, charged with hydrogen gas, and stirred for 16 h at room temperature. The hydrogen was then evacuated and nitrogen was charged into the bottle. The catalyst was removed by filtration through a pad of Celite and the filtrate concentrated under reduced pressure to afford 188b (2.7 g, 97%). MS: [M+H]$^+$ 279

Example 188c tert-Butyl 4-(6-(5-bromo-1-methyl-2-oxo-1,2-dihydropyridin-3-ylamino)pyridine-3-yl)piperazine-1-carboxylate 188c

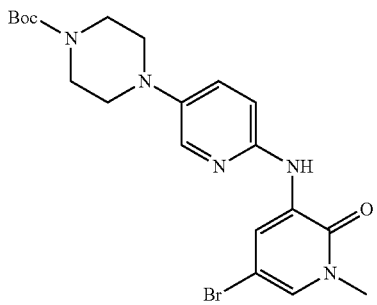

A 100-mL single-neck round-bottomed flask equipped with a magnetic stirrer and reflux condenser was charged with 1,4-dioxane (50 mL), 188b (1.3 g, 4.7 mmol), 3,5-dibromo-1-methylpyridin-2(1H)-one (1.24 g, 4.7 mmol), and cesium carbonate (3.8 g, 12 mmol). After bubbling nitrogen through the resulting mixture for 30 minutes, XantPhos (272 mg, 0.47 mmol) and tris(dibenzylideneacetone)dipalladium(0) (430 mg, 0.47 mmol) were added, and the reaction mixture was heated at reflux for 3 h. After this time the reaction was cooled to room temperature, partitioned between ethyl acetate (100 mL) and water (100 mL), and filtered. The aqueous layer was separated and extracted with ethyl acetate (50 mL×2). The organic layers were combined, washed with brine (50 mL), and dried over sodium sulfate. The drying agent was removed by filtration and the filtrate was concentrated under reduced pressure. The residue was purified on flash column eluting with 50:1 methylene chloride/methanol to afford 188c (1.3 g, 59%). MS: [M+H]$^+$ 464.

Example 188d 5-Bromo-1-methyl-3-(5-(piperazin-1-yl)pyridin-2-ylamino)pyridin-2(1H)-one 188d

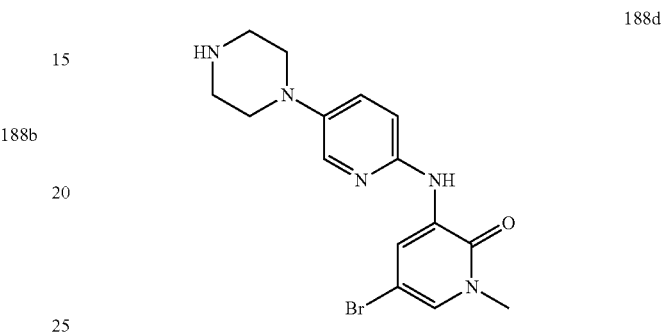

A mixture of 188c (3.6 g, 7.8 mmol) and 4.0 M HCl/dioxane (10 mL) was stirred for 5 h at room temperature. It was then concentrated at reduced pressure. The residue was basified with aqueous 1.0M NaOH and extracted with methylene chloride. The combined organic layers were washed with water and concentrated under reduced pressure to give 188d (2.46 g, 87%). MS: [M+H]$^+$ 364.

Example 188e 5-Bromo-1-methyl-3-(5-(4-(oxetan-3-yl)piperazin-1-yl)pyridin-2-ylamino)pyridin-2(1H)-one 188e

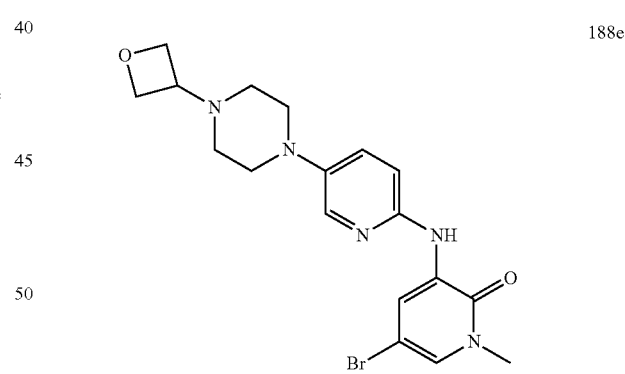

A mixture of 188d (2.75 g, 7.5 mmol), oxetan-3-one (1.6 g, 22.7 mmol), NaBH$_3$CN (4.75 g, 22.5 mmol), and zinc chloride (3 g, 22.7 mmol) in methanol (125 mL) was stirred for 5 hours at 50 degree. The mixture was added to water and extracted with methylene chloride for three times. The organic layers were concentrated under reduced pressure. The residue was purified by column chromatography eluting with 25:1 methylene chloride/methanol to give 188e (1.92 g, 61%). MS: [M+H]$^+$ 420. $^1$H NMR (500 MHz, DMSO) δ 8.58 (d, J=2.5, 1H), 8.55 (s, 1H), 7.94 (d, J=3, 1H), 7.54 (d, J=2.5, 1H), 7.39 (dd, J=3, 1H), 7.25 (d, J=4, 1H), 4.56 (t, J=6.5, 2H), 4.46 (t, J=6.5, 2H), 3.50 (s, 3H), 3.43 (m, 1H), 3.01 (m, 4H), 2.40 (m, 4H).

Example 188f 2-(1-Methyl-5-(5-(4-(oxetan-3-yl)piperazin-1-yl)pyridin-2-ylamino)-6-oxo-1,6-dihydropyridin-3-yl)-6-(1-oxo-3,4,6,7,8,9-hexahydropyrazino[1,2-a]indol-2(1H)-yl)benzyl Acetate 188f

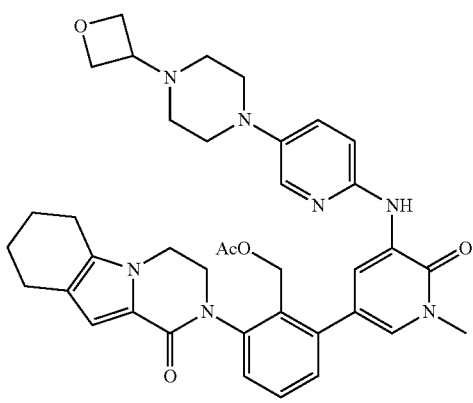

188f

Following Example 148b, 464 mg of 2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 114a and 420 mg of 188e were reacted to give 188f as a yellow solid (360 mg, 54%). LCMS: [M+H]+ 678

Following Example 148, 270 mg of 188f was converted to 188 as a white solid (144 mg, 54%). LCMS: [M+H]+ 635. $^1$H NMR (500 MHz, CDCl3) δ: 8.55 (d, J=2.5, 1H), 7.89 (d, J=3, 1H), 7.80 (s, 1H), 7.47-7.41 (m, 3H), 7.26-7.21 (m, 2H), 6.85 (s, 1H), 6.83 (d, J=8.5, 1H), 4.72-4.65 (m, 3H), 4.59 (d, J=10.5, 1H), 4.43-4.36 (m, 2H), 4.20-4.13 (m, 3H), 3.93-3.89 (m, 1H), 3.59-3.57 (m, 1H), 3.15 (s, 3H), 3.05 (m, 1H), 2.6-2.51 (m, 7H), 1.89 (s, 2H), 1.78 (S, 2H).

Example 189 10-[5-Fluoro-2-(hydroxymethyl)-3-[1-methyl-6-oxo-5-(pyrimidin-4-ylamino)-1,6-dihydropyridin-3-yl]phenyl]-4,4-dimethyl-1,10-diazatricyclo-[6.4.0.0$^{2,6}$]dodeca-2(6),7-dien-9-one 189

Example 189a 2-Bromo-4-fluoro-6-(9-oxo-4,4-dimethyl-1,10diazatricyclo[6.4.0.0$^{2,6}$]-dodeca-2(6),7-dien-10-yl)benzyl Acetate 189a

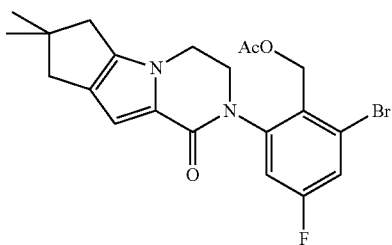

189a

A sealed tube was equipped with a magnetic stirrer and charged with 167e (740 mg, 3.6 mmol), 2,6-dibromo-4-fluorobenzyl acetate 197c (2.4 g, 7.2 mmol) and cesium carbonate (2.6 g, 7.9 mmol) in 1,4-dioxane (36 mL). After bubbling nitrogen through the solution for 30 min, Xantphos (250 mg, 0.43 mmol) and tris(dibenzylideneacetone)dipalladium(0) (260 mg, 0.29 mmol) were added, and the reaction mixture was heated to 100° C. for 16 h. After this time, H$_2$O (50 mL) and ethyl acetate (50 mL) were added. The aqueous layer was separated and extracted with ethyl acetate (2×50 mL). The combined organic extracts were washed with brine (100 mL) and dried over sodium sulfate. The resulting residue was purified by column chromatography eluting with a gradient of 100% hexanes—100% Ethyl acetate to afford a 56% yield (910 mg) of 189a.

Example 189b 10-[5-Fluoro-2-(acetoxymethyl)-3-[1-methyl-6-oxo-5-(pyrimidin-4-ylamino)-1,6-dihydropyridin-3-yl]phenyl]-4,4-dimethyl-1,10-diazatricyclo[6.4.0.0$^{2,6}$]dodeca-2(6),7-dien-9-one 189b

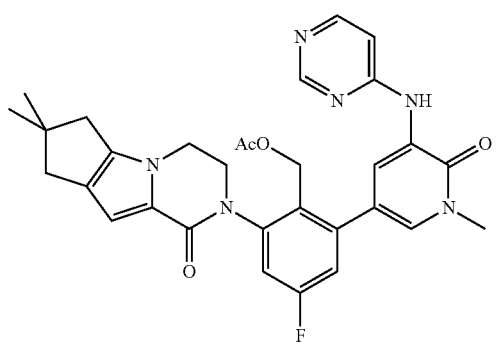

189b

A microwave tube equipped with a magnetic stirrer was charged with 1-methyl-3-(pyrimidin-4-ylamino)-5-(4,4,5,5-tetramethyl-1,3,2-dioxaborolan-2-yl)pyridin-2(1H)-one 109c (170 mg, 0.5 mmol), 189a (150 mg, 0.33 mmol), 1,2-dimethoxyethane (4 mL) and 1M aqueous sodium carbonate (1 mL). After bubbling N$_2$ for 15 min, Pd(PPh$_3$)$_4$ (19 mg, 0.02 mmol) was added. The mixture was heated in microwave to 130° C. for 10 min. After this time, Ethyl acetate (5 mL) and water (5 mL) were added. The separated aqueous layer was extracted with ethyl acetate (2×5 mL). The combined organics were washed with brine (10 mL), dried over sodium sulfate, filtered and concentrated under reduced pressure. The resulting residue was purified by column chromatography eluting with a gradient of CH$_2$Cl$_2$—60:35:5 methylene chloride:diethyl ether:methanol to afford a 37% yield (71 mg) of 189b.

A 25 mL round bottom flask with a magnetic stirrer was charged with 189b (71 mg, 0.12 mmol), lithium hydroxide (26 mg, 0.6 mmol), THF (0.6 mL), isopropanol (0.6 mL) and water (1.2 mL). The mixture stirred at rt for 1 h. After this time, ethyl acetate (5 mL) and water (5 mL) were added. The separated aqueous layer was extracted with ethyl acetate (2×5 mL). The combined organics were washed with brine (10 mL), dried over sodium sulfate, filtered and concentrated under reduced pressure. The resulting residue was purified by column chromatography eluting with a gradient of C methylene chloride—60:35:5 CH$_2$Cl$_2$:diethyl ether:methanol to afford a 58% yield (38 mg) of 189. MS (ESI+) m/z 529.7 (M+H).

Example 190 10-[3-(5-{[5-(4-Ethylpiperazin-1-yl)pyridine-2-yl]amino}-1-methyl-6-oxo-1,6-dihydropyridin-3-yl)-2-(hydroxymethyl)phenyl]-4,4-dimethyl-1,10-diazatricyclo[6.4.0.0$^{2,6}$]dodeca-2(6),7-dien-9-one 190

Example 190a 3-(5-(4-Ethylpiperazin-1-yl)pyridin-2-ylamino)-1-methyl-5-(4,4,5,5-tetramethyl-1,3,2-dioxaborolan-2-yl)pyridin-2(1H)-one 190a

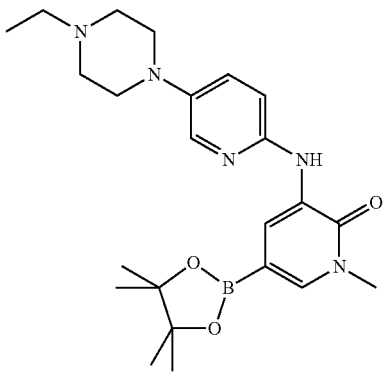 [SMILES: CCN1CCN(c2ccc(Nc3cc(B4OC(C)(C)C(C)(C)O4)cn(C)c3=O)nc2)CC1]

To a round-bottomed flask equipped with a stirring bar, 5-bromo-3-(5-(4-ethylpiperazin-1-yl)pyridin-2-ylamino)-1-methylpyridin-2(1H)-one 138c (305.6 mg, 0.696 mmol), 4,4,4',4',5,5,5',5'-octamethyl-2,2'-bi(1,3,2-dioxaborolane) (185.4 g, 0.730 mmol), Pd$_2$(dba)$_3$ (63.7 mg, 0.070 mmol), X-Phos (66.3 mg, 0.139 mmol), KOAc (102.4 mg, 1.043 mmol), and dioxane (5 mL) were added. The mixture was heated at 90° C. for 4 hrs. The resulting mixture was filtered through celite, washed with ethyl acetate (200 mL). The organic phase was washed with water (50 mL), dried over MgSO$_4$, and removed solvent in vacuo to yield the crude product 190a which was used directly in the next step.

Example 190b 10-[3-(5-{[5-(4-Ethylpiperazin-1-yl)pyridine-2-yl]amino}-1-methyl-6-oxo-1,6-dihydropyridin-3-yl)-2-(acetoxymethyl)phenyl]-4,4-dimethyl-1,10-diazatricyclo[6.4.0.0$^{2,6}$]dodeca-2(6),7-dien-9-one 190b

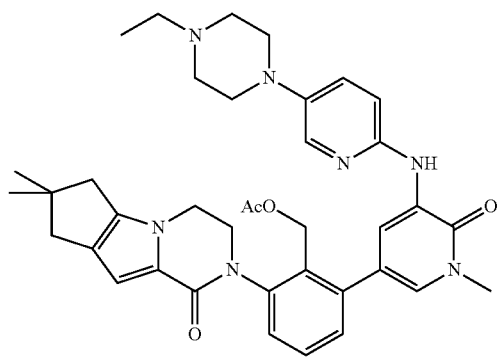

To a microwave tube equipped with a stirring bar, bromide 167f (150 mg, 0.348 mmol), 190a (306 mg, 0.696 mmol), Pd(PPh$_3$)$_4$ (40.2 mg, 0.0348 mmol), Na$_2$CO$_3$ aqueous solution (1.0 N, 1.15 mL, 1.15 mmol), DME (4 mL) were added. The mixture was reacted in microwave at 130° C. for 10 min. methylene chloride (200 mL) was added and the resulting mixture was washed with water (3×30 mL), brine (30 mL×1), dried over MgSO$_4$, filtered, and removed solvent in vacuo. Silica gel column chromatography (methanol:methylene chloride=5:95) gave 190b.

To a round-bottomed flask equipped with a stirring bar, 190b, THF (3 mL), isopropanol (3 mL), water (3 mL), LiOH monohydrate (200 mg) were added. The resulting mixture was stirred at RT for 1 hr. Removed all the solvent in vacuo and the resulting residue was added to methylene chloride (200 mL), the solution was washed with water (3×30 mL), brine (30 mL), dried over MgSO$_4$, filtered, and removed solvent in vacuo. Silica gel column chromatography (MeOH:methylene chloride=10:90) gave 190 as a yellow solid, 16 mg. MS (ESI+) m/z 622.5 (M+H).

Example 191 10-[3-(5-{[5-(4-Ethylpiperazin-1-yl)pyridine-2-yl]amino}-1-methyl-6-oxo-1,6-dihydropyridin-3-yl)-2-(hydroxymethyl)phenyl]-4,4-dimethyl-1,10-diazatricyclo-[6.4.0.0$^{2,6}$]dodeca-2(6),7-dien-9-one 191

Example 191a 10-[3-(5-{[5-(4-Ethylpiperazin-1-yl)pyridine-2-yl]amino}-1-methyl-6-oxo-1,6-dihydropyridin-3-yl)-2-(hydroxymethyl)phenyl]-4,4-dimethyl-1,10-diazatricyclo[6.4.0.0$^{2,6}$]dodeca-2(6),7-dien-9-one 191a

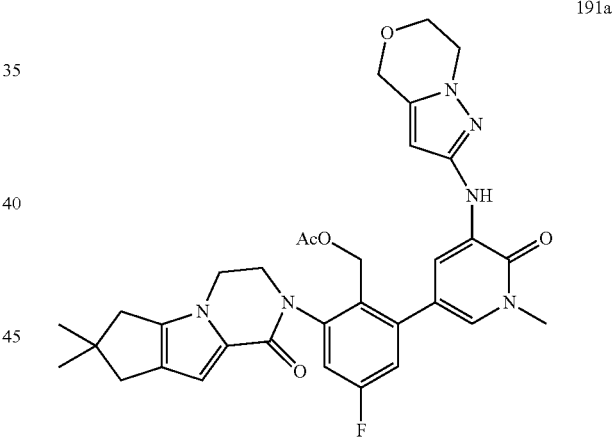

A microwave tube equipped with a magnetic stirrer was charged with 3-(6,7-dihydro-4H-pyrazolo[5,1-c][1,4]oxazin-2-ylamino)-1-methyl-5-(4,4,5,5-tetramethyl-1,3,2-dioxaborolan-2-yl)pyridin-2(1H)-one 150a (200 mg, 0.5 mmol), 189a (150 mg, 0.34 mmol), 1,2-dimethoxyethane (4 mL) and 1M aqueous sodium carbonate (1 mL). After bubbling N$_2$ for 15 min, Pd(PPh$_3$)$_4$ (19 mg, 0.02 mmol) was added. The mixture was heated in microwave to 130° C. for 10 min. After this time, ethyl acetate (5 mL) and water (5 mL) were added. The separated aqueous layer was extracted with ethyl acetate (2×5 mL). The combined organics were washed with brine (10 mL), dried over sodium sulfate, filtered and concentrated under reduced pressure. The resulting residue was purified by column chromatography eluting with a gradient of methylene chloride—60:35:5 CH$_2$Cl$_2$:diethyl ether:methanol to afford a 59% yield (125 mg) of 191a.

A 25 mL round bottom flask with a magnetic stirrer was charged with 191a (130 mg, 0.2 mmol), lithium hydroxide (43 mg, 1.0 mmol), THF (1 mL), isopropanol (1 mL) and water (2 mL). The mixture stirred at rt for 30 min. After this time, ethyl acetate (5 mL) and water (5 mL) were added. The separated aqueous layer was extracted with ethyl acetate (2×5 mL). The combined organics were washed with brine (10 mL), dried over sodium sulfate, filtered and concentrated under reduced pressure. The resulting residue was purified by column chromatography eluting with a gradient of methylene chloride—60:35:5 $CH_2Cl_2$:diethyl ether:methanol to afford a 59% yield (68 mg) of 191. MS (ESI+) m/z 573.4 (M+H).

Example 192 6-(3-(5-(6,7-Dihydro-4H-pyrazolo[5,1-c][1,4]oxazin-2-ylamino)-1-methyl-6-oxo-1,6-dihydropyridin-3-yl)-5-fluoro-2-(hydroxymethyl)phenyl)-2,3-(5,5-dimethyl-5,6-dihydro-4H-cyclopenta)-5,6-dihydrothieno[2,3-c]pyridin-7(4H)-one 192

A 100-mL three-neck round-bottomed flask equipped with a magnetic stirrer and reflux condenser was charged with 182c (300 mg, 0.513 mmol), 110c (167 mg, 0.513 mmol), sodium carbonate (218 mg, 2.05 mmol), water (6 mL) and 1,4-dioxane (30 mL). After bubbling nitrogen through the resulting suspension for 20 min, tetrakis(triphenyl-phosphine)-palladium(0) (60.0 mg, 0.051 mmol) was added, and the reaction mixture was heated at 100° C. for 4 h. After this time, the reaction mixture was cooled to room temperature and filtered, and the filter cake was washed with a 1:10 mixture of methanol and methylene chloride (30 mL). The filtrate was concentrated under reduced pressure to afford a brown residue. Another 50-mL single-neck round-bottomed flask equipped with a magnetic stirrer and reflux condenser was charged with the residue thus obtained, tetrabutylammonium fluoride (1.0 M in THF, 2 mL, 2.00 mmol) and THF (6 mL). The mixture was stirred at room temperature for 1.5 h. After this time, the reaction mixture was concentrated under reduced pressure. The resulting residue was purified by flash chromatography to afford a 36% (110 mg) yield of 192 as an off-white solid: mp 170-172° C.; $^1$H NMR (500 MHz, DMSO-$d_6$) δ 8.21 (s, 1H), 7.99 (d, 1H, J=2.0 Hz), 7.32 (dd, 1H, J=9.0, 3.0 Hz), 7.28 (d, 1H, J=2.0 Hz), 7.15 (dd, 1H, J=9.0, 3.0 Hz), 5.93 (s, 1H), 4.86 (t, 1H, J=5.0 Hz)

Example 193 5-(2-(Hydroxymethyl)-3-(6,6-dimethyl-3,4,6,7-tetrahydro-5H-cyclopenta[4,5]thieno[2,3-c]pyridine-1(2H)-yl))-1-methyl-3-(pyridin-3-ylamino)pyrazin-2(1H)-one 193

Following Example 204, reaction of 111b (132 mg, 0.466 mmol) with 131a (300 mg, 0.606 mmol) afforded a 31% yield (75 mg) of 193 as an off-white solid: mp 135-136° C.; $^1$H NMR (500 MHz, DMSO-$d_6$) δ 9.53 (s, 1H), 9.15 (d, 1H, J=1.9 Hz), 8.42 (m, 1H), 8.17 (dd, 1H, J=4.5, 1.4 Hz), 7.54 (dd, 1H, J=7.4, 1.0 Hz), 7.47 (m, 2H), 7.34 (dd, 1H, J=8.0, 1.5 Hz), 7.30 (m, 1H), 4.82 (m, 1H), 4.46 (m, 2H), 4.01 (m, 1H), 3.86 (m, 1H), 3.56 (s, 3H), 3.02 (m, 1H), 2.88 (m, 1H), 2.75 (s, 2H), 2.54 (d, 2H, J=6.0 Hz), 1.23 (s, 6H); MS (ESI+) m/z 528.2 (M+H).

Example 194 5-(2-(Hydroxymethyl)-3-(6,6-dimethyl-3,4,6,7-tetrahydro-5H-cyclopenta[4,5]thieno[2,3-c]pyridine-1(2H)-yl)-1-methyl-3-(5-(4-methylpiperazin-1-yl)pyridin-2-ylamino)pyridin-2(1H)-one 194

Following Example 204, reaction of 197e (176 mg, 0.466 mmol) with 131a (300 mg, 0.606 mmol) afforded a brown residue. A 100-mL single-neck round-bottomed flask equipped with a magnetic stirrer was charged with the above crude residue, THF (8 mL), methanol (4 mL), water (4 mL) and lithium hydroxide monohydrate (196 mg, 4.66 mmol). The mixture was stirred for 2 h at room temperature and then concentrated in vacuo. The residue was partitioned between a 20% (v/v) solution of methanol in methylene chloride (150 mL) and water (30 mL). The organic layer was separated, and the aqueous layer was extracted with a 20% (v/v) solution of methanol in methylene chloride (3×30 mL). The combined organic layers were dried over sodium sulfate and concentrated under reduced pressure. The residue was purified by column chromatography (silica, 0% to 10% methanol/methylene chloride) to afford a 33% yield (95 mg) of 194 as an off-white solid: mp 142-143° C.; $^1$H NMR (500 MHz, DMSO-$d_6$) δ 8.54 (d, 1H, J=2.5 Hz), 8.33 (s, 1H), 7.85 (d, 1H, J=3.0 Hz), 7.45 (t, 1H, J=7.4 Hz), 7.35 (m, 2H), 7.32 (m, 2H), 7.20 (d, 1H, J=9.3 Hz), 4.84 (m, 1H), 4.32 (m, 2H), 4.03 (m, 1H), 3.85 (m, 1H), 3.58 (s, 3H), 3.03 (m, 5H), 2.87 (m, 1H), 2.75 (s, 2H), 2.53 (m, 2H), 2.43 (m, 4H), 2.20 (s, 3H), 1.23 (s, 6H); MS (ESI+) m/z 625.3 (M+H).

Example 195 5-[2-(Hydroxymethyl)-3-{1-oxo-1H,2H,3H,4H,6H,7H,8H,9H-pyrazino-[1,2-a]indol-2-yl}phenyl]-1-methyl-3-({5-[4-(propan-2-yl)piperazin-1-yl]pyridine-2-yl}amino)-1,2-dihydropyridin-2-one 195

Following Example 138, 5-bromo-1-methyl-3-(5-(4-(1-methylethyl)piperazin-1-yl)pyridin-2-ylamino)pyridin-2(1H)-one 220a was converted to 75 mg of 195 as a white solid. MS (ESI+) m/z 622 (M+H).

Example 196 10-(3-{5-[(1,5-Dimethyl-1H-pyrazol-3-yl)amino]-1-methyl-6-oxo-1,6-dihydropyridin-3-yl}-5-fluoro-2-(hydroxymethyl)phenyl)-4,4-dimethyl-1,10-diazatricyclo[6.4.0.0$^{2,6}$]dodeca-2(6),7-dien-9-one 196

Example 196a 3-(1,5-Dimethyl-1H-pyrazol-3-ylamino)-1-methyl-5-(4,4,5,5-tetramethyl-1,3,2-dioxaborolan-2-yl)pyridin-2(1H)-one 196a

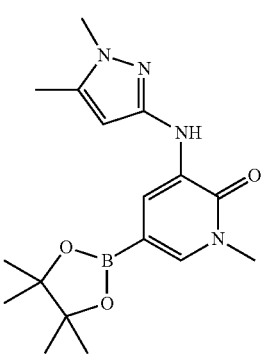

196a

A sealed tube equipped with a magnetic stirrer was charged with 5-bromo-3-(1,5-dimethyl-1H-pyrazol-3-ylamino)-1-methylpyridin-2(1H)-one 142a (380 mg, 1.4 mmol), 4,4,4',4',5,5,5',5'-octamethyl-2,2'-bi(1,3,2-dioxaborolane) (690 mg, 2.7 mmol), potassium acetate (401 mg, 4.1 mmol) and 1,4-dioxane (34 mL). After bubbling nitrogen through the resulting suspension for 30 min, [1,1'-bis(diphenylphosphino)ferrocene]dichloro-palladium(II) complex with methylene chloride (Pd Cl$_2$dppf:CH$_2$Cl$_2$ (1:1), 110 mg, 0.14 mmol) was then added, and the reaction was stirred at 105° C. for 16 h. After this time, the mixture was cooled to ambient temperature, partition between water (20 mL) and ethyl acetate (20 mL). The separated aqueous layer was extracted with ethyl acetate (2×10 mL). The combined organics were washed with brine (30 mL), dried over sodium sulfate, filtered and concentrated under reduced pressure. The resulting crude 196a was used in the next step without further purification.

Example 196b 10-(3-{5-[(1,5-Dimethyl-1H-pyrazol-3-yl)amino]-1-methyl-6-oxo-1,6-dihydropyridin-3-yl}-5-fluoro-2-(acetoxymethyl)phenyl)-4,4-dimethyl-1,10-diazatricyclo[6.4.0.0$^{2,6}$]dodeca-2(6),7-dien-9-one 196b

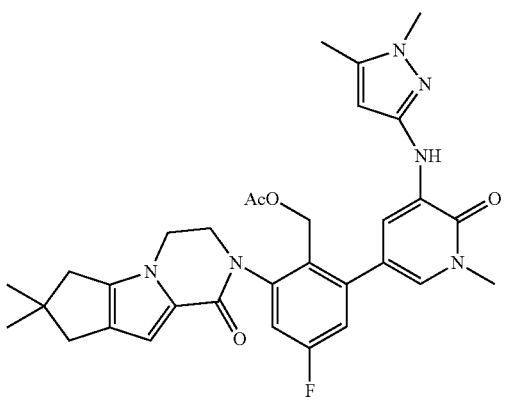

A microwave tube equipped with a magnetic stirrer was charged with 196a (450 mg, 1.3 mmol), 189a (240 mg, 0.5 mmol), DME (4 mL) and 1M aqueous sodium carbonate (1.5 mL). After bubbling N2 for 15 min, Pd(PPh$_3$)$_4$ (31 mg, 0.03 mmol) was added. The mixture was heated in microwave to 130° C. for 10 min. After this time, EtOAc (5 mL) and water (5 mL) were added. The separated aqueous layer was extracted with EtOAc (2×5 mL). The combined organics were washed with brine (10 mL), dried over sodium sulfate, filtered and concentrated under reduced pressure. The resulting residue was purified by column chromatography eluting with a gradient of methylene chloride—60:35:5 methylene chloride:diethyl ether:methanol to afford a 83% yield (260 mg) of 196b.

A 25 mL round bottom flask with a magnetic stirrer was charged with 196b (260 mg, 0.5 mmol), lithium hydroxide (94 mg, 2.2 mmol), THF (2 mL), isopropanol (2 mL) and water (5 mL). The mixture stirred at rt for 30 min. After this time, ethyl acetate (5 mL) and water (5 mL) were added. The separated aqueous layer was extracted with ethyl acetate (2×5 mL). The combined organics were washed with brine (10 mL), dried over sodium sulfate, filtered and concentrated under reduced pressure. The resulting residue was purified by column chromatography using the Biotage KPNH 12+M column eluting with a gradient of hexanes—ethyl acetate to afford a 46% yield (110 mg) of 196. MS (ESI+) m/z 545.4 (M+H).

Example 197 2-(5-fluoro-2-(hydroxymethyl)-3-(1-methyl-5-(5-(4-methylpiperazin-1-yl)pyridin-2-ylamino)-6-oxo-1,6-dihydropyridin-3-yl)phenyl)-3,4,6,7,8,9-hexahydropyrazino[1,2-a]indol-1(2H)-one 197

Example 197a 2,6-Dibromo-4-fluorobenzaldehyde 197a

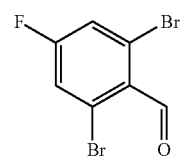

A solution of 1,3-dibromo-5-fluoro-2-iodobenzene (50 g, 132 mmol) in anhydrous toluene (300 mL) cooled to −35° C. was added the solution of isopropylmagnesium chloride (84 mL, 171 mmol, 2.0 M in diethyl ether) over a period of 30 minutes while maintaining the internal temperature below −25° C. A clear brown solution was obtained. Stirring was continued for 1.5 h. Then anhydrous DMF (34 mL, 436 mmol) was added over a period of 30 minutes. The temperature of the reaction mixture increased to −19° C. The reaction mixture was warmed to 10° C. (room temperature) over 1 h and stirred at this temperature for 1.5 h. The reaction was quenched with saturated aqueous NH$_4$Cl (100 mL), filtered and evaporated under reduced pressure. The residue was purified by silica-gel column chromatography (eluting with petroleum ether/ethyl acetate: from 50:1 to 20:1) to give 197a (20 g, yield 54%) as a yellow solid.

Example 197b
2,6-Dibromo-4-fluorophenyl)methanol 197b

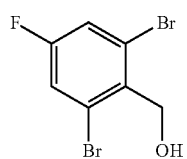

A solution of 197a (20 g, 71 mmol) in ethanol (500 mL) was added NaBH$_4$ (10 g, 284 mmol). The mixture was stirred at room temperature (10° C.) for 4 h. TLC showed the start material disappeared. The reaction was quenched with HCl solution (150 mL, 1 M). Most of ethanol was evaporated at reduced pressure. The residue was extracted by ethyl acetate (3×500 mL). The organic layers was combined and dried with anhydrous Na$_2$SO$_4$, evaporated in vacuo. The residue was purified by silica-gel column chromatography (eluting with petroleum ether/ethyl acetate: from 50:1 to 20:1) to give 197b (15 g, yield 75%) as a white solid.

Example 197c 2,6-Dibromo-4-fluorobenzyl acetate 197c

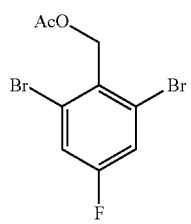

A 500-mL single-neck round-bottomed flask equipped with a magnetic stirrer and nitrogen inlet was charged with 197b (23.0 g, 81.0 mmol), triethylamine (25.0 g, 247 mmol) in anhydrous methylene chloride (100 mL). Acetic anhydride (10.0 g, 98.0 mmol) was added and this mixture was stirred at room temperature for 16 h. After this time, the mixture was diluted with methylene chloride (100 mL) and washed with saturated aqueous sodium bicarbonate (100 mL). The layers were separated and the aqueous layer was extracted with methylene chloride (2×20 mL). The organic extracts were combined and dried over sodium sulfate. The drying agent was removed by filtration. The filtrate was concentrated under reduced pressure, and the resulting residue was purified by flash column chromatography (silica, 0% to 50% ethyl acetate/hexanes) to afford 197c in 87% yield (23.0 g) as a white solid.

Example 197d 2-Bromo-4-fluoro-6-(1-oxo-3,4,6,7,8,9-hexahydropyrazino[1,2-a]indol-2(1H)-yl)benzyl Acetate 197d

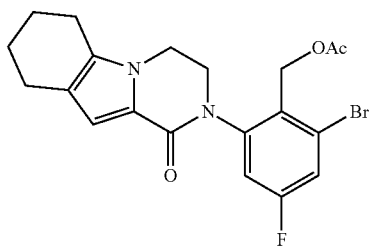

A 250-mL single-neck round-bottomed flask equipped with a magnetic stirrer was charged with ethyl 1-(2-aminoethyl)-4,5,6,7-tetrahydro-1H-indole-2-carboxylate 101k (3.8 g, 20 mmol), 197c (20 g, 60 mmol), Xantphos (1.2 g, 2 mmol), tris(dibenzylideneacetone)dipalladium(0) (1.8 g, 2 mmol), Cs$_2$CO$_3$ (16 g, 50 mmol), and 1,4-dioxane (120 mL). The system was evacuated and then refilled with N$_2$. A reflux condenser was attached to the flask, and the reaction mixture was heated at 100° C. for 16 h. It was then cooled to room temperature and filtered. The filtrate was concentrated under reduced pressure, and the resulting residue was purified by flash column chromatography eluting with 5:1 petroleum ether/ethyl acetate to afford 197d in 60% yield (5.2 g) as a white solid. MS: [M+H]$^+$ 435. $^1$H NMR (500 MHz, DMSO) δ 7.70 (dd, J=3, 1H), 7.48 (dd, J=3, 1H), 6.52 (s, 1H), 5.01 (m, 2H), 4.18 (m, 2H), 4.02 (m, 1H), 3.73 (m, 1H), 2.60 (m, 2H), 2.45 (m, 2H), 1.98 (s, 3H), 1.77 (m, 2H), 1.68 (m, 2H).

Example 197f 1-Methyl-3-[5-(4-methyl-piperazin-1-yl)-pyridin-2-ylamino]-5-(4,4,5,5-tetramethyl-[1,3,2]dioxaborolan-2-yl)-1H-pyridin-2-one 197f

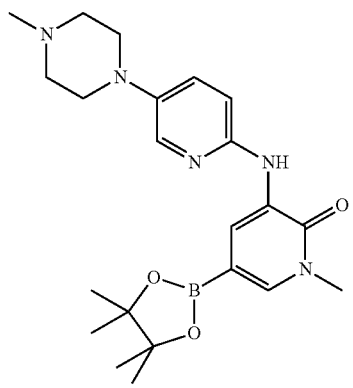

A 1-L single-neck round-bottomed flask equipped with a magnetic stirrer and thermoregulator was purged with nitrogen and charged with 197e, prepared according to US 2009/0318448, (10.0 g, 0.027 mol), bis(pinacolato)diboron (8.06 g, 0.032 mol), potassium acetate (10.4 g, 0.11 mol) and 1,4-dioxane (200 mL). After a stream of nitrogen was passed through the resulting suspension for 30 min., Pd(dppf)Cl$_2$CH$_2$Cl$_2$ (582 mg, 0.795 mmol) was added. The resulting reaction mixture was stirred at reflux for 3 h. Then, it was cooled to room temperature, partitioned between water (400 mL) and ethyl acetate (600 mL) and filtered through a pad of Celite. The organic phase was extracted, dried over sodium sulfate, filtered and concentrated. The residue was triturated with a mixture of diethyl ether (50 mL) and hexanes (250 mL), and the suspension was filtered. The filter cake was dried under vacuum at room temperature to afford a 27% yield (3.04 g) of 197f as a brown solid.

Example 197g 4-Fluoro-2-(1-methyl-5-(5-(4-methylpiperazin-1-yl)pyridin-2-ylamino)-6-oxo-1,6-dihydropyridin-3-yl)-6-(1-oxo-3,4,6,7,8,9-hexahydropyrazino[1,2-a]indol-2(1H)-yl)benzyl Acetate 197g

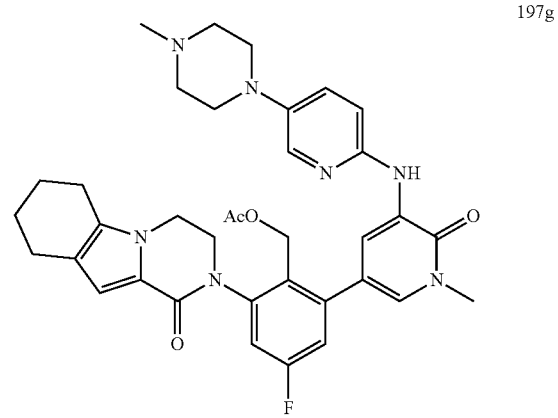 [SMILES: CC(=O)OCc1c(-c2cc(Nc3ccc(N4CCN(C)CC4)cn3)c(=O)n(C)c2)cc(F)cc1N1CCn2c(cc3c2CCCC3)C1=O]

In a 10-mL glass vessel equipped with a magnetic stirring bar were placed 197f (244 mg, 0.58 mmol), 197d (200 mg, 0.46 mmol), Pd(PPh$_3$)$_4$ (33 mg, 0.030 mmol) in 2 N Na$_2$CO$_3$ (1 mL) and DME (2 mL). The vessel was sealed with a septum and placed into the microwave cavity. After the reaction mixture was stirred at 125° C. for 7 min., it was purified by flash chromatography (dichloromethane:methanol, 85:15) to give 30% (90 mg) of 197g as a solid.

A 100-mL, single-necked, round-bottomed flask equipped with a magnetic stirring bar was charged with 197g (90 mg, 0.14 mmol), LiOH hydrate (60 mg, 1.4 mmol), THF (2 mL), i-PrOH (2 mL), and water (2 mL). After the reaction mixture was stirred at room temperature for 3 h, it was partitioned between dichloromethane (5 mL) and water (5 mL), and the organic phase was extracted with dichloromethane (5 mL×3). The combined organic phases were washed with water (5 mL×2) and brine (5 mL×1), dried (Na$_2$SO$_4$), and concentrated. The crude product was re-dissolved in dichloromethane (3 mL). To this solution was added hexane (10 mL) and the resulting precipitates were filtered to give 81% yield (69 mg) of 197. MS (ESI+) m/z 612.5 (M+H)

Example 198 10-[5-Fluoro-2-(hydroxymethyl)-3-(1-methyl-5-{[5-(4-methylpiperazin-1-yl)pyridin-2-yl]amino}-6-oxo-1,6-dihydropyridin-3-yl)phenyl]-4,4-dimethyl-1,10-diazatricyclo[6.4.0.0$^{2,6}$]dodeca-2(6),7-dien-9-one 198

Example 198a 2,6-Dibromo-4-fluorobenzaldehyde 198a

A solution of 1,3-dibromo-5-fluoro-2-iodobenzene (50 g, 132 mmol) in anhydrous toluene (300 mL) cooled to −35° was added the solution of isopropylmagnesium chloride (84 mL, 171 mmol, 2.0 M in Et$_2$O) over a period of 30 minute while maintaining the internal temperature below −25° (FIG. 6). A clear brown solution was obtained. Stirring was continued for 1.5 h. Then anhydrous DMF (34 mL, 436 mmol) was added over a period of 30 minutes. The temperature of the reaction mixture increased to −19°. The reaction mixture was warmed to 10° (room temperature) over 1 h and stirred at this temperature for 1.5 h. The reaction was quenched with saturated aqueous NH$_4$Cl (100 mL), filtered and evaporated under reduced pressure. The residue was purified by silica-gel column chromatography (eluting with petroleum ether/ethyl acetate: from 50:1 to 20:1) to give 198a (20 g, yield 54%) as a yellow solid.

Example 198b
2,6-Dibromo-4-fluorophenyl)methanol 198b

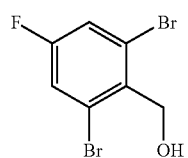

A solution of 198a (20 g, 71 mmol) in EtOH (500 mL) was added NaBH$_4$ (10 g, 284 mmol). The mixture was stirred at room temperature (10° C.) for 4 h. TLC showed the start material disappeared. The reaction was quenched with HCl solution (150 mL, 1 M). Most of EtOH was evaporated at reduced pressure. The residue was extracted by ethyl acetate (3×500 mL). The organic layers was combined and dried with anhy. Na$_2$SO$_4$, evaporated in vacuo. The residue was purified by silica-gel column chromatography (eluting with petroleum ether/ethyl acetate: from 50:1 to 20:1) to give 198b (15 g, yield 75%) as a white solid.

Example 198c 2,6-Dibromo-4-fluorobenzyl acetate 198c

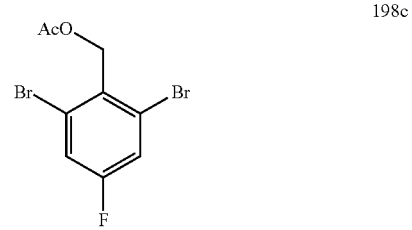

A 500-mL single-neck round-bottomed flask equipped with a magnetic stirrer and nitrogen inlet was charged with 198b (23.0 g, 81.0 mmol), triethylamine (25.0 g, 247 mmol) in anhydrous methylene chloride (100 mL). Acetic anhydride (10.0 g, 98.0 mmol) was added and this mixture was stirred at room temperature for 16 h. After this time, the mixture was diluted with methylene chloride (100 mL) and washed with saturated aqueous sodium bicarbonate (100 mL). The layers were separated and the aqueous layer was extracted with methylene chloride (2×20 mL). The organic extracts were combined and dried over sodium sulfate. The drying agent was removed by filtration. The filtrate was concentrated under reduced pressure, and the resulting residue was purified by flash column chromatography (silica, 0% to 50% ethyl acetate/hexanes) to afford 198c in 87% yield (23.0 g) as a white solid.

Example 198d 2-Bromo-4-fluoro-6-(1-oxo-3,4,6,7,8,9-hexahydropyrazino[1,2-a]indol-2(1H)-yl)benzyl acetate 198d

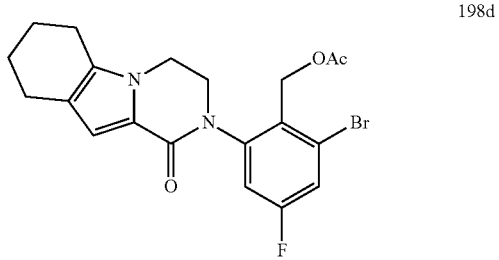 [SMILES: CC(=O)OCc1c(Br)cc(F)cc1N1CCn2c(cc3c2CCCC3)C1=O]

A 250-mL single-neck round-bottomed flask equipped with a magnetic stirrer was charged with ethyl 1-(2-aminoethyl)-4,5,6,7-tetrahydro-1H-indole-2-carboxylate 101k (3.8 g, 20 mmol), 198c (20 g, 60 mmol), Xantphos (1.2 g, 2 mmol), tris(dibenzylideneacetone)dipalladium(0) (1.8 g, 2 mmol), Cs$_2$CO$_3$ (16 g, 50 mmol), and 1,4-dioxane (120 mL). The system was evacuated and then refilled with N$_2$. A reflux condenser was attached to the flask, and the reaction mixture was heated at 100° C. for 16 h. It was then cooled to room temperature and filtered. The filtrate was concentrated under reduced pressure, and the resulting residue was purified by flash column chromatography eluting with 5:1 PE/EA to afford 198d in 60% yield (5.2 g) as a white solid. MS:

[M+H]+ 435. ¹H NMR (500 MHz, DMSO) δ 7.70 (dd, J=3, 1H), 7.48 (dd, J=3, 1H), 6.52 (s, 1H), 5.01 (m, 2H), 4.18 (m, 2H), 4.02 (m, 1H), 3.73 (m, 1H), 2.60 (m, 2H), 2.45 (m, 2H), 1.98 (s, 3H), 1.77 (m, 2H), 1.68 (m, 2H).

Example 198e 5-bromo-1-methyl-3-[5-(4-methyl-piperazin-1-yl)-pyridin-2-ylamino]-1H-pyridin-2-one 198e

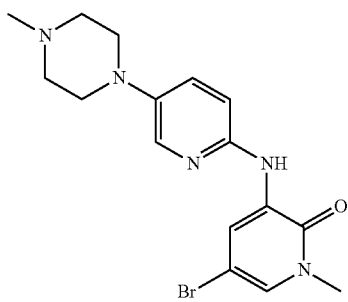

Step 1: 1-methyl-4-(6-nitropyridin-3-yl)piperazine

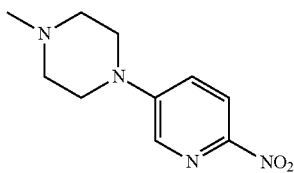 [SMILES: CN1CCN(c2ccc([N+](=O)[O-])nc2)CC1]

According to US 2009/0318448, into a solution of 5-bromo-2-nitropyridine (2.0 g, 9.85 mmol) in DMSO (10 mL) was added K2CO3 (2.72 g, 19.7 mmol) and 1-methylpiperazine (1.64 mL, 14.8 mmol), and tetrabutylammonium iodide (36 mg). The mixture was stirred at 120 degree C. for overnight. It was allowed to cool down and acidified with 1N HCl. The mixture was extracted with DCM. The aqueous layer was basified with saturated Na2CO3, and further extracted with DCM. The combined organic layers were dried over Na2SO4 and concentrated to give a brown solid, which was washed with small amount of water. The solid was dried under vacuum to give 2.16 g of 1-methyl-4-(6-nitropyridin-3-yl)piperazine (99% yield) as a yellow powder. LCMS: (M+H)+ 223

Step 2: 5-(4-methylpiperazin-1-yl)pyridin-2-amine

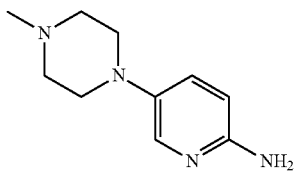

The suspension of 1-methyl-4-(6-nitropyridin-3-yl)piperazine (5 g, 22.5 mmol), NH4Cl (12 g, 225 mmol), and Fe (5 g, 5 mmol) was stirred in EtOH/H2O (1:1) (100 mL) at 80° C. for 3 h. TLC showed starting material 1-methyl-4-(6-nitropyridin-3-yl)piperazine disappeared. After filtration on a pad of Celite, the solvent was removed under vacuum. EA and brine were added into the mixture and the organic layer was separated, dried over Na2SO4 and concentrated at reduced pressure to give 2.5 g of 5-(4-methylpiperazin-1-yl)pyridin-2-amine (yield 60%). LCMS: (M+H)+ 193.

Step 3

5-(4-methylpiperazin-1-yl)pyridin-2-amine (1 g, 10.5 mmol), 3,5-dibromo-1-methylpyridin-2(1H)-one (1.87 g, 7 mmol), and Cs2CO3 (5 g, 21 mmol) were added to dioxane (30 mL) in a sealed tube. After bubbling nitrogen through the resulting solution for 15 minutes, Xantphos (405 mg, 0.7 mmol) and tris(dibenzylideneacetone)dipalladium(0) (320 mg, 0.35 mmol) were added, and the reaction mixture was stirred at 100° C. for 0.5 h. After filtration, the solid was washed by warm EA, and the filtrate was concentrated to afford the crude product as a black solid. The crude product was the re-crystallized from MeOH to give 1.26 g (64%) of 198e. LCMS: (M+H)+ 380. ¹H NMR (500 MHz, DMSO) δ 8.57 (d, J=2.5, 1H), 8.54 (s, 1H), 7.93 (d, J=3, 1H), 7.44 (d, J=2.5, 1H), 7.38 (dd, J=3.5, 2H), 7.24 (d, J=4.5, 1H), 3.50 (s, 3H), 3.07 (m, 4H), 2.44 (m, 4H), 2.21 (s, 3H).

Example 198f 1-Methyl-3-[5-(4-methyl-piperazin-1-yl)-pyridin-2-ylamino]-5-(4,4,5,5-tetramethyl-[1,3,2]dioxaborolan-2-yl)-1H-pyridin-2-one 198f

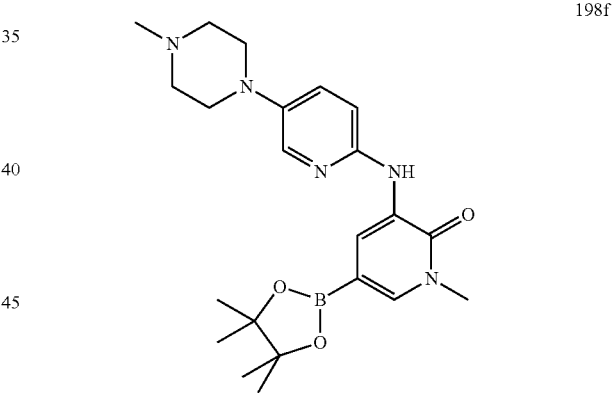

A 1-L single-neck round-bottomed flask equipped with a magnetic stirrer and thermoregulator was purged with nitrogen and charged with 198e (10.0 g, 0.027 mol), bis(pinacolato)diboron (8.06 g, 0.032 mol), potassium acetate (10.4 g, 0.11 mol) and 1,4-dioxane (200 mL). After a stream of nitrogen was passed through the resulting suspension for 30 min., Pd(dppf)Cl₂CH₂Cl₂ (582 mg, 0.795 mmol) was added. The resulting reaction mixture was stirred at reflux for 3 h. Then, it was cooled to room temperature, partitioned between water (400 mL) and ethyl acetate (600 mL) and filtered through a pad of Celite. The organic phase was extracted, dried over sodium sulfate, filtered and concentrated. The residue was triturated with a mixture of diethyl ether (50 mL) and hexanes (250 mL), and the suspension was filtered. The filter cake was dried under vacuum at room temperature to afford a 27% yield (3.04 g) of 198f as brown solids.

Example 198g 4-Fluoro-2-(1-methyl-5-(5-(4-methylpiperazin-1-yl)pyridin-2-ylamino)-6-oxo-1,6-dihydropyridin-3-yl)-6-(1-oxo-3,4,6,7,8,9-hexahydropyrazino[1,2-a]indol-2(1H)-yl)benzyl acetate 198g

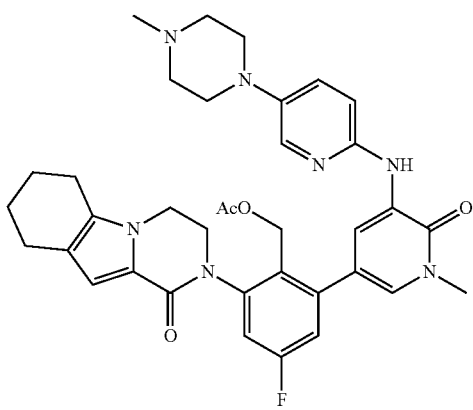

In a 10-mL glass vessel equipped with a magnetic stirring bar were placed 198f (244 mg, 0.58 mmol), 198d (200 mg, 0.46 mmol), Pd(PPh$_3$)$_4$ (33 mg, 0.030 mmol) in 2 N Na$_2$CO$_3$ (1 mL) and DME (2 mL). The vessel was sealed with a septum and placed into the microwave cavity. After the reaction mixture was stirred at 125° C. for 7 min., it was purified by flash chromatography (dichloromethane:MeOH, 85:15) to give 30% (90 mg) of 198g as solids.

Following Example 148, 198g was converted to 75 mg of 198 as a white solid. MS (ESI+) m/z 626.6 (M+H).

Example 199 5-[5-Fluoro-2-(hydroxymethyl)-3-[1-methyl-5-({5-[(1-methylazetidin-3-yl)oxy]pyridin-2-yl}amino)-6-oxo-1,6-dihydropyridin-3-yl]phenyl]-8-thia-5-azatricyclo[7.4.0.0$^{2,7}$]trideca-1(9),2(7)-dien-6-one 199

Example 199a tert-Butyl 3-Iodoazetidine-1-carboxylate 199a

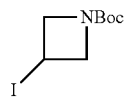

A solution of tert-butyl 3-hydroxyazetidine-1-carboxylate (25-3) (3.5 g, 0.02 mol) in toluene (200 mL) was treated with imidazole (4.08 g, 0.06 mol), PPh$_3$ (0.6 g, 0.04 mol), and I$_2$ (7.62 g, 0.03 mol). The mixture was heated at 100° C. for 1 h and cooled down to room temperature. It was then poured into saturated NaHCO$_3$ solution (30 mL). Excess PPh$_3$ was destroyed by addition of iodine until I$_2$ coloration persisted in organic layer. The mixture was washed with 5% Na$_2$SO$_3$ solution, dried over Na$_2$SO$_4$, and evaporated in vacuo. The residue was purified on silica gel column to give 199a (5.31 g, 93%). MS: [M+H]$^+$ 284.

Example 199b tert-Butyl 3-(6-Nitropyridin-3-yloxy)azetidine-1-carboxylate 199b

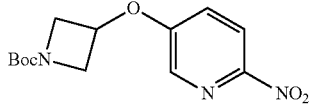

A mixture of 199a (2.24 g, 7.9 mmol), 6-nitropyridin-3-ol (1 g, 7.2 mmol) and Cs$_2$CO$_3$ (2.6 g, 7.9 mmol) in DMF (8 mL) was heated at 125° C. in a sealed tube for overnight. The mixture was filtered off and washed with ethyl acetate (20 mL×2). The filtrate was evaporated in vacuo and the residue was purified on reverse phase Combi-flash to give 199b (1.25 g, 59%). MS: [M+H]$^+$ 296.

Example 199c tert-Butyl 3-(6-Aminopyridin-3-yloxy)azetidine-1-carboxylate 199c

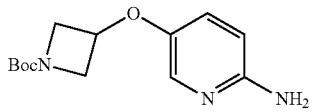

A 100-mL Parr hydrogenation bottle was purged with nitrogen and charged with 199b (1.07 g, 3.6 mmol), 10% palladium on carbon (50% wet, 0.3 g) and methanol (60 mL). The bottle was evacuated, charged with hydrogen gas to a pressure of 25 psi, and shaken for 2 h on a Parr hydrogenation apparatus. The hydrogen was then evacuated and nitrogen charged to the bottle. The catalyst was removed by filtration through a pad of Celite and the filtrate was concentrated under reduced pressure to afford 199c (0.95 g, 99%). MS: [M+H]$^+$ 266.

Example 199d tert-Butyl 3-(6-(5-Bromo-1-methyl-2-oxo-1,2-dihydropyridin-3-ylamino)pyridin-3-yloxy)azetidine-1-carboxylate 199d

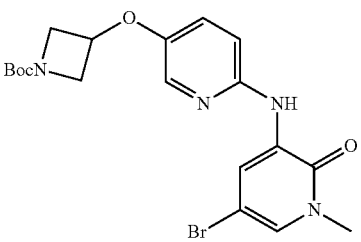 [SMILES: Cn1cc(Br)cc(Nc2ccc(OC3CN(C(=O)OC(C)(C)C)C3)cn2)c1=O]

A mixture of 199c (950 mg, 3.6 mmol), XantPhos (125 mg, 0.29 mmol), Pd$_2$dba$_3$ (260 mg, 0.29 mmol), 3,5-dibromo-1-methylpyridin-2(1H)-one (1.03 g, 3.9 mmol) and Cs$_2$CO$_3$ (1.8 g. 7.2 mmol) in 1,4-dioxane (20 mL) was heated at reflux for 2 h. After the completion of the reaction, the mixture was filtered off and washed with methanol (100 mL). The filtrate was evaporated in vacuo. The residue was purified on reverse phase Combi-flash to give 199d (1.46 g, 91%). MS: [M+H]$^+$ 451.

Example 199e 3-(5-(Azetidin-3-yloxy)pyridin-2-ylamino)-5-bromo-1-methylpyridin-2(1H)-one hydrochloride 199e

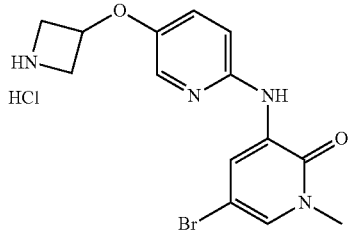 [SMILES: Cl ; Cn1cc(Br)cc(Nc2ccc(OC3CNC3)cn2)c1=O]

A mixture of 199d (1.46 g, 3.2 mmol) and HCl/1,4-dioxane (3.2 mL, 12.8 mmol, 4 M) in methanol (20 mL) was heated at 80° C. for 1 h. The mixture was concentrated under reduced pressure to give 199e (1.24 g, 99%). MS: [M+H]$^+$ 351.

Example 199f 5-Bromo-1-methyl-3-(5-(1-methyl-azetidin-3-yloxy)pyridin-2-ylamino)-pyridine-2(1H)-one 199f

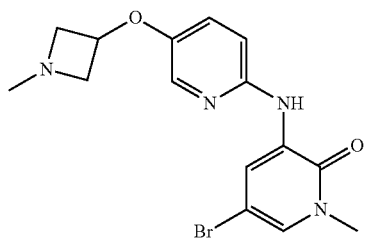 [SMILES: CN1CC(Oc2ccc(Nc3cc(Br)cn(C)c3=O)nc2)C1]

A mixture of 199e (1.24 g, 3.2 mmol), HCHO solution (15 mL, 37% in water), acetic acid (1 mL) and NaBH(OAc)$_3$ (1.36 g, 6.4 mmol) in methanol (10 mL) was stirred at room temperature for 4 h. The solvent was evaporated in vacuo and the residue was extracted with ethyl acetate (20 mL×3). The combined extracts were dried over sodium sulfate and concentrated under reduced pressure. The residue was purified on reverse phase Combi-flash to give 199f (940 mg, 80%). MS: [M+H]$^+$ 365.

Example 199g {4-Fluoro-2-[1-methyl-5-({5-[(1-methylazetidin-3-yl)oxy]pyridin-2-yl}amino)-6-oxo-1,6-dihydropyridin-3-yl]-6-{6-oxo-8-thia-5azatricyclo[7.4.0.0$^{2,7}$]-trideca-1(9),2(7)-dien-5-yl}phenyl}methyl Acetate 199g

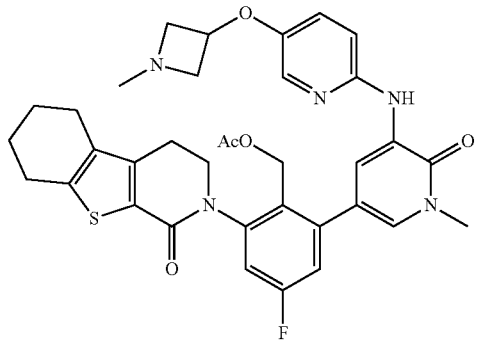 [SMILES: CC(=O)OCc1c(-c2cc(Nc3ccc(OC4CN(C)C4)cn3)c(=O)n(C)c2)cc(F)cc1N1CCc2c(sc3c2CCCC3)C1=O]

A mixture of 199f (434 mg, 1.2 mmol), (4-fluoro-2-{6-oxo-8-thia-5-azatricyclo[7.4.0.0$^{2,7}$]trideca-1(9),2(7)-dien-5-yl}-6-(4,4,5,5-tetramethyl-1,3,2-dioxaborolan-2-yl)phenyl) methyl acetate 212b (600 mg, 1.2 mmol), PdCl$_2$(dppf) (134 mg, 0.18 mmol), K$_3$PO$_4$ (150 mg), and NaOAc (100 mg) in MeCN (8 mL) and water (2 mL) was heated at 110° C. in a sealed tube for 2 h. The solvent was evaporated in vacuo. The residue was purified on reverse phase Combi-flash to give 199g (320 mg, 41%). MS: [M+H]$^+$ 658.

A mixture of 199g (320 mg, 0.49 mmol) and LiOH hydrate (409 mg, 9.8 mmol) in isopropanol (20 mL) and water (3 mL) was stirred at 30° C. for 2 h. The mixture was evaporated in vacuo and the residue was extracted with ethyl acetate (20 mL×2). The combined extracts were concentrated under reduced pressure. The residue was purified on prep-HPLC to give 199 (30 mg, 10%). MS: [M+H]$^+$ 616. $^1$H NMR (500 MHz, CDCl3) δ 8.52 (d, J=2.0, 1H), 7.82 (s, 1H), 7.75 (d, J=2.5, 1H), 7.48 (d, J=2.0, 1H), 7.16-7.14 (m, 1H), 7.11-7.09 (m, 1H), 6.98-6.96 (m, 1H), 6.79 (d, J=9.0, 1H), 4.76-7.72 (m, 1H), 4.56 (d, J=11.5, 1H), 4.32-4.25 (m, 1H), 4.19-4.07 (m, 2H), 3.97-3.80 (m, 3H), 3.69 (s, 3H), 3.23-3.15 (m, 2H), 3.00-2.81 (m, 4H), 2.59-2.50 (m, 2H), 2.47 (s, 2H), 1.93-1.83 (m, 4H).

Example 200 2-(3-(5-(5-(Azetidin-1-ylmethyl)-1-methyl-1H-pyrazol-3-ylamino)-1-methyl-6-oxo-1,6-dihydropyridin-3-yl)-5-fluoro-2-(hydroxymethyl) phenyl)-3,4,6,7,8,9-hexahydropyrazino[1,2-a]indol-1(2H)-one 200

Example 200a 5-(Azetidin-1-ylmethyl)-1-methyl-3-nitro-1H-pyrazole 200a

Following Example 156e, 5-(bromomethyl)-1-methyl-3-nitro-1H-pyrazole 156d (1.76 g, 8 mmol), azetidine (550 mg, 9.6 mmol), di-isopropylethylamine (1.75 mL, 10 mmol) and methylene chloride (40 mL) were stirred at room temperature for 3-5 h. Work-up and concentrated under reduced pressure to afford 5-(azetidin-1-ylmethyl)-1-methyl-3-nitro-1H-pyrazole 200a (quant.) as yellow oil, which was used without further purification for the next step. MS (ESI+) m/z 197.1 (M+H).

Example 200b 5-(Azetidin-1-ylmethyl)-1-methyl-1H-pyrazol-3-amine 200b

Following Example 156f, 10% palladium on carbon (30% wet, 480 mg dry weight) and a solution of 200a (1.6 g, 8 mmol) in ethanol (50 mL) were reacted. The reaction mixture was filtered through a pad of Celite 521. The filter cake was washed with ethanol (2×30 mL), and the combined filtrates were concentrated to dryness under reduced pressure to afford 5-(azetidin-1-ylmethyl)-1-methyl-1H-pyrazol-3-amine 200b (quantitative) as yellow oil. MS (ESI+) m/z 167.1 (M+H).

Example 200c 3-(5-(Azetidin-1-ylmethyl)-1-methyl-1H-pyrazol-3-ylamino)-5-bromo-1-methylpyridin-2(1H)-one 200c Following Example 156g, 200b (350 mg, 2 mmol), 3,5-dibromo-1-methyl-1H-pyridin-2-one (0.54 g, 2 mmol), cesium carbonate (1.3 g, 4 mmol), tris(dibenzylideneacetone)dipalladium(0) (0.18 g, 0.2 mmol), Xantphos (0.23 g, 0.4 mmol) and 1,4-dioxane (20 mL) were heated at 100° C. for 8 hours. Work-up and flash column chromatography (silica, 3:1 methylene chloride/methanol) give a 98% yield (0.69 g) of 3-(5-(azetidin-1-ylmethyl)-1-methyl-1H-pyrazol-3-ylamino)-5-bromo-1-methylpyridin-2(1H)-one 200c as a yellow solid. MS (ESI+) m/z 354.1 (M+H).

Example 200d 2-(5-(5-(Azetidin-1-ylmethyl)-1-methyl-1H-pyrazol-3-ylamino)-1-methyl-6-oxo-1,6-dihydropyridin-3-yl)-4-fluoro-6-(1-oxo-3,4,6,7,8,9-hexahydropyrazino[1,2-a]indol-2(1H)-yl)benzyl Acetate 200d Following Example 121b, 4-fluoro-2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 210d (202 mg, 0.42 mmol), 3-(5-(azetidin-1-ylmethyl)-1-methyl-1H-pyrazol-3-ylamino)-5-bromo-1-methylpyridin-2(1H)-one 200c (105 mg, 0.3 mmol), 1M sodium carbonate solution (1.2 mL, 1.2 mmol), tetrakis(triphenylphosphine)palladium (0) (18 mg, 0.015 mmol) and 1,2-Dimethoxyethane (3 mL) were heated at 130° C. for 10 minutes in the microwave reactor. Work-up and the resulting residue was purified by flash column chromatography (silica, 3:1 methylene chloride/methanol) to give 180 mg compound 200d (quant., contain 3% 200) as a yellow residue: MS (ESI+) m/z 628.1 (M+H).

Intermediate 200d (0.3 mmol) was deprotected using Example 121, using THF (1 mL), water (0.5 mL), isopropanol (1 mL) and lithium hydroxide monohydrate (80 mg, 1.93 mmol). Work-up and the resulting residue was purified by flash column chromatography (NH-silica, ethyl acetate/hexanes) to afford a 25% yield (two steps, 45 mg) of 200 as a light pink solid: MS (ESI+) m/z 586.6 (M+H).

Example 201 2-(5-(5-(4-Ethylpiperazin-1-yl)pyridin-2-ylamino)-1-methyl-6-oxo-1,6-dihydropyridin-3-yl)-6-(1-oxo-3,4,6,7,8,9-hexahydropyrazino[1,2-a]indol-2(1H)-yl)benzyl Alcohol 201

Example 201b 2-(5-(5-(4-Ethylpiperazin-1-yl)pyridin-2-ylamino)-1-methyl-6-oxo-1,6-dihydropyridin-3-yl)-6-(1-oxo-3,4,6,7,8,9-hexahydropyrazino[1,2-a]indol-2(1H)-yl)benzyl Acetate 201b

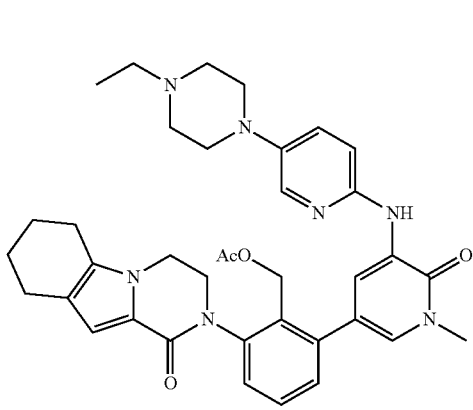

A 44-mL sealed tube equipped with a magnetic stirrer was charged with 138e (190 mg, 0.49 mmol), 4,4,4',4',5,5,5',5'-octamethyl-2,2'-bi(1,3,2-dioxaborolane (200 mg, 0.79 mmol), potassium acetate (190 mg, 2.0 mmol) and 1,4-dioxane (5 mL). After the mixture was degassed for 30 minutes, Pd(dppf)Cl$_2$.CH$_2$Cl$_2$ (40 mg, 0.049 mmol) was added. The resulting reaction mixture was stirred at 105° C. for 6 h. Then, it was cooled to room temperature and filtered through a pad of Celite. The filtrate was concentrated, and the crude boronolate product was redissolved in DME (2 mL) and transferred into a 10-mL microwave reaction vessel. To this solution was added 2-bromo-4-fluoro-6-(1-oxo-3,4,6,7,8,9-hexahydropyrazino[1,2-a]indol-2(1H)-yl)benzyl acetate 197d (171 mg, 0.39 mmol), Pd(PPh$_3$)$_4$ (30 mg, 0.025 mmol), and 2 N Na$_2$CO$_3$ (2 mL). Then, the reaction mixture was degassed for 5 minutes and placed into the microwave cavity. After the reaction mixture was stirred at 125° C. for 7 min., it was purified by flash chromatography (dichloromethane:MeOH, 85:15) to give 46% (120 mg) of 201b as solids.

A 100-mL, single-necked, round-bottomed flask equipped with a magnetic stirring bar was charged with 2-(5-(5-(4-ethylpiperazin-1-yl)pyridin-2-ylamino)-1-methyl-6-oxo-1,6-dihydropyridin-3-yl)-6-(1-oxo-3,4,6,7,8,9-hexahydropyrazino[1,2-a]indol-2(1H)-yl)benzyl acetate 201b (120 mg, 0.18 mmol), LiOH.H$_2$O (80 mg, 1.8 mmol), THF (2 mL), isopropanol (2 mL), and water (2 mL). After the reaction mixture was stirred at room temperature for 3 h, it was partitioned between dichloromethane (5 mL) and water (5 mL), and the organic phase was extracted with dichloromethane (3×5 mL). The combined organic phases were washed with water 2×5 mL) and brine (5 mL), dried (Na$_2$SO$_4$), and concentrated. The crude product was redissolved in dichloromethane (3 mL). To this solution was added hexane (10 mL) and the resulting precipitates were filtered to give 40% yield (45 mg) of 201; MS(ESI$^+$) m/z 626.4 (M+H).

Example 202 5-[5-fluoro-2-(hydroxymethyl)-3-{1-oxo-1H,2H,3H,4H,6H,7H,8H,9H-pyrazino[1,2-a]indol-2-yl}phenyl]-1-methyl-3-{[5-(1-methylpyrrolidin-2-yl)pyridine-2-yl]amino}-1,2-dihydropyridin-2-one 202

Example 202a 5-Bromo-1-methyl-3-(5-(1-methylpyrrolidin-2-yl)pyridin-2-ylamino)pyridin-2(1H)-one 202a

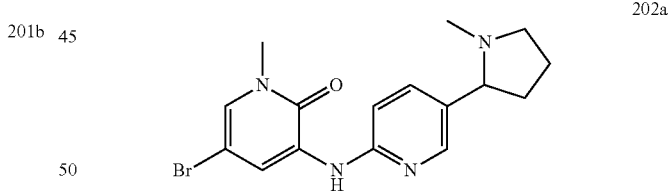

Following Example 142a, 5-(1-methylpyrrolidin-2-yl)pyridin-2-amine (500 mg, 2 mmol), 3,5-dibromo-1-methylpyridin-2(1H)-one (0.54 g, 2 mmol), cesium carbonate (1.9 g, 6 mmol), tris(dibenzylidene-acetone)dipalladium(0) (0.18 g, 0.2 mmol), Xantphos (0.23 g, 0.4 mmol) and 1,4-dioxane (20 mL) were heated at 100° C. for 8 hours. Work-up and flash column chromatography (silica, 9:1 methylene chloride/methanol) give a 82% yield (0.6 g) of 5-bromo-1-methyl-3-(5-(1-methylpyrrolidin-2-yl)pyridin-2-ylamino)pyridin-2(1H)-one 202a as a green solid: MS (ESI+) m/z 365.0 (M+H).

Following Example 121b, 4-fluoro-2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 210d (338 mg, 0.7 mmol), 202a (181 mg, 0.5 mmol), 1M sodium carbonate solution (2 mL, 2 mmol), tetrakis(triphenylphosphine)palladium(0) (29 mg, 0.025 mmol) and 1,2-dimethoxyethane (5 mL) were reacted. Work-up and flash column chromatography (silica, 3:1 methylene chloride/methanol) give a mixture (200 mg) of 4-fluoro-2-(1-methyl-5-(5-(1-methylpyrrolidin-2-yl)pyridin-2-ylamino)-6-oxo-1,6-dihydropyridin-3-yl)-6-(1-oxo-3,4,6,7,8,9-hexahydropyrazino[1,2-a]indol-2(1H)-yl)benzyl acetate and 202 as a yellow residue.

The above residue was deprotected following Example 121, except using a mixture of THF (1 mL), water (0.5 mL), isopropanol (1 mL) and lithium hydroxide monohydrate (55 mg, 1.2 mmol). Work-up and flash column chromatography (NH-silica, ethyl acetate/hexanes) give a 32% yield (60 mg) of 202 as a yellow solid: MS (ESI+) m/z 597.4 (M+H).

Example 203 5-(3-(6,6-Dimethyl-5,7-dihydro-5H-cyclopenta[4,5]thieno[2,3-c]pyridine-1(2H)-yl)-2-(hydroxymethyl)phenyl)-1-methyl-3-(pyrimidin-4-ylamino)pyridin-2(1H)-one 203

A 100-mL single-neck round-bottomed flask equipped with a magnetic stirrer and nitrogen inlet was charged with 105i (226 mg, 0.506 mmol), 109c (200 mg, 0.610 mmol), sodium carbonate (160 mg, 1.51 mmol), water (2 mL) and 1,4-dioxane (8 mL). After bubbling nitrogen through the resulting suspension for 30 min, tetrakis(triphenyl-phosphine)palladium(0) (60 mg, 0.052 mmol) was added. A reflux condenser was attached to the flask, and the reaction mixture was heated at 100° C. for 2 h. After this time, the mixture was diluted with 90:10 methylene chloride/methanol (100 mL) and water (75 mL), and the layers were separated. The aqueous layer was extracted with 90:10 methylene chloride/methanol (2×50 mL), and the combined organic layers were washed with brine (100 mL) and dried over sodium sulfate. The drying agent was removed by filtration. The filtrate was concentrated under reduced pressure, and the resulting residue was dissolved in a mixture of THF (3 mL), water (3 mL) and methanol (3 mL). Lithium hydroxide monohydrate (61 mg, 1.45 mmol) was added, and the reaction was stirred at room temperature for 2 h. After this time, the mixture was diluted with 90:10 methylene chloride/methanol (100 mL) and water (50 mL), and the layers were separated. The aqueous layer was extracted with 90:10 methylene chloride/methanol (2×75 mL), and the combined organic layers were washed with brine (100 mL) and dried over sodium sulfate. The drying agent was removed by filtration. The filtrate was concentrated under reduced pressure, and the resulting residue was purified by flash column chromatography (silica, 0% to 10% methanol/methylene chloride) followed by trituration with methanol (10 mL) to afford 203 in 37% yield (57 mg) as an amorphous white solid: mp 170-171° C.; $^1$H NMR (500 MHz, DMSO-$d_6$) δ 9.18 (s, 1H), 8.74 (d, 1H, J=3.5 Hz), 8.65 (s, 1H), 8.29 (d, 1H, J=10.0 Hz), 7.93 (d, 1H, J=10.0 Hz), 7.57 (d, 1H, J=3.5 Hz), 7.43 (t, 1H, J=13.0 Hz), 7.32 (m, 2H), 7.24 (d, 1H, J=13.0 Hz), 7.19 (d, 1H, J=13.0 Hz), 4.83 (m, 1H), 4.38 (d, 2H, J=6.5 Hz), 3.60 (s, 3H), 2.90 (s, 2H), 2.74 (s, 2H), 1.28 (s, 6H); MS (ESI+) m/z 526.2 (M+H).

Example 204 5-(5-Fluoro-2-(hydroxymethyl)-3-(6,6-dimethyl-3,4,6,7-tetrahydro-5H-cyclopenta[4,5]thieno[2,3-c]pyridine-1(2H)-yl)-1-methyl-3-(5-(4-methylpiperazin-1-yl)pyridin-2-ylamino)pyridin-2(1H) 204

A 100-mL three-neck round-bottomed flask equipped with a reflux condenser, magnetic stirrer and nitrogen inlet was charged with 197e (170 mg, 0.450 mmol), 182c (300 mg, 0.513 mmol), sodium carbonate (143 mg, 1.35 mmol), water (2 mL) and 1,4-dioxane (8 mL). After bubbling nitrogen through the resulting suspension for 30 min, tetrakis(triphenylphosphine)palladium(0) (52 mg, 0.045 mmol) was added, and the reaction mixture was heated at reflux for 2 h. After that time, the mixture was cooled to room temperature and diluted with methylene chloride (100 mL) and water (30 mL). The organic layer was separated, and the aqueous layer was extracted with methylene chloride (3×30 mL). The combined organic layers were dried over sodium sulfate and concentrated under reduced pressure to afford brown residue.

A 100-mL single-neck round-bottomed flask equipped with a magnetic stirrer was purged with nitrogen and charged with the above crude residue, THF (10 mL) and a 1 M solution of tetrabutylammonium fluoride in THF (4.50 mmol, 4.5 mL). The resulting mixture was stirred at room temperature for 1 h. After this time, the mixture was diluted with methylene chloride (100 mL) and washed with water (30 mL). The organic layer was separated, and the aqueous layer was extracted with methylene chloride (3×30 mL). The combined organic layers were dried over sodium sulfate and concentrated under reduced pressure. The residue was purified by column chromatography (silica, 0% to 10% methanol/methylene chloride) to afford a 53% yield (154 mg) of 204 as an off-white solid: mp 143-145° C.; $^1$H NMR (500 MHz, DMSO-$d_6$) δ 8.54 (d, 1H, J=2.5 Hz), 8.35 (s, 1H), 7.86 (d, 1H, J=3.0 Hz), 7.34 (m, 3H), 7.21 (d, 1H, J=8.9 Hz), 7.17 (dd, 1H, J=9.3, 3.0 Hz), 4.85 (m, 1H), 4.32 (m, 2H), 4.04 (m, 1H), 3.85 (m, 1H), 3.58 (s, 3H), 3.03 (m, 5H), 2.87 (m, 1H), 2.75 (s, 2H), 2.53 (m, 2H), 2.43 (m, 4H), 2.20 (s, 3H), 1.23 (s, 6H); MS (ESI+) m/z 643.3 (M+H).

Example 205 2-(5-Fluoro-2-(hydroxymethyl)-3-(1-methyl-5-(6-methyl-5,6,7,8-tetrahydro-1,6-naphthyridin-2-ylamino)-6-oxo-1,6-dihydropyridin-3-yl)phenyl)-3,4,6,7,8,9-hexahydropyrazino[1,2-a]indol-1(2H)-one 205

Example 205a 5-Bromo-1-methyl-3-(5,6,7,8-tetrahydro-1,6-naphthyridin-2-ylamino)pyridin-2(1H)-one 205a

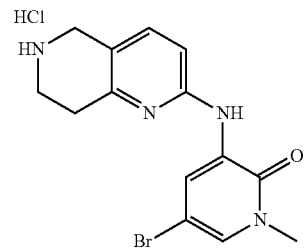 [SMILES: Cl ; Cn1cc(Br)cc(Nc2ccc3c(n2)CCNC3)c1=O]

tert-Butyl 2-(5-bromo-1-methyl-2-oxo-1,2-dihydropyridin-3-ylamino)-7,8-dihydro-1,6-naphthyridine-6(5H)-carboxylate 158c (3.2 g, 7.4 mmol) was suspended in methylene chloride (20 mL), saturated hydrogen chloride in dioxane (20 mL) was added dropwise. The reaction mixture was stirred for 20 minutes and concentrated under reduced pressure to give 205a, which was used without further purification in the next step. LC/MS: m/z 336 (M+H)$^+$

Example 205b 5-Bromo-1-methyl-3-(6-methyl-5,6,7,8-tetrahydro-1,6-naphthyridin-2-ylamino)pyridin-2(1H)-one 205b A mixture of 205a (2.75 g, 7.5 mmol), formaldehyde (37 percent in water, 30 ml, 375 mmol), NaBH(OAc)$_3$ (4.75 g, 22.5 mmol) and acetic acid (25 ml, 150 mmol) in methanol (125 ml) was stirred for 4 hours at room temperature. The mixture was then brought to basic condition with saturated NaOH solution and extracted with ethyl acetate. The organic layer was dried over Na$_2$SO$_4$ and evaporated under reduced pressure. The residue was purified by column chromatography eluting with 4:1 ethyle acetate/methanol to give 205b (2.0 g, 77%). LC/MS: m/z 349 (M+H)$^+$

Example 205c 4-Fluoro-2-(1-methyl-5-(6-methyl-5,6,7,8-tetrahydro-1,6-naphthyridin-2-ylamino)-6-oxo-1,6-dihydropyridin-3-yl)-6-(1-oxo-3,4,6,7,8,9-hexahydropyrazino[1,2-a]indol-2(1H)-yl)benzyl Acetate 205c A 15 mL microwave reaction vial with a magnetic stirrer was charged with 205b (0.35 g, 1 mmol), 4-fluoro-2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 210d (0.48 g, 1 mmol), potassium phosphate (0.54 g, 2 mmol), sodium acetate (0.17 g, 2 mmol), acetonitrile (10 mL), water (1 mL), and 1,1'-bis(diphenylphosphino)ferrocene-palladium(II) dichloride dichloromethane (0.08 g, 0.1 mmol). The mixture was heated at 110° C. for 2 hours under argon atmosphere. After this time, the mixture was cooled to room temperature and filtered. The filtrate was concentrated under reduced pressure and the residue was purified by column-chromatography eluting with 40:1 DMC/methanol to give 205c (0.22 g, 36%). LC/MS: m/z 625 (M+H)$^+$ A 25 mL round bottomed flask with a magnetic stirrer was charged with compound 4-fluoro-2-(1-methyl-5-(6-methyl-5,6,7,8-tetrahydro-1,6-naphthyridin-2-ylamino)-6-oxo-1,6-dihydropyridin-3-yl)-6-(1-oxo-3,4,6,7,8,9-hexahydropyrazino[1,2-a]indol-2(1H)-yl)benzyl acetate 205c (0.2 g, 0.32 mmol), LiOH (2 g, 48 mmol), THF (5 mL), isopropanol (5 mL) and water (2 mL). The reaction mixture was stirred at room temperature for 30 minutes and filtered. The filtrate was concentrated under reduced pressure and the residue was purified by prep-HPLC to give 205 (100 mg, 53%). LC/MS: m/z 583 (M+H)$^+$. $^1$H NMR (500 MHz, DMSO) δ 8.79 (d, J=2, 1H), 8.45 (s, 1H), 7.44 (d, J=2, 1H), 7.31 (m, 2H), 7.20 (m, 1H), 7.08 (d, J=9, 1H), 6.52 (s, 1H), 4.89 (m, 1H), 4.34 (m, 2H), 4.17 (m, 3H), 3.89 (m, 1H), 3.59 (s, 3H), 3.38 (m, 2H), 2.75 (m, 2H), 2.62 (m, 4H), 2.51 (m, 2H), 2.33 (s, 3H), 1.70 (m, 4H).

Example 206 2-(2-(Hydroxymethyl)-3-(1-methyl-5-(1-(2-(methylamino)ethyl)-1H-pyrazol-3-ylamino)-6-oxo-1,6-dihydropyridin-3-yl)phenyl)-3,4,6,7,8,9-hexahydropyrazino[1,2-a]indol-1(2H)-one 206

Example 206a 2-(2-(3-Nitro-1H-pyrazol-1-yl)ethyl)isoindoline-1,3-dione 206a

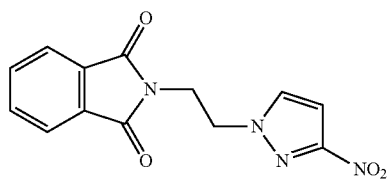

A solution of 4-nitro-1H-pyrazole (10 g, 88.5 mmol) in anhydrous DMF (250 mL) was treated with 60% dispersion of NaH in mineral oil (4.6 g, 115 mmol) while stirring under nitrogen. After effervescence the reaction was stirred for an additional 30 minutes. At this time the reaction was treated with 2-(2-bromoethyl)isoindoline-1,3-dione (18-2) (25 g, 97.3 mmol) and continued to stir under nitrogen for 3 hours. Water (50 mL) was then added slowly and the mixture was filtered to give 206a as a white solid (20 g, 80%), which was used directly without further purification. LCMS: (M+H)+ 287.

Example 206b 2-(3-Nitro-1H-pyrazol-1-yl)ethanamine 206b

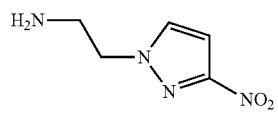

A solution of 206a (2.0 g, 7.0 mmol) in ethanol (30 mL) was added hydrazine hydrate (1 mL, 21 mmol) and the mixture was stirred at room temperature for 3 hours. The mixture was evaporated and the residue was purified by silica-gel eluting with 10:1 methylene chloride/methanol to give 206b as a white solid (0.8 g, 80%). MS: (M+H)$^+$ 157.

Example 206c tert-Butyl 2-(3-Nitro-1H-pyrazol-1-yl)ethylcarbamate 206c

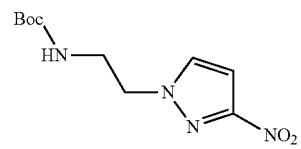

To a solution of 206b (18 g, 115 mmol) in methylene chloride (400 mL) was added (Boc)$_2$O (50 g, 230 mmol) and triethylamine (35 g, 346 mmol). The mixture was stirred at room temperature for 5 hours. It was then evaporated and purified by silical-gel column eluting with 1:1 petroleum ether/ethyl acetate to give 206c as a white solid (24 g, 80%). MS: (M+H)$^+$ 257.

Example 206d tert-Butyl Methyl(2-(3-nitro-1H-pyrazol-1-yl)ethyl)carbamate 206d

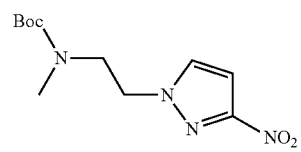

To a solution of 206c (5 g, 19.5 mmol) in THF (40 mL) was added NaH (938 mg, 23.4 mmol). The reaction mixture was stirred at room temperature for 30 minutes. Iodomethane (1.7 mL, 25.4 mmol) was added and the mixture was stirred for additional 15 hours. It was then evaporated and purified by silical-gel column eluting with 2:1 petroleum ether/ethyl acetate to give 206d as a white solid (4.5 g, 85%). MS: (M+H)$^+$ 271.

Example 206e tert-Butyl 2-(3-Amino-1H-pyrazol-1-yl)ethyl(methyl)carbamate 206e

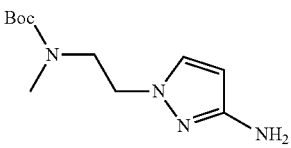

To a solution of 206d (4.5 g, 1.7 mmol) in ethanol (40 mL) was added Fe (4.7 g, 8.5 mmol) and NH₄Cl (900 mg, 17 mmol). The reaction mixture was stirred at room temperature for 4 hours. It was then evaporated and purified by silical-gel column eluting with 2:1 petroleum ether/ethyl acetate to give 206e as a brown solid (3.2 g, 80%). MS: (M+H)⁺ 241.

Example 206f tert-Butyl 2-(3-(5-Bromo-1-methyl-2-oxo-1,2-dihydropyridin-3-ylamino)-1H-pyrazol-1-yl)ethyl(methyl)carbamate 206f

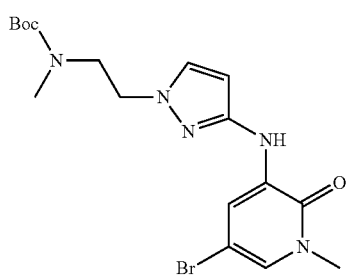

A mixture of (206e (2 g, 8.3 mmol), 3,5-dibromo-1-methylpyridin-2(1H)-one (2.2 g, 8.3 mmol), XantPhos (482 mg, 0.83 mmol), Pd₂(dba)₃ (762 mg, 0.83 mmol) and Cs₂CO₃ (6.8 g, 21 mmol) in dioxane (80 mL) was heated at 100° C. for 15 h under nitrogen. It was then filtered, evaporated in vacuo, and purified by silical-gel column eluting with 1:2 petroleum ether/ethyl acetate to give 206f as a yellow solid (2.7 g, 77%). MS: (M+H)⁺ 426.

Example 206g 2-(5-(1-(2-(tert-Butoxycarbonyl(methyl)amino)ethyl)-1H-pyrazol-3-ylamino)-1-methyl-6-oxo-1,6-dihydropyridin-3-yl)-6-(1-oxo-3,4,6,7,8,9-hexahydro-pyrazino[1,2-a]indol-2(1H)-yl)benzyl Acetate 206g

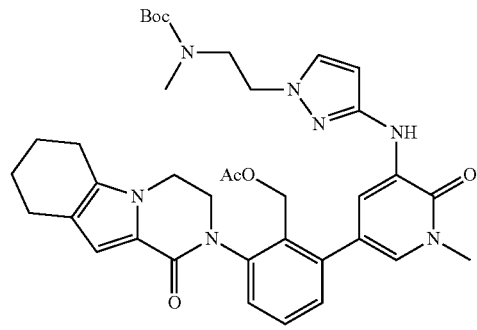

A mixture of 206f (800 mg, 1.9 mmol), 2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate (114a) (873 mg, 1.9 mmol), CH₃COONa (309 mg, 3.8 mmol), PdCl₂(dppf) (153 mg, 0.19 mmol) and K₃PO₄ (1 g, 3.8 mmol) suspended in CH₃CN (30 mL) and H₂O (2 mL) was heated at 110° C. for 15 h under argon atmosphere. It was then evaporated and the residue was purified by reverse phase Combi-flash eluting with 0.3% NH₄HCO₃ in 1:4 water/CH₃CN to give 206g as a brown solid (800 mg, 63%). MS: (M+H)⁺ 684

Example 206h tert-Butyl 2-(3-(5-(2-(Hydroxymethyl)-3-(1-oxo-3,4,6,7,8,9-hexahydropyrazino[1,2-a]indol-2(1H)-yl)phenyl)-1-methyl-2-oxo-1,2-dihydropyridin-3-ylamino)-1H-pyrazol-1-yl)ethyl(methyl)carbamate 206h

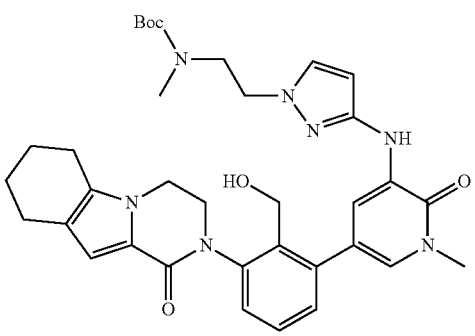

To a solution of 206g (750 mg, 1.1 mmol) in propan-2-ol (15 mL), tetrahydrofuran (15 mL), and water (5 mL) was added LiOH (2.6 g, 110 mmol). The mixture was stirred at 30° C. for 2 h. It was then evaporated and the residue was purified by reverse phase Combi-flash eluting with 0.3% NH₄HCO₃ in 1:3 water/CH₃CN to give 206h as a brown solid (500 mg, 71%). MS: (M+H)⁺ 642

A solution of 206h (500 mg, 0.78 mmol) in HCl/ethyl acetate (5 mL) was stirred at room temperature for 2 h. It was then evaporated and the residue was purified by prep-HPLC to afford 206 as a brown solid (134 mg, 35%). MS: (M+H)⁺542. ¹H NMR (500 MHz, MeOD) δ 1.79 (s, 2H), 1.89 (s, 2H), 2.35 (s, 3H), 2.54-2.56 (t, J=6 Hz, 2H), 2.63-2.67 (m, 2H), 2.97-2.99 (t, J=6 Hz, 2H), 3.71 (s, 3H), 4.00-4.03 (m, 1H), 4.14-4.23 (m, 5H), 4.50-4.60 (m, 2H), 6.06-6.07 (d, 1H), 6.71 (s, 1H), 7.23-7.24 (d, 1H), 7.37-7.43 (m, 2H), 7.49-7.52 (m, 2H), 8.01-8.02 (d, 1H).

Example 207 2-(3-(5-(5-(3-Hydroxy-3-methylazetidin-1-yl)pyridin-2-ylamino)-1-methyl-6-oxo-1,6-dihydropyridin-3-yl)-2-(hydroxymethyl)phenyl)-3,4,6,7,8,9-hexahydropyrazino[1,2-a]indol-1(2H)-one 207

Example 207a
3-Methyl-1-(6-nitropyridin-3-yl)azetidin-3-ol 207a

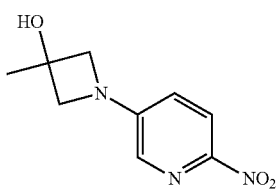

A mixture of 5-bromo-2-nitropyridine (3.28 g, 16.3 mmol), XantPhos (1.13 g, 1.96 mmol), Pd$_2$dba$_3$ (1.19 g, 1.30 mmol), 3-methylazetidin-3-ol hydrochloride (2 g, 16.3 mmol) and Cs$_2$CO$_3$ (15.9 g, 48.9 mmol) in 1,4-dioxane (70 mL) was heated at reflux for 2 h. After the completion of the reaction, the mixture was filtered off, and washed with MeOH (100 mL). The filtrate was evaporated in vacuo and the residue was purified on reverse phase Combi-flash to give 207a (2.5 g, 71%). MS: [M+H]$^+$ 210.

Example 207b
1-(6-Aminopyridin-3-yl)-3-methylazetidin-3-ol 207b

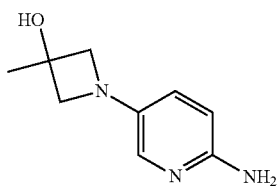

A 100-mL Parr hydrogenation bottle was purged with nitrogen and charged with 207a (2.3 g, 11 mmol), 10% palladium on carbon (50% wet, 1.0 g) and methanol (100 mL). The bottle was evacuated, charged with hydrogen gas to a pressure of 25 psi and shaken for 2 h on a Pan hydrogenation apparatus. The hydrogen was then evacuated and nitrogen charged to the bottle. The catalyst was removed by filtration through a pad of Celite and the filtrate was concentrated under reduced pressure to afford 207b (1.85 g, 92%). MS: [M+H]$^+$ 180.

Example 207c 5-Bromo-3-(5-(3-hydroxy-3-methyl-azetidin-1-yl)pyridin-2-ylamino)-1-methylpyridin-2(1H)-one 207c

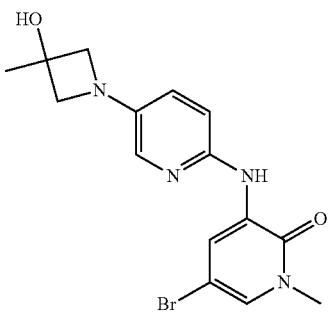 [SMILES: Cn1cc(Br)cc(Nc2ccc(N3CC(C)(O)C3)cn2)c1=O]

A mixture of 207b (1.84 g, 10.3 mmol), XantPhos (714 mg, 1.24 mmol), Pd$_2$dba$_3$ (755 mg, 0.82 mmol), 3,5-di-bromo-1-methylpyridin-2(1H)-one (3.27 g, 12.3 mmol) and Cs$_2$CO$_3$ (10 g, 30.9 mmol) in 1,4-dioxane (50 mL) was heated at reflux for 2 h. After the completion of the reaction, the mixture was filtered off, and washed with MeOH (100 mL). The filtrate was evaporated in vacuo and the residue was purified on reverse phase Combi-flash to give 207c (2.11 g, 54%). MS: [M+H]$^+$ 365.

Example 207d 2-(5-(5-(3-Hydroxy-3-methylazeti-din-1-yl)pyridin-2-ylamino)-1-methyl-6-oxo-1,6-dihydropyridin-3-yl)-6-(1-oxo-3,4,6,7,8,9-hexahy-dropyrazino[1,2-a]indol-2(1H)-yl)benzyl Acetate 207d

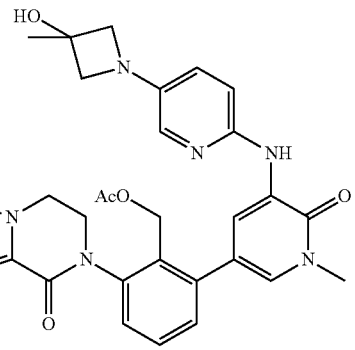

A mixture of 207c (364 mg, 1.0 mmol), 2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 114a (510 mg, 1.1 mmol), PdCl$_2$(dppf) (110 mg, 0.15 mmol), K$_3$PO$_4$ (100 mg), and NaOAc (50 mg) in MeCN (20 mL) and water (4 mL) was heated at reflux for 2 h. The solvent was evaporated in vacuo and the residue was purified on reverse phase Combi-flash to give 207d (267 mg, 43%). MS: [M+H]$^+$ 623.

A mixture of 207d (350 mg, 0.56 mmol) and LiOH hydrate (236 mg, 5.6 mmol) in $^i$PrOH (20 mL) and water (4 mL) was stirred at 30° C. for 2 h. The mixture was evaporated in vacuo and the residue was extracted with ethyl acetate (20 mL×2). The combined extracts were concentrated under reduced pressure. And the residue was purified on prep-HPLC to give 207 (130 mg, 40%). MS: [M+H]$^+$ 581. $^1$H NMR (500 MHz, DMSO) δ 8.48 (s, 1H), 8.25 (s, 1H), 7.48-7.44 (m, 2H), 7.34-7.28 (m, 3H), 7.17 (d, J=8.5, 1H), 6.89-6.87 (m, 1H), 6.51 (s, 1H), 5.47 (s, 1H), 4.84-4.83 (m, 1H), 4.33 (d, J=4.5, 2H), 4.18-4.06 (m, 3H), 3.90-3.86 (m, 1H), 3.70 (d, J=7.5, 2H), 3.58 (s, 3H), 3.53-3.52 (m, 2H), 2.64-2.54 (m, 2H), 2.47-2.45 (m, 2H), 1.82-1.75 (m, 2H), 1.73-1.65 (m, 2H), 1.43 (s, 3H).

Example 208 2-(3-(5-(6-Ethyl-5,6,7,8-tetrahydro-1,6-naphthyridin-2-ylamino)-1-methyl-6-oxo-1,6-di-hydropyridin-3-yl)-5-fluoro-2-(hydroxymethyl)phe-nyl)-3,4,6,7,8,9-hexahydropyrazino[1,2-a]indol-1(2H)-one 208

Example 208a 2-(5-(6-Ethyl-5,6,7,8-tetrahydro-1,6-naphthyridin-2-ylamino)-1-methyl-6-oxo-1,6-dihy-dropyridin-3-yl)-4-fluoro-6-(1-oxo-3,4,6,7,8,9-hexa-hydropyrazino[1,2-a]indol-2(1H)-yl)benzyl Acetate 208a

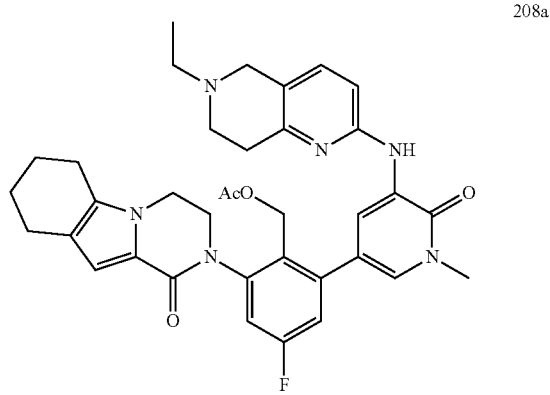 [SMILES: CCN1CCc2nc(Nc3cc(-c4cc(F)cc(N5CCn6c(cc7c6CCCC7)C5=O)c4COC(C)=O)cn(C)c3=O)ccc2C1]

Following Example 136e, 5-bromo-3-(6-ethyl-5,6,7,8-tetrahydro-1,6-naphthyridin-2-ylamino)-1-methylpyridin-2(1H)-one and 4-fluoro-2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 210d was converted to 208a in 42% yield. LCMS: (M+H)+ 639

Following Example 136, 208a was converted to 208 in 40% yield. LCMS: (M+H)+ 597. $^1$H NMR (500 MHz, DMSO) δ 8.80 (d, J=2, 1H), 8.45 (s, 1H), 7.45 (d, J=2, 1H), 7.31 (m, 2H), 7.20 (dd, J=10, 1H), 7.07 (d, J=9, 1H), 6.53 (s, 1H), 4.36 (s, 2H), 4.14 (m, 3H), 3.90 (m, 1H), 3.60 (s, 3H), 2.74 (m, 2H), 2.68 (m, 2H), 2.59 (m, 2H), 2.47 (m, 3H), 1.79 (m, 2H), 1.69 (m, 2H), 1.08 (t, J=7.5, 3H).

Example 209 5-[2-(Hydroxymethyl)-3-[1-methyl-5-({5-[4-(oxetan-3-yl)piperazin-1-yl]pyridine-2-yl}amino)-6-oxo-1,6-dihydropyridin-3-yl]phenyl]-8-thia-5-azatricyclo[7.4.0.0$^{2,7}$]trideca-1(9),2(7)-dien-6-one 209

Example 209a {2-[1-Methyl-5-({5-[4-(oxetan-3-yl)piperazin-1-yl]pyridin-2-yl}amino)-6-oxopyridin-3-yl]-6-{6-oxo-8-thia-5-azatricyclo[7.4.0.0$^{2,7}$]trideca-1(9),2(7)-dien-5-yl}phenyl}methyl Acetate 209a

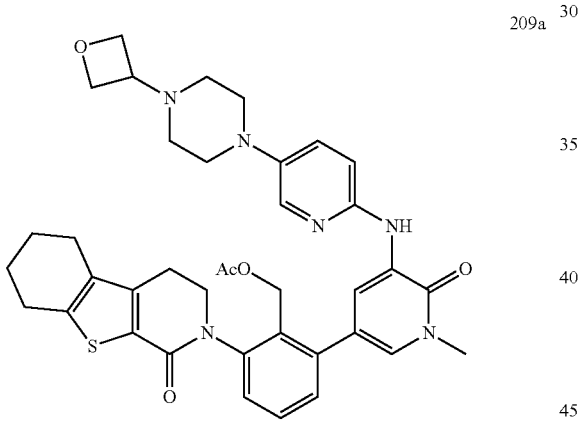

Following Example 148c, 481 mg of 111a and 420 mg of 5-bromo-1-methyl-3-(5-(4-(oxetan-3-yl)piperazin-1-yl)pyridine-2-ylamino)pyridin-2(1H)-one 188e were reacted to give 209a as a yellow solid (347 mg, 50%). MS: [M+H]+ 695

Following Example 148, 230 mg of 209a was converted to 209 as a white solid (108 mg, 50%). MS: [M+H]+ 653. $^1$H NMR (500 MHz, DMSO) δ 8.56 (d, J=2.5, 1H), 8.37 (s, 1H), 7.86 (d, J=3.0, 1H), 7.45 (d, J=7.5, 1H), 7.36-7.30 (m, 4H), 7.23 (d, J=9.0, 1H), 4.82 (s, 1H), 4.55 (t, J=6.5, 2H), 4.45 (t, J=6.0, 2H), 4.35 (s, 2H), 4.02 (m, 1H), 3.82 (m, 1H), 3.58 (s, 3H), 3.42 (m, 2H), 3.06 (t, J=4.5, 4H), 2.92-2.80 (m, 2H), 2.78 (s, 2H), 2.53 (m, 1H), 2.38 (s, 4H), 1.80 (s, 4H).

Example 210 2-(5-fluoro-2-(hydroxymethyl)-3-(1-methyl-5-(5-(4-(oxetan-3-yl)piperazin-1-yl)pyridin-2-ylamino)-6-oxo-1,6-dihydropyridin-3-yl)phenyl)-3,4,6,7,8,9-hexahydropyrazino[1,2-a]indol-1(2H)-one 210

Example 210a 5-Bromo-1-methyl-3-[5-(4-tert-butoxycarbonylpiperazin-1-yl)-pyridin-2-ylamine 210a

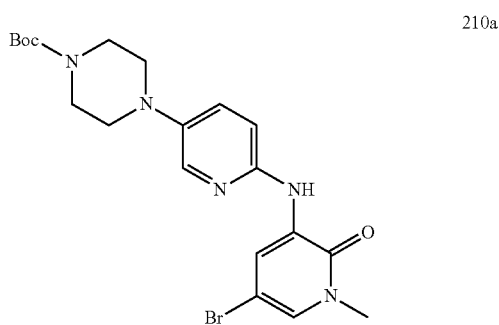 [SMILES: Cn1cc(Br)cc(Nc2ccc(N3CCN(C(=O)OC(C)(C)C)CC3)cn2)c1=O]

Step 1: tert-Butyl 4-(6-Nitropyridin-3-yl)piperazine-1-carboxylate

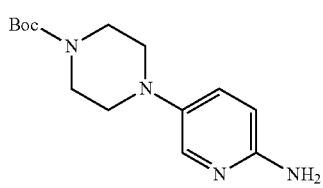 [SMILES: CC(C)(C)OC(=O)N1CCN(c2ccc(N)nc2)CC1]

To solution of 5-bromo-2-nitropyridine (30 g, 148 mmol) in DMSO (1 L) were added K$_2$CO$_3$ (40 g, 296 mmol) and tert-butyl piperazine-1-carboxylate (28 g, 148 mmol). The mixture was stirred at 65° C. overnight. After cooling down, it was poured into water (2 L). The solid precipitated was collected and dried under vacuum. It was then purified by flash column eluting with PE:EA (20:1) and then DCM to give 17 gm of tert-butyl 4-(6-nitropyridin-3-yl)piperazine-1-carboxylate as a yellow solid (37% yield). MS: [M+H]+ 309

Step 2: tert-Butyl 4-(6-Aminopyridin-3-yl)piperazine-1-carboxylate

A 500-mL bottle was purged with nitrogen and charged with tert-butyl 4-(6-nitropyridin-3-yl)piperazine-1-carboxylate (3.1 g, 10 mmol), 10% palladium on carbon (50% wet, 1 g) and ethanol (100 mL). The bottle was evacuated, charged with hydrogen gas, and stirred for 16 h at room temperature. The hydrogen was then evacuated and nitrogen charged into the bottle. The catalyst was removed by filtration through a pad of Celite and the filtrate concentrated under reduced pressure to afford tert-butyl 4-(6-aminopyridin-3-yl)piperazine-1-carboxylate (2.7 g, 97%). MS: [M+H]+ 279

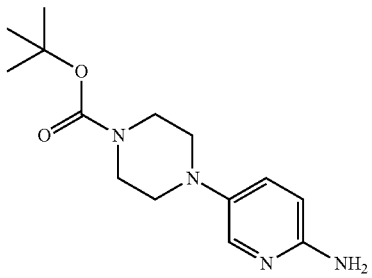 [SMILES: CC(C)(C)OC(=O)N1CCN(c2ccc(N)nc2)CC1]

Step 3

A 100-mL single-neck round-bottomed flask equipped with a magnetic stirrer and reflux condenser was charged with 1,4-dioxane (50 mL), tert-butyl 4-(6-aminopyridin-3-yl)piperazine-1-carboxylate, prepared according to U.S. Pat. No. 7,456,168, (1.3 g, 4.7 mmol), 3,5-dibromo-1-methyl-pyridin-2(1H)-one (1.24 g, 4.7 mmol) and cesium carbonate (3.8 g, 12 mmol). After bubbling nitrogen through the resulting solution for 30 min, Xantphos (272 mg, 0.47 mmol) and tris(dibenzylideneacetone)dipalladium(0) (430 mg, 0.47 mmol) were added, and the reaction mixture was heated at reflux for 3 h. After this time the reaction was cooled to room temperature, partitioned between ethyl acetate (100 mL) and water (100 mL) and filtered. The aqueous layer was separated and extracted with ethyl acetate (2×50 mL). The organic layers were combined and washed with brine (50 mL) and dried over sodium sulfate. The drying agent was removed by filtration and the filtrate was concentrated under reduced pressure. The residue was purified on flash column eluting with DCM:MeOH (50:1) to afford 210a (1.3 g, 59%). MS: [M+H]+ 464.

Example 210b 5-Bromo-1-methyl-3-[5-(piperazin-1-yl)-pyridin-2-ylamino]-1H-pyridin-2-one 210b

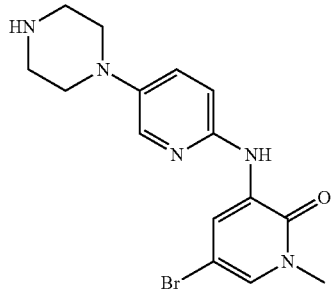

Compound 210a (3.6 g, 7.8 mmol) was suspended in 4.0 M HCl/dioxane (10 mL). The reaction mixture was stirred for 5 h at room temperature and concentrated at reduced pressure. The desired product was basified with aqueous 1.0 M NaOH and was extracted with methylene chloride. The combined organic layers were washed with H2O and concentrated under reduced pressure to give 2.46 g of 210b with an 87% yield. MS: [M+H]+ 364.

Example 210c 5-Bromo-1-methyl-3-[5-(4-(oxetan-3-yl)piperazin-1-yl)-pyridin-2-ylamino]-1H-pyridin-2-one 210c

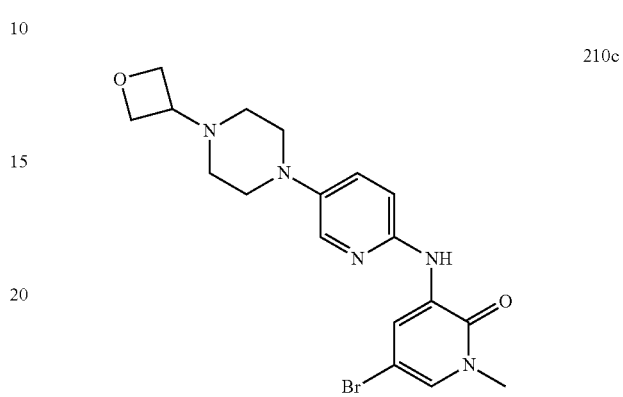

A mixture of 210b (2.75 g, 7.5 mmol), oxetan-3-one (1.6 g, 22.7 mmol), NaBH3CN (4.75 g, 22.5 mmol) and zinc chloride (3 g, 22.7 mmol) in methanol (125 mL) was stirred for 5 hours at 50 degree. The mixture was added to water and extracted with methylene chloride three times. The organic layers were concentrated under reduced pressure. The residue was purified by column-chromatography eluting with methylene chloride: methanol=25:1 to give 210c (1.92 g, 61%). MS: [M+H]+ 420. 1H NMR (500 MHz, DMSO) δ 8.58 (d, J=2.5, 1H), 8.55 (s, 1H), 7.94 (d, J=3, 1H), 7.54 (d, J=2.5, 1H), 7.39 (dd, J=3, 1H), 7.25 (d, J=4, 1H), 4.56 (t, J=6.5, 2H), 4.46 (t, J=6.5, 2H), 3.50 (s, 3H), 3.43 (m, 1H), 3.01 (m, 4H), 2.40 (m, 4H).

Example 210d 2-(4,4,5,5-Tetramethyl-[1,3,2]dioxa-borolan-2-yl)-4-fluoro-6-(1-oxo-3,4,6,7,8,9-hexahydropyrazino[1,2-a]indol-2(1H)-yl)benzyl Acetate 210d

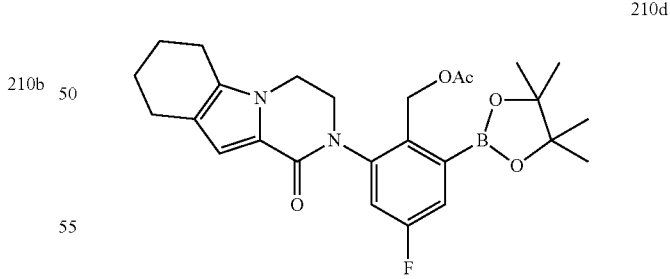

A 250-mL single-neck round-bottomed flask equipped with a magnetic stirrer was charged with 197d (3.8 g, 8.65 mmol), bis(pinacolato)diboron (11 g, 43.25 mmol), Pd(dppf)Cl2 (0.4 g, 0.5 mmol), KOAc (2.5 g, 26 mmol), and 1,4-dioxane (150 mL). The system was evacuated and then refilled with N2. A reflux condenser was attached to the flask, and the reaction mixture was heated at 100° C. for 15 h. It was then cooled to room temperature and filtered. The filtrate was concentrated under reduced pressure, and the Example 210e 5-Fluoro-2-(1-methyl-5-(5-(4-(oxetan-3-yl)piperazin-1-yl)pyridin-2-ylamino)-6-oxo-1,6-dihydropyridin-3-yl)-6-(1-oxo-3,4,6,7,8,9-hexahydropyrazino[1,2-a]indol-2(1H)-yl)benzyl Acetate 210e

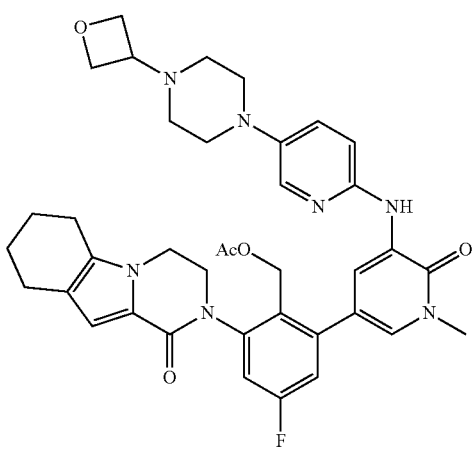

A sealed tube was charged with the mixture of 210d (337 mg, 0.7 mmol), 210c (294 mg, 0.7 mmol), Pd(dppf)Cl$_2$ (33 mg, 0.04 mmol), K$_3$PO$_4$·3H$_2$O (372 mg, 1.4 mmol), and NaOAc (115 mg, 1.4 mmol) in 20 mL CH$_3$CN. The system was evacuated and refilled with N$_2$. The reaction mixture was heated at 110° C. for 2 h. It was then cooled to room temperature and filtered. The filtrate was concentrated under reduced pressure, and the resulting residue was purified by flash column chromatography eluting with 30:1 DCM/MeOH to afford 210e in 54% yield (263 mg) as a yellow solid. MS: [M+H]$^+$ 696.

At room temperature, to the solution of 210e (250 mg, 0.36 mol) in THF/iso-propanol/water (6 mL/6 mL/2 mL) was added LiOH (87 mg, 3.6 mmol) while stirring. This mixture was stirred for 0.5 h. Then, 20 mL of water was added and extracted with ethyl acetate (30 mL×3). The combined organic layer was dried with Na$_2$SO$_4$ and concentrated to get a yellow solid which was further purified by prep-HPLC to afford 210 as a white solid (134 mg, 57% yield). LCMS: [M+H]$^+$ 654. $^1$H NMR (500 MHz, MEOD) δ 8.53 (d, J=2.5, 1H), 7.93 (d, J=3, 1H), 7.42 (dd, J=3, 1H), 7.34 (d, J=2.5, 1H), 7.23 (s, 1H), 7.21 (s, 1H), 7.03 (d, J=4.5, 1H), 6.72 (s, 1H), 4.73 (t, J=2, 2H), 4.64 (t, J=1.5, 2H), 4.51 (m, 2H), 4.21 (s, 3H), 4.03 (m, 1H), 3.71 (s, 3H), 3.57 (m, 1H), 3.17 (t, J=4.5, 4H), 2.65 (m, 2H), 2.55 (m, 6H), 1.90 (m, 2H), 1.79 (m, 2H)

Example 211 5-[5-Fluoro-2-(hydroxymethyl)-3-[1-methyl-5-({5-[4-(oxetan-3-yl)piperazin-1-yl]pyridin-2-yl}amino)-6-oxo-1,6-dihydropyridin-3-yl]phenyl]-8-thia-5-azatricyclo[7.4.0.0$^{2,7}$]trideca-1(9),2(7)-dien-6-one 211

Example 211a {4-Fluoro-2-[1-methyl-5-({5-[4-(oxetan-3-yl)piperazin-1-yl]pyridin-2-yl}amino)-6-oxo-1,6-dihydropyridin-3-yl]-6-{6-oxo-8-thia-5-azatricyclo[7.4.0.0$^{2,7}$]-trideca-1(9),2(7)-dien-5-yl}phenyl}methyl Acetate 211a

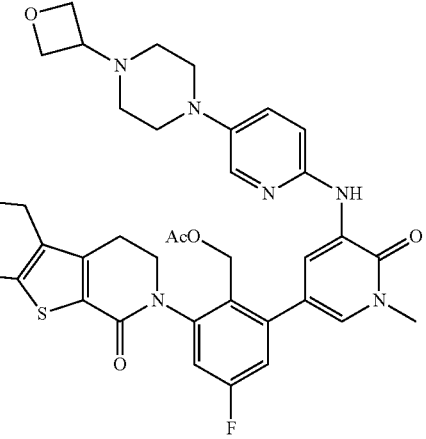

Following Example 148h, 400 mg of (4-fluoro-2-{6-oxo-8-thia-5-azatricyclo[7.4.0.0$^{2,7}$]trideca-1(9),2(7)-dien-5-yl}-6-(4,4,5,5-tetramethyl-1,3,2-dioxaborolan-2-yl)phenyl) methyl acetate 212b and 336 mg of 5-bromo-1-methyl-3-(5-(4-(oxetan-3-yl)piperazin-1-yl)pyridin-2-ylamino) pyridine-2(1H)-one 210c were reacted to give 211a as a yellow solid (319 mg, 56%). LCMS: (M+H)$^+$ 713

Following Example 148, 270 mg of 211a was converted to 211 as a white solid (120 mg, 48%). LCMS: [M+H]$^+$ 671. $^1$H NMR (500 MHz, DMSO) δ 8.56 (s, 1H), 8.39 (s, 1H), 7.87 (s, 1H), 7.38-7.16 (m, 5H), 4.8 (s, 1H), 4.56 (t, J=6.5 2H), 4.46 (t, J=6.5, 2H), 4.33 (s, 1H), 4.05 (m, 1H), 3.87 (m, 1H), 3.58 (s, 3H), 3.43 (t, J=6, 2H), 3.06 (m, 4H), 2.88-2.78 (m, 4H), 2.38 (t, J=5, 1H), 1.79 (m, 4H).

Example 212 5-[5-Fluoro-2-(hydroxymethyl)-3-(1-methyl-5-{[5-(4-methylpiperazin-1-yl)pyridine-2-yl]amino}-6-oxo-1,6-dihydropyridin-3-yl)phenyl]-8-thia-5-azatricyclo[7.4.0.0$^{2,7}$]trideca-1(9),2(7)-dien-6-one 212

Example 212a 2-Bromo-4-fluoro-6-(1-oxo-3,4,5,6,7,8-hexahydrobenzothieno[2,3-c]pyridin-2(1H)-yl) benzyl Acetate 212a

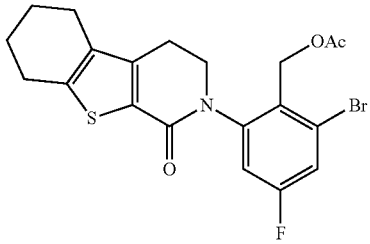

A solution of 104e (3 g, 14.5 mmol), 2,6-dibromo-4-fluorobenzyl acetate 197c (14 g, 43.5 mmol), Xantphos (839 mg, 1.45 mmol), $Pd_2(dba)_3$ (1.33 g, 1.45 mmol) and $Cs_2CO_3$ (9.4 g, 29 mmol) in dioxane (200 mL) was heated at 100° C. for 15 h under nitrogen. After filtration, the filtrate was evaporated in vacuo and purified by flash column eluting with ethyl acetate/petroleum ether (1:1) to give 212a (5 g, yield 77%) as a yellow solid. LCMS: $(M+H)^+$ 452. $^1H$ NMR (500 MHz, DMSO) δ 7.71 (dd, J=2.5, 1H), 7.51 (dd, J=3, 1H), 5.04 (m, 1H), 4.10 (m, 1H), 3.68 (m, 1H), 2.86 (m, 2H), 2.77 (m, 2H), 2.55 (m, 3H), 1.98 (s, 3H), 1.78 (m, 4H).

Example 212b 2-(4,4,5,5-Tetramethyl-[1,3,2]dioxaborolan-2-yl)-4-fluoro-6-(1-oxo-3,4,5,6,7,8-hexahydrobenzothieno[2,3-c]pyridin-2(1H)-yl)benzyl Acetate 212b

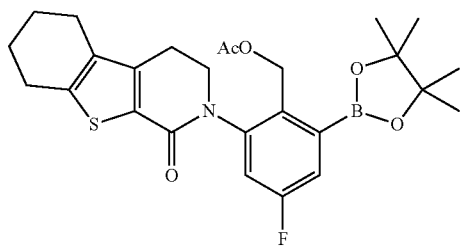

212b

A solution of 212a (3 g, 6.65 mmol), 4,4,4',4',5,5,5',5'-octamethyl-2,2'-bis(1,3,2-dioxa-borolane) (10 g, 40 mmol) in dioxane (160 mL) was added $PdCl_2(dppf)$ (543 mg, 0.66 mmol) and $CH_3COOK$ (3.9 g, 40 mmol). The mixture was stirred at 100° for 15 h under argon atmosphere. The mixture was filtered and evaporated in vacuo and purified by flash column eluting with ethyl acetate/petroleum ether (1:2) to give 212b (2.5 g, yield 76%) as a yellow solid. LCMS: $(M+H)^+$ 500

Example 212c [4-Fluoro-2-(1-methyl-5-{[5-(4-methylpiperazin-1-yl)pyridin-2-yl]amino}-6-oxo-1,6-dihydropyridin-3-yl)-6-{6-oxo-8-thia-5-azatricyclo[7.4.0.0$^{2,7}$]-trideca-1(9),2(7)-dien-5-yl}phenyl]methyl Acetate 212c

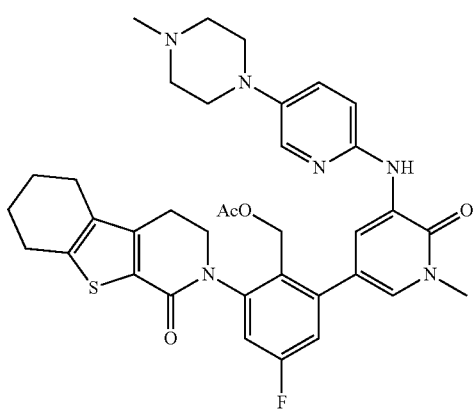

212c

A 25 mL sealed tube was charged with 212b (990 mg, 2 mmol), 5-bromo-1-methyl-3-(5-(4-methylpiperazin-1-yl)pyridin-2-ylamino)pyridine-2(1H)-one 198e (500 mg, 1.3 mmol), $CH_3COONa$ (220 mg, 2.6 mmol), $K_3PO_4$ (700 mg, 2.6 mmol), and $PdCl_2(dppf)$ (110 mg, 0.13 mmol) suspended in $CH_3CN$ (25 mL) and water (1 mL). The mixture was heated at 110° C. for 2 hours. It was evaporated and the residue was purified by silical-gel column eluting with 20:1 methylene chloride/methanol to give 212c as a brown solid (500 mg, 56%). LCMS: $[M+H]^+$ 670

To a solution of 212c (500 mg, 0.75 mmol) in propan-2-ol (8 mL), tetrahydrofuran (8 mL), and water (1.5 mL) was added LiOH (964 mg, 40 mmol). The mixture was stirred at 30° C. for 2 h. Then, 20 mL $H_2O$ was added and the mixture was extracted with ethyl acetate (3×30 mL). The combined organic layer was dried with $Na_2SO_4$ and concentrated to give a yellow solid, which was further purified by prep-HPLC to give 212 as a white solid (200 mg, 48%). LCMS: $[M+H]^+$ 629. $^1H$ NMR (500 MHz, DMSO-$d_6$) δ 8.56 (d, J=2, 1H), 8.37 (s, 1H), 7.85 (d, J=2.5, 1H), 7.34 (m, 3H), 7.19 (m, 2H), 4.86 (s, 1H), 4.32 (s, 2H), 4.05 (m, 1H), 3.87 (m, 1H), 3.57 (s, 3H), 3.02 (m, 4H), 2.96 (m, 1H), 2.87 (m, 1H), 2.77 (m, 2H), 2.54 (m, 1H), 2.43 (m, 4H), 2.19 (s, 3H), 1.79 (m, 4H).

Example 213 2-(5-Fluoro-2-(hydroxymethyl)-3-(1-methyl-5-(5-(1-methylazetidin-3-yl)pyridin-2-ylamino)-6-oxo-1,6-dihydropyridin-3-yl)phenyl)-3,4,6,7,8,9-hexahydropyrazino[1,2-a]indol-1(2H)-one 213

Example 213a 4-Fluoro-2-(1-methyl-5-(5-(1-methylazetidin-3-yl)pyridin-2-ylamino)-6-oxo-1,6-dihydropyridin-3-yl)-6-(1-oxo-3,4,6,7,8,9-hexahydropyrazino[1,2-a]indol-2(1H)-yl)benzyl Acetate 213a

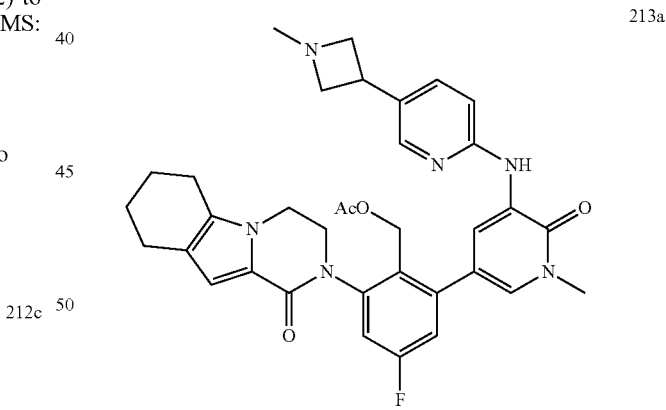

213a

Following Example 148b, 482 mg of 4-fluoro-2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 210d and 350 mg 5-bromo-1-methyl-3-(5-(1-methylazetidin-3-yl)pyridin-2-ylamino)pyridin-2(1H)-one 172a, were reacted to give 213a as a yellow solid (324 mg, 52%). MS: $[M+H]^+$ 625.

Following the procedures as described for 148 and starting with 220 mg of 213a, compound 213 was obtained as a white solid (82 mg, 40%). MS: $[M+H]^+$ 583. $^1H$ NMR (500 MHz, CDCl3) δ 8.64 (d, J=2.0, 1H), 8.13 (d, J=2.5, 1H), 7.89 (s, 1H), 7.58 (m, 1H), 7.50 (d, J=2.5, 1H), 7.16 (dd, J=9.0, 1H), 6.96 (dd, J=8.5, 1H), 6.86 (s, 1H), 6.83 (d, J=8.5, 1H), 4.55 (d, J=11.5, 1H), 4.40 (s, 1H), 4.30 (s, 1H), 4.16 (m, 2H), 3.91 (m, 1H), 3.72 (m, 5H), 3.60 (m, 1H), 3.14 (t, J=7.0, 2H), 2.59 (m, 4H), 2.38 (s, 3H), 1.90-1.79 (m, 5H).

Example 214 2-(5-Fluoro-2-(hydroxymethyl)-3-(4-methyl-6-(4-(1-(oxetan-3-yl)piperidin-4-yl)phenylamino)-5-oxo-4,5-dihydropyrazin-2-yl)phenyl)-3,4,6,7,8,9-hexahydropyrazino[1,2-a]indol-1(2H)-one 214

Example 214a 5-Bromo-1-methyl-3-(4-(piperidin-4-yl)phenylamino)pyrazin-2(1H)-one 214a Compound 214a was synthesized using the same procedure as for 121c, except using tert-butyl 4-(4-(6-bromo-4-methyl-3-oxo-3,4-dihydropyrazin-2-ylamino)phenyl)-piperidine-1-carboxylate (121a) (0.53 g, 1.08 mmol), trifluoroacetic acid (0.9 mL, 10.8 mmol) and methylene chloride (20 mL). Work-up and concentration afforded a quantitative yield of 214a (390 mg) as yellow oil, which was used without purification in the next step.

Example 214b 5-Bromo-1-methyl-3-(4-(1-(oxetan-3-yl)piperidin-4-yl)phenylamino)-pyrazin-2(1H)-one 214b A 100-mL sealed tube with a magnetic stirrer was purged with nitrogen and charged with 214a (390 mg, 1.08 mmol), oxetan-3-one (800 mg, 11 mmol) and methanol (10 mL). A suspension of sodium cyanoborohydride (208 mg, 3.3 mmol) and zinc chloride (225 mg, 1.65 mmol) in methanol (10 mL) was added, and the reaction was heated at 48° C. for 12 hours. After this time, the reaction mixture was concentrated, and the residue was partitioned between ethyl acetate (50 mL) and 10% aqueous potassium carbonate (10 mL). The aqueous layer was extracted with ethyl acetate (3×30 mL). The combined organic layers were dried over sodium sulfate and concentrated under reduced pressure. The resulting residue was purified by column chromatography (silica, 60:35:5 methylene chloride/diethyl ethyl/methanol) to afford a 60% yield (270 mg) of 5-bromo-1-methyl-3-(4-(1-(oxetan-3-yl)piperidin-4-yl)phenylamino)pyrazin-2(1H)-one (214b) as a yellow solid: MS (ESI+) m/z 421.2 (M+H).

Example 214c 4-Fluoro-2-(4-methyl-6-(4-(1-(oxetan-3-yl)piperidin-4-yl)phenylamino)-5-oxo-4,5-dihydropyrazin-2-yl)-6-(1-oxo-3,4,6,7,8,9-hexahydropyrazino[1,2-a]indol-2(1H)-yl)benzyl Acetate 214c Following Example 121b, 4-fluoro-2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 210d (217 mg, 0.45 mmol), 214b (158 mg, 0.375 mmol), 1M sodium carbonate solution (1.5 mL, 1.5 mmol), tetrakis(triphenylphosphine)palladium(0) (22 mg, 0.019 mmol) and 1,2-dimethoxyethane (3.5 mL) were heated at 130° C. for 15 minutes in the microwave reactor. Work-up and flash column chromatography (silica, 60:35:5 methylene chloride/diethyl ether/methanol) give a 62% yield (160 mg) of 214c as brown oil: MS (ESI+) m/z 696.1 (M+H).

Compound 214 was synthesized using the same procedure as for 121, except using a mixture of THF (1 mL), water (0.5 mL) and isopropanol (1 mL), 214c (160 mg, 0.23 mmol) and lithium hydroxide monohydrate (80 mg, 2 mmol). Work-up and flash column chromatography (NH-silica, ethyl acetate/ Hexanes) give a 34% yield (52 mg) of 214 as a yellow solid: MS (ESI+) m/z 653.6 (M+H).

Example 215 10-[5-Fluoro-2-(hydroxymethyl)-3-(4-methyl-6-{[4-(1-methylazetidin-3-yl)phenyl]amino}-5-oxo-4,5-dihydropyrazin-2-yl)phenyl]-4,4-dimethyl-1,10-diazatricyclo[6.4.0.0²,⁶]dodeca-2(6),7-dien-9-one 215

Example 215a 10-[5-Fluoro-2-(acetoxymethyl)-3-(4-methyl-6-{[4-(1-methylazetidin-3-yl)phenyl]amino}-5-oxo-4,5-dihydropyrazin-2-yl)phenyl]-4,4-dimethyl-1,10-diazatricyclo[6.4.0.0²,⁶]dodeca-2(6),7-dien-9-one 215a A 44-mL sealed tube equipped with a magnetic stirrer was charged with 298c (160 mg, 0.48 mmol), 4,4,4',4',5,5,5',5'-octamethyl-2,2'-bi-1,3,2-dioxaborolane (180 mg, 0.71 mmol), potassium acetate (188 mg, 1.9 mmol) and 1,4-dioxane (5 mL). After the mixture was degassed for 30 minutes, Pd(dppf)Cl₂.CH₂Cl₂ (39 mg, 0.048 mmol) was added. The resulting reaction mixture was stirred at 105° C. for 4 h. Then, it was cooled to room temperature and filtered through a pad of Celite. The filtrate was concentrated, and the crude mixture was redissolved in 1,2-dimethoxyethane (2 mL) and transferred into a 10-mL microwave reaction vessel. To this solution was added 10-[2-(acetoxy-methyl)-3-bromo-5-fluorophenyl]-4,4-dimethyl-1,10-diazatricyclo [6.4.0.0²,⁶]dodeca-2(6),7-dien-9-one 189a (172 mg, 0.38 mmol), Pd(PPh₃)₄ (30 mg, 0.024 mmol), and 2 N Na₂CO₃ (2 mL). Then, the reaction mixture was degassed for 5 minutes and placed into the microwave cavity. After the reaction mixture was stirred at 125° C. for 10 min., it was purified by flash chromatography (dichloromethane:methanol, 3:1) to give 20% (49 mg) of 215a.

A 25-mL, single-necked, round-bottomed flask equipped with a magnetic stirring bar was charged with 215a (49 mg, 0.077 mmol), LiOH.H₂O (16 mg, 0.38 mmol), THF (2 mL), isopropanol (2 mL), and water (2 mL). After the reaction mixture was stirred at room temperature for 3 h, it was partitioned between dichloromethane (5 mL) and water (5 mL), and the organic phase was extracted with dichloromethane (3×5 mL). The combined organic phases were washed with water (2×5 mL) and brine (5 mL), dried (Na₂SO₄), and concentrated. The crude product was re-dissolved in dichloromethane (3 mL). To this solution was added hexane (10 mL) and the resulting precipitate was filtered to give 74% yield (34 mg) of 215. MS(ESI⁺) m/z 597.5 (M+H).

Example 216 Di-sodium 2-(1-Methyl-6-oxo-5-(pyrimidin-4-ylamino)-1,6-dihydro-pyridin-3-yl)-6-(6,6-Dimethyl-3,4,6,7-tetrahydro-5H-cyclopenta[4,5]thieno[2,3-c]pyridine-1(2H)-yl)benzyl Phosphate 216

Example 216a Bis(2-cyanoethyl) 2-(1-Methyl-6-oxo-5-(pyrimidin-4-ylamino)-1,6-dihydropyridin-3-yl)-6-(6,6-Dimethyl-3,4,6,7-tetrahydro-5H-cyclopenta[4,5]thieno-[2,3-c]pyridine-1(2H)-yl)benzyl Phosphate 216a

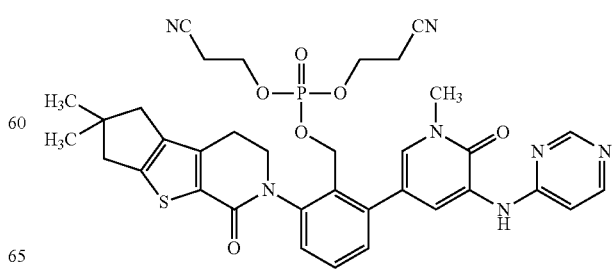

A 250-mL single-neck round-bottomed flask equipped with a magnetic stirrer and nitrogen inlet was charged with 105 (850 mg, 1.61 mmol), 1H-tetrazole (451 mg, 6.44 mmol) and methylene chloride (20 mL). A solution of bis(2-cyanoethyl)-N,N-diisopropyl phosphoramidite (1.31 g, 4.83 mmol) in methylene chloride (5 mL) was added at room temperature, and the reaction mixture was stirred for 3 h under nitrogen atmosphere. After this time, the reaction mixture was cooled to 0° C. and a 5.5 M solution of tert-butyl hydroperoxide in decane (2.00 mL, 11.0 mmol) was added dropwise, and the reaction mixture was stirred at 0° C. for 3 h under nitrogen atmosphere. After this time, the mixture was concentrated under reduced pressure to a volume of 5 mL, and the resulting suspension was loaded on a silica gel column and eluted with 90:10 methylene chloride/methanol to afford 216a in 39% yield (450 mg) as a white semi-solid: $^1$H NMR (500 MHz, CDCl$_3$) δ 8.77 (d, J=0.5 Hz, 1H), 8.73 (d, J=2.0 Hz, 1H), 8.36 (d, J=5.5 Hz, 1H), 8.17 (s, 1H), 7.55 (t, J=7.5 Hz, 1H), 7.38-7.35 (m, 2H), 7.09 (d, J=2.0 Hz, 1H), 6.76 (dd, J=6.0, 1.5 Hz, 1H), 5.21-5.14 (m, 2H), 4.15-4.04 (m, 5H), 3.86-3.83 (m, 1H), 3.72 (s, 3H), 3.21-3.18 (m, 1H), 2.90-2.82 (m, 1H), 2.79 (d, J=3.5 Hz, 2H), 2.63-2.48 (m, 6H), 1.28 (s, 3H), 1.27 (s, 3H); MS (ESI+) m/z 714.2 (M+H).

Example 216b Di-ammonium 2-(1-Methyl-6-oxo-5-(pyrimidin-4-ylamino)-1,6-dihydro-pyridin-3-yl)-6-(6,6-Dimethyl-3,4,6,7-tetrahydro-5H-cyclopenta[4,5]thieno[2,3-c]pyridine-1(2H)-yl)benzyl Phosphate 216b

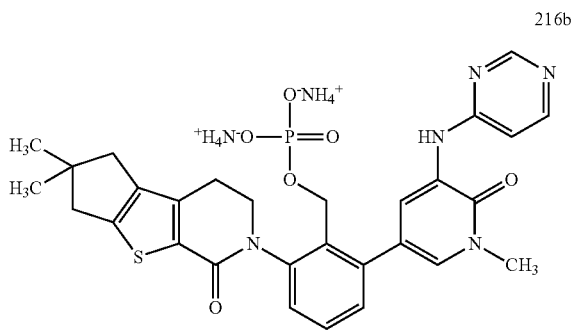

A 250-mL single-neck round-bottomed flask equipped with a magnetic stirrer and nitrogen inlet was charged with 216a (450 mg, 0.631 mmol) and acetonitrile (8 mL), and the mixture was cooled to 0° C. Triethylamine (4 mL) was added followed bis trimethyl-silyl trifluoroacetamide (4 mL), and the mixture was stirred at room temperature for 40 h. After this time, the mixture was concentrated under reduced pressure and the resulting residue was purified by flash column chromatography (silica, 40:20:40 chloroform/methanol/ammonia) to afford 216b in 52% yield (210 mg) as an amorphous yellow solid: mp 260-262° C. d; $^1$H NMR (500 MHz, DMSO-d$_6$) δ 9.12 (s, 1H), 8.66 (s, 1H), 8.62 (d, J=2.0 Hz, 1H), 8.27 (d, J=4.0 Hz, 1H), 7.54 (s, 1H), 7.43 (t, J=7.5 Hz, 1H), 7.32-7.27 (m, 3H), 7.15 (br s, 2H), 4.69 (d, J=9.0 Hz, 1H), 4.46 (d, J=7.0 Hz, 1H), 3.87-3.83 (m, 3H), 3.57 (s, 3H), 3.36-3.17 (br s, 8H), 2.77-2.63 (m, 3H), 1.23 (s, 3H), 1.21 (s, 3H); MS (ESI+) m/z 608.2 (M+H for C$_{29}$H$_{30}$N$_5$O$_6$PS).

A 200-mL single-neck round-bottomed flask equipped with a magnetic stirrer was charged with 216b (210 mg, 0.327 mmol), methanol (10 mL) and water (5 mL). A 0.1 M solution of sodium hydroxide in water (6.50 mL, 0.65 mmol) was added at room temperature, and the mixture was stirred for 30 min. After this time, the mixture was concentrated under reduced pressure and dried under vacuum at 45° C. for 14 h to afford 216 in 92% yield (197 mg) as an amorphous yellow solid: mp 256-258° C. dec; $^1$H NMR (500 MHz, DMSO-d$_6$/D$_2$O (15:1)) d 8.65 (s, 1H), 8.63 (d, J=1.5 Hz, 1H), 8.28 (d, J=6.0 Hz, 1H), 8.09 (d, J=1.5 Hz, 1H), 7.47 (t, J=7.5 Hz, 1H), 7.38 (d, J=7.5 Hz, 1H), 7.24 (d, J=7.5 Hz, 1H), 7.16 (d, J=6.0 Hz, 1H), 4.72 (d, J=9.5 Hz, 1H), 4.45 (d, J=8.0 Hz, 1H), 4.23-4.21 (m, 1H), 3.83-3.78 (m, 1H), 3.71 (s, 3H), 3.48-3.41 (m, 1H), 2.78-2.73 (m, 3H), 2.59-2.49 (m, 2H), 1.23 (s, 3H), 1.22 (s, 3H); MS (ESI+) m/z 608.2 (M+H for C$_{29}$H$_{30}$N$_5$O$_6$PS).

Example 217 5-(5-Fluoro-2-(hydroxymethyl)-3-(6,6-Dimethyl-3,4,6,7-tetrahydro-5H-cyclopenta[4,5]thieno[2,3-c]pyridine-1(2H)-yl)-3-(5-(4-(2-fluoroethyl)piperazin-1-yl)pyridin-2-ylamino)-1-methylpyridin-2(1H)-one 217

Example 217a 1-(6-Nitropyridin-3-yl)piperazine 217a

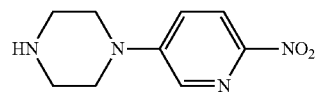

A 250-mL three-neck round-bottomed flask equipped with a magnetic stirrer and reflux condenser was charged with 2-nitro-5-bromopyridine (5.00 g, 24.6 mmol), piperazine (5.66 g, 65.7 mmol) and acetonitrile (70 mL). The reaction mixture was heated at reflux for 20 h. After this time, the reaction mixture was cooled to room temperature and concentrated under reduced pressure. The residue was diluted with ethyl acetate (200 mL) and washed with saturated aqueous sodium bicarbonate (100 mL). The organic layer was dried over sodium sulfate, filtered and concentrated under reduced pressure. The resulting residue was titrated with hexane/ethyl acetate (1:1, 30 mL) to afford 217a in 41% yield (2.10 g) as a yellow solid: mp 113-115° C.; $^1$H NMR (500 MHz, DMSO-d$_6$) δ 8.23 (d, 1H, J=3.5 Hz), 8.13 (d, 1H, J=9.0 Hz), 7.44 (dd, 1H, J=9.0, 3.5 Hz), 3.41 (t, 4H, J=5.0 Hz), 2.82 (t, 4H, J=5.0 Hz), 1.90 (s, 1H); MS (ESI+) m/z 209.1 (M+H).

Example 217b 1-(2-Fluoroethyl)-4-(6-nitropyridin-3-yl)piperazine 217b

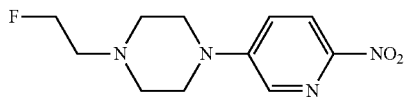

A 250-mL single-neck round-bottomed flask equipped with a magnetic stirrer, reflux condenser, and nitrogen inlet was charged with 217a (598 mg, 2.87 mmol), 1-bromo-2-fluoroethane (1.09 g, 8.61 mmol), potassium carbonate (1.19 g, 8.61 mmol), THF (10 mL) and DMF (10 mL). The reaction mixture was heated at 85° C. for 14 h under nitrogen atmosphere. After this time, the mixture was diluted with 90:10 methylene chloride/methanol (100 mL) and water (75 mL), and the layers were separated. The aqueous layer was extracted with 90:10 methylene chloride/methanol (50 mL), and the combined organic layers were washed with brine (100 mL) and dried over sodium sulfate. The drying agent was removed by filtration. The filtrate was concentrated under reduced pressure, and the resulting residue was purified by flash column chromatography (silica, 95:5 methylene chloride/methanol) to afford 217b in 63% yield (460 mg) as a yellow semi-solid: $^1$H NMR (500 MHz, CDCl$_3$) δ 8.16 (d, J=9.0 Hz, 1H), 8.14 (d, J=3.0 Hz, 1H), 7.21 (dd, J=9.0, 2.0 Hz, 1H), 4.67 (t, J=5.0 Hz, 1H), 4.57 (t, J=5.0 Hz, 1H), 3.49 (t, J=5.0 Hz, 4H), 2.81 (t, J=5.0 Hz, 1H), 2.75 (t, J=5.0 Hz, 1H), 2.73 (t, J=5.5 Hz, 4H); MS (ESI+) m/z 255.1 (M+H).

Example 217c 5-(4-(2-Fluoroethyl)piperazin-1-yl)pyridin-2-amine 217c

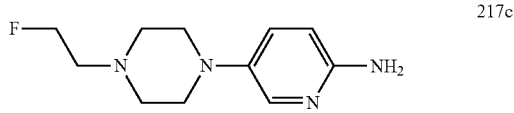

A 250-mL Parr reactor bottle was purged with nitrogen and charged with 10% palladium on carbon (50% wet, 75 mg dry weight) and a solution of 217b (455 mg, 1.79 mmol) in ethanol (20 mL). The bottle was attached to a Parr hydrogenator, evacuated, charged with hydrogen gas to a pressure of 50 psi and shaken for 3 h. After this time, the hydrogen was evacuated, and nitrogen was charged into the bottle. Celite 521 (3.50 g) was added, and the mixture was filtered through a pad of Celite 521. The filter cake was washed with ethanol (2×50 mL), and the combined filtrates were concentrated to dryness under reduced pressure to afford a quantitative yield of 217c (425 mg) as a yellow semi-solid: $^1$H NMR (500 MHz, CDCl$_3$) δ 7.75 (d, J=3.0 Hz, 1H), 7.20 (dd, J=9.0, 3.0 Hz, 1H), 6.51 (d, J=8.5 Hz, 1H), 4.66 (t, J=5.0 Hz, 1H), 4.56 (t, J=5.0 Hz, 1H), 4.35-4.15 (br s, 2H), 3.08 (t, J=5.0 Hz, 4H), 2.79 (t, J=5.0 Hz, 1H), 2.74 (t, J=4.5 Hz, 1H), 2.71 (t, J=5.0 Hz, 4H); MS (ESI+) m/z 225.1 (M+H).

Example 217d 5-Bromo-3-(5-(4-(2-fluoroethyl)piperazin-1-yl)pyridin-2-ylamino)-1-methylpyridin-2(1H)-one 217d

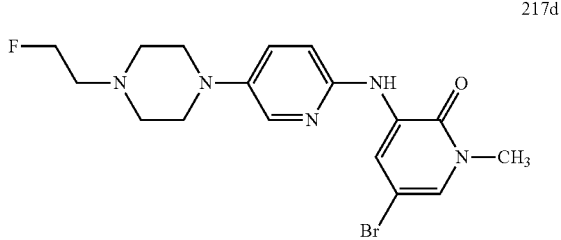 [SMILES: Cn1cc(Br)cc(Nc2ccc(N3CCN(CCF)CC3)cn2)c1=O]

A 100-mL single-neck round-bottomed flask equipped with a magnetic stirrer and nitrogen inlet was charged with 217c (402 mg, 1.79 mmol), 3,5-dibromo-1-methyl-pyridin-2(1H)-one (478 mg, 1.79 mmol), cesium carbonate (1.75 g, 5.37 mmol) and 1,4-dioxane (15 mL). After bubbling nitrogen through the resulting suspension for 30 min, Xantphos (93 mg, 0.161 mmol) and tris(dibenzylideneacetone)dipalladium(0) (82 mg, 0.090 mmol) were added. A reflux condenser was attached to the flask, and the reaction mixture was heated at 100° C. for 3 h. After this time, the mixture was cooled to room temperature and diluted with 90:10 methylene chloride/methanol (100 mL) and water (75 mL), and the layers were separated. The aqueous layer was extracted with 90:10 methylene chloride/methanol (2×50 mL), and the combined organic layers were washed with brine and dried over sodium sulfate. The drying agent was removed by filtration. The filtrate was concentrated under reduced pressure, and the resulting residue was purified by flash column chromatography (silica, 95:5 methylene chloride/methanol) to afford 217d in 62% yield (459 mg) as an amorphous yellow solid: mp 141-143° C.; $^1$H NMR (500 MHz, CDCl$_3$) δ 8.57 (d, J=2.0 Hz, 1H), 7.99 (d, J=3.0 Hz, 1H), 7.74 (s, 1H), 7.24 (d, J=3.0 Hz, 1H), 6.93 (d, J=2.0 Hz, 1H), 6.76 (d, J=9.0 Hz, 1H), 4.67 (t, J=5.0 Hz, 1H), 4.57 (t, J=5.0 Hz, 1H), 3.59 (s, 3H), 3.16 (t, J=5.0 Hz, 4H), 2.80 (t, J=5.0 Hz, 1H), 2.75 (t, J=5.0 Hz, 1H), 2.73 (t, J=5.5 Hz, 4H); MS (ESI+) m/z 410.1 (M+H)

A 100-mL single-neck round-bottomed flask equipped with a magnetic stirrer and nitrogen inlet was charged with 217d (177 mg, 0.431 mmol), 182c (315 mg, 0.539 mmol), sodium carbonate (100 mg, 0.862 mmol), water (2 mL) and 1,4-dioxane (10 mL). After bubbling nitrogen through the resulting suspension for 30 min, tetrakis(tripheny-1phosphine)palladium(0) (100 mg, 0.086 mmol) was added. A reflux condenser was attached to the flask, and the reaction mixture was heated at 90° C. for 1 h. After this time, the mixture was diluted with 90:10 methylene chloride/methanol (100 mL) and water (75 mL), and the layers were separated. The aqueous layer was extracted with 90:10 methylene chloride/methanol (2×50 mL), and the combined organic layers were washed with brine (100 mL) and dried over sodium sulfate. The drying agent was removed by filtration. The filtrate was concentrated under reduced pressure, and the resulting residue was dissolved in a mixture of THF. A 1.0 M solution of tetra-butyl-ammonium fluoride in THF (1.10 mL, 1.10 mmol) was added, and the mixture was stirred at room temperature for 3 h. After this time, the mixture was diluted with 90:10 methylene chloride/methanol (75 mL) and water (50 mL), and the layers were separated. The aqueous layer was extracted with 90:10 methylene chloride/methanol (2×50 mL), and the combined organic layers were washed with brine (100 mL) and dried over sodium sulfate. The drying agent was removed by filtration. The filtrate was concentrated under reduced pressure, and the resulting residue was purified by flash column chromatography (silica, 95:5 methylene chloride/methanol) to afford 217 in 25% yield (73 mg) as an amorphous yellow solid: mp 158-160° C.; $^1$H NMR (500 MHz, DMSO-d$_6$) δ 8.55 (d, J=2.0 Hz, 1H), 8.35 (s, 1H), 7.86 (d, J=3.0 Hz, 1H), 7.37-7.31 (m, 3H), 7.22 (d, J=9.0 Hz, 1H), 7.17 (dd, J=9.5, 3.0 Hz, 1H), 4.85 (t, J=4.0 Hz, 1H), 4.61 (t, J=5.0 Hz, 1H), 4.51 (t, J=5.0 Hz, 1H), 4.35-4.30 (m, 2H), 4.08-4.02 (m, 1H), 3.87-3.82 (m, 1H), 3.58 (s, 3H), 3.05-2.99 (m, 5H), 2.91-2.87 (m, 1H), 2.75 (s, 2H), 2.68 (t, J=5.0 Hz, 1H), 2.62 (t, J=4.5 Hz, 1H), 2.57-2.53 (m, 4H), 2.52 (d, J=4.5 Hz, 2H), 1.23 (s, 6H); MS (ESI+) m/z 675.3 (M+H).

Example 218 5-(3-{5-[(6-ethyl-5,6,7,8-tetrahydro-1,
6-naphthyridin-2-yl)amino]-1-methyl-6-oxo-1,6-
dihydropyridin-3-yl}-5-fluoro-2-(hydroxymethyl)
phenyl)-8-thia-5-azatricyclo[7.4.0.0$^{2,7}$]trideca-1(9),2
(7)-dien-6-one 218

Example 218a (2-{5-[(6-Ethyl-5,6,7,8-tetrahydro-1,
6-naphthyridin-2-yl)amino]-1-methyl-6-oxo-1,6-
dihydropyridin-3-yl}-4-fluoro-6-{6-oxo-8-thia-5-
azatricyclo[7.4.0.0$^{2,7}$]trideca-1(9),2(7)-dien-5-
yl}phenyl)methyl Acetate 218a

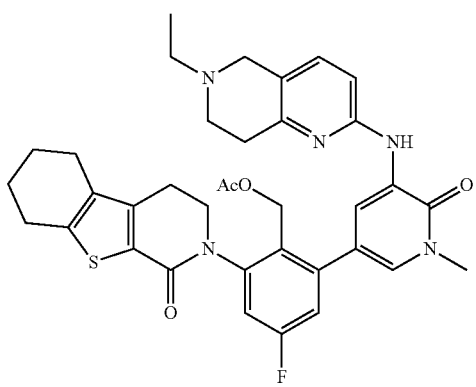

218a

A 25 mL sealed tube was charged with (2-{6-oxo-8-thia-
5-azatricyclo[7.4.0.0$^{2,7}$]-trideca-1(9),2(7)-dien-5-yl}-6-(4,
4,5,5-tetramethyl-1,3,2-dioxaborolan-2-yl)phenyl)-methyl
acetate (212b) (893 mg, 1.8 mmol), 5-bromo-3-(6-ethyl-5,
6,7,8-tetrahydro-1,6-naphthyridin-2-ylamino)-1-methyl-
pyridin-2(1H)-one (500 mg, 1.4 mmol), CH$_3$COONa (226
mg, 2.75 mmol), K$_3$PO$_4$ (733 mg, 2.75 mmol), PdCl$_2$(dppf)
(112 mg, 0.14 mmol) suspended in CH$_3$CN (25 mL) and
H$_2$O (1 mL). The mixture was stirred at 110° C. for 2 hours.
After reaction the solvent was evaporated and the residue
was purified by silical-gel column eluting with 20:1 methylene chloride/methanol to give 218a as a brown solid (400
mg, 44%). MS: (M+H)$^+$ 656.

To a solution of 218a (350 mg, 0.53 mmol) in propan-2-ol
(10 mL), tetrahydrofuran (10 mL), and water (2 mL) was
added LiOH (1.28 g, 53 mmol). The mixture was stirred at
30° C. for 2 h. After reaction the mixture was evaporated and
the residue was purified by prep-HPLC to afford 218 as a
yellow solid (124 mg, 38%). MS: (M+H)$^+$ 614. $^1$H NMR
(500 MHz, DMSO) δ 1.06-1.09 (t, J=7.5 Hz, 3H), 1.80 (s,
4H), 2.55-2.58 (m, 2H), 2.67-2.68 (d, 2H), 2.74-2.79 (d,
4H), 2.85-2.98 (m, 2H), 3.43 (s, 2H), 3.60 (s, 3H), 3.87-3.89
(m, 1H), 4.05-4.07 (m, 1H), 4.37-4.38 (d, 2H), 4.87-4.89 (t,
J=4.5 Hz, 1H), 7.07-7.09 (d, 1H), 7.19-7.21 (m, 1H), 7.29-
7.34 (m, 2H), 7.45-7.46 (d, 1H), 8.46 (s, 1H), 8.79-8.80 (d,
1H).

Example 219 5-[5-Fluoro-2-(hydroxymethyl)-3-(1-
methyl-5-{[6-(oxetan-3-yl)-5,6,7,8-tetrahydro-1,6-
naphthyridin-2-yl]amino}-6-oxo-1,6-dihydropyridin-
3-yl)phenyl]-8-thia-5-azatricyclo[7.4.0.0$^{2,7}$]trideca-1
(9),2(7)-dien-6-one 219

Example 219a 5-Bromo-1-methyl-3-(6-(oxetan-3-
yl)-5,6,7,8-tetrahydro-1,6-naphthyridin-2-ylamino)
pyridin-2(1H)-one 219a

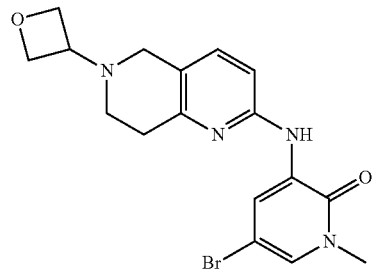

219a

A mixture of 5-bromo-1-methyl-3-(5,6,7,8-tetrahydro-1,
6-naphthyridin-2-ylamino)pyridine-2(1H)-one hydrochloride 205a (800 mg, 2.16 mmol), oxetan-3-one (778 mg, 10.8
mmol), NaBH$_3$CN (681 mg, 10.8 mmol), and zinc chloride
(1.47 g, 10.8 mmol) in methanol (30 mL) was stirred for 4
hours at 50° C. The mixture was added to H$_2$O (30 mL) and
extracted with DCM (50 mL×3). The organic layers were
concentrated under reduced pressure. The residue was purified by column chromatography eluting with 10:1 ethyl
acetate/methanol to give 219a as a yellow solid (750 mg,
89%). MS: [M+H]$^+$ 391.

Example 219b [4-Fluoro-2-(1-methyl-5-{[6-(oxetan-
3-yl)-5,6,7,8-tetrahydro-1,6-naphthyridin-2-yl]
amino}-6-oxo-1,6-dihydropyridin-3-yl)-6-{6-oxo-8-
thia-5-azatricyclo[7.4.0.0$^{2,7}$]trideca-1(9),2(7)-dien-5-
yl}phenyl]methyl Acetate 219b

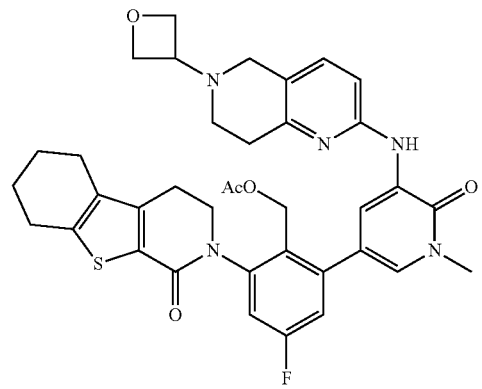

219b

A 25 mL sealed tube was charged with (2-{6-oxo-8-thia-
5-azatricyclo-[7.4.0.0$^{2,7}$]trideca-1(9),2(7)-dien-5-yl}-6-(4,
4,5,5-tetramethyl-1,3,2-dioxaborolan-2-yl)phenyl)methyl
acetate 212b (512 mg, 1.0 mmol), 219a (400 mg, 1.0 mmol), CH₃COONa (168 mg, 2.0 mmol), K₃PO₄ (546 mg, 2.0 mmol), and PdCl₂(dppf) (84 mg, 0.1 mmol) suspended in CH₃CN (25 mL) and H₂O (1 mL). The mixture was stirred in at 110° C. for 2 hours. After reaction the mixture was evaporated and the residue was purified by column chromatography eluting with 10:1 methylene chloride/methanol to give 219b as a brown solid (450 mg, 64%). MS: (M+H)⁺ 684.

A solution of 219b (400 mg, 0.58 mmol) in propan-2-ol (12 mL), tetrahydrofuran (12 mL), and water (2 mL) was added LiOH (1.4 g, 58 mmol). The mixture was stirred at 30° C. for 2 h. After reaction the mixture was evaporated and the residue was purified by prep-HPLC to afford 219 as a yellow solid (213 mg, 57%). MS: (M+H)⁺ 642. ¹H NMR (500 MHz, DMSO) δ 1.80 (s, 4H), 2.55-2.58 (m, 3H), 2.77-2.79 (d, 4H), 2.85-2.89 (m, 1H), 2.96-2.98 (m, 1H), 3.36 (s, 2H), 3.60-3.61 (d, 4H), 3.87-3.89 (m, 1H), 4.05-4.07 (m, 1H), 4.37-4.38 (d, 2H), 4.50-4.52 (t, J=5 Hz, 2H), 4.59-4.62 (t, J=6.5 Hz, 2H), 4.87-4.90 (t, J=4 Hz, 2H), 7.08-7.10 (d, 1H), 7.19-7.21 (m, 1H), 7.29-7.34 (m, 2H), 7.45-7.46 (d, 1H), 8.46 (s, 1H), 8.79-8.80 (d, 1H).

Example 220 5-[5-Fluoro-2-(hydroxymethyl)-3-[1-methyl-6-oxo-5-({5-[4-(propan-2-yl)piperazin-1-yl]pyridin-2-yl}amino)-1,6-dihydropyridin-3-yl]phenyl]-8-thia-5-azatricyclo[7.4.0.02,7]trideca-1(9),2(7)-dien-6-one 220

Example 220a 5-Bromo-3-(5-(4-isopropylpiperazin-1-yl)pyridin-2-ylamino)-1-methylpyridin-2(1H)-one 220a

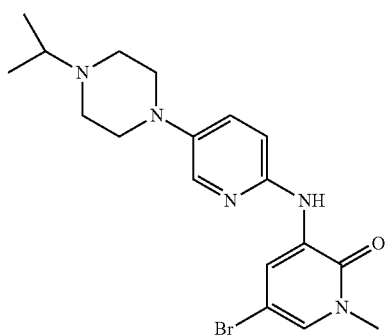

A mixture of 5-bromo-1-methyl-3-(5-(piperazin-1-yl)pyridin-2-ylamino)pyridin-2(1H)-one 188d (1.2 g, 3.3 mmol), and acetone (1.0 g, 16.5 mmol) in methanol/acetic acid (30 mL/3 mL) was stirred for 5 minutes at room temperature, followed by the addition of NaBH(OAc)₃ (3.5 g, 16.5 mmol). The mixture was stirred at 50° C. for 2 h. It was cooled to room temperature and H₂O (50 mL) was added. The mixture was extracted with DCM (50 mL) three times. The organic layers were concentrated under reduced pressure and the residue was purified by column chromatography eluting with 25:1 DCM/methanol to give 220a (2.97 g, 81%). MS: [M+H]⁺ 406. ¹H NMR (500 MHz, DMSO) δ 8.58 (d, J=3.0, 1H), 8.53 (s, 1H), 7.92 (d, J=3.0, 1H), 7.44 (d, J=2.5, 1H), 7.37 (d, J=2.5, 1H), 7.25 (d, J=8, 1H), 3.51 (s, 3H), 3.06 (t, J=4.5, 4H), 2.69 (s, 1H), 2.57-2.50 (m, 4H), 1.00 (d, J=7, 6H).

Example 220b {4-Fluoro-2-[1-methyl-6-oxo-5-({5-[4-(propan-2-yl)piperazin-1-yl]pyridin-2-yl}amino)-1,6-dihydropyridin-3-yl]-6-{6-oxo-8-thia-5-azatricyclo-[7.4.0.0²,⁷]trideca-1(9),2(7)-dien-5-yl}phenyl}methyl Acetate 220b

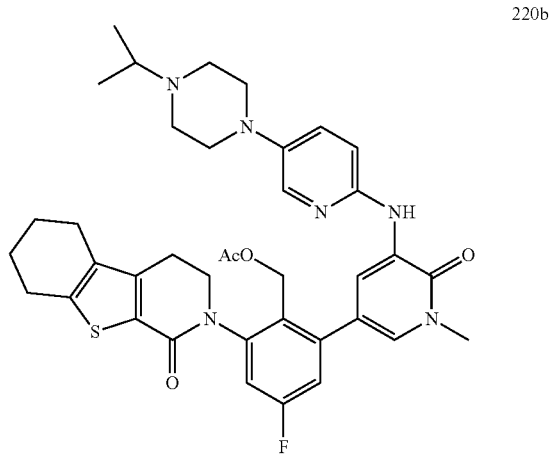 [SMILES: CC(=O)OCc1c(-c2cc(Nc3ccc(N4CCN(C(C)C)CC4)cn3)c(=O)n(C)c2)cc(F)cc1N1CCc2c(sc3c2CCCC3)C1=O]

Following the procedures as described for 148b and starting with 400 mg of (4-fluoro-2-{6-oxo-8-thia-5-azatricyclo[7.4.0.0²,⁷]trideca-1(9),2(7)-dien-5-yl}-6-(4,4,5,5-tetramethyl-1,3,2-dioxaborolan-2-yl)phenyl)methyl acetate 212b and 340 mg 5-bromo-3-(5-(4-isopropylpiperazin-1-yl)pyridin-2-ylamino)-1-methylpyridin-2(1H)-one 220a, compound 220b was obtained as a yellow solid (446 mg, 82%). MS: [M+H]⁺ 699

Following the procedures as described for 148 and starting with 200 mg of 220b, compound 220 was obtained as a white solid (70 mg, 37%). MS: [M+H]⁺ 657. ¹H NMR (500 MHz, DMSO) δ 8.56 (d, J=2.5, 1H), 8.37 (s, 1H), 7.85 (d, J=2.5, 1H), 7.34 (m, 3H), 7.23 (m, 2H), 4.68 (s, 1H), 4.32 (s, 2H), 4.06 (s, 1H), 3.85 (s, 1H), 3.58 (s, 3H), 3.02 (s, 4H), 2.78 (m, 4H), 2.55 (m, 7H), 1.80 (d, J=3.5, 4H), 1.00 (d, J=7, 6H).

Example 221 5-[5-Fluoro-2-(hydroxymethyl)-3-{4-methyl-6-[(2-methyl-1,2,3,4-tetrahydroisoquinolin-6-yl)amino]-5-oxo-4,5-dihydropyrazin-2-yl}phenyl]-8-thia-5-azatricyclo[7.4.0.0²,⁷]trideca-1(9),2(7)-dien-6-one 221

Example 221a 5-Bromo-1-methyl-3-(1,2,3,4-tetrahydroisoquinolin-6-ylamino)pyrazin-2(1H)-one 221a

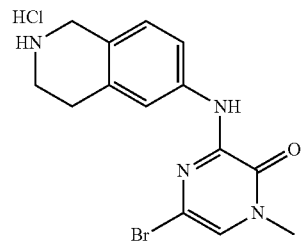 [SMILES: Cl ; Cn1cc(Br)nc(Nc2ccc3c(c2)CCNC3)c1=O]

To a solution of tert-butyl 6-(6-bromo-4-methyl-3-oxo-3,4-dihydropyrazin-2-ylamino)-3,4-dihydroisoquinoline-2(1H)-carboxylate 120a (3.6 g, 8.3 mmol) in dioxane (10 mL) was added saturated hydrogen chloride solution in dioxane (20 mL) dropwise. The reaction mixture was stirred for 20 minutes and concentrated under reduced pressure to give 221a, which was used without further purification in the next step. LC/MS: m/z 336 (M+H)+

Example 221b 5-Bromo-1-methyl-3-(2-methyl-1,2,3,4-tetrahydroisoquinolin-6-ylamino)pyrazin-2(1H)-one 221b

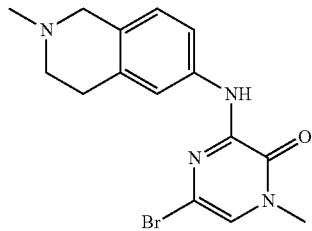 [SMILES: CN1CCc2cc(Nc3nc(Br)cn(C)c3=O)ccc2C1]

A mixture of 221a (2.75 g, 7.5 mmol), formaldehyde (37% in H$_2$O, 30 mL, 375 mmol), NaBH(OAc)$_3$ (4.75 g, 22.5 mmol), and AcOH (25 ml, 150 mmol) in methanol (125 ml) was stirred for 4 hours at room temperature. The mixture was then brought to basic condition with saturated NaOH solution and extracted with ethyl acetate. The organic layer was dried over Na$_2$SO$_4$ and evaporated under reduced pressure. The residue was purified by column chromatography eluting with 4:1 ethyl acetate/methanol to give 221b. (0.9 g, 34.4%) LC/MS: m/z 350 (M+H)+

Example 221c (4-Fluoro-2-{4-methyl-6-[(2-methyl-1,2,3,4-tetrahydroisoquinolin-6-yl)amino]-5-oxo-4,5-dihydropyrazin-2-yl}-6-{6-oxo-8-thia-5-azatricyclo[7.4.0.0$^{2,7}$]-trideca-1(9), 2(7)-dien-5-yl}phenyl) methyl Acetate 221c

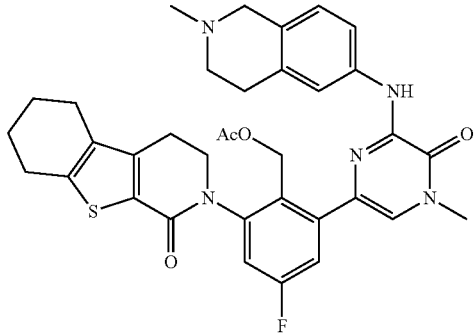

A 15 mL microwave vial with a magnetic stirrer was charged with 5-bromo-1-methyl-3-(2-methyl-1,2,3,4-tetrahydroisoquinolin-6-ylamino)pyrazin-2(1H)-one (0.42 g, 1.2 mmol), 212b (0.6 g, 1.2 mmol), potassium phosphate (0.64 g, 2.4 mmol), sodium acetate (0.2 g, 2.4 mmol), acetonitrile (10 mL), water (1 mL), and 1,1'-bis(diphenylphosphino)ferrocene-palladium(II) dichloride dichloromethane (0.1 g, 0.12 mmol). The reaction mixture was heated at 110° C. for 2 hours under argon atmosphere. After this time, the mixture was cooled to room temperature and filtered. The filtrate was concentrated under reduced pressure and the residue was purified by column chromatography eluting with 40:1 DMC/methanol to give 221c (0.667 g, 86.6%). LC/MS: m/z 642 (M+H)+

A 25 mL round bottomed flask with a magnetic stirrer was charged with 221c (0.647 g, 1.0 mmol), LiOH (2.1 g, 50 mmol), THF (10 mL), isopropanol (10 mL) and water (5 mL). The reaction mixture was stirred at room temperature for 30 minutes and filtered. The filtrate was concentrated under reduced pressure. The residue was purified by prep-HPLC to give 221. LC/MS: m/z 600 (M+H)+. $^1$H NMR (500 MHz, DMSO) δ 9.13 (s, 1H), 7.80 (s, 1H), 7.62 (d, J=8.5, 1H), 7.51 (s, 1H), 7.39 (d, J=10, 1H), 7.30 (d, J=6.5, 1H), 6.97 (d, J=8.5, 1H), 4.86 (m, 1H), 44.51 (m, 3H), 4.41 (m, 1H), 4.05 (m, 1H), 3.87 (m, 1H), 3.55 (m, 6H), 2.77 (m, 3H), 2.55 (m, 3H), 2.31 (m, 3H), 1.80 (m, 4H).

Example 222 5-[5-Fluoro-2-(hydroxymethyl)-3-(4-methyl-6-{[2-(oxetan-3-yl)-1,2,3,4-tetrahydroisoquinolin-6-yl]amino}-5-oxo-4,5-dihydropyrazin-2-yl)phenyl]-8-thia-5-azatricyclo[7.4.0.0$^{2,7}$]trideca-1(9),2(7)-dien-6-one 222

Example 222a 5-Bromo-1-methyl-3-(2-(oxetan-3-yl)-1,2,3,4-tetrahydroisoquinolin-6-ylamino)pyrazin-2(1H)-one 222a

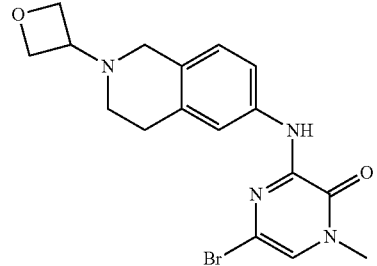 [SMILES: Cn1cc(Br)nc(Nc2ccc3c(c2)CCN(C2COC2)C3)c1=O]

A mixture of 5-bromo-1-methyl-3-(1,2,3,4-tetrahydroisoquinolin-6-ylamino)pyrazin-2(1H)-one 221a (2.75 g, 7.5 mmol), oxetan-3-one (2.5 g, 37.5 mmol), NaBH$_3$CN (4.75 g, 22.5 mmol) and zinc chloride (5 g, 37.5 mmol) in methanol (125 ml) was stirred for 4 hours at room temperature. The mixture was filtered and the filtrate was concentrated under reduced pressure. The residue was purified by column chromatography eluting with 20:1 DCM/methanol to 222a (0.76 g, 25.9%). LC/MS: m/z 392 (M+H)+.

Example 222b [4-Fluoro-2-(4-methyl-6-{[2-(oxetan-3-yl)-1,2,3,4-tetrahydroisoquinolin-6-yl]amino}-5-oxo-4,5-dihydropyrazin-2-yl)-6-{6-oxo-8-thia-5-azatricyclo[7.4.0.0$^{2,7}$]trideca-1(9),2(7)-dien-5-yl}phenyl]methyl Acetate 222b

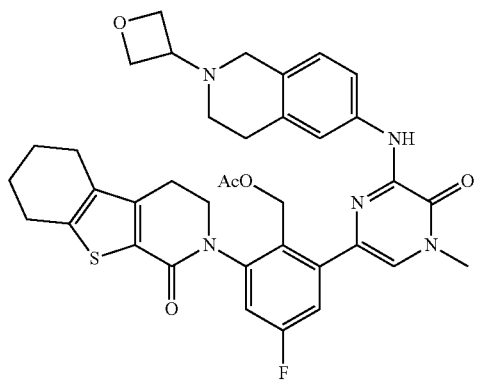 [SMILES: CC(=O)OCc1c(-c2cn(C)c(=O)c(Nc3ccc4c(c3)CCN(C3COC3)C4)n2)cc(F)cc1N1CCc2c(sc3c2CCCC3)C1=O]

A 250 mL round bottomed flask with a magnetic stirrer was charged with 222a (0.31 g, 0.8 mmol), (4-fluoro-2-{6-oxo-8-thia-5-azatricyclo[7.4.0.0$^{2,7}$]-trideca-1(9),2(7)-dien-5-yl}-6-(4,4,5,5-tetramethyl-1,3,2-dioxaborolan-2-yl)phenyl)-methyl acetate 212b (0.4 g, 0.8 mmol), potassium phosphate (0.43 g, 1.6 mmol), sodium acetate (0.13 g, 1.6 mmol), acetonitrile (30 mL), water (2 mL), and 1,1'-bis(diphenyl-phosphino)ferrocene-palladium(II)dichloride dichloromethane (0.07 g, 0.08 mmol). The reaction mixture was refluxed for overnight under argon atmosphere. After this time, the mixture was cooled to room temperature and filtered. The filtrate was concentrated under reduced pressure. The residue was purified by column chromatography eluting with 40:1 methylene chloride/methanol to give 222b (0.491 g, 89.3%). LC/MS: m/z 684(M+H)$^+$ A 25 mL round bottomed flask with a magnetic stirrer was charged with 222b (0.471 g, 0.69 mmol), LiOH (1.45 g, 34.5 mmol), THF (10 mL), isopropanol (10 mL) and water (5 mL). The reaction mixture was stirred at room temperature for 30 minutes and filtered. The filtrate was concentrated under reduced pressure. The residue was purified by prep-HPLC to give 222 as a white solid (20 mg, 11%). LC/MS: m/z 642 (M+H)$^+$. $^1$H NMR (500 MHz, DMSO) δ 9.14 (s, 1H), 7.82 (s, 1H), 7.63 (d, J=8.5, 1H), 7.51 (s, 1H), 7.39 (d, J=10, 1H), 7.30 (d, J=6.5, 1H), 6.97 (d, J=8.5, 1H), 4.86 (m, 1H), 4.84 (m, 2H), 4.51 (m, 3H), 4.41 (m, 1H), 4.05 (m, 1H), 3.87 (m, 1H), 3.55 (m, 5H), 2.88 (m, 1H), 2.77 (m, 1H), 2.53 (m, 4H), 1.80 (m, 4H), 1.23 (m, 2H).

Example 223 5-[5-Fluoro-2-(hydroxymethyl)-3-{1-methyl-5-[(6-methyl-5,6,7,8-tetrahydro-1,6-naphthyridin-2-yl)amino]-6-oxo-1,6-dihydropyridin-3-yl}phenyl]-8-thia-5-azatricyclo[7.4.0.0$^{2,7}$]trideca-1(9),2(7)-dien-6-one 223

Example 223a (4-Fluoro-2-{1-methyl-5-[(6-methyl-5,6,7,8-tetrahydro-1,6-naphthyridin-2-yl)amino]-6-oxo-1,6-dihydropyridin-3-yl}-6-{6-oxo-8-thia-5-azatricyclo[7.4.0.0$^{2,7}$]trideca-1(9),2(7)-dien-5-yl}phenyl)methyl Acetate 223a

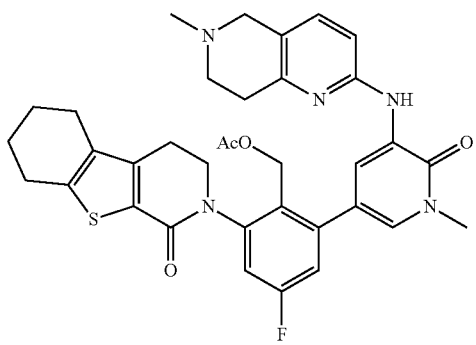

223a

Following the procedures as described for 136e and starting with 5-bromo-1-methyl-3-(6-methyl-5,6,7,8-tetrahydro-1,6-naphthyridin-2-ylamino)pyridine-2(1H)-one 205b and (4-fluoro-2-{6-oxo-8-thia-5-azatricyclo[7.4.0.0$^{2,7}$]trideca-1(9),2(7)-dien-5-yl}-6-(4,4,5,5-tetramethyl-1,3,2-dioxaborolan-2-yl)phenyl)methyl acetate 212b, compound 223a was obtained in 50% yield.

Following the procedures as described for compound 136f and starting with 223a, compound 223 was obtained in 33% yield. LCMS: (M+H)$^+$ 600. $^1$H NMR (500 MHz, MEOD) δ 8.87 (d, J=2, 1H), 7.40 (d, J=2.5, 1H), 7.35 (d, J=8, 1H), 7.23 (s, 1H), 7.21 (s, 1H), 6.88 (d, J=8, 1H), 4.56 (m, 2H), 4.16 (m, 1H), 4.01 (m, 1H), 3.72 (s, 3H), 3.57 (s, 2H), 3.05 (m, 1H), 2.95 (m, 3H), 2.84 (m, 4H), 2.59 (m, 2H), 2.49 (s, 3H), 1.90 (m, 4H).

Example 224 10-[5-Fluoro-2-(hydroxymethyl)-3-{1-methyl-5-[(5-{[methyl(propan-2-yl)amino]methyl}pyridine-2-yl)amino]-6-oxo-1,6-dihydropyridin-3-yl}phenyl]-4,4-dimethyl-1,10-diazatricyclo[6.4.0.0$^{2,6}$]dodeca-2(6),7-dien-9-one 224

Example 224a 10-[5-Fluoro-2-(acetoxymethyl)-3-{1-methyl-5-[(5-{[methyl(propan-2-yl)amino]methyl}pyridine-2-yl)amino]-6-oxo-1,6-dihydropyridin-3-yl}phenyl]-4,4-dimethyl-1,10-diazatricyclo[6.4.0.0$^{2,6}$]dodeca-2(6),7-dien-9-one 224a Following Example 186f, 186e (365 mg, 0.64 mmol) and 189 (230 mg, 0.51 mmol) were reacted to give 224a (80 mg, 20% yield).

Following Example 186, 224a (80 mg, 0.12 mmol), 1N LiOH (0.61 mL), THF (2 mL) and isopropanol (2 mL) were reacted and triturated with EtOAc to give 224 (57 mg, 76% yield). MS (ESI+) m/z 613.6 (M+H).

Example 225 2-(2-(Hydroxymethyl)-3-(1-methyl-5-(5-methyl-1H-pyrazol-3-ylamino)-6-oxo-1,6-dihydropyridin-3-yl)phenyl)-3,4,6,7,8,9-hexahydropyrido[3,4-b]indolizin-1(2H)-one 225

Using the same general procedure as described for 118, reaction of 112a (200 mg, 0.706 mmol) and 118f (330 mg, 0.710 mmol) afforded a 17% yield (60 mg) of 225 as a green-yellow solid: mp 199-200° C.; $^1$H NMR (500 MHz, DMSO-d$_6$) δ 11.69 (s, 1H), 7.99 (s, 1H), 7.93 (s, 1H), 7.41 (t, 1H, J=8.0 Hz), 7.25 (d, 3H, J=8.5 Hz), 6.00 (s, 1H), 5.86 (s, 1H), 4.69 (br s, 1H), 4.31 (m, 2H), 3.97 (m, 1H), 3.91 (m, 1H), 3.79 (m, 2H), 3.56 (s, 3H), 3.01 (m, 1H), 2.90 (m, 1H), 2.70 (m, 2H), 2.15 (s, 3H), 1.90 (m, 2H), 1.74 (m, 2H); MS (ESI+) m/z 499.2 (M+H).

Example 226 2-(2-(Hydroxymethyl)-3-(1-methyl-6-oxo-5-(5,6,7,8-tetrahydro-2,6-naphthyridin-3-ylamino)-1,6-dihydropyridin-3-yl)phenyl)-3,4,6,7,8,9-hexahydropyrido[3,4-b]indolizin-1(2H)-one 226

Example 226a tert-Butyl 7-(5-Bromo-1-methyl-2-oxo-1,2-dihydropyridin-3-ylamino)-3,4-dihydro-2,6-naphthyridine-2(1H)-carboxylate 226a

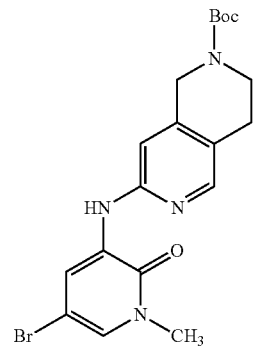

226a

A 100-mL three-neck round-bottomed flask equipped with a magnetic stirrer, nitrogen inlet and reflux condenser was charged with 3,5-dibromo-1-methylpyridin-2(1H)-one (536 mg, 2.01 mmol), tert-butyl 7-amino-3,4-dihydro-2,6-naphthyridine-2(1H)-carboxylate (500 mg, 2.01 mmol), cesium carbonate (1.44 g, 4.40 mmol) and 1,4-dioxane (30 mL). After bubbling nitrogen through the resulting mixture for 20 minutes, Xantphos (98.4 mg, 0.170 mmol) and tris(dibenzylideneacetone)dipalladium(0) (91.6 mg, 0.100 mmol) were added, and the reaction mixture was heated at 100° C. for 6 h. After this time, the reaction was cooled to room temperature, filtered and concentrated under reduced pressure. The resulting residue was purified by flash chromatography to afford a 96% yield (840 mg) of 226a as a yellow solid: mp 126-128° C.; $^1$H NMR (500 MHz, CDCl$_3$) δ 8.60 (d, 1H, J=2.5 Hz), 8.10 (s, 1H), 7.79 (s, 1H), 6.95 (d, 1H, J=2.5 Hz), 6.55 (s, 1H), 4.53 (s, 2H), 3.64 (t, 2H, J=5.0 Hz), 3.59 (s, 3H), 2.77 (t, 2H, J=5.0 Hz), 1.49 (s, 9H); MS (ESI+) m/z 435.0 (M+H).

Example 226b 5-Bromo-1-methyl-3-(5,6,7,8-tetrahydro-2,6-naphthyridin-3-ylamino)pyridin-2(1H)-one 226b

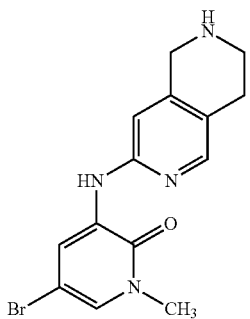

A 50-mL single-neck round-bottomed flask equipped with a magnetic stirrer was purged with nitrogen and charged with 226a (840 mg, 1.94 mmol) and methylene chloride (12 mL). Trifluoroacetic acid (6 mL) was added. The reaction was stirred at room temperature for 2 h. After this time, the reaction mixture was evaporated under reduced pressure. The residue 226b was directly used in the following step.

A 100-mL three-neck round-bottomed flask equipped with a magnetic stirrer and reflux condenser was charged with ½ of the amount of crude 226b prepared above (0.898 mmol presumed), 118f (416 mg, 0.898 mmol), sodium carbonate (381 mg, 3.59 mmol), water (4 mL) and 1,4-dioxane (20 mL). After bubbling nitrogen through the resulting suspension for 20 min, tetrakis(triphenylphosphine)palladium(0) (104 mg, 0.090 mmol) was added, and the reaction mixture was heated at 100° C. for 4 h. After this time, the reaction mixture was cooled to room temperature and filtered, and the filter cake was washed with a 1:10 mixture of methanol and methylene chloride (30 mL). The filtrate was concentrated under reduced pressure to afford a brown residue. Another 50-mL single-neck round-bottomed flask equipped with a magnetic stirrer and reflux condenser was charged with residue obtained above, THF (10 mL), ethanol (10 mL), water (10 mL) and lithium hydroxide (86.0 mg, 3.59 mmol). The mixture was stirred at 50° C. for 2 h. After this time, the reaction mixture was concentrated under reduced pressure. The resulting residue was purified by flash chromatography to afford a 7.7% (38 mg) yield of 226 as an off-white solid: mp 197-199° C.; $^1$H NMR (500 MHz, DMSO-d$_6$) δ 8.53 (d, 1H, J=2.0 Hz), 8.23 (s, 1H), 7.90 (s, 1H), 7.43 (t, 1H, J=7.5 Hz), 7.35 (d, 1H, J=2.0 Hz), 7.28 (s, 1H), 7.27 (s, 1H), 6.93 (s, 1H), 6.00 (s, 1H), 4.72 (t, 1H, J=5.0 Hz), 4.32 (d, 2H, J=5.0 Hz), 3.96 (m, 1H), 3.90 (m, 1H), 3.82 (m, 2H), 3.75 (s, 2H), 3.58 (s, 3H), 3.00 (m, 1H), 2.94 (m, 1H), 2.90 (t, 2H, J=5.0 Hz), 2.70 (m, 2H), 2.56 (m, 2H), 1.92 (m, 2H), 1.76 (m, 2H); MS (ESI+) m/z 551.2 (M+H).

Example 227 2-(3-(5-(5-(Azetidin-3-yl)pyridin-2-ylamino)-1-methyl-6-oxo-1,6-dihydropyridin-3-yl)-2-(hydroxymethyl)phenyl)-3,4,6,7,8,9-hexahydropyrido[3,4-b]indolizin-1(2H)-one 227

A 100-mL single-neck round-bottomed flask equipped with a magnetic stirrer and nitrogen inlet was charged with 155n (312 mg, 0.931 mmol), 118f (472 mg, 1.12 mmol), sodium carbonate (296 mg, 2.79 mmol), DMF (2 mL), water (2 mL) and 1,4-dioxane (10 mL). After bubbling nitrogen through the resulting suspension for 30 min, tetrakis-(triphenylphosphine)palladium(0) (215 mg, 0.186 mmol) was added. A reflux condenser was attached to the flask, and the reaction mixture was heated at 100° C. for 14 h. After this time, the mixture was diluted with 90:10 methylene chloride/methanol (100 mL) and water (75 mL), and the layers were separated. The aqueous layer was extracted with 90:10 methylene chloride/methanol (2×50 mL), and the combined organic layers were washed with brine (100 mL) and dried over sodium sulfate. The drying agent was removed by filtration. The filtrate was concentrated under reduced pressure, and the resulting residue was dissolved in a mixture of THF (5 mL), water (5 mL) and methanol (5 mL). Lithium hydroxide monohydrate (195 mg, 4.66 mmol) was added, and the mixture was stirred at room temperature for 3 h. After this time, the mixture was diluted with 90:10 methylene chloride/methanol (100 mL) and water (50 mL), and the layers were separated. The aqueous layer was extracted with 90:10 methylene chloride/methanol (2×75 mL), and the combined organic layers were washed with brine (100 mL) and dried over sodium sulfate. The drying agent was removed by filtration. The filtrate was concentrated under reduced pressure, and the resulting residue was purified by flash column chromatography (silica, 90:10 methylene chloride/methanol) to afford 227 in 7% yield (36 mg) as an amorphous off-white solid: mp 227-229° C.; $^1$H NMR (500 MHz, DMSO-d$_6$) δ 8.66 (d, J=1.5 Hz, 1H), 8.53 (s, 1H), 8.11 (s, 1H), 7.68 (d, J=7.0 Hz, 1H), 7.44 (t, J=8.0 Hz, 1H), 7.39 (s, 1H), 7.29 (m, 3H), 6.01 (s, 1H), 4.72 (t, J=4.5 Hz, 1H), 4.33 (s, 2H), 3.99-3.88 (m, 3H), 3.84-3.75 (m, 2H), 3.59 (m, 3H), 3.51 (m, 5H), 3.02-2.91 (m, 2H), 2.72 (t, J=5.5 Hz, 2H), 1.92 (t, J=5.0 Hz, 2H), 1.77-1.73 (m, 2H); MS (ESI+) m/z 551.2 (M+H).

Example 228 2-(2-(Hydroxymethyl)-3-(4-methyl-5-oxo-6-(1,2,3,4-tetrahydroisoquinolin-7-ylamino)-4,5-dihydropyrazin-2-yl)phenyl)-3,4,6,7,8,9-hexahydropyrido[3,4-b]indolizin-1(2H)-one 228

Using the same general procedure as described for the preparation of 226, reaction of 153a (400 mg, 1.19 mmol) with 118f (718 mg, 1.55 mmol) followed by hydrolysis gave a 12% yield (88 mg) of 228 as a white solid: mp 218-220° C.; $^1$H NMR (500 MHz, DMSO-d$_6$) δ 9.03 (s, 1H), 7.73 (s, 1H), 7.63 (dd, 1H, J=7.5, 2.0 Hz), 7.52 (dd, 1H, J=7.5, 2.0 Hz), 7.43 (t, 2H, J=8.0 Hz), 7.25 (dd, 1H, J=7.5, 1.0 Hz), 6.90 (d, 1H, J=8.0 Hz), 6.00 (s, 1H), 4.71 (dd, 1H, J=7.0, 3.5 Hz), 4.46 (m, 2H), 3.94 (m, 2H), 3.82 (m, 2H), 3.77 (s, 2H), 3.54 (s, 3H), 3.00 (m, 1H), 2.93 (m, 1H), 2.90 (t, 2H, J=5.0 Hz), 2.70 (t, 2H, J=6.0 Hz), 2.62 (t, 2H, J=6.0 Hz), 2.45 (m, 1H), 1.92 (m, 2H), 1.76 (m, 2H); MS (ESI+) m/z 551.2 (M+H).

Example 229 2-(2-(Hydroxymethyl)-3-(1-methyl-5-(5-(1-methylpyrrolidin-2-yl)pyridin-2-ylamino)-6-oxo-1,6-dihydropyridin-3-yl)phenyl)-3,4,6,7,8,9-hexahydropyrido[3,4-b]indolizin-1(2H)-one 229

Example 229a 5-Bromo-1-methyl-3-(5-(1-methyl-pyrrolidin-2-yl)pyridin-2-ylamino)pyridin-2(1H)-one 229a

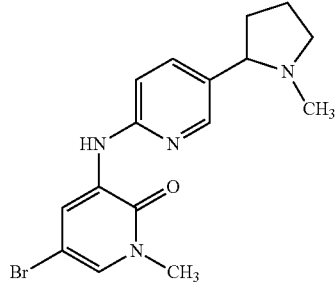

Using the same general procedure as described for the preparation of 226b, reaction of 3,5-dibromo-1-methylpyridin-2(1H)-one (1.51 g, 5.65 mmol) with 5-(1-methylpyrrolidin-2-yl)-2-amino pyridine (1.00 g, 5.65 mmol) gave an 81% yield (1.65 g) of 229a as a yellow solid: mp 143-145° C.; $^1$H NMR (300 MHz, DMSO-$d_6$) δ 8.73 (s, 1H), 8.68 (d, 1H, J=2.4 Hz), 8.15 (d, 1H, J=2.1 Hz), 7.55 (dd, 1H, J=8.9, 2.1 Hz), 7.52 (s, 1H), 7.30 (d, 1H, J=8.9 Hz), 3.52 (s, 3H), 3.13 (t, 1H, J=7.5 Hz), 2.99 (t, 1H, J=7.5 Hz), 2.19 (m, 1H), 2.10 (m, 1H), 2.05 (s, 3H), 1.79 (m, 2H), 1.71 (m, 1H); MS (ESI+) m/z 363.3 (M+H).

Using the same general procedure as described for the preparation of 226, reaction of 229a (500 mg, 1.38 mmol) with 118f (705 mg, 1.52 mmol) followed by a hydrolysis gave a 27% yield (215 mg) of 229 as a white solid: mp 146-148° C.; $^1$H NMR (500 MHz, DMSO-$d_6$) δ 8.67 (dd, 1H, J=2.0 Hz), 8.52 (s, 1H), 8.05 (s, 1H), 7.53 (dd, 1H, J=8.5, 2.5 Hz), 7.44 (t, 1H, J=8.0 Hz), 7.39 (d, 1H, J=2.5 Hz), 7.29-7.24 (m, 3H), 6.00 (s, 1H), 4.72 (t, 1H, J=5.0 Hz), 4.32 (d, 2H, J=5.0 Hz), 3.99 (m, 1H), 3.90 (m, 1H), 3.81 (m, 2H), 3.58 (s, 3H), 3.11 (t, 1H, J=8.0 Hz), 3.00 (m, 1H), 2.93 (m, 2H), 2.71 (t, 2H, J=6.0 Hz), 2.17 (q, 1H, J=9.0 Hz), 2.06 (m, 1H), 2.03 (s, 3H), 1.92 (t, 2H, J=6.0 Hz), 1.83-1.72 (m, 4H), 1.59 (m, 1H); MS (ESI+) m/z 579.2 (M+H).

Example 230 10-[3-(5-{[5-(Azetidin-1-ylmethyl)-1-methyl-1H-pyrazol-3-yl]amino}-1-methyl-6-oxo-1,6-dihydropyridin-3-yl)-5-fluoro-2-(hydroxymethyl)phenyl]-4,4-dimethyl-1,10-diazatricyclo[6.4.0.0$^{2,6}$]dodeca-2(6),7-dien-9-one 230

Example 230a 2-(4,4,5,5-Tetramethyl-[1,3,2]dioxaborolan-2-yl)-4-fluoro-6-(9-oxo-4,4-dimethyl-1,10diazatricyclo[6.4.0.0$^{2,6}$]-dodeca-2(6),7-dien-10-yl) benzyl Acetate 230a

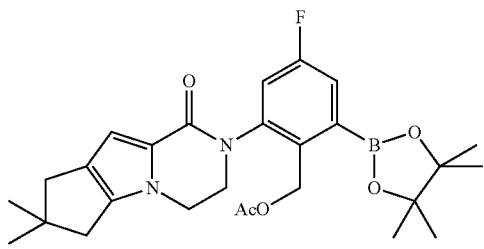

Following Example 211d, 2-Bromo-4-fluoro-6-(9-oxo-4,4-dimethyl-1,10diazatricyclo[6.4.0.0$^{2,6}$]-dodeca-2(6),7-dien-10-yl)benzyl Acetate 189a (450 mg, 1.0 mmol), 4,4,4',4',5,5,5',5'-octamethyl-2,2'-bi(1,3,2-dioxaborolane) (635 mg, 2.5 mmol), potassium acetate (393 mg, 4.0 mmol), bis(diphenylphosphino)-ferrocene]dichloropalladium(II) complex with CH$_2$Cl$_2$ (Pd Cl$_2$dppf:CH$_2$Cl$_2$ (1:1), 66 mg, 0.08 mmol) and 1,4-dioxane (20 mL) were heated at 100° C. for 5 h. The reaction mixture was cooled to room temperature and filtered through a pad of Celite 521. The filter cake was washed with Ethyl Acetate (2×25 mL), and the combined filtrates were concentrated to dryness under reduced pressure to afford compound 230a (quantitative yield) as black oil, which was used directly for the next step. MS (ESI+) m/z 497.3 (M+H).

Example 230b 10-[3-(5-{[5-(Azetidin-1-ylmethyl)-1-methyl-1H-pyrazol-3-yl]amino}-1-methyl-6-oxo-1,6-dihydropyridin-3-yl)-5-fluoro-2-(acetoxymethyl)phenyl]-4,4-dimethyl-1,10-diazatricyclo[6.4.0.0$^{2,6}$]dodeca-2(6),7-dien-9-one 230b Example 230b was synthesized using the same procedure as 121b, except using compound 230a (223 mg, 0.45 mmol), 3-(5-(azetidin-1-ylmethyl)-1-methyl-1H-pyrazol-3-ylamino)-5-bromo-1-methylpyridin-2(1H)-one (200c) (160 mg, 0.45 mmol), 1M sodium carbonate solution (1.5 mL, 1.5 mmol), tetrakis(triphenylphosphine)palladium(0) (26 mg, 0.022 mmol) and 1,2-dimethoxyethane (4.5 mL). The reaction mixture was heated at 130° C. for 15 minutes in the microwave reactor. Work-up and flash column chromatography (silica, 9:1 methylene chloride/methanol) give a 43% yield (120 mg) of compound 230b as brown oil: MS (ESI+) m/z 643.1 (M+H).

Following the same procedure as 121, except using a mixture of THF (1 mL), water (0.5 mL) and isopropanol (1 mL), compound 230b (120 mg, 0.2 mmol) and lithium hydroxide monohydrate (50 mg, 1.2 mmol) were reacted. Work-up and flash column chromatography (NH-silica, ethyl acetate/hexanes) give a 30% yield (36 mg) of compound 230 as a light green solid: MS (ESI+) m/z 600.6 (M+H).

Example 231 2-(5-fluoro-2-(hydroxymethyl)-3-(4-methyl-6-(2-methylisoindolin-5-ylamino)-5-oxo-4,5-dihydropyrazin-2-yl)phenyl)-3,4,6,7,8,9-hexahydropyrazino[1,2-a]indol-1(2H)-one 231

Example 231a 5-Nitroisoindoline 231a

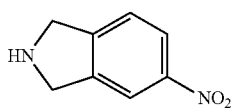

To the suspension of isoindoline (2 g, 16.8 mmol) in 98% H$_2$SO$_4$ (10 mL) was added dropwise the mixture of concentrated nitric acid (2 mL) and 98% sulfuric acid (2 mL) at 0° C. The mixture was stirred at 0° C. for 45 minutes. The resulting yellow solution was then poured into ice water. The white solid precipitate was collected by filtration. The solid was washed with water (20 mL×2) and dried in vacuum to afford 231a as a white solid (700 mg, 51%). MS: [M+H]+ 165.

Example 231b tert-Butyl 5-Nitroisoindoline-2-carboxylate 231b

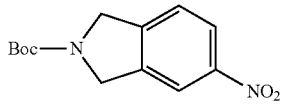

231b

The mixture of 5-nitroisoindoline (600 mg, 3.66 mmol) and (Boc)$_2$O (1.6 g, 7.31 mmol) in THF (30 mL) was stirred at room temperature for 2 h. The resulting red solution was then concentrated under reduced pressure and the residue was purified by flash column chromatography eluting with 5:1 petroleum ether/ethyl acetate to afford 231b as a yellow solid (750 mg, 80%). MS: [M+H]$^+$ 209.

Example 231c tert-Butyl 5-Aminoisoindoline-2-carboxylate 231c

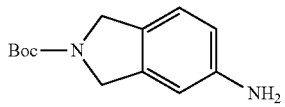

231c

A 100-mL single-neck round-bottomed flask equipped with a magnetic stirrer was charged with tert-butyl 5-nitroisoindoline-2-carboxylate (650 mg, 2.5 mmol) and C$_2$H$_5$OH (50 mL). This solution was hydrogenated with Pd/C (160 mg) at room temperature for 15 h. It was then filtered and the filtrate was concentrated under reduced pressure to afford 231c as a yellow oil (585 mg, 99%), which was used in the next step without further purification. MS: [M+H]$^+$ 179.

Example 231d tert-Butyl 5-(6-Bromo-4-methyl-3-oxo-3,4-dihydropyrazin-2-ylamino)isoindoline-2-carboxylate 231d

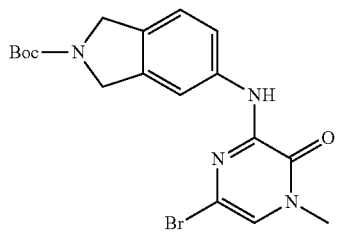

231d

Following the procedures as described for 129a and starting with 600 mg of tert-butyl 5-aminoisoindoline-2-carboxylate (231c) and 685 mg of 3,5-dibromo-1-methylpyrazin-2(1H)-one, 231d was obtained as a yellow solid (732 mg, 68%). MS: [M+H]$^+$ 421.

Example 231e 5-Bromo-3-(isoindolin-5-ylamino)-1-methylpyrazin-2(1H)-one 231e

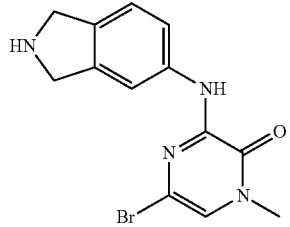

231e

Following the procedures as described for 129b and starting with 460 mg of tert-butyl 5-(6-bromo-4-methyl-3-oxo-3,4-dihydropyrazin-2-ylamino)isoindoline-2-carboxylate, 231e was obtained as a yellow solid (352 mg, 99%). MS: [M+H]$^+$ 321

Example 231f 5-Bromo-1-methyl-3-(2-methylisoindolin-5-ylamino)pyrazin-2(1H)-one 231f

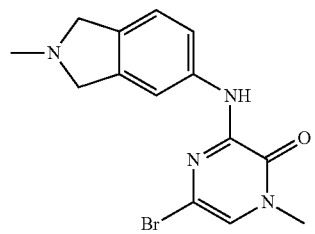

231f

Following the procedures as described for 220a and starting with 336 mg of 5-bromo-3-(isoindolin-5-ylamino)-1-methylpyrazin-2(1H)-one, compound 231f was obtained as a yellow solid (237 mg, 75%). MS: [M+H]$^+$ 337. $^1$H NMR (500 MHz, CDCl3) δ 8.31 (s, 1H), 7.67 (s, 1H), 7.52 (t, J=7.0, 1H), 7.18 (d, J=8.0, 1H), 6.74 (s, 1H), 3.94 (s, 2H), 3.89 (s, 2H), 3.52 (s, 3H), 2.60 (s, 3H).

Example 231g 4-Fluoro-2-(4-methyl-6-(2-methylisoindolin-5-ylamino)-5-oxo-4,5-dihydropyrazin-2-yl)-6-(1-oxo-3,4,6,7,8,9-hexahydropyrazino[1,2-a]indol-2(1H)-yl)benzyl Acetate 231g

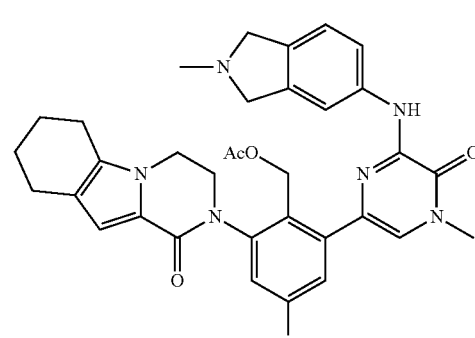

231g

Following the procedures as described for compound 148h and starting with 400 mg of 4-fluoro-2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 210d and 278 mg of 5-bromo-1-methyl-3-(2-methylisoindolin-5-ylamino)pyrazin-2(1H)-one 231f, compound 231g was obtained as a yellow solid (258 mg, 51%). MS: [M+H]$^+$ 611.

Following Example 148, 231g was converted to 231 as a white solid (116 mg, 50%). $^1$H NMR (500 MHz, DMSO) δ 9.23 (s, 1H), 7.90 (s, 1H), 7.73 (d, J=8, 1H), 7.51 (s, 1H), 7.37 (dd, J=10.0, 1H), 7.31 (dd, J=10.0, 1H), 7.13 (d, J=8.0, 1H), 6.53 (s, 1H), 4.88 (s, 1H), 4.50 (d, J=8.0, 1H), 4.50 (d, J=11.5, 1H), 4.40 (m, 1H), 4.13 (m, 3H), 3.89 (m, 1H), 3.78 (m, 4H), 3.52 (s, 3H), 2.59 (m, 2H), 2.48 (m, 5H), 1.79 (s, 2H), 1.70 (s, 2H).

Example 232 5-[5-fluoro-2-(hydroxymethyl)-3-{4-methyl-6-[(2-methyl-2,3-dihydro-1H-isoindol-5-yl)amino]-5-oxo-4,5-dihydropyrazin-2-yl}phenyl]-8-thia-5-azatricyclo[7.4.0.0$^{2,7}$]trideca-1(9),2(7)-dien-6-one 232

Example 232a (4-Fluoro-2-{4-methyl-6-[(2-methyl-2,3-dihydro-1H-isoindol-5-yl)amino]-5-oxo-4,5-dihydropyrazin-2-yl}-6-{6-oxo-8-thia-5azatricyclo[7.4.0.0$^{2,7}$]-trideca-1(9),2(7)-dien-5-yl}phenyl) methyl Acetate 232a

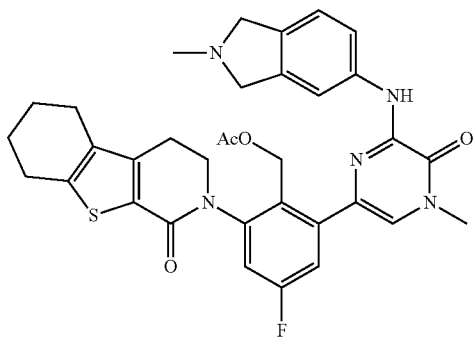

232a

Following the procedures as described for 148h and starting with 499 mg of (4-fluoro-2-{6-oxo-8-thia-5-azatricyclo[7.4.0.0$^{2,7}$]trideca-1(9),2(7)-dien-5-yl}-6-(4,4,5,5-tetramethyl-1,3,2-dioxaborolan-2-yl)phenyl)methyl acetate 212b and 335 mg of 5-bromo-1-methyl-3-(2-methylisoindolin-5-ylamino)pyrazin-2(1H)-one, compound 232a was obtained as a yellow solid (320 mg, 51%). MS: [M+H]$^+$ 628.

Following the procedures as described for 148 and starting with 300 mg of 232a, compound 232 was obtained as a white solid (117 mg, 42%). $^1$H NMR (500 MHz, DMSO) δ 9.23 (s, 1H), 7.90 (s, 1H), 7.72 (s, 1H), 7.51 (d, J=8.0, 1H), 7.36 (s, 1H), 7.31 (s, 1H), 7.13 (s, 1H), 4.85 (s, 1H), 4.50 (s, 1H), 4.40 (m, 1H), 4.05 (s, 1H), 3.87 (s, 1H), 3.78 (d, J=6.5, 4H), 3.56 (s, 3H), 3.33 (s, 3H), 2.97 (s, 1H), 2.87 (s, 1H), 2.79 (s, 2H), 2.50 (m, 3H), 1.80 (s, 4H).

Example 233 5-[3-(5-{[5-(1-Ethylazetidin-3-yl)pyridin-2-yl]amino}-1-methyl-6-oxo-1,6-dihydropyridin-3-yl)-5-fluoro-2-(hydroxymethyl)phenyl]-8-thia-5-azatricyclo[7.4.0.0$^{2,7}$]trideca-1(9),2(7)-dien-6-one 233

Example 233a [2-(5-{[5-(1-Ethylazetidin-3-yl)pyridin-2-yl]amino}-1-methyl-6-oxo-1,6-dihydropyridin-3-yl)-4-fluoro-6-{6-oxo-8-thia-5-azatricyclo[7.4.0.0$^{2,7}$]trideca-1(9),2(7)-dien-5-yl}phenyl]methyl Acetate 233a

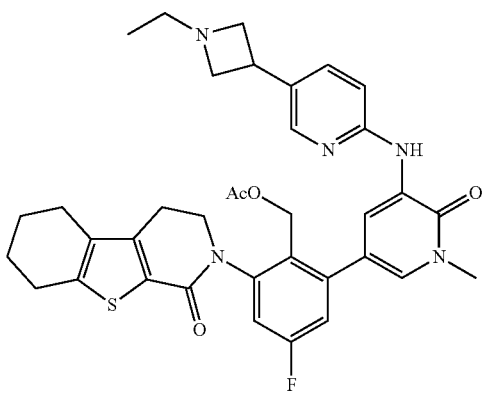 [SMILES: CCN1CC(c2ccc(Nc3cc(-c4cc(F)cc(N5CCc6c(sc7c6CCCC7)C5=O)c4COC(C)=O)cn(C)c3=O)nc2)C1]

Following the procedures as described for 136e and starting with 5-bromo-3-(5-(1-ethylazetidin-3-yl)pyridin-2-ylamino)-1-methylpyridin-2(1H)-one (250a) and (4-fluoro-2-{6-oxo-8-thia-5-azatricyclo[7.4.0.0$^{2,7}$]trideca-1(9),2(7)-dien-5-yl}-6-(4,4,5,5-tetramethyl-1,3,2-dioxaborolan-2-yl)phenyl)methyl acetate 212b, compound 233a was obtained in 67% yield. LCMS: (M+H)$^+$ 597

Following the procedures as described for 136 and starting with 233a, compound 233 was obtained in 58% yield. LCMS: (M+H)$^+$ 614. $^1$H NMR (500 MHz, DMSO) δ 8.66 (d, J=2, 1H), 8.56 (s, 1H), 8.11 (d, J=2, 1H), 7.65 (dd, J=9, 1H), 7.41 (d, J=2, 1H), 7.33 (dd, J=9.5, 1H), 7.28 (d, J=8, 1H), 7.18 (dd, J=9, 1H), 4.86 (t, J=4, 1H), 4.32 (d, J=4.5, 2H), 4.05 (m, 1H), 3.86 (m, 1H), 3.59 (s, 3H), 3.49 (m, 3H), 2.97 (m, 3H), 2.86 (m, 1H), 2.78 (m, 2H), 2.56 (m, 1H), 2.40 (m, 2H), 1.79 (m, 4H), 0.87 (t, J=7, 3H).

Example 234 2-(5-Fluoro-2-(hydroxymethyl)-3-(1-methyl-5-(5-methyl-4,5,6,7-tetrahydropyrazolo[1,5-a]pyrazin-2-ylamino)-6-oxo-1,6-dihydropyridin-3-yl)phenyl)-3,4,6,7,8,9-hexahydropyrazino[1,2-a]indol-1(2H)-one 234

Example 234a {4-Fluoro-2-[1-methyl-5-({5-methyl-4H,5H,6H,7H-pyrazolo[1,5-a]pyrazin-2-yl}amino)-6-oxo-1,6-dihydropyridin-3-yl]-6-{1-oxo-1H,2H,3H,4H,-6H,7H,8H,9H-pyrazino[1,2-a]indol-2-yl}phenyl}methyl Acetate 234a

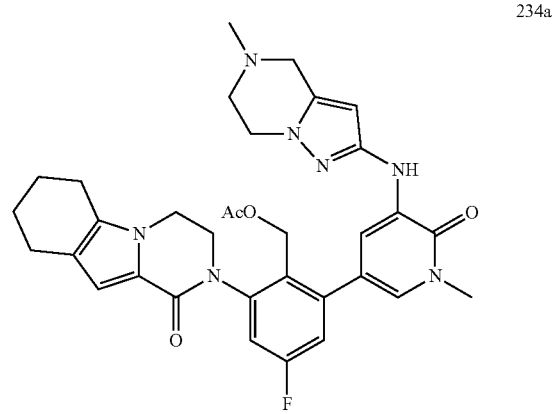 [SMILES: CC(=O)OCc1c(-c2cc(Nc3cc4n(n3)CCN(C)C4)c(=O)n(C)c2)cc(F)cc1N1CCn2c(cc3c2CCCC3)C1=O]

A 25 mL sealed tube was charged with 4-fluoro-2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate (210d) (500 mg, 1.0 mmol), 5-bromo-1-methyl-3-(5-methyl-4,5,6,7-tetrahydropyrazolo[1,5-a]pyrazin-2-ylamino)pyridin-2(1H)-one (146a) (350 mg, 1.0 mmol), CH₃COONa (170 mg, 2.0 mmol), K₃PO₄ (552 mg, 2.0 mmol), PdCl₂(dppf) (85 mg, 0.1 mmol) suspended in CH₃CN (25 mL) and H₂O (1 mL). The mixture was heated at 110° C. for 2 hours. It was then evaporated and the residue was purified by silical-gel column eluting with 20:1 methylene chloride/methanol to give 234a as a brown solid (400 mg, 63%). MS: (M+H)⁺ 614.

A solution of 234a (400 mg, 0.65 mmol) in propan-2-ol (10 mL), tetrahydrofuran (10 mL) and water (2 mL) was added LiOH (1.57 g, 65 mmol). The mixture was stirred at 30° C. for 2 h. It was then evaporated and the residue was purified by prep-HPLC to afford 234 as a yellow solid (119 mg, 32%). MS: (M+H)⁺ 572. ¹H NMR (500 MHz, MEOD) δ 1.78-1.80 (t, 2H), 1.89-1.90 (d, 2H), 2.49 (s, 3H), 2.54-2.56 (t, J=6 Hz, 2H), 2.64-2.66 (m, 2H), 2.94-2.96 (t, 2H), 3.64 (s, 2H), 3.67 (s, 3H), 4.04-4.06 (m, 3H), 4.20 (s, 3H), 4.46-4.51 (m, 2H), 5.89 (s, 1H), 6.72 (s, 1H), 7.20-7.22 (d, 2H), 7.26-7.27 (d, 1H), 7.91 (s, 1H).

Example 235 5-(5-Fluoro-2-(hydroxymethyl)-3-(6,6-dimethyl-3,4,6,7-tetrahydro-5H-cyclopenta[4,5]thieno[2,3-c]pyridine-1(2H)-yl)phenyl)-1-methyl-3-(2-methylisoindolin-5-ylamino)pyrazin-2(1H)-one 235

A 100-mL three-neck round-bottomed flask equipped with a reflux condenser, magnetic stirrer and nitrogen inlet was charged with 231e (150 mg, 0.447 mmol), 131a (340 mg, 0.581 mmol), sodium carbonate (142 mg, 1.34 mmol), water (2 mL) and 1,4-dioxane (8 mL). After bubbling nitrogen through the resulting suspension for 30 min, tetrakis-(triphenylphosphine)palladium(0) (52 mg, 0.045 mmol) was added, and the reaction mixture was heated at reflux for 2 h. After that time, the mixture was cooled to room temperature and diluted with methylene chloride (100 mL) and water (30 mL). The organic layer was separated, and the aqueous layer was extracted with methylene chloride (3×30 mL). The combined organic layers were dried over sodium sulfate and concentrated under reduced pressure to afford a brown residue. A 100-mL single-neck round-bottomed flask equipped with a magnetic stirrer was purged with nitrogen and charged with the crude residue, THF (10 mL) and a 1 M solution of tetrabutylammonium fluoride in THF (4.50 mmol, 4.5 mL). The resulting mixture was stirred at room temperature for 2 h. After this time, the mixture was diluted with methylene chloride (100 mL) and washed with water (30 mL). The organic layer was separated, and the aqueous layer was extracted with methylene chloride (3×30 mL). The combined organic layers were dried over sodium sulfate and concentrated under reduced pressure. The residue was purified by column chromatography (silica, 0% to 10% methanol/methylene chloride) to afford a 44% yield (120 mg) of 235 as an off-white solid: mp 218-220° C. (dec); ¹H NMR (500 MHz, DMSO-d₆) δ 9.21 (s, 1H), 7.89 (d, 1H, J=1.0 Hz), 7.70 (dd, 1H, J=8.1, 2.0 Hz), 7.50 (s, 1H), 7.34 (dd, 1H, J=9.9, 3.0 Hz), 7.30 (dd, 1H, J=9.1, 2.5 Hz), 7.13 (d, 1H, J=8.0 Hz), 4.82 (m, 1H), 4.50 (m, 1H), 4.04 (m, 1H), 4.04 (m, 1H), 3.84 (m, 1H), 3.75 (m, 4H), 3.54 (s, 3H), 3.02 (m, 1H), 2.89 (m, 1H), 2.75 (s, 2H), 2.53 (d, 2H, J=6.5 Hz), 2.46 (s, 3H), 1.23 (s, 6H); MS (ESI+) m/z 600.2 (M+H).

Example 236 5-(5-Fluoro-2-(hydroxymethyl)-3-(6,6-dimethyl-3,4,6,7-tetrahydro-5H-cyclopenta[4,5]thieno[2,3-c]pyridine-1(2H)-yl)-3-(5-(3-methylazetidin-1-yl)pyridin-2-ylamino)-1-methylpyridin-2(1H)-one 236

Example 236a
5-(3-Methylazetidin-1-yl)-2-nitropyridine 236a

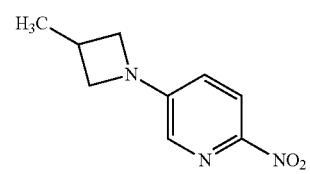

A 500-mL single-neck round-bottomed flask equipped with a magnetic stirrer and nitrogen inlet was charged with 3-methylazetidinium benzenesulfonate (4.02 g, 17.5 mmol), 2-nitro-5-bromo pyridine (3.56 g, 17.5 mmol), cesium carbonate (28.5 g, 87.7 mmol) and 1,4-dioxane (50 mL). After bubbling nitrogen through the resulting suspension for 30 min, Xantphos (862 mg, 1.50 mmol) and tris(dibenzylideneacetone)dipalladium(0) (800 mg, 0.900 mmol) were added. A reflux condenser was attached to the flask, and the reaction mixture was heated at reflux for 3 h. After this time, the mixture was cooled to room temperature and diluted with 90:10 methylene chloride/methanol (100 mL) and water (75 mL), and the layers were separated. The aqueous layer was extracted with 90:10 methylene chloride/methanol (2×50 mL), and the combined organic extracts were washed with brine and dried over sodium sulfate. The drying agent was removed by filtration. The filtrate was concentrated under reduced pressure, and the resulting residue was purified by flash column chromatography (silica, 0% to 80% ethyl acetate/hexanes) to afford 236a in 69% yield (2.35 g) as an amorphous yellow solid: mp 141-143° C.; ¹H NMR (500 MHz, CDCl₃) δ 8.12 (d, 1H, J=9.0 Hz), 7.60 (d, 1H, J=2.5 Hz), 6.66 (dd, 1H, J=9.0, 2.5 Hz), 4.23 (t, 2H, J=8.5 Hz), 3.68 (m, 2H), 2.99 (m, 1H), 1.36 (d, 3H, J=7.0 Hz); MS (ESI+) m/z 194.0 (M+H)

Example 236b
5-(3-Methylazetidin-1-yl)pyridin-2-amine 236b

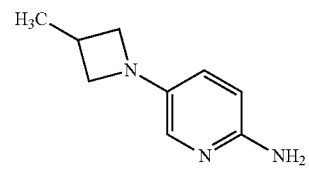

A 250-mL Parr reactor bottle was purged with nitrogen and charged with 10% palladium on carbon (50% wet, 800 mg dry weight) and a solution of 236a (2.58 g, 13.4 mmol) in a mixture of ethanol (25 mL) and ethyl acetate (25 mL). The bottle was attached to a Parr hydrogenator, evacuated, charged with hydrogen gas to a pressure of 50 psi and shaken for 3 h. After this time, the hydrogen was evacuated, and nitrogen was charged into the bottle. Celite 521 (3.50 g) was added, and the mixture was filtered through a pad of Celite 521. The filter cake was washed with ethanol (2×50 mL), and the combined filtrates were concentrated to dryness under reduced pressure to afford a quantitative yield of 236b (2.21 g) as a purple oil: $^1$H NMR (500 MHz, DMSO-$d_6$) δ 7.19 (d, 1H, J=3.0 Hz), 6.66 (dd, 1H, J=9.0, 3.0 Hz), 6.36 (d, 1H, J=8.5 Hz), 5.13 (br s, 2H), 3.81 (t, 2H, J=7.5 Hz), 3.21 (t, 2H, J=6.5 Hz), 2.70 (m, 1H), 1.18 (d, 3H, J=7.0 Hz); MS (ESI+) m/z 164.1 (M+H).

Example 236c 5-Bromo-1-methyl-3-(5-(3-methyl-azetidin-1-yl)pyridin-2-ylamino)pyridin-2(1H)-one 236c

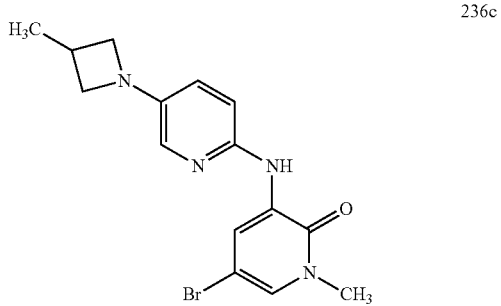

Using the same procedure as described for the preparation of 121a, a reaction of 236b (1.04 g, 6.40 mmol) with 3,5-dibromo-1-methylpyridin-2(1H)-one (1.90 g, 7.12 mmol) afforded a 44% yield (980 mg) of 236c as a brown solid: mp 135-136° C.; $^1$H NMR (500 MHz, DMSO-$d_6$) δ 8.49 (d, 1H, J=5.5 Hz), 8.42 (s, 1H), 7.50 (d, 1H, J=4.5 Hz), 7.41 (d, 1H, J=7.0 Hz), 7.20 (d, 1H, J=14.5 Hz), 6.85 (dd, 1H, J=14.5, 5.0 Hz), 3.91 (m, 2H), 3.49 (s, 3H), 3.34 (m, 2H), 2.75 (m, 1H), 1.21 (d, 3H, J=11.5 Hz; MS (ESI+) m/z 350.2 (M+H).

A 100-mL single-neck round-bottomed flask equipped with a magnetic stirrer and nitrogen inlet was charged with 236c (140 mg, 0.400 mmol), 182c (304 mg, 0.520 mmol), sodium carbonate (130 mg, 1.23 mmol), water (2 mL) and 1,4-dioxane (10 mL). After bubbling nitrogen through the resulting suspension for 30 min, tetrakis(triphenyl-phosphine)palladium(0) (50 mg, 0.043 mmol) was added. A reflux condenser was attached to the flask, and the reaction mixture was heated at reflux for 2 h. After this time, the mixture was diluted with 90:10 methylene chloride/methanol (100 mL) and water (75 mL), and the layers were separated. The aqueous layer was extracted with 90:10 methylene chloride/methanol (2×50 mL), and the combined organic layers were washed with brine (100 mL) and dried over sodium sulfate. The drying agent was removed by filtration. The filtrate was concentrated under reduced pressure, and the resulting residue was dissolved in THF. A 1 M solution of tetrabutylammonium fluoride in THF (1.20 mL, 1.20 mmol) was added, and the mixture was stirred at room temperature for 14 h. After this time, the mixture was diluted with 90:10 methylene chloride/methanol (75 mL) and water (50 mL), and the layers were separated. The aqueous layer was extracted with 90:10 methylene chloride/methanol (2×50 mL), and the combined organic extracts were washed with brine (100 mL) and dried over sodium sulfate. The drying agent was removed by filtration. The filtrate was concentrated under reduced pressure, and the resulting residue was purified by flash column chromatography (silica, 0% to 10% methylene chloride/methanol) to afford 236 in 14% yield (35 mg) as an amorphous brown solid: mp 170-171° C.; $^1$H NMR (500 MHz, DMSO-$d_6$) δ 8.45 (d, 1H, J=2.5 Hz), 8.22 (s, 1H), 7.31 (m, 2H), 7.15 (m, 2H), 6.83 (dd, 1H, J=9.0, 3.0 Hz), 4.83 (t, 1H, J=4.5 Hz), 4.32 (m, 2H), 4.05 (m, 1H), 3.88 (m, 3H), 3.02 (m, 1H), 2.89 (m, 1H), 2.75 (s, 3H), 2.54 (m, 4H); MS (ESI+) m/z 614.3 (M+H).

Example 237 6-(3-(5-(4-(Oxetan-3-yl)piperazin-1-yl)pyridin-2-ylamino)-1-methyl-6-oxo-1,6-dihydro-pyridin-3-yl)-5-fluoro-2-(hydroxymethyl)phenyl)-2,3-(5,5-dimethyl-5,6-dihydro-4H-cyclopenta)-5,6-dihydrothieno[2,3-c]pyridin-7(4H)-one 237

A 100-mL three-neck round-bottomed flask equipped with a magnetic stirrer and reflux condenser was charged with 210c (160 mg, 0.382 mmol), 182c (300 mg, 0.512 mmol), sodium carbonate (162 mg, 1.53 mmol), water (6 mL) and 1,4-dioxane (30 mL). After bubbling nitrogen through the resulting suspension for 20 min, tetrakis(triphenyl-phosphine)-palladium(0) (44.0 mg, 0.038 mmol) was added, and the reaction mixture was heated at 100° C. for 4 h. After this time, the reaction mixture was cooled to room temperature and filtered, and the filter cake was washed with a 1:10 mixture of methanol and methylene chloride (30 mL). The filtrate was concentrated under reduced pressure to afford a brown residue. Another 50-mL single-neck round-bottomed flask equipped with a magnetic stirrer and reflux condenser was charged with the residue obtained above, tetrabutylammonium fluoride (1.0 M in THF, 1.54 mL, 1.54 mmol) and THF (10 mL). The mixture was stirred at room temperature for 1.5 h. After this time, the reaction mixture was concentrated under reduced pressure. The resulting residue was purified by flash chromatography to afford a 24% (86 mg) yield of 237 as a yellow solid: mp 175-177° C.; $^1$H NMR (500 MHz, DMSO-$d_6$) d 8.55 (d, 1H, J=2.0 Hz), 8.36 (s, 1H), 7.86 (d, 1H, J=3.0 Hz), 7.35 (m, 3H), 7.22 (d, 1H, J=9.0 Hz), 7.16 (dd, 1H, J=9.0, 3.0 Hz), 4.85 (t, 1H, J=5.0 Hz), 4.55 (t, 2H, J=6.5 Hz), 4.45 (t, 2H, J=6.0 Hz), 4.32 (m, 2H), 4.04 (m, 1H), 3.86 (m, 1H), 3.58 (s, 3H), 3.44 (m, 1H), 3.06 (t, 4H, J=4.5 Hz), 3.03 (m, 1H), 2.89 (m, 1H), 2.75 (s, 2H), 2.52 (m, 2H), 2.38 (t, 4H, J=4.5 Hz); MS (ESI+) m/z 685.4 (M+H).

Example 238 10-[3-(5-{[5-(4-Ethylpiperazin-1-yl)pyridine-2-yl]amino}-1-methyl-6-oxo-1,6-dihydro-pyridin-3-yl)-5-fluoro-2-(hydroxymethyl)phenyl]-4,4-dimethyl-1,10-diazatricyclo[6.4.0.0$^{2,6}$]dodeca-2(6),7-dien-9-one 238

Example 238a 10-[3-(5-{[5-(4-Ethylpiperazin-1-yl)pyridine-2-yl]amino}-1-methyl-6-oxo-1,6-dihydro-pyridin-3-yl)-5-fluoro-2-(acetoxymethyl)phenyl]-4,4-dimethyl-1,10-diazatricyclo[6.4.0.0$^{2,6}$]dodeca-2(6),7-dien-9-one 238a

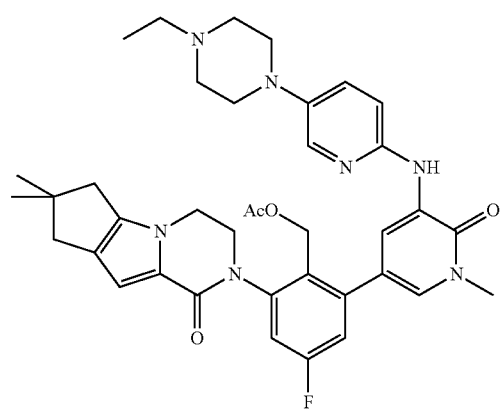

To a microwave tube equipped with a stirring bar, 189a (381.9 mg, 0.850 mmol), 3-(5-(4-ethylpiperazin-1-yl)pyridin-2-ylamino)-1-methyl-5-(4,4,5,5-tetramethyl-1,3,2-dioxaborolan-2-yl)pyridin-2(1H)-one (201a) (560 mg, 1.275 mmol), Pd(PPh$_3$)$_4$ (49.1 mg, 0.043 mmol), Na$_2$CO$_3$ aqueous solution (1.0 N, 2.81 mL, 2.81 mmol), 1,2-dimethoxyethane (4 mL) were added. The mixture was reacted in microwave at 130° C. for 10 min. methylene chloride (200 mL) was added and the resulting mixture was washed with water (30 mL×3), brine (30 mL×1), dried over MgSO$_4$, filtered, and removed solvent in vacuo. Silica gel column chromatography (methanol:methylene chloride=5:95) gave 238a.

To a round-bottomed flask equipped with a stirring bar, 238a, THF (5 mL), i-PrOH (5 mL), H$_2$O (5 mL), LiOH H$_2$O (200 mg) were added. The resulting mixture was stirred at RT for 1 hr. The solvent was removed in vacuo and the resulting residue was added to methylene chloride (200 mL), the solution was washed with water (30 mL×3), brine (30 mL×1), dried over MgSO$_4$, filtered, and removed solvent in vacuo. Silica gel column chromatography (MeOH:methylene chloride/10:90) gave 238 53 as a pink solid, 143 mg. MS (ESI+) m/z 640.6 (M+H).

Example 239 5-(5-Fluoro-2-(hydroxymethyl)-3-(6,6-dimethyl-3,4,6,7-tetrahydro-5H-cyclopenta[4,5]thieno[2,3-c]pyridine-1(2H)-yl)-3-(5-(4-isopropylpiperazin-1-yl)pyridin-2-ylamino)-1-methylpyridin-2(1H)-one 239

Using the same procedure as described for 236, a reaction of 220a (165 mg, 0.410 mmol) with 182c (312 mg, 0.533 mmol) afforded a 21% yield (57 mg) of 239 as an off-white solid: mp 191-192° C.; $^1$H NMR (500 MHz, DMSO-d$_6$) δ 8.54 (d, 1H, J=2.0 Hz), 8.34 (s, 1H), 7.85 (d, 1H, J=3.0 Hz), 7.33 (m, 3H), 7.20 (d, 1H, J=9.0 Hz), 7.15 (dd, 1H, J=9.0, 3.0 Hz), 4.84 (t, 1H, J=4.0 Hz), 4.32 (m, 2H), 4.04 (m, 1H), 3.84 (m, 1H), 3.57 (s, 3H), 3.02 (m, 5H), 2.87 (m, 1H), 2.75 (br s, 2H), 2.63 (m, 1H), 2.55 (m, 6H), 1.22 (s, 6H), 0.98 (d, 6H, J=3.0 Hz); MS (ESI+) m/z 671.3 (M+H).

Example 240 5-(3-(6,6-Dimethyl-3,4,6,7-tetrahydro-5H-cyclopenta[4,5]thieno[2,3-c]pyridine-1(2H)-yl)-5-fluoro-2-(hydroxymethyl)phenyl)-1-methyl-3-(6-methyl-5,6,7,8-tetrahydro-1,6-naphthyridin-2-ylamino)pyridin-2(1H)-one 240

A 100-mL single-neck round-bottomed flask equipped with a magnetic stirrer and reflux condenser was purged with nitrogen and charged with 182c (300 mg, 0.513 mmol), 205b (138 mg, 0.394 mmol), sodium carbonate (125 mg, 1.18 mmol), 1,4-dioxane (8 mL) and water (2 mL). This mixture was degassed with nitrogen for 30 min. Tetrakis(triphenylphosphine)palladium (46 mg, 0.039 mmol) was added. After heating at reflux for 2 h, the reaction mixture was cooled to room temperature and partitioned between water (40 mL) and methylene chloride (100 mL). The layers were separated, and the aqueous phase was extracted with methylene chloride (2×50 mL). The organic extracts were combined, dried over sodium sulfate, filtered and concentrated under reduced pressure. The resulting residue was dissolved in THF (3 mL), and tetrabuty-ammonium fluoride trihydrate (372 mg, 1.18 mmol) was added. After stirring at room temperature for 2 h, the reaction mixture was partitioned between water (20 mL) and methylene chloride (20 mL). The layers were separated, and the aqueous phase was extracted with methylene chloride (2×20 mL). The organic extracts were combined, dried over sodium sulfate, filtered and concentrated under reduced pressure. The resulting residue was purified by flash chromatography to afford 240 in 22% yield (53 mg) as a yellow solid: mp 142-143° C.; $^1$H NMR (500 MHz, DMSO-d$_6$) δ 8.77 (d, 1H, J=2.0 Hz), 8.43 (s, 1H), 7.44 (d, 1H, J=2.0 Hz), 7.31 (dd, 1H, J=9.5, 2.5 Hz), 7.27 (d, 1H, J=8.0 Hz), 7.19 (dd, 1H, J=9.5, 2.5 Hz), 7.06 (d, 1H, J=8.0 Hz), 4.86 (m, 1H), 4.38 (m, 2H), 4.04 (m, 1H), 3.84 (m, 1H), 3.59 (s, 3H), 3.38 (s, 2H), 3.03 (m, 1H), 2.89 (m, 1H), 2.75 (s, 4H), 2.62 (m, 2H), 2.53 (m, 2H), 2.34 (s, 3H), 1.23 (s, 6H); MS (ESI+) m/z 614.3 (M+H).

Example 241 5-(3-(6,6-Dimethyl-3,4,6,7-tetrahydro-5H-cyclopenta[4,5]thieno[2,3-c]pyridine-1(2H)-yl)-5-fluoro-2-(hydroxymethyl)phenyl)-1-methyl-3-(6-ethyl-5,6,7,8-tetrahydro-1,6-naphthyridin-2-ylamino)pyridin-2(1H)-one 241

Using the same general procedure as described for the preparation of 240, reaction of 5-bromo-3-(6-ethyl-5,6,7,8-tetrahydro-1,6-naphthyridin-2-ylamino)-1-methylpyridin-2(1H)-one (143 mg, 0.394 mmol) with 182c (300 mg, 0.513 mmol) gave a 28% yield (70 mg) of 241 as a yellow solid: mp 134-135° C.; $^1$H NMR (500 MHz, DMSO-d$_6$) δ 8.78 (d, 1H, J=2.0 Hz), 8.43 (s, 1H), 7.44 (d, 1H, J=2.0 Hz), 7.31 (dd, 1H, J=9.5, 2.5 Hz), 7.28 (d, 1H, J=8.0 Hz), 7.18 (dd, 1H, J=9.5, 2.5 Hz), 7.06 (d, 1H, J=8.0 Hz), 4.86 (m, 1H), 4.38 (m, 2H), 4.04 (m, 1H), 3.84 (m, 1H), 3.59 (s, 3H), 3.43 (s, 2H), 3.03 (m, 1H), 2.89 (m, 1H), 2.75 (s, 4H), 2.62 (m, 2H), 2.53 (m, 2H), 2.50 (m, 2H), 1.23 (s, 6H), 1.08 (t, 3H, J=7.0 Hz); MS (ESI+) m/z 628 (M+H).

Example 242 5-[5-Fluoro-2-(hydroxymethyl)-3-{1-oxo-1H,2H,3H,4H,6H,7H,8H,9H-pyrazino[1,2-a]indol-2-yl}phenyl]-1-methyl-3-{[5-(1-methylpiperidin-4-yl)pyridine-2-yl]amino}-1,2-dihydropyridin-2-one 242

Example 242a 4-Fluoro-2-(1-methyl-5-(5-(1-methylpiperidin-4-yl)pyridin-2-ylamino)-6-oxo-1,6-dihydropyridin-3-yl)-6-(1-oxo-3,4,6,7,8,9-hexahydropyrazino[1,2-a]indol-2(1H)-yl)benzyl Acetate 242a

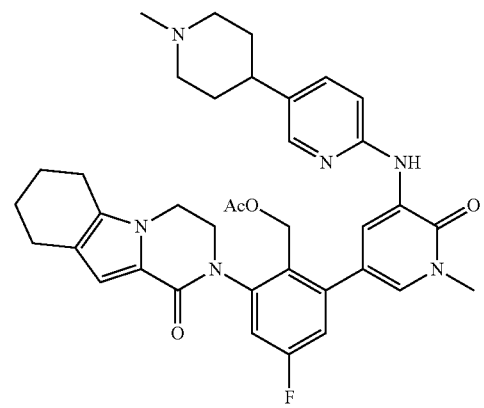 [SMILES: CC(=O)OCc1c(-c2cc(Nc3ccc(C4CCN(C)CC4)cn3)c(=O)n(C)c2)cc(F)cc1N1CCn2c(cc3c2CCCC3)C1=O]

To a microwave tube equipped with a stirring bar, 5-bromo-1-methyl-3-(5-(1-methylpiperidin-4-yl)pyridin-2-ylamino)pyridin-2(1H)-one (130c) (240 mg, 0.636 mmol), 4-fluoro-2-(1-oxo-3,4,6,7,8,9-hexahydropyrazino[1,2-a]indol-2(1H)-yl)-6-(4,4,5,5-tetramethyl-1,3,2-dioxaborolan-2- yl)benzyl acetate 210d (336 mg, 0.763 mmol), Pd(PPh$_3$)$_4$ (37 mg, 0.0318 mmol), Na$_2$CO$_3$ aqueous solution (1.0 N, 2.1 mL, 2.1 mmol), 1,2-dimethoxyethane (4.2 mL) were added. The mixture was reacted in microwave at 130° C. for 10 min. methylene chloride (200 mL) was added and the resulting mixture was washed with water (3×30 mL), brine (30 mL), dried over MgSO$_4$, filtered, and removed solvent in vacuo. Silica gel column chromatography (methanol: methylene chloride=5:95) gave 242a.

To a round-bottomed flask equipped with a stirring bar, 242a, THF (5 mL), i-PrOH (5 mL), H$_2$O (5 mL), LiOH H$_2$O (300 mg) were added. The resulting mixture was stirred at RT for 1 hr. Removed all the solvent in vacuo and the resulting residue was added to methylene chloride (200 mL), the solution was washed with water (30 mL×3), brine (30 mL×1), dried over MgSO$_4$, filtered, and removed solvent in vacuo. Silica gel column chromatography (MeOH: methylene chloride=10:90) gave 242 as a brown solid, 56 mg. MS (ESI+) m/z 611.5 (M+H).

Example 243 10-[5-Fluoro-2-(hydroxymethyl)-3-(1-methyl-5-{[5-(1-methylpyrrolidin-2-yl)pyridine-2-yl]amino}-6-oxo-1,6-dihydropyridin-3-yl)phenyl]-4,4-dimethyl-1,10-diazatricyclo[6.4.0.0$^{2,6}$]dodeca-2(6),7-dien-9-one 243

Example 243a 10-[5-Fluoro-2-(acetoxymethyl)-3-(1-methyl-5-{[5-(1-methylpyrrolidin-2-yl)pyridine-2-yl]amino}-6-oxo-1,6-dihydropyridin-3-yl)phenyl]-4,4-dimethyl-1,10-diazatricyclo[6.4.0.0$^{2,6}$]dodeca-2(6),7-dien-9-one 243a Example 243a was synthesized using the same procedure as 121b, except using compound 230a (446 mg, 0.9 mmol), 5-bromo-1-methyl-3-(5-(1-methylpyrrolidin-2-yl)pyridin-2-ylamino)pyridin-2(1H)-one (229a) (281 mg, 0.8 mmol), 1M sodium carbonate solution (2.7 mL, 2.7 mmol), tetrakis (triphenylphosphine)-palladium(0) (47 mg, 0.040 mmol) and 1,2-dimethoxyethane (6.5 mL). The reaction mixture was heated at 130° C. for 15 minutes in the microwave reactor. Work-up and flash column chromato-graphy (silica, 9:1 methylene chloride/methanol) give a 67% yield (350 mg) of 243a as brown oil: MS (ESI+) m/z 653.1 (M+H).

Following Example 121, except using a mixture of THF (2 mL), water (1 mL) and isopropanol (2 mL), compound 243a (350 mg, 0.54 mmol) and lithium hydroxide monohydrate (150 mg, 3.5 mmol). Work-up and flash column chromatography (NH-silica, ethyl acetate/hexanes) give a 29% yield (95 mg) of compound 243 as a pale yellow solid: MS (ESI+) m/z 611.5 (M+H).

Example 244 10-[5-Fluoro-2-(hydroxymethyl)-3-[4-methyl-6-({4-[1-(oxetan-3-yl)piperidin-4-yl]phenyl}amino)-5-oxo-4,5-dihydropyrazin-2-yl]phenyl]-4,4-dimethyl-1,10-diazatricyclo[6.4.0.0$^{2,6}$]dodeca-2(6),7-dien-9-one 244

Example 244a 10-[5-Fluoro-2-(acetoxymethyl)-3-[4-methyl-6-({4-[1-(oxetan-3-yl)piperidin-4-yl]phenyl}amino)-5-oxo-4,5-dihydropyrazin-2-yl]phenyl]-4,4-dimethyl-1,10-diazatricyclo[6.4.0.0$^{2,6}$]dodeca-2(6),7-dien-9-one 244a Following Example 121b, except using compound 230a (188 mg, 0.38 mmol), 5-bromo-1-methyl-3-(4-(1-(oxetan-3-yl)piperidin-4-yl)phenylamino)pyrazin-2(1H)-one 214b (160 mg, 0.38 mmol), 1M sodium carbonate solution (1.5 mL, 1.5 mmol), tetrakis(triphenylphosphine)palladium(0) (22 mg, 0.019 mmol) and 1,2-dimethoxyethane (5 mL). The reaction mixture was heated at 130° C. for 15 minutes in the microwave reactor. Work-up and flash column chromatography (silica, 60:35:5 methylene chloride/diethyl ether/methanol) give a mixture (270 mg) of compound 244a and 244 as yellow oil.

The mixture from 244a (270 mg) was deprotected using the same procedure as 121, except using a mixture of THF (2 mL), water (1 mL) and isopropanol (2 mL) and Lithium hydroxide monohydrate (85 mg, 2 mmol). Work-up and flash column chromatography (NH-silica, ethyl acetate/hexanes) give a 63% yield (167 mg) of compound 244 as a pale yellow solid: MS (ESI+) m/z 667.6 (M+H).

Example 245 10-[5-Fluoro-2-(hydroxymethyl)-3-[1-methyl-6-oxo-5-({5-[4-(propan-2-yl)piperazin-1-yl]-pyridin-2-yl}amino)-1,6-dihydropyridin-3-yl]phenyl]-4,4-dimethyl-1,10-diazatricyclo[6.4.0.0$^{2,6}$]dodeca-2(6),7-dien-9-one 245

Example 245a 10-[5-Fluoro-2-(acetoxymethyl)-3-[1-methyl-6-oxo-5-({5-[4-(propan-2-yl)piperazin-1-yl]-pyridin-2-yl}amino)-1,6-dihydropyridin-3-yl]phenyl]-4,4-dimethyl-1,10-diazatricyclo[6.4.0.0$^{2,6}$]dodeca-2(6),7-dien-9-one 245a A 44-mL sealed tube equipped with a magnetic stirrer was charged with 220a (400 mg, 1.0 mmol), 7 (508 mg, 2.0 mmol), potassium acetate (392 mg, 4.0 mmol) and 1,4-dioxane (10 mL). After the mixture was degassed for 30 minutes, Pd(dppf)Cl$_2$.CH$_2$Cl$_2$ (82 mg, 0.10 mmol) was added. The resulting reaction mixture was stirred at 105° C. for 6 h. Then, it was cooled to room temperature and filtered through a pad of Celite. The filtrate was concentrated, and the crude mixture was redissolved in DME (2 mL) and transferred into a 10-mL microwave reaction vessel. To this solution was added 10-[2-(acetoxymethyl)-3-bromo-5-fluorophenyl]-4,4-dimethyl-1,10-diazatricyclo-[6.4.0.0$^{2,6}$]dodeca-2(6),7-dien-9-one (189a) (270 mg, 0.60 mmol), Pd(PPh$_3$)$_4$ (50 mg, 0.050 mmol), and 2 N Na$_2$CO$_3$ (2 mL). Then, the reaction mixture was degassed for 5 minutes and placed into the microwave cavity. After the reaction mixture was stirred at 125° C. for 7 min., it was purified by flash chromatography (dichloromethane:methanol, 85:15) to give 49% (150 mg) of 245a.

A 100-mL, single-necked, round-bottomed flask equipped with a magnetic stirring bar was charged with 245a (150 mg, 0.22 mmol), LiOH.H$_2$O (100 mg, 2.2 mmol), THF (2 mL), isopropanol (2 mL), and water (2 mL). After the reaction mixture was stirred at room temperature for 3 h, it was partitioned between dichloromethane (5 mL) and water (5 mL), and the organic phase was extracted with dichloromethane (5 mL×3). The combined organic phases were washed with water (5 mL×2) and brine (5 mL×1), dried (Na$_2$SO$_4$), and concentrated. The crude product was redissolved in dichloromethane (3 mL). To this solution was added hexane (10 mL) and the resulting precipitates were filtered to give 49% yield (70 mg) of 245. MS(ESI$^+$) m/z 654.6 (M+H).

Example 246 10-[5-Fluoro-2-(hydroxymethyl)-3-[1-methyl-5-({5-methyl-4H,5H,6H,7H-pyrazolo[1,5-a]pyrazin-2-yl}amino)-6-oxo-1,6-dihydropyridin-3-yl]phenyl]-4,4-dimethyl-1,10-diazatricyclo[6.4.0.0$^{2,6}$]dodeca-2(6),7-dien-9-one 246

Example 246a 10-[5-Fluoro-2-(acetoxymethyl)-3-[1-methyl-5-({5-methyl-4H,5H,6H,7H-pyrazolo[1,5-a]pyrazin-2-yl}amino)-6-oxo-1,6-dihydropyridin-3-yl]phenyl]-4,4-dimethyl-1,10-diazatricyclo[6.4.0.0$^{2,6}$]dodeca-2(6),7-dien-9-one 246a

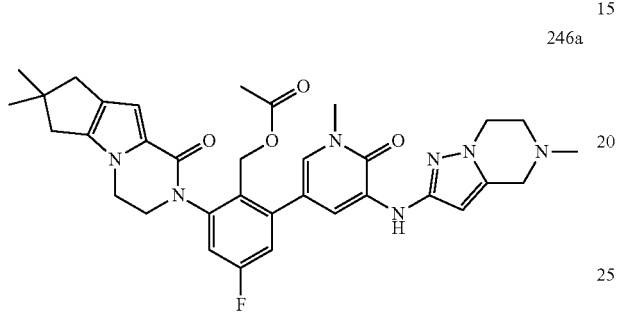

246a

A microwave tube equipped with a magnetic stirrer was charged with 5-bromo-1-methyl-3-(5-methyl-4,5,6,7-tetrahydropyrazolo[1,5-a]pyrazin-2-ylamino)pyridin-2(1H)-one 146a (210 mg, 0.6 mmol), 230a (460 mg, 0.9 mmol), 1,2-dimethoxyethane (8 mL) and 1M aqueous sodium carbonate (2 mL). After bubbling N$_2$ for 15 min, Pd(PPh$_3$)$_4$ (36 mg, 0.03 mmol) was added. The mixture was heated in microwave to 135° C. for 15 min. After this time, ethyl acetate (5 mL) and water (5 mL) were added. The separated aqueous layer was extracted with ethyl acetate (2×5 mL). The combined organics were washed with brine (10 mL), dried over sodium sulfate, filtered and concentrated under reduced pressure. The resulting residue was purified by column chromatography eluting with a gradient of methylene chloride—60:35:5 methylene chloride/diethyl ether/methanol to afford a 37% yield (140 mg) of 246a.

A 25 mL round bottom flask with a magnetic stirrer was charged with 246a (140 mg, 0.2 mmol), lithium hydroxide (200 mg, 4.8 mmol), THF (3 mL), isopropanol (3 mL) and water (2 mL). The mixture stirred at rt for 1 h. After this time, ethyl acetate (5 mL) and water (5 mL) were added. The separated aqueous layer was extracted with ethyl acetate (2×5 mL). The combined organics were washed with brine (10 mL), dried over sodium sulfate, filtered and concentrated under reduced pressure. The resulting residue was purified by column chromatography using the Biotage KPNH 12+M column eluting with a gradient of hexanes—ethyl acetate to afford a 86% yield (120 mg) of 246. MS (ESI+) m/z 586.6 (M+H).

Example 247 10-[5-Fluoro-2-(hydroxymethyl)-3-{4-methyl-6-[(2-methyl-1,2,3,4-tetrahydroisoquinolin-6-yl)amino]-5-oxo-4,5-dihydropyrazin-2-yl}phenyl]-4,4-dimethyl-7-thia-10-azatricyclo[6.4.0.0$^{2,6}$]dodeca-1(8),2(6)-dien-9-one 247

Example 247a (2-Bromo-6-{4,4-dimethyl-9-oxo-7-thia-10-azatricyclo[6.4.0.0$^{2,6}$]dodeca-1(8),2(6)-dien-10-yl}-4-fluorophenyl)methyl Acetate 247a

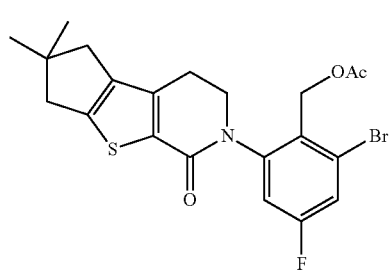

247a

A mixture of 4,4-dimethyl-7-thia-10-azatricyclo[6.4.0.0$^{2,6}$]dodeca-1(8),2(6)-dien-9-one (105h) (2 g, 9.05 mmol), 2,6-dibromo-4-fluorobenzyl acetate (197c)(8.8 g, 27.15 mmol), XantPhos (524 mg, 0.9 mmol), Pd$_2$(dba)$_3$ (828 mg, 0.9 mmol) and Cs$_2$CO$_3$ (5.9 g, 18 mmol) in dioxane (200 mL) was heated at 100° C. for 15 h under nitrogen. The reaction mixture was filtered and the filtrated was evaporated in vacuo. The residue was purified by silical-gel column eluting with 1:1 ethyl acetate/petroleum ether to give 247a as a yellow solid (3 g, 71%). MS: (M+H)$^+$ 466.

Example 247b (2-{4,4-Dimethyl-9-oxo-7-thia-10-azatricyclo[6.4.0.0$^{2,6}$]dodeca-1(8),2(6)-dien-10-yl}-4-fluoro-6-(tetramethyl-1,3,2-dioxaborolan-2-yl)phenyl)methyl Acetate 247b

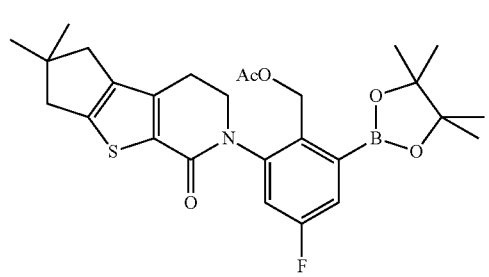

247b

A solution of 247a (3 g, 6.45 mmol), 4,4,4',4',5,5,5',5'-octamethyl-2,2'-bi(1,3,2-dioxaborolane) (9.8 g, 38.7 mmol) in dioxane (160 mL) was added PdCl$_2$(dppf) (525 mg, 0.65 mmol) and CH$_3$COOK (3.8 g, 38.7 mmol). The mixture was stirred at 100° C. for 15 h under argon atmosphere. After reaction the mixture was filtered and evaporated in vacuo and the residue was purified by silical-gel column eluting with 1:2 ethyl acetate/petroleum ether to give 247b as a yellow solid (2.5 g, 76%). MS: (M+H)$^+$ 514.

Example 247c (2-{4,4-Dimethyl-9-oxo-7-thia-10-azatricyclo[6.4.0.0²,⁶]dodeca-1(8),2(6)-dien-10-yl}-4-fluoro-6-{4-methyl-6-[(2-methyl-1,2,3,4-tetrahydroisoquinolin-6-yl)amino]-5-oxo-4,5-dihydropyrazin-2-yl}phenyl)methyl Acetate 247c 247c

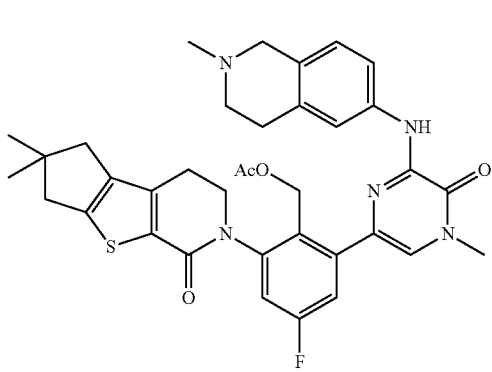

A 25 mL sealed tube was charged with 247b (590 mg, 1.15 mmol), 5-bromo-1-methyl-3-(2-methyl-1,2,3,4-tetrahydroisoquinolin-6-ylamino)pyrazin-2(1H)-one 221b (400 mg, 1.15 mmol), CH₃COONa (189 mg, 2.3 mmol), K₃PO₄ (611 mg, 2.3 mmol), PdCl₂(dppf) (94 mg, 0.11 mmol) suspended in CH₃CN (25 mL) and water (1 mL). The mixture was heated at 110° C. for 2 hours. The mixture was evaporated and the residue was purified by silical-gel column eluting with 20:1 methylene chloride/methanol to give 247c as a brown solid (400 mg, 53%). MS: (M+H)⁺ 656.

A solution of 247c (400 mg, 0.61 mmol) in propan-2-ol (8 mL), tetrahydrofuran (8 mL) and water (1.5 mL) was added LiOH (1.46 g, 61 mmol). The mixture was stirred at 30° C. for 2 h. It was then evaporated and the residue was purified by prep-HPLC to afford 247 as a yellow solid (124 mg, 33%). MS: (M+H)⁺ 614. ¹H NMR (500 MHz, MeOD) δ 1.29 (s, 6H), 2.46 (s, 3H), 2.59-2.60 (d, 2H), 2.74-2.76 (t, 2H), 2.81 (s, 2H), 2.93-2.98 (m, 3H), 3.07-3.09 (m, 1H), 3.59 (s, 2H), 3.64 (s, 3H), 3.95-3.97 (m, 1H), 4.01-4.12 (m, 1H), 4.48-4.51 (d, 1H), 4.58-4.61 (d, 1H), 7.03-7.05 (d, 1H), 7.18-7.21 (m, 1H), 7.38-7.41 (m, 2H), 7.52-7.54 (d, 1H), 7.64 (s, 1H).

Example 248 10-(3-{6-[(2-Ethyl-1,2,3,4-tetrahydroisoquinolin-6-yl)amino]-4-methyl-5-oxo-4,5-dihydropyrazin-2-yl}-5-fluoro-2-(hydroxymethyl)phenyl)-4,4-dimethyl-7-thia-10-azatricyclo[6.4.0.0²,⁶]dodeca-1(8),2(6)-dien-9-one 248

Example 248a 5-Bromo-3-(2-ethyl-1,2,3,4-tetrahydroisoquinolin-6-ylamino)-1-methylpyrazin-2(1H)-one 248a 248a

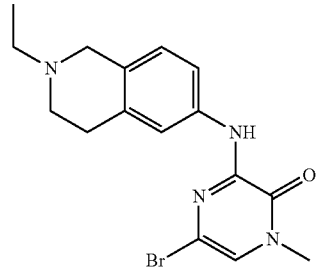

Following the procedures as described for 220a and starting with 385 mg of 5-bromo-1-methyl-3-(1,2,3,4-tetrahydroisoquinolin-6-ylamino)pyrazin-2(1H)-one (221a), 248a was obtained as yellow solid (292 mg, 70%). MS: [M+H]⁺ 364.

Example 248b 2-{4,4-Dimethyl-9-oxo-7-thia-10-azatricyclo[6.4.0.0²,⁶]dodeca-1(8),2(6)-dien-10-yl}-6-{6-[(2-ethyl-1,2,3,4-tetrahydroisoquinolin-6-yl)amino]-4-methyl-5-oxo-4,5-dihydropyrazin-2-yl}-4-fluorophenyl)methyl Acetate 248b 248b

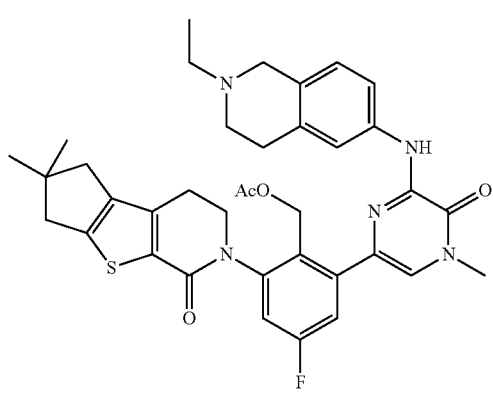

Following the procedures as described for 129a and starting with 400 mg of (2-{4,4-dimethyl-9-oxo-7-thia-10-azatricyclo[6.4.0.0²,⁶]dodeca-1(8),2(6)-dien-10-yl}-4-fluoro-6-(4,4,5,5-tetramethyl-1,3,2-dioxaborolan-2-yl)phenyl)methyl acetate (247b) and 283 mg of 5-bromo-3-(2-ethyl-1,2,3,4-tetrahydroisoquinolin-6-ylamino)-1-methylpyrazin-2(1H)-one, 248b was obtained as a yellow solid (260 mg, 50%).

Following the procedures as described for 148 and starting with 230 mg of 248b, 127 mg of 248 was obtained as a white solid (59%). ¹H NMR (500 MHz, DMSO) δ 9.15 (s, 1H), 7.81 (s, 1H), 7.63 (dd, J=8, 1H), 7.52 (s, 1H), 7.39 (dd, J=9.5, 1H), 7.31 (d, J=9.5, 1H), 6.97 (d, J=8.0, 1H), 4.88 (s, 1H), 4.50 (s, 1H), 4.45 (s, 1H), 4.04 (m, 1H), 3.84 (m, 1H), 3.54 (s, 3H), 3.47 (s, 2H), 3.03 (m, 1H), 2.91 (m, 1H), 2.76 (s, 3H), 2.62-2.45 (m, 6H), 1.23 (s, 6H), 1.08 (t, J=7.5, 3H).

Example 249 10-[5-Fluoro-2-(hydroxymethyl)-3-(4-methyl-6-{[2-(oxetan-3-yl)-1,2,3,4-tetrahydroisoquinolin-6-yl]amino}-5-oxo-4,5-dihydropyrazin-2-yl)phenyl]-4,4-dimethyl-7-thia-10-azatricyclo[6.4.0.0²,⁶]dodeca-1(8),2(6)-dien-9-one 249

Example 249a (2-{4,4-Dimethyl-9-oxo-7-thia-10-azatricyclo[6.4.0.0²,⁶]dodeca-1(8),2(6)-dien-10-yl}-4-fluoro-6-(4-methyl-6-{[2-(oxetan-3-yl)-1,2,3,4-tetrahydroisoquinolin-6-yl]amino}-5-oxo-4,5-dihydropyrazin-2-yl)phenyl)methyl Acetate 249a 249a

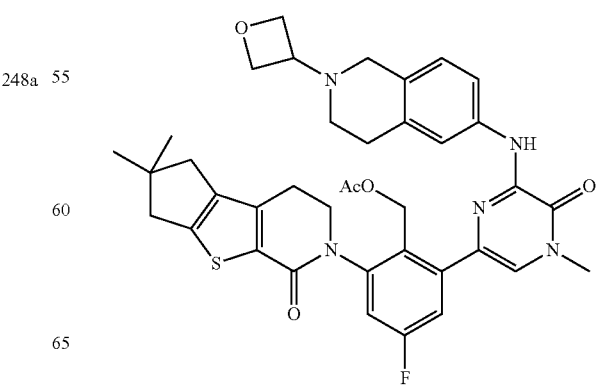

Following the procedures as described for 148b and starting with 247b and 305 mg of 222a, 277 mg of 249a was obtained as a yellow solid (51%). MS: [M+H]+ 698.

Following the procedures as described for compound 148 and starting with 250 mg of 249a, 117 mg of 249 was obtained as a white solid (50%). ¹H NMR (500 MHz, DMSO) δ 9.17 (s, 1H), 7.85 (d, J=1.5, 1H), 7.65 (dd, J=8, 1H), 7.52 (s, 1H), 7.39 (dd, J=9.5, 1H), 7.31 (d, J=9.5, 1H), 6.97 (d, J=8.0, 1H), 4.80 (s, 1H), 4.61 (m, 2H), 4.52 (m, 1H), 4.43 (m, 1H), 4.04 (m, 1H), 3.85 (m, 1H), 3.56 (m, 4H), 3.34 (s, 2H), 3.01-2.57 (m, 6H), 2.53 (m, 5H), 1.23 (s, 6H).

Example 250 2-(3-(5-(5-(1-Ethylazetidin-3-yl)pyridin-2-ylamino)-1-methyl-6-oxo-1,6-dihydropyridin-3-yl)-5-fluoro-2-(hydroxymethyl)phenyl)-3,4,6,7,8,9-hexahydropyrazino[1,2-a]indol-1(2H)-one 250

Example 250a 5-Bromo-3-(5-(1-ethylazetidin-3-yl)pyridin-2-ylamino)-1-methylpyridin-2(1H)-one 250a

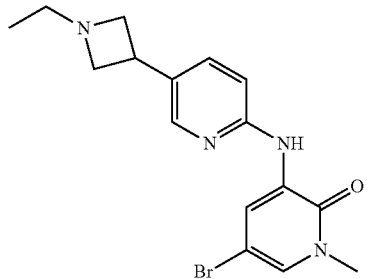 [SMILES: CCN1CC(c2ccc(Nc3cc(Br)cn(C)c3=O)nc2)C1]

To a solution of 3-(5-(azetidin-3-yl)pyridin-2-ylamino)-5-bromo-1-methylpyridin-2(1H)-one 155n (crude, 4.6 mmol) in methanol (50 mL) and acetic acid (5 mL) at 0° C., was added CH₃CHO (40% wt in H₂O) (10 g, 92 mmol) followed by the addition of NaBH(CH₃O)₃ (20 g, 92 mmol) in small portions over a period of 1 h. After the reaction was finished, the mixture was adjusted to pH>7 with 2N NaOH. Then the mixture was extracted with DCM (80 mL×3), dried over Na₂SO₄ and concentrated to get a yellow solid, which was purified on flash column eluting with 50:1 DCM/MeOH containing 0.5% Et₃N to afford 250a as a yellow solid (43%, two steps). LCMS: (M+H)+ 364. ¹H NMR (500 MHz, DMSO) δ 8.72 (s, 1H), 8.66 (d, J=3, 1H), 8.21 (d, J=3, 1H), 7.68 (dd, J=9, 1H), 7.52 (d, J=2.5, 1H), 7.32 (d, J=9, 1H), 3.54 (m, 6H), 2.99 (m, 2H), 2.42 (m, 2H), 0.89 (t, J=7, 3H).

Example 250b 2-(5-(5-(1-Ethylazetidin-3-yl)pyridin-2-ylamino)-1-methyl-6-oxo-1,6-dihydropyridin-3-yl)-4-fluoro-6-(1-oxo-3,4,6,7,8,9-hexahydropyrazino[1,2-a]indol-2(1H)-yl)benzyl Acetate 250b

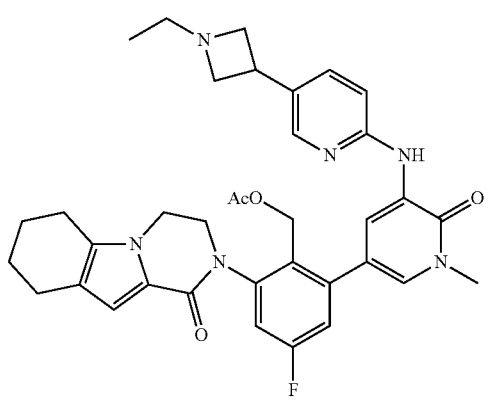 [SMILES: CCN1CC(c2ccc(Nc3cc(-c4cc(F)cc(N5CCn6c(cc7c6CCCC7)C5=O)c4COC(C)=O)cn(C)c3=O)nc2)C1]

Following Example 136e, starting with 250a and 4-fluoro-2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 210d, a 65% yield of 250b was obtained. LCMS: (M+H)+ 639

Following Example 135, starting with 250b, a 63% yield of 250 was obtained. LCMS: (M+H)+ 597. ¹H NMR (500 MHz, DMSO) δ 8.66 (d, J=2, 1H), 8.56 (s, 1H), 8.11 (d, J=1.5, 1H), 7.66 (dd, J=8.5, 1H), 7.42 (d, J=2.5, 1H), 7.33 (dd, J=9.5, 1H), 7.28 (d, J=8.5, 1H), 7.19 (dd, J=9, 1H), 6.53 (s, 1H), 4.87 (t, J=4, 1H), 4.31 (d, J=4.5, 2H), 4.15 (m, 3H), 3.89 (m, 1H), 3.59 (s, 3H), 3.47 (m, 3H), 2.97 (m, 2H), 2.62 (m, 3H), 2.40 (m, 3H), 1.79 (m, 2H), 1.69 (m, 2H), 0.88 (t, J=7, 3H).

Example 251 5-(5-Fluoro-2-(hydroxymethyl)-3-(6,6-dimethyl-3,4,6,7-tetrahydro-5H-cyclopenta[4,5]thieno[2,3-c]pyridine-1(2H)-yl)-3-(5-(1-methylazetidin-3-yloxy))-1-methylpyridin-2(1H)-one 251

Example 251a tert-Butyl 3-(6-Nitropyridin-3-yloxy)azetidine-1-carboxylate 251a

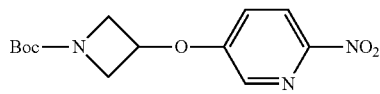

A 100-mL single-neck round-bottomed flask equipped with a magnetic stirrer and reflux condenser was charged with 2-nitro-5-hydroxypyridine (2.00 g, 14.3 mmol), tert-butyl 3-iodoazetidine-1-carboxylate (6.06 g, 21.5 mmol), sodium hydride (800 mg, 20.2 mmol) and DMF (30 mL). The reaction mixture was heated at 110° C. for 24 h. After this time, the reaction mixture was cooled to room temperature and concentrated under reduced pressure. The residue was diluted with ethyl acetate (200 mL) and washed with saturated aqueous sodium bicarbonate (100 mL). The organic layer was dried over sodium sulfate, filtered and concentrated under reduced pressure. The resulting residue was purified by flash chromatography to afford 251a in 95% yield (4.00 g) as a yellow oil: ¹H NMR (500 MHz, CDCl₃) δ 8.27 (d, 1H, J=9.0 Hz), 8.14 (d, 1H, J=3.0 Hz), 7.26 (dd, 1H, J=9.0, 3.0 Hz), 5.04 (m, 1H), 4.39 (m, 2H), 4.06 (m, 2H), 1.44 (s, 9H); MS (ESI+) m/z 196.1 (M-Boc+H).

Example 251b tert-Butyl 3-(6-Aminopyridin-3-yloxy)azetidine-1-carboxylate 251b

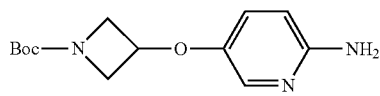

A 250-mL Parr reactor bottle was purged with nitrogen and charged with platinum oxide (200 mg), 251a (2.00 g, 6.78 mmol), ethyl acetate (30 mL) and ethanol (30 mL). The bottle was attached to a Parr hydrogenator, evacuated, charged with hydrogen gas to a pressure of 50 psi and shaken for 20 h. After this time, the hydrogen was evacuated, and nitrogen was charged into the bottle. Celite 521 (10.0 g) was added, and the mixture was filtered through a pad of Celite 521. The filter cake was washed with methanol (2×50 mL), and the combined filtrates were concentrated to dryness under reduced pressure to afford a 100% yield (2.01 g) of 251b as a white solid: mp 83-84° C.; $^1$H NMR (500 MHz, DMSO-$d_6$) δ 7.53 (d, 1H, J=3.0 Hz), 7.04 (dd, 1H, J=9.0, 3.0 Hz), 6.41 (d, 1H, J=9.0 Hz), 5.32 (br s, 2H), 4.21 (t, 2H, J=6.5 Hz), 3.75 (t, 2H, J=6.5 Hz), 3.25 (m, 1H), 1.37 (s, 9H); MS (ESI+) m/z 266.2 (M+H).

Example 251c tert-Butyl 3-(6-(5-Bromo-1-methyl-2-oxo-1,2-dihydropyridin-3-ylamino)pyridin-3-yloxy)azetidine-1-carboxylate 251c

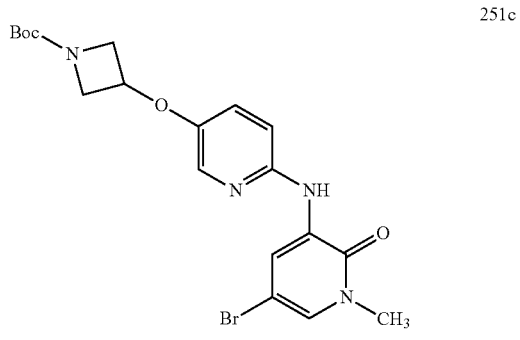 [SMILES: Cn1cc(Br)cc(Nc2ccc(OC3CN(C(=O)OC(C)(C)C)C3)cn2)c1=O]

Using the same procedure as described for the preparation of 250a, reaction of 251b (1.01 g, 3.80 mmol) with 3,5-dibromo-1-methylpyridin-2(1H)-one (1.01 g, 3.80 mmol) afforded an 81% yield (1.40 mg) of 251c as a brown solid: mp 120-121° C.; $^1$H NMR (500 MHz, DMSO-$d_6$) δ 8.70 (s, 1H), 8.57 (d, 1H, J=2.5 Hz), 7.86 (d, 1H, J=3.0 Hz), 7.48 (d, 1H, J=2.5 Hz), 7.35 (d, 1H, J=9.0 Hz), 7.28 (m, 1H), 4.95 (m, 1H), 4.3 (m, 2H), 3.80 (m, 2H), 3.50 (s, 3H), 1.38 (s, 9H); MS (ESI+) m/z 452.3 (M+H).

Example 251d 3-(5-(Azetidin-3-yloxy)pyridin-2-ylamino)-5-bromo-1-methylpyridin-2(1H)-one 251d

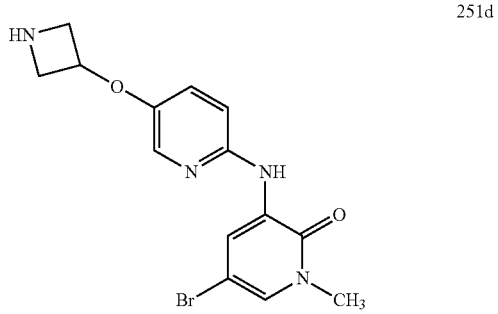 [SMILES: Cn1cc(Br)cc(Nc2ccc(OC3CNC3)cn2)c1=O]

A 250-mL single-neck round-bottomed flask equipped with a magnetic stirrer was charged with 251c (1.14 g, 3.10 mmol), methylene chloride (10 mL) and trifluoroacetic acid (5 mL). The reaction mixture was stirred at room temperature for 2 h. After this time, the mixture was concentrated under reduced pressure. The resulting residue was diluted with methylene chloride (100 mL) and washed with saturated aqueous sodium bicarbonate (50 mL). The aqueous layer was extracted with methylene chloride (2×50 mL) and the combined organic extracts were dried over sodium sulfate, filtered and concentrated to afford a 92% yield (1.10 g) of 251d as a colorless oil. This compound was used directly for the next step without any purification: $^1$H NMR (500 MHz, DMSO-$d_6$) δ 8.65 (s, 1H), 8.55 (d, 1H, J=2.5 Hz), 7.82 (d, 1H, J=3.0 Hz), 7.48 (d, 1H, J=2.5 Hz), 7.30 (d, 1H, J=9.0 Hz), 7.21 (m, 1H), 4.95 (t, 1H, J=6.0 Hz), 3.76 (m, 1H), 3.48 (m, 5H); MS (ESI+) m/z 353.0 (M+H).

Example 251e 5-Bromo-1-methyl-3-(5-(1-methylazetidin-3-yloxy)pyridin-2-ylamino)pyridin-2(1H)-one 251e

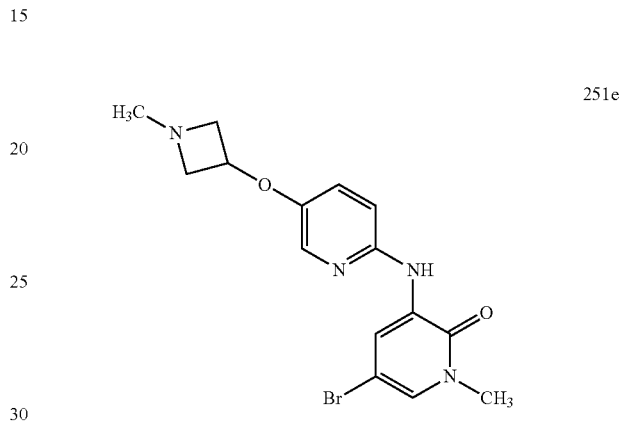

A 250-mL single-neck round-bottomed flask equipped with a magnetic stirrer was purged with nitrogen and charged with 251d (1.10 g, 2.95 mmol), 37% solution of formaldehyde in water (111 mg, 3.70 mmol) and methanol (15 mL). A suspension of sodium cyanoborohydride (540 mg, 8.60 mmol) and zinc chloride (600 mg, 4.40 mmol) in methanol (10 mL) was added, and the reaction was stirred at room temperature for 4 h. After this time, the reaction mixture was concentrated, and the residue was partitioned between 90:10 methylene chloride/methanol (250 mL) and 10% aqueous potassium carbonate (100 mL). The aqueous layer was extracted with 90:10 methylene chloride/methanol (3×150 mL). The combined organic extracts were dried over sodium sulfate, filtered and concentrated under reduced pressure. The resulting residue was purified by column chromatography (silica, 0% to 50% methanol/methylene chloride) to afford a 80% yield (830 mg) of 251e as an brown solid: mp 100-101° C.; $^1$H NMR (500 MHz, DMSO-$d_6$) δ 8.66 (s, 1H), 8.55 (d, 1H, J=2.5 Hz), 7.86 (d, 1H, J=3.0 Hz), 7.47 (d, 1 h, J=2.5 Hz), 7.31 (d, 1H, J=9.0 Hz), 7.24 (dd, 1H, J=9.5, 3.5 Hz), 4.76 (m, 1H), 3.77 (t, 2H, J=7.5 Hz), 3.50 (s, 3H), 3.03 (t, 2H, J=7.5 Hz), 2.26 (s, 3H); MS (ESI+) m/z 366.0 (M+H).

Using the same procedure as described for the preparation of 239, a reaction of 251e (145 mg, 0.400 mmol) with 182c (304 mg, 0.520 mmol) afforded a 15% yield (37 mg) of 251 as a off-white solid: mp 160-161° C.; $^1$H NMR (500 MHz, DMSO-$d_6$) δ 8.53 (d, 1H, J=2.5 Hz), 8.49 (s, 1H), 7.77 (d, 1H, J=2.5 Hz), 7.36 (d, 1H, J=2.0 Hz), 7.32 (dd, 1H, J=9.0, 2.5 Hz), 7.27 (d, 1H, J=9.0 Hz), 7.22 (dd, 1H, J=9.0, 2.5 Hz), 7.16 (dd, 1H, J=9.0, 2.5 Hz), 4.84 (t, 1H, J=4.0 Hz), 4.69 (m, 1H), 4.30 (m, 2H), 3.84 (m, 2H), 3.69 (m, 2H), 3.58 (s, 3H), 3.02 (m, 1H), 2.92 (m, 3H), 2.75 (m, 2H), 2.54 (m, 2H), 2.27 (s, 3H); MS (ESI+) m/z 630.3 (M+H).

Example 252 10-[5-fluoro-2-(hydroxymethyl)-3-(1-methyl-5-{[5-(oxetan-3-yl)-4H,5H,6H,7H-pyrazolo[1,5-a]pyrazin-2-yl]amino}-6-oxo-1,6-dihydropyridin-3-yl)phenyl]-4,4-dimethyl-1,10-diazatricyclo[6.4.0.0$^{2,6}$]dodeca-2(6),7-dien-9-one 252

Example 252a 5-bromo-1-methyl-3-(5-(oxetan-3-yl)-4,5,6,7-tetrahydropyrazolo[1,5-a]pyrazin-2-ylamino)pyridin-2(1H)-one 252a

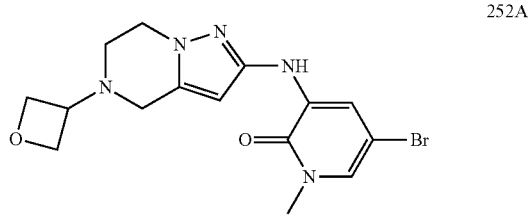 [SMILES: Cn1cc(Br)cc(Nc2cc3n(n2)CCN(C2COC2)C3)c1=O]

252A

Following Example 214b, 5-bromo-1-methyl-3-(4,5,6,7-tetrahydropyrazolo[1,5-a]pyrazin-2-ylamino)pyridin-2(1H)-one 126a (250 mg, 0.78 mmol), oxetan-3-one (600 mg, 8.3 mmol) were dissolved in methanol (8 mL). Sodium cyanoborohydride (148 mg, 3 mmol) and zinc chloride (165 mg, 1.5 mmol) in methanol (8 mL) was added, and the reaction was heated at 48° C. for 12 hours. Work-up and flash column chromatography (silica, 60:35:5 methylene chloride/diethyl ether/methanol) afford a 34% yield (100 mg) of 252a as a light green solid: MS (ESI+) m/z 382.1 (M+H).

Following Example 121b, except using 230a (135 mg, 0.26 mmol), 252a (100 mg, 0.26 mmol), 1M sodium carbonate solution (1 mL, 1 mmol), tetrakis(tripheny-phosphine)palladium(0) (15 mg, 0.013 mmol) and 1,2-dimethoxyethane (2.5 mL). The reaction mixture was heated at 130° C. for 15 minutes in the microwave reactor. Work-up and flash column chromatography (silica, 60:35:5 methylene chloride/diethyl ether/methanol) give a mixture (80 mg) of 252b and 252 as yellow oil. This mixture (80 mg) was deprotected using the same procedure 121, except using a mixture of THF (1 mL), water (0.5 mL) and isopropanol (1 mL) and Lithium hydroxide monohydrate (25 mg, 0.6 mmol). Work-up and flash column chromatography (NH-silica, Ethyl Acetate/Hexanes) give a 40% yield (30 mg) of 252 as a white solid: MS (ESI+) m/z 628.5 (M+H).

Example 253 5-[5-Fluoro-2-(hydroxymethyl)-3-{1-oxo-1H,2H,3H,4H,6H,7H,8H,9H-pyrazino[1,2-a]indol-2-yl}phenyl]-1-methyl-3-({5-[(2R)-1-methyl-pyrrolidin-2-yl]pyridine-2-yl}amino)-1,2-dihydropyridin-2-one 253

Example 254 5-[5-Fluoro-2-(hydroxymethyl)-3-{1-oxo-1H,2H,3H,4H,6H,7H,8H,9H-pyrazino[1,2-a]indol-2-yl}phenyl]-1-methyl-3-({5-[(2S)-1-methyl-pyrrolidin-2-yl]pyridine-2-yl}amino)-1,2-dihydropyridin-2-one 254

Examples 253 and 254 are enantiomers of racemate 202. The racemic mixture 202 was subjected to chiral separation on a Chiralpak AD, 4.6×50 mm, 3 mm column (mobile phase 55% isopropanol (w/0.1% triethylamine)/45% CO$_2$, flow rate 5 mL/min) at 40° C. to give individual enantiomers, with 254 eluting first, followed by 253 last. Examples 253 MS (ESI+) m/z 597.4 (M+H). Examples 254 MS (ESI+) m/z 597.4 (M+H).

Example 255 5-[5-Fluoro-2-(hydroxymethyl)-3-{1-oxo-1H,2H,3H,4H,6H,7H,8H,9H-pyrazino[1,2-a]indol-2-yl}phenyl]-1-methyl-3-{[5-(morpholin-4-yl)pyridin-2-yl]amino}-1,2-dihydropyridin-2-one 255

Example 255a 4-(6-Nitropyridin-3-yl)morpholine 255a

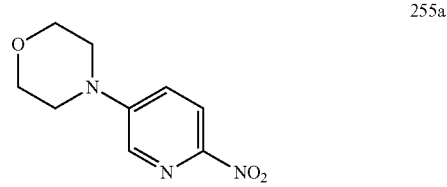 [SMILES: Nc1ccc(N2CCOCC2)cn1]

255a

Following the procedures as described for 188a and starting with 2 g of 5-bromo-2-nitropyridine and 968 mg morpholine, 255a was obtained as a yellow solid (1 g, 50%). MS: [M+H]$^+$ 210. $^1$H NMR (500 MHz, CDCl3) δ 8.18 (d, J=9.0, 1H), 8.15 (d, J=3.0, 1H), 7.22 (dd, J=3.0, 1H), 3.90 (t, J=5.0, 4H), 3.42 (t, J=5.0, 4H).

Example 255b 5-Morpholinopyridin-2-amine 255b

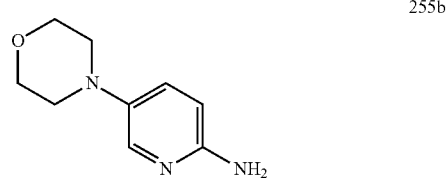

255b

Following the procedures as described for 188b and starting with 1 g of 4-(6-nitropyridin-3-yl)morpholine, 255b was obtained as a yellow solid (840 mg, 98%). MS: [M+H]$^+$ 210

Example 255c 5-Bromo-1-methyl-3-(5-morpholinopyridin-2-ylamino)pyridin-2(1H)-one 255c

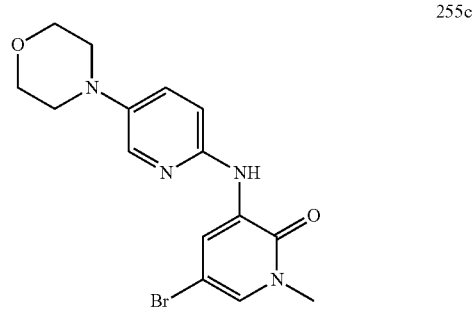 [SMILES: Cn1cc(Br)cc(Nc2ccc(N3CCOCC3)cn2)c1=O]

255c

Following the procedures as described for 188c and starting with 3,5-dibromo-1-methylpyridin-2(1H)-one (1.15 g, 4.3 mmol) and 5-morpholinopyridin-2-amine (770 mg, 4.3 mmol), 255c was obtained as a yellow solid (986 mg, 63%). MS: [M+H]$^+$ 365

Example 255d 4-Fluoro-2-(1-methyl-5-(5-morpholinopyridin-2-ylamino)-6-oxo-1,6-dihydropyridin-3-yl)-6-(1-oxo-3,4,6,7,8,9-hexahydropyrazino[1,2-a]indol-2(1H)-yl)benzyl Acetate 255d

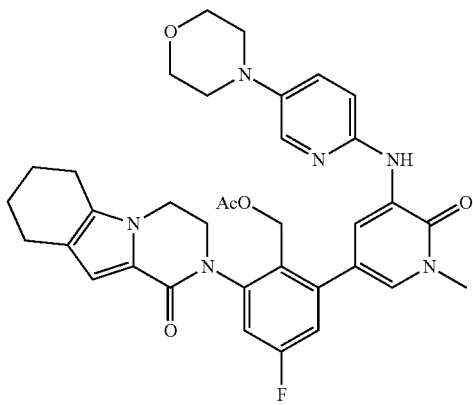

Following the procedures as described for 148c and starting with 400 mg of 4-fluoro-2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 210d and 302 mg of 5-bromo-1-methyl-3-(5-morpholinopyridin-2-ylamino)pyridin-2(1H)-one, 255d was obtained as a yellow solid (281 mg, 53%). MS: [M+H]⁺ 641

Following the procedures as described for 148 and starting with 270 mg of 4-fluoro-2-(1-methyl-5-(5-morpholinopyridin-2-ylamino)-6-oxo-1,6-dihydropyridin-3-yl)-6-(1-oxo-3,4,6,7,8,9-hexahydropyrazino[1,2-a]indol-2(1H)-yl)benzyl acetate, 255 was obtained as a white solid (103 mg, 41%). MS: [M+H]⁺ 599. $^1$H NMR (500 MHz, DMSO) δ 8.56 (d, J=2.0, 1H), 8.38 (s, 1H), 7.87 (d, J=3.0, 1H), 7.36-7.32 (m, 3H), 7.25 (d, J=9.5, 2H), 7.19 (d, J=9.0, 1H), 6.52 (s, 1H), 4.87 (s, 1H), 4.32 (d, J=4, 2H), 4.15 (m, 3H), 3.82 (m, 1H), 3.72 (t, J=4.0, 1H), 3.50 (s, 3H), 3.02 (t, J=4.5, 3H), 2.61 (m, 2H), 2.47 (m, 2H), 1.80 (s, 2H), 1.68 (S, 2H).

Example 256 10-[5-Fluoro-2-(hydroxymethyl)-3-(1-methyl-5-{[5-(morpholin-4-yl)pyridine-2-yl]amino}-6-oxo-1,6-dihydropyridin-3-yl)phenyl]-4,4-dimethyl-7-thia-10-azatricyclo[6.4.0.0²,⁶]dodeca-1(8),2(6)-dien-9-one 256

Example 256a (2-{4,4-Dimethyl-9-oxo-7-thia-10-azatricyclo[6.4.0.0²,⁶]dodeca-1(8),2(6)-dien-10-yl}-4-fluoro-6-(1-methyl-5-{[5-(morpholin-4-yl)pyridin-2-yl]amino}-6-oxo-1,6-dihydropyridin-3-yl)phenyl)methyl Acetate 256a

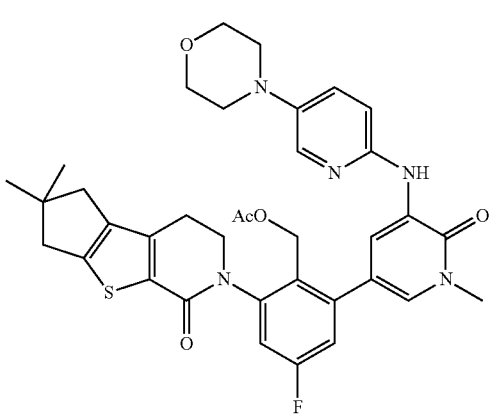

Following Example 148b, starting with 400 mg of (2-{4,4-dimethyl-9-oxo-7-thia-10-azatricyclo[6.4.0.0²,⁶]dodeca-1(8),2(6)-dien-10-yl}-4-fluoro-6-(4,4,5,5-tetramethyl-1,3,2-dioxaborolan-2-yl)phenyl)methyl acetate 247b and 284 mg 5-bromo-1-methyl-3-(5-morpholinopyridin-2-ylamino)pyridin-2(1H)-one 255c, 277 mg of 256a was obtained as a yellow solid (53%). MS: [M+H]⁺ 672

Following Example 148, starting with 270 mg of 256a, 103 mg of 256 was obtained as a white solid (41%). MS: [M+H]⁺ 630. $^1$H NMR (500 MHz, DMSO) δ 8.56 (d, J=2.0, 1H), 8.38 (s, 1H), 7.88 (d, J=3.0, 1H), 7.36-7.32 (m, 3H), 7.25 (d, J=9.5, 2H), 7.19 (d, J=9.0, 1H), 4.85 (s, 1H), 4.32 (d, J=4, 2H), 4.07 (m, 3H), 3.86 (m, 1H), 3.72 (t, J=4.0, 1H), 3.50 (s, 3H), 3.02 (t, J=4.5, 3H), 2.89 (m, 1H), 2.76 (s, 2H), 2.53 (m, 2H), 1.23 (s, 6H).

Example 257 10-[3-(5-{[5-(1-Ethylazetidin-3-yl)pyridin-2-yl]amino}-1-methyl-6-oxo-1,6-dihydropyridin-3-yl)-5-fluoro-2-(hydroxymethyl)phenyl]-4,4-dimethyl-7-thia-10-azatricyclo[6.4.0.0²,⁶]dodeca-1(8),2(6)-dien-9-one 257

Example 257a (2-{4,4-Dimethyl-9-oxo-7-thia-10-azatricyclo[6.4.0.0²,⁶]dodeca-1(8),2(6)-dien-10-yl}-6-(5-{[5-(1-ethylazetidin-3-yl)pyridin-2-yl]amino}-1-methyl-6-oxo-1,6-dihydropyridin-3-yl)-4-fluorophenyl)methyl Acetate 257a

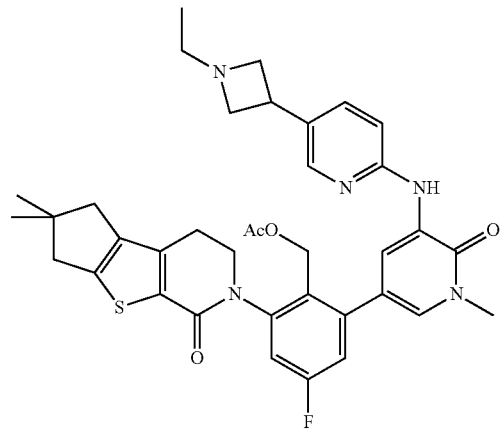 [SMILES: CCN1CC(c2ccc(Nc3cc(-c4cc(F)cc(N5CCc6c(sc7c6CC(C)(C)C7)C5=O)c4COC(C)=O)cn(C)c3=O)nc2)C1]

Following Example 136a, starting with 5-bromo-3-(5-(1-ethylazetidin-3-yl)pyridin-2-ylamino)-1-methylpyridin-2(1H)-one 250a and (2-{4,4-dimethyl-9-oxo-7-thia-10-azatricyclo[6.4.0.0²,⁶]dodeca-1(8),2(6)-dien-10-yl}-4-fluoro-6-(4,4,5,5-tetramethyl-1,3,2-dioxaborolan-2-yl)phenyl)methyl acetate 247b, compound 257a was obtained in 37% yield.

Following Example 136, starting with 257a, compound 257 was obtained in 46% yield. LCMS: (M+H)⁺ 628. $^1$H NMR (500 MHz, DMSO) δ 8.66 (d, J=2, 1H), 8.55 (s, 1H), 8.12 (d, J=2.5, 1H), 7.65 (dd, J=8.5, 1H), 7.42 (d, J=2, 1H), 7.33 (dd, J=9.5, 1H), 7.28 (d, J=9, 1H), 7.19 (dd, J=9, 1H), 4.86 (t, J=4, 1H), 4.33 (m, 2H), 4.05 (m, 1H), 3.86 (m, 1H), 3.59 (s, 3H), 3.49 (m, 3H), 3.04 (m, 1H), 2.97 (m, 2H), 2.89 (m, 1H), 2.76 (s, 2H), 2.55 (m, 2H), 2.40 (m, 2H), 1.79 (m, 4H), 1.23 (s, 6H), 0.88 (t, J=7, 3H).

Example 258 2-(5-Fluoro-2-(hydroxymethyl)-3-(1-methyl-5-(2-(oxetan-3-yl)-1,2,3,4-tetrahydroisoquinolin-6-ylamino)-6-oxo-1,6-dihydropyridin-3-yl)phenyl)-3,4,6,7,8,9-hexahydropyrazino[1,2-a]indol-1(2H)-one 258

Example 258a tert-Butyl 6-(5-Bromo-1-methyl-2-oxo-1,2-dihydropyridin-3-ylamino)-3,4-dihydroisoquinoline-2(1H)-carboxylate 258a

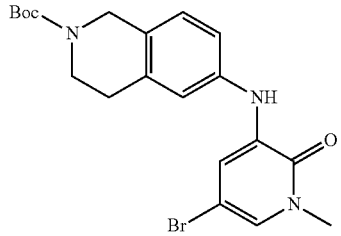 [SMILES: Cn1cc(Br)cc(Nc2ccc3c(c2)CCN(C(=O)OC(C)(C)C)C3)c1=O]

A 100 mL round bottomed flask was charged with tert-butyl 6-amino-3,4-dihydroisoquinoline-2(1H)-carboxylate (2 g, 8 mmol), 3,5-dibromo-1-methylpyridin-2(1H)-one (1.8 g, 6.7 mmol), cesium carbonate (4.4 g, 13.4 mmol), Xant-Phos (0.41 g, 0.7 mmol), tris(dibenzylideneacetone)dipalladium(0) (0.64 g, 0.7 mmol) and 1,4-dioxane (50 mL). The reaction mixture was refluxed under argon atmosphere for 2 h. After this time, the mixture was cooled to room temperature and filtered. The filtrate was concentrated under reduced pressure. The residue was purified by column chromatography eluting with 25:1 dichloromethane/methanol to give 258a (2.18 g, 63%). LC/MS: m/z 435 (M+H)$^+$ Example 258b 5-Bromo-1-methyl-3-(1,2,3,4-tetrahydroisoquinolin-6-ylamino)pyridine-2(1H)-one 258b

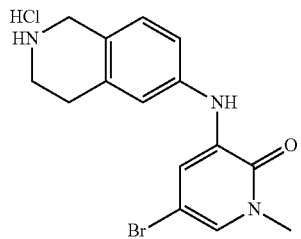 [SMILES: Cl ; Cn1cc(Br)cc(Nc2ccc3c(c2)CCNC3)c1=O]

Compound 258a (2.18 g, 5 mmol) was suspended in dioxane (10 mL). Saturated hydrogen chloride in dioxane (20 mL) was added dropwise. The reaction mixture was stirred for 20 minutes and concentrated under reduced pressure to afford 258b, which was used without further purification in the next step. LC/MS: m/z 335 (M+H)$^+$ Example 258c 5-Bromo-1-methyl-3-(2-(oxetan-3-yl)-1,2,3,4-tetrahydroisoquinolin-6-ylamino)pyridin-2(1H)-one 258c

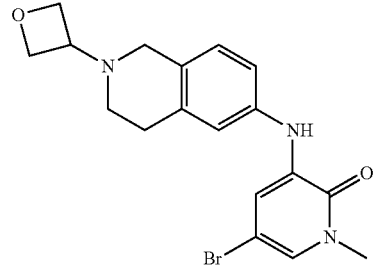 [SMILES: Cn1cc(Br)cc(Nc2ccc3c(c2)CCN(C2COC2)C3)c1=O]

A mixture of 258b (1.7 g, 5 mmol), oxetan-3-one (1.8 g, 25 mmol), NaBH$_3$CN (1 g, 15 mmol) and zinc chloride (3.4 g, 25 mmol) in methanol (50 mL) was stirred for 4 hours at room temperature. The mixture was filtered and the filtrate was concentrated under reduced pressure. The residue was purified by column chromatography eluting with 25:1 dichloromethane/methanol to give 258c (1.8 g, 92%). LC/MS: m/z 391 (M+H)$^+$ Example 258d 4-Fluoro-2-(1-methyl-5-(2-(oxetan-3-yl)-1,2,3,4-tetrahydroisoquinolin-6-ylamino)-6-oxo-1,6-dihydropyridin-3-yl)-6-(1-oxo-3,4,6,7,8,9-hexahydropyrazino[1,2-a]indol-2(1H)-yl)benzyl Acetate 258d

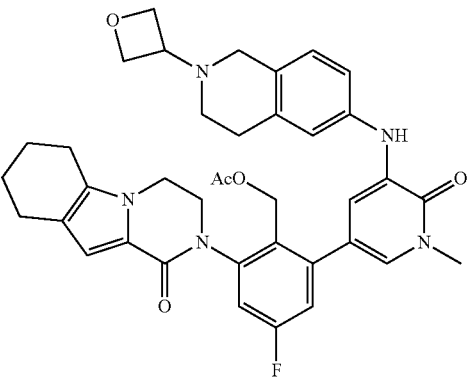 [SMILES: CC(=O)OCc1c(-c2cc(Nc3ccc4c(c3)CCN(C3COC3)C4)c(=O)n(C)c2)cc(F)cc1N1CCn2c(cc3c2CCCC3)C1=O]

A 15 mL microwave reaction vial with a magnetic stirrer was charged with 258c (0.39 g, 1 mmol), 4-fluoro-2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 210d (0.48 g, 1 mmol), potassium phosphate (0.54 g, 2 mmol), sodium acetate (0.17 g, 2 mmol), acetonitrile (10 mL), water (1 mL), and 1,1'-bis(diphenylphosphino)ferrocene-palladium(II)dichloride dichloromethane (0.08 g, 0.1 mmol). The reaction mixture was heated at 110° C. for 2 hours under argon atmosphere. After this time, the mixture was cooled to room temperature and filtered. The filtrate was concentrated under reduced pressure. The residue was purified by column chromatography eluting with 40:1 dichloromethane/methanol to give 258d (0.3 g, 50%). LC/MS: m/z 666 (M+H)$^+$ A 25 mL round bottomed flask with a magnetic stirrer was charged with 258d (0.6 g, 0.9 mmol), LiOH (2 g, 48 mmol), THF (5 mL), isopropanol (5 mL) and water (2 mL). The reaction mixture was stirred at room temperature for 30 minutes and filtered. The filtrate was concentrated under reduced pressure. The residue was purified by prep-HPLC to give 258. LC/MS: m/z 624 (M+H)+. 1H NMR (500 MHz, DMSO) δ 7.62 (s, 1H), 7.82 (s, 1H), 7.34 (m, 3H), 7.20 (m, 1H), 7.09 (m, 2H), 6.94 (m, 1H), 4.86 (m, 1H), 4.96 (m, 1H), 4.60 (m, 2H), 4.51 (m, 2H), 4.31 (m, 2H), 4.14 (m, 3H), 3.87 (m, 1H), 3.58 (m, 4H), 3.33 (m, 3H), 2.75 (m, 2H), 2.60 (m, 3H), 2.50 (m, 3H), 1.78 (m, 4H).

Example 259 5-[2-(Hydroxymethyl)-3-[1-methyl-5-({5-methyl-4H,5H,6H,7H-pyrazolo[1,5-a]pyrazin-2-yl}amino)-6-oxo-1,6-dihydropyridin-3-yl]phenyl]-8-thia-5-azatricyclo[7.4.0.0$^{2,7}$]trideca-1(9),2(7)-dien-6-one 259

Example 259a {2-[1-Methyl-5-({5-methyl-4H,5H,6H,7H-pyrazolo[1,5-a]pyrazin-2-yl}amino)-6-oxo-1,6-dihydropyridin-3-yl]-6-{6-oxo-8-thia-5 azatricyclo[7.4.0.0$^{2,7}$]-trideca-1(9),2(7)-dien-5-yl}phenyl}methyl Acetate 259a

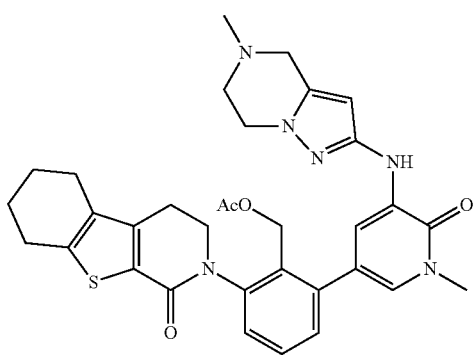

A 25 mL sealed tube was charged with (2-{6-oxo-8-thia-5-azatricyclo[7.4.0.0$^{2,7}$]-trideca-1(9),2(7)-dien-5-yl}-6-(4,4,5,5-tetramethyl-1,3,2-dioxaborolan-2-yl)phenyl)-methyl acetate 111a (571 mg, 1.2 mmol), 5-bromo-1-methyl-3-(5-methyl-4,5,6,7-tetrahydropyrazolo[1,5-a]pyrazin-2-ylamino)pyridin-2(1H)-one 146a (400 mg, 1.2 mmol), CH$_3$COONa (195 mg, 2.4 mmol), K$_3$PO$_4$ (631 mg, 2.4 mmol), PdCl$_2$(dppf) (97 mg, 0.12 mmol) suspended in CH$_3$CN (25 mL) and H$_2$O (1 mL). The mixture was heated at 110° C. for 2 hours. It was then evaporated and the residue was purified by column chromatography eluting with 20:1 methylene chloride/methanol to give 259a as a brown solid (500 mg, 69%). MS: (M+H)+ 613.

A solution of 259a (500 mg, 0.82 mmol) in propan-2-ol (10 mL), tetrahydrofuran (10 mL) and water (2 mL) was added LiOH (1.96 g, 82 mmol). The mixture was stirred at 30° C. for 2 h. It was then evaporated and the residue was purified by prep-HPLC to afford 259 as a yellow solid (159 mg, 34%). MS: (M+H)+ 571. 1H NMR (500 MHz, DMSO) δ 1.79 (s, 4H), 2.35 (s, 2H), 2.53-2.55 (m, 1H), 2.76-2.79 (m, 4H), 2.84-2.88 (m, 1H), 2.96-2.98 (m, 1H), 3.48 (s, 2H), 3.57 (s, 3H), 3.87-3.93 (m, 3H), 3.99-4.03 (m, 1H), 4.35 (s, 2H), 4.81 (s, 1H), 5.88 (s, 1H), 7.23-7.24 (d, 2H), 7.29-7.34 (m, 2H), 7.43-7.46 (d, 1H), 7.97-7.98 (d, 1H), 8.10 (s, 1H).

Example 260 10-[5-Fluoro-2-(hydroxymethyl)-3-(1-methyl-5-{[5-(1-methylpiperidin-4-yl)pyridine-2-yl]amino}-6-oxo-1,6-dihydropyridin-3-yl)phenyl]-4,4-dimethyl-1,10-diazatricyclo[6.4.0.0$^{2,6}$]dodeca-2(6),7-dien-9-one 260

Example 260a 10-[5-Fluoro-2-(acetoxymethyl)-3-(1-methyl-5-{[5-(1-methylpiperidin-4-yl)pyridine-2-yl]amino}-6-oxo-1,6-dihydropyridin-3-yl)phenyl]-4,4-dimethyl-1,10-diazatricyclo[6.4.0.0$^{2,6}$]dodeca-2(6),7-dien-9-one 260a

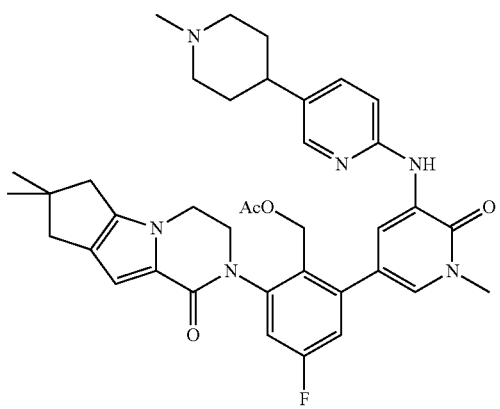 [SMILES: CC(=O)OCc1c(-c2cc(Nc3ccc(C4CCN(C)CC4)cn3)c(=O)n(C)c2)cc(F)cc1N1CCn2c(cc3c2CC(C)(C)C3)C1=O]

To a microwave tube equipped with a stirring bar, 5-bromo-1-methyl-3-(5-(1-methylpiperidin-4-yl)pyridin-2-ylamino)pyridin-2(1H)-one 130c (162 mg, 0.429 mmol), boronic ester 212b (347 mg, 0.700 mmol), Pd(PPh$_3$)$_4$ (24.8 mg, 0.022 mmol), Na$_2$CO$_3$ aqueous solution (1.0 N, 1.42 mL, 1.42 mmol), 1,2-dimethoxyethane (4.0 mL) were added. The mixture was reacted in microwave at 130° C. for 15 min. Dichloromethane (200 mL) was added and the resulting mixture was washed with water (3×30 mL), brine (30 mL×1), dried over MgSO$_4$, filtered, and removed solvent in vacuo. Silica gel column chromatography (methanol:dichloromethane=5:95) gave 260a.

To a round-bottomed flask equipped with a stirring bar, 260a, THF (5 mL), i-PrOH (5 mL), H$_2$O (5 mL), LiOH H$_2$O (300 mg) were added. The resulting mixture was stirred at RT for 1 hr. Removed all the solvent in vacuo and the resulting residue was added to dichloromethane (200 mL), the solution was washed with water (3×30 mL), brine (30 mL), dried over MgSO$_4$, filtered, and removed solvent in vacuo. Silica gel column chromatography (MeOH:dichloromethane=10:90) gave alcohol 260 as yellow solids, 48 mg. MS (ESI+) m/z 625.5 (M+H).

Example 261 10-[5-Fluoro-2-(hydroxymethyl)-3-{1-methyl-5-[(6-methyl-5,6,7,8-tetrahydro-1,6-naphthyridin-2-yl)amino]-6-oxo-1,6-dihydropyridin-3-yl}phenyl]-4,4-dimethyl-1,10-diazatricyclo[6.4.0.0$^{2,6}$]dodeca-2(6),7-dien-9-one 261

Example 261a 10-[5-Fluoro-2-(acetoxymethyl)-3-{1-methyl-5-[(6-methyl-5,6,7,8-tetrahydro-1,6-naphthyridin-2-yl)amino]-6-oxo-1,6-dihydropyridin-3-yl}phenyl]-4,4-dimethyl-1,10-diazatricyclo[6.4.0.0$^{2,6}$]dodeca-2(6),7-dien-9-one 261a In a 10-mL microwave reaction vessel equipped with a magnetic stirring bar were placed 5-bromo-1-methyl-3-(6- methyl-5,6,7,8-tetrahydro-1,6-naphthyridin-2-ylamino)pyridin-2(1H)-one 205b (150 mg, 0.43 mmol), 10-[2-(acetoxymethyl)-3-(4,4,5,5-tetramethyl-[1,3,2]dioxaborolan-2-yl)-5-fluorophenyl]-4,4-dimethyl-1,10-diazatricyclo[6.4.0.0$^{2,6}$]dodeca-2(6),7-dien-9-one 230a (248 mg, 0.50 mmol), Pd(PPh$_3$)$_4$ (30 mg, 0.026 mmol) in 2 N Na$_2$CO$_3$ (2 mL) and 1,2-dimethoxyethane (2 mL). After the reaction mixture was stirred at 125° C. for 10 minutes, it was purified by flash chromatography (dichloromethane:methanol, 3:1) to give 36% (100 mg) of 261a as a solid.

A 25-mL, single-necked, round-bottomed flask equipped with a magnetic stirring bar was charged with 261a (100 mg, 0.16 mmol), LiOH.H$_2$O (200 mg, 4.8 mmol), THF (2 mL), isopropanol (2 mL), and water (2 mL). After the reaction mixture was stirred at room temperature for 2 h, it was partitioned between dichloromethane (5 mL) and water (5 mL), and the organic phase was extracted with dichloromethane (5 mL×3). The combined organic phases were washed with water (2×5 mL) and brine (5 mL), dried (Na$_2$SO$_4$), and concentrated. The crude product was redissolved in dichloromethane (3 mL). To this solution was added hexane (10 mL) and the resulting precipitate was filtered to give 36% yield (34 mg) of 261. MS(ESI$^+$) m/z 597.5 (M+H).

Example 262 10-[3-(5-{[5-(1-Ethylazetidin-3-yl)pyridine-2-yl]amino}-1-methyl-6-oxo-1,6-dihydropyridin-3-yl)-5-fluoro-2-(hydroxymethyl)phenyl]-4,4-dimethyl-1,10-diazatricyclo[6.4.0.0$^{2,6}$]dodeca-2(6),7-dien-9-one 262

Examples 262a and 262b

Following Example 271a, 262b was produced using 250a (305 mg, 0.84 mmol) in Step 1 and using 189a (302 mg, 0.67 mmol) in Step 2 in Example 271b. The product was purified via column chromatography: ISCO 12 g silica, 0-10% MeOH, to give desired product 262b (105 mg, 19% yield).

Following Example 119, 262a (105 mg, 0.36 mmol), 1N LiOH (0.8 mL), THF (2 mL) and isopropanol (2 mL) were reacted to give 262 (85 mg, 87% yield). MS (ESI+) m/z 611.5 (M+H).

Example 263 2-(5-Fluoro-2-(hydroxymethyl)-3-(5-(2-methoxypyrimidin-4-ylamino)-1-methyl-6-oxo-1,6-dihydropyridin-3-yl)phenyl)-3,4,6,7,8,9-hexahydropyrazino[1,2-a]indol-1(2H)-one 263

Example 263a 5-Bromo-3-(2-methoxypyrimidin-4-ylamino)-1-methylpyridin-2(1H)-one 263a Following Example 112a, 2-methoxypyrimidin-4-amine (0.625 g, 5 mmol), 3,5-dibromo-1-methyl-1H-pyridin-2-one (1.34 g, 5 mmol), cesium carbonate (4.88 g, 15 mmol), tris(dibenzylideneacetone)-dipalladium(0) (0.465 g, 0.5 mmol), Xantphos (0.58 g, 1 mmol) and 1,4-dioxane (50 mL) were heated at 100° C. for 24 hours. The mixture was cooled to room temperature, and filtered through a pad of Celite 521. The filter cake was washed with 9:1 methylene chloride/methanol (2×25 mL), and the combined filtrates were concentrated to dryness. The residue was dissolve in methylene chloride, diethyl ethyl was added, and the resulting precipitate was filtered to give a quantitative yield (1.57 g) of 263a as a green solid: MS (ESI+) m/z 313.1 (M+H).

Example 263b 4-Fluoro-2-(5-(2-methoxypyrimidin-4-ylamino)-1-methyl-6-oxo-1,6-dihydropyridin-3-yl)-6-(1-oxo-3,4,6,7,8,9-hexahydropyrazino[1,2-a]indol-2(1H)-yl)benzyl acetate 263b Following Example 121b, 263a (158 mg, 0.5 mmol), 4-fluoro-2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 210d (242 mg, 0.5 mmol), 1M sodium carbonate solution (2 mL, 2 mmol), tetrakis(triphenylphosphine)palladium(0) (29 mg, 0.025 mmol) and 1,2-dimethoxyethane (5 mL) were heated at 130° C. for 15 minutes in the microwave reactor. Work-up and flash column chromatography (silica, 60:35:5 methylene chloride/diethyl ether/methanol) gave a 98% yield (290 mg) of 263b as yellow oil: MS (ESI+) m/z 587.6 (M+H).

Following Example 121, a mixture of THF (2 mL), water (1 mL) and isopropanol (2 mL), 263b (290 mg, 0.5 mmol) and lithium hydroxide monohydrate (105 mg, 2.5 mmol) were reacted. Work-up and flash column chromatography (NH-silica, ethyl acetate/hexanes) gave a 26% yield (70 mg) of 263 as a solid: MS (ESI+) m/z 545.1 (M+H).

Example 264 10-[5-Fluoro-2-(hydroxymethyl)-3-[1-methyl-5-({5-[1-(oxetan-3-yl)piperidin-4-yl]pyridine-2-yl}amino)-6-oxo-1,6-dihydropyridin-3-yl]phenyl]-4,4-dimethyl-1,10-diazatricyclo[6.4.0.0$^{2,6}$]dodeca-2(6),7-dien-9-one 264

Example 264a tert-Butyl 4-(6-(5-Bromo-1-methyl-2-oxo-1,2-dihydropyridin-3-ylamino)pyridin-3-yl)piperidine-1-carboxylate 264a Following Example 112a, tert-butyl 4-(6-aminopyridin-3-yl)piperidine-1-carboxylate (1.9 g, 5.5 mmol), 3,5-dibromo-1-methylpyridin-2(1H)-one (1.47 g, 5.5 mmol), cesium carbonate (5.36 g, 16.5 mmol), tris(dibenzylideneacetone)dipalladium(0) (0.53 g, 0.55 mmol), Xantphos (0.63 g, 1.1 mmol) and 1,4-dioxane (50 mL) were heated at 100° C. for 8 hours. Work-up and concentrated to dryness. Wash the resulting solid with diethyl ether, filtered and give 56% yield (1.4 g) of 264a as a grey solid: MS (ESI+) m/z 465.2 (M+H).

Example 264b 5-Bromo-1-methyl-3-(5-(piperidin-4-yl)pyridin-2-ylamino)pyridin-2(1H)-one 264b Following Example 121c, 264a (0.58 g, 1.25 mmol), trifluoroacetic acid (0.96 mL, 12.5 mmol) and methylene chloride (20 mL) were reacted. Work-up and concentrated to afford a quantitative yield of 264b (454 mg) as yellow oil, which was used without purification in the next step. MS (ESI+) m/z 365.2 (M+H).

Example 264c 5-Bromo-1-methyl-3-(5-(1-(oxetan-3-yl)piperidin-4-yl)pyridin-2-ylamino)pyridin-2(1H)-one 264c Following Example 214b, 264b (450 mg, 1.25 mmol), oxetan-3-one (800 mg, 11.1 mmol) in methanol (10 mL) were mixed. Sodium cyanoborohydride (236 mg, 3.75 mmol) and zinc chloride (256 mg, 1.88 mmol) in methanol (10 mL) was added, and the reaction was heated at 48° C. for 12 hours. Work-up and flash column chromatography (silica, 60:35:5 methylene chloride/diethyl ether/methanol) afford a 30% yield (160 mg) of 264c as a light green solid: MS (ESI+) m/z 421.1 (M+H).

Following Example 121b, 264c (160 mg, 0.38 mmol), 230a (188 mg, 0.38 mmol), 1M sodium carbonate solution (1.5 mL, 1.5 mmol), tetrakis(triphenylphosphine)-palladium (0) (22 mg, 0.019 mmol) and 1,2-dimethoxyethane (3.5 mL) were heated at 130° C. for 15 minutes in the microwave reactor. Work-up and flash column chromatography (silica, 9:1 methylene chloride/methanol) gave a mixture (110 mg) of compound 264c and 264 as yellow oil. The mixture (110 mg) was deprotected using the same procedure as for 121, except using a mixture of THF (1 mL), water (0.5 mL) and isopropanol (1 mL), and lithium hydroxide monohydrate (50 mg, 1.2 mmol). Work-up and flash column chromatography (NH-silica, ethyl acetate/hexanes) give a 56% yield (60 mg) of compound 264 as a yellow solid: MS (ESI+) m/z 667.6 (M+H).

Example 265 2-(5-Fluoro-2-(hydroxymethyl)-3-(1-methyl-5-(5-(1-(oxetan-3-yl)piperidin-4-yl)pyridin-2-ylamino)-6-oxo-1,6-dihydropyridin-3-yl)phenyl)-3,4,6,7,8,9-hexahydropyrazino[1,2-a]indol-1(2H)-one 265

Example 265a 4-Fluoro-2-(1-methyl-5-(5-(1-(oxetan-3-yl)piperidin-4-yl)pyridin-2-ylamino)-6-oxo-1,6-dihydropyridin-3-yl)-6-(1-oxo-3,4,6,7,8,9-hexahydropyrazino[1,2-a]indol-2(1H)-yl)benzyl Acetate 265a Following Example 121b, 264c (210 mg, 0.5 mmol), 4-fluoro-2-(1-oxo-3,4,6,7,8,9-hexahydro-pyrazino[1,2-a]indol-2(1H)-yl)-6-(4,4,5,5-tetramethyl-1,3,2-dioxaborolan-2-yl)benzyl acetate 210d (242 mg, 0.5 mmol), 1M sodium carbonate solution (2 mL, 2 mmol), tetrakis(triphenylphosphine)palladium(0) (29 mg, 0.025 mmol) and 1,2-dimethoxyethane (5 mL) were heated at 130° C. for 15 minutes in the microwave reactor. Work-up and flash column chromatography (silica, 9:1 methylene chloride/methanol) gave a 69% yield (240 mg) of 265a as brown oil: MS (ESI+) m/z 695.5 (M+H).

Following Example 121, a mixture of THF (2 mL), water (1 mL) and isopropanol (2 mL), 265a (240 mg, 0.35 mmol) and lithium hydroxide monohydrate (100 mg, 2.5 mmol) were reacted. Work-up and flash column chromatography (NH-silica, ethyl acetate/hexanes) give a 30% yield (70 mg) of 265 as a yellow solid: MS (ESI+) m/z 653.6 (M+H).

Example 266 10-[5-Fluoro-2-(hydroxymethyl)-3-{4-methyl-6-[(2-methyl-1,2,3,4-tetrahydroisoquinolin-6-yl)amino]-5-oxo-4,5-dihydropyrazin-2-yl}phenyl]-4,4-dimethyl-1,10-diazatricyclo[6.4.0.0²,⁶]dodeca-2(6),7-dien-9-one 266

Example 266a 5-Bromo-1-methyl-3-(2-methyl-1,2,3,4-tetrahydroisoquinolin-6-ylamino)pyridin-2(1H)-one 266a

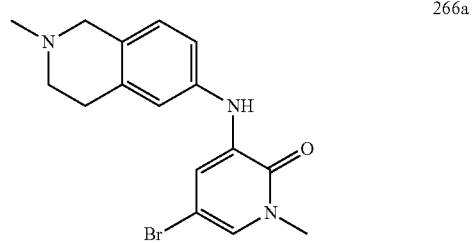 [SMILES: CN1CCc2cc(Nc3cc(Br)cn(C)c3=O)ccc2C1]

266a

A 100 mL round bottom flask with a magnetic stirrer was charged with 258b (350 mg, 0.8 mmol), formaldehyde (37% aqueous soln, 4.1 mmol), NaBH₃CN (150 mg, 2.4 mmol), ZnCl₂ (170 mg, 1.2 mmol) in methanol (46 mL). The mixture was stirred for 16 h at room temperature. After this time, the mixture was concentrated under reduced pressure and 10% aqueous K₂CO₃ (25 mL). The desired product crashed out of this mixture and was filtered. Upon washing with diethyl ether (20 mL) afforded a 85% yield (240 mg) of 266a.

Example 266b 10-[5-Fluoro-2-(acetoxymethyl)-3-{4-methyl-6-[(2-methyl-1,2,3,4-tetrahydroisoquinolin-6-yl)amino]-5-oxo-4,5-dihydropyrazin-2-yl}phenyl]-4,4-dimethyl-1,10-diazatricyclo[6.4.0.0²,⁶]dodeca-2(6),7-dien-9-one 266b

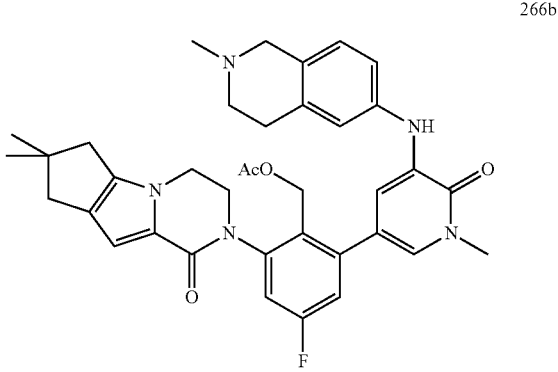 [SMILES: CC(=O)OCc1c(-c2cc(Nc3ccc4c(c3)CCN(C)C4)c(=O)n(C)c2)cc(F)cc1N1CCn2c(cc3c2CC(C)(C)C3)C1=O]

266b

A microwave tube equipped with a magnetic stirrer was charged with 266a (240 mg, 0.7 mmol), 210d (460 mg, 0.9 mmol), 1,2-dimethoxyethane (8 mL) and 1M aqueous sodium carbonate (2 mL). After bubbling N₂ for 15 min, Pd(PPh₃)₄ (40 mg, 0.03 mmol) was added. The mixture was heated in microwave to 120° C. for 10 min. After this time, ethyl acetate (5 mL) and water (5 mL) were added. The separated aqueous layer was extracted with ethyl acetate (2×5 mL). The combined organics were washed with brine (10 mL), dried over sodium sulfate, filtered and concentrated under reduced pressure. The resulting residue was purified by column chromatography eluting with a gradient of methylene chloride—9:1 methylene chloride:methanol to afford a 27% yield (120 mg) of 266b.

A 25 mL round bottom flask with a magnetic stirrer was charged with 266b (120 mg, 0.2 mmol), lithium hydroxide (40 mg, 0.9 mmol), THF (1 mL), isopropanol (1 mL) and water (2 mL). The mixture stirred at rt for 30 min. After this time, ethyl acetate (5 mL) and water (5 mL) were added. The separated aqueous layer was extracted with ethyl acetate (2×5 mL). The combined organics were washed with brine (10 mL), dried over sodium sulfate, filtered and concentrated under reduced pressure. The resulting residue was purified by column chromatography using the Biotage KPNH 12+M column eluting with a gradient of hexanes—ethyl acetate to afford a 45% yield (50 mg) of 266. MS (ESI+) m/z 597.4 (M+H).

Example 267 5-[5-Fluoro-2-(hydroxymethyl)-3-(1-methyl-5-{[5-(1-methylpiperidin-4-yl)pyridin-2-yl]amino}-6-oxo-1,6-dihydropyridin-3-yl)phenyl]-8-thia-5-azatricyclo[7.4.0.0$^{2,7}$]trideca-1(9),2(7)-dien-6-one 267

Example 267a [4-Fluoro-2-(1-methyl-5-{[5-(1-methylpiperidin-4-yl)pyridin-2-yl]amino}-6-oxo-1,6-dihydropyridin-3-yl)-6-{6-oxo-8-thia-5-azatricyclo[7.4.0.0$^{2,7}$]-trideca-1(9),2(7)-dien-5-yl}phenyl] methyl Acetate 267a

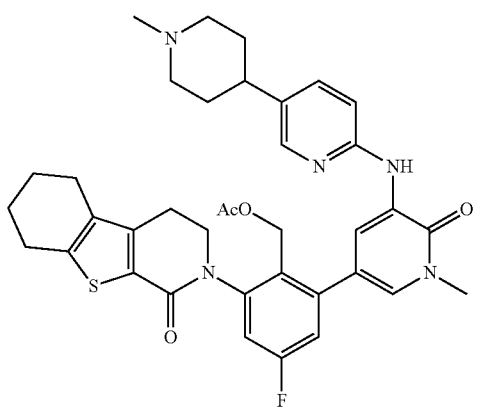

A sealed tube was charged with the mixture of 5-bromo-1-methyl-3-(5-(1-methylpiperidin-4-yl)pyridin-2-ylamino)pyridin-2(1H)-one 130c (400 mg, 1.0 mmol), (4-fluoro-2-{6-oxo-8-thia-5-azatricyclo[7.4.0.0$^{2,7}$]trideca-1(9),2(7)-dien-5-yl}-6-(4,4,5,5-tetramethyl-1,3,2-dioxaborolan-2-yl)phenyl)methyl acetate 247b (534 mg, 1.0 mmol), Pd(dppf)Cl$_2$ (87 mg, 0.1 mmol), K$_3$PO$_4$·3H$_2$O (569 mg, 2.0 mmol), and NaOAc (175 mg, 2.0 mmol) in CH$_3$CN (20 mL). The system was evacuated and then refilled with N$_2$. And the reaction mixture was heated at 110° C. for 2 h. Then, the mixture was cooled to room temperature and filtered. The filtrate was concentrated under reduced pressure and the resulting residue was purified by column chromatography eluting with 10:1 methylene chloride/methanol to give 267a as a brown solid (350 mg, 49%). MS: [M+H]$^+$ 670.

A solution of 267a (100 mg, 0.15 mmol) in propan-2-ol (5 mL), tetrahydrofuran (5 mL) and water (1 mL) was added LiOH (358 mg, 15 mmol). The mixture was stirred at 30° C. for 2 h. It was then evaporated and the residue was purified by prep-HPLC to afford 267 as a yellow solid (18 mg, 19%). MS: (M+H)$^+$ 628. $^1$H NMR (500 MHz, MEOD) δ 1.83-1.96 (m, 8H), 2.53-2.66 (m, 8H), 2.85 (t, 2H), 2.92-2.97 (m, 1H), 3.04-3.07 (m, 1H), 3.23-3.26 (d, 2H), 3.98-4.01 (m, 1H), 4.12-4.15 (m, 1H), 4.48-4.55 (m, 2H), 7.05 (d, 1H), 7.20-7.23 (m, 2H), 7.39 (d, 1H), 7.55-7.57 (m, 1H), 8.12 (s, 1H), 8.65 (s, 1H).

Example 268 5-{3-[5-({5-[2-(Dimethylamino)ethoxy]pyridin-2-yl}amino)-1-methyl-6-oxo-1,6-dihydropyridin-3-yl]-5-fluoro-2-(hydroxymethyl)phenyl}-8-thia-5-azatricyclo[7.4.0.0$^{2,7}$]trideca-1(9),2(7)-dien-6-one 268

Example 268a N,N-Dimethyl-2-(6-nitropyridin-3-yloxy)ethanamine 268a

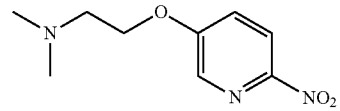

A mixture of 6-nitropyridin-3-ol (0.5 g, 3.57 mmol), 2-chloro-N,N-dimethylethanamine hydrochloride (0.61 g, 4.29 mmol) and Cs$_2$CO$_3$ (2.56 g, 7.85 mmol) in DMF (7 mL) was stirred at 120° C. in a sealed tube for 15 hr. The mixture was filtered and the filtrate was worked up with ethyl acetate and water. The aqueous phase was extracted with ethyl acetate. The combined extracts were dried over sodium sulfate and concentrated under reduced pressure. The residue was purified on flash column to give 268a (0.46 g, 61%). MS: [M+H]$^+$ 212.

Example 268b 5-(2-(Dimethylamino)ethoxy)pyridin-2-amine 268b

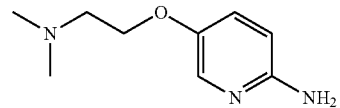

A 100-mL Parr hydrogenation bottle was purged with nitrogen and charged with 268a (0.92 g, 4.36 mmol), 10% palladium on carbon (50% wet, 0.2 g) and methanol (30 mL). The bottle was evacuated, charged with hydrogen gas to a pressure of 25 psi and shaken for 2 h on a Parr hydrogenation apparatus. The hydrogen was then evacuated and nitrogen charged to the bottle. The catalyst was removed by filtration through a pad of Celite and the filtrate was concentrated under reduced pressure to afford 268b (0.66 g, 83%). MS: [M+H]$^+$ 182.

Example 268c 5-Bromo-3-(5-(2-(dimethylamino)ethoxy)pyridin-2-ylamino)-1-methy-1pyridin-2(1H)-one 268c

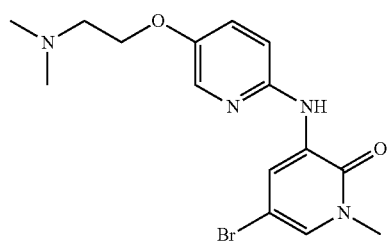 [SMILES: CN(C)CCOc1ccc(Nc2cc(Br)cn(C)c2=O)nc1]

A mixture of 268b (570 mg, 3.15 mmol), XantPhos (109 mg, 0.19 mmol), Pd$_2$dba$_3$ (230 mg, 0.25 mmol), 3,5-dibromo-1-methylpyridin-2(1H)-one (918 mg, 3.46 mmol) and Cs$_2$CO$_3$ (2.05 g. 6.3 mmol) in 1,4-dioxane (20 mL) was heated at reflux for 2 h. After the completion of the reaction, the mixture was filtered off and washed with methanol (100 mL). The filtrate was evaporated in vacuo. The residue was purified on reverse phase Combi-flash to give 268c (922 mg, 80%). MS: [M+H]$^+$ 367.

Example 268d {2-[5-({5-[2-(Dimethylamino)ethoxy]pyridin-2-yl}amino)-1-methyl-6-oxo-1,6-dihydropyridin-3-yl]-4-fluoro-6-{6-oxo-8-thia-5-azatricyclo[7.4.0.0$^{2,7}$]trideca-1(9),2(7)-dien-5-yl}phenyl}methyl Acetate 268d

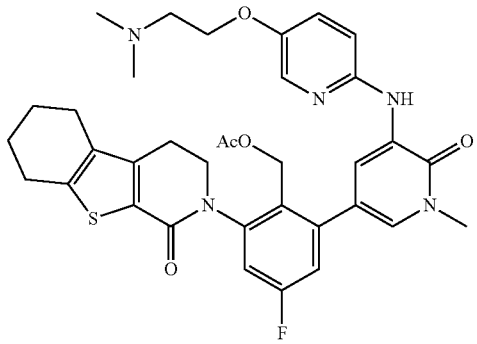 [SMILES: CC(=O)OCc1c(-c2cc(Nc3ccc(OCCN(C)C)cn3)c(=O)n(C)c2)cc(F)cc1N1CCc2c(sc3c2CCCC3)C1=O]

A mixture of 268c (360 mg, 0.99 mmol), (4-fluoro-2-{6-oxo-8-thia-5-azatricyclo[7.4.0.0$^{2,7}$]trideca-1(9),2(7)-dien-5-yl}-6-(4,4,5,5-tetramethyl-1,3,2-dioxaborolan-2-yl)phenyl) methyl acetate 212b (494 mg, 0.99 mmol), PdCl$_2$(dppf) (86 mg, 0.12 mmol), K$_3$PO$_4$ (150 mg), and NaOAc (50 mg) in MeCN (6 mL) and water (2 mL) was heated at 110° C. in a sealed tube for 2 h. The solvent was evaporated in vacuo. The residue was purified on reverse phase Combi-flash to give 268d (367 mg, 60%). MS: [M+H]$^+$ 660.

A mixture of 268d (700 mg, 1.06 mmol) and LiOH hydrate (446 mg, 10.6 mmol) in isopropanol (15 mL) and water (5 mL) was stirred at 30° C. for 2 h. The mixture was evaporated in vacuo and the residue was extracted with ethyl acetate (2×20 mL). The combined extracts were concentrated under reduced pressure. The residue was purified on prep-HPLC to give 268 (94 mg, 14%). MS: [M+H]$^+$ 618. $^1$H NMR (500 MHz, CDCl3) δ 8.54 (d, J=2.0, 1H), 7.95 (d, J=3.0, 1H), 7.80 (s, 1H), 7.48 (d, J=2.5, 1H), 7.23-7.21 (m, 1H), 7.16-7.14 (m, 1H), 6.98-6.96 (m, 1H), 6.81 (d, J=9.0, 1H), 4.57 (d, J=11.5, 1H), 4.30 (t, J=10.5, 1H), 4.20-4.02 (m, 4H), 3.87-3.80 (m, 1H), 3.69 (s, 3H), 3.00-2.84 (m, 4H), 2.75-2.73 (m, 2H), 2.59-2.48 (m, 2H), 2.37 (s, 6H), 1.94-1.83 (m, 4H).

Example 269 5-[3-(5-{[5-(4-Ethylpiperazin-1-yl)pyridine-2-yl]amino}-1-methyl-6-oxo-1,6-dihydropyridin-3-yl)-5-fluoro-2-(hydroxymethyl)phenyl]-8-thia-5-azatricyclo-[7.4.0.0$^{2,7}$]trideca-1(9),2(7)-dien-6-one 269

Example 269a 5-[3-(5-{[5-(4-Ethylpiperazin-1-yl)pyridine-2-yl]amino}-1-methyl-6-oxo-1,6-dihydropyridin-3-yl)-5-fluoro-2-(hydroxymethyl)phenyl]-8-thia-5-azatricyclo-[7.4.0.0$^{2,7}$]trideca-1(9),2(7)-dien-6-one 269a

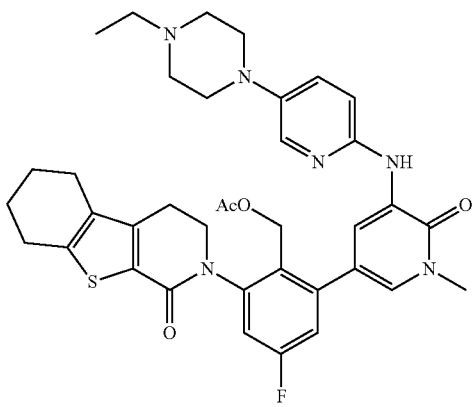 [SMILES: CCN1CCN(c2ccc(Nc3cc(-c4cc(F)cc(N5CCc6c(sc7c6CCCC7)C5=O)c4COC(C)=O)cn(C)c3=O)nc2)CC1]

To a microwave tube equipped with a stirring bar, 5-bromo-3-(5-(4-ethyl-piperazin-1-yl)pyridin-2-ylamino)-1-methylpyridin-2(1H)-one 138c (300 mg, 0.765 mmol), boronic ester 212b (420.1 mg, 0.841 mmol), Pd(PPh$_3$)$_4$ (44.2 mg, 0.038 mmol), Na$_2$CO$_3$ aqueous solution (1.0 N, 2.52 mL, 2.52 mmol), 1,2-dimethoxyethane (4.0 mL) were added. The mixture was reacted in microwave at 130° C. for 15 min. Methylene chloride (200 mL) was added and the resulting mixture was washed with water (3×30 mL), brine (30 mL), dried over MgSO$_4$, filtered, and removed solvent in vacuo. Silica gel column chromatography (methanol:methylene chloride=5:95) gave acetate 269a.

To a round-bottomed flask equipped with a stirring bar, 269a, THF (5 mL), isopropanol (5 mL), water (5 mL), LiOH H$_2$O (300 mg) were added. The resulting mixture was stirred at RT for 1 hr. The solvent was removed in vacuo and the resulting residue was added to methylene chloride (200 mL), the solution was washed with water (3×30 mL), brine (30 mL), dried over MgSO$_4$, filtered, and removed solvent in vacuo. Silica gel column chromatography (methanol:methylene chloride=10:90) gave 269 as a light brown solid, 158 mg. MS (ESI+) m/z 643.4 (M+H).

Example 270 3-(5-((2-(Dimethylamino)ethyl)(methyl)amino)pyridin-2-ylamino)-5-(5-fluoro-2-(hydroxymethyl)-3-(6,6-dimethyl-3,4,6,7-tetrahydro-5H-cyclopenta-[4,5]thieno[2,3-c]pyridine-1(2H)-yl)phenyl)-1-methylpyridin-2(1H)-one 270

Example 270a N$^1$,N$^1$,N$^2$-Trimethyl-N$^2$-(6-nitropyridin-3-yl)ethane-1,2-diamine 270a

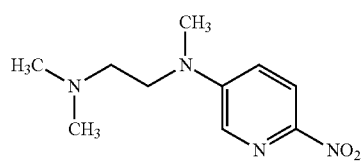

A 100-mL round-bottomed flask equipped with a magnetic stirrer was charged with 1e (3.00 g, 14.8 mmol), $N^1,N^1,N^2$-trimethylethane-1,2-diamine (2.26 g, 22.2 mmol) and N,N-dimethylacetamide (10 mL). N,N-di-isopropylethylamine (3.69 g, 28.6 mmol) and tetrabutylammonium iodide (8.18 g, 22.8 mmol) were added, and the reaction mixture was stirred at 90° C. for 14 h. After this time, the reaction was cooled to room temperature and poured into water (20 mL). The resulting mixture was extracted with ethyl acetate (100 mL). The organic layer was separated and dried over sodium sulfate. The drying agent was removed by filtration, and the filtrate was concentrated under reduced pressure. Purification of the resulting residue by column chromatography afforded 270a in 75% yield (2.50 g) as a yellow oil: $^1$H NMR (300 MHz, CDCl$_3$) δ 8.15 (d, 1H, J=9.1 Hz), 7.98 (d, 1H, J=3.2 Hz), 7.00 (dd, 1H, J=9.1, 3.2 Hz), 3.58 (t, 1H, J=6.9 Hz), 3.14 (s, 3H), 2.52 (t, 2H, J=7.1 Hz), 2.29 (s, 6H); MS (ESI+) m/z 225.1 (M+H).

Example 270b $N^5$-(2-(Dimethylamino)ethyl)-$N^5$-methylpyridine-2,5-diamine 270b

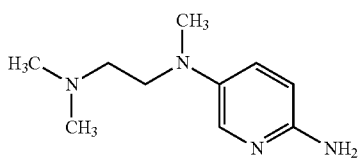

A 250-mL Parr reactor bottle was purged with nitrogen and charged with 10% palladium on carbon (50% wet, 1.00 g dry weight) and a solution of 270a (2.20 g, 9.80 mmol) in ethanol (150 mL). The bottle was attached to a Parr hydrogenator, evacuated, charged with hydrogen gas to a pressure of 50 psi and shaken for 3 h. After this time, the hydrogen was evacuated, and nitrogen was charged into the bottle. Celite 521 (1.00 g) was added, and the mixture was filtered through a pad of Celite 521. The filter cake was washed with ethanol (2×25 mL), and the combined filtrates were concentrated to dryness under reduced pressure to afford a quantitative yield of 270b (1.91 g) as a purple oil: $^1$H NMR (500 MHz, CDCl$_3$) δ 7.67 (d, 1H, J=2.9 Hz), 7.05 (dd, 1H, J=8.5, 2.9 Hz), 6.48 (dd, 1H, J=8.9, 0.5 Hz), 4.04 (br s, 2H), 3.28 (t, 2H, J=7.1 Hz), 2.84 (s, 3H), 2.43 (t, 2H, J=7.4 Hz), 2.26 (s, 6H); MS (ESI+) m/z 195.2 (M+H).

Example 270c 5-Bromo-3-(5-((2-(dimethylamino)ethyl)(methyl)amino)pyridin-2-ylamino)-1-methyl-pyridin-2(1H)-one 270c

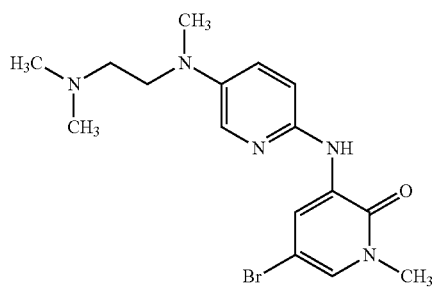

A 100-mL two-neck round-bottomed flask equipped with a reflux condenser, magnetic stirrer and nitrogen inlet was charged with 270b (1.00 g, 5.20 mmol), 3,5-dibromo-1-methylpyridin-2(1H)-one (1.53 g, 5.72 mmol), cesium carbonate (5.09 g, 15.6 mmol), and 1,4-dioxane (52 mL). After bubbling nitrogen through the resulting suspension for 30 min, Xantphos (257 mg, 0.442 mmol) and tris(dibenzylidene-acetone)dipalladium(0) (239 mg, 0.260 mmol) were added, and the reaction mixture was heated at reflux for 3 h. After this time, the mixture was cooled to room temperature and diluted with ethyl acetate (150 mL) and water (30 mL). The organic layer was separated, and the aqueous layer was extracted with ethyl acetate (3×150 mL). The combined organic layers were dried over sodium sulfate and concentrated under reduced pressure. The residue was triturated with methanol (20 mL) to afford a 63% yield (700 mg) of 270c as an off-white solid: mp 161-163° C.; $^1$H NMR (300 MHz, DMSO-d$_6$) δ 8.50 (d, 1H, J=2.3 Hz), 8.39 (s, 1H), 7.75 (d, 1H, J=2.4 Hz), 7.40 (d, 1H, J=2.4 Hz), 7.17 (m, 2H), 3.50 (s, 3H), 3.56 (t, 2H, J=6.9 Hz), 2.86 (s, 3H), 2.35 (t, 2H, J=7.1 Hz), 2.16 (s, 6H); MS (ESI+) m/z 380.1 (M+H).

Example 270d 3-(5-((2-(Dimethylamino)ethyl)(methyl)amino)pyridin-2-ylamino)-1-methyl-5-(4,4,5,5-tetramethyl-1,3,2-dioxaborolan-2-yl)pyridin-2(1H)-one 270d

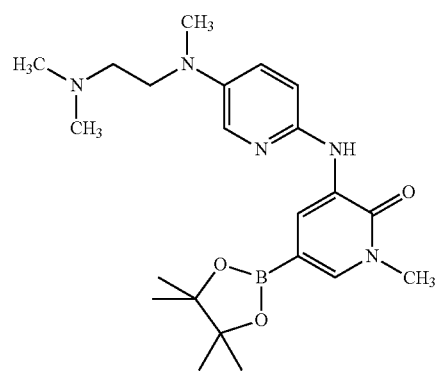

A 100-mL single-neck round-bottomed flask equipped with a reflux condenser, magnetic stirrer and nitrogen inlet was charged with 270c (500 mg, 1.32 mmol), 4,4,4',4',5,5,5',5'-octamethyl-2,2'-bi-1,3,2-dioxaborolane (668 mg, 2.63 mmol), potassium acetate (389 mg, 3.96 mmol), and 1,4-dioxane (10 mL). After bubbling nitrogen through the resulting suspension for 30 min, [1,1'-bis(diphenylphosphino)ferrocene]dichloropalladium(II) (97 mg, 0.132 mmol) was added, and the reaction mixture was heated at reflux for 1 h. After this time, the mixture was cooled to room temperature and diluted with ethyl acetate (150 mL) and water (30 mL). The organic layer was separated, and the aqueous layer was extracted with ethyl acetate (3×150 mL). The combined organic layers were dried over sodium sulfate and concentrated under reduced pressure to afford 270d in a crude quantitative yield. The residue was used without further purification.

A 50-mL three-neck round-bottomed flask equipped with a reflux condenser, magnetic stirrer and nitrogen inlet was charged with 247a (420 mg, 0.901 mmol), 270d (290 mg, 0.690 mmol), sodium carbonate (220 mg, 2.07 mmol), water (2 mL) and 1,4-dioxane (8 mL). After bubbling nitrogen through the resulting suspension for 30 min, tetrakis(triphenylphosphine)palladium(0) (80 mg, 0.069 mmol) was added, and the reaction mixture was heated at reflux for 2 h. After this time, the mixture was cooled to room temperature and diluted with ethyl acetate (150 mL) and water (30 mL). The organic layer was separated, and the aqueous layer was extracted with ethyl acetate (3×150 mL). The combined organic layers were dried over sodium sulfate and concentrated under reduced pressure. The residue was dissolved in a mixture of THF (10 mL), methanol (10 mL) and water (10 mL). Lithium hydroxide monohydrate (420 mg, 10.0 mmol) was added to the resulting solution. The mixture was stirred for 2 h at room temperature and then concentrated in vacuo. The residue was partitioned between ethyl acetate (150 mL) and water (30 mL). The organic layer was separated, and the aqueous layer was extracted with a 20% (v/v) solution of methanol in methylene chloride (3×150 mL). The combined organic layers were dried over sodium sulfate and concentrated under reduced pressure. The residue was purified by column chromatography (silica, 0% to 20% methanol/methylene chloride) to afford a 14% yield (53 mg) of 270 as an off-white solid: mp 106-107° C.; $^1$H NMR (500 MHz, DMSO-$d_6$) δ 8.45 (d, 1H, J=2.5 Hz), 8.20 (s, 1H), 7.69 (d, 1H, J=2.5 Hz), 7.32 (m, 2H), 7.17 (m, 3H), 4.84 (t, 1H, J=4.0 Hz), 4.33 (m, 2H), 4.04 (m, 1H), 3.84 (m, 1H), 3.58 (s, 3H), 3.03 (m, 1H), 2.89 (m, 1H), 2.75 (s, 2H), 2.53 (d, 2H, J=8.9 Hz), 2.32 (t, 2H, J=7.2 Hz), 2.14 (s, 6H), 1.23 (s, 6H); MS (ESI+) m/z 645.3 (M+H).

Example 271 10-[5-Fluoro-2-(hydroxymethyl)-3-(1-methyl-5-{[5-(1-methylazetidin-3-yl)pyridine-2-yl]amino}-6-oxo-1,6-dihydropyridin-3-yl)phenyl]-4,4-dimethyl-1,10-diazatricyclo[6.4.0.0$^{2,6}$]dodeca-2(6),7-dien-9-one 271

Example 271a 10-[5-Fluoro-2-(acetoxymethyl)-3-(1-methyl-5-{[5-(1-methylazetidin-3-yl)pyridine-2-yl]amino}-6-oxo-1,6-dihydropyridin-3-yl)phenyl]-4,4-dimethyl-1,10-diazatricyclo[6.4.0.0$^{2,6}$]dodeca-2(6),7-dien-9-one 271a

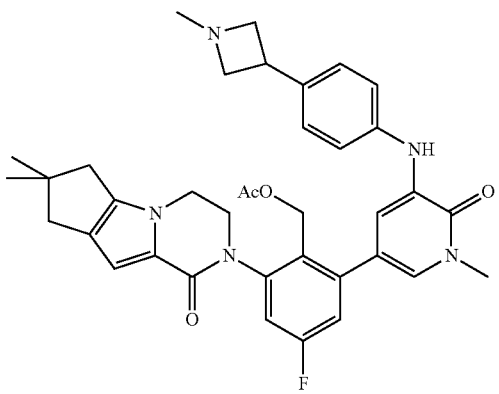

A microwave tube equipped with a magnetic stirrer was charged with 5-bromo-1-methyl-3-(5-(1-methylazetidin-3-yl)pyridin-2-ylamino)pyridin-2(1H)-one (172a) (216 mg, 0.6 mmol), 230a (390 mg, 0.8 mmol), 1,2-dimethoxyethane (8 mL) and 1M aqueous sodium carbonate (2 mL). After bubbling N$_2$ for 15 min, Pd(PPh$_3$)$_4$ (36 mg, 0.03 mmol) was added. The mixture was heated in microwave to 130° C. for 15 min. After this time, ethyl acetate (5 mL) and water (5 mL) were added. The separated aqueous layer was extracted with ethyl acetate (2×5 mL). The combined organics were washed with brine (10 mL), dried over sodium sulfate, filtered and concentrated under reduced pressure. The resulting residue was purified by column chromatography eluting with a gradient of methylene chloride—9:1 methylene chloride:methanol to afford a 30% yield (120 mg) of 271a.

A 25 mL round bottom flask with a magnetic stirrer was charged with 271a (110 mg, 0.2 mmol), lithium hydroxide (40 mg, 0.9 mmol), THF (1 mL), isopropanol (1 mL) and water (2 mL). The mixture stirred at rt for 30 min. After this time, ethyl acetate (5 mL) and water (5 mL) were added. The separated aqueous layer was extracted with ethyl acetate (2×5 mL). The combined organics were washed with brine (10 mL), dried over sodium sulfate, filtered and concentrated under reduced pressure. The resulting residue was purified by column chromatography using the Biotage KPNH 12+M column eluting with a gradient of hexanes—ethyl acetate to afford an 88% yield (94 mg) of 271. MS (ESI+) m/z 597.4 (M+H).

Example 272 10-[3-(5-{[5-(4-Ethylpiperazin-1-yl)pyridine-2-yl]amino}-1-methyl-6-oxo-1,6-dihydropyridin-3-yl)-5-fluoro-2-(hydroxymethyl)phenyl]-4,4-dimethyl-7-thia-10-azatricyclo[6.4.0.0$^{2,6}$]dodeca-1(8),2(6)-dien-9-one 272

Example 272a 10-[3-(5-{[5-(4-Ethylpiperazin-1-yl)pyridine-2-yl]amino}-1-methyl-6-oxo-1,6-dihydropyridin-3-yl)-5-fluoro-2-(acetoxymethyl)phenyl]-4,4-dimethyl-7-thia-10-azatricyclo[6.4.0.0$^{2,6}$]dodeca-1(8),2(6)-dien-9-one 272a

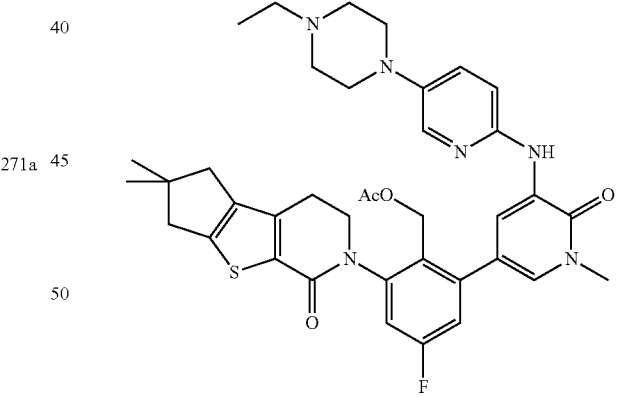

To a microwave tube equipped with a stirring bar, 182b (270 mg, 0.579 mmol), 3-(5-(4-ethylpiperazin-1-yl)pyridin-2-ylamino)-1-methyl-5-(4,4,5,5-tetramethyl-1,3,2-dioxaborolan-2-yl)pyridin-2(1H)-one 201a (382 mg, 0.868 mmol), Pd(PPh$_3$)$_4$ (34 mg, 0.029 mmol), Na$_2$CO$_3$ aqueous solution (1.0 N, 1.91 mL, 1.91 mmol), 1,2-dimethoxyethane (4.0 mL) were added. The mixture was reacted in microwave at 130° C. for 15 min. Methylene chloride (200 mL) was added and the resulting mixture was washed with water (30 mL×3), brine (30 mL×1), dried over MgSO$_4$, filtered, and removed solvent in vacuo. Silica gel column chromatography (methanol:methylene chloride=5:95) gave 272a.

To a round-bottomed flask equipped with a stirring bar, 272a, THF (5 mL), isopropanol (5 mL), water (5 mL), LiOH H$_2$O (300 mg) were added. The resulting mixture was stirred at RT for 1 hr. The solvent was removed in vacuo and the resulting residue was added to methylene chloride (200 mL), the solution was washed with water (30 mL×3), brine (30 mL×1), dried over MgSO$_4$, filtered, and removed solvent in vacuo. Silica gel column chromatography (methanol:methylene chloride=10:90) gave 272 as yellow solids, 143 mg. MS (ESI+) m/z 657.6 (M+H).

Example 273 10-{5-Fluoro-3-[5-({5-[4-(2-fluoroethyl)piperazin-1-yl]pyridine-2-yl}amino)-1-methyl-6-oxo-1,6-dihydropyridin-3-yl]-2-(hydroxymethyl)phenyl}-4,4-dimethyl-1,10-diazatricyclo[6.4.0.0$^{2,6}$]dodeca-2(6),7-dien-9-one 273

Example 273b 10-{5-Fluoro-3-[5-({5-[4-(2-fluoroethyl)piperazin-1-yl]pyridine-2-yl}amino)-1-methyl-6-oxo-1,6-dihydropyridin-3-yl]-2-(acetoxymethyl)phenyl}-4,4-dimethyl-1,10-diazatricyclo[6.4.0.0$^{2,6}$]dodeca-2(6),7-dien-9-one 273b

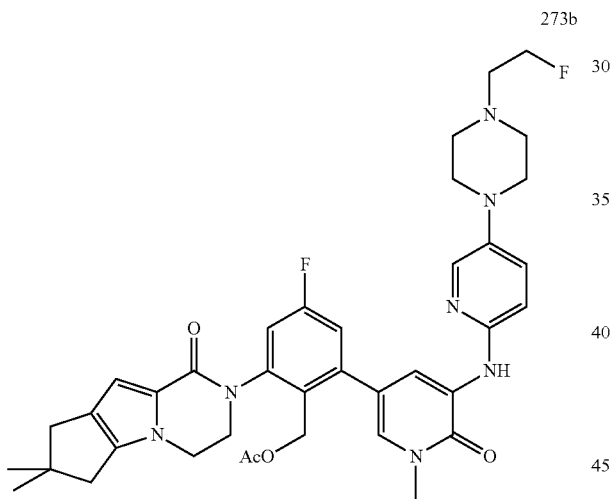

Following Example 186f, 273a (which was prepared in situ from 217d using conditions analogous to those used to prepare 270d) (200 mg, 0.49 mmol) and 189a (176 mg, 0.39 mmol) were reacted to give 273b (115 mg, 33% yield).

Following Example 186, 273b (115 mg, 0.16 mmol), 1N LiOH (0.82 mL), THF (3 mL) and isopropanol (3 mL) were reacted and purified via HPLC (acetonitrile/water/TFA). To the residue was added ethyl acetate and saturated aqueous sodium bicarbonate and the mixture stirred for ~15 min. The layers were separated and the organics were washed with brine, dried over anhydrous sodium sulfate, filtered and concentrated under vacuum to give 273 (23 mg, 22% yield). MS (ESI+) m/z 658.5 (M+H).

Example 274 10-[5-Fluoro-2-(hydroxymethyl)-3-(1-methyl-5-{[5-(morpholin-4-ylmethyl)pyridine-2-yl]amino}-6-oxo-1,6-dihydropyridin-3-yl)phenyl]-4,4-dimethyl-1,10-diazatricyclo[6.4.0.0$^{2,6}$]dodeca-2(6), 7-dien-9-one 274

Example 274a 5-Bromo-1-methyl-3-(5-(morpholinomethyl)pyridin-2-ylamino)pyridin-2(1H)-one 274a

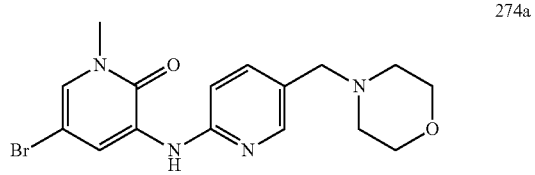 [SMILES: Cn1cc(Br)cc(Nc2ccc(CN3CCOCC3)cn2)c1=O]

Following Example 186d, compound 274a was prepared.

Example 274c 10-[5-Fluoro-2-(acetoxymethyl)-3-(1-methyl-5-{[5-(morpholin-4-ylmethyl)pyridine-2-yl]amino}-6-oxo-1,6-dihydropyridin-3-yl)phenyl]-4,4-dimethyl-1,10-diazatricyclo[6.4.0.0$^{2,6}$]dodeca-2(6),7-dien-9-one 274c

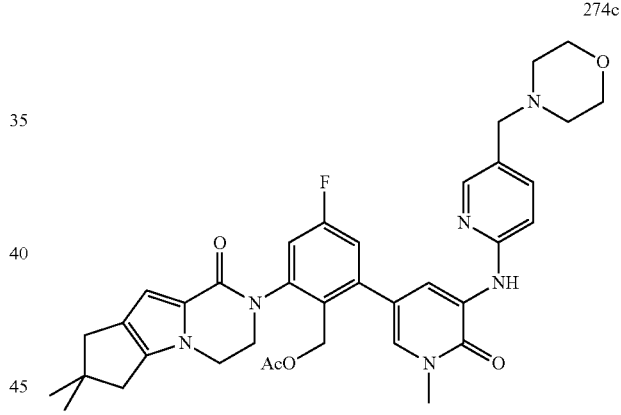

Following Examples 186e and 186f, 274a (300 mg, 0.79 mmol) in Step 1 to afford 274b in situ and then reacting with 189a (284 mg, 0.63 mmol) in Step 2 gave 274c (250 mg, 46% yield).

Following Example 119, 274c (250 mg, 0.36 mmol), 1N LiOH (1.5 mL), THF (3 mL) and isopropanol (3 mL) were reacted, purified via column chromatography: ISCO 12 g silica, 0-10% methanol, then triturated with methylene chloride/diethylether to give 274 (89 mg, 39% yield). MS (ESI+) m/z 627.5 (M+H).

Example 275 2-(2-(Hydroxymethyl)-3-(1-methyl-5-(5-(4-methylpiperazin-1-yl)pyridin-2-ylamino)-6-oxo-1,6-dihydropyridin-3-yl)phenyl)-3,4,6,7,8,9-hexahydropyrido[3,4-b]indolizin-1(2H)-one 275

A 100-mL single-neck round-bottomed flask equipped with a magnetic stirrer and nitrogen inlet was charged with 197e (210 mg, 0.560 mmol), 118f (330 mg, 0.710 mmol), sodium carbonate (175 mg, 1.70 mmol), water (2 mL) and 1,4-dioxane (8 mL). After bubbling nitrogen through the resulting suspension for 30 min, tetrakis(triphenyl-phosphine)palladium(0) (64 mg, 0.055 mmol) was added. A reflux condenser was attached to the flask, and the reaction mixture was heated at 100° C. for 2 h. After this time, the mixture was diluted with 90:10 methylene chloride/methanol (100 mL) and water (75 mL), and the layers were separated. The aqueous layer was extracted with 90:10 methylene chloride/methanol (2×50 mL), and the combined organic extracts were washed with brine (100 mL) and dried over sodium sulfate. The drying agent was removed by filtration. The filtrate was concentrated under reduced pressure, and the resulting residue was dissolved in a mixture of THF (3 mL), water (3 mL) and methanol (3 mL). Lithium hydroxide monohydrate (100 mg, 2.40 mmol) was added, and the reaction was stirred at room temperature for 2 h. After this time, the mixture was diluted with 90:10 methylene chloride/methanol (100 mL) and water (50 mL), and the layers were separated. The aqueous layer was extracted with 90:10 methylene chloride/methanol (2×75 mL), and the combined organic extracts were dried over sodium sulfate. The drying agent was removed by filtration. The filtrate was concentrated under reduced pressure, and the resulting residue was purified by flash column chromatography (silica, 0% to 10% methanol/methylene chloride) to afford 275 in 8% yield (35 mg) as an amorphous off-white solid: mp 180-181° C.; $^1$H NMR (500 MHz, DMSO-$d_6$) δ 8.54 (d, 1H, J=2.5 Hz), 8.31 (s, 1H), 7.84 (d, 1H, J=2.5 Hz), 7.42 (t, 1H, J=8.0 Hz), 7.35 (m, 1H), 7.26 (d, 2H, J=8.0 Hz), 7.19 (d, 1H, J=9.0 Hz), 6.00 (s, 1H), 4.69 (t, 1H, J=5.0 Hz), 4.31 (d, 2H, J=4.5 Hz), 3.99 (m, 1H), 3.95 (m, 1H), 3.88 (m, 2H), 3.57 (s, 3H), 3.05 (m, 5H), 2.90 (m, 1H), 2.70 (t, 2H, J=6.0 Hz), 2.42 (m, 5H), 2.19 (s, 3H), 1.91 (m, 2H), 2.73 (m, 2H); MS (ESI+) m/z 594.3 (M+H).

Example 276 10-[5-Fluoro-2-(hydroxymethyl)-3-{1-methyl-5-[(5-methyl-1H-pyrazol-3-yl)amino]-6-oxo-1,6-dihydropyridin-3-yl}phenyl]-4,4-dimethyl-1,10-diazatricyclo[6.4.0.0$^{2,6}$]dodeca-2(6),7-dien-9-one 276

Example 276a 10-[5-Fluoro-2-(hydroxymethyl)-3-{1-methyl-5-[(5-methyl-1H-pyrazol-3-yl)amino]-6-oxo-1,6-dihydropyridin-3-yl}phenyl]-4,4-dimethyl-1,10-diazatricyclo[6.4.0.0$^{2,6}$]dodeca-2(6),7-dien-9-one 276a

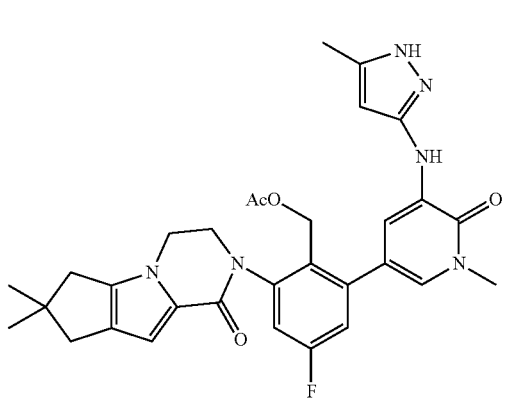

276a

A microwave tube equipped with a magnetic stirrer was charged with 5-bromo-1-methyl-3-(5-methyl-1H-pyrazol-3-ylamino)pyridin-2(1H)-one 112a (150 mg, 0.5 mmol), 230a (350 mg, 0.7 mmol), 1,2-dimethoxyethane (6.4 mL) and 1M aqueous sodium carbonate (1.6 mL). After bubbling N$_2$ for 15 min, Pd(PPh$_3$)$_4$ (31 mg, 0.03 mmol) was added. The mixture was heated in microwave to 130° C. for 15 min. After this time, ethyl acetate (5 mL) and water (5 mL) were added. The separated aqueous layer was extracted with ethyl acetate (2×5 mL). The combined organics were washed with brine (10 mL), dried over sodium sulfate, filtered and concentrated under reduced pressure. The resulting residue was purified by column chromatography eluting with a gradient of methylene chloride—60:35:5 methylene chloride:diethyl ether:methanol to afford a 16% yield (50 mg) of 276a.

A 25 mL round bottom flask with a magnetic stirrer was charged with 276a (50 mg, 0.1 mmol), lithium hydroxide (18 mg, 0.4 mmol), THF (0.4 mL), isopropanol (0.4 mL) and water (1 mL). The mixture stirred at rt for 30 min. After this time, ethyl acetate (5 mL) and water (5 mL) were added. The separated aqueous layer was extracted with ethyl acetate (2×5 mL). The combined organics were washed with brine (10 mL), dried over sodium sulfate and filtered. The mixture was concentrated under reduced pressure to near dryness when the desired product crashed out and was filtered. Upon washing with diethyl ether (10 mL) afforded an 87% yield (40 mg) of 276. MS (ESI+) m/z 531.4 (M+H).

Example 277 5-[5-Fluoro-2-(hydroxymethyl)-3-{1-methyl-5-[(5-{[methyl(propan-2-yl)amino]methyl}pyridine-2-yl)amino]-6-oxo-1,6-dihydropyridin-3-yl}phenyl]-8-thia-5-azatricyclo[7.4.0.0$^{2,7}$]trideca-1(9),2(7)-dien-6-one 277

Example 277a 5-[5-Fluoro-2-(acetoxymethyl)-3-{1-methyl-5-[(5-{[methyl(propan-2-yl)amino]methyl}pyridine-2-yl)amino]-6-oxo-1,6-dihydropyridin-3-yl}phenyl]-8-thia-5-azatricyclo[7.4.0.0$^{2,7}$]trideca-1(9),2(7)-dien-6-one 277a Following Example 186, 186e (270 mg, 0.74 mmol) produced in situ was reacted with 212a (267 mg, 0.59 mmol) in Step 2. Purified by column chromatography: ISCO 12 g silica, 50-100% ethyl acetate/hexanes then 0-15% MeOH/CH2Cl2 to give 277a (270 mg, 55% yield).

Following Example 119, 277a (270 mg, 0.41 mmol), 1N LiOH (2.0 mL), THF (4 mL) and isopropanol (4 mL) were reacted, and triturated with ether to give 277 (185 mg, 73% yield). MS (ESI+) m/z 616.4 (M+H).

Example 278 10-[5-Fluoro-2-(hydroxymethyl)-3-(4-methyl-6-{[4-(1-methylpiperidin-4-yl)phenyl]amino}-5-oxo-4,5-dihydropyrazin-2-yl)phenyl]-4,4-dimethyl-7-thia-10-azatricyclo[6.4.0.0$^{2,6}$]dodeca-1(8),2(6)-dien-9-one 278

Example 278a 10-[5-Fluoro-3-(4-methyl-6-{[4-(1-methylpiperidin-4-yl)phenyl]amino}-5-oxo-4,5-dihydropyrazin-2-yl)benzyl acetate]-4,4-dimethyl-7-thia-10-azatricyclo-[6.4.0.0$^{2,6}$]dodeca-1(8),2(6)-dien-9-one 278a

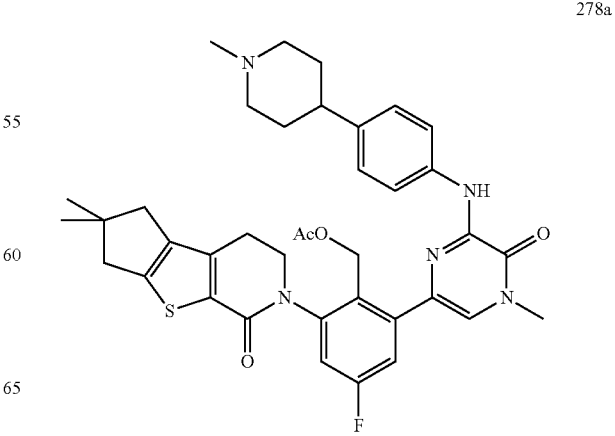

278a

Following Example 136d, 282c and (2-{4,4-dimethyl-9-oxo-7-thia-10-azatricyclo[6.4.0.0^{2,6}]dodeca-1(8),2(6)-dien-10-yl}-4-fluoro-6-(4,4,5,5-tetramethyl-1,3,2-dioxaborolan-2-yl)phenyl)methyl acetate 247b were reacted to give 278a in 62% yield. LCMS: (M+H)$^+$ 684

Following Example 136, 278a was converted to 278 in 39% yield. LCMS: (M+H)$^+$ 642. $^1$H NMR (500 MHz, DMSO) δ 9.22 (s, 1H), 7.90 (s, 1H), 7.87 (s, 1H), 7.48 (s, 1H), 7.36 (dd, J=9.5, 1H), 7.31 (dd, J=9, 1H), 7.16 (s, 1H), 7.14 (s, 1H), 4.46 (m, 2H), 4.05 (m, 2H), 3.85 (m, 2H), 3.54 (s, 3H), 3.01 (m, 1H), 2.92 (m, 3H), 2.75 (s, 2H), 2.53 (m, 2H), 2.44 (m, 1H), 2.27 (s, 3H), 2.13 (m, 2H), 1.70 (m, 4H), 1.22 (s, 6H).

Example 279 10-[5-Fluoro-2-(hydroxymethyl)-3-[1-methyl-5-({5-methyl-4H,5H,6H,7H-pyrazolo[1,5-a]pyrazin-2-yl}amino)-6-oxo-1,6-dihydropyridin-3-yl]phenyl]-4,4-dimethyl-7-thia-10-azatricyclo[6.4.0.0$^{2,6}$]dodeca-1(8),2(6)-dien-9-one 279

Example 279a (2-{4,4-Dimethyl-9-oxo-7-thia-10-azatricyclo[6.4.0.0$^{2,6}$dodeca-1(8),2(6)-dien-10-yl}-4-fluoro-6-[1-methyl-5-({5-methyl-4H,5H,6H,7H-pyrazolo[1,5-a]pyrazin-2-yl}amino)-6-oxo-1,6-dihydropyridin-3-yl]phenyl)methyl Acetate 279a

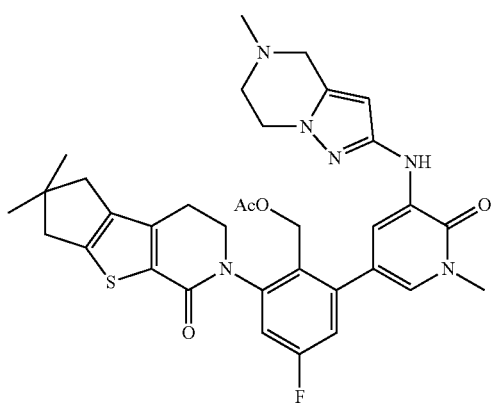

A 25 mL sealed tube was charged with 5-bromo-1-methyl-3-(5-methyl-4,5,6,7-tetrahydropyrazolo[1,5-a]pyrazin-2-ylamino)pyridin-2(1H)-one 146a (340 mg, 1.0 mmol), (2-{4,4-dimethyl-9-oxo-7-thia-10-azatricyclo[6.4.0.0$^{2,6}$]dodeca-1(8),2(6)-dien-10-yl}-4-fluoro-6-(4,4,5,5-tetramethyl-1,3,2-dioxaborolan-2-yl)phenyl)methyl acetate 247b (480 mg, 1.0 mmol), CH$_3$COONa (168 mg, 2.0 mmol), K$_3$PO$_4$ (546 mg, 2.0 mmol), PdCl$_2$(dppf) (84 mg, 0.1 mmol) suspended in CH$_3$CN (25 mL) and water (1 mL). The mixture was heated at 110° C. for 2 hours, evaporated, and the residue was purified by column chromatography eluting with 15:1 methylene chloride/methanol to give 279a as a brown solid (300 mg, 46%). MS: (M+H)$^+$ 645.

To a solution of 279a (300 mg, 0.46 mmol) in propan-2-ol (10 mL), tetrahydrofuran (10 mL) and water (2 mL) was added LiOH (1.1 g, 57 mmol). The mixture was stirred at 30° C. for 2 h. It was then evaporated and the residue was purified by prep-HPLC to afford 279 as a white solid (99 mg, 35%). MS: (M+H)$^+$ 603. $^1$H NMR (500 MHz, MEOD) δ 1.29 (d, 6H), 2.49 (s, 3H), 2.59 (d, 2H), 2.81 (s, 2H), 2.94-2.97 (m, 3H), 3.07-3.14 (m, 1H), 3.64 (s, 2H), 3.70 (s, 3H), 3.97-3.99 (m, 1H), 4.05-4.07 (t, 2H), 4.12-4.15 (m, 1H), 4.47-4.54 (m, 2H), 5.89 (s, 1H), 7.19-7.22 (m, 2H), 7.26 (d, 1H), 7.91 (s, 1H).

Example 280 10-[5-Fluoro-2-(hydroxymethyl)-3-(1-methyl-5-{[6-(oxetan-3-yl)-5,6,7,8-tetrahydro-1,6-naphthyridin-2-yl]amino}-6-oxo-1,6-dihydropyridin-3-yl)phenyl]-4,4-dimethyl-7-thia-10-azatricyclo[6.4.0.0$^{2,6}$]dodeca-1(8),2(6)-dien-9-one 280

Example 280a (2-{4,4-Dimethyl-9-oxo-7-thia-10-azatricyclo[6.4.0.0$^{2,6}$]dodeca-1(8),2(6)-dien-10-yl}-4-fluoro-6-(1-methyl-5-{[6-(oxetan-3-yl)-5,6,7,8-tetrahydro-1,6-naph-thyridin-2-yl]amino}-6-oxo-1,6-dihydropyridin-3-yl)phenyl)methyl Acetate 280a

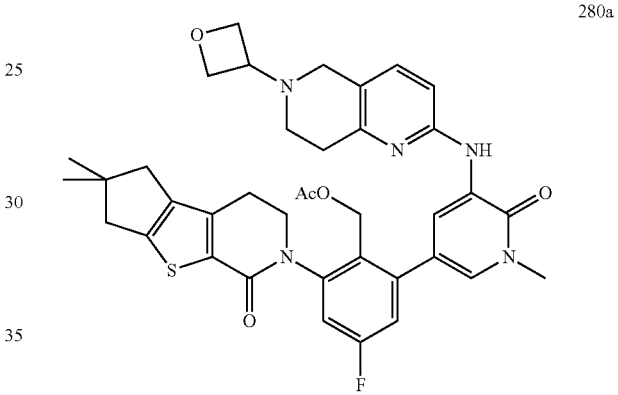

A 25 mL sealed tube was charged with 5-bromo-1-methyl-3-(6-(oxetan-3-yl)-5,6,7,8-tetrahydro-1,6-naphthyridin-2-ylamino)pyridin-2(1H)-one 219a (400 mg, 1.0 mmol), (2-{4,4-dimethyl-9-oxo-7-thia-10-azatricyclo[6.4.0.0$^{2,6}$]dodeca-1(8),2(6)-dien-10-yl}-4-fluoro-6-(4,4,5,5-tetramethyl-1,3,2-dioxaborolan-2-yl)phenyl)methyl acetate 247b (493 mg, 1.0 mmol), CH$_3$COONa (168 mg, 2.0 mmol), K$_3$PO$_4$ (546 mg, 2.0 mmol), PdCl$_2$(dppf) (84 mg, 0.1 mmol) suspended in CH$_3$CN (25 mL) and H$_2$O (1 mL). The mixture was heated at 110° C. for 2 hours. It was then evaporated and the residue was purified by column chromatography eluting with 20:1 methylene chloride/methanol (20:1) to give 280a as a brown solid (400 mg, 56%). MS: (M+H)$^+$ 698.

To a solution of 280a (400 mg, 0.57 mmol) in propan-2-ol (10 mL), tetrahydrofuran (10 mL) and water (2 mL) was added LiOH (1.4 g, 57 mmol). The mixture was stirred at 30° C. for 2 h. It was then evaporated and the residue was purified by prep-HPLC to afford 280 as a white solid (52 mg, 14%). MS: (M+H)$^+$ 656. $^1$H NMR (500 MHz, MEOD) δ 1.29 (d, 6H), 2.56-2.63 (q, 2H), 2.70-2.72 (t, 2H), 2.81 (s, 2H), 2.93-2.99 (m, 3H), 3.08-3.12 (m, 1H), 3.47 (s, 2H), 3.72-3.74 (m, 4H), 3.96-4.01 (m, 1H), 4.13-4.18 (m, 1H), 4.51-4.60 (q, 2H), 4.68-4.71 (t, 2H), 4.76-4.79 (t, 2H), 6.89 (d, 1H), 7.21-7.23 (d, 2H), 7.34 (d, 1H), 7.40 (s, 1H), 8.78 (s, 1H).

Example 281 5-[5-Fluoro-2-(hydroxymethyl)-3-(4-methyl-6-{[4-(1-methylpiperidin-4-yl)phenyl]amino}-5-oxo-4,5-dihydropyrazin-2-yl)phenyl]-8-thia-5-azatricyclo[7.4.0.0$^{2,7}$]trideca-1(9),2(7)-dien-6-one 281

Example 281a [4-Fluoro-2-(4-methyl-6-{[4-(1-methylpiperidin-4-yl)phenyl]amino}-5-oxo-4,5-dihydropyrazin-2-yl)-6-{6-oxo-8-thia-5-azatricyclo[7.4.0.0$^{2,7}$]trideca-1(9),2(7)-dien-5-yl}phenyl]methyl acetate 281a

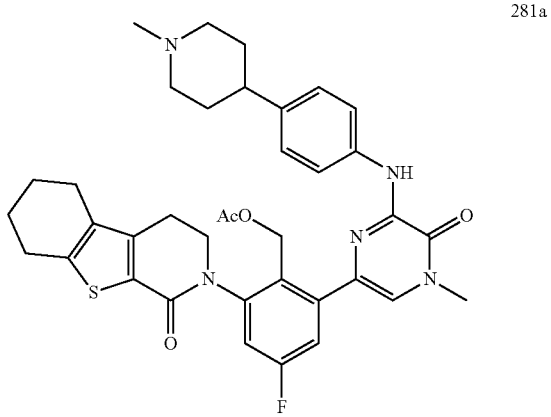 [SMILES: CC(=O)OCc1c(-c2cn(C)c(=O)c(Nc3ccc(C4CCN(C)CC4)cc3)n2)cc(F)cc1N1CCc2c(sc3c2CCCC3)C1=O]

Following Example 136d, 282c) and (4-fluoro-2-{6-oxo-8-thia-5-azatricyclo[7.4.0.0$^{2,7}$]trideca-1(9),2(7)-dien-5-yl}-6-(4,4,5,5-tetramethyl-1,3,2-dioxaborolan-2-yl)phenyl)methyl acetate 212b were reacted to give 281a in 73% yield. LCMS: (M+H)$^+$ 670

Following Example 136, 281a was converted to 281 in 70% yield. LCMS: (M+H)$^+$ 628. $^1$H NMR (500 MHz, DMSO) δ 9.21 (s, 1H), 7.87 (s, 1H), 7.85 (s, 1H), 7.47 (s, 1H), 7.35 (dd, J=10, 1H), 7.30 (dd, J=9, 1H), 7.16 (s, 1H), 7.14 (s, 1H), 4.84 (m, 1H), 4.48 (m, 1H), 4.40 (m, 1H), 3.86 (m, 1H), 3.53 (s, 3H), 2.96 (m, 1H), 2.87 (m, 4H), 2.78 (m, 2H), 2.42 (m, 2H), 2.19 (s, 3H), 1.96 (m, 2H), 1.80 (m, 4H), 1.62 (m, 5H).

Example 282 2-(5-Fluoro-2-(hydroxymethyl)-3-(4-methyl-6-(4-(1-methylpiperidin-4-yl)phenylamino)-5-oxo-4,5-dihydropyrazin-2-yl)phenyl)-3,4,6,7,8,9-hexahydropyrazino[1,2-a]indol-1(2H)-one 282

Example 282a tert-Butyl 4-(4-(6-Bromo-4-methyl-3-oxo-3,4-dihydropyrazin-2-ylamino)phenyl)piperidine-1-carboxylate 282a

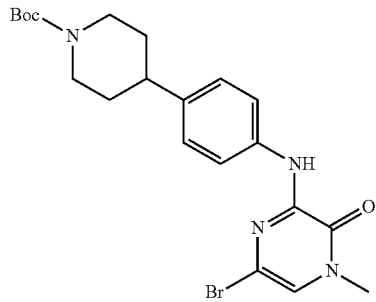

A mixture of tert-butyl 4-(4-aminophenyl)piperidine-1-carboxylate (2.5 g, 9.06 mmol) and 3,5-dibromo-1-methyl-pyrazin-2(1H)-one (2.2 g, 8.23 mmol) in isopropanol (30 mL) was heated at 85° C. for 15 h. After the reaction was finished, it was filtered and the solid was washed with isopropanol to afford 282a as a white solid (2.9 g, 80%). LCMS: (M+H)$^+$ 463

Example 282b 5-Bromo-1-methyl-3-(4-(piperidin-4-yl)phenylamino)pyrazin-2(1H)-one 282b

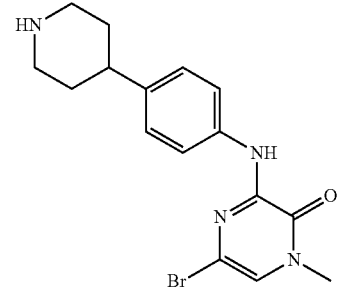

Following Example 247a, 282a was converted to 282b in 99% yield.

Example 282c 5-Bromo-1-methyl-3-(4-(1-methylpiperidin-4-yl)phenylamino)pyrazin-2(1H)-one 282c

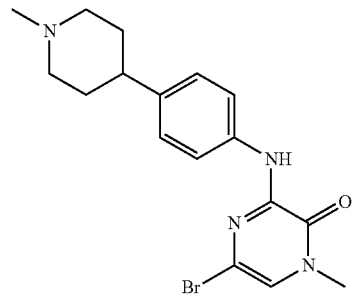

Following Example 247b, 282b was converted to 282c in 65% yield.

Example 282d 4-Fluoro-2-(4-methyl-6-(4-(1-methylpiperidin-4-yl)phenylamino)-5-oxo-4,5-dihydropyrazin-2-yl)-6-(1-oxo-3,4,6,7,8,9-hexahydropyrazino[1,2-a]indol-2(1H)-yl)benzyl acetate 282d

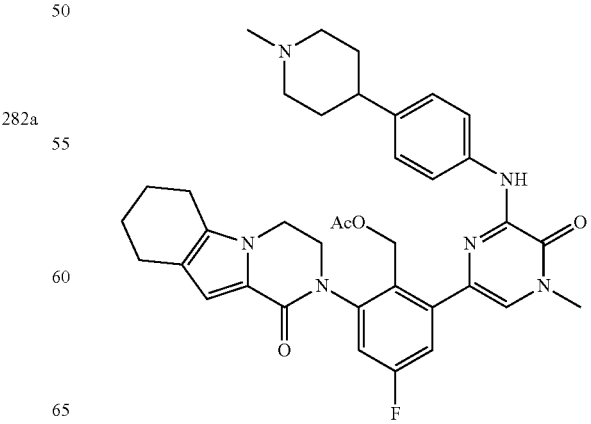

Following Example 247c, 282c and 4-fluoro-2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 210d were reacted to give 282d in 41% yield.

Following Example 136, 282d was converted to 282 in 36% yield. LCMS: (M+H)⁺ 611. ¹H NMR (500 MHz, DMSO) δ 9.22 (s, 1H), 7.90 (s, 1H), 7.88 (s, 1H), 7.49 (s, 1H), 7.36 (dd, J=9.5, 1H), 7.30 (dd, J=9.5, 1H), 7.17 (s, 1H), 7.15 (s, 1H), 6.54 (s, 1H), 4.47 (m, 2H), 4.15 (m, 3H), 3.88 (m, 2H), 2.91 (m, 2H), 2.59 (m, 2H), 3.05 (m, 1H), 2.46 (m, 3H), 2.25 (s, 3H), 2.07 (m, 2H), 1.80 (m, 2H), 1.70 (m, 6H).

Example 283 2-(5-Fluoro-2-(hydroxymethyl)-3-(4-methyl-6-(2-methyl-1,2,3,4-tetrahydroisoquinolin-6-ylamino)-5-oxo-4,5-dihydropyrazin-2-yl)phenyl)-3,4,6,7,8,9-hexahydropyrazino[1,2-a]indol-1(2H)-one 283

Example 283a 4-Fluoro-2-(4-methyl-6-(2-methyl-1,2,3,4-tetrahydroisoquinolin-6-ylamino)-5-oxo-4,5-dihydropyrazin-2-yl)-6-(1-oxo-3,4,6,7,8,9-hexahydropyrazino[1,2-a]indol-2(1H)-yl)benzyl acetate 283a

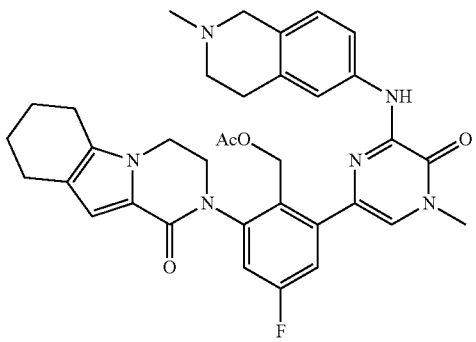

Following Example 148b, 290 mg of 4-fluoro-2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 210d and 209 mg 5-bromo-1-methyl-3-(2-methyl-1,2,3,4-tetrahydroisoquinolin-6-ylamino)pyrazin-2(1H)-one 221b were reacted to give 283a as a yellow solid (217 mg, 58%). MS: [M+H]⁺ 699

Following Example 148, 283a was converted to 283 as a white solid (84 mg, 43%). ¹H NMR (500 MHz, DMSO) δ 9.15 (s, 1H), 7.82 (s, 1H), 7.65 (d, J=8, 1H), 7.52 (s, 1H), 7.39 (dd, J=10, 1H), 7.31 (dd, J=10, 1H), 6.96 (d, J=8.0, 1H), 6.53 (s, 1H), 4.87 (s, 1H), 4.49 (m, 1H), 4.42 (m, 1H), 4.13 (m, 3H), 3.88 (m, 1H), 3.54 (s, 3H), 3.41 (s, 2H), 3.30 (s, 1H), 2.76 (d, J=5.5, 6H), 2.58 (m, 5H), 23.2 (s, 3H), 1.79 (s, 2H), 1.70 (s, 2H).

Example 284 10-(3-{5-[(6-Ethyl-5,6,7,8-tetrahydro-1,6-naphthyridin-2-yl)amino]-1-methyl-6-oxo-1,6-dihydropyridin-3-yl}-5-fluoro-2-(hydroxymethyl)phenyl)-4,4-dimethyl-1,10-diazatricyclo[6.4.0.0²,⁶]dodeca-2(6),7-dien-9-one 284

In a 48-mL sealed tube equipped with a magnetic stirring bar were placed 5-bromo-1-methyl-3-(6-ethyl-5,6,7,8-tetrahydro-1,6-naphthyridin-2-ylamino)pyridin-2(1H)-one (143 mg, 0.4 mmol), 10-[2-(acetoxymethyl)-3-(4,4,5,5-tetramethyl[1,3,2]-dioxaborolan-2-yl)-5-fluorophenyl]-4,4-dimethyl-1,10-diazatricyclo[6.4.0.0²,⁶]-dodeca-2(6),7-dien-9-one 230a (496 mg, 1.0 mmol), Pd(PPh₃)₄ (23 mg, 0.020 mmol) in 2 N Na₂CO₃ (4 mL) and DME (4 mL). After the reaction mixture was stirred at 100° C. for 1 h, it was purified by flash chromatography (dichloromethane:methanol, 3:1) to give 7% (18 mg) of 284 MS(ESI⁺) m/z 611.5 (M+H).

Example 285 10-{3-[5-({5-Ethyl-4H,5H,6H,7H-pyrazolo[1,5-a]pyrazin-2-yl}amino)-1-methyl-6-oxo-1,6-dihydropyridin-3-yl]-5-fluoro-2-(hydroxymethyl)phenyl}-4,4-dimethyl-1,10-diazatricyclo[6.4.0.0²,⁶]dodeca-2(6),7-dien-9-one 285

Example 285a 5-Ethyl-2-nitro-4,5,6,7-tetrahydropyrazolo[1,5-a]pyrazine 285a

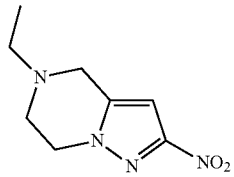

A sealed tube equipped with a magnetic stirrer was charged with 1-(2-bromoethyl)-5-(bromomethyl)-3-nitro-1H-pyrazole 101c (2.8 g, 9 mmol) 2M ethylamine solution in THF (27 mL). The resulting mixture was heated to 35° C. overnight. After this time, the reaction mixture was concentrated under reduced pressure, and to the residue was added water (50 mL) and ethyl acetate (50 mL). The aqueous layer was separated and extracted with ethyl acetate (2×50 mL). The combined organic extracts were washed with brine (100 mL) and dried over sodium sulfate. The resulting solution was concentrated under reduced pressure to afford a 100% yield (1.8 g) of crude 285a.

Example 285b 5-Ethyl-4,5,6,7-tetrahydropyrazolo[1,5-a]pyrazin-2-amine 285b

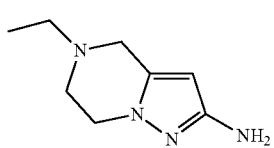

A 500-mL Parr hydrogenation bottle was charged with 285a (1.8 g, 9 mmol), 10% palladium on carbon (50% wet, 500 mg dry weight) and ethanol (100 mL). The bottle was evacuated, charged with hydrogen gas to a pressure of 50 psi and shaken for 1 h on a Parr hydrogenation apparatus. The catalyst was removed by filtration through a pad of Celite 521 washing with 1:1 methylene chloride:methanol (500 mL). The resulting solution was concentrated under reduced pressure to afford a 71% yield (1.7 g) of crude 285b.

Example 285c 5-Bromo-3-(5-ethyl-4,5,6,7-tetrahydropyrazolo[1,5-a]pyrazin-2-ylamino)-1-methylpyridin-2(1H)-one 285c

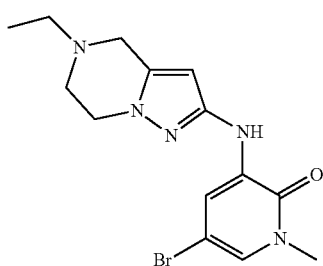

A sealed tube was equipped with a magnetic stirrer and charged with 285b (1.1 g, 6.4 mmol), 3,5-dibromo-1-methylpyridin-2(1H)-one 5 (1.7 g, 6.4 mmol) and cesium carbonate (4.6 g, 14 mmol) in 1,4-dioxane (64 mL). After bubbling nitrogen through the solution for 30 min, Xantphos (440 mg, 0.8 mmol) and tris(dibenzylideneacetone)dipalladium(0) (400 mg, 0.5 mmol) were added, and the reaction mixture was heated to 100° C. for 16 h. After this time, water (50 mL) and ethyl acetate (50 mL) were added. The aqueous layer was separated and extracted with ethyl acetate (2×50 mL). The combined organic extracts were washed with brine (100 mL) and dried over sodium sulfate. The resulting residue was purified by column chromatography eluting with a gradient of methylene chloride—60:35:5 methylene chloride:diethyl ether:methanol to afford a 28% yield (620 mg) of 285c.

Example 285d 10-{3-[5-({5-Ethyl-4H,5H,6H,7H-pyrazolo[1,5-a]pyrazin-2-yl}amino)-1-methyl-6-oxo-1,6-dihydropyridin-3-yl]-5-fluoro-2-(acetoxymethyl)phenyl}-4,4-dimethyl-1,10-diazatricyclo[6.4.0.0$^{2,6}$]dodeca-2(6),7-dien-9-one 285d

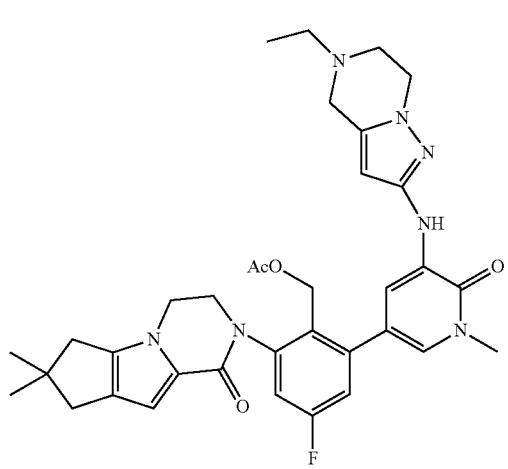

A microwave tube equipped with a magnetic stirrer was charged with 285c (190 mg, 0.5 mmol), 230a (350 mg, 0.7 mmol), 1,2-dimethoxyethane (6.4 mL) and 1M aqueous sodium carbonate (1.6 mL). After bubbling N$_2$ for 15 min, Pd(PPh$_3$)$_4$ (31 mg, 0.03 mmol) was added. The mixture was heated in microwave to 130° C. for 15 min. After this time, ethyl acetate (5 mL) and water (5 mL) were added. The separated aqueous layer was extracted with ethyl acetate (2×5 mL). The combined organics were washed with brine (10 mL), dried over sodium sulfate, filtered and concentrated under reduced pressure. The resulting residue was purified by column chromatography eluting with a gradient of methylene chloride—60:35:5 methylene chloride:diethyl ether:methanol to afford a 35% yield (120 mg) of 285d.

A 25 mL round bottom flask with a magnetic stirrer was charged with 285d (120 mg, 0.2 mmol), lithium hydroxide (40 mg, 1 mmol), THF (1 mL), isopropanol (1 mL) and water (2 mL). The mixture stirred at rt for 30 min. After this time, ethyl acetate (5 mL) and water (5 mL) were added. The separated aqueous layer was extracted with ethyl acetate (2×5 mL). The combined organics were washed with brine (10 mL), dried over sodium sulfate and filtered. The mixture was concentrated under reduced pressure to near dryness when the desired product crashed out and was filtered. Washing with diethyl ether (10 mL) afforded an 78% yield (90 mg) of 285. MS (ESI+) m/z 600.6 (M+H).

Example 286 2-(3-(5-(5-((2-(Dimethylamino)ethyl)(methyl)amino)pyridin-2-ylamino)-1-methyl-6-oxo-1,6-dihydropyridin-3-yl)-5-fluoro-2-(hydroxymethyl)phenyl)-3,4,5,6,7,8-hexahydrobenzothieno[2,3-c]pyridin-1(2H)-one 286

Following Example 270, reaction of 212a (550 mg, 1.20 mmol) and 270d (428 mg, 1.00 mmol) afforded a 8% yield (49 mg) of 286 as an off-white solid: mp 122-123° C.; $^1$H NMR (500 MHz, DMSO-d$_6$) δ 8.45 (d, 1H, J=2.0 Hz), 8.20 (s, 1H), 7.69 (d, 1H, J=2.4 Hz), 7.31 (m, 2H), 7.17 (m, 3H), 4.83 (t, 1H, J=4.6 Hz), 4.32 (d, 2H, J=4.3 Hz), 4.06 (m, 1H), 3.87 (m, 1H), 3.58 (s, 3H), 2.96 (m, 1H), 2.86 (m, 1H), 2.83 (s, 3H), 2.78 (m, 2H), 2.54 (m, 1H), 2.32 (t, 2H, J=7.0 Hz), 2.14 (s, 6H), 1.80 (m, 4H); MS (ESI+) m/z 631.3 (M+H).

Example 287 5-(5-Fluoro-2-(hydroxymethyl)-3-(6,6-dimethyl-3,4,6,7-tetrahydro-5H-cyclopenta[4,5]thieno[2,3-c]pyridine-1(2H)-yl)phenyl)-1-methyl-3-(5-(1-methylpyrrolidin-3-yl)pyridin-2-ylamino)pyridin-2(1H)-one 287

Example 287a 1-Methyl-3-(5-(1-methylpyrrolidin-3-yl)pyridin-2-ylamino)-5-(4,4,5,5-tetramethyl-1,3,2-dioxaborolan-2-yl)pyridin-2(1H)-one 287a

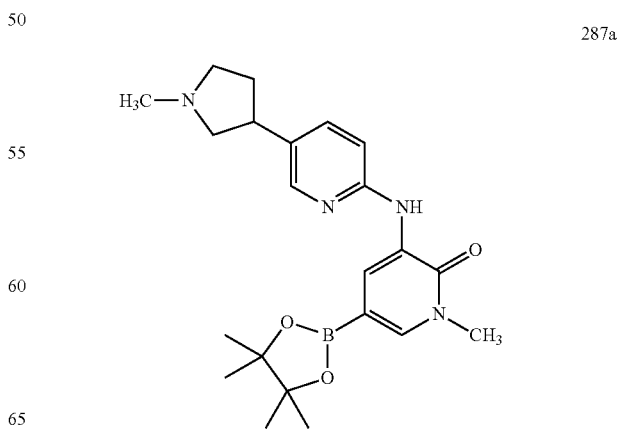

A 100-mL single-neck round-bottomed flask equipped with a magnetic stirrer and nitrogen inlet was charged with 202a (481 mg, 1.33 mmol), 4,4,4',4',5,5,5',5'-octamethyl-2,2'-bi-1,3,2-dioxaborolane (675 mg, 2.66 mmol), potassium acetate (392 mg, 3.99 mmol) and 1,4-dioxane (12 mL). After bubbling nitrogen through the resulting suspension for 30 min, Pd(dppf)Cl$_2$ (97.0 mg, 0.133 mmol) was added. A reflux condenser was attached to the flask, and the reaction mixture was heated at 100° C. for 3 h. After this time, the mixture was diluted with ethyl acetate (100 mL) and water (75 mL), and the layers were separated. The aqueous layer was extracted with ethyl acetate (2×50 mL), and the combined organic layers were washed with brine (100 mL) and dried over sodium sulfate. The drying agent was removed by filtration. The filtrate was concentrated under reduced pressure to afford crude 287a in quantitative yield (548 mg) as a brown semi-solid. The crude mixture was used in the next reaction without further purification: MS (ESI+) m/z 411.2 (M+H).

A 250-mL single-neck round-bottomed flask equipped with a magnetic stirrer and nitrogen inlet was charged with crude 287a (274 mg, 0.668 mmol, presuming quantitative yield), 247a (420 mg, 0.865 mmol), sodium carbonate (207 mg, 1.99 mmol), water (2 mL) and 1,4-dioxane (10 mL). After bubbling nitrogen through the resulting suspension for 30 min, tetrakis(triphenylphosphine)palladium(0) (151 mg, 0.133 mmol) was added. A reflux condenser was attached to the flask, and the reaction mixture was heated at 90° C. for 1 h. After this time, the mixture was diluted with 90:10 methylene chloride/methanol (100 mL) and water (75 mL), and the layers were separated. The aqueous layer was extracted with 90:10 methylene chloride/methanol (2×50 mL), and the combined organic layers were washed with brine (100 mL) and dried over sodium sulfate. The drying agent was removed by filtration. The filtrate was concentrated under reduced pressure, and the resulting residue was dissolved in THF (5 mL), water (5 mL) and methanol (5 mL). Lithium hydroxide monohydrate (47 mg, 1.12 mmol) was added, and the mixture was stirred at room temperature for 2 h. After this time, the mixture was diluted with 90:10 methylene chloride/methanol (100 mL) and water (50 mL), and the layers were separated. The aqueous layer was extracted with 90:10 methylene chloride/methanol (2×75 mL), and the combined organic layers were washed with brine (100 mL) and dried over sodium sulfate. The drying agent was removed by filtration. The filtrate was concentrated under reduced pressure, and the resulting residue was purified by flash column chromatography (silica, 80:20 methylene chloride/methanol) to afford 287 in 27% yield (110 mg) as an amorphous off-white solid: mp 181-183° C.; $^1$H NMR (500 MHz, DMSO-d$_6$) δ 8.64 (d, J=2.0 Hz, 1H), 8.49 (s, 1H), 8.07 (d, J=2.5 Hz, 1H), 7.54 (dd, J=8.5, 2.5 Hz, 1H), 7.40 (d, J=2.0 Hz, 1H), 7.34 (dd, J=9.0, 2.5 Hz, 1H), 7.25 (d, J=8.5 Hz, 1H), 7.19 (dd, J=9.5, 2.5 Hz, 1H), 4.86 (t, J=4.0 Hz, 1H), 4.34-4.32 (m, 2H), 4.10-4.03 (m, 1H), 3.87-3.83 (m, 1H), 3.59 (s, 3H), 3.25-3.20 (m, 1H), 3.05-2.99 (m, 1H), 2.91-2.87 (m, 1H), 2.81-2.77 (m, 1H), 2.75 (s, 2H), 2.60-2.58 (m, 2H), 2.55-2.50 (m, 2H), 2.49-2.32 (m, 1H), 2.27 (s, 3H), 2.22-2.17 (m, 1H), 1.71-1.67 (m, 1H), 1.23 (s, 6H); MS (ESI+) m/z 628.3 (M+H).

Example 288 2-(5-Fluoro-2-(hydroxymethyl)-3-(1-methyl-5-(5-(1-methylpyrrolidin-2-yl)pyridin-2-ylamino)-6-oxo-1,6-dihydropyridin-3-yl)phenyl)-3,4,5,6,7,8-hexahydrobenzothieno[2,3-c]pyridin-1(2H)-one 288

Following Example 286, reaction of 212a (450 mg, 1.04 mmol) and 287b (328 mg, 0.810 mmol) afforded a 26% yield (130 mg) of 288 as an off-white solid: mp 164-166° C.; $^1$H NMR (500 MHz, DMSO-d$_6$) δ 8.67 (d, 1H, J=2.0 Hz), 8.55 (s, 1H), 8.06 (d, 1H, J=2.4 Hz), 7.53 (dd, 1H, J=8.5, 2.4 Hz), 7.41 (d, 1H, J=2.4 Hz), 7.32 (dd, 1H, J=9.1, 2.1 Hz), 7.26 (d, 1H, J=9.0 Hz), 7.19 (dd, 1H, J=9.0, 2.0 Hz), 4.85 (t, 1H, J=4.2 Hz), 4.32 (m, 2H), 4.04 (m, 1H), 3.87 (m, 1H), 3.59 (s, 3H), 3.13 (m, 1H), 2.95 (m, 2H), 2.84 (m, 1H), 2.78 (m, 2H), 2.54 (m, 1H), 2.18 (q, 1H, J=4.0 Hz), 2.04 (m, 4H), 1.80 (m, 6H), 1.58 (m, 1H); MS (ESI+) m/z 614.3 (M+H).

Example 289 2-(5-Fluoro-2-(hydroxymethyl)-3-(1-methyl-5-(5-morpholinopyridin-2-ylamino)-6-oxo-1,6-dihydropyridin-3-yl)phenyl)-3,4,5,6,7,8-hexahydrobenzothieno[2,3-c]pyridin-1(2H)-one 289

Example 289a 1-Methyl-3-(5-morpholinopyridin-2-ylamino)-5-(4,4,5,5-tetra-methyl1,3,2-dioxaborolan-2-yl)pyridin-2(1H)-one 289a

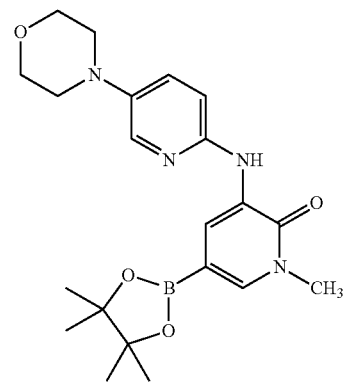

289a

A 250-mL single-neck round-bottomed flask equipped with a magnetic stirrer and nitrogen inlet was charged with 255c (610 mg, 1.70 mmol), 4,4,4',4',5,5,5',5'-octamethyl-2,2'-bi-1,3,2-dioxaborolane (850 mg, 3.40 mmol), potassium acetate (492 mg, 5.00 mmol) and 1,4-dioxane (20 mL). After bubbling nitrogen through the resulting suspension for 30 min, Pd(dppf)Cl$_2$/CH$_2$Cl$_2$ (122 mg, 0.200 mmol) was added. A reflux condenser was attached to the flask, and the reaction mixture was heated at 90° C. for 2 h. After this time, the mixture was diluted with ethyl acetate (100 mL) and water (75 mL), and the layers were separated. The aqueous layer was extracted with ethyl acetate (50 mL), and the combined organic extracts were washed with brine (50 mL) and dried over sodium sulfate. The drying agent was removed by filtration. The filtrate was concentrated under reduced pressure, and the resulting residue was purified by trituration with hexanes/ethyl acetate (80:20, 25 mL) to afford 289a in quantitative yield (688 mg) as a brown solid: mp 100-101° C.; $^1$H NMR (500 MHz, DMSO-d$_6$) δ 8.45 (d, 1H, J=1.5 Hz), 8.21 (s, 1H), 7.91 (s, 1H), 7.89 (d, 1H, J=3.0 Hz), 7.66 (d, 1H, J=6.5 Hz), 7.14 (d, 1H, J=9.0 Hz), 3.73 (t, 4H, J=4.5 Hz), 3.55 (s, 3H), 3.05 (t, 4H, J=4.5 Hz), 1.29 (s, 12H); MS (ESI+) m/z 413.0 (M+H)

A 100-mL single-neck round-bottomed flask equipped with a magnetic stirrer and reflux condenser was purged with nitrogen and charged with 289a (485 mg, 0.415 mmol), 247a (488 mg, 1.10 mmol), sodium carbonate (264 mg, 2.50 mmol), 1,4-dioxane (8 mL) and water (2 mL). This mixture was degassed with nitrogen for 30 min. Tetrakis(triphenylphosphine)palladium (96 mg, 0.083 mmol) was added. After heating at 100° C. for 2 h, the reaction mixture was cooled to room temperature and partitioned between water (40 mL) and methylene chloride (100 mL). The layers were separated, and the aqueous phase was extracted with methylene chloride (2×50 mL). The organic extracts were combined, dried over sodium sulfate, filtered and concentrated under reduced pressure. The resulting residue was dissolved in methanol (5 mL), and potassium carbonate (745 mg, 5.40 mmol) was added. After stirring at room temperature for 1 h, the reaction mixture was partitioned between water (20 mL) and methylene chloride (20 mL). The layers were separated, and the aqueous phase was extracted with methylene chloride (2×20 mL). The organic extracts were combined, dried over sodium sulfate, filtered and concentrated under reduced pressure. The resulting residue was purified by flash column chromatography (silica, 0% to 15% methanol/methylene chloride) to afford 289 in 51% yield (130 mg) as a yellow solid: mp 220-221° C.; $^1$H NMR (500 MHz, DMSO-$d_6$) δ 8.55 (d, 1H, J=2.0 Hz), 8.37 (s, 1H), 7.87 (d, 1H, J=3.0 Hz), 7.34 (m, 3H), 7.23 (d, 1H, J=9.0 Hz), 7.16 (dd, 1H, J=9.5, 3.0 Hz), 4.83 (t, 1H, J=4.0 Hz), 4.32 (m, 2H), 4.05 (m, 1H), 3.86 (m, 1H), 3.71 (t, 4H, J=4.5 Hz), 3.58 (s, 3H), 3.01 (t, 4H, J=4.5 Hz), 2.98 (m, 1H), 2.87 (m, 1H), 2.77 (m, 2H), 2.54 (m, 1H), 1.79 (m, 4H); MS (ESI+) m/z 616.2 (M+H).

Example 290 10-[5-Fluoro-2-(hydroxymethyl)-3-[1-methyl-5-({5-[(2S)-1-methylpyrrolidin-2-yl]pyridine-2-yl}amino)-6-oxo-1,6-dihydropyridin-3-yl]phenyl]-4,4-dimethyl-1,10-diazatricyclo[6.4.0.0$^{2,6}$]dodeca-2(6),7-dien-9-one 290

Example 291 10-[5-Fluoro-2-(hydroxymethyl)-3-[1-methyl-5-({5-[(2R)-1-methylpyrrolidin-2-yl]pyridine-2-yl}amino)-6-oxo-1,6-dihydropyridin-3-yl]phenyl]-4,4-dimethyl-1,10-diazatricyclo[6.4.0.0$^{2,6}$]dodeca-2(6),7-dien-9-one 291

Compounds 290 and 291 are enantiomers of racemate 243. The racemic mixture 243 was subjected to chiral separation on a Chiralpak AD, 4.6×50 mm, 3 mm column (mobile phase 45% isopropanol (w/0.1% triethylamine)/55% CO$_2$, flow rate 5 mL/min) at 40° C. to give individual enantiomers, with 290 eluting first: MS (ESI+) m/z 611.5 (M+H) and Example 291 eluting last: MS (ESI+) m/z 611.5 (M+H).

Example 292 10-[5-Fluoro-2-(hydroxymethyl)-3-(1-methyl-5-{[6-(oxetan-3-yl)-5,6,7,8-tetrahydro-1,6-naphthyridin-2-yl]amino}-6-oxo-1,6-dihydropyridin-3-yl)phenyl]-4,4-dimethyl-1,10-diazatricyclo[6.4.0.0$^{2,6}$]dodeca-2(6),7-dien-9-one 292

Example 292a 10-[5-Fluoro-2-(acetoxymethyl)-3-(1-methyl-5-{[6-(oxetan-3-yl)-5,6,7,8-tetrahydro-1,6-naphthyridin-2-yl]amino}-6-oxo-1,6-dihydropyridin-3-yl)phenyl]-4,4-dimethyl-1,10-diazatricyclo[6.4.0.0$^{2,6}$]dodeca-2(6),7-dien-9-one 292a In a 10-mL microwave reaction vessel equipped with a magnetic stirring bar were placed 5-bromo-1-methyl-3-(6-(oxetan-3-yl)-5,6,7,8-tetrahydro-1,6-naphthyridin-2-ylamino)pyridin-2(1H)-one 219a (250 mg, 0.64 mmol), 10-[2-(acetoxymethyl)-3-(4,4,5,5-tetramethyl-[1,3,2]dioxaborolan-2-yl)-5-fluorophenyl]-4,4-dimethyl-1,10-diazatricyclo[6.4.0.0$^{2,6}$]dodeca-2(6),7-dien-9-one 230a (635 mg, 1.3 mmol), Pd(PPh$_3$)$_4$ (37 mg, 0.03 mmol) in 2 N Na$_2$CO$_3$ (2 mL) and 1,2-dimethoxyethane (2 mL). After the reaction mixture was stirred at 125° C. for 10 minutes, it was purified by flash chromatography (dichloromethane:methanol, 3:1) to give 12% (50 mg) of 292a as a solid.

A 25-mL, single-necked, round-bottomed flask equipped with a magnetic stirring bar was charged with 292a (50 mg, 0.078 mmol), LiOH.H$_2$O (50 mg, 1.2 mmol), THF (2 mL), i-PrOH (2 mL), and water (2 mL). After the reaction mixture was stirred at room temperature for 2 h, it was partitioned between dichloromethane (5 mL) and water (5 mL), and the organic phase was extracted with dichloromethane (5 mL×3). The combined organic phases were washed with water (5 mL×2) and brine (5 mL×1), dried (Na$_2$SO$_4$), and concentrated. The crude product was re-dissolved in dichloromethane (3 mL). To this solution was added hexane (10 mL) and the resulting precipitates were filtered to give 12% yield (6 mg) of 292 MS(ESI+) m/z 639.5 (M+H).

Example 293 2-(5-Fluoro-2-(hydroxymethyl)-3-(1-methyl-5-(5-(1-methylazetidin-3-yloxy)pyridin-2-ylamino)-6-oxo-1,6-dihydropyridin-3-yl)phenyl)-3,4,6,7,8,9-hexahydropyrazino[1,2-a]indol-1(2H)-one 293

Example 293a 4-Fluoro-2-(1-methyl-5-(5-(1-methylazetidin-3-yloxy)pyridin-2-ylamino)-6-oxo-1,6-dihydropyridin-3-yl)-6-(1-oxo-3,4,6,7,8,9-hexahydropyrazino[1,2-a]indol-2(1H)-yl)benzyl Acetate 293a

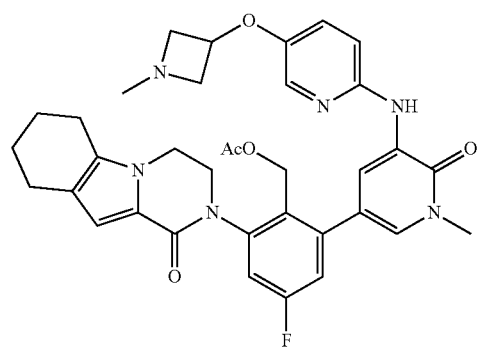 [SMILES: CC(=O)OCc1c(-c2cc(Nc3ccc(OC4CN(C)C4)cn3)c(=O)n(C)c2)cc(F)cc1N1CCn2c(cc3c2CCCC3)C1=O]

A mixture of 5-bromo-1-methyl-3-(5-(1-methylazetidin-3-yloxy)pyridin-2-ylamino)pyridine-2(1H)-one 199f (200 mg, 0.55 mmol), 4-fluoro-2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 210d (270 mg, 0.56 mmol), PdCl$_2$(dppf) (40 mg, 0.055 mmol), K$_3$PO$_4$ (150 mg), NaOAc (50 mg) in MeCN (8 mL) and water (2 mL) was heated at 110° C. in a sealed tube for 2 h. The solvent was evaporated in vacuo. The residue was purified on reverse phase Combi-flash to give 293a (307 mg, 70%). MS: [M+H]$^+$ 641.

A mixture of 293a (287 mg, 0.45 mmol) and LiOH hydrate (188 mg, 4.5 mmol) in isopropanol (25 mL) and water (5 mL) was stirred at 30° C. for 2 h. The mixture was evaporated in vacuo and the residue was extracted with ethyl acetate (20 mL×2). The combined extracts were concentrated under reduced pressure. And the residue was purified on prep-HPLC to give 293 (60 mg, 25%). MS: [M+H]$^+$ 599. $^1$H NMR (500 MHz, CDCl3) δ 8.51 (s, 1H), 7.81 (s, 1H), 7.74 (s, 1H), 7.48 (s, 1H), 7.16-7.14 (m, 1H), 7.11-7.09 (m, 1H), 6.95-6.93 (m, 1H), 6.86 (s, 1H), 6.79 (d, J=9.0, 1H), 4.76-4.72 (m, 1H), 4.53 (d, J=8.5, 1H), 4.34-4.25 (m, 2H), 4.20-4.13 (m, 3H), 3.95-3.84 (m, 3H), 3.69 (s, 3H), 3.24-3.13 (m, 2H), 2.64-2.52 (m, 4H), 2.46 (s, 3H), 1.93-1.84 (m, 2H), 1.81-1.75 (m, 2H).

Example 294 10-[5-Fluoro-2-(hydroxymethyl)-3-(4-methyl-6-{[4-(1-methylpiperidin-4-yl)phenyl]amino}-5-oxo-4,5-dihydropyrazin-2-yl)phenyl]-4,4-dimethyl-1,10-diazatricyclo[6.4.0.0$^{2,6}$]dodeca-2(6),7-dien-9-one 294

Example 294a (2-{4,4-Dimethyl-9-oxo-1,10-diazatricyclo[6.4.0.0$^{2,6}$]dodeca-2(6),7-dien-10-yl}-4-fluoro-6-(4-methyl-6-{[4-(1-methylpiperidin-4-yl)phenyl]amino}-5-oxo-4,5-dihydropyrazin-2-yl)phenyl)methyl Acetate 294a

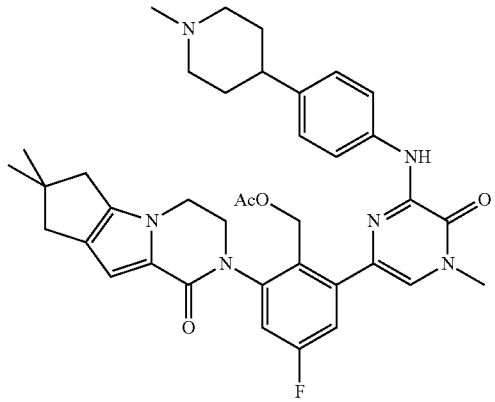

294a

Following Example 150b, 282c and (2-{4,4-dimethyl-9-oxo-7-thia-10-azatricyclo[6.4.0.0$^{2,6}$]dodeca-1(8),2(6)-dien-10-yl}-4-fluoro-6-(4,4,5,5-tetramethyl-1,3,2-dioxaborolan-2-yl)phenyl)methyl acetate 230a were reacted to give 294a in 81% yield. LCMS: (M+H)$^+$ 667

Following Example 150, 294a was converted to 294 in 47% yield. LCMS: (M+H)$^+$ 625. $^1$H NMR (500 MHz, DMSO) δ 9.20 (s, 1H), 7.89 (s, 1H), 7.87 (s, 1H), 7.48 (s, 1H), 7.36 (dd, J=10, 1H), 7.31 (dd, J=9.5, 1H), 7.17 (s, 1H), 7.15 (s, 1H), 6.52 (s, 1H), 4.85 (m, 1H), 4.49 (m, 1H), 4.40 (m, 1H), 4.20 (m, 2H), 4.12 (m, 1H), 3.87 (m, 1H), 3.54 (s, 3H), 2.84 (d, J=10.5, 1H), 2.57 (s, 2H), 2.42 (s, 2H), 2.38 (m, 1H), 2.18 (s, 3H), 1.93 (t, J=9, 2H), 1.66 (m, 4H), 1.22 (s, 6H).

Example 295 10-[5-Fluoro-2-(hydroxymethyl)-3-(1-methyl-5-{[5-(1-methylpiperidin-4-yl)pyridin-2-yl]amino}-6-oxo-1,6-dihydropyridin-3-yl)phenyl]-4,4-dimethyl-7-thia-10-azatricyclo[6.4.0.0$^{2,6}$]dodeca-1(8),2(6)-dien-9-one 295

Example 295a (2-{4,4-Dimethyl-9-oxo-7-thia-10-azatricyclo[6.4.0.0$^{2,6}$]dodeca-1(8),2(6)-dien-10-yl}-4-fluoro-6-(1-methyl-5-{[5-(1-methylpiperidin-4-yl)pyridin-2-yl]amino}-6-oxo-1,6-dihydropyridin-3-yl)phenyl)methyl Acetate 295a

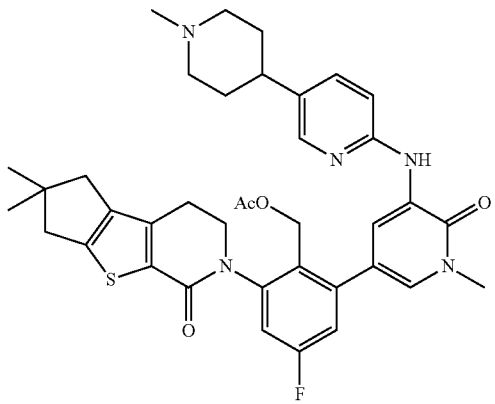

295a

A sealed tube was charged with the mixture of 5-bromo-1-methyl-3-(5-(1-methylpiperidin-4-yl)pyridin-2-ylamino)pyridin-2(1H)-one 282c (350 mg, 0.93 mmol), (2-{4,4-dimethyl-9-oxo-7-thia-10-azatricyclo[6.4.0.0$^{2,6}$]dodeca-1(8), 2(6)-dien-10-yl}-4-fluoro-6-(4,4,5,5-tetramethyl-1,3,2-dioxaborolan-2-yl)phenyl)methyl acetate 247b (448 mg, 0.93 mmol), Pd(dppf)Cl$_2$ (76 mg, 0.09 mmol), K$_3$PO$_4$.3H$_2$O (495 mg, 1.86 mmol), and NaOAc (153 mg, 1.86 mmol) in CH$_3$CN (20 mL). The system was evacuated and then refilled with N$_2$. And the reaction mixture was heated at 110° C. for 2 h. The mixture was cooled to room temperature and filtered. The filtrate was concentrated under reduced pressure and the resulting residue was purified by flash column chromatography eluting with 15:1 methylene chloride/methanol to give 295a as a brown solid (300 mg, 47%). MS: [M+H]$^+$ 684

A solution of 295a (250 mg, 0.37 mmol) in propan-2-ol (8 mL), tetrahydrofuran (8 mL) and water (1 mL) was added LiOH (878 mg, 37 mmol) was stirred at 30° C. for 2 h. It was then evaporated and the residue was purified by prep-HPLC to afford 295 as a yellow solid (76 mg, 32%). MS: (M+H)$^+$ 642. $^1$H NMR (500 MHz, MEOD) δ 1.29 (d, 6H), 1.94-2.02 (m, 2H), 2.18 (d, 2H), 2.56-2.64 (m, 2H), 2.81 (s, 2H), 2.94-3.03 (m, 5H), 3.08-3.19 (m, 3H), 3.66 (d, 1H), 3.74 (s, 3H), 3.92-3.97 (m, 1H), 4.14-4.19 (m, 1H), 4.50 (s, 1H), 7.21-7.28 (m, 2H), 7.84 (s, 1H), 7.95 (d, 1H), 8.13 (s, 1H).

Example 296 10-{3-[5-({5-[2-(Dimethylamino)ethoxy]pyridin-2-yl}amino)-1-methyl-6-oxo-1,6-dihydropyridin-3-yl]-5-fluoro-2-(hydroxymethyl)phenyl}-4,4-dimethyl-7-thia-10-azatricyclo[6.4.0.0$^{2,6}$]dodeca-1(8),2(6)-dien-9-one 296

Example 296a (2-{4,4-Dimethyl-9-oxo-7-thia-10-azatricyclo[6.4.0.0$^{2,6}$]dodeca-1(8),2(6)-dien-10-yl}-6-[5-({5-[2-(dimethylamino)ethoxy]pyridin-2-yl}amino)-1-methyl-6-oxo-1,6-dihydropyridin-3-yl]-4-fluorophenyl)methyl Acetate 296a

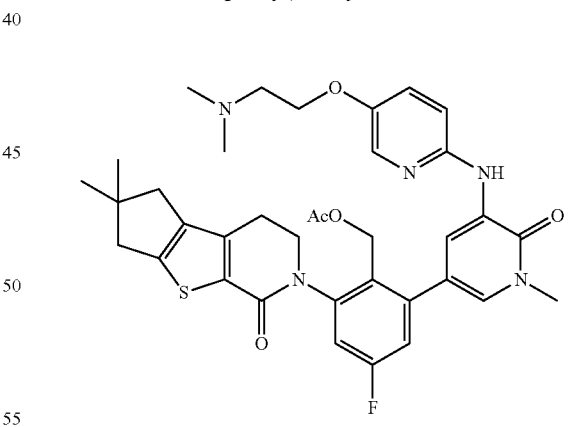

A mixture of 5-bromo-3-(5-(2-(dimethylamino)ethoxy)pyridin-2-ylamino)-1-methylpyridin-2(1H)-one 268c (244 mg, 0.67 mmol), (2-{4,4-dimethyl-9-oxo-7-thia-10-azatricyclo[6.4.0.0$^{2,6}$]dodeca-1(8),2(6)-dien-10-yl}-4-fluoro-6-(4,4,5,5-tetramethyl-1,3,2-dioxaborolan-2-yl)phenyl)methyl acetate 247b (342 mg, 0.67 mmol), PdCl$_2$(dppf) (59 mg, 0.08 mmol), K$_3$PO$_4$ (150 mg), and NaOAc (50 mg) in MeCN (6 mL) and water (2 mL) was heated at 110° C. in a sealed tube for 2 h. The solvent was evaporated in vacuo and the residue was purified on reverse phase Combi-flash to give 296a (287 mg, 60%). MS: [M+H]$^+$ 674.

A mixture of 296a (186 mg, 0.28 mmol) and LiOH hydrate (116 mg, 2.8 mmol) in isopropanol (25 mL) and water (5 mL) was stirred at 30° C. for 2 h. The mixture was evaporated in vacuo and the residue was extracted with ethyl acetate (20 mL×2). The combined extracts were concentrated under reduced pressure and the residue was purified on prep-HPLC to give 296 (126 mg, 71%). MS: [M+H]+ 632.

Example 297 2-(3-(5-(5-(2-(Dimethylamino)ethoxy)pyridin-2-ylamino)-1-methyl-6-oxo-1,6-dihydropyridin-3-yl)-5-fluoro-2-(hydroxymethyl)phenyl)-3,4,6,7,8,9-hexahydropyrazino[1,2-a]indol-1(2H)-one 297

Example 297a 2-(5-(5-(2-(Dimethylamino)ethoxy)pyridin-2-ylamino)-1-methyl-6-oxo-1,6-dihydropyridin-3-yl)-4-fluoro-6-(1-oxo-3,4,6,7,8,9-hexahydropyrazino[1,2-a]indol-2(1H)-yl)benzyl Acetate 297a

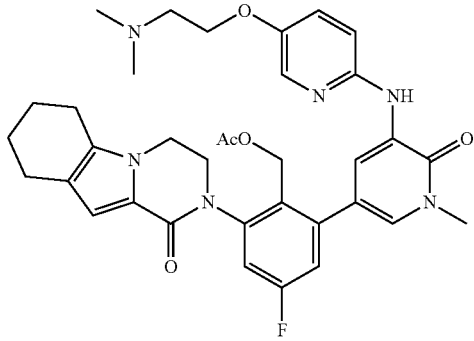 [SMILES: CC(=O)OCc1c(-c2cc(Nc3ccc(OCCN(C)C)cn3)c(=O)n(C)c2)cc(F)cc1N1CCn2c(cc3c2CCCC3)C1=O]

A mixture of 5-bromo-3-(5-(2-(dimethylamino)ethoxy)pyridin-2-ylamino)-1-methylpyridin-2(1H)-one 268c (205 mg, 0.56 mmol), 4-fluoro-2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 210d (270 mg, 0.56 mmol), PdCl2(dppf) (51 mg, 0.07 mmol), K3PO4 (100 mg), and NaOAc (40 mg) in MeCN (6 mL) and water (2 mL) was heated at 110° C. in a sealed tube for 2 h. The solvent was evaporated in vacuo. The residue was purified on reverse phase Combi-flash to give 297a (206 mg, 50%). MS: [M+H]+ 643.

A mixture of 297a (186 mg, 0.29 mmol) and LiOH hydrate (122 mg, 2.9 mmol) in isopropanol (15 mL) and water (3 mL) was stirred at 30° C. for 2 h. The mixture was evaporated in vacuo and the residue was extracted with ethyl acetate (20 mL×2). The combined extracts were concentrated under reduced pressure and the residue was purified on prep-HPLC to give 297 (84 mg, 48%). MS: [M+H]+ 601.
1H NMR (500 MHz, CDCl3) δ 8.53 (d, J=2.5, 1H), 7.94 (d, J=3.0, 1H), 7.80 (s, 1H), 7.47 (d, J=2.0, 1H), 7.23-7.21 (m, 1H), 7.16-7.14 (m, 1H), 6.95-6.93 (m, 1H), 6.86 (s, 1H), 6.81 (d, J=9.0, 1H), 4.55 (d, J=10.5, 1H), 4.40-4.26 (m, 2H), 4.22-4.15 (m, 3H), 4.15-4.04 (m, 2H), 3.94-3.86 (m, 1H), 3.69 (s, 3H), 2.75-2.73 (m, 2H), 2.62-2.54 (m, 4H), 2.37 (s, 6H), 1.92-1.86 (m, 2H), 1.82-1.76 (m, 2H).

Example 298 10-[5-fluoro-2-(hydroxymethyl)-3-(4-methyl-6-{[4-(1-methylazetidin-3-yl)phenyl]amino}-5-oxopyrazin-2-yl)phenyl]-4,4-dimethyl-7-thia-10-azatricyclo[6.4.0.0²,⁶]dodeca-1(8),2(6)-dien-9-one 298

Example 298a tert-Butyl 3-(4-Aminophenyl)azetidine-1-carboxylate 298a

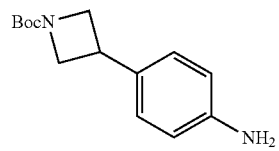

A mixture of tert-butyl 3-iodoazetidine-1-carboxylate (1 g, 3.53 mmol), 4-aminophenylboronic acid (630 mg, 4.59 mmol), NiI2 (66 mg, 0.212 mmol), NaHMDS (1.94 g, 10.6 mmol), (1R,2S)-2-aminocyclohexanol (24 mg, 0.212 mmol) in isopropanol (8 mL) was stirred at 150° C. in microwave for 2 h. It was then evaporated and the residue was dissolved with water and ethyl acetate. The water phase was separated and extracted with ethyl acetate. The combined extracts were dried over sodium sulfate and concentrated under reduced pressure. The residue was purified with column chromatography to give 298a (360 mg, 40%). MS: [M+H]+ 249.

Example 298b tert-Butyl 3-(4-(6-Bromo-4-methyl-3-oxo-3,4-dihydropyrazin-2-ylamino)phenyl)azetidine-1-carboxylate 298b

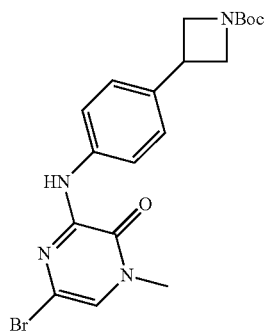

A mixture of 298a (500 mg, 2.02 mmol), 3,5-dibromo-1-methylpyrazin-2(1H)-one (536 mg, 2.02 mmol) and triethylamine (0.6 mL, 4.04 mmol) in isopropanol (10 mL) was heated at reflux for 4 days. The solvent was evaporated in vacuo and the residue was purified on reverse phase Combi-flash to afford 298b (690 mg, 66%). MS: [M+H]+ 435.

Example 298c 3-(4-(Azetidin-3-yl)phenylamino)-5-bromo-1-methylpyrazin-2(1H)-one Hydrochloride 298c

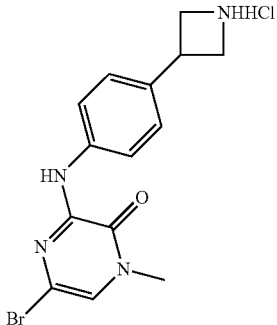

A mixture of 298b (690 mg, 1.6 mmol) and HCl/1,4-dioxane (8M, 8 mL) in methanol (30 mL) was stirred at room temperature overnight. The mixture was evaporated in vacuo and the residue was purified on reverse phase Combi-flash to give 298c (100 mg, 17%). MS: [M+H]$^+$ 335.

Example 298d 5-Bromo-1-methyl-3-(4-(1-methyl-azetidin-3-yl)phenylamino)pyrazin-2(1H)-one 298d

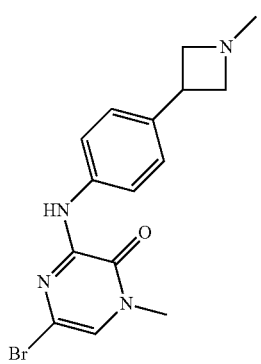 [SMILES: CN1CC(c2ccc(Nc3nc(Br)cn(C)c3=O)cc2)C1]

A mixture of 298c (100 mg, 0.24 mmol), NaBH(OAc)$_3$ (100 mg, 0.48 mmol), HCHO (10 mL) and acetic acid (1 mL) in methanol (15 mL) was stirred at room temperature for 4 h. The solvent was evaporated in vacuo and the residue was neutralized with NaHCO$_3$ solution until pH 8 was reached. The mixture was extracted with ethyl acetate. The combined extracts were dried over sodium sulfate and concentrated under reduced pressure to give 298d (100 mg), which was used for the next step without further purification. MS: [M+H]$^+$ 349.

Example 298e (2-{4,4-Dimethyl-9-oxo-7-thia-10-azatricyclo[6.4.0.0$^{2,6}$]dodeca-1(8),2(6)-dien-10-yl}-4-fluoro-6-(4-methyl-6-{[4-(1-methylazetidin-3-yl)phenyl]amino}-5-oxo-4,5-dihydropyrazin-2-yl)phenyl)methyl Acetate 298e

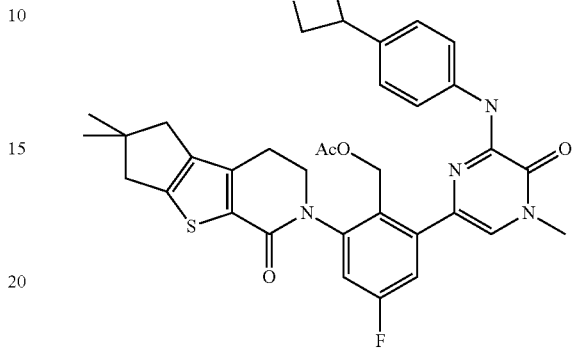

To a sealed tube was charged a mixture of (2-{4,4-Dimethyl-9-oxo-7-thia-10-azatricyclo[6.4.0.0$^{2,6}$]dodeca-1(8),2(6)-dien-10-yl}-4-fluoro-6-(tetramethyl-1,3,2-dioxaborolan-2-yl)phenyl)methyl Acetate 247b (100 mg, 0.19 mmol), 5-bromo-1-methyl-3-(4-(1-methylazetidin-3-yl)phenylamino)pyrazin-2(1H)-one 298d (68 mg, 0.19 mmol), PdCl$_2$(dppf) (14 mg, 0.019 mmol), K$_3$PO$_4$ (60 mg), and NaOAc (30 mg) in MeCN (5 mL) and water (1 mL). It was heated at 110° C. for 2 h. The solvent was evaporated in vacuo and the residue was purified on reverse phase Combi-flash to give 298e (100 mg, 82%). MS: [M+H]$^+$ 656.

A mixture of 298e (100 mg, 0.16 mmol) and LiOH hydrate (66 mg, 1.6 mmol) in isopropanol (10 mL) and water (2 mL) was stirred at 30° C. for 2 h. The mixture was evaporated in vacuo and the residue was extracted with ethyl acetate (2×20 mL). The combined extracts were concentrated under reduced pressure. And the residue was purified on pre-HPLC to give 298 (60 mg, 63%). MS: [M+H]$^+$ 614. $^1$H NMR (500 MHz, CDCl3) δ 8.29 (s, 1H), 7.72 (d, J=7.5, 2H), 7.55 (s, 1H), 7.45-7.43 (m, 1H), 7.30 (s, 1H), 7.01-6.99 (m, 1H), 4.56 (d, J=11.5, 1H), 4.41-4.30 (m, 2H), 4.10-4.05 (m, 1H), 3.90-3.85 (m, 1H), 3.82-3.72 (m, 2H), 3.64 (s, 3H), 3.22-3.10 (m, 2H), 3.04-2.97 (m, 1H), 2.93-2.88 (m, 1H), 2.79 (s, 2H), 2.57-2.50 (m, 2H), 2.39 (s, 3H), 1.27 (s, 6H).

Example 299 10-[5-Fluoro-2-(hydroxymethyl)-3-[1-methyl-5-({5-[1-(oxetan-3-yl)piperidin-4-yl]pyridine-2-yl}amino)-6-oxo-1,6-dihydropyridin-3-yl]phenyl]-4,4-dimethyl-7-thia-10-azatricyclo[6.4.0.0$^{2,6}$]dodeca-1(8),2(6)-dien-9-one 299

Following Example 121b, compound 247b (256 mg, 0.5 mmol), 5-bromo-1-methyl-3-(5-(1-(oxetan-3-yl)piperidin-4-yl)pyridin-2-ylamino)pyridin-2(1H)-one 264e (210 mg, 0.5 mmol), 1M sodium carbonate solution (2 mL, 2 mmol), tetrakis(triphenylphosphine)palladium(0) (29 mg, 0.025 mmol) and 1,2-dimethoxyethane (5 mL) were reacted. The reaction mixture was heated at 130° C. for 15 minutes in the microwave reactor. Work-up and flash column chromatography (silica, 9:1 methylene chloride/methanol) give a mixture of compound 299a and 299 as yellow oil.

The above residue (0.5 mmol) was deprotected using the same procedure as 121, except using a mixture of THF (2 mL), water (1 mL) and isopropanol (2 mL and lithium hydroxide monohydrate (105 mg, 2.5 mmol). Work-up and flash column chromatography (NH-silica, ethyl acetate/hexanes) give a 12% yield (40 mg) of 299 as a pale yellow solid: MS (ESI+) m/z 684.5 (M+H).

Example 300 10-[5-Fluoro-2-(hydroxymethyl)-3-[1-methyl-5-({5-[1-(oxetan-3-yl)piperidin-4-yl]pyridine-2-yl}amino)-6-oxo-1,6-dihydropyridin-3-yl]phenyl]-4,4-dimethyl-7-thia-10-azatricyclo[6.4.0.0²,⁶]dodeca-1(8),2(6)-dien-9-one 300

Example 300a 5-Bromo-3-(2-methoxypyrimidin-4-ylamino)-1-methylpyridin-2(1H)-one 300a Following Example 121a, 2-methoxypyrimidin-4-amine (0.625 g, 5 mmol), 3,5-dibromo-1-methyl-1H-pyridin-2-one (1.34 g, 5 mmol), cesium carbonate (4.88 g, 15 mmol), tris(dibenzylideneacetone)-dipalladium(0) (0.465 g, 0.5 mmol), Xantphos (0.58 g, 1 mmol) and 1,4-dioxane (50 mL) were reacted. The reaction mixture was heated at 100° C. for 24 hours, then cool to room temperature, and filtered through a pad of Celite 521. The filter cake was washed with 9:1 methylene chloride/methanol (2×25 mL), and the combined filtrates were concentrated to dryness. The residue was dissolve in methylene chloride, diethyl ethyl was added, and the resulting precipitate was filtered to give a quantitative yield (1.57 g) of 300a as a green solid: MS (ESI+) m/z 313.1 (M+H).

Example 300b 10-[5-Fluoro-2-(acetoxymethyl)-3-[1-methyl-5-({5-[1-(oxetan-3-yl)piperidin-4-yl]pyridine-2-yl}amino)-6-oxo-1,6-dihydropyridin-3-yl]phenyl]-4,4-dimethyl-7-thia-10-azatricyclo[6.4.0.0²,⁶]dodeca-1(8),2(6)-dien-9-one 300b Following Example 121b, 300a (242 mg, 0.5 mmol), 230a (210 mg, 0.5 mmol), 1M sodium carbonate solution (2 mL, 2 mmol), tetrakis(triphenylphosphine)palladium(0) (29 mg, 0.025 mmol) and 1,2-dimethoxyethane (5 mL). The reaction mixture was heated at 130° C. for 15 minutes in the microwave reactor. Work-up and flash column chromatography (silica, 60:35:5 methylene chloride/diethyl ether/methanol) give a 67% yield (200 mg) of 300b as a yellow solid: MS (ESI+) m/z 602.4 (M+H).

Following Example 121, a mixture of THF (2 mL), water (1 mL) and isopropanol (2 mL), 300b (200 mg, 0.33 mmol) and lithium hydroxide monohydrate (105 mg, 2.5 mmol). Work-up and flash column chromatography (NH-silica, Ethyl Acetate/Hexanes) give a 29% yield (55 mg) of compound 300 as a white solid: MS (ESI+) m/z 559.4 (M+H).

Example 301 2-(2-(Hydroxymethyl)-3-(1-methyl-6-oxo-5-(5-(piperazin-1-yl)pyridin-2-ylamino)-1,6-dihydropyridin-3-yl)phenyl)-3,4,6,7,8,9-hexahydropyrazino[1,2-a]indol-1(2H)-one 301

Example 301a tert-Butyl 4-(6-(5-Bromo-1-methyl-2-oxo-1,2-dihydropyridin-3-ylamino)pyridin-3-yl)piperazine-1-carboxylate 301a

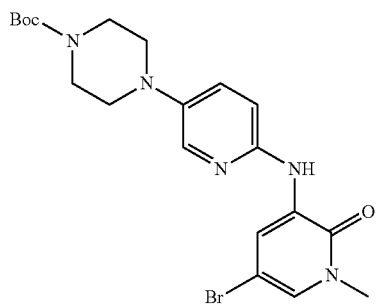 [SMILES: Cn1cc(Br)cc(Nc2ccc(N3CCN(C(=O)OC(C)(C)C)CC3)cn2)c1=O]

To a round-bottomed flask equipped with a stirring bar, tert-butyl 4-(6-aminopyridin-3-yl)piperazine-1-carboxylate (2.00 g, 7.18 mmol), 3,5-dibromo-1-methylpyridin-2(1H)-one (2.87 g, 10.77 mmol), Pd₂(dba)₃ (657 mg, 0.718 mmol), XantPhos (665 mg, 1.15 mmol), Cs₂CO₃ (7.72 g, 23.7 mmol) and dioxane (40 mL) were added. The reaction mixture was heated at 100° C. for 40 hrs. Ethyl acetate (200 mL) was added and the resulting mixture was washed with water (30 mL×3), brine (30 mL×1), dried over MgSO₄, filtered, and removed solvent in vacuo. Methylene chloride/ether (1:2, 5 mL) was added followed by sonication, the precipitate was filtered as 301a, yellow solids, 1.946 g (58%).

Example 301b tert-Butyl 4-(6-(5-(2-(Acetoxymethyl)-3-(1-oxo-3,4,6,7,8,9-hexa-hydropyrazino[1,2-a]indol-2(1H)-yl)phenyl)-1-methyl-2-oxo-1,2-dihydropyridin-3-ylamino)pyridin-3-yl)piperazine-1-carboxylate 301b

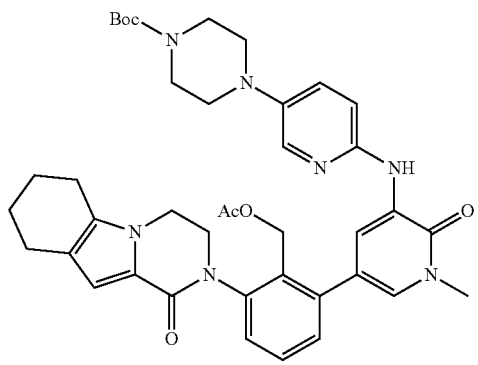 [SMILES: CC(=O)OCc1c(-c2cc(Nc3ccc(N4CCN(C(=O)OC(C)(C)C)CC4)cn3)c(=O)n(C)c2)cccc1N1CCn2c(cc3c2CCCC3)C1=O]

To a microwave tube equipped with a stirring bar, 301a (500 mg, 1.077 mmol), 2-(2-(hydroxymethyl)-3-(4,4,5,5-tetramethyl-1,3,2-dioxaborolan-2-yl)phenyl)-3,4,6,7,8,9-hexahydropyrazino[1,2-a]indol-1(2H)-one 114a (546 mg, 1.292 mmol), Pd(PPh₃)₄(62 mg, 0.054 mmol), Na₂CO₃ aqueous solution (1.0 N, 3.55 mL, 3.55 mmol), 1,2-dimethoxyethane (4.3 mL) were added. The mixture was reacted in microwave at 130° C. for 10 min. Methylene chloride (200 mL) was added and the resulting mixture was washed with water (3×30 mL), brine (30 mL), dried over MgSO₄, filtered, and removed solvent in vacuo. Silica gel column chromatography (methanol:methylene chloride=5:95) gave 301b.

To a round-bottomed flask equipped with a stirring bar, 301b, methylene chloride (10 mL) was added. The solution was cooled to 0° C. in an ice-water bath. TFA (1 mL) was added and the resulting solution was stirred overnight. Removed all the volatiles in vacuo, and to the bottle THF (5 mL), isopropanol (5 mL), H₂O (5 mL), LiOH monohydrate (300 mg) were added. The resulting mixture was stirred at RT for 1 hr. Removed all the solvent in vacuo and the resulting residue was added to methylene chloride (200 mL), the solution was washed with water (3×30 mL), brine (30 mL), dried over MgSO₄, filtered, and removed solvent in vacuo. Silica gel column (methanol:methylene chloride=10:90) followed by prep-HPLC gave 301 as a yellow solid, 9 mg. MS (ESI+) m/z 580.4 (M+H).

Example 302 10-(3-{5-[(1-Ethyl-5-methyl-1H-pyrazol-3-yl)amino]-1-methyl-6-oxo-1,6-dihydropyridin-3-yl}-5-fluoro-2-(hydroxymethyl)phenyl)-4,4-dimethyl-1,10-diazatricyclo[6.4.0.0$^{2,6}$]dodeca-2(6),7-dien-9-one 302

Example 302a 5-Bromo-3-(1-ethyl-5-methyl-1H-pyrazol-3-ylamino)-1-methylpyridin-2(1H)-one 302a

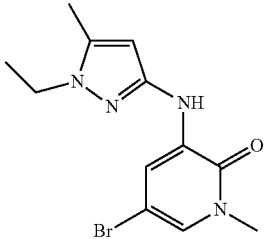

A sealed tube was equipped with a magnetic stirrer and charged with 1-ethyl-5-methyl-1H-pyrazol-3-amine (870 mg, 7 mmol), 3,5-dibromo-1-methylpyridin-2(1H)-one (1.9 g, 7 mmol) and cesium carbonate (5 g, 15 mmol) in 1,4-dioxane (69 mL). After bubbling nitrogen through the solution for 30 min, Xantphos (480 mg, 0.8 mmol) and tris(dibenzylideneacetone)dipalladium(0) (450 mg, 0.5 mmol) were added, and the reaction mixture was heated to 100° C. for 16 h. After this time, water (50 mL) and ethyl acetate (50 mL) were added. The aqueous layer was separated and extracted with ethyl acetate (2×50 mL). The combined organic extracts were washed with brine (100 mL) and dried over sodium sulfate. The mixture was concentrated under reduced pressure to near dryness when the desired product crashed out and was filtered. Washing with diethyl ether (10 mL) afforded a 40% yield (870 mg) of 302a.

Example 302b 10-(3-{5-[(1-Ethyl-5-methyl-1H-pyrazol-3-yl)amino]-1-methyl-6-oxo-1,6-dihydropyridin-3-yl}-5-fluoro-2-(acetoxymethyl)phenyl)-4,4-dimethyl-1,10-diazatricyclo[6.4.0.0$^{2,6}$]dodeca-2(6),7-dien-9-one 302b

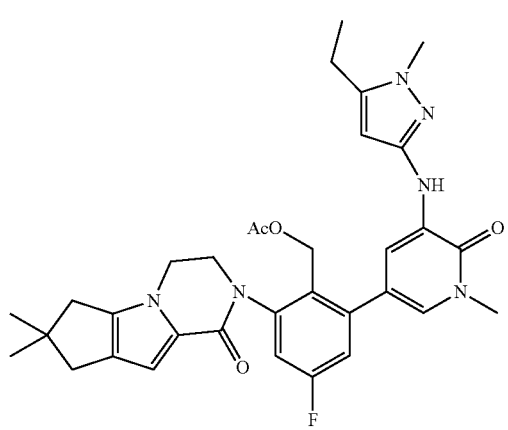

A microwave tube equipped with a magnetic stirrer was charged with 302a (170 mg, 0.5 mmol), 230a (350 mg, 0.7 mmol), 1,2-dimethoxyethane (4 mL) and 1M aqueous sodium carbonate (1.6 mL). After bubbling $N_2$ for 15 min, Pd(PPh$_3$)$_4$ (31 mg, 0.03 mmol) was added. The mixture was heated in microwave to 130° C. for 15 min. After this time, ethyl acetate (5 mL) and water (5 mL) were added. The separated aqueous layer was extracted with ethyl acetate (2×5 mL). The combined organics were washed with brine (10 mL), dried over sodium sulfate, filtered and concentrated under reduced pressure. The resulting residue was purified by column chromatography eluting with a gradient of methylene chloride—60:35:5 methylene chloride:diethyl ether:methanol to afford a 60% yield (190 mg) of 302b.

A 25 mL round bottom flask with a magnetic stirrer was charged with 302b (190 mg, 0.3 mmol), lithium hydroxide (70 mg, 1.6 mmol), THF (1.6 mL), isopropanol (1.6 mL) and water (3.2 mL). The mixture stirred at room temperature for 2 h. After this time, ethyl acetate (5 mL) and water (5 mL) were added. The separated aqueous layer was extracted with ethyl acetate (2×5 mL). The combined organics were washed with brine (10 mL), dried over sodium sulfate and filtered. The mixture was concentrated under reduced pressure to near dryness when the desired product crashed out and was filtered. Upon washing with diethyl ether (10 mL) afforded a 51% yield (90 mg) of 302. MS (ESI+) m/z 559.4 (M+H).

Example 303 5-[5-Fluoro-2-(hydroxymethyl)-3-[1-methyl-5-({5-[1-(oxetan-3-yl)piperidin-4-yl]pyridine-2-yl}amino)-6-oxo-1,6-dihydropyridin-3-yl]phenyl]-8-thia-5-azatricyclo[7.4.0.0$^{2,7}$]trideca-1(9),2(7)-dien-6-one 303

Following Example 299, compound 212b was converted to 303. MS (ESI+) m/z 670.3 (M+H).

Example 304 10-[5-Fluoro-2-(hydroxymethyl)-3-[1-methyl-5-({5-[4-(oxetan-3-yl)piperazin-1-yl]pyridine-2-yl}amino)-6-oxo-1,6-dihydropyridin-3-yl]phenyl]-4,4-dimethyl-1,10-diazatricyclo[6.4.0.0$^{2,6}$]dodeca-2(6),7-dien-9-one 304

To a solution of (2-{4,4-dimethyl-9-oxo-1,10-diazatricyclo[6.4.0.0$^{2,6}$]dodeca-2(6),7-dien-10-yl}-4-fluoro-6-[1-methyl-5-({5-[4-(oxetan-3-yl)piperazin-1-yl]pyridin-2-yl}amino)-6-oxo-1,6-dihydropyridin-3-yl]phenyl)methyl acetate (200 mg, 0.28 mmol) in THF/iPA/H$_2$O (6 mL/6 mL/2 mL) at room temperature was added LiOH (70 mg, 2.9 mmol) while stirring. This mixture was stirred for 0.5 h. Then, 20 mL H$_2$O was added and the mixture was extracted with ethyl acetate (30 mL×3). The combined organic layers were dried with Na$_2$SO$_4$ and concentrated to give a yellow solid which was further purified by prep-HPLC to afford 304 as a white solid (100 mg, 53%). LCMS: [M+H]$^+$ 668. $^1$H NMR (500 MHz, DMSO): δ 1.23 (s, 6H), 2.37-2.39 (m, 5H), 2.53-2.57 (m, 2H), 3.07 (s, 4H), 3.43-3.45 (m, 2H), 3.60 (s, 3H), 3.85-3.87 (m, 1H), 4.16-1.19 (m, 3H), 4.32 (d, J=6.0 Hz, 2H), 4.45-4.50 (m, 2H), 4.54-4.58 (m, 2H), 4.86 (s, 1H), 6.47-6.51 (m, 1H), 7.18-7.25 (m, 2H), 7.34-7.39 (m, 3H), 7.83-7.86 (m, 1H), 8.35-8.37 (m, 1H), 8.53-8.56 (m, 1H).

Example 305 5-[2-(Hydroxymethyl)-3-[4-methyl-6-({4-[1-(oxetan-3-yl)piperidin-4-yl]phenyl}amino)-5-oxo-4,5-dihydropyrazin-2-yl]phenyl]-8-thia-5-azatricyclo[7.4.0.0²,⁷]trideca-1(9),2(7)-dien-6-one 305

Example 305a {2-[4-Methyl-6-({4-[1-(oxetan-3-yl)piperidin-4-yl]phenyl}amino)-5-oxo-4,5-dihydropyrazin-2-yl]-6-{6-oxo-8-thia-5-azatricyclo[7.4.0.0²,⁷]trideca-1(9),2(7)-dien-5-yl}phenyl}methyl Acetate 305a

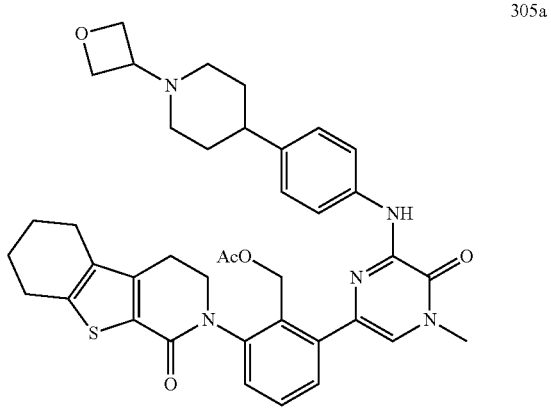 [SMILES: CC(=O)OCc1c(-c2cn(C)c(=O)c(Nc3ccc(C4CCN(C5COC5)CC4)cc3)n2)cccc1N1CCc2c(sc3c2CCCC3)C1=O]

Following Example 136e, 5-bromo-1-methyl-3-(4-(1-(oxetan-3-yl)piperidin-4-yl)phenylamino)pyrazin-2(1H)-one 214b and (2-{6-oxo-8-thia-5-azatricyclo[7.4.0.0²,⁷]trideca-1(9),2(7)-dien-5-yl}-6-(4,4,5,5-tetramethyl-1,3,2-dioxaborolan-2-yl)phenyl)methyl acetate 111a afforded 305a in 68% yield. LCMS: (M+H)⁺ 694

Following Example 136, 305a was converted to 305 in 51% yield. LCMS: (M+H)⁺ 652. ¹H NMR (500 MHz, DMSO) δ 9.18 (s, 1H), 7.88 (s, 1H), 7.86 (s, 1H), 7.52 (d, J=7.5, 1H), 7.46 (t, J=7.5, 1H), 7.38 (s, 1H), 7.17 (s, 1H), 7.32 (d, J=7.5, 1H), 7.15 (d, J=8.5, 2H), 4.78 (m, 1H), 4.52 (m, 3H), 4.43 (m, 3H), 4.01 (m, 1H), 3.87 (m, 1H), 3.54 (s, 3H), 3.37 (m, 1H), 2.96 (m, 1H), 2.86 (m, 1H), 2.78 (m, 4H), 2.43 (m, 2H), 1.82 (s, 6H), 1.72 (m, 2H), 1.60 (m, 2H).

Example 306 10-[2-(Hydroxymethyl)-3-[1-methyl-6-oxo-5-(pyrimidin-4-ylamino)-1,6-dihydropyridazin-3-yl]phenyl]-4,4-dimethyl-7-thia-10-azatricyclo[6.4.0.0²,⁶]dodeca-1(8),2(6)-dien-9-one 306

Example 306b 10-[2-(Acetoxymethyl)-3-[1-methyl-6-oxo-5-(pyrimidin-4-ylamino)-1,6-dihydropyridazin-3-yl]phenyl]-4,4-dimethyl-7-thia-10-azatricyclo[6.4.0.0²,⁶]dodeca-1(8),2(6)-dien-9-one 306b

Step 1

In a pressure flask was placed 5-chloro-1-methyl-3-(pyrimidin-4-ylamino)pyridazin-2(1H)-one (300 mg, 1.26 mmol), 4,4,4',4',5,5,5',5'-octamethyl-2,2'-bi(1,3,2-dioxaborolane) (577 mg, 2.27 mmol), potassium acetate (247 mg, 2.32 mmol), X-Phos (2-Dicyclohexylphosphino-2',6'-triisopropylbiphenyl) (120 mg, 20 mol %), and Tris(dibenzylideneacetone)dipalladium(0) (115 mg, 10 mol %) The flask was evacuated and filled with N₂ 3×, dioxane (12 mL) was added, the vessel sealed and heated to 90° C. for 2 hrs. The reaction was allowed to cool then diluted with ethyl acetate, and filtered through a pad of celite and concentrated under reduced pressure to give 306a which was used directly in the next step.

Step 2

306a was dissolved in dioxane (7 mL) and transferred to a pressure flask containing 189a (448 mg, 1.0 mmol), 10% K₂CO₃/water (2.5 ml) and bis(di-tert-butyl(4-dimethylaminophenyl)phosphine)dichloropalladium(II) (45 mg, 5 mol %). The flask was sealed and heated to 100° C. overnight. The reaction was then diluted with ethyl acetate and water, separated, washed with brine 3×, dried over Na₂SO₄, filtered, and concentrated under reduced pressure. The residue was purified by chromatography: ISCO 24 g silica, eluting with 50-100% ethyl acetate/hexanes, to give 306b (250 mg, 35% yield over 2 steps).

Following Example 119, 306b (250 mg, 0.44 mmol), 1N LiOH (2.2 mL), THF (4.5 mL) and isopropanol (4.5 mL) were reacted. The product was triturated with ether and dried under vacuum to give 306 (185 mg, 80% yield) as an off-white solid. MS (ESI+) m/z 529.3 (M+H).

Example 307 2-(2-(Hydroxymethyl)-3-(1-methyl-5-(5-(4-methylpiperazin-1-yl)pyridin-2-ylamino)-6-oxo-1,6-dihydropyridazin-3-yl)phenyl)-3,4,6,7,8,9-hexahydropyrazino[1,2-a]indol-1(2H)-one 307

Example 307a 6-Chloro-2-methyl-4-(5-(4-methylpiperazin-1-yl)pyridin-2-ylamino)pyridazin-3(2H)-one 307a

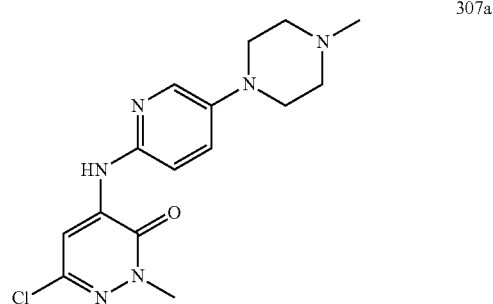 [SMILES: CN1CCN(c2ccc(Nc3cc(Cl)nn(C)c3=O)nc2)CC1]

Following Example 119b, 4-bromo-6-chloro-2-methylpyridazin-3(2H)-one (1.5 g, 6.7 mmol), 5-(4-methyl-piperazin-1-yl)-pyridin-2-ylamine (1.3 g, 6.7 mmol), cesium carbonate (4.8 g, 39.4 mmol), and Xantphos (330 mg, 8.5 mol %), dioxane (50 ml) and tris(dibenzylideneacetone)dipalladium(0) (307 mg, 5 mol %) were reacted. Purified via column chromatography: ISCO 40 g silica, 50-100% ethyl acetate/hexanes then 0-10% methanol to give 307a (1.2 g, 53%) as a light tan solid.

Example 307c 2-(2-(Acetoxymethyl)-3-(1-methyl-5-(5-(4-methylpiperazin-1-yl)pyridin-2-ylamino)-6-oxo-1,6-dihydropyridazin-3-yl)phenyl)-3,4,6,7,8,9-hexahydropyrazino[1,2-a]indol-1(2H)-one 307c

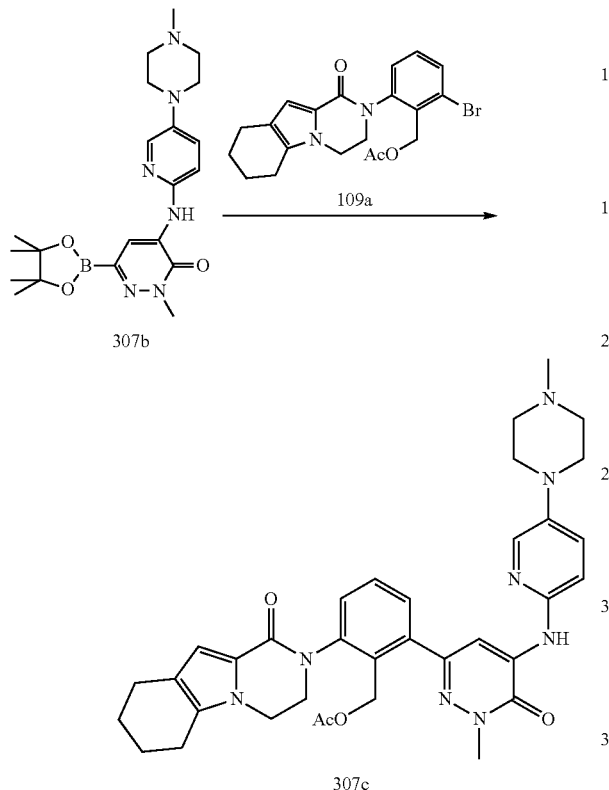

Following Example 306b, 307a (422 mg, 1.26 mmol) was converted to the boron intermediate 307b, which was coupled under Suzuki conditions with 109a (420 mg, 1.0 mmol). The crude product was purified via column chromatography: ISCO 24 g silica, 50-100% ethyl acetate/hexanes then 0-10% MeOH, to give 307c (285 mg, 36% yield).

Following Example 119, 307c (285 mg, 0.45 mmol), 1N LiOH (2.2 mL), THF (5 mL) and isopropanol (5 mL) were reacted, triturated with ethyl acetate and dried under vacuum to give 307 (115 mg, 43% yield) as slightly yellow solid. MS (ESI+) m/z 595.6 (M+H).

Example 308 5-[5-Fluoro-2-(Hydroxymethyl)-3-(1-methyl-5-{[5-(1-methylpyrrolidin-3-yl)pyridine-2-yl]amino}-6-oxo-1,6-dihydropyridin-3-yl)phenyl]-8-thia-5-azatricyclo-[7.4.0.0²,⁷]trideca-1(9),2(7)-dien-6-one 308

Following Example 270, reaction of boronate 212b with bromide 202a yielded 308. MS (ESI+) m/z 614.3 (M+H).

Example 309 5-[2-(Hydroxymethyl)-3-{1-oxo-1H,2H,3H,4H,6H,7H,8H,9H-pyrido[3,4-b]indolizin-2-yl}phenyl]-1-methyl-3-{4H,6H,7H-pyrazolo[3,2-c][1,4]oxazin-2-ylamino}-1,2-dihydropyridin-2-one 309

Following Example 270, reaction of boronate 113a with bromide 110c yielded 309. MS (ESI+) m/z 541.2 (M+H).

Example 310 3-{[5-(4-Ethylpiperazin-1-yl)pyridine-2-yl]amino}-5-[2-(hydroxymethyl)-3-{1-oxo-1H,2H,3H,4H,6H,7H,8H,9H-pyrido[3,4-b]indolizin-2-yl}phenyl]-1-methyl-1,2-dihydropyridin-2-one 310

Following Example 270, reaction of boronate 113a with bromide 138c yielded 310. MS (ESI+) m/z 608.3 (M+H).

Example 311 10-[2-(Hydroxymethyl)-3-[1-methyl-5-({5-[4-(oxetan-3-yl)piperazin-1-yl]pyridine-2-yl}amino)-6-oxo-1,6-dihydropyridin-3-yl]phenyl]-4,4-dimethyl-1,10-diazatricyclo[6.4.0.0²,⁶]dodeca-2(6),7-dien-9-one 311

Example 311a (2-{4,4-Dimethyl-9-oxo-1,10-diazatricyclo[6.4.0.0²,⁶]dodeca-2(6),7-dien-10-yl}-6-[1-methyl-5-({5-[4-(oxetan-3-yl)piperazin-1-yl]pyridin-2-yl}amino)-6-oxo-1,6-dihydropyridin-3-yl]phenyl) methyl Acetate 311a

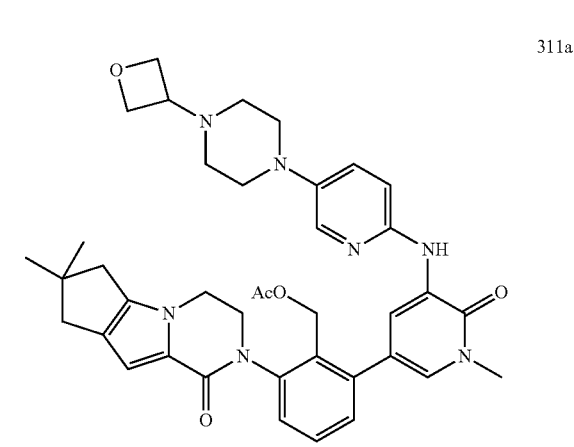 [SMILES: CC(=O)OCc1c(-c2cc(Nc3ccc(N4CCN(C5COC5)CC4)cn3)c(=O)n(C)c2)cccc1N1CCn2c(cc3c2CC(C)(C)C3)C1=O]

A sealed tube was charged with the mixture of (2-{4,4-dimethyl-9-oxo-1,10-diazatricyclo[6.4.0.02,6]dodeca-2(6),7-dien-10-yl}-6-(4,4,5,5-tetramethyl-1,3,2-dioxaborolan-2-yl)phenyl)methyl acetate (335 mg, 0.7 mmol), 5-bromo-1-methyl-3-(5-(4-(oxetan-3-yl)piperazin-1-yl)pyridin-2-ylamino)pyridin-2(1H)-one 188e (294 mg, 0.7 mmol), Pd(dppf)Cl₂ (33 mg, 0.04 mmol), K₃PO₄·3H₂O (372 mg, 1.4 mmol), and NaOAc (115 mg, 1.4 mmol) in CH₃CN (20 mL). The system was evacuated and refilled with N₂. The reaction mixture was heated at 110° C. for 2 h. It was then cooled to room temperature and filtered. The filtrate was concentrated under reduced pressure and the resulting residue was purified by flash column chromatography eluting with 30:1 methylene chloride/methanol to afford 311a as a yellow solid (208 mg, 43%). MS: [M+H]⁺ 692.

At room temperature, to the solution of 311a (200 mg, 0.29 mol) in THF/isopropanol/water (6 mL/6 mL/2 mL) was added LiOH (70 mg, 2.9 mmol) while stirring. This mixture was stirred for 0.5 h. Then, 20 mL water was added and the mixture was extracted with ethyl acetate (3×30 mL). The combined organic layer was dried with Na₂SO₄ and concentrated to give a yellow solid which was further purified by prep-HPLC to afford 311 as a white solid (100 mg, 53%). LCMS: [M+H]⁺ 650. ¹H NMR (500 MHz, DMSO) δ 1.22 (s, 6H), 2.37-2.42 (m, 6H), 2.54-2.56 (m, 1H), 3.06 (d, J=4.5 Hz, 4H), 3.41-3.44 (m, 2H), 3.59 (s, 3H), 3.85-3.90 (m, 1H), 4.08-4.21 (m, 3H), 4.35 (d, J=4.5 Hz, 2H), 4.45-4.47 (m, 2H), 4.54-4.57 (m, 2H), 4.84-4.86 (m, 1H), 6.45 (s, 1H), 7.22 (d, J=9.0 Hz, 1H), 7.31-7.47 (m, 4H), 7.44-7.47 (m, 1H), 7.86 (d, J=3.0 Hz, 1H), 8.37 (s, 1H), 8.56 (d, J=2.0 Hz, 1H).

Example 312 10-[2-(Hydroxymethyl)-3-[1-methyl-5-({5-[4-(oxetan-3-yl)piperazin-1-yl]pyridine-2-yl}amino)-6-oxo-1,6-dihydropyridin-3-yl]phenyl]-4,4-dimethyl-7-thia-10-azatricyclo[6.4.0.0$^{2,6}$]dodeca-1(8),2(6)-dien-9-one 312

Example 312a (2-{4,4-Dimethyl-9-oxo-7-thia-10-azatricyclo[6.4.0.0$^{2,6}$]dodeca-1(8),2(6)-dien-10-yl}-6-[1-methyl-5-({5-[4-(oxetan-3-yl)piperazin-1-yl]pyridin-2-yl}amino)-6-oxo-1,6-dihydropyridin-3-yl]phenyl)methyl Acetate 312a Following Example 136e, 5-bromo-1-methyl-3-(5-(4-(oxetan-3-yl)piperazin-1-yl)pyridin-2-ylamino)pyridin-2(1H)-one (24-7) and (2-{4,4-dimethyl-9-oxo-7-thia-10-azatricyclo[6.4.0.0$^{2,6}$]dodeca-1(8),2(6)-dien-10-yl}-6-(tetramethyl-1,3,2-dioxaborolan-2-yl)phenyl)methyl acetate 131a was converted to 312a in 63% yield. LCMS: (M+H)$^+$ 709

Following Example 136, 312a was converted to 312 in 60% yield. LCMS: (M+H)$^+$ 667. $^1$H NMR (500 MHz, MEOD) δ 8.52 (s, 1H), 7.93 (m, 1H), 7.50 (m, 1H), 7.42 (m, 3H), 7.30 (s, 1H), 7.05 (m, 1H), 4.73 (t, J=6.5, 2H), 4.64 (t, J=6, 2H), 4.56 (m, 2H), 4.14 (m, 1H), 3.98 (m, 1H), 3.71 (s, 3H), 3.67 (m, 1H), 3.16 (m, 4H), 3.11 (m, 1H), 2.96 (m, 1H), 2.81 (s, 2H), 2.60 (m, 2H), 2.53 (s, 4H), 1.29 (d, J=3, 6H).

Example 313 5-[5-Fluoro-2-(hydroxymethyl)-3-(1-methyl-5-{[5-(2S)-(1-methylpyrrolidin-2-yl)pyridine-2-yl]amino}-6-oxo-1,6-dihydropyridin-3-yl)phenyl]-8-thia-5-azatricyclo[7.4.0.0$^{2,7}$]trideca-1(9),2(7)-dien-6-one 313

Example 314 5-[5-Fluoro-2-(hydroxymethyl)-3-(1-methyl-5-{[5-(2R)-(1-methylpyrrolidin-2-yl)pyridine-2-yl]amino}-6-oxo-1,6-dihydropyridin-3-yl)phenyl]-8-thia-5-azatricyclo[7.4.0.0$^{2,7}$]trideca-1(9),2(7)-dien-6-one 314

Compounds 313 and 314 are enantiomers of racemate 288. The racemic mixture 288 was subjected to chiral separation on a Chiralpak AD, 4.6×50 mm, 3 mm column (mobile phase 55% isopropanol (w/0.1% triethylamine)/45% CO$_2$, flow rate 5 mL/min) at 40° C. to give individual enantiomers, with 313 eluting first, and 314 eluting last.

Example 315 5-[2-(Hydroxymethyl)-3-(1-methyl-5-{[5-(1-methylpiperidin-4-yl)pyridine-2-yl]amino}-6-oxo-1,6-dihydropyridin-3-yl)phenyl]-8-thia-5-azatricyclo[7.4.0.0$^{2,7}$]trideca-1(9),2(7)-dien-6-one 315

Example 315a [2-(1-Methyl-5-{[5-(1-methylpiperidin-4-yl)pyridin-2-yl]amino}-6-oxo-1,6-dihydropyridin-3-yl)-6-{6-oxo-8-thia-5-azatricyclo[7.4.0.0$^{2,7}$]trideca-1(9),2(7)-dien-5-yl}phenyl]methyl Acetate 315a

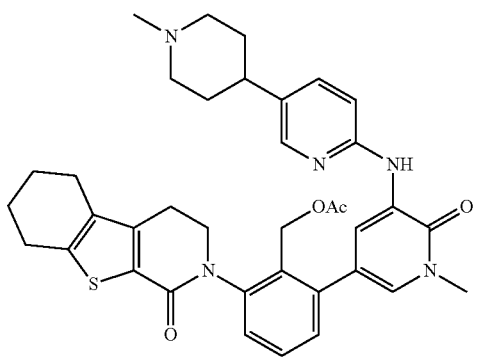

315a

A sealed tube was charged with the mixture of 5-bromo-1-methyl-3-(5-(1-methylpiperidin-4-yl)pyridin-2-ylamino)pyridin-2(1H)-one 130c (400 mg, 1.06 mmol), (2-{6-oxo-8-thia-5-azatricyclo[7.4.0.0$^{2,7}$]trideca-1(9),2(7)-dien-5-yl}-6-(4,4,5,5-tetramethyl-1,3,2-dioxaborolan-2-yl)phenyl)methyl acetate 111a (512 mg, 1.06 mmol), Pd(dppf)Cl$_2$ (87 mg, 0.1 mmol), K$_3$PO$_4$.3H$_2$O (566 mg, 2.12 mmol), and NaOAc (174 mg, 2.12 mmol) in CH$_3$CN (25 mL). The system was evacuated and then refilled with N$_2$. The reaction mixture was heated at 110° C. for 2 h. Then, the mixture was cooled to room temperature and filtered. The filtrate was concentrated under reduced pressure and the resulting residue was purified by flash column chromatography eluting with 10:1 methylene chloride/methanol to give 315a as a brown solid (300 mg, 43%). MS: [M+H]$^+$ 652

A solution of 315a (250 mg, 0.38 mmol) in propan-2-ol (10 mL), tetrahydrofuran (10 mL) and water (1.5 mL) was added LiOH (922 mg, 38 mmol). The mixture was stirred at 30° C. for 2 h. It was then evaporated and the residue was purified by reverse phase Combi-flash eluting with 0.3% NH$_4$HCO$_3$ in 1:4 water/CH$_3$CN to give 315 as a white solid (37 mg, 16%). MS: (M+H)$^+$ 610. $^1$H NMR (500 MHz, MeOD) δ 1.74-1.84 (m, 4H), 1.87-1.95 (m, 4H), 2.13-2.18 (t, J=11.5, 2 H), 2.32 (s, 3H), 2.52-2.61 (m, 3H), 2.85-2.87 (t, J=4.5, 2 H), 2.92-3.06 (m, 4H), 3.71 (s, 3H), 3.99-4.03 (m, 1H), 4.12-4.17 (m, 1H), 4.52-4.59 (m, 2H), 7.03 (d, 1H), 7.34 (d, 1H), 7.39 (d, 1H), 7.42 (d, 1H), 7.51 (d, 1H), 7.56 (d, 1H), 8.08 (s, 1H), 8.62 (s, 1H).

Example 316 5-[5-Fluoro-2-(hydroxymethyl)-3-{1-oxo-1H,2H,3H,4H,6H,7H,8H,9H-pyrazino[1,2-a]indol-2-yl}phenyl]-1-methyl-3-[(4-(1-methylazetidin-3-yl)phenyl)amino)-1,2-dihydropyrazin-2-one 316

Example 316a 4-Fluoro-2-(4-methyl-6-(4-(1-methylazetidin-3-yl)phenylamino)-5-oxo-4,5-dihydropyrazin-2-yl)-6-(1-oxo-3,4,6,7,8,9-hexahydropyrazino[1,2-a]indol-2(1H)-yl)benzyl Acetate 316a

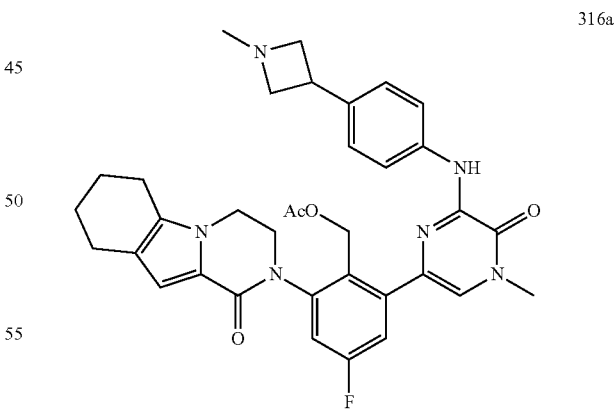

316a

A sealed tube was charged with the mixture of 5-bromo-1-methyl-3-(4-(1-methylazetidin-3-yl)phenylamino)pyrazin-2(1H)-one 298c (200 mg, 0.58 mmol), 4-fluoro-2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 210d (280 mg, 0.58 mmol), Pd(dppf)Cl$_2$ (40 mg, 0.06 mmol), K$_3$PO$_4$.3H$_2$O (300 mg, 1.16 mmol), and NaOAc (100 mg, 1.16 mmol) in CH$_3$CN (20 mL). The system was evacuated and then refilled with $N_2$. And the reaction mixture was heated at 110° C. for 3 h. Then, the mixture was cooled to room temperature and filtered. The filtrate was concentrated under reduced pressure and the resulting residue was purified by flash column chromatography eluting with 15:1 methylene chloride/methanol to give 216a as a brown solid (150 mg, 42%). MS: [M+H]+ 625

A solution of 316a (130 mg, 0.21 mmol) in propan-2-ol (7 mL), tetrahydrofuran (7 mL), and water (1 mL) was added LiOH (500 mg, 21 mmol). The mixture was stirred at 30° C. for 2 h. It was evaporated and the residue was purified by prep-HPLC to afford 316 as a white solid (14 mg, 12%). MS: (M+H)+ 583. $^1$H NMR (500 MHz, MEOD) δ 1.77-1.81 (m, 2H), 1.89-1.95 (m, 2H), 2.46 (s, 3H), 2.55 (t, J=6, 2 H), 2.60-2.68 (m, 2H), 3.64 (s, 3H), 3.73-3.77 (m, 1H), 3.85 (s, 2H), 4.16-4.27 (m, 1H), 4.46-4.59 (m, 2H), 6.72 (s, 1H), 7.19-7.21 (d, 1H), 7.8-7.30 (d, 2H), 7.31-7.41 (dd, 2H), 7.78 (d, 2H).

Example 317 10-[2-(Hydroxymethyl)-3-(1-methyl-5-{[5-(oxetan-3-yl)-4H,5H,6H,7H-pyrazolo[1,5-a]pyrazin-2-yl]amino}-6-oxo-1,6-dihydropyridin-3-yl)phenyl]-4,4-dimethyl-7-thia-10-azatricyclo[6.4.0.0$^{2,6}$]dodeca-1(8),2(6)-dien-9-one 317

Example 317a (2-{4,4-Dimethyl-9-oxo-7-thia-10-azatricyclo[6.4.0.0$^{2,6}$]dodeca-1(8),2(6)-dien-10-yl}-6-(1-methyl-5-{[5-(oxetan-3-yl)-4H,5H,6H,7H-pyrazolo[1,5-a]pyrazin-2-yl]amino}-6-oxo-1,6-dihydropyridin-3-yl)phenyl)methyl Acetate 317a

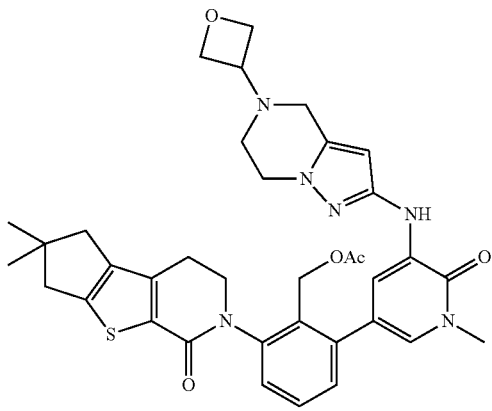

A sealed tube was charged with the mixture of 5-bromo-1-methyl-3-(5-(oxetan-3-yl)-4,5,6,7-tetrahydropyrazolo[1,5-a]pyrazin-2-ylamino)pyridin-2(1H)-one 252a (275 mg, 0.7 mmol), (2-{4,4-dimethyl-9-oxo-7-thia-10-azatricyclo[6.4.0.0$^{2,6}$]dodeca-1(8),2(6)-dien-10-yl}-4-fluoro-6-(4,4,5,5-tetramethyl-1,3,2-dioxaborolan-2-yl)phenyl)methyl acetate 131a (356 mg, 0.7 mmol), Pd(dppf)Cl$_2$ (59 mg, 0.07 mmol), $K_3PO_4 \cdot 3H_2O$ (317 mg, 1.4 mmol), and NaOAc (118 mg, 1.4 mmol) in $CH_3CN$ (20 mL). The system was evacuated and refilled with $N_2$. The reaction mixture was heated at 110° C. for 2 h. It was then cooled to room temperature and filtered. The filtrate was concentrated under reduced pressure and the resulting residue was purified by flash column chromatography eluting with 30:1 methylene chloride/methanol to afford 317a as a yellow solid (300 mg, 61%). MS: [M+H]+ 669.

At room temperature, to the solution of 317a (300 mg, 0.5 mol) in THF/isopropanol/water (6 mL/6 mL/2 mL) was added LiOH (70 mg, 2.9 mmol) while stirring. This mixture was stirred for 0.5 h. Then, 20 mL $H_2O$ was added and the mixture was extracted with ethyl acetate (3×30 mL). The combined organic layer was dried with $Na_2SO_4$ and concentrated to get a yellow solid, which was further purified by prep-HPLC to afford 317 as a white solid (93 mg, 28%). MS: [M+H]+ 627. $^1$H NMR (500 MHz, DMSO) δ 1.24 (s, 6H), 2.65 (s, 1H), 2.75 (d, J=8.5 Hz, 4H), 2.88-2.91 (m, 1H), 3.00-3.03 (m, 1H), 3.50 (s, 2H), 3.57 (s, 3H), 3.67 (t, J=6.0 Hz, 1H), 3.84-3.89 (m, 1H), 3.93 (t, J=6.0 Hz, 2H), 4.00-4.05 (m, 1H), 4.34-4.36 (m, 2H), 4.49 (t, J=6.0 Hz, 2H), 4.59 (t, J=7.0 Hz, 2H), 4.83 (d, J=5.0 Hz, 1H), 5.91 (s, 1H), 7.24 (d, J=2.0 Hz, 1H), 7.24-7.35 (m, 2H), 7.45 (t, J=7.0 Hz, 1H), 7.98 (d, J=2.0 Hz, 1H), 8.13 (s, 1H).

Example 318 10-[5-Fluoro-2-(hydroxymethyl)-3-(1-methyl-5-{[5-(oxetan-3-yl)-4H,5H,6H,7H-pyrazolo[1,5-a]pyrazin-2-yl]amino}-6-oxo-1,6-dihydropyridin-3-yl)phenyl]-4,4-dimethyl-7-thia-10-azatricyclo[6.4.0.0$^{2,6}$]dodeca-1(8),2(6)-dien-9-one 318

Example 318a (2-{4,4-Dimethyl-9-oxo-7-thia-10-azatricyclo[6.4.0.0$^{2,6}$]dodeca-1(8),2(6)-dien-10-yl}-4-fluoro-6-(1-methyl-5-{[5-(oxetan-3-yl)-4H,5H,6H,7H-pyrazolo[1,5-a]pyrazin-2-yl]amino}-6-oxo-1,6-dihydropyridin-3-yl)phenyl)methyl Acetate 318a

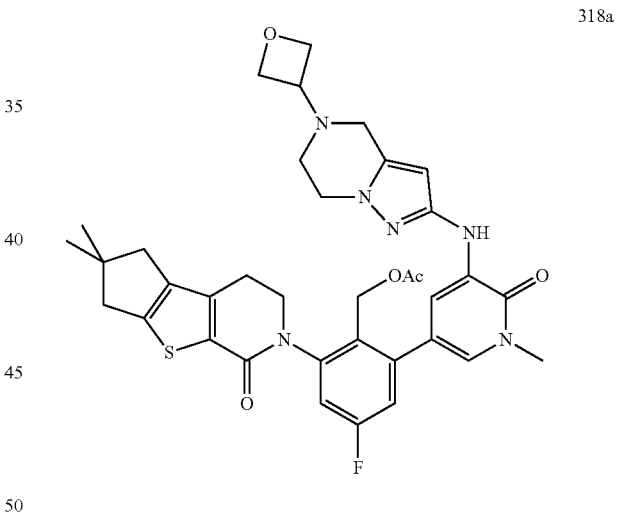

A sealed tube was charged with the mixture of (2-{4,4-dimethyl-9-oxo-7-thia-10-azatricyclo[6.4.0.0$^{2,6}$]dodeca-1(8),2(6)-dien-10-yl}-4-fluoro-6-(4,4,5,5-tetramethyl-1,3,2-dioxaborolan-2-yl)phenyl)methyl acetate 247b (300 mg, 0.584 mmol), 5-bromo-1-methyl-3-(5-(oxetan-3-yl)-4,5,6,7-tetrahydropyrazolo[1,5-a]pyrazin-2-ylamino)pyridin-2(1H)-one 252a (222 mg, 0.584 mmol), Pd(dppf)Cl$_2$ (48 mg, 0.0584 mmol), $K_3PO_4 \cdot 3H_2O$ (311 mg, 1.168 mmol), and NaOAc (96 mg, 1.168 mmol) in $CH_3CN$ (20 mL). The system was evacuated and then refilled with $N_2$. And the reaction mixture was heated at 110° C. for 2 h. Then, the mixture was cooled to room temperature and filtered. The filtrate was concentrated under reduced pressure and the resulting residue was purified by flash column chromatography eluting with 30:1 methylene chloride/methanol to afford 318a as a yellow solid (304 mg, 74%). MS: [M+H]+ 687.

To a solution of 318a (300 mg, 0.44 mol) in THF/isopropanol/water (6 mL/6 mL/2 mL) was added LiOH (100 mg, 4.16 mmol) at room temperature. The mixture was stirred for 0.5 h. Then, 20 mL H$_2$O was added and the mixture was extracted with ethyl acetate (30 mL×3). The combined organic layer was dried with Na$_2$SO$_4$ and concentrated to give a yellow solid, which was further purified by prep-HPLC to afford 318 as a white solid (68.7 mg, 52.3%). $^1$H NMR (500 MHz, DMSO) δ 8.17 (s, 1H), 7.98 (d, J=6 Hz, 1H), 7.30 (t, 2H), 7.17 (t, 1H), 5.91 (s, 1H), 4.88 (t, 1H), 4.58 (t, 2H), 4.48 (t, 2H), 4.32 (d, 1H), 4.05 (t, 1H), 4.02 (m, 3H), 3.94 (m, 2H), 3.92 (s, 1H), 3.83 (s, 1H), 3.30 (s, 1H), 3.02 (m, 1H), 2.88 (s, 4H), 2.73 (s, 2H), 1.20 (s, 6H)

Example 319 2-(2-(Hydroxymethyl)-3-(1-methyl-5-(5-(oxetan-3-yl)-4,5,6,7-tetrahydropyrazolo[1,5-a]pyrazin-2-ylamino)-6-oxo-1,6-dihydropyridin-3-yl)phenyl)-3,4,6,7,8,9-hexahydropyrazino[1,2-a]indol-1(2H)-one 319

Example 319a [2-(1-Methyl-5-{[5-(oxetan-3-yl)-4H,5H,6H,7H-pyrazolo[1,5-a]pyrazin-2-yl]amino}-6-oxo-1,6-dihydropyridin-3-yl)-6-{1-oxo-1H,2H,3H,4H,6H,7H,8H,9H-pyrazino[1,2-a]indol-2-yl}phenyl]methyl Acetate 319a

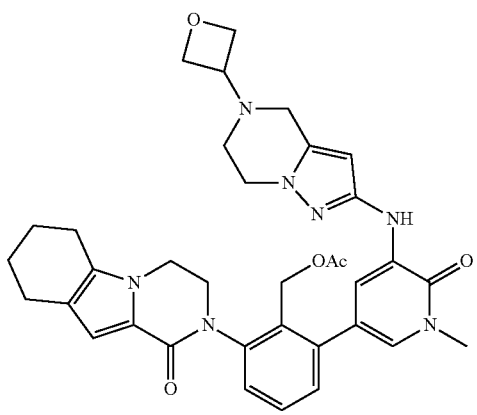

319a

A sealed tube was charged with the mixture of 5-bromo-1-methyl-3-(5-(oxetan-3-yl)-4,5,6,7-tetrahydropyrazolo[1,5-a]pyrazin-2-ylamino)pyridin-2(1H)-one 252a (265 mg, 0.7 mmol), 2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 114a (320 mg, 0.7 mmol), Pd(dppf)Cl$_2$ (56 mg, 0.07 mmol), K$_3$PO$_4$·3H$_2$O (367 mg, 1.4 mmol), and NaOAc (113 mg, 1.4 mmol) in CH$_3$CN (20 mL). The system was evacuated and refilled with N$_2$. The reaction mixture was heated at 110° C. for 2 h. It was then cooled to room temperature and filtered. The filtrate was concentrated under reduced pressure and the resulting residue was purified by flash column chromatography eluting with 30:1 methylene chloride/methanol to afford 319a as a yellow solid (200 mg, 38%). MS: [M+H]$^+$ 638.

At room temperature, to the solution of 319a (150 mg, 0.24 mol) in THF/isopropanol/water (6 mL/6 mL/2 mL) was added LiOH (70 mg, 2.9 mmol) while stirring. This mixture was stirred for 0.5 h. Then, 20 mL water was added and the mixture was extracted with ethyl acetate (3×30 mL). The combined organic layer was dried with Na$_2$SO$_4$ and concentrated to give a yellow solid, which was further purified by prep-HPLC to afford 319 as a white solid (50 mg, 28%). MS: [M+H]$^+$ 596. $^1$H NMR (500 MHz, DMSO) δ 1.23 (t, J=7.0 Hz, 2H), 1.70-2.08 (m, 5H), 2.74-2.76 (m, 2H), 3.50 (s, 2H), 3.57 (s, 3H), 3.67 (s, 1H), 3.91-3.94 (m, 3H), 4.03-4.16 (m, 4H), 4.35 (s, 2H), 4.48-4.50 (m, 2H), 4.58-4.60 (m, 2H), 4.61 (s, 1H), 5.91 (s, 1H), 6.51 (s, 1H), 7.23 (s, 1H), 7.30-7.34 (m, 2H), 7.44-7.47 (m, 1H), 7.98 (d, J=2.0 Hz, 1H), 8.12 (s, 1H).

Example 320 2-(5-Fluoro-2-(hydroxymethyl)-3-(1-methyl-5-(5-(4-(oxetan-3-yl)piperazin-1-yl)pyridin-2-ylamino)-6-oxo-1,6-dihydropyridin-3-yl)phenyl)-3,4,6,7,8,9-hexahydropyrazino[1,2-a]indol-1(2H)-one 320

Example 320a N-Methyl(1-methyl-3-nitro-1H-pyrazol-5-yl)methanamine 320a

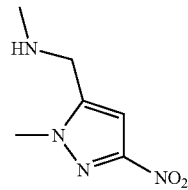

To a stirred solution of MeNH$_2$ (30% wt in H$_2$O) (2.5 g, 20 mmol) in acetone (10 mL) at 0° C. (ice bath) was added K$_2$CO$_3$ (415 mg, 3 mmol), followed by the dropwise addition of a solution of 5-(bromomethyl)-1-methyl-3-nitro-1H-pyrazole (220 mg, 1 mmol) in acetone (5 mL). The reaction mixture was then warmed to room temperature and stirred for 3 h. The solvent was removed and the residue was extracted with methylene chloride (15 mL×3), dried over Na$_2$SO$_4$ and concentrated to afford 320a as a yellow oil (170 mg, 99%), which was used in the next step without additional purification. LCMS: (M+H)$^+$ 171

Example 320b N-Methyl-N-((1-methyl-3-nitro-1H-pyrazol-5-yl)methyl)oxetan-3-amine 320b

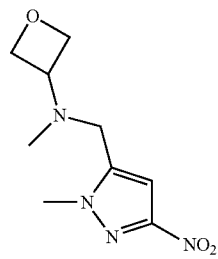 [SMILES: CN(Cc1cc([N+](=O)[O-])nn1C)C1COC1]

To a mixture of 320a (170 mg, 1 mmol) in methanol (4 mL), ZnCl$_2$ (1 mmol/L in diethyl ether) (2 mL, 2 mmol) and oxetan-3-one (150 mg, 2 mmol) were added at room temperature under nitrogen protection, followed by the addition of NaBH$_3$CN (130 mg, 2 mmol). The reaction mixture was warmed to 50° C. and stirred for 3 h. The mixture was then cooled to room temperature and the solvent was removed. The residue was purified on flash column eluting with 50:1 methylene chloride/methanol to afford 320b as a yellow solid (180 mg, 80%, two steps). LCMS: (M+H)+ 227. ¹H NMR (500 MHz, DMSO) δ 6.99 (s, 1H), 4.52 (t, J=6.5, 2H), 4.42 (t, J=6, 2H), 3.98 (s, 3H), 3.63 (m, 1H), 3.50 (s, 2H), 2.03 (s, 3H).

Example 320c 1-Methyl-5-((methyl(oxetan-3-yl)amino)methyl)-1H-pyrazol-3-amine 320c

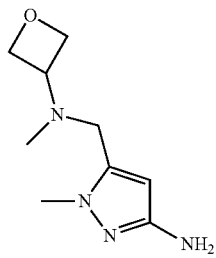

To a solution of 320b (1.8 g, 7.96 mmol) in ethanol (20 mL) and water (20 mL), NH₄Cl (3.3 g, 63.6 mmol) and iron powder (1.80 g, 31.8 mmol) were added. The reaction mixture was heated at 70° C. for 2 h. After that, the mixture was cooled to room temperature and filtered. The filtrate was evaporated and the residue was extracted with methylene chloride (30 mL×3), dried Na₂SO₄, and concentrated to afford the crude product, which was purified on flash column eluting with 50:1 methylene chloride/methanol containing 0.5% triethylamine to afford 320c as a yellow oil (1.3 g, 83%). LCMS: (M+H)+ 197

Example 320d 5-Bromo-1-methyl-3-(1-methyl-5-((methyl(oxetan-3-yl)amino)methyl)-1H-pyrazol-3-ylamino)pyridin-2(1H)-one 320d

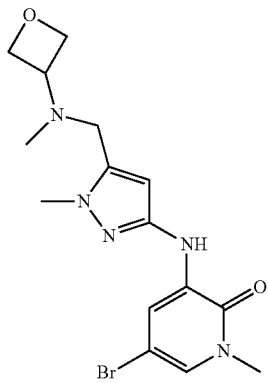 [SMILES: CN(Cc1cc(Nc2cc(Br)cn(C)c2=O)nn1C)C1COC1]

Following Example 136d, 320c and 3,5-dibromo-1-methylpyridin-2(1H)-one were reacted to give 320d in 63% yield. LCMS: (M+H)+ 383. ¹H NMR (500 MHz, DMSO) δ 8.35 (s, 1H), 7.99 (d, J=2.5, 1H), 7.36 (d, J=2.5, 1H), 5.99 (s, 1H), 4.50 (t, J=7, 2H), 4.40 (t, J=6.5, 2H), 3.77 (s, 3H), 3.57 (m, 1H), 3.49 (s, 3H), 3.35 (s, 2H), 2.01 (s, 3H).

Example 320e 4-Fluoro-2-(1-methyl-5-(1-methyl-5-((methyl(oxetan-3-yl)amino)methyl)-1H-pyrazol-3-ylamino)-6-oxo-1,6-dihydropyridin-3-yl)-6-(1-oxo-3,4,6,7,8,9-hexahydropyrazino[1,2-a]indol-2(1H)-yl) benzyl Acetate 320e

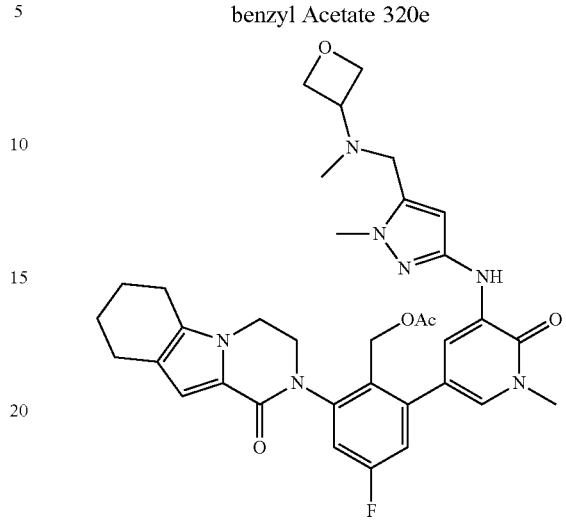

Following Example 136e, 210d was converted to 320e in 71% yield.

Following Example 136, 320e was converted to 320 in 66% yield. LCMS: (M+H)+ 616. ¹H NMR (500 MHz, DMSO) δ 8.07 (s, 1H), 7.97 (s, 1H), 7.30 (m, 2H), 7.17 (d, J=9.5, 1H), 6.53 (s, 1H), 6.02 (s, 1H), 4.88 (m, 1H), 4.50 (t, J=6.5, 2H), 4.40 (t, J=5.5, 2H), 4.32 (s, 2H), 4.14 (m, 3H), 3.89 (m, 1H), 3.70 (s, 3H), 3.57 (m, 4H), 2.59 (m, 2H), 2.47 (m, 2H), 2.00 (s, 3H), 1.80 (m, 2H), 1.70 (m, 2H).

Example 321 10-[5-Fluoro-2-(Hydroxymethyl)-3-{1-methyl-5-[(1-methyl-5-{[methyl(oxetan-3-yl)amino]methyl}-1H-pyrazol-3-yl)amino]-6-oxo-1,6-dihydropyridin-3-yl}phenyl]-4,4-dimethyl-1,10-diazatricyclo[6.4.0.0²,⁶]dodeca-2(6),7-dien-9-one 321

Example 321a (2-{4,4-Dimethyl-9-oxo-1,10-diazatricyclo[6.4.0.0²,⁶]dodeca-2(6),7-dien-10-yl}-4-fluoro-6-{1-methyl-5-[(1-methyl-5-{[methyl(oxetan-3-yl)amino]methyl}-1H-pyrazol-3-yl)amino]-6-oxo-1,6-dihydropyridin-3-yl}phenyl)methyl 321a

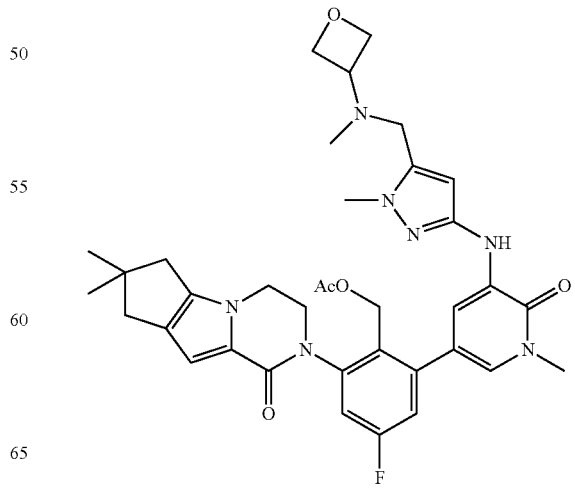

Following Example 136e, 5-bromo-1-methyl-3-(1-methyl-5-((methyl(oxetan-3-yl)amino)methyl)-1H-pyrazol-3-ylamino)pyridin-2(1H)-one 320d and 230a were reacted to give 321a in 65% yield. LCMS: (M+H)+ 672

Following Example 136, 321a was converted to 321 in 59% yield. LCMS: (M+H)+ 630. ¹H NMR (500 MHz, DMSO) δ 8.07 (s, 1H), 7.97 (d, J=2.5, 1H), 7.33 (d, J=2.5, 1H), 7.31 (d, J=3, 1H), 7.29 (d, J=2, 1H), 7.17 (dd, J=9.5, 1H), 6.51 (s, 1H), 6.02 (s, 1H), 4.89 (t, J=4.5, 1H), 4.50 (t, J=6.5, 2H), 4.40 (t, J=6, 2H), 4.33 (d, J=4.5, 2H), 4.21 (m, 2H), 4.13 (m, 1H), 3.88 (m, 1H), 3.70 (s, 3H), 3.57 (m, 4H), 2.57 (s, 2H), 2.42 (s, 2H), 2.00 (s, 3H), 1.22 (s, 6H).

Example 322 10-[5-Fluoro-2-(hydroxymethyl)-3-{1-methyl-5-[(1-methyl-5-{[methyl(oxetan-3-yl)amino] methyl}-1H-pyrazol-3-yl)amino]-6-oxo-1,6-dihydropyridin-3-yl}phenyl]-4,4-dimethyl-7-thia-10-azatricyclo[6.4.0.0²,⁶]dodeca-1(8),2(6)-dien-9-one 322

Example 322a (2-{4,4-Dimethyl-9-oxo-7-thia-10-azatricyclo[6.4.0.0²,⁶]dodeca-1(8),2(6)-dien-10-yl}-4-fluoro-6-[1-methyl-5-{(1-methyl-5-{[methyl(oxetan-3-yl)amino]methyl}-1H-pyrazol-3-yl)amino]-6-oxo-1,6-dihydropyridin-3-yl}phenyl)methyl acetate 322a A sealed tube was charged with the mixture of 5-bromo-1-methyl-3-(1-methyl-5-((methyl(oxetan-3-yl)amino) methyl)-1H-pyrazol-3-ylamino)pyridin-2(1H)-one 320d (250 mg, 0.65 mmol), (2-{4,4-dimethyl-9-oxo-7-thia-10-azatricyclo[6.4.0.0²,⁶]dodeca-1(8),2(6)-dien-10-yl}-4-fluoro-6-(4,4,5,5-tetramethyl-1,3,2-dioxaborolan-2-yl)phenyl)methyl acetate 247b (334 mg, 0.65 mmol), Pd(dppf)Cl₂ (55 mg, 0.07 mmol), K₃PO₄.3H₂O (345 mg, 1.3 mmol), and NaOAc (105 mg, 1.3 mmol) in CH₃CN (20 mL). The system was evacuated and refilled with N₂. The reaction mixture was heated at 110° C. for 2 h. It was then cooled to room temperature and filtered. The filtrate was concentrated under reduced pressure and the resulting residue was purified by flash column chromatography eluting with 30:1 methylene chloride/methanol to afford 322a as a yellow solid (300 mg, 56%). MS: [M+H]+ 689.

At room temperature, to a solution of 322a (250 mg, 0.35 mol) in THF/isopropanol/water (6 mL/6 mL/2 mL) was added LiOH (70 mg, 2.9 mmol) while stirring. This mixture was stirred for 0.5 h. Then, 20 mL water was added and the mixture was extracted with ethyl acetate (30 mL×3). The combined organic layer was dried with Na₂SO₄ and concentrated to yield a yellow solid, which was further purified by prep-HPLC to afford 322 as a white solid (94 mg, 36%). MS: [M+H]+ 647. ¹H NMR (500 MHz, DMSO) δ 1.23 (s, 6H), 2.01 (s, 3H), 2.50-2.52 (m, 2H), 2.76 (s, 2H), 2.88-2.91 (m, 1H), 3.04 (s, 1H), 3.55-3.57 (m, 4H), 3.70 (s, 3H), 3.86 (t, J=6.0 Hz, 1H), 4.06 (d, J=5.5 Hz, 1H), 4.33-4.41 (m, 4H), 4.50 (t, J=6.5 Hz, 2H), 4.88 (t, J=5.0 Hz, 1H), 6.02 (s, 1H), 7.16-7.18 (m, 1H), 7.29-7.34 (m, 2H), 7.97 (d, J=2.5 Hz, 1H), 8.07 (s, 1H).

Example 323 10-[2-(Hydroxymethyl)-3-(1-methyl-5-{[5-(1-methylpiperidin-4-yl)pyridin-2-yl]amino}-6-oxopyridin-3-yl)phenyl]-4,4-dimethyl-1,10-diazatricyclo[6.4.0.0²,⁶]dodeca-2(6),7-dien-9-one 323

Example 323a (2-{4,4-Dimethyl-9-oxo-1,10-diazatricyclo[6.4.0.0²,⁶]dodeca-2(6),7-dien-10-yl}-6-(1-methyl-5-{[5-(1-methylpiperidin-4-yl)pyridin-2-yl] amino}-6-oxo-1,6-dihydropyridin-3-yl)phenyl) methyl Acetate 323a

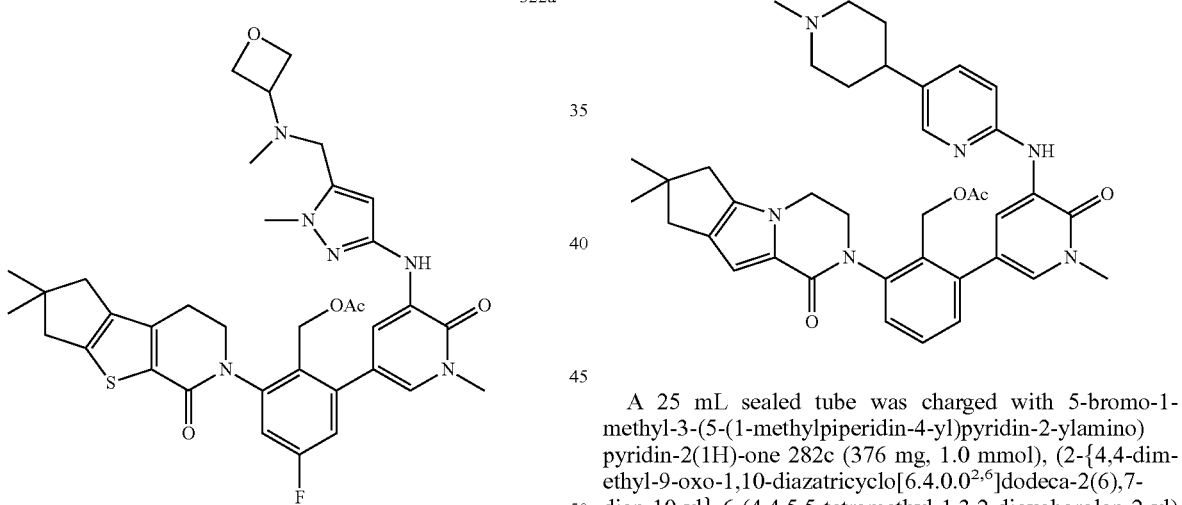

A 25 mL sealed tube was charged with 5-bromo-1-methyl-3-(5-(1-methylpiperidin-4-yl)pyridin-2-ylamino) pyridin-2(1H)-one 282c (376 mg, 1.0 mmol), (2-{4,4-dimethyl-9-oxo-1,10-diazatricyclo[6.4.0.0²,⁶]dodeca-2(6),7-dien-10-yl}-6-(4,4,5,5-tetramethyl-1,3,2-dioxaborolan-2-yl) phenyl)methyl acetate (478 mg, 1.0 mmol), CH₃COONa (168 mg, 2.0 mmol), K₃PO₄ (546 mg, 2.0 mmol), PdCl₂ (dppf) (84 mg, 0.1 mmol) suspended in CH₃CN (25 mL) and H₂O (1 mL). The mixture was heated at 110° C. for 2 hours. It was then evaporated and the residue was purified by column chromatography eluting with 15:1 methylene chloride/methanol to give 323a as a brown solid (278 mg, 43%). MS: (M+H)+ 649.

A solution of 323a (200 mg, 0.3 mmol) in propan-2-ol (10 mL), tetrahydrofuran (10 mL) and water (2 mL) was added LiOH (1.1 g, 57 mmol). The mixture was stirred at 30° C. for 2 h. It was then evaporated and the residue was purified by prep-HPLC to afford 323 as a white solid (41 mg, 22%). MS: (M+H)+ 607. ¹H NMR (500 MHz, DMSO) δ 8.65 (s, 1H), 8.50 (s, 1H), 8.05 (s, 1H), 7.51 (m, 2H), 7.46 (m, 3H), 7.31 (d, J=8.5, 1H), 6.50 (s, 1H), 4.83 (m, 1H), 4.39 (m, 2H), 4.13 (m, 1H), 3.85 (m, 1H), 3.59 (s, 3H), 3.03 (m, 1H), 2.91

(m, 3H), 2.84 (m, 2H), 2.64 (m, 1H), 2.46 (m, 1H), 2.17 (s, 3H), 1.80 (m, 2H), 1.60 (m, 4H), 1.22 (s, 6H).

Example 324 5-[5-Fluoro-2-(hydroxymethyl)-3-{1-methyl-5-[(1-methyl-5-{[methyl(oxetan-3-yl)amino]methyl}-1H-pyrazol-3-yl)amino]-6-oxo-1,6-dihydropyridin-3-yl}phenyl]-8-thia-5-azatricyclo[7.4.0.0$^{2,7}$]trideca-1(9),2(7)-dien-6-one 324

Example 324a (4-Fluoro-2-{1-methyl-5-[(1-methyl-5-{[methyl(oxetan-3-yl)amino]methyl}-1H-pyrazol-3-yl)amino]-6-oxo-1,6-dihydropyridin-3-yl}-6-{6-oxo-8-thia-5-azatricyclo[7.4.0.0$^{2,7}$]trideca-1(9),2(7)-dien-5-yl}phenyl)methyl Acetate 324a

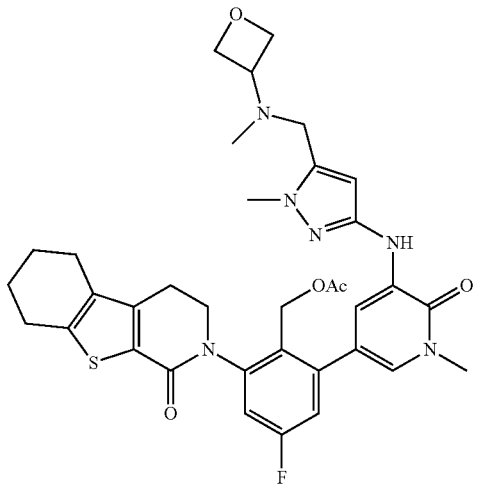 [SMILES: CC(=O)OCc1c(-c2cc(Nc3cc(CN(C)C4COC4)n(C)n3)c(=O)n(C)c2)cc(F)cc1N1CCn2c(cc3c2CCCC3)C1=O]

324a

A sealed tube was charged with the mixture of 5-bromo-1-methyl-3-(1-methyl-5-((methyl(oxetan-3-yl)amino)methyl)-1H-pyrazol-3-ylamino)pyridin-2(1H)-one 320d (150 mg, 0.39 mmol), (4-fluoro-2-{6-oxo-8-thia-5-azatricyclo[7.4.0.0$^{2,7}$]trideca-1(9),2(7)-dien-5-yl}-6-(4,4,5,5-tetramethyl-1,3,2-dioxaborolan-2-yl)phenyl)methyl acetate 247b (195 mg, 0.39 mmol), Pd(dppf)Cl$_2$ (33 mg, 0.04 mmol), K$_3$PO$_4$.3H$_2$O (207 mg, 0.78 mmol), and NaOAc (63 mg, 0.78 mmol) in CH$_3$CN (20 mL). The system was evacuated and refilled with N$_2$. The reaction mixture was heated at 110° C. for 2 h. It was then cooled to room temperature and filtered. The filtrate was concentrated under reduced pressure and the resulting residue was purified by flash column chromatography eluting with 30:1 methylene chloride/methanol to afford 324a as a yellow solid (150 mg, 56%). MS: [M+H]$^+$ 675.

At room temperature, to a solution of 324a (150 mg, 0.22 mol) in THF/isopropanol/water (6 mL/6 mL/2 mL) was added LiOH (70 mg, 2.9 mmol) while stirring. This mixture was stirred for 0.5 h. Then, 20 mL H$_2$O was added and extracted with ethyl acetate (3×30 mL). The combined organic layer was dried with Na$_2$SO$_4$ and concentrated to get a yellow solid, which was further purified by prep-HPLC to afford 324 as a white solid (43 mg, 31%). MS: [M+H]$^+$ 633. $^1$H NMR (500 MHz, DMSO) δ 1.75-1.80 (m, 4H), 2.00 (s, 4H), 2.85 (s, 4H), 2.36 (s, 1H), 2.64 (s, 1H), 2.78 (s, 2H), 2.83-2.89 (m, 1H), 2.94-3.01 (m, 1H), 3.58 (s, 3H), 3.69 (s, 3H), 3.86-3.89 (m, 1H), 4.02-4.07 (m, 1H), 4.32 (d, J=3.0 Hz, 2H), 4.39 (t, J=6.5 Hz, 2H), 4.49 (t, J=6.5 Hz, 2H), 4.85 (d, J=4.5 Hz, 1H), 6.01 (s, 1H), 7.15-7.18 (m, 1H), 7.28-7.32 (m, 2H), 7.96 (d, J=2.0 Hz, 1H), 8.06 (s, 1H).

Example 325 10-[2-(Hydroxymethyl)-3-(1-methyl-5-{[5-(1-methylpiperidin-4-yl)pyridine-2-yl]amino}-6-oxopyridin-3-yl)phenyl]-4,4-dimethyl-7-thia-10-azatricyclo[6.4.0.0$^{2,6}$]dodeca-1(8),2(6)-dien-9-one 325

Example 325a (2-{4,4-Dimethyl-9-oxo-7-thia-10-azatricyclo[6.4.0.0$^{2,6}$]dodeca-1(8),2(6)-dien-10-yl}-6-(1-methyl-5-{[5-(1-methylpiperidin-4-yl)pyridin-2-yl]amino}-6-oxopyridin-3-yl)phenyl)methyl Acetate 325a

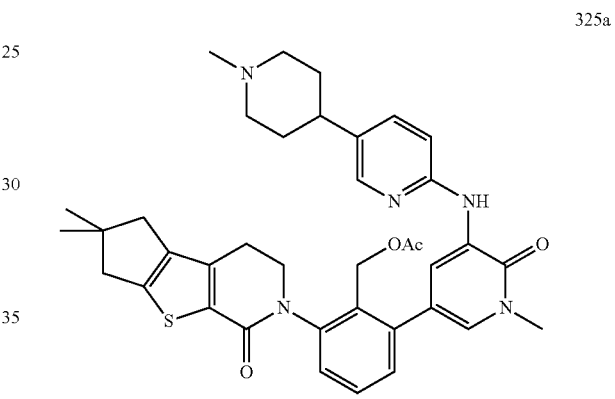

325a

A 25 mL sealed tube is charged with 5-bromo-1-methyl-3-(5-(1-methylpiperidin-4-yl)pyridine-2-ylamino)pyridin-2(1H)-one 282c (376 mg, 1.0 mmol), (2-{4,4-dimethyl-9-oxo-7-thia-10-azatricyclo[6.4.0.0$^{2,6}$]}dodeca-1(8),2(6)-dien-10-yl}-6-(4,4,5,5-tetramethyl-1,3,2-dioxaborolan-2-yl)phenyl)methyl acetate 131a (495 mg, 1.0 mmol), CH$_3$COONa (168 mg, 2.0 mmol), K$_3$PO$_4$ (546 mg, 2.0 mmol), PdCl$_2$(dppf) (84 mg, 0.1 mmol) suspended in CH$_3$CN (25 mL) and water (1 mL). The mixture was heated at 110° C. for 2 hours. It was then evaporated and the residue was purified by column chromatography eluting with 50:1 methylene chloride/methanol to give 325a as a brown solid (278 mg, 42%). MS: (M+H)$^+$ 666.

A solution of 325a (200 mg, 0.3 mmol) in isopropanol (10 mL), and tetrahydrofuran (10 mL) and water (2 mL) was added LiOH (1.1 g, 57 mmol). The mixture was stirred at 30° C. for 2 h. It was then evaporated and the residue was purified by prep-HPLC to afford 325 as a white solid (54 mg, 29%). MS: (M+H)$^+$ 624. $^1$H NMR (500 MHz, DMSO) δ 8.66 (s, 1H), 8.50 (s, 1H), 8.10 (s, 1H), 7.51 (m, 2H), 7.46 (m, 3H), 7.31 (d, J=8.5, 1H), 4.83 (m, 1H), 4.39 (m, 2H), 4.13 (m, 1H), 3.85 (m, 1H), 3.59 (s, 3H), 3.03 (m, 1H), 2.91 (m, 3H), 2.84 (m, 2H), 2.64 (m, 1H), 2.46 (m, 1H), 2.23 (s, 3H), 1.80 (m, 2H), 1.66 (m, 4H), 1.20 (s, 6H).

Example 326 2-(5-Fluoro-2-(hydroxymethyl)-3-(1-methyl-5-(5-(4-methylpiperazin-1-yl)pyridin-2-ylamino)-6-oxo-1,6-dihydropyridin-3-yl)phenyl)-3,4-dihydropyrazino[1,2-a]indol-1(2H)-one 326

Example 326a 4-Fluoro-2-(1-oxo-3,4-dihydropyrazino[1,2-a]indol-2(1H)-yl)-6-(4,4,5,5-tetramethyl-1,3,2-dioxaborolan-2-yl)benzyl Acetate 326a

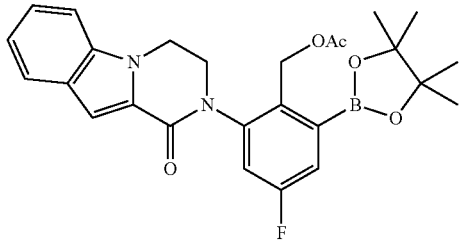

Following Examples 102c and 102d, 326a was prepared.

Example 326b 4-fluoro-2-(1-methyl-5-(5-(4-methylpiperazin-1-yl)pyridin-2-ylamino)-6-oxo-1,6-dihydropyridin-3-yl)-6-(1-oxo-3,4-dihydropyrazino[1,2-a]indol-2(1H)-yl)benzyl acetate 326b

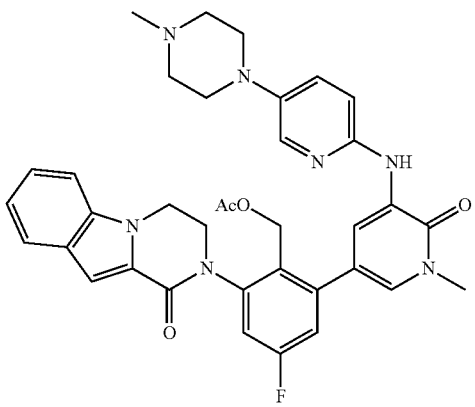

Following Example 148h, 478 mg of 326a and 378 mg 5-bromo-1-methyl-3-(5-(4-methylpiperazin-1-yl)pyridin-2-ylamino)pyridin-2(1H)-one 197d were reacted to give 326b was obtained as a yellow solid (324 mg, 50%). MS: [M+H]$^+$ 650.

Following Example 148, 260 mg of 326b was converted to 326 as a white solid (100 mg, 41%). MS: [M+H]$^+$ 607. $^1$H NMR (500 MHz, DMSO) δ 8.58 (d, J=2.0, 1H), 8.39 (s, 1H), 7.87 (d, J=3.0, 1H), 7.73 (d, J=8.0, 1H), 7.63 (d, J=8.0, 1H), 7.46 (dd, J=9.0, 1H), 7.36 (m, 3H), 7.23 (m, 2H), 7.17 (m, 2H), 4.99 (d, J=4.5, 1H), 4.65 (m, 1H), 4.50 (m, 1H), 4.38 (s, 2H), 4.29 (m, 1H), 4.10 (m, 1H), 3.59 (s, 3H), 3.04 (t, J=4.0, 4H), 4.36 (t, J=4.0, 4H), 2.20 (s, 3H).

Example 327 2-(5-Fluoro-2-(hydroxymethyl)-3-(4-methyl-6-(4-(4-(oxetan-3-yl)piperazin-1-yl)phenylamino)-5-oxo-4,5-dihydropyrazin-2-yl)phenyl)-3,4,6,7,8,9-hexahydropyrazino[1,2-a]indol-1(2H)-one 327

Example 327a tert-Butyl 4-(4-Nitrophenyl)piperazine-1-carboxylate 327a

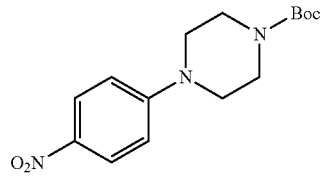

Following Example 188a, 1-fluoro-4-nitrobenzene (2.8 g, 20 mmol) and N-Boc-piperazine (11 g, 60 mmol) were reacted to give 327a as a yellow solid (3 g, 51%). MS: [M+H]$^+$ 308.

Example 327b tert-Butyl 4-(4-Aminophenyl)piperazine-1-carboxylate 327b

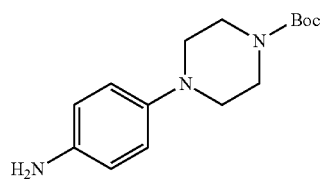

Following Example 188b, 327a was reduced to 327b as a yellow solid (1.35 g, 99%). MS: [M+H]$^+$ 278.

Example 327c tert-Butyl 4-(4-(6-Bromo-4-methyl-3-oxo-3,4-dihydropyrazin-2-ylamino)phenyl)piperazine-1-carboxylate 327c

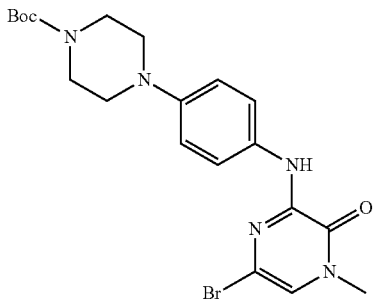

Following Example 188c, 327b (2.6 g, 9.4 mmol) and 3,5-dibromo-1-methylpyrazin-2(1H)-one (2.5 g, 9.4 mmol) were reacted to give 327c as a yellow solid (2.96 g, 68%). MS: [M+H]$^+$ 464.

Example 327d 5-Bromo-1-methyl-3-(4-(piperazin-1-yl)phenylamino)pyrazin-2(1H)-one 327d

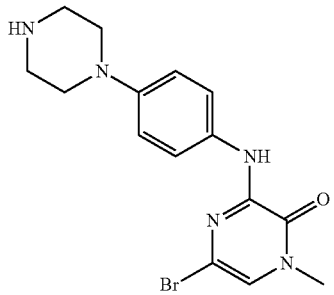

Following Example 188d, 327c was deprotected to give 327d as a yellow solid (1.57 g, 99%). MS: [M+H]+ 364.

Example 327e 5-Bromo-1-methyl-3-(4-(4-(oxetan-3-yl)piperazin-1yl)phenyl-amino)pyrazin-2(1H)-one 327e

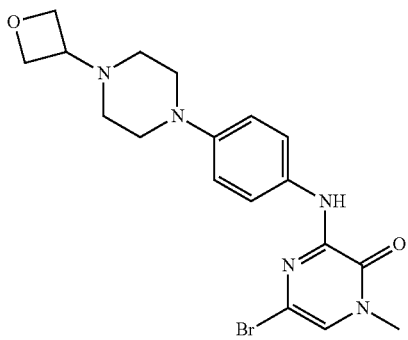

Following Example 188e, 1.2 g (3 mmol) of 327d was converted to 327e as a yellow solid (943 mg, 75%). MS: [M+H]+ 420.

Example 327f 4-Fluoro-2-(4-methyl-6-(4-(4-(oxetan-3-yl)piperazin-1-yl)phenylamino)-5-oxo-4,5-dihydropyrazin-2-yl)-6-(1-oxo-3,4,6,7,8,9-hexahydropyrazino[1,2-a]indol-2(1H)-yl)benzyl Acetate 327f

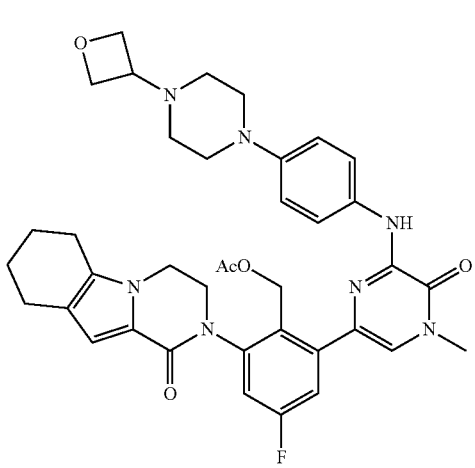

Following Example 148h, 300 mg of 4-fluoro-2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 210d and 287 mg of 327e were reacted to give 327f as a yellow solid (220 mg, 51%). LCMS: [M+H]+ 696

Following Example 148, 220 mg of 327f was converted to 327 as a white solid (87 mg, 42%). ¹H NMR (500 MHz, DMSO) δ 9.11 (s, 1H), 7.81 (d, J=8.5, 1H), 7.43 (s, 1H), 7.35 (t, J=7.0, 1H), 7.29 (d, J=9.0, 1H), 6.88 (d, J=8.5, 2H), 6.53 (s, 1H), 4.86 (s, 1H), 4.56 (t, J=6.5, 2H), 4.67 (d, t=5.5, 3H), 4.42 (m, 1H), 4.11 (m, 3H), 3.89 (m, 1H), 3.53 (s, 3H), 3.43 (s, 1H), 3.10 (t, J=4.5, 4H), 2.62 (m, 2H), 2.46 (m, 2H), 2.39 (t, J=4.5, 4H), 1.79 (s, 2H), 1.70 (s, 2H).

Example 328 2-(5-Fluoro-2-(hydroxymethyl)-3-(1-methyl-5-(5-(4-(oxetan-3-yl)piperazin-1-yl)pyridin-2-ylamino)-6-oxo-1,6-dihydropyridazin-3-yl)phenyl)-3,4,6,7,8,9-hexahydropyrazino[1,2-a]indol-1(2H)-one 328

Example 328a 4-(6-(6-Chloro-2-methyl-3-oxo-2,3-dihydropyridazin-4-yl-amino)pyridin-3-yl)piperazine-1-carboxylate 328a

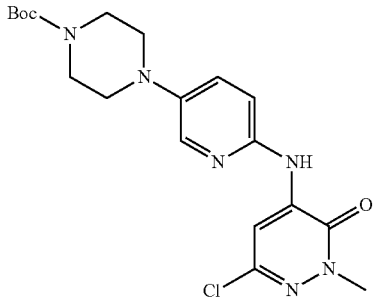

A 100-mL single-neck round-bottomed flask equipped with a magnetic stirrer and reflux condenser was charged with 1,4-dioxane (50 mL), tert-butyl 4-(6-aminopyridin-3-yl)piperazine-1-carboxylate 188b (2.0 g, 7.2 mmol), 4-bromo-6-chloro-2-methyl-pyridin-3(2H)-one (1.6 g, 7.2 mmol) and cesium carbonate (4.7 g, 14.4 mmol). After bubbling nitrogen through the resulting mixture for 30 minutes, XantPhos (500 mg, 0.9 mmol) and tris(dibenzylideneacetone)dipalladium(0) (450 mg, 0.45 mmol) was added, and the reaction mixture was heated at reflux for 3 h. After this time the reaction was cooled to room temperature, partitioned between ethyl acetate (100 mL) and water (100 mL), and filtered. The aqueous layer was separated and extracted with ethyl acetate (50 mL×2). The organic layers were combined, washed with brine (50 mL), and dried over sodium sulfate. The drying agent was removed by filtration and the filtrate was concentrated under reduced pressure. The residue was purified on flash column eluting with petroleum ether/ethyl acetate to afford 328a (1.4 g, 43%). MS: [M+H]+ 421

Example 328b 6-Chloro-2-methyl-4-(5-(piperazin-1-yl)pyridin-2-ylamino)pyridazin-3(2H)-one Hydrochloride 328b

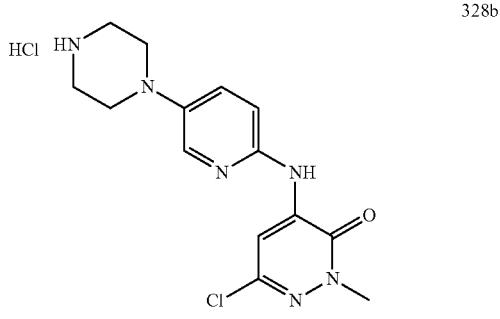 [SMILES: Cl ; Cn1nc(Cl)cc(Nc2ccc(N3CCNCC3)cn2)c1=O]

Intermediate 328a (1.4 g, 3.3 mmol) was suspended in 4.0 M HCl/dioxane (10 mL). The reaction mixture was stirred at room temperature for 2 h and concentrated under reduced pressure to give 328b (1.1 g, 96%). MS: [M+H]$^+$ 321.

Example 328c 6-Chloro-2-methyl-4-(5-(4-(oxetan-3-yl)piperazin-1-yl)pyridin-2-ylamino)pyridazin-3(2H)-one 328c

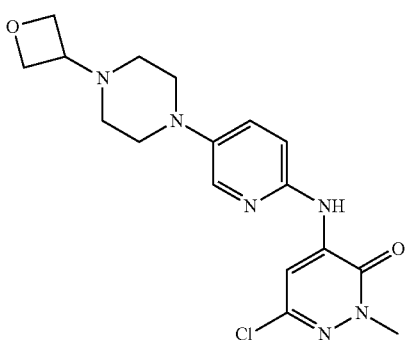

A mixture of 328b (1.2 g, 3.5 mmol), oxetan-3-one (0.5 g, 7.0 mmol), NaBH$_3$CN (0.44 g, 7.0 mmol) and zinc chloride (0.93 g, 7.0 mmol) in methanol (125 ml) was stirred at 50 degree for 3.5 hours. The mixture was added to water and extracted with methylene chloride. The organic layers were combined and concentrated under reduced pressure. The residue was purified by column chromatography eluting with 25:1 methylene chloride/methanol to give 328c (0.63 g, 50%). MS: [M+H]$^+$ 377.

Example 328d 4-Fluoro-2-(1-methyl-5-(5-(4-(oxetan-3-yl)piperazin-1-yl)pyridin-2-ylamino)-6-oxo-1,6-dihydropyridazin-3-yl)-6-(1-oxo-3,4,6,7,8,9-hexahydropyrazino[1,2-a]indol-2(1H)-yl)benzyl Acetate 328d

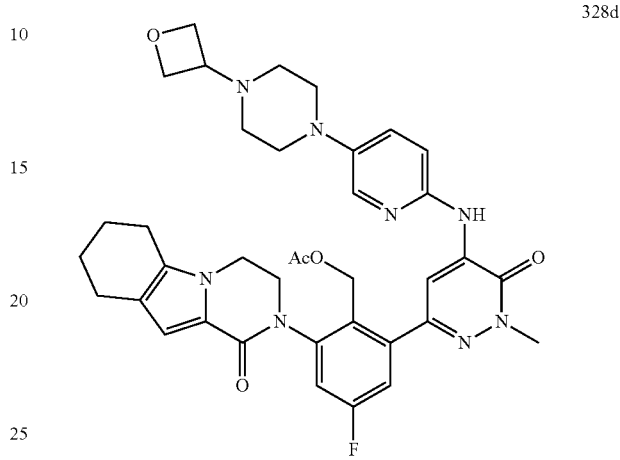

A sealed tube was charged with the mixture of 4-fluoro-2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 210d (420 mg, 0.9 mmol), 328c (300 mg, 0.78 mmol), Pd(dppf)Cl$_2$ (66 mg, 0.078 mmol), K$_3$PO$_4$·3H$_2$O (360 mg, 1.56 mmol), and NaOAc (130 mg, 1.56 mmol) in CH$_3$CN (20 ml). The system was evacuated and then refilled with N$_2$. And the reaction mixture was heated at 110° C. for 2 h. Then, the mixture was cooled to room temperature and filtered. The filtrate was concentrated under reduced pressure and the resulting residue was purified by flash column chromatography eluting with 30:1 methylene chloride/methanol to afford 328d as a yellow solid (400 mg, 72%). MS: [M+H]$^+$ 696.

To the solution of 328d (350 mg, 0.5 mol) in THF/iPA/H$_2$O (6 ml/6 ml/2 ml) was added LiOH (600 mg, 25 mmol) while stirring at room temperature. And this mixture was stirred for 0.5 h. Then, 20 mL water was added and resulting mixture was extracted with ethyl acetate (30 mL×3). The combined organic layer was dried with Na$_2$SO$_4$ and concentrated to give a yellow solid, which was further purified by prep-HPLC to afford 328 as a white solid (100 mg, 27%). $^1$H NMR (500 MHz, DMSO) δ 9.25 (s, 1H), 8.41 (s, 1H), 7.97 (d, J=3.5 Hz, 1H), 7.39-7.45 (m, 3H), 7.25-7.28 (m, 1H), 6.52 (s, 1H), 4.66 (t, J=5.0 Hz, 2H), 4.55 (t, J=6.5 Hz, 2H), 4.41-4.46 (m, 3H), 4.31-4.34 (m, 1H), 4.11-4.18 (m, 3H), 3.85-3.87 (m, 1H), 3.77 (s, 3H), 3.43 (t, J=6.5 Hz, 1H), 3.12 (t, J=5.0 Hz, 4H), 2.54-2.63 (m, 2H), 2.46 (t, J=6.0 Hz, 2H), 2.39 (t, J=5.0 Hz, 4H), 1.79 (t, J=5.5 Hz, 2H), 1.69 (s, 2H).

Example 329 5-[5-Fluoro-2-(hydroxymethyl)-3-(1-methyl-5-{[5-(4-methylpiperazin-1-yl)pyridin-2-yl]amino}-6-oxo-1,6-dihydropyridin-3-yl)phenyl]-8-thia-5-azatricyclo[7.4.0.0²,⁷]trideca-1(9),2(7),10,12-tetraen-6-one 329

Example 329a (2Z)-3-(1-Benzothiophen-3-yl)prop-2-enoic Acid 329a

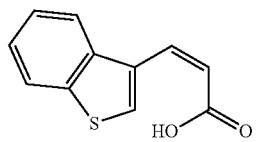

329a

A suspension of benzo[b]thiophene-3-carbaldehyde (4.9 g, 30 mol), malonic acid (6.6 g, 60 mmol) and piperidine (1 mL) in 100 mL anhydrous pyridine was heated at 110° C. for overnight. The reaction mixture was cooled to room temperature and the solvent was removed in vacuo. The residue was taken up in 100 mL of water and 1 N hydrochloric acid was added to adjust the pH of this solution to ca. 3. The resulting suspension was filtered and the yellow solid was collected, washed with water (3×30 mL) dried in vacuo to give 329a as a yellow solid (5.5 g, 89%). MS: [M+H]⁺ 205.

Example 329b 3-(1-Benzothiophen-3-yl)propanoic Acid 329b

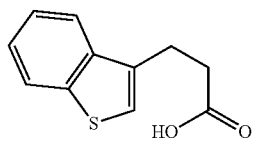

329b

A suspension of 329a (5.5 g, 27 mmol) and 10% Pd/C (600 mg) in 1:1 methanol/ethyl acetate (100 mL) was hydrogenated in a Parr apparatus at 50 psi for overnight. The mixture was filtered through a pad of Celite and the filtrate was concentrated under reduced pressure to give crude 329b as a brown solid (5.0 g, 90%), which was used without further purification for the next step. MS: [M+H]⁺ 207. ¹H NMR (500 MHz, CDCl3) δ 2.81-2.84 (t, J=8.5, 2H), 3.18-3.21 (m, 2H), 7.16 (s, 1H), 7.34-7.41 (m, 2H), 7.74-7.76 (d, 1H), 7.85-7.87 (d, 1H).

Example 329c 3-(1-Benzothiophen-3-yl)propanoyl Chloride 329c

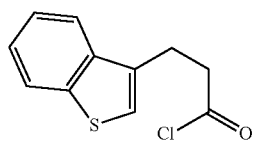

329c

Intermediate 329b (5.0 g, 24 mmol) in sulfurous dichloride (15 mL) was heated at 100° C. for 4 hours. The mixture was cooled to room temperature and the solvent was evaporated in vacuo. 30 mL methylene chloride was added to the residue and the resulting mixture was evaporated under reduced pressure to give 329c as a brown solid (5.3 g, 97%), which was used without further purification for the next step. MS: [M+H]⁺ 225.

Example 329d 7-Thiatricyclo[6.4.0.0²,⁶]dodeca-1(8),2(6),9,11-tetraen-5-one 329d

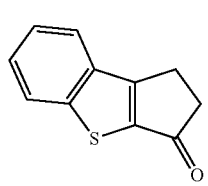

329d

To 329c (5.0 g, 22.3 mmol) in methylene chloride (50 mL) was added anhydrous aluminum trichloride (5.9 g, 44.6 mmol). The mixture was stirred at room temperature for overnight. The reaction solution was evaporated in vacuo and the residue was purified by column chromatography eluting with 20:1 methylene chloride/methanol to give 329d as a yellow solid (2.3 g, 55%). MS: [M+H]⁺ 189. ¹H NMR (500 MHz, CDCl3) δ 3.05-3.07 (m, 2H), 3.21-3.23 (m, 2H), 7.45-7.52 (m, 2H), 7.88-7.91 (m, 2H).

Example 329e N-[(5Z)-7-Thiatricyclo[6.4.0.0²,⁶]dodeca-1(8),2(6),9,11-tetraen-5-ylidene]hydroxylamine 329e

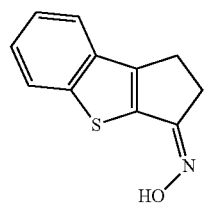

329e

To a solution of NH₂OH.HCl (18.4 g, 266 mmol) in MeOH (600 mL) at 0° C. was slowly added CH₃COONa (21.8 g, 266 mmol). After stirring at 0° C. for 30 min, 329d (10 g, 53 mmol) was added. The reaction solution was allowed to warm to room temperature and stirred for overnight. It was then evaporated in vacuo. 100 mL of water was added to the residue and the resulting mixture was extracted with ethyl acetate (500 mL×3). The organic layers were combined, washed with brine (50 mL), and dried over sodium sulfate. The drying agent was removed by filtration and the filtrate was concentrated under reduced pressure to give 329e as a yellow solid (10 g, 92%). MS: [M+H]⁺ 203.

Example 329f 8-Thia-5-azatricyclo[7.4.0.0²,⁷]tri-deca-1(9),2(7),10,12-tetraen-6-one 329f

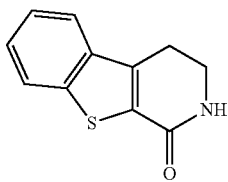

329f

A solution of 329e (5 g, 25 mmol) in PPA (80 mL) was stirred at 150° C. in an oil bath for overnight. The reaction was cooled to room temperature and diluted with 150 mL of water/ice. The solid was collected by filtration, washed with 3×50 mL of water and dried in a vacuum oven under reduced pressure to afford the crude product, which was further purified by column chromatography eluting with 1:1 ethyl acetate/petroleum ether to give 329f as a yellow solid (3 g, 60%). MS: [M+H]⁺ 204

Example 329g (2-Bromo-4-fluoro-6-{6-oxo-8-thia-5-azatricyclo[7.4.0.0²,⁷]trideca-1(9),2(7),10,12-tetraen-5-yl}phenyl)methyl Acetate 329g

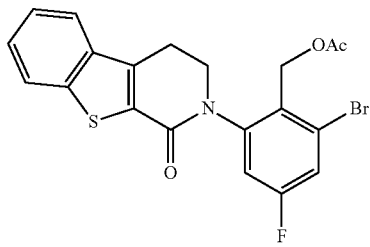

329g

A mixture of 329f (700 mg, 3.4 mmol), 197c (3.35 g, 10.2 mmol), XantPhos (200 mg, 0.34 mmol), Pd₂(dba)₃ (316 mg, 0.34 mmol) and Cs₂CO₃ (2.25 g, 6.8 mmol) in dioxane (50 mL) was heated at 100° C. for 15 h under argon atmosphere. It was then filtered and evaporated in vacuo. The residue was purified by column chromatography eluting with 1:3 ethyl acetate/petroleum ether to give 329g as a white solid (500 mg, 33%). MS: [M+H]⁺ 448.

Example 329h [4-Fluoro-2-(1-methyl-5-{[5-(4-methylpiperazin-1-yl)pyridin-2-yl]amino}-6-oxo-1,6-dihydropyridin-3-yl)-6-{6-oxo-8-thia-5azatricyclo[7.4.0.0²,⁷]-trideca-1(9),2(7),10,12-tetraen-5-yl}phenyl]methyl 329h

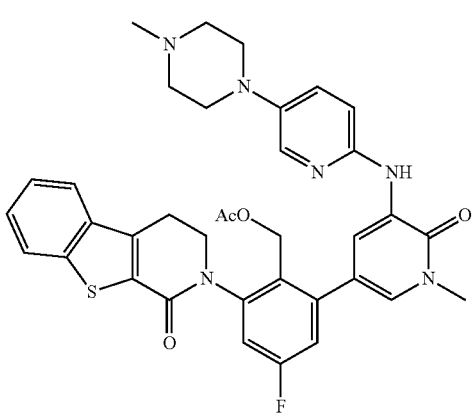

329h

A sealed tube was charged with the mixture of 329g (300 mg, 0.66 mmol), 1-methyl-5-(5-(4-methylpiperazin-1-yl)pyridin-2-ylamino)-6-oxo-1,6-dihydropyridin-3-ylboronic acid 197f (690 mg, 1.32 mmol), Pd(dppf)Cl₂ (54 mg, 0.066 mmol), and Na₂CO₃ (141 mg, 1.32 mmol) in DMF (22 mL). The system was evacuated and then refilled with N₂. And the reaction mixture was heated at 130° C. in microwave for 1 h. Then, the mixture was cooled to room temperature and filtered. The filtrate was concentrated under reduced pressure and the resulting residue was purified by column chromatography eluting with 15:1 methylene chloride/methanol to give 329h as a brown solid (300 mg, 67%). MS: [M+H]⁺ 667.

At room temperature, to a solution of 329h (250 mg, 0.38 mol) in THF/isopropanol/water (10 mL/10 mL/2 mL) was added LiOH (90 mg, 38 mmol) while stirring. This mixture was stirred for 2 h. Then, 20 mL water was added and resulting mixture was extracted with ethyl acetate (30 mL×3). The combined organic layer was dried with Na₂SO₄ and concentrated to give a yellow solid, which was further purified by prep-HPLC to afford 329 as a brown solid (37 mg, 16%). MS: [M+H]⁺ 625. ¹H NMR (500 MHz, MEOD) δ 1.31 (s, 3H), 2.39 (s, 4H), 2.65-2.69 (m, 4H), 3.30-3.33 (m, 2H), 3.68 (s, 3H), 4.11-4.16 (m, 1H), 4.24-4.30 (m, 1H), 4.50-4.56 (m, 2H), 6.99 (d, 1H), 7.20 (d, 1H), 7.22 (d, 1H), 7.30 (s, 1H), 7.36-7.38 (m, 1H), 7.47-7.54 (m, 2H), 7.89-7.95 (m, 2H), 7.97 (d, 1H), 8.53 (s, 1H).

Example 330 2-(5-Fluoro-2-(hydroxymethyl)-3-(1-methyl-5-(6-(4-(oxetan-3-yl)piperazin-1-yl)pyridazin-3-ylamino)-6-oxo-1,6-dihydropyridin-3-yl)phenyl)-3,4,6,7,8,9-hexahydropyrazino[1,2-a]indol-1(2H)-one 330

Example 330a tert-Butyl 4-(6-Aminopyridazin-3-yl)piperazine-1-carboxylate 330a

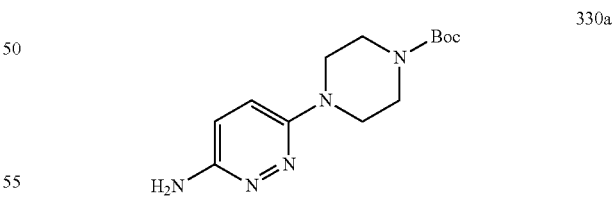

330a

A 100-mL single-neck round-bottomed flask equipped with a magnetic stirrer was charged with 6-chloropyridazin-3-amine (2.58 g, 20 mmol) and N-Boc-piperazine (22.3 g, 120 mmol). The reaction mixture was heated at 140° C. and stirred for 2 h. It was then cooled to room temperature and the resulting solid was washed with ethyl acetate (100 mL), and the resulting residue was purified by flash column chromatography eluting with 30:1 methylene chloride/methanol to afford 330a as a yellow solid (3.5 g, 60%). MS: [M+H]⁺ 280.

Example 330b tert-Butyl 4-(6-(5-Bromo-1-methyl-2-oxo-1,2-dihydropyridin-3-ylamino)pyridazin-3-yl)piperazine-1-carboxylate 330b

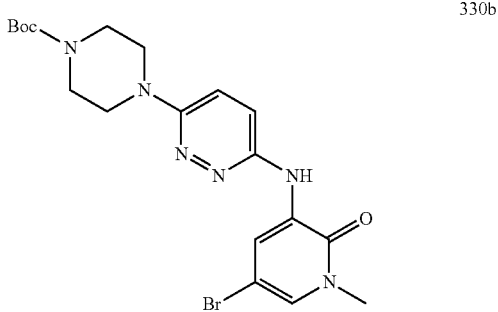

330b

Following Example 188c, 3,5-dibromo-1-methylpyridin-2(1H)-one (536 mg, 2.0 mmol) and 330a (558 mg, 2.0 mmol) were reacted to give 330b as a yellow solid (560 mg, 60%). MS: [M+H]$^+$ 467

Example 330c 5-Bromo-1-methyl-3-(6-(piperazin-1-yl)pyridazin-3-ylamino)pyridin-2(1H)-one 330c

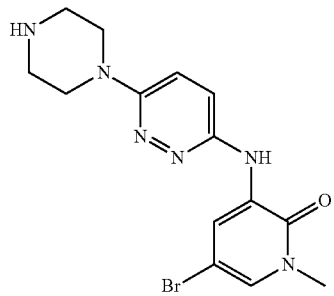

330c

Following Example 188d, 560 mg (1.2 mmol) of 330b was deprotected to give 330c as a yellow solid (440 mg, 99%). MS: [M+H]$^+$ 367.

Example 330d 5-Bromo-1-methyl-3-(6-(4-(oxetan-3-yl)piperazin-1-yl)pyridazin-3-ylamino)pyridin-2(1H)-one 330d

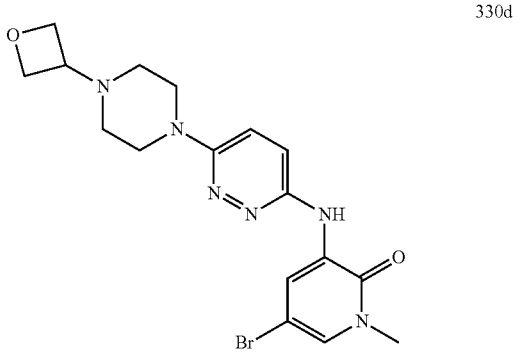

330d

Following Example 210a, 400 mg (1.1 mmol) of 330c was converted to 330d as a yellow solid (312 mg, 68%). MS: [M+H]$^+$ 421

Example 330e 4-Fluoro-2-(1-methyl-5-(6-(4-(oxetan-3-yl)piperazin-1-yl)pyridazin-3-ylamino)-6-oxo-1,6-dihydropyridin-3-yl)-6-(1-oxo-3,4,6,7,8,9-hexahydropyrazino[1,2-a]indol-2(1H)-yl)benzyl Acetate 330e

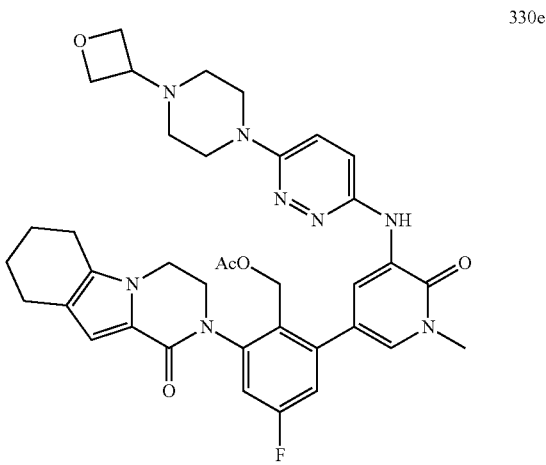 [SMILES: CC(=O)OCc1c(-c2cc(Nc3ccc(N4CCN(C5COC5)CC4)nn3)c(=O)n(C)c2)cc(F)cc1N1CCn2c(cc3c2CCCC3)C1=O]

330e

Following Example 210a, 207 mg of 4-fluoro-2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 210d (0.43 mmol) and 180 mg of 330d (0.43 mmol) were reacted to give 330e as a yellow solid (156 mg, 51%). MS: [M+H]$^+$ 697.

Following Example 210, 330e (150 mg 0.22 mmol) was hydrolyzed to give 330 as a yellow solid (60 mg, 42%). LCMS: [M+H]$^+$ 655. $^1$H NMR (500 MHz, CDCl3) δ 8.67 (d, J=2.5, 1H), 7.77 (s, 1H), 7.48 (d, J=2.0, 1H), 7.12 (dd, J=8.5, 1H), 6.98 (m, 3H), 6.86 (s, 1H), 4.69 (m, 4H), 4.51 (d, J=11, 1H), 4.20 (m, 5H), 3.86 (m, 1H), 3.71 (s, 3H), 3.56 (m, 5H), 2.60 (m, 4H), 2.47 (m, 4H), 1.90 (s, 2H), 1.80 (s, 2H).

Example 331 2-(5-Fluoro-2-(hydroxymethyl)-3-(4-methyl-6-(6-(4-methyl piperazin-1-yl)pyridine-3-ylamino)-5-oxo-4,5-dihydropyrazin-2-yl)phenyl)-3,4,6,7,8,9-hexahydropyrazino[1,2-a]indol-1(2H) 331

Example 331a 5-Bromo-1-methyl-3-(6-(4-methyl-piperazin-1-yl)pyridine-3-ylamino) pyrazin-2(1H)-one 331a

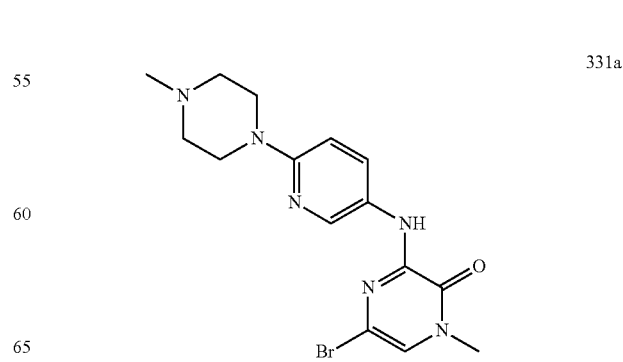

331a

A mixture of 6-(4-methylpiperazin-1-yl)pyridin-3-amine (1 g, 5.2 mmol) prepared according to US 2009/0318448, 3,5-dibromo-1-methylpyrazin-2(1H)-one (1.7 g, 6.2 mmol), and isopropanol (20 mL) was stirred at reflux for 16 h. After the reaction was completed, the solvent was removed to give 331a as a brown solid (500 mg, 30%). MS: [M+H]$^+$ 379.

Example 331b 4-Fluoro-2-(4-methyl-6-(6-(4-methylpiperazin-1-yl)pyridin-3-ylamino)-5-oxo-4,5-dihydropyrazin-2-yl)-6-(1-oxo-3,4,6,7,8,9-hexahydropyrazino[1,2-a]indol-2(1H)-yl)benzyl Acetate 331b

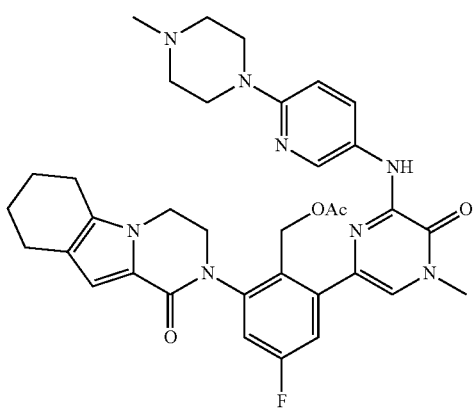

A sealed tube was charged with the mixture of 331a (400 mg, 1 mmol), 4-fluoro-2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 210d (578 mg, 1.2 mmol), Pd(dppf)Cl$_2$ (82 mg, 0.1 mmol), K$_3$PO$_4$.3H$_2$O (760 mg, 2 mmol), and NaOAc (164 mg, 2 mmol) in CH$_3$CN (10 mL). The system was evacuated and then refilled with N$_2$ and the reaction mixture was heated at 110° C. for 2 h. The mixture was then cooled to room temperature and filtered. The filtrate was concentrated under reduced pressure and the resulting residue was purified by flash column chromatography eluting with 50:1 methylene chloride/methanol to afford 331b as a yellow solid (100 mg, 14%). MS: [M+H]$^+$ 655.

To the solution of 331b (100 mg, 0.15 mmol) in THF/isopropanol/water (2 mL/2 mL/1 mL) was added LiOH (15 mg, 0.75 mmol). The reaction mixture was stirred at 30° C. for 1 h. Then, 20 mL water was added and the mixture was extracted with ethyl acetate (90 mL×3). The combined organic layer was dried with Na$_2$SO$_4$ and concentrated to give yellow solid, which was purified by prep-HPLC to give 331 as a yellow solid (42 mg, 45%). MS: [M+H]$^+$ 613. $^1$H NMR (500 MHz, DMSO) δ 9.26 (s, 1H), 8.67 (d, J=2.5, 1H), 8.35 (q, J=2.5, 1H), 7.44 (s, 1H), 7.32 (m, 2H), 6.82-6.80 (d, J=9, 1H), 6.52 (s, 1H), 4.46-4.36 (m, 2H), 4.16-4.09 (m, 3H), 3.88-3.87 (m, 1H), 3.52 (s, 3H), 3.40-3.34 (m, 5H), 2.60-2.57 (m, 2H), 2.51-2.45 (m, 2H), 2.39-2.37 (m, 4H), 2.20 (s, 3H), 1.79-1.69 (m, 4H).

Example 332 2-(5-Fluoro-2-(hydroxymethyl)-3-(1-methyl-5-(5-(4-methyl-2-oxopiperazin-1-yl)pyridin-2-ylamino)-6-oxo-1,6-dihydropyridin-3-yl)phenyl)-3,4,6,7,8,9-hexahydropyrazino[1,2-a]indol-1(2H)-one 332

Example 332a tert-Butyl 3-Oxopiperazine-1-carboxylate 332a

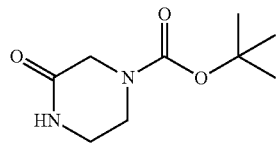

To a dry 100 mL one necked round bottom flask equipped with a stirring bar was added piperazin-2-one (5.0 g, 50 mmol), anhydrous dichloromethane (60 mL), and Et$_3$N (3.2 mL, 22.5 mmol) and the reaction mixture was stirred for 1 h at room temperature. The organic layer was concentrated under reduced pressure to afford 332a (10 g, 99%).

Example 332b tert-Butyl 4-(6-Nitropyridin-3-yl)-3-oxopiperazine-1-carboxylate 332b

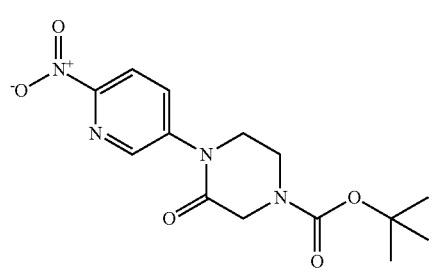

A microwave vial was charged with 332a (1.5 g, 7.5 mmol) in 30 mL of anhydrous 1,4-dioxane, 5-bromo-2-nitropyridine (1.27 g, 6.25 mmol), diacetoxypalladium (71.8 mg, 0.32 mmol), Xantphos (278 mg, 0.48 mmol), and Cs$_2$CO$_3$ (2.04 g, 6.25 mmol). After three cycles of vacuum/argon flash, it was heated at 120° C. under microwave irradiation for 1.5 h. The reaction mixture was filtered and the filtrate was evaporated in vacuum. The residue was purified by silica gel-column chromatography eluting with 3:1 petroleum ether/ethyl acetate to afford 332b as a yellow solid (1.1 g, 54%). MS: [M+H]$^+$ 323. $^1$H NMR (500 MHz, CDCl$_3$) δ 8.68 (d, J=2.5 Hz, 1H), 8.31 (d, J=9 Hz, 1H), 8.15 (m, 1H), 4.33 (s, 2H), 3.91 (m, 4H).

Example 332c tert-Butyl 4-(6-Aminopyridin-3-yl)-3-oxopiperazine-1-carboxylate 332c

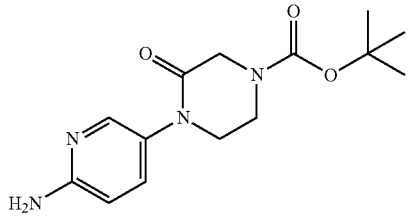

To a solution of 332b (1.1 g, 3.4 mmol) in methanol (20 mL) was added Pd/C (10%) (250 mg). After three cycles of vacuum/H$_2$ flash, the mixture was stirred under H$_2$ at room temperature for 10 h. The mixture was filtered and the filtrate was evaporated in vacuo to afford 332c (946 mg, 95%), which was used for the next step without further purification. MS: [M+H]$^+$ 293.

Example 332d tert-Butyl 4-(6-(5-Bromo-1-methyl-2-oxo-1,2-dihydropyridin-3-ylamino)pyridin-3-yl)-3-oxopiperazine-1-carboxylate 332d

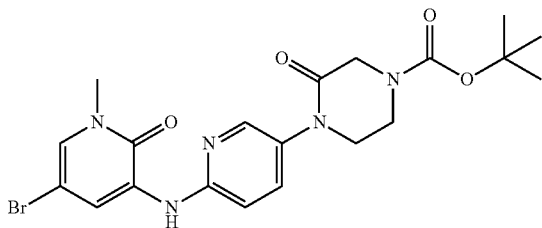

A reaction vessel was charged with 332c (946 mg, 3.2 mmol) in 40 mL of anhydrous 1,4-dioxane, 3,5-dibromo-1-methylpyridin-2(1H)-one (1.11 g, 4.2 mmol), tris(dibenzylideneacetone)dipalladium(0) (146 mg, 0.16 mmol), Xantphos (185 mg, 0.32 mmol), and Cs$_2$CO$_3$ (2.6 g, 8.0 mmol). After three cycles of vacuum/Argon flash, it was stirred at 110° C. for 4 h. The reaction mixture was filtered and the filtrate was evaporated in vacuum. The crude was purified by silica-gel column chromatography eluting with 50:1 methylene chloride/methanol to afford 332d as a yellow solid (706 mg, 46%). MS: [M+H]$^+$ 479.

Example 332e 1-(6-(5-Bromo-1-methyl-2-oxo-1,2-dihydropyridin-3-ylamino)pyridin-3-yl) piperazin-2-one 332e A 50-mL round-bottomed flask equipped with a magnetic stirrer and reflux condenser was charged with HCl in 1,4-dioxane (20 mL) and 332d (706 mg, 1.47 mmol). The mixture was stirred for at 65° C. for 6 h. It was then concentrated under reduced pressure to afford 332e as a yellow solid (500 mg, 90%). MS: [M+H]$^+$ 379.

Example 332f 1-(6-(5-Bromo-1-methyl-2-oxo-1,2-dihydropyridin-3-ylamino)pyridin-3-yl)-4-methyl-piperazin-2-one 332f

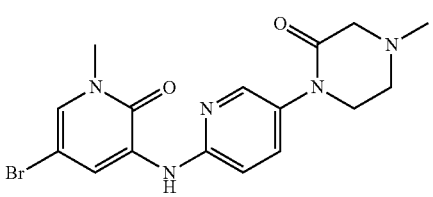

To a solution of 1-(6-(5-bromo-1-methyl-2-oxo-1,2-dihydropyridin-3-ylamino)pyridin-3-yl)piperazin-2-one (332e) (500 mg, 1.32 mmol) in methanol (20 mL) was added Na(OAc)$_3$BH (2.0 g, 13.2 mmol), formaldehyde (30% aq., 8 mL), and acetic acid (2.7 mL, 45 mmol). The mixture was stirred for 4 h. The pH of the reaction mixture was adjust to 11~13 by adding NaOH (1M). It was then extracted with methylene chloride three times. The combined organic exact was dried over anhydrous Na$_2$SO$_4$, filtered, and evaporated in vacuo. The residue was purified by silica-gel column eluting with 50:1 methylene chloride/methanol to afford 332f as a gray solid (312 mg, 60%). MS: [M+H]$^+$ 393. $^1$H NMR (500 MHz, CDCl$_3$) δ 8.61 (d, J=2.5 Hz, 1H), 8.17 (d, J=2.5 Hz, 1H), 7.88 (s, 1H), 7.45 (dd, J=9 Hz, 1H), 6.92 (d, J=2.5 Hz, 1H), 6.74 (d, J=9 Hz, 1H), 3.64 (m, 2H), 3.53 (s, 3H), 3.22 (s, 2H), 2.74 (m, 2H), 2.35 (s, 3H).

Example 332g 4-Fluoro-2-(1-methyl-5-(5-(4-methyl-2-oxopiperazin-1-yl)pyridin-2-ylamino)-6-oxo-1,6-dihydropyridin-3-yl)-6-(1-oxo-3,4,6,7,8,9-hexahydropyrazino[1,2-a]indol-2(1H)-yl)benzyl acetate 332g A reaction vessel was charged with the mixture of 1-(6-(5-bromo-1-methyl-2-oxo-1,2-dihydropyridin-3-ylamino)pyridin-3-yl)-4-methylpiperazin-2-one (332f) (0.3 g, 0.76 mmol),4-fluoro-2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 210d (0.37 g, 0.76 mmol), PdCl$_2$(dppf) (65 mg, 0.076 mmol), K$_3$PO$_4$ (325 mg, 1.53 mmol), and NaOAc (125 mg, 1.53 mmol) in MeCN (15 mL) and water (1 mL). It was then bubbled with argon for 15 min and heated at 110° C. for 3 h. After evaporation of solvent in vacuo, the residue was purified on silica-gel column eluting with 50:1 methylene chloride/methanol to afford 332g (0.4 g, 63%). MS: [M+H]$^+$ 668.

A mixture of 332g (350 mg, 0.52 mmol) and LiOH hydrate (1.1 g, 26 mmol) in isopropanol (3 mL), THF (3 mL) and water (3 mL) was stirred at 30° C. for 1 h. The mixture was evaporated in vacuo, and the residue was extracted with methylene chloride (30 mL×3). The combined extracts were concentrated under reduced pressure and the residue was purified on silica gel column eluting with 50:1 methylene chloride/methanol to afford 332 as a yellow solid (120 mg, 32%). MS: [M+H]$^+$ 626. $^1$H NMR (500 MHz, CDCl$_3$) δ 8.78 (d, J=2 Hz, 1H), 8.17 (d, J=2.5 Hz, 1H), 7.58 (dd, J=8.5 Hz, 1H), 7.42 (d, J=2.5 Hz, 1H), 7.23 (s, 1H), 7.21 (s, 1H), 7.12 (d, J=9 Hz, 1H), 6.73 (s, 1H), 4.53 (m, 2H), 4.22 (s, 2H), 4.03 (m, 1H), 3.73 (s, 4H), 3.27 (s, 2H), 2.87 (m, 2H), 2.65 (m, 1H), 2.55 (m, 2H), 2.43 (s, 3H), 1.89 (m, 2H), 1.79 (m, 2H).

Example 333 2-(5-Fluoro-2-(methoxymethyl)-3-(1-methyl-5-(5-(4-methylpiperazin-1-yl)pyridin-2-ylamino)-6-oxo-1,6-dihydropyridin-3-yl)phenyl)-3,4,6,7,8,9-hexahydropyrazino[1,2-a]indol-1(2H)-one 333

To a solution of 2-(5-fluoro-2-(hydroxymethyl)-3-(1-methyl-5-(5-(4-methylpiperazin-1-yl)pyridin-2-ylamino)-6-oxo-1,6-dihydropyridin-3-yl)phenyl)-3,4,6,7,8,9-hexahydropyrazino[1,2-a]indol-1(2H)-one 197 (200 mg, 0.33 mmol) and $K_2CO_3$ (135 mg, 0.99 mmol) in DMF (30 mL) was added the solution of iodomethane (70 mg, 0.50 mmol) in DMF (5 mL) at room temperature. The reaction mixture was stirred for 1 h. It was then filtered and the residue was purified by prep-HPLC to afford 333 as a yellow solid (165 mg, 80%). MS: $[M+H]^+$ 626. $^1$H NMR (500 MHz, DMSO) δ 8.59 (d, J=2.0, 1H), 8.49 (s, 1H), 7.97 (d, J=2.0, 1H), 7.44 (s, 1H), 7.39 (s, 1H), 7.32 (m, 2H), 7.17 (m, 1H), 6.52 (s, 1H), 4.31 (s, 2H), 4.14 (m, 3H), 3.88 (s, 1H), 3.56 (s, 3H), 3.54 (s, 4H), 3.44 (s, 4H), 3.12 (s, 6H), 2.58 (m, 2H), 2.46 (s, 2H), 1.79 (s, 2H), 1.68 (s, 2H).

Example 334 {4-Fluoro-2-[1-methyl-5-({5-[4-(oxetan-3-yl)piperazin-1-yl]pyridin-2-yl}amino)-6-oxo-1,6-dihydropyridin-3-yl]-6-{7-oxo-3,6-diazatetracyclo[9.2.1.0$^{2,10}$0.0$^{3,8}$]tetradeca-2(10),8-dien-6-yl}phenyl}methyl Acetate 334

Example 334a 3-Chlorobicyclo[2.2.1]hept-2-ene-2-carbaldehyde 334a

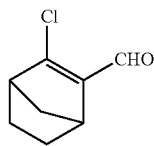

A 250-mL three-neck round-bottomed flask equipped with a magnetic stirrer and reflux condenser was purged with nitrogen and charged with anhydrous 1,2-dichloroethane (24 mL) and anhydrous DMF (9.12 g, 125 mmol). The reaction mixture was cooled to 0° C., and phosphorus oxychloride (15.3 g, 100 mmol) was added over a period of 5 minutes, while maintaining the reaction temperature between 0 and 10° C. The cooling bath was removed, and the reaction was stirred at room temperature for 30 minutes. A solution of bicyclo[2.2.1]heptan-2-one (5.50 g, 50.0 mmol) in 1,2-dichloroethane (10 mL) was added and the resulting mixture was heated at 80° C. for overnight. After this time, the reaction was poured into a solution of potassium monohydrogenphosphate (43.5 g, 250 mmol) in water (200 mL) and stirred for 15 minutes. The organic layer was separated and concentrated under reduced pressure. The residue was dissolved in methylene chloride (300 mL) and washed with water (2×50 mL). The methylene chloride layer was dried over sodium sulfate, filtered, and concentrated under reduced pressure. The residue was purified by column chromatography eluting with 1:100 ethyl acetate/petroleum ether to give 334a as a yellow oil (2.2 g, 28%). MS: $[M+H]^+$ 157. $^1$H NMR (500 MHz, CDCl3) δ 9.80 (s, 1H), 3.07 (d, J=1.7 Hz, 1H), 1.95-1.77 (m, 2H), 1.67 (t, J=8.9 Hz, 1H), 1.41-1.17 (m, 3H).

Example 334b (E)-Ethyl 3-(3-Chlorobicyclo[2.2.1]hept-2-en-2-yl)acrylate 334b

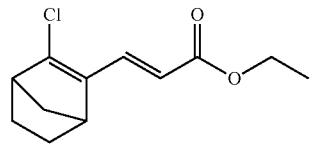

To a solution of 334a (9.0 g, 57.7 mmol) in methylene chloride (250 mL) was added ethyl 2-(triphenyl-λ$^5$-phosphanylidene)acetate (20 g, 57.7 mmol). The mixture was stirred at room temperature for overnight. After reaction the reaction solution was evaporated in vacuo. The residue was purified by column chromatography eluting with 1:100 ethyl acetate/petroleum ether to give 334b as a yellow oil (6.0 g, 46%). MS: $[M+H]^+$ 227.

Example 334c Ethyl 3-Azatricyclo[5.2.1.0$^{2,6}$]deca-2(6),4-diene-4-carboxylate 334c

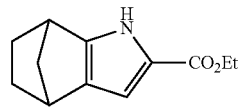

To a solution of 334b (5.0 g, 22 mmol) in DMSO (30 mL) was added $NaN_3$ (2.2 g, 33 mmol) and the mixture was heated at 105° C. for 6 hours. Water (13 mL) was added to reaction the mixture after cooling down to room temperature, and resulting mixture was extracted with methylene chloride (50 mL×3). The organic phase was dried ($Na_2SO_4$) and evaporated to dryness. The residue was purified by column chromatography eluting with 20:1 methylene chloride/methanol to give 334c as a brown solid (2.7 g, 60%). MS: $[M+H]^+$ 206. $^1$H NMR (500 MHz, CDCl3) δ 11.51 (s, 1H), 6.45 (dd, 1H), 4.14-4.19 (m, 2H), 3.25 (d, 2H), 1.79-1.82 (m, 2H), 1.73 (d, 1H), 1.22-1.25 (t, J=6.5, 3H), 0.89-0.91 (m, 2H).

Example 334d Ethyl 3-(Cyanomethyl)-3-azatricyclo[5.2.1.0$^{2,6}$]deca-2(6),4-diene-4-carboxylate 334d

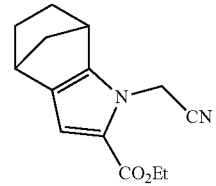

To a solution of 334c (3.0 g, 14.6 mmol) in anhydrous DMF (30 mL) was added NaH (880 mg, 22 mmol). The mixture was stirred at room temperature for 30 minutes. 2-Bromoacetonitrile (3.5 g, 29.3 mmol) was added and the resulting mixture was heated at 65° C. for 1 hour. It was then cooled to room temperature and stirred for overnight. After reaction water (30 mL) was added and the reaction mixture was extracted with ethyl acetate (3×200 mL). The organic phase was evaporated to dryness. The residue was purified by column chromatography eluting with 20:1 methylene chloride/methanol to give 334d as a brown solid (2.6 g, 72%). MS: [M+H]+ 245.

Example 334e Ethyl 3-(2-Aminoethyl)-3-azatricyclo[5.2.1.0$^{2,6}$]deca-2(6),4-diene-4-carboxylate 334e

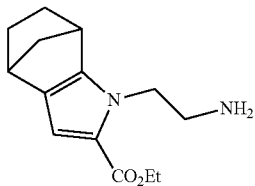

A suspension of 334d (4.0 g, 16 mmol) and Raney Ni (400 mg) in methanol (60 mL) was hydrogenated in a Parr apparatus at 50 psi for overnight. The mixture was filtered through a pad of Celite and the filtrate was concentrated under reduced pressure. The residue was purified by column chromatography eluting with 20:1 methylene chloride/methanol to give 334e as a yellow solid (2 g, 50%). MS: [M+H]+ 249.

Example 334f 3,6-Diazatetracyclo[9.2.1.0$^{2,10}$.0$^{3,8}$]tetradeca-2(10),8-dien-7-one 334f

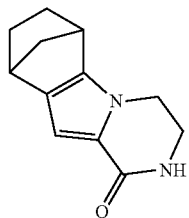

To a solution of ethyl 3-(2-aminoethyl)-3-azatricyclo[5.2.1.0$^{2,6}$]deca-2(6),4-diene-4-carboxylate (334e) (1.8 g, 7.2 mmol) in ethanol (40 mL) was added sodium meth-oxide (2.5 g, 36 mmol). The mixture was heated at 65° C. for 12 hours. It was then cooled to room temperature. The solvent was evaporated to dryness. The residue was purified by column chromatography eluting with 20:1 methylene chloride/methanol to give 334f as a brown solid (800 mg, 53%). MS: [M+H]+ 203.

Example 334g (2-Bromo-4-fluoro-6-{7-oxo-3,6-diazatetracyclo[9.2.1.0$^{2,10}$.0$^{3,8}$]tetradeca-2(10),8-dien-6-yl}phenyl)methyl Acetate 334g

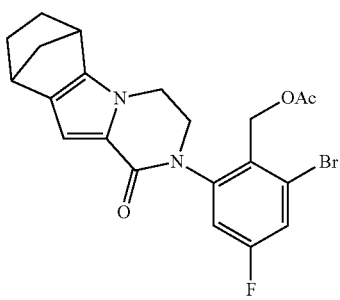

Into a sealed tube was charged with 334f (800 mg, 4 mmol) and 197c (3.8 g, 12 mmol) in dioxane (25 mL), and cesium carbonate (2.6 g, 8 mmol). After bubbling nitrogen through the resulting solution for 30 min, XantPhos (230 mg, 0.4 mmol) and tris(dibenzylideneacetone)-dipalladium (0) (362 mg, 0.4 mmol) were added, and the reaction mixture was heated at 100° C. for 4 h. After this time the reaction was cooled to room temperature, and partitioned between ethyl acetate (100 mL) and water (100 mL). The aqueous layer was separated and extracted with ethyl acetate (50 mL×3). The organic layers were combined, washed with brine (20 mL×3), and dried over sodium sulfate. The drying agent was removed by filtration and the filtrate was concentrated under reduced pressure. The residue was purified by column chromatography eluting with 1:5 ethyl acetate/petroleum ether to give 334g as a brown solid (1.3 g, 72%). MS: [M+H]+ 447.

Example 334h (4-Fluoro-2-{7-oxo-3,6-diazatetracyclo[9.2.1.0$^{2,10}$.0$^{3,8}$]tetradeca-2(10),8-dien-6-yl}-6-(tetramethyl-1,3,2-dioxaborolan-2-yl)phenyl)methyl Acetate 334h

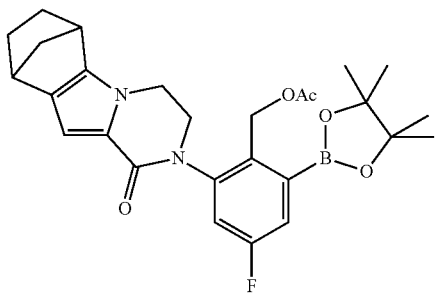

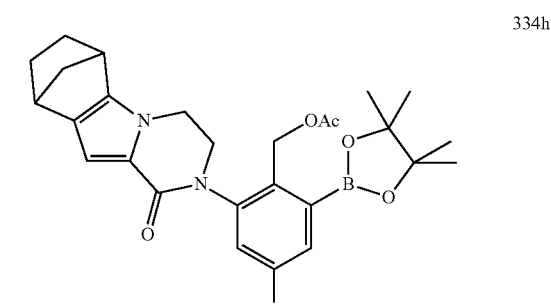

To a solution of 334g (450 mg, 1.0 mmol) and 4,4,4',4',5,5,5',5'-octamethyl-2,2'-bi(1,3,2-dioxaborolane) (770 mg, 3.0 mmol) in dioxane (40 mL) was added PdCl$_2$(dppf) (82 mg, 0.1 mmol) and CH$_3$COOK (593 mg, 6 mmol). The mixture was stirred at 100° C. for 12 h under argon atmosphere. After reaction the mixture was filtered and evaporated in vacuo. The residue was purified by column chromatography eluting with 1:4 ethyl acetate/petroleum ether to give 334h as a brown solid (400 mg, 80%). MS: [M+H]+ 495.

Example 334i {4-Fluoro-2-[1-methyl-5-({5-[4-(oxetan-3-yl)piperazin-1-yl]pyridin-2-yl}amino)-6-oxo-1,6-dihydropyridin-3-yl]-6-{7-oxo-3,6-diazatetracyclo[9.2.1.0$^{2,10}$.0$^{3,8}$]tetradeca-2(10),8-dien-6-yl}phenyl}methyl Acetate 334i

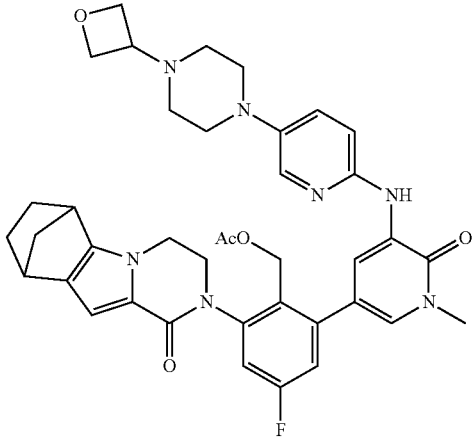

334i

A sealed tube was charged with 334h (300 mg, 0.6 mmol), 188e (254 mg, 0.6 mmol), Na$_2$CO$_3$ (129 mg, 1.2 mmol), PdCl$_2$(dppf) (50 mg, 0.06 mmol) suspended in DMF (20 mL), and H$_2$O (1 mL). The mixture was stirred at 80° C. for 5 hours. After reaction the mixture was partitioned between ethyl acetate and water. The organic phase was washed with water (2×), dried over sodium sulfate and concentrated. The residue was purified by reverse phase Combi-flash eluting with 0.3% NH$_4$HCO$_3$ in 1:5 water/CH$_3$CN to give 334i as a brown solid (300 mg, 70%). MS: (M+H)$^+$ 708.

At room temperature, to the solution of 334i (280 mg, 0.4 mol) in THF/isopropanol/water (10 mL/10 mL/2 mL) was added LiOH (950 mg, 40 mmol) while stirring. This mixture was stirred for 2 h. Then, 20 mL water was added and resulting mixture was extracted with ethyl acetate (3×30 mL). The combined organic layer was dried with Na$_2$SO$_4$ and concentrated to give a yellow solid, which was further purified by reverse phase Combi-flash eluting with 0.3% NH$_4$HCO$_3$ in 1:4 water/CH$_3$CN to give 334 as a white solid (160 mg, 67%). MS: [M+H]$^+$ 666. $^1$H NMR (500 MHz, MEOD) δ 8.53 (s, 1H), 7.93 (d, 1H), 7.43 (d, 1H), 7.34 (s, 1H), 7.20-7.22 (m, 2H), 7.04 (d, 1H), 6.67 (s 1H), 4.72-4.75 (t, J=6.5, 1H), 4.63-4.66 (t, J=6, 2H), 4.47-4.56 (M, 2H), 4.21-4.39 (m, 3H), 3.98-4.06 (m, 1H), 3.71 (s, 3H), 3.56-3.60 (m, 1H), 3.48 (s, 1H), 3.17-3.19 (t, J=4.5, 4H), 2.71 (s, 1H), 2.53-2.55 (t, J=5, 4H), 1.88-1.95 (m,3H), 1.67-1.69 (m, 1H), 1.04-1.17 (m, 2H).

Example 335 2-(5-fluoro-2-(hydroxymethyl)-3-(1-methyl-5-(5-(5-methylhexahydropyrrolo[3,4-c]pyrrol-2(1H)-yl)pyridin-2-ylamino)-6-oxo-1,6-dihydropyridin-3-yl)phenyl)-3,4,6,7,8,9-hexahydropyrazino[1,2-a]indol-1(2H)-one 335

Example 335a tert-Butyl 5-(6-Nitropyridin-3-yl)-hexahydropyrrolo[3,4-c]pyrrole-2(1H)-carboxylate 335a

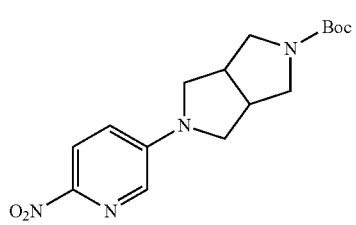

335a

Following Example 188a, reaction of 404 mg of tert-butyl hexahydropyrrolo[3,4-c]pyrrole-2(1H)-carboxylate (2 mmol) and 566 mg 5-fluoro-2-nitropyridine (1.1 mmol) gave 335a as a yellow solid (234 mg, 35%). MS: [M+H]$^+$ 335. $^1$H NMR (500 MHz, DMSO) δ 8.18 (d, J=9.0, 1H), 7.87 (d, J=3.5, 1H), 7.06 (dd, J=9.0, 1H), 3.66 (s, 2H), 3.55 (s, 2H), 3.36 (s, 2H), 3.18 (s, 2H), 3.05 (s, 2H), 1.39 (s, 9H).

Example 335b tert-Butyl 5-(6-Aminopyridin-3-yl)-hexahydropyrrolo[3,4-c]pyrrole-2(1H)-carboxylate 335b

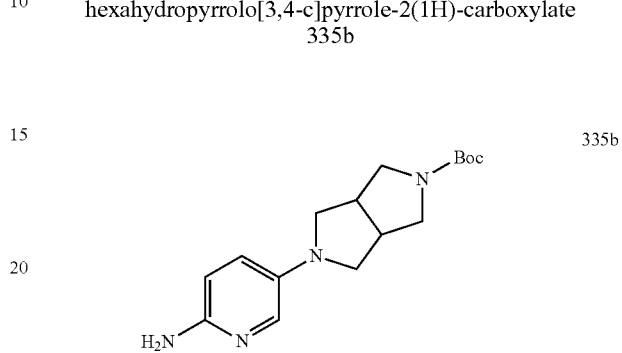

335b

Following Example 188b, 234 mg of 335a (0.7 mmol) was reduced to give 335b as a yellow solid (213 mg, 99%). MS: [M+H]$^+$ 305

Example 335c tert-Butyl 5-(6-(5-Bromo-1-methyl-2-oxo-1,2-dihydropyridin-3-ylamino)pyridine-3-yl)-hexahydropyrrolo[3,4-c]pyrrole-2(1H)-carboxylate 335c

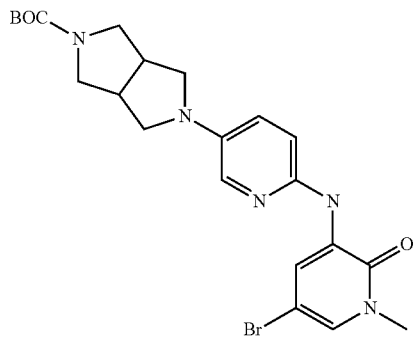 [SMILES: Cn1cc(Br)cc(Nc2ccc(N3CC4CN(C(=O)OC(C)(C)C)CC4C3)cn2)c1=O]

335c

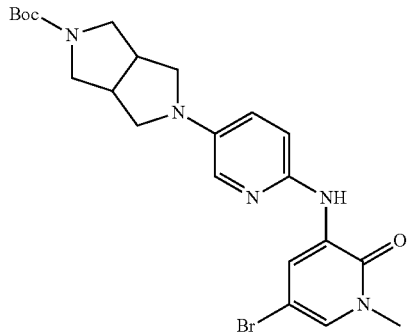

Following Example 188c, 3,5-dibromo-1-methylpyridin-2(1H)-one (212 mg, 0.79 mmol) and 335b (200 mg, 0.66 mmol) were reacted to give 335c as a yellow solid (194 mg, 60%). MS: [M+H]+ 492

Example 335d 5-Bromo-3-(5-(hexahydropyrrolo[3,4-c]pyrrol-2(1H)-yl)pyridin-2-ylamino-1-methyl-pyridin-2(1H)-one 335d

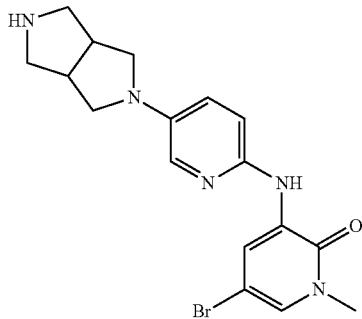

Following Example 188d, 194 mg (0.4 mmol) of 335c was deprotected to give 335d as a yellow solid (154 mg, 99%). MS: [M+H]+ 392

Example 335e 5-Bromo-1-methyl-3-(5-(5-methyl-hexahydropyrrolo[3,4-c]pyrrol-2(1H)-yl)pyridin-2-ylamino)pyridin-2(1H)-one 335e

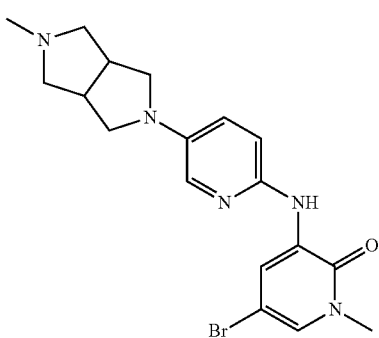

Following Example 188e, 154 mg (0.4 mmol) of 335d was methylated to give 335e as a yellow solid (119 mg, 75%). MS: [M+H]+ 404.

Example 335f 4-Fluoro-2-(1-methyl-5-(5-(5-methyl-hexahydropyrrolo[3,4-c]pyrrol-2(1H)-yl)pyridin-2-ylamino)-6-oxo-1,6-dihydropyridin-3-yl)-6-(1-oxo-3,4,6,7,8,9-hexahydropyrazino[1,2-a]indol-2(1H)-yl) benzyl Acetate 335f

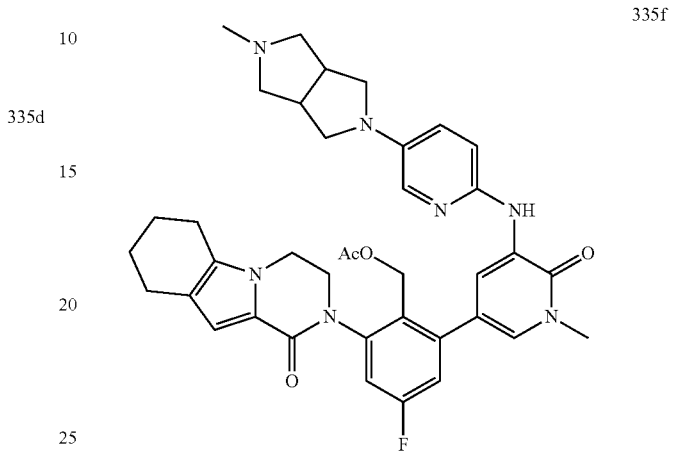

Following Examples 148h, 142 mg of 4-fluoro-2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 210d (0.29 mmol) and 119 mg of 335e (0.29 mmol) were reacted to give 335f as a yellow solid (100 mg, 51%). LCMS: [M+H]+ 680

Following Example 148, 100 mg of 335f (0.15 mmol), 335 was obtained as a white solid (39 mg, 42%). $^1$H NMR (500 MHz, CDCl3) δ 8.45 (d, J=2.0, 1H), 7.70 (d, J=2.5, 1H), 7.67 (s, 1H), 7.42 (d, J=2.5, 1H), 7.17 (m, 1H), 7.04 (dd, J=9.0, 1H), 6.95 (dd, J=6.0, 1H), 6.86 (s, 1H), 6.79 (d, J=9.0, 1H), 4.54 (d, J=11.0, 1H), 4.31 (m, 1H), 4.16 (m, 3H), 3.91 (m, 1H), 3.70 (s, 3H), 3.27 (s, 2H), 3.18 (s, 2H), 2.99 (s, 2H), 2.83 (s, 2H), 2.59 (m, 4H), 2.46 (m, 2H), 2.38 (s, 3H), 1.90 (s, 2H), 1.80 (s, 2H).

Example 336 2-(5-Fluoro-3-(5-(5-(3-(fluoromethyl)-4-methylpiperazin-1-yl)pyridin-2-ylamino)-1-methyl-6-oxo-1,6-dihydropyridin-3-yl)-2-(hydroxymethyl)phenyl)-3,4,6,7,8,9-hexahydropyrazino[1,2-a]indol-1(2H)-one 336

Example 336a 1-tert-Butyl 2-Methyl 4-benzylpiperazine-1,2-dicarboxylate 336a

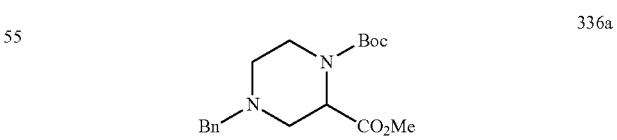

To a dry 100 mL round bottom flask equipped with a stirring bar under $N_2$ was added 1-tert-butyl 2-methyl piperazine-1,2-dicarboxylate (5 g, 20.5 mmol), anhydrous acetonitrile (60 mL), benzyl bromide (2.7 mL, 22.5 mmol), and triethylamine (8.5 mL, 61.5 mmol). The reaction mixture was heated at 71° C. for 45 minutes and concentrated under reduced pressure. It was then diluted with methylene chloride and washed with water and brine. The organic layer was dried over Na₂SO₄, filtered, and concentrated under reduced pressure. The crude compound was purified by flash column chromato-graphy eluting with 8:1 petroleum either/ethyl acetate to afford 336a (4.5 g, 66%). MS: [M+H]⁺ 335. ¹H NMR (500 MHz, CDCl₃) δ 7.28 (m, 5H), 4.60 (m, 1H), 3.78 (m, 4H), 3.57 (m, 1H), 3.43 (m, 1H), 3.28 (m, 2H), 2.77 (m, 1H), 2.19 (m, 1H), 2.11 (m, 1H), 1.47 (s, 5H), 1.42 (s, 4H).

Example 336b
(4-Benzyl-1-methylpiperazin-2-yl)methanol 336b

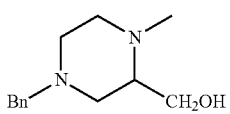

To a solution of 336a (1 g, 2.99 mmol) in 100 mL of anhydrous tetrahydrofuran was slowly added lithium aluminum hydride (342 mg, 8.98 mmol) at 0° C. and the mixture was stirred for 30 min. Then, it was refluxed for 3 h and the reaction mixture was poured onto ice portionwise. The resulting mixture was filtered and the filtrate was evaporated in vacuo. After addition of 100 mL brine to the residue, it was extracted with methylene chloride (100 mL×3). The combined organic layer was dried over Na₂SO₄, filtered, and concentrated to afford 336b as yellow oil (0.60 g, 91%). MS: [M+H]⁺ 221.

Example 336c
4-Benzyl-2-(fluoromethyl)-1-methylpiperazine 336c

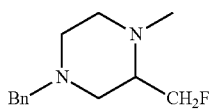

To an ice-cooled solution of diethylaminosulfur trifluoride (10.8 mL, 81.8 mmol) in methylene chloride under N₂ was added 336b (9.0 g, 40.9 mmol) in methylene chloride dropwise. The yellow solution was stirred at 0° C. for 1 h and then room temperature for 15 h. The reaction mixture was then diluted with NaHCO₃, and the organic layer was separated and dried over Na₂SO₄. The crude product was purified on silica gel column chromatography eluting with 50:1 methylene chloride/methanol to afford 336c as a yellow oil (3.0 g, 33%). MS: [M+H]⁺ 223. ¹H NMR (500 MHz, DMSO) δ 7.28 (m, 5H), 4.50 (m, 0.5H), 4.43 (m, 1H), 4.35 (m, 0.5H), 3.45 (s, 2H), 2.67 (m, 2H), 2.60 (m, 1H), 2.29 (m, 1H), 2.24 (s, 3H), 2.20 (m, 1H), 2.11 (m, 1H), 1.94 (m, 1H).

Example 336d 2-(Fluoromethyl)-1-methylpiperazine 336d

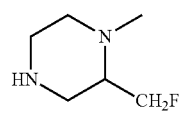

A 250-mL single-neck round-bottomed flask equipped with a magnetic stirrer was charged with 336c (3.0 g, 13.5 mmol), methanol (80 mL), and Pd/C (10%) (300 mg). The reaction mixture was stirred at 25° C. under H₂ for 15 h. After the reaction was finished, it was filtered and concentrated to afford 336d as a yellow oil (1.6 g, 90%).

Example 336e 2-(Fluoromethyl)-1-methyl-4-(6-nitropyridin-3-yl)piperazine 336e

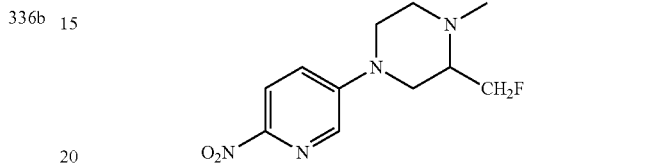

A 100-mL single-neck round-bottomed flask equipped with a magnetic stirrer and reflux condenser was charged with 1,4-dioxane (50 mL), 336d (1.6 g, 12.1 mmol), 5-bromo-2-nitropyridine (3.7 g, 18.2 mmol), and cesium carbonate (9.9 g, 30.2 mmol). After bubbling nitrogen through the resulting solution for 30 min, Xantphos (700 mg, 0.12 mmol) and tris(dibenzylideneacetone)-dipalladium (0) (550 mg, 0.06 mmol) were added. After three cycles of vacuum/argon flash, the reaction mixture was heated at reflux for 15 h. After this time the reaction was cooled to room temperature, filtered, and concentrated to afford a black solid as a crude product, which was further purified by column chromatography eluting with 100:1 methylene chloride/methanol to afford 336e as a yellow solid (2.6 g, 76%). MS: [M+H]⁺ 255. ¹H NMR (500 MHz, MeOD) δ 8.20 (m, 2H), 7.52 (dd, J=9, 1H), 4.72 (m, 0.5H), 4.64 (m, 1H), 4.56 (m, 0.5H), 4.01 (m, 1H), 3.94 (m, 1H), 3.19 (m, 1H), 3.06 (m, 1H), 3.00 (m, 1H), 2.50 (m, 2H), 2.46 (s, 3H).

Example 336f 5-(3-(Fluoromethyl)-4-methylpiperazin-1-yl)pyridin-2-amine 336f

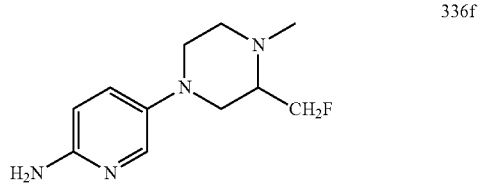

A 250-mL single-neck round-bottomed flask equipped with a magnetic stirrer was charged with 336e (2.6 g, 10.2 mmol), methanol (50 mL), and Pd/C (10%) (260 mg). The reaction mixture was stirred under H₂ for 15 h. After the reaction was finished, it was filtered and concentrated to afford 336f as a black oil, which was used in the next step without further purification. MS: [M+H]⁺ 225.

Example 336g 5-Bromo-3-(5-(3-(fluoromethyl)-4-methylpiperazin-1-yl)pyridin-2-ylamino)-1-methyl-pyridin-2(1H)-one 336g

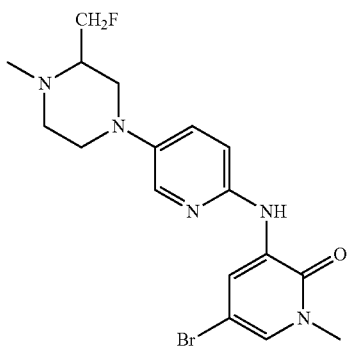

336g

A 100-mL single-neck round-bottomed flask equipped with a magnetic stirrer and reflux condenser was charged with 1,4-dioxane (60 mL), 336f (crude, 14.1 mmol), 3,5-dibromo-1-methylpyridin-2(1H)-one (4.5 g, 16.9 mmol), and cesium carbonate (11.5 g, 35.2 mmol). After bubbling nitrogen through the resulting solution for 30 min, Xantphos (820 mg, 1.41 mmol) and tris(dibenzylideneacetone)dipalladium(0) (645 mg, 0.7 mmol) were added. After three cycles of vacuum/argon flash, the reaction mixture was heated at reflux for 15 h. The reaction was cooled to room temperature, filtered and concentrated to afford a black solid, which was purified by column chromatography eluting with methylene chloride/methanol (from 100:1 to 50:1) to afford 336g as a yellow solid (3.1 g, 50%). MS: [M+H]$^+$ 410.

Example 336h 4-Fluoro-2-(5-(5-(3-(fluoromethyl)-4-methylpiperazin-1-yl)pyridin-2-ylamino)-1-methyl-6-oxo-1,6-dihydropyridin-3-yl)-6-(1-oxo-3,4,6,7,8,9-hexahydropyrazino[1,2-a]indol-2(1H)-yl) benzyl Acetate 336h

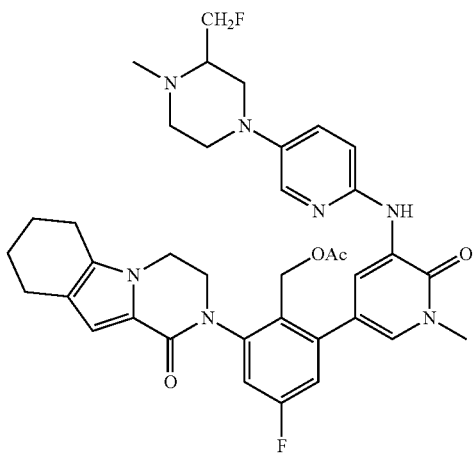

336h

A reaction vessel was charged with a mixture of 336g (1 g, 2.4 mmol), 4-fluoro-2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate 210d (1.3 g, 2.68 mmol), PdCl$_2$(dppf) (190 mg, 0.24 mmol), K$_3$PO$_4$ (1 g, 4.8 mmol), and NaOAc (390 mg, 4.8 mmol) in MeCN (15 mL) and water (1.5 mL). It was bubbled with nitrogen for 30 min and then heated at 110° C. for 3 h. The solvent was evaporated in vacuum and the residue was purified on silica gel column chromatography eluting with 5:1 methylene chloride/methanol to afford 336h (0.80 g, 45%). MS: [M+H]$^+$ 686.

A mixture of 336h (750 mg, 1.09 mmol) and LiOH hydrate (2.3 g, 55 mmol) in isopropanol (10 mL), THF (10 mL), and water (10 mL) was stirred at 30° C. for 1 h. The mixture was evaporated in vacuo, and the residue was extracted with methylene chloride (30 mL×3). The combined extracts were concentrated under reduced pressure and the residue was purified on silica gel column eluting with 50:1 methylene chloride/methanol to afford 336 as a yellow solid (700 mg, 93%). MS: [M+H]$^+$ 644. $^1$H NMR (500 MHz, MeOD) δ 8.54 (d, J=2 Hz, 1H), 7.92 (d, J=1.5 Hz, 1H), 7.42 (m, 1H), 7.33 (m, 1H), 7.22 (s, 1H), 7.20 (s, 1H), 7.02 (m, 1H), 6.72 (s, 1H), 4.46-4.69 (m, 4H), 4.20 (s, 3H), 4.02 (m, 1H), 3.70 (s, 3H), 3.49 (d, J=11.5 Hz, 1H), 3.42 (d, J=11.5 Hz, 1H), 2.94 (m, 1H), 2.85 (m, 1H), 2.71 (m, 1H), 2.64 (m, 2H), 2.56 (m, 4H), 2.44 (s, 3H), 1.88 (m, 2H), 1.79, (m, 2H).

Example 337 6-[5-Fluoro-2-(hydroxymethyl)-3-{1-methyl-6-oxo-5-[(pyrimidin-4-yl)amino]-1,6-dihydropyridin-3-yl}phenyl]-3,6-diazatetracyclo[9.2.1.0$^{2,10}$.0$^{3,8}$]tetradeca-2(10),8-dien-7-one 337

Example 337a (4-Fluoro-2-{1-methyl-6-oxo-5-[(pyrimidin-4-yl)amino]-1,6-dihydro-pyridin-3-yl}-6-{7-oxo-3,6-diazatetracyclo[9.2.1.0$^{2,10}$.0$^{3,8}$]tetradeca-2(10),8-dien-6-yl}phenyl)methyl Acetate 337a

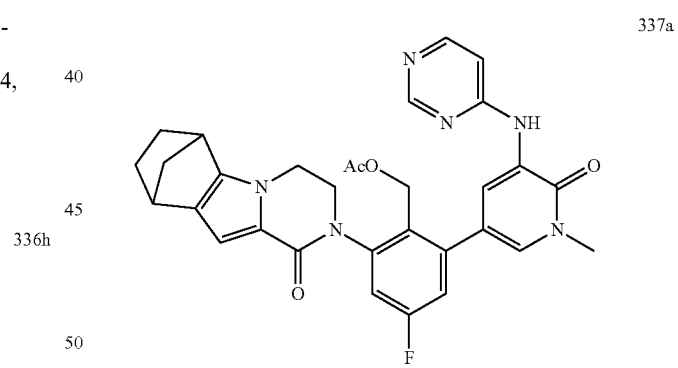

337a

A sealed tube was charged with (2-bromo-4-fluoro-6-{7-oxo-3,6-diazatetracyclo-[9.2.1.0$^{2,10}$.0$^{3,8}$]tetradeca-2(10),8-dien-6-yl}phenyl)methyl acetate 334g (400 mg, 0.9 mmol), 1-methyl-3-(pyrimidin-4-ylamino)-5-(4,4,5,5-tetramethyl-1,3,2-dioxaborolan-2-yl)pyridin-2(1H)-one 109c (294 mg, 0.9 mmol), Na$_2$CO$_3$ (190 mg, 1.8 mmol), and PdCl$_2$(dppf) (73 mg, 0.09 mmol) suspended in DMF (20 mL) and water (1 mL). The mixture was stirred at 60° C. for 6 hours. It was then partitioned between water and ethyl acetate. The organic phase was washed with water and evaporated to dryness. The residue was purified by column chromatography eluting with 15:1 methylene chloride/methanol to give 337a as a brown solid (300 mg, 58%). MS: [M+H]$^+$ 569.

At room temperature, to the solution of 337a (270 mg, 0.47 mol) in THF/isopropanol/water (10 mL/10 mL/2 mL)

was added LiOH (1.1 g, 47 mmol) while stirring. This mixture was stirred for 2 h. Then, 20 mL water was added and the resulting mixture was extracted with ethyl acetate (30 mL×3). The combined organic layer was dried with $Na_2SO_4$ and concentrated to get a yellow solid, which was further purified by reverse phase Combi-flash eluting with 0.3% $NH_4HCO_3$ in 1:5 water/$CH_3CN$ to give 337 as a white solid (138 mg, 48%). MS: [M+H]$^+$ 527. $^1$H NMR (500 MHz, MEOD) δ 8.87 (s, 1H), 8.67 (s, 1H), 8.29 (d, 1H), 7.55 (s, 1H), 7.22-7.24 (m, 2H), 7.10 (d, 1H), 6.68 (d, 1H), 4.48-4.55 (m, 2H), 4.18-4.40 (m, 3H), 3.98-4.06 (m, 1H), 3.72 (s, 3H), 3.45-3.48 (m, 1H), 1.88-1.98 (m, 3H), 1.67-1.69 (m, 1H), 1.30 (m, 1H), 1.12-1.17 (m, 1H), 1.02-1.07 (m, 1H).

Example 338 2-(5-Fluoro-2-(hydroxymethyl)-3-(1-methyl-5-(5-(4-methyl-1,4-diazepan-1-yl)pyridin-2-ylamino)-6-oxo-1,6-dihydropyridin-3-yl)phenyl)-3,4,6,7,8,9-hexahydropyrazino[1,2-a]indol-1(2H)-one 338

Example 338a
1-Methyl-4-(6-nitropyridin-3-yl)-1,4-diazepane 338a

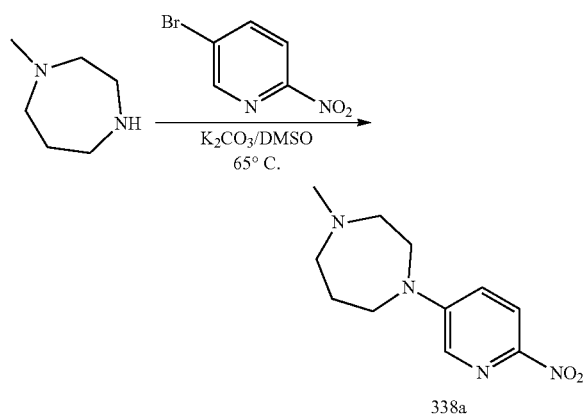

To a solution of 1-methyl-1,4-diazepane (1 g, 8.8 mmol) in DMSO (20 mL) were added $K_2CO_3$ (2.4 g, 18 mmol) and 5-bromo-2-nitropyridine (51-7) (1.78 g, 8.8 mmol). The mixture was stirred at 65° C. for overnight. It was allowed to cool to room temperature and poured into water. The resulting solid was collected and dried under vacuum. The solid was further purified by flash column eluting with 3:1 petroleum ether/ethyl acetate and then methylene chloride to give 338a as a yellow solid (800 mg, 69%). MS: [M+H]$^+$ 236.

Example 338b
1-Methyl-4-(6-nitropyridin-3-yl)-1,4-diazepane 338b

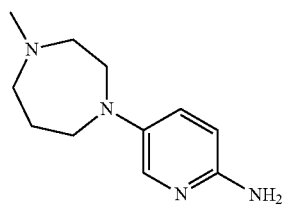

A 500-mL bottle was purged with nitrogen and charged with 338a (0.8 g, 3.4 mmol), 10% palladium on carbon (50% wet, 100 mg) and methanol (100 mL). The bottle was evacuated, charged with hydrogen gas, and stirred at room temperature for 16 h. The hydrogen was then evacuated and nitrogen charged to the bottle. The catalyst was removed by filtration through a pad of Celite and the filtrate was concentrated under reduced pressure to afford 338b (0.6 g, crude). MS: [M+H]$^+$ 207.

Example 338c 5-Bromo-1-methyl-3-(5-(4-methyl-1,4-diazepan-1-yl)pyridin-2-ylamino)pyridine-2(1H)-one 338c

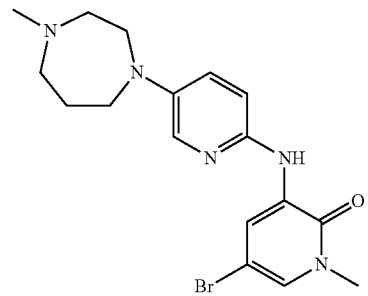

A 100-mL single-neck round-bottomed flask equipped with a magnetic stirrer and reflux condenser was charged with 338b (968 mg, 4.7 mmol), 3,5-dibromo-1-methylpyridin-2(1H)-one (1.24 g, 4.7 mmol) and cesium carbonate (3.8 g, 12 mmol). After bubbling nitrogen through the resulting solution for 30 minutes, XantPhos (272 mg, 0.47 mmol) and tris(dibenzylideneacetone)dipalladium(0) (430 mg, 0.47 mmol) were added. The reaction mixture was heated at reflux for 3 h. After this time the reaction was cooled to room temperature, partitioned between ethyl acetate (100 mL) and water (100 mL), and filtered. The aqueous layer was separated and extracted with ethyl acetate (2×50 mL). The organic layers were combined, washed with brine (50 mL), and dried over sodium sulfate. The drying agent was removed by filtration and the filtrate was concentrated under reduced pressure. The residue was purified on flash column eluting with petroleum ether/ethyl acetate to afford 338c (918 mg, 50%). MS: [M+H]$^+$ 392.

Example 338d 4-Fluoro-2-(1-methyl-5-(5-(4-methyl-1,4-diazepan-1-yl)pyridine-2-ylamino)-6-oxo-1,6-dihydropyridin-3-yl)-6-(1-oxo-3,4,6,7,8,9-hexahydropyrazino[1,2-a]indol-2(1H)-yl)benzyl Acetate 338d

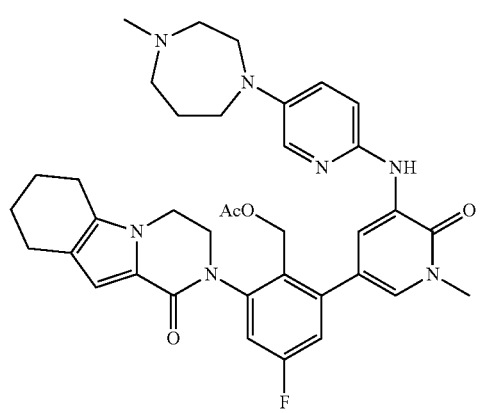

A sealed tube was charged with the mixture of 338c (274 mg, 0.7 mmol), 210d (337 mg, 0.7 mmol), Pd(dppf)Cl$_2$ (33 mg, 0.04 mmol), K$_3$PO$_4$.3H$_2$O (372 mg, 1.4 mmol), and NaOAc (115 mg, 1.4 mmol) in CH$_3$CN (20 ml). The system was evacuated and then refilled with N$_2$. And the reaction mixture was heated at 110° C. under microwave irradiation for 3 h. The mixture was cooled to room temperature and filtered. The filtrate was concentrated under reduced pressure and the resulting residue was purified by flash column chromatography eluting with 30:1 methylene chloride/methanol to afford 338d as a yellow solid (120 mg, 43%). MS: [M+H]$^+$ 668.

A solution of 338d (120 mg, 0.18 mmol) in propan-2-ol (10 mL), tetrahydrofuran (10 mL) and water (2 mL) was added LiOH (1.1 g, 57 mmol). The mixture was stirred at 30° C. for 2 h. It was then evaporated and the residue was purified by prep-HPLC to afford 338 as a white solid (60 mg, 54%). MS: (M+H)$^+$ 626. $^1$H NMR (500 MHz, MeOD) δ 8.18 (s, 1H), 7.62 (s, 1H), 7.16 (s, 1H), 7.06 (m, 3H), 6.88 (d, J=11.5, 2H), 6.59 (s, 1H), 4.38 (m, 2H), 4.07 (m 3H), 3.87 (m, 1H), 3.57 (s, 3H), 3.42 (m, 2H), 3.31 (m, 2H), 3.20 (s, 3H), 2.60 (m, 2H), 2.50 (m, 4H), 2.42 (m, 2H), 1.75 (m, 6H).

Example 339 5-[5-fluoro-2-(hydroxymethyl)-3-[1-methyl-5-({5-[4-(oxetan-3-yl)piperazin-1-yl]pyridine-2-yl}amino)-6-oxo-1,6-dihydropyridin-3-yl]phenyl]-8-thia-4,5-diazatricyclo[7.4.0.0$^{2,7}$]-trideca-1(9),2(7),3(4)-trien-6-one 339

Example 339a [4-Fluoro-2-(1-methyl-5-{[5-(4-(oxetan-3-yl)piperazin-1-yl)pyridine-2-yl]amino}-6-oxo-1,6-dihydropyridin-3-yl)-6-{6-oxo-8-thia-4,5-diazatricyclo[7.4.0.0$^{2,7}$]trideca-1(9),2(7),3-trien-5-yl}phenyl]methyl Acetate 339a

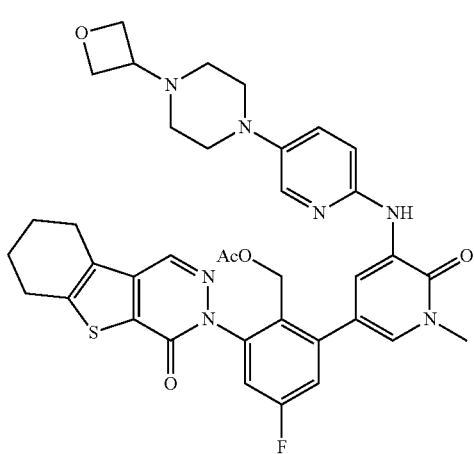

Following Example 210e, 150 mg (0.30 mmol) of (4-fluoro-2-{6-oxo-8-thia-4,5-diazatricyclo[7.4.0.0$^{2,7}$]trideca-1(9),2(7),3-trine-5-yl}-6-(tetramethyl-1,3,2-dioxaborolan-2-yl)phenyl)methyl acetate 341b was converted to 339a as a yellow solid (129 mg, 60%). MS: [M+H]$^+$ 712

Following Example 148, 120 mg of 339a (0.17 mmol) was converted to 339 as a white solid (56 mg, 50%). MS: [M+H]$^+$ 670. $^1$H NMR (500 MHz, DMSO) δ 8.56 (d, J=3.0 Hz, 1H), 8.48 (s, 1H), 8.41 (s, 1H), 7.88 (d, J=3.0 Hz, 1H), 7.37 (m, 4H), 7.23 (d, J=9.5 Hz, 1H), 4.60 (t, J=10.0 Hz, 1H), 4.56 (t, J=13.0 Hz, 2H), 4.46 (t, J=12.0 Hz, 2H), 4.28 (s, 2H), 3.58 (s, 3H), 3.43 (m, 1H), 3.07 (t, J=9.0 Hz, 4H) 2.93 (s, 2H), 2.85 (s, 2H), 2.38 (t, J=9.0 Hz, 4H), 1.87 (m, 4H).

Example 340 2-(5-Fluoro-2-(hydroxymethyl)-3-(1-methyl-5-(5-(4-methylpiperazin-1-ylpyridin-2-ylamino)-6-oxo-1,6-dihydropyridin-3-yl)phenyl)-3,4,6,7,8,9-hexahydro-6,9-methanopyrazino[1,2-a]indol-1(2H)-one 340

Example 340a {4-Fluoro-2-[1-methyl-5-({5-[4-methylpiperazin-1-yl]pyridin-2yl}amino)-6-oxo-1,6-dihydropyridin-3-yl]-6-{7-oxo-3,6-diazatetracyclo[9.2.1.0$^{2,10}$.0$^{3,8}$]tetradeca-2(10),8-dien-6-yl}phenyl}methyl Acetate 340a

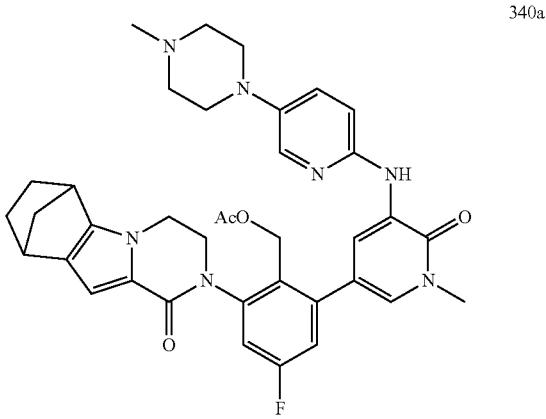 [SMILES: CC(=O)OCc1c(-c2cc(Nc3ccc(N4CCN(C)CC4)cn3)c(=O)n(C)c2)cc(F)cc1N1CCn2c(cc3c2C2CCC3C2)C1=O]

A microwave vial equipped with a magnetic stirrer was charged with (2-bromo-4-fluoro-6-{7-oxo-3,6-diazatetracyclo[9.2.1.0$^{2,10}$.0$^{3,8}$]tetradeca-2(10),8-dien-6-yl}phenyl)methyl acetate 334g (293 mg, 0.65 mmol), 1-methyl-5-(5-(4-methylpiperazin-1-yl)pyridine-2-ylamino)-6-oxo-1,6-dihydropyridin-3-ylboronic acid 197f (450 mg, 1.3 mmol), PdCl$_2$(dppf) (54 mg, 0.065 mmol), 2.0 M Na$_2$CO$_3$ (2.0 equiv), and 1,2-dimethoxyethane (18 mL). After three cycles of vacuum/argon flash, the mixture was heated at 130° C. under microwave irradiation for 0.5 h. It was then filtered and the filtrate was evaporated in vacuo. The residue was purified on flash column chromatography eluting with 10:1 dichloromethane/methanol to afford 340a as a brown solid (130 mg, 33%). LCMS: [M+H]$^+$ 666

A mixture of 340a (130 mg, 0.20 mmol) and LiOH (470 mg, 20.0 mmol) in isopropanol/THF (1:1, 10 mL) and water (3 mL) was stirred at 30° C. for 2 h. The mixture was evaporated in vacuo and the residue was extracted with ethyl acetate (30 mL×2). The combined ethyl acetate extract was concentrated under reduced pressure and the residue was purified with prep-HPLC to afford 340 (50 mg, 41%). LCMS: [M+H]$^+$ 624. $^1$H NMR (500 MHz, MEOD) δ 8.54 (s, 1H), 7.93 (s, 1H), 7.41-7.43 (m, 1H), 7.34 (s, 1H), 7.20-7.22 (m, 2H), 7.02-7.04 (d, J=9.0 Hz, 1H), 6.67-6.68 (d, J=3.0 Hz, 1H), 4.46-4.55 (m, 2H), 4.18-4.38 (m, 3H), 3.98-4.06 (m, 1H), 3.71 (s, 3H), 3.46-3.48 (m, 1H), 3.14-3.18 (m, 4H), 2.62-2.64 (t, J=4.5 Hz, 4H), 2.36 (s, 3H), 1.88-1.95 (m, 3H), 1.67-1.69 (m, 1H), 1.01-1.30 (m, 2H).

Example 341 5-[5-Fluoro-2-(hydroxymethyl)-3-(1-methyl-5-{[5-(4-methylpiperazin-1-yl)pyridin-2-yl]amino}-6-oxo-1,6-dihydropyridin-3-yl)phenyl]-8-thia-4,5-diazatricyclo[7.4.0.0²,⁷]trideca-1(9),2(7),3-trien-6-one 341

Example 341a (2-Bromo-4-fluoro-6-{6-oxo-8-thia-4,5-diazatricyclo[7.4.0.0²,⁷]trideca-1(9),2(7),3-trien-5-yl}phenyl)methyl acetate 341a

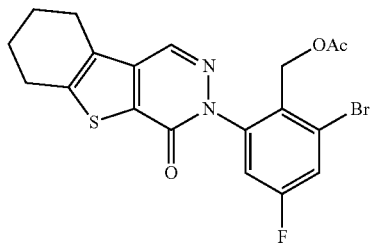

A 100-mL single-neck round-bottomed flask equipped with a magnetic stirrer was charged with 8-thia-4,5-diazatricyclo[7.4.0.0²,⁷]trideca-1(9),2(7),3-trien-6-one (1 g, 4.85 mmol), 2,6-dibromo-4-fluorobenzyl acetate 197c (4.8 g, 14.6 mmol), copper(I) iodide (553 mg, 2.9 mmol), $N^1,N^2$-dimethylethane-1,2-diamine (512 mg, 5.82 mmol), $Cs_2CO_3$ (3.2 g, 9.7 mmol), and 1,4-dioxane (50 mL). The system was evacuated and then refilled with $N_2$. A reflux condenser was attached to the flask, and the reaction mixture was heated at 100° C. for 16 h. It was then cooled to room temperature and filtered. The filtrate was concentrated under reduced pressure and the resulting residue was purified by flash column chromatography eluting with 5:1 petroleum ether/ethyl acetate to afford 341a as a yellow solid (437 mg, 20%). MS: [M+H]⁺ 451.

Example 341b (4-Fluoro-2-{6-oxo-8-thia-4,5-diazatricyclo[7.4.0.0²,⁷]trideca-1(9),2(7),3-trine-5-yl}-6-(tetramethyl-1,3,2-dioxaborolan-2-yl)phenyl)methyl acetate 341b

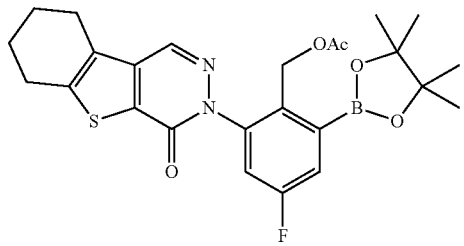

Following Example 210d, 341a (400 mg 0.88 mmol) was converted to 341b as a yellow solid (353 mg, 80%). MS: [M+H]⁺ 499

Example 341c [4-Fluoro-2-(1-methyl-5-{[5-(4-methylpiperazin-1-yl)pyridin-2-yl]amino}-6-oxo-1,6-dihydropyridin-3-yl)-6-{6-oxo-8-thia-4,5-diazatricyclo-[7.4.0.0²,⁷]trideca-1(9),2(7),3-trien-5-yl}phenyl]methyl Acetate 341c

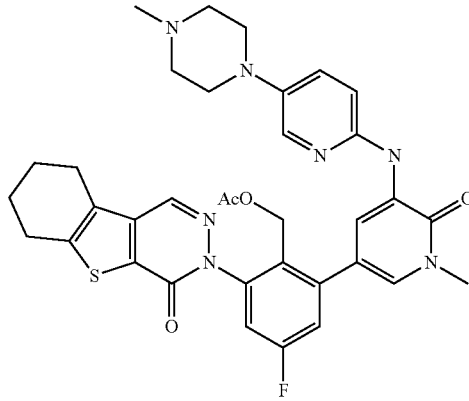

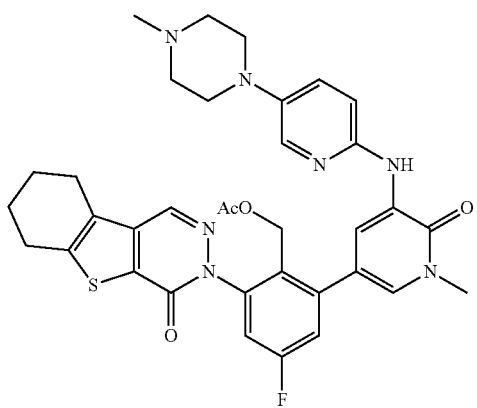

Following Example 210a, 180 mg (0.36 mmol) of 341b was converted to 341c as a yellow solid (120 mg, 50%). MS: [M+H]⁺ 670

Following Example 148, 120 mg of 341c (0.18 mmol) was converted to 341 as a white solid (46 mg, 41%). MS: [M+H]⁺ 628. ¹H NMR (500 MHz, CDCl3) δ 8.58 (d, J=2.5, 1H), 8.26 (s, 1H), 7.95 (d, J=3.0, 1H), 7.77 (s, 1H), 7.45 (d, J=2.0, 1H), 7.31 (m, 1H), 7.25 (m, 1H), 7.11 (dd, J=8.0, 1H), 6.82 (d, J=9.0, 1H), 4.31 (s, 1H), 4.01 (s, 1H), 3.71 (s, 3H), 3.15 (t, J=4.5, 4H), 2.99 (t, J=5.0, 2H), 2.87 (t, J=5.5, 2H), 2.60 (t, J=5.0, 4H), 2.37 (s, 3H), 1.99 (s, 4H).

Example 342 2-(5-Fluoro-2-(hydroxymethyl)-3-(1-methyl-5-(6-(4-methylpiperazin-1-yl)pyridazin-3-ylamino)-6-oxo-1,6-dihydropyridin-3-yl)phenyl)-3,4,6,7,8,9-hexahydropyrazino[1,2-a]indol-1(2H)-one 342

Example 342a
6-(4-Methylpiperazin-1-yl)pyridazin-3-amine 342a

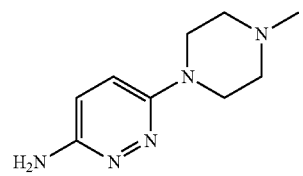

A sealed tube equipped with a magnetic stirrer was charged with 6-chloro-pyridazin-3-amine (1.3 g, 10 mmol) and 1-methylpiperazine (15 mL). The reaction mixture was heated at 170° C. for 3 h. It was then cooled to room temperature and concentrated under reduced pressure. The resulting residue was washed with CH$_3$CN (20 mL) to afford 342a as a yellow solid (1.5 g, 78%). MS: [M+H]$^+$ 194. $^1$H NMR (500 MHz, DMSO) δ 7.12 (d, J=9.0 Hz, 1H), 6.74 (d, J=9.0 Hz, 1H), 5.72 (s, 2H), 3.27 (t, J=4.5 Hz, 4H), 2.40 (t, J=4.5 Hz, 4H), 2.20 (s, 3H).

Example 342b 5-Bromo-1-methyl-3-(6-(4-methyl-piperazin-1-yl)pyridazin-3-ylamino)-pyridin-2(1H)-one 342b

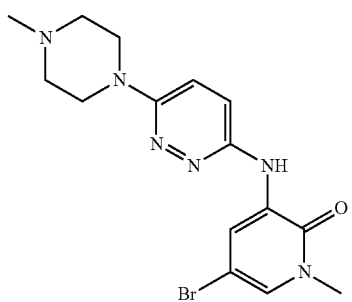

342b

Following Example 188c, 342a (580 mg, 3.0 mmol) was converted to 342b as a yellow solid (920 mg, 80%). MS: [M+H]$^+$ 381

Example 342c 4-Fluoro-2-(1-methyl-5-(6-(4-methylpiperazin-1-yl)pyridazin-3-ylamino)-6-oxo-1,6-dihydropyridin-3-yl)-6-(1-oxo-3,4,6,7,8,9-hexahydropyrazino[1,2-a]indol-2(1H)-yl)benzyl Acetate 342c

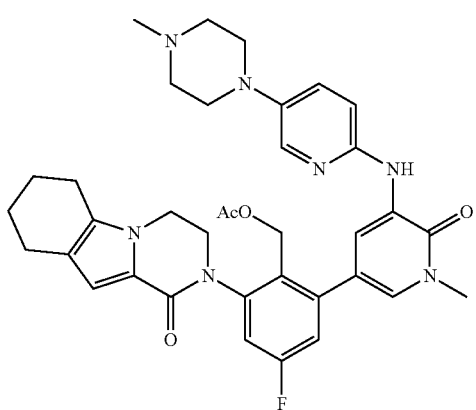

342c

Following Example 188f, 482 mg of 342b (1.0 mmol) and 379 mg of 5-bromo-1-methyl-3-(6-(4-methylpiperazin-1-yl)pyridazin-3-ylamino)pyridin-2(1H)-one (1.0 mmol) were reacted to give 342c as a yellow solid (261 mg, 40%). MS: [M+H]$^+$ 655.

Following Example 188, 342c (150 mg 0.23 mmol) was converted to 342 as a white solid (73 mg, 52%). LCMS: [M+H]$^+$ 613. $^1$H NMR (500 MHz, CDCl$_3$) δ 8.68 (d, J=2.5 Hz, 1H), 7.76 (s, 1H), 7.46 (d, J=2.0 Hz, 1H), 7.12 (dd, J=9.0 Hz, 1H), 7.0 (m, 2H), 6.90 (dd, J=9.0 Hz, 1H), 6.86 (s, 1H), 4.50 (dd, J=11.0 Hz, 1H), 4.27 (m, 2H), 4.16 (m, 3H), 3.88 (m, 1H), 3.71 (s, 3H), 3.54 (m, 4H), 2.58 (m, 7H), 2.35 (s, 3H), 1.90 (m, 2H), 1.71 (m, 2H).

Example 901 Biochemical Btk Assay

A generalized procedure for a standard biochemical Btk Kinase Assay that can be used to test Formula I compounds is as follows. A master mix minus Btk enzyme is prepared containing 1× Cell Signaling kinase buffer (25 mM Tris-HCl, pH 7.5, 5 mM beta-glycerophosphate, 2 mM dithiothreitol, 0.1 mM Na$_3$VO$_4$, 10 mM MgCl$_2$), 0.5 μM Promega PTK Biotinylated peptide substrate 2, and 0.01% BSA. A master mix plus Btk enzyme is prepared containing 1× Cell Signaling kinase buffer, 0.5 μM PTK Biotinylated peptide substrate 2, 0.01% BSA, and 100 ng/well (0.06 mU/well) Btk enzyme. Btk enzyme is prepared as follows: full length human wildtype Btk (accession number NM-000061) with a C-terminal V5 and 6×His tag was subcloned into pFastBac vector for making baculovirus carrying this epitope-tagged Btk. Generation of baculovirus is done based on Invitrogen's instructions detailed in its published protocol "Bac-to-Bac Baculovirus Expression Systems" (Cat. Nos. 10359-016 and 10608-016). Passage 3 virus is used to infect Sf9 cells to overexpress the recombinant Btk protein. The Btk protein is then purified to homogeneity using Ni-NTA column. The purity of the final protein preparation is greater than 95% based on the sensitive Sypro-Ruby staining. A solution of 200 μM ATP is prepared in water and adjusted to pH7.4 with 1N NaOH. A quantity of 1.25 μL of compounds in 5% DMSO is transferred to a 96-well ½ area Costar polystyrene plate. Compounds are tested singly and with an 11-point dose-responsive curve (starting concentration is 10 μM; 1:2 dilution). A quantity of 18.75 μL of master mix minus enzyme (as a negative control) and master mix plus enzyme is transferred to appropriate wells in 96-well ½ area costar polystyrene plate. 5 μL of 200 μM ATP is added to that mixture in the 96-well ½ area Costar polystyrene plate for final ATP concentration of 40 μM. The reaction is allowed to incubate for 1 hour at room temperature. The reaction is stopped with Perkin Elmer 1× detection buffer containing 30 mM EDTA, 20 nM SA-APC, and 1 nM PT66 Ab. The plate is read using time-resolved fluorescence with a Perkin Elmer Envision using excitation filter 330 nm, emission filter 665 nm, and 2$^{nd}$ emission filter 615 nm. IC$_{50}$ values are subsequently calculated. Alternatively, the Lanthascreen assay can be used to evaluate Btk activity through quantification of its phosphorylated peptide product. The FRET (Fluorescence Resonance Energy Transfer) that occurs between the fluorescein on the peptide product and the terbium on the detection antibody decreases with the addition of inhibitors of Btk that reduce the phosphorylation of the peptide. In a final reaction volume of 25 uL, Btk (h) (0.1 ng/25 ul reaction) is incubated with 50 mM Hepes pH 7.5, 10 mM MgCl2, 2 mM MnCl$_2$, 2 mM DTT, 0.2 mM NaVO4, 0.01% BSA, and 0.4 uM fluorescein poly-GAT. The reaction is initiated by the addition of ATP to 25 uM (Km of ATP). After incubation for 60 minutes at room temperature, the reaction is stopped by the addition of a final concentration of 2 nM Tb-PY20 detection antibody in 60 mM EDTA for 30 minutes at room temperature. Detection is determined on a Perkin Elmer Envision with 340 nM excitation and emission at 495 nm and 520 nm. Exemplary Btk inhibition IC50 values are in Tables 1, 2, and 3.

Example 902 Ramos Cell Btk Assay

Another generalized procedure for a standard cellular Btk Kinase Assay that can be used to test Formula I compounds is as follows. Ramos cells are incubated at a density of $0.5 \times 10^7$ cells/ml in the presence of test compound for 1 hr at 37° C. Cells are then stimulated by incubating with 10 µg/ml anti-human IgM F(ab)$_2$ for 5 minutes at 37° C. Cells are pelleted, lysed, and a protein assay is performed on the cleared lysate. Equal protein amounts of each sample are subject to SDS-PAGE and western blotting with either anti-phosphoBtk(Tyr223) antibody (Cell Signaling Technology #3531; Epitomics, cat. #2207-1) or phosphoBtk (Tyr551) antibody (BD Transduction Labs #558034) to assess Btk autophosphorylation or an anti-Btk antibody (BD Transduction Labs #611116) to control for total amounts of Btk in each lysate.

Example 903 B-Cell Proliferation Assay

A generalized procedure for a standard cellular B-cell proliferation assay that can be used to test Formula I compounds is as follows. B-cells are purified from spleens of 8-16 week old Balb/c mice using a B-cell isolation kit (Miltenyi Biotech, Cat #130-090-862). Testing compounds are diluted in 0.25% DMSO and incubated with $2.5 \times 10^5$ purified mouse splenic B-cells for 30 min prior to addition of 10 µg/ml of an anti-mouse IgM antibody (Southern Biotechnology Associates Cat #1022-01) in a final volume of 100 µl. Following 24 hr incubation, 1 µCi $^3$H-thymidine is added and plates are incubated an additional 36 hr prior to harvest using the manufacturer's protocol for SPA[$^3$H] thymidine uptake assay system (Amersham Biosciences #RPNQ 0130). SPA-bead based fluorescence is counted in a microbeta counter (Wallace Triplex 1450, Perkin Elmer).

Example 904 T Cell Proliferation Assay

A generalized procedure for a standard T cell proliferation assay that can be used to test Formula I compounds is as follows. T cells are purified from spleens of 8-16 week old Balb/c mice using a Pan T cell isolation kit (Miltenyi Biotech, Cat #130-090-861). Testing compounds are diluted in 0.25% DMSO and incubated with $2.5 \times 10^5$ purified mouse splenic T cells in a final volume of 100 µl in flat clear bottom plates precoated for 90 min at 37° C. with 10 µg/ml each of anti-CD3 (BD #553057) and anti-CD28 (BD #553294) antibodies. Following 24 hr incubation, 1 µCi $^3$H-thymidine is added and plates are incubated an additional 36 hr prior to harvest using the manufacturer's protocol for SPA[$^3$H] thymidine uptake assay system (Amersham Biosciences # RPNQ 0130). SPA-bead based fluorescence was counted in a microbeta counter (Wallace Triplex 1450, Perkin Elmer).

Example 905 CD86 Inhibition Assay

A generalized procedure for a standard assay for the inhibition of B cell activity that can be used to test Formula I compounds is as follows. Total mouse splenocytes are purified from spleens of 8-16 week old Balb/c mice by red blood cell lysis (BD Pharmingen #555899). Testing compounds are diluted to 0.5% DMSO and incubated with $1.25 \times 10^6$ splenocytes in a final volume of 200 µl in flat clear bottom plates (Falcon 353072) for 60 min at 37° C. Cells are then stimulated with the addition of 15 µg/ml IgM (Jackson ImmunoResearch 115-006-020), and incubated for 24 hr at 37° C., 5% CO$_2$. Following the 24 hr incubation, cells are transferred to conical bottom clear 96-well plates and pelleted by centrifugation at 1200×g×5 min. Cells are pre-blocked by CD16/CD32 (BD Pharmingen #553142), followed by triple staining with CD19-FITC (BD Pharmingen #553785), CD86-PE (BD Pharmingen #553692), and 7AAD (BD Pharmingen #51-68981E). Cells are sorted on a BD FACSCalibur and gated on the CD19$^+$/7AAD$^-$ population. The levels of CD86 surface expression on the gated population is measured versus test compound concentration. Exemplary results are in Table 4.

TABLE 4

| Compound | CD86 inhibition EC$_{50}$ (mM) |
|---|---|
| 105 | 0.064 |
| 110 | 0.022 |
| 113 | 0.021 |
| 114 | 0.188 |
| 115 | 0.078 |
| 197 | 0.022 |
| 210 | 0.010 |
| 211 | 0.009 |
| 212 | 0.009 |
| 273 | 0.003 |
| 277 | 0.028 |
| 284 | 0.006 |
| 285 | 0.011 |
| 286 | 0.004 |
| 289 | 0.010 |
| 290 | 0.010 |
| 296 | 0.001 |
| 299 | 0.009 |
| 300 | 0.009 |
| 308 | 0.063 |
| 311 | 0.030 |
| 313 | 0.006 |
| 318 | 0.018 |
| 319 | 0.016 |
| 321 | 0.044 |

Example 906 B-ALL Cell Survival Assay

The following is a procedure for a standard B-ALL (acute lymphoblastic leukemia) cell survival study using an XTT readout to measure the number of viable cells. This assay can be used to test Formula I compounds for their ability to inhibit the survival of B-ALL cells in culture. One human B-cell acute lymphoblastic leukemia line that can be used is SUP-B15, a human Pre-B-cell ALL line that is available from the ATCC.

SUP-B15 pre-B-ALL cells are plated in multiple 96-well microtiter plates in 100 µl of Iscove's media+20% FBS at a concentration of $5 \times 10^5$ cells/ml. Test compounds are then added with a final conc. of 0.4% DMSO. Cells are incubated at 37° C. with 5% CO$_2$ for up to 3 days. After 3 days cells are split 1:3 into fresh 96-well plates containing the test compound and allowed to grow up to an additional 3 days. After each 24 h period, 50 ul of an XTT solution is added to one of the replicate 96-well plates and absorbance readings are taken at 2, 4 and 20 hours following manufacturer's directions. The reading taken with an OD for DMSO only treated cells within the linear range of the assay (0.5-1.5) is then taken and the percentage of viable cells in the compound treated wells are measured versus the DMSO only treated cells.

Example 907 CD69 Whole Blood Assay

Human blood is obtained from healthy volunteers, with the following restrictions: 1 week drug-free, non-smokers. Blood (approximately 20 mls to test 8 compounds) is collected by venipuncture into Vacutainer® (Becton, Dickinson and Co.) tubes with sodium heparin.

Solutions of Formula I compounds at 10 mM in DMSO are diluted 1:10 in 100% DMSO, then are diluted by three-fold serial dilutions in 100% DMSO for a ten point dose-response curve. The compounds are further diluted 1:10 in PBS and then an aliquot of 5.5 µl of each compound is added in duplicate to a 2 ml 96-well plate; 5.5 µl of 10% DMSO in PBS is added as control and no-stimulus wells. Human whole blood—HWB (100 µl) is added to each well. After mixing the plates are incubated at 37° C., 5% $CO_2$, 100% humidity for 30 minutes. Goat F(ab')2 anti-human IgM (10 µl of a 500 µg/ml solution, 50 µg/ml final) is added to each well (except the no-stimulus wells) with mixing and the plates are incubated for an additional 20 hours. At the end of the 20 hour incubation, samples are incubated with fluorescent labeled antibodies for 30 minutes, at 37° C., 5% $CO_2$, 100% humidity. Include induced control, unstained and single stains for compensation adjustments and initial voltage settings. Samples are then lysed with PharM Lyse™ (BD Biosciences Pharmingen) according to the manufacturer's instructions. Samples are then transferred to a 96 well plate suitable to be run on the BD Biosciences HTS 96 well system on the LSRII machine. Data acquired and Mean Fluorescence Intensity values were obtained using BD Biosciences DIVA Software. Results are initially analyzed by FACS analysis software (Flow Jo). The IC50 for test compounds is defined as the concentration which decreases by 50% the percent positive of CD69 cells that are also CD20 positive stimulated by anti-IgM (average of 8 control wells, after subtraction of the average of 8 wells for the no-stimulus background). The IC50 values are calculated by Prism version 5, using a nonlinear regression curve fit.

Exemplary IC50 values of selected compounds from Tables 1, 2, and 3 in the CD69 Whole Blood Assay include:

| Compound No. | IC50 (micromolar) |
| --- | --- |
| 105 | 0.088 |
| 197 | 0.023 |
| 304 | 0.035 |
| 311 | 0.044 |
| 339 | 0.053 |
| 341 | 0.024 |
| 322 | 0.053 |
| 323 | 0.024 |

We claim:
1. A compound selected from Formula I:

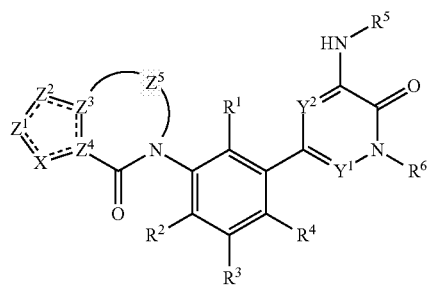

or stereoisomers, tautomers, or pharmaceutically acceptable salts thereof, wherein:

$R^1$ is H, D, F, Cl, CN, $NH_2$, $NHCH_3$, —$N(CH_3)_2$, —OH, —$OCH_3$, —$OCH_2CH_3$, —$OCH_2CH_2OH$, heteroaryl selected from imidazolyl and pyrazolyl, heterocyclyl selected from oxetanyl and azetidinyl, and $C_1$-$C_3$ alkyl;

$R^2$, $R^3$ and $R^4$ are independently selected from H, D, F, Cl, —$NH_2$, —$NHCH_3$, —$N(CH_3)_2$, —OH, —$OCH_3$, —$OCH_2CH_3$, —$OCH_2CH_2OH$, and $C_1$-$C_3$ alkyl;

$R^5$ is optionally substituted $C_6$-$C_{20}$ aryl, $C_3$-$C_{12}$ carbocyclyl, $C_2$-$C_{20}$ heterocyclyl, $C_1$-$C_{20}$ heteroaryl, —($C_6$-$C_{20}$ aryl)-($C_2$-$C_{20}$ heterocyclyl), —($C_1$-$C_{20}$ heteroaryl)-($C_2$-$C_{20}$ heterocyclyl), —($C_1$-$C_{20}$ heteroaryl)-($C_1$-$C_6$ alkyl), or —($C_1$-$C_{20}$ heteroaryl)-C(=O)—($C_2$-$C_{20}$ heterocyclyl);

$R^6$ is H, F, —$NH_2$, —OH, or optionally substituted $C_1$-$C_3$ alkyl;

X is S, S(=O), S(=O)$_2$, N, $NR^6$, O, or $CR^7$;

$R^7$ is independently selected from H, D, F, Cl, —$CH_3$, —$CH_2CH_3$, —CN, —$CH_2F$, —$CHF_2$, —$CF_3$, —$NH_2$, —OH, and —$OCH_3$;

$Y^1$ and $Y^2$ are independently selected from $CR^6$ and N;

$Z^1$, $Z^2$, $Z^3$, and $Z^4$ are independently selected from C, $CR^7$, and N;

$Z^5$ is selected from —$C(R^3)_2$—, —C(=O)—;

one of $Z^1$ and $Z^2$, or X and $Z^1$, where X is not S, S(=O), or S(=O)$_2$, forms a five-, six-, or seven-membered aryl, carbocyclyl, heterocyclyl or heteroaryl ring;

where alkyl, carbocyclyl, heterocyclyl, aryl, and heteroaryl are optionally substituted with one or more groups independently selected from D, F, Cl, Br, I, —$CH_3$, —$CH_2CH_3$, —$CH_2CH(CH_3)_2$, —$CH_2OH$, —$CH_2CH_2OH$, —$C(CH_3)_2OH$, —$CH(OH)CH(CH_3)_2$, —$C(CH_3)_2CH_2OH$, —$CH_2CH_2SO_2CH_3$, —$CH_2OP(O)(OH)_2$, —CN, —$CH_2F$, —$CHF_2$, —$CF_3$, —$CO_2H$, —$COCH_3$, —$CO_2CH_3$, —$CO_2C(CH_3)_3$, —$COCH(OH)CH_3$, —$CONH_2$, —$CONHCH_3$, —$CON(CH_3)_2$, —$C(CH_3)_2CONH_2$, —$NO_2$, —$NH_2$, —$NHCH_3$, —$N(CH_3)_2$, —$NHCOCH_3$, —$N(CH_3)COCH_3$, —$NHS(O)_2CH_3$, —$N(CH_3)C(CH_3)_2CONH_2$, —$N(CH_3)CH_2CH_2S(O)_2CH_3$, =O, —OH, —$OCH_3$, —$OCH_2CH_2N(CH_3)_2$, —$OP(O)(OH)_2$, —$S(O)_2N(CH_3)_2$, —$SCH_3$, —$CH_2OCH_3$, —$S(O)_2CH_3$, cyclopropyl, azetidinyl, 1-methylazetidin-3-yl)oxy, N-methyl-N-oxetan-3-ylamino, azetidin-1-ylmethyl, oxetanyl, and morpholino.

2. The compound of claim 1 selected from Formulas Ia-c:
Ia
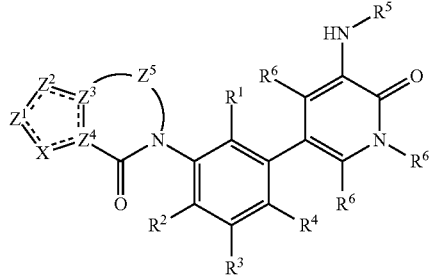
Ib
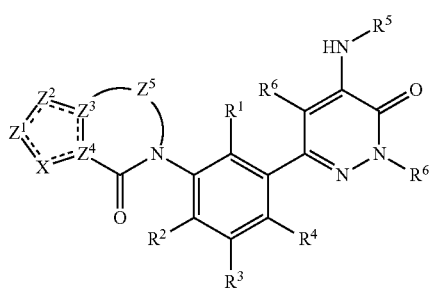
Ic
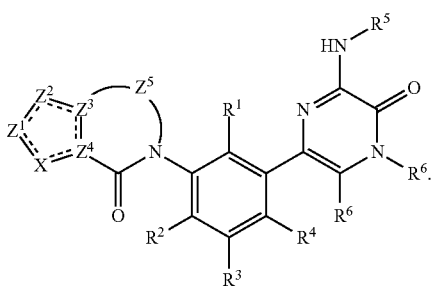
3. The compound of claim 1 selected from Formulas Id-f:
Id
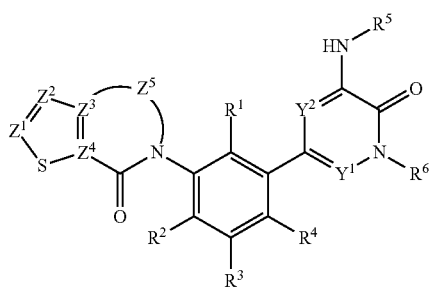
Ie
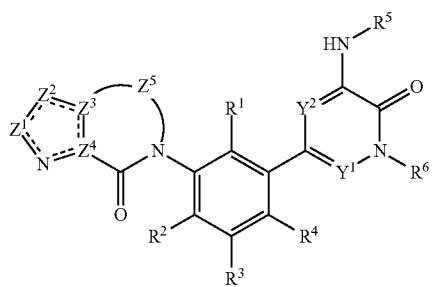
If
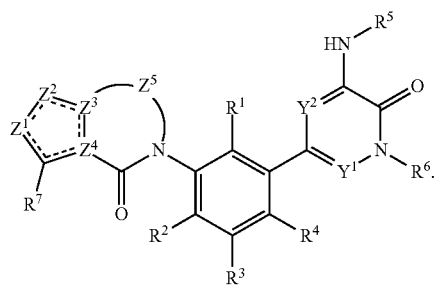
4. The compound of claim 1 selected from Formulas Ig-n:
Ig
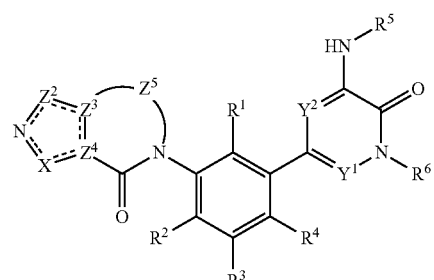
Ih
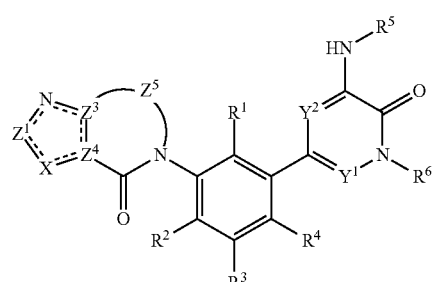
Ii
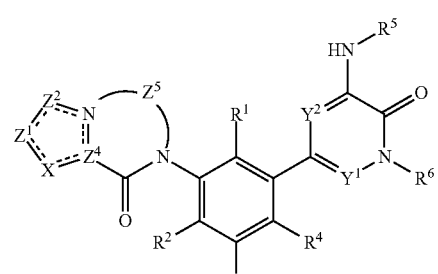
Ij
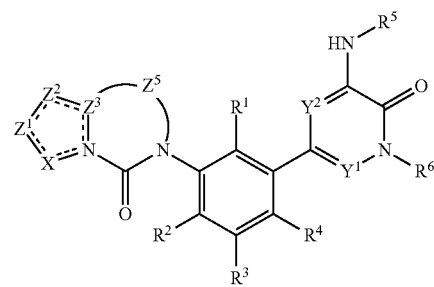

Ik
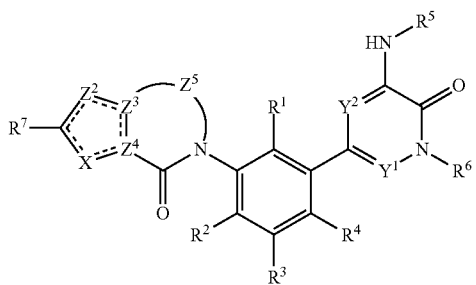
Il
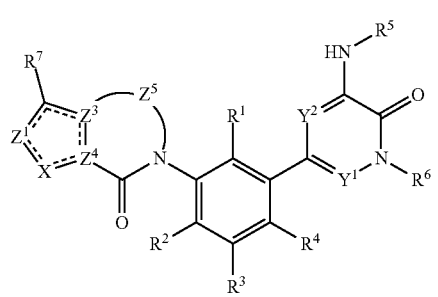
Im
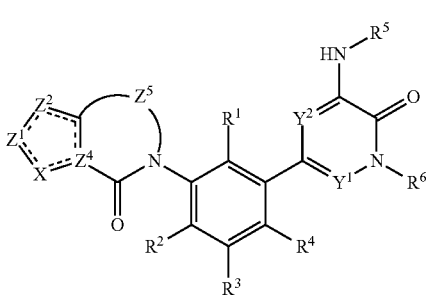
In
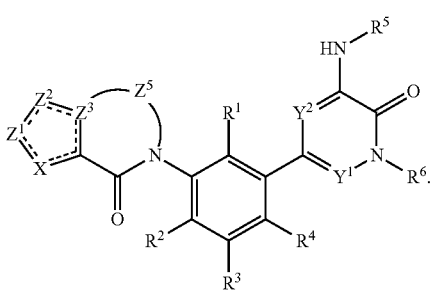
5. The compound of claim 1 selected from Formulas Io-t:
Io
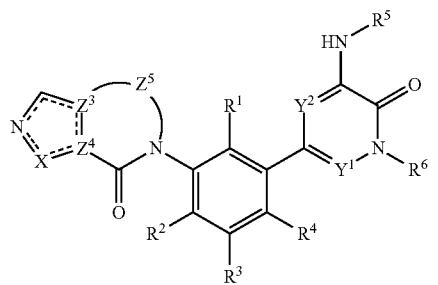
Ip
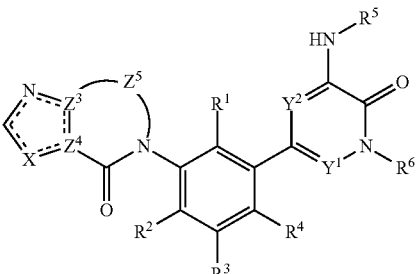
Iq
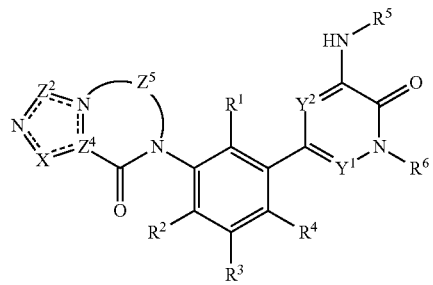
Ir
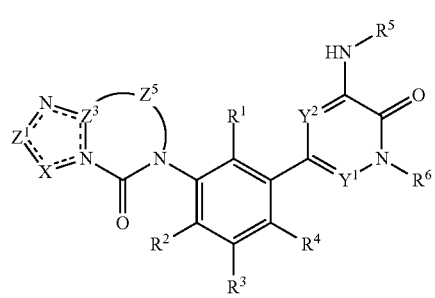
Is
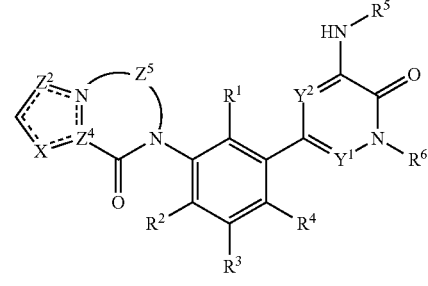
It
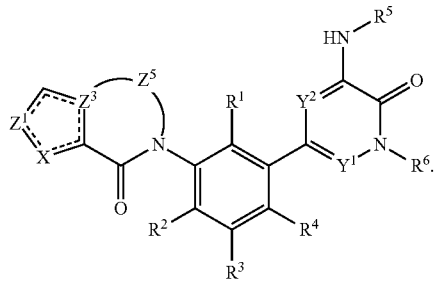
6. The compound of claim 1 where $Z^1$ and $Z^2$ forms a five-, six-, or seven-membered aryl, carbocyclyl, heterocyclyl or heteroaryl ring, and selected from Formulas Iaa-ap:

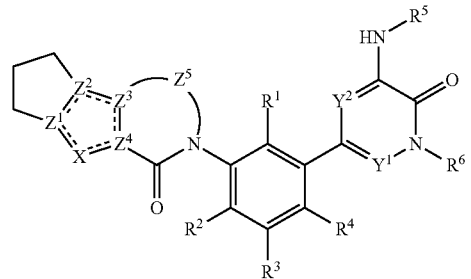
Iaa
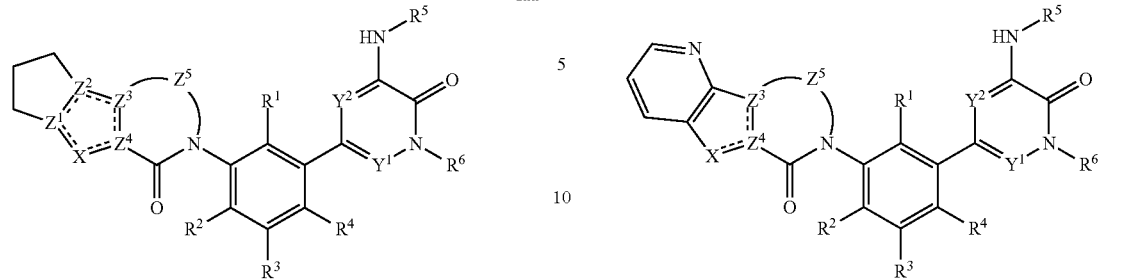
Iaf
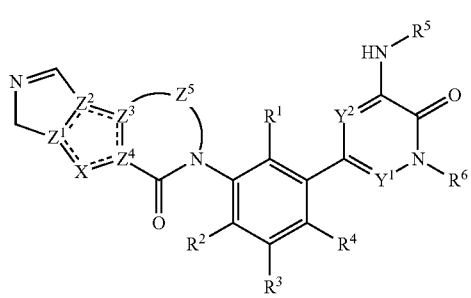
Iab
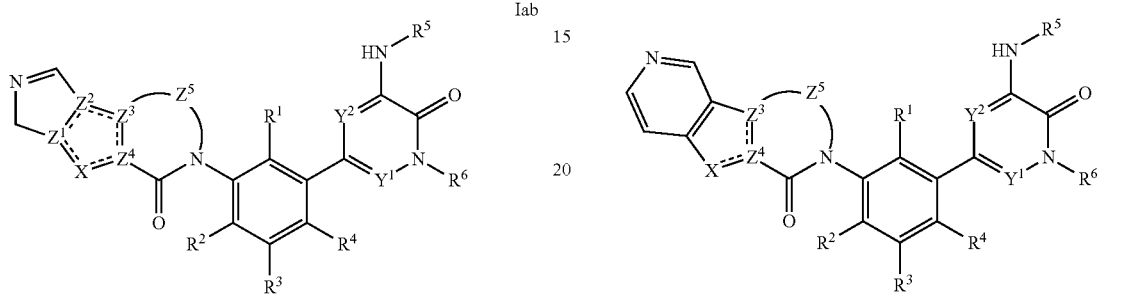
Iag
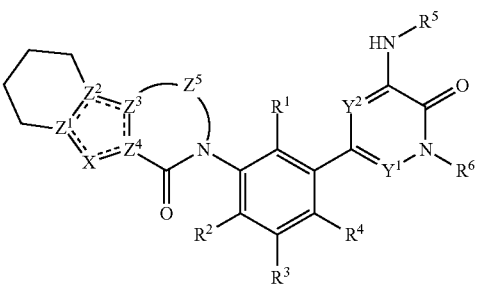
Iac
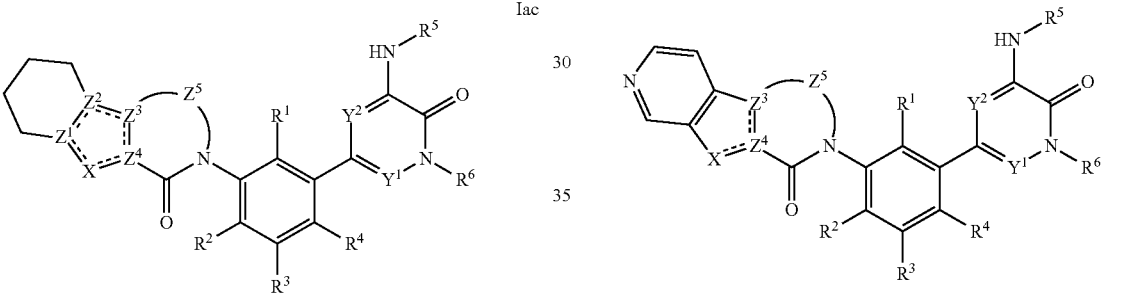
Iah
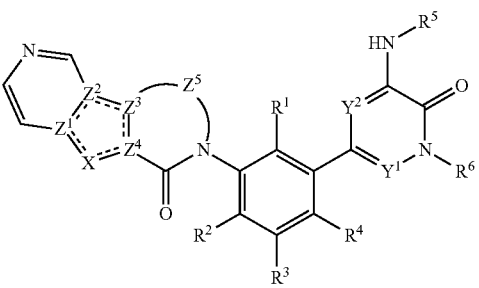
Iad
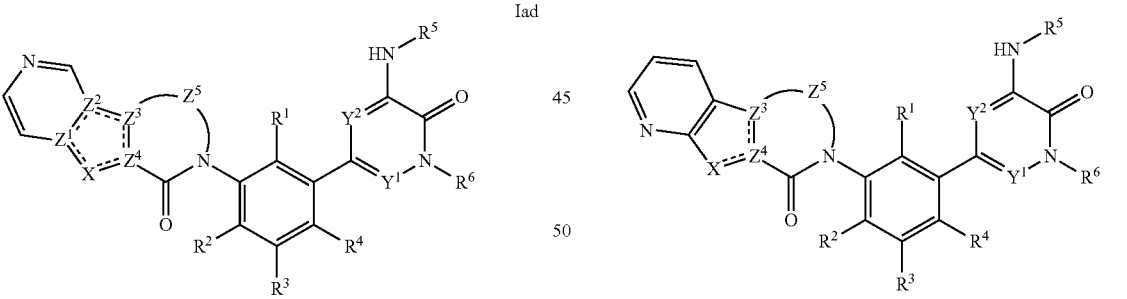
Iai
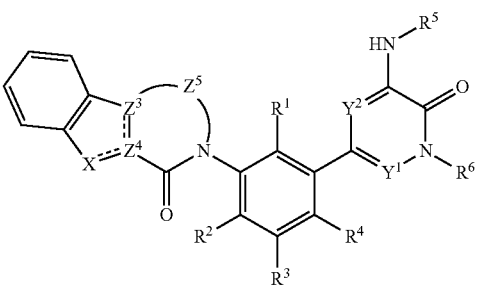
Iae
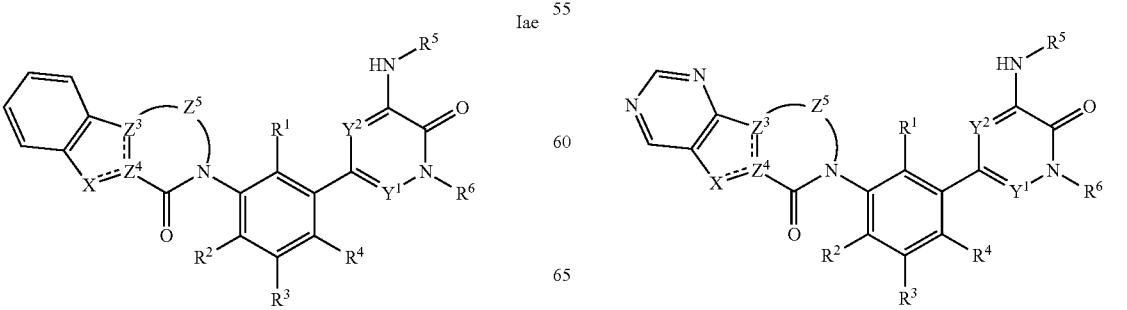
Iaj Iak
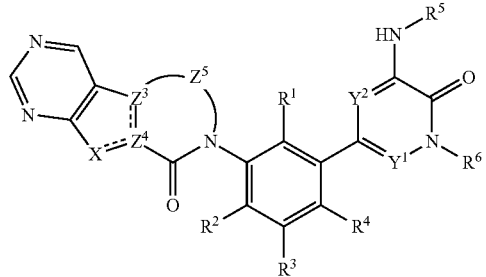
Ial
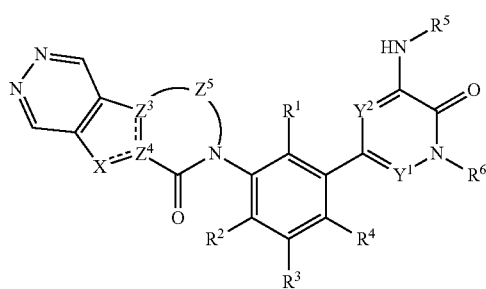
Iam
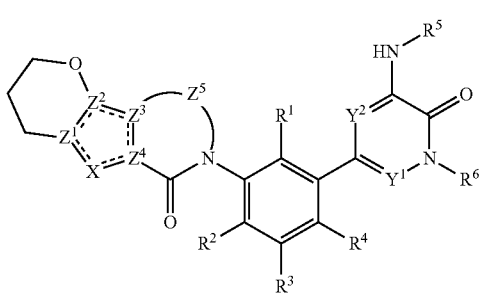
Ian
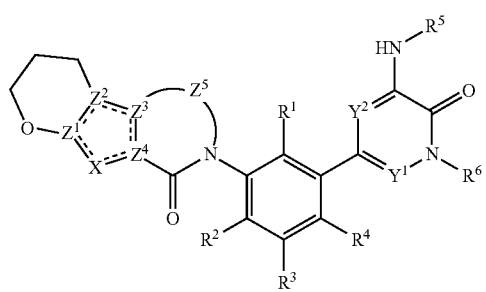
Iao
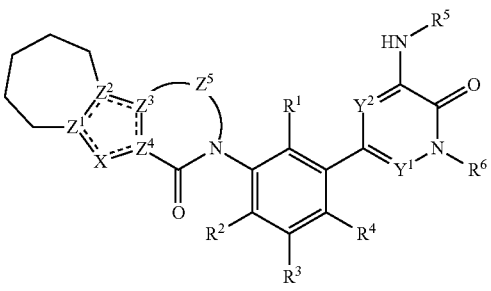
Iap
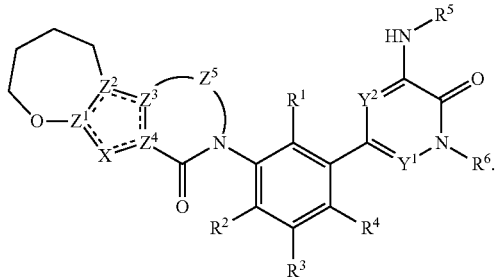
7. The compound of claim 1 where X and Z', and X is not S, forms a five-, six-, or seven-membered aryl, carbocyclyl, heterocyclyl or heteroaryl ring, and selected from Formulas Iaq-bf:
Iaq
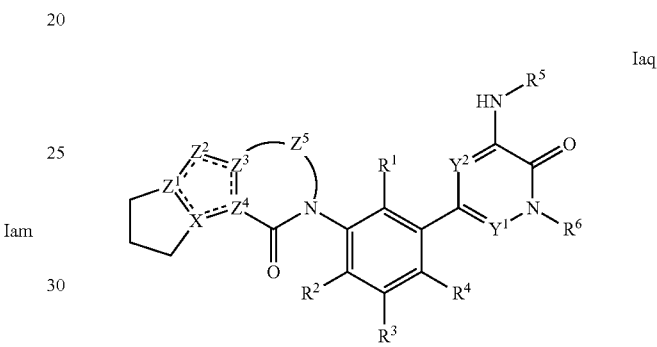
Iar
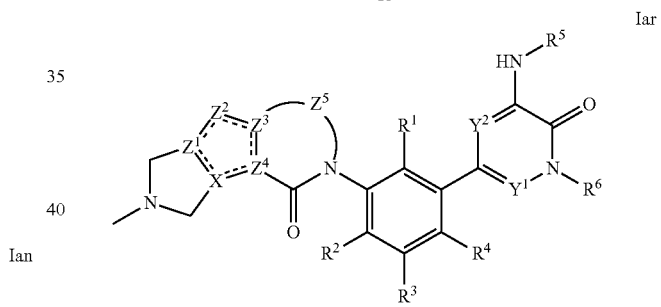
Ias
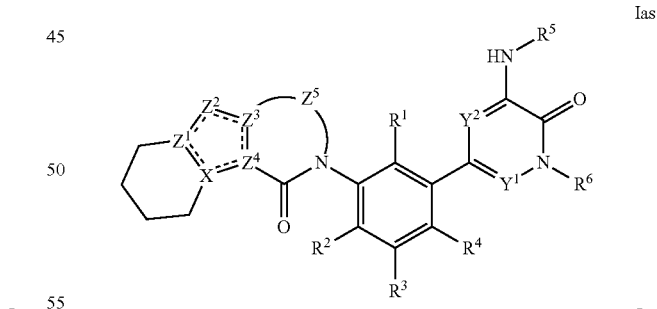
Iat
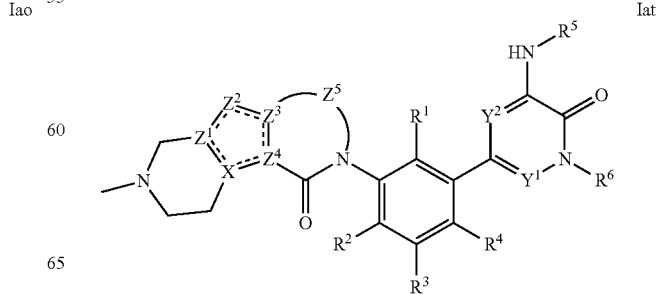

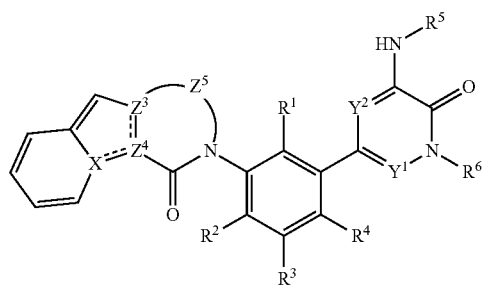
Iau
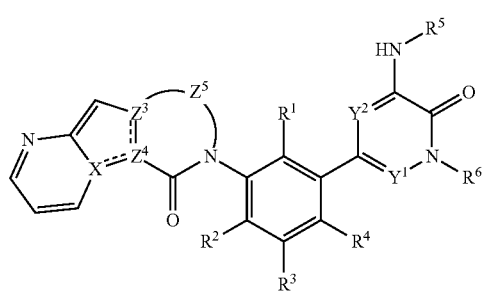
Iav
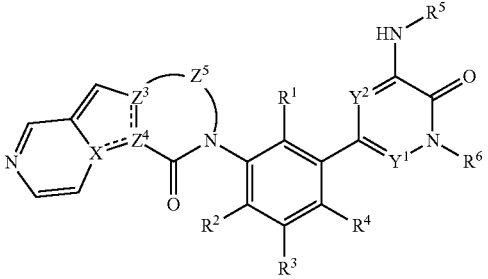
Iaw
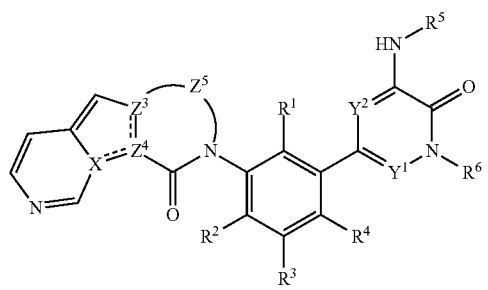
Iax
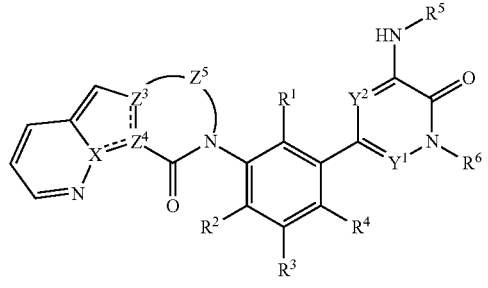
Iay
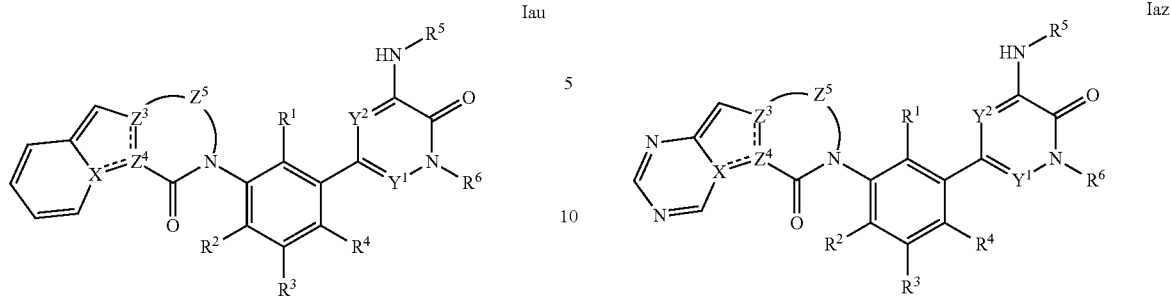
Iaz
Iba
Ibb
Ibc
Ibd

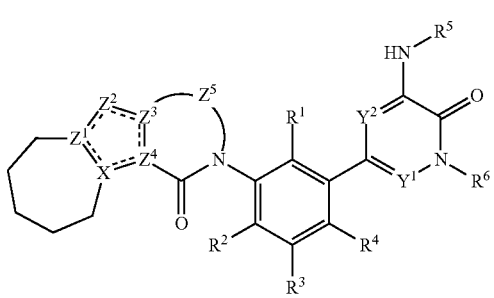

Ibe

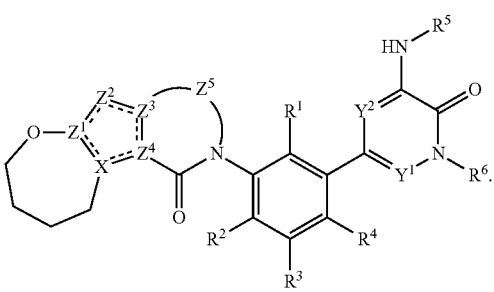

Ibf

8. The compound of claim 1 wherein $R^1$, $R^2$, $R^3$, and $R^4$ are each H.

9. The compound of claim 1 wherein $R^1$ is selected from F, —$CH_3$, —$CH_2F$, —$CHF_2$, and —$CF_3$.

10. The compound of claim 1 wherein R is —$CH_2OH$.

11. The compound of claim 1 wherein $R^3$ is F.

12. The compound of claim 1 wherein $R^1$ is —$CH_2OH$, $R^2$ and $R^4$ are each H, and $R^3$ is F.

13. The compound of claim 1 wherein $R^5$ is optionally substituted $C_6$-$C_{20}$ aryl selected from phenyl and naphthyl.

14. The compound of claim 1 wherein $R^5$ is optionally substituted $C_3$-$C_{12}$ carbocyclyl selected from cyclopropyl, cyclobutyl, cyclopentyl, cyclohexyl, and cycloheptyl.

15. The compound of claim 1 wherein $R^5$ is optionally substituted $C_2$-$C_{20}$ heterocyclyl selected from oxetanyl, azetidinyl, pyrrolidinyl, tetrahydrofuryl, piperidinyl, piperazinyl, morpholinyl, and tetrahydropyranyl.

16. The compound of claim 1 wherein $R^5$ is optionally substituted $C_1$-$C_{20}$ heteroaryl selected from pyrazolyl, pyridinyl, pyrimidinyl, 5-methyl-4,5,6,7-tetrahydropyrazolo[1,5-a]pyrazin-2-yl, 5-acetyl-4,5,6,7-tetrahydropyrazolo[1,5-a]pyrazin-2-yl, 6,7-dihydro-4H-pyrazolo[5,1-c][1,4]oxazin-2-yl, and 1-methyl-5-(5-(4-methylpiperazin-1-yl)pyridin-2-yl.

17. The compound of claim 1 wherein $R^5$ is substituted with one or more groups selected from F, Cl, —$CH_3$, cyclopropyl, azetidinyl, oxetanyl, and morpholino.

18. The compound of claim 1 wherein $R^5$ is selected from the structures:

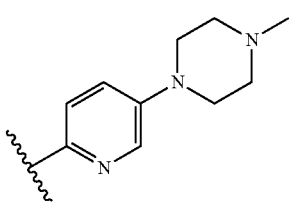

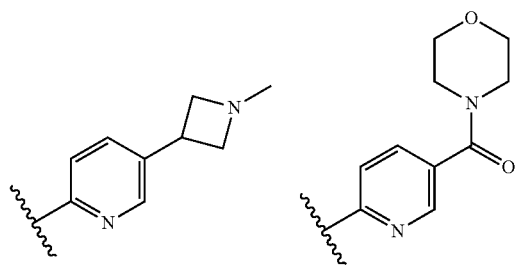

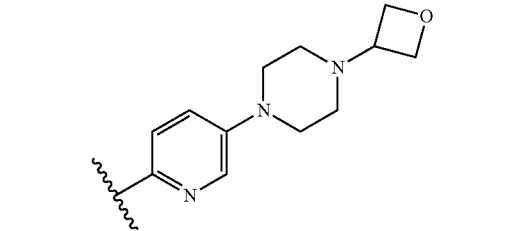

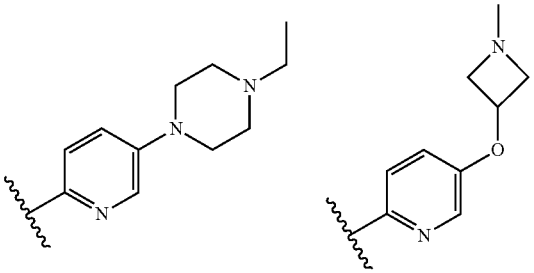

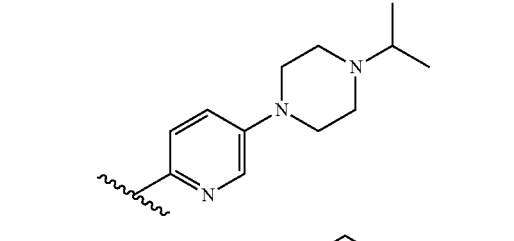

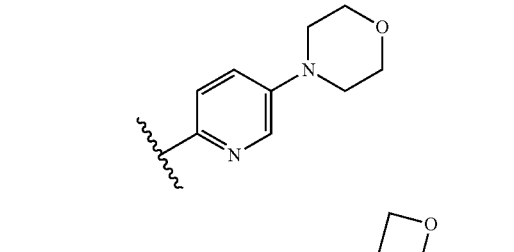

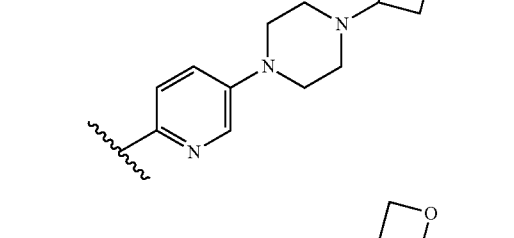

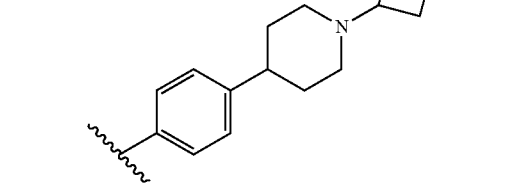

535
-continued

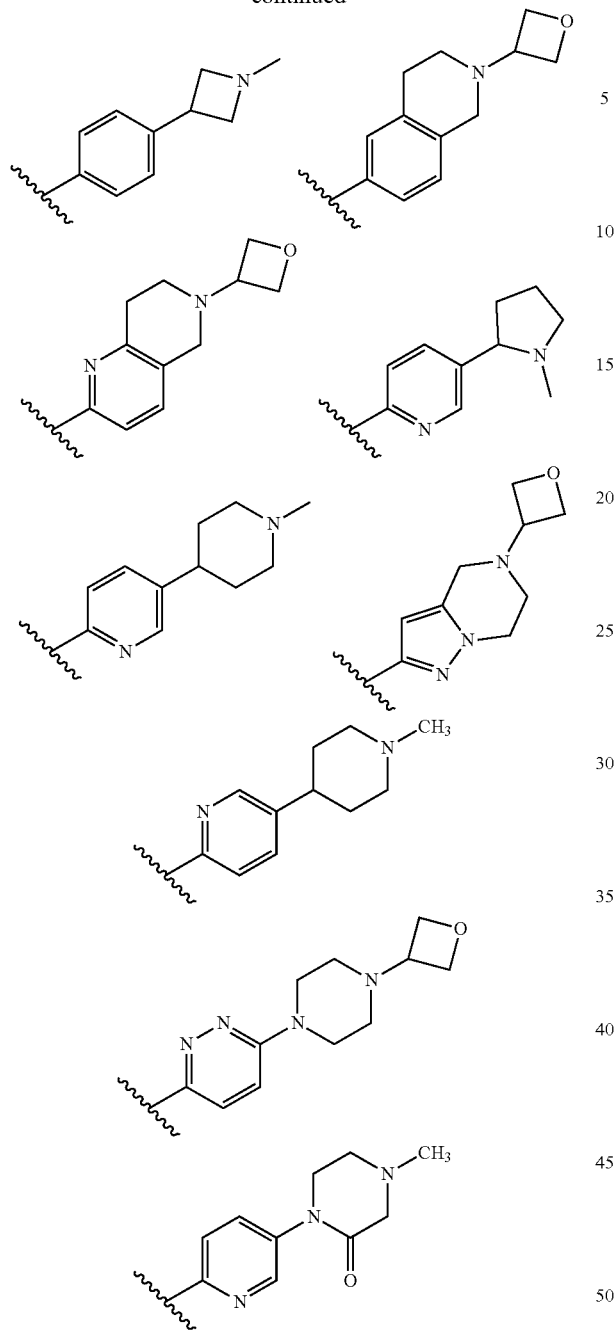

536
-continued

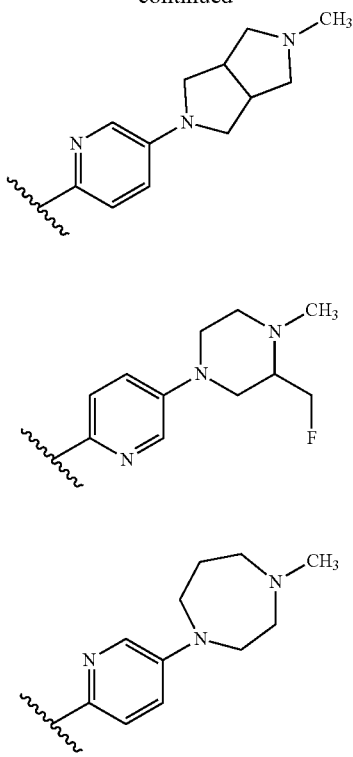

where the wavy line indicates the site of attachment.

19. The compound of claim 1 wherein $R^6$ is H.

20. The compound of claim 1 wherein X is S.

21. The compound of claim 1 wherein X is N.

22. The compound of claim 1 wherein X is $CR^7$.

23. The compound of claim 1 wherein $Y^1$ is $CR^6$ and $Y^2$ is N.

24. The compound of claim 1 wherein $Y^1$ is N and $Y^2$ is $CR^6$.

25. The compound of claim 1 wherein $Y^1$ and $Y^2$ are each $CR^6$.

26. A pharmaceutical composition comprised of a compound of claim 1 and a pharmaceutically acceptable carrier, glidant, diluent, or excipient.

27. The pharmaceutical composition of to claim 1, further comprising a second therapeutic agent.

* * * * *